US011179383B2

(12) United States Patent
Blomgren et al.

(10) Patent No.: US 11,179,383 B2
(45) Date of Patent: Nov. 23, 2021

(54) COMPOUNDS FOR INHIBITION OF α4β7 INTEGRIN

(71) Applicant: Gilead Sciences, Inc., Foster City, CA (US)

(72) Inventors: Peter A. Blomgren, Issaquah, WA (US); Taryn Campbell, Seattle, WA (US); Jayaraman Chandrasekhar, Redmond, WA (US); Christopher T. Clark, Seattle, WA (US); Julian A. Codelli, Seattle, WA (US); Kevin S. Currie, North Bend, WA (US); Jeffrey E. Kropf, Issaquah, WA (US); Yasamin Moazami, Seattle, WA (US); Nicole Nava, Seattle, WA (US); Leena Patel, Seattle, WA (US); Stephane Perreault, Brier, WA (US); Jason K. Perry, San Francisco, CA (US); Kassandra F. Sedillo, Princeton, NJ (US); Natalie Seeger, Seattle, WA (US); Kirk L. Stevens, Bothell, WA (US); Jennifer Anne Treiberg, Redmond, WA (US); Suet C. Yeung, Redmond, WA (US); Zhongdong Zhao, Bellevue, WA (US)

(73) Assignee: GILEAD SCIENCES, INC., Foster City, CA (US)

( * ) Notice: Subject to any disclaimer, the term of this patent is extended or adjusted under 35 U.S.C. 154(b) by 0 days.

(21) Appl. No.: 16/667,572

(22) Filed: Oct. 29, 2019

(65) Prior Publication Data
US 2020/0163953 A1    May 28, 2020

Related U.S. Application Data

(60) Provisional application No. 62/752,854, filed on Oct. 30, 2018.

(51) Int. Cl.
| | |
|---|---|
| *C07D 215/02* | (2006.01) |
| *A61K 31/47* | (2006.01) |
| *A61K 31/352* | (2006.01) |
| *A61K 31/4709* | (2006.01) |
| *A61K 31/497* | (2006.01) |
| *A61K 31/501* | (2006.01) |
| *A61K 31/513* | (2006.01) |
| *A61K 31/5377* | (2006.01) |
| *A61K 31/541* | (2006.01) |
| *C07D 215/14* | (2006.01) |
| *C07D 311/58* | (2006.01) |

(Continued)

(52) U.S. Cl.
CPC ............ *A61K 31/47* (2013.01); *A61K 31/352* (2013.01); *A61K 31/4709* (2013.01); *A61K 31/497* (2013.01); *A61K 31/501* (2013.01); *A61K 31/513* (2013.01); *A61K 31/5377* (2013.01); *A61K 31/541* (2013.01); *C07D 215/14* (2013.01); *C07D 311/58* (2013.01); *C07D 401/10* (2013.01); *C07D 403/10* (2013.01); *C07D 405/10* (2013.01); *C07D 413/12* (2013.01); *C07D 413/14* (2013.01); *C07D 417/10* (2013.01); *C07D 471/04* (2013.01); *C07D 519/00* (2013.01)

(58) Field of Classification Search
CPC .. C07D 215/02; C07D 413/12; C07D 413/14; A61K 31/311; A61K 31/314; A61K 31/5377; A61P 29/00
USPC ........... 546/152; 514/311, 314, 234.2, 235.2; 544/117, 128
See application file for complete search history.

(56) References Cited

U.S. PATENT DOCUMENTS

| 6,511,961 B1 | 1/2003 | Takahashi et al. |
| 6,521,666 B1 | 2/2003 | Sircar et al. |

(Continued)

FOREIGN PATENT DOCUMENTS

| CN | 105483206 A | 4/2016 |
| CN | 106995439 A | 8/2017 |

(Continued)

OTHER PUBLICATIONS

Notice of Allowance and Search Report dated Nov. 4, 2020 for Taiwanese Appl. No. 108139338.

(Continued)

*Primary Examiner* — Charanjit Aulakh

(57) ABSTRACT

The present disclosure provides a compound of Formula (I):

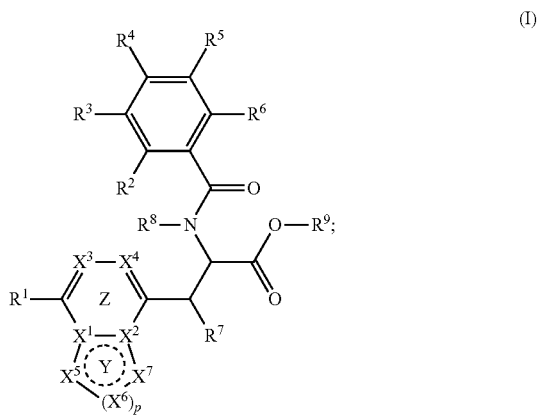

or a pharmaceutically acceptable salt thereof as described herein. The present disclosure also provides pharmaceutical compositions comprising a compound of Formula (I), processes for preparing compounds of Formula (I), and therapeutic methods for treating inflammatory disease.

20 Claims, No Drawings

(51) Int. Cl.
　　　*C07D 401/10*　　(2006.01)
　　　*C07D 403/10*　　(2006.01)
　　　*C07D 405/10*　　(2006.01)
　　　*C07D 413/12*　　(2006.01)
　　　*C07D 413/14*　　(2006.01)
　　　*C07D 417/10*　　(2006.01)
　　　*C07D 471/04*　　(2006.01)
　　　*C07D 519/00*　　(2006.01)

(56) References Cited

U.S. PATENT DOCUMENTS

| | | |
|---|---|---|
| 6,806,312 B2 | 10/2004 | Sasagawa et al. |
| 7,105,520 B2 | 9/2006 | Suzuki et al. |
| 7,335,673 B2 | 2/2008 | Hoshina et al. |
| 7,361,679 B2 | 4/2008 | Ikegami et al. |
| 7,566,724 B2 | 7/2009 | Hirano et al. |
| 8,546,610 B2 | 10/2013 | Kataoka et al. |
| 9,216,174 B2 | 12/2015 | Shen et al. |
| 9,533,985 B2 | 1/2017 | Ueno et al. |
| 9,822,110 B2 | 11/2017 | Ueno et al. |
| 2003/0114490 A1 | 6/2003 | Tanaka et al. |
| 2003/0130320 A1 | 7/2003 | Suzuki et al. |
| 2003/0149083 A1 | 8/2003 | Tanaka et al. |
| 2003/0220268 A1 | 11/2003 | Makino et al. |
| 2003/0220318 A1 | 11/2003 | Suzuki et al. |
| 2004/0039040 A1 | 2/2004 | Takahashi et al. |
| 2004/0077693 A1 | 4/2004 | Artis et al. |
| 2004/0087574 A1 | 5/2004 | Takahashi et al. |
| 2004/0110945 A1 | 6/2004 | Nakayama et al. |
| 2004/0132783 A1 | 7/2004 | Ono et al. |
| 2004/0235848 A1 | 11/2004 | Okuzumi et al. |
| 2004/0236147 A1 | 11/2004 | Chiba et al. |
| 2004/0259908 A1 | 12/2004 | Ikegami et al. |
| 2005/0101779 A1 | 5/2005 | Sagi et al. |
| 2005/0187284 A1 | 8/2005 | Artis et al. |
| 2005/0222141 A1 | 10/2005 | Sagi et al. |
| 2005/0261291 A1 | 11/2005 | Kawahara et al. |
| 2006/0009476 A1 | 1/2006 | Kataoka et al. |
| 2006/0204572 A1 | 9/2006 | Higuchi et al. |
| 2006/0204574 A1 | 9/2006 | Ogawa et al. |
| 2006/0223836 A1 | 10/2006 | Makino et al. |
| 2006/0241132 A1 | 10/2006 | Ishigaki et al. |
| 2007/0105936 A1 | 5/2007 | Ono et al. |
| 2007/0232601 A1 | 10/2007 | Yoneda et al. |
| 2007/0269835 A1 | 11/2007 | Katayama et al. |
| 2008/0075719 A1 | 3/2008 | Chan et al. |
| 2008/0108634 A1 | 5/2008 | Sagi et al. |
| 2008/0108637 A1 | 5/2008 | Fujita et al. |
| 2008/0161566 A1 | 7/2008 | Kotake et al. |
| 2008/0280909 A1 | 11/2008 | Okuzumi et al. |
| 2009/0048236 A1 | 2/2009 | Suzuki et al. |
| 2009/0163715 A1 | 6/2009 | Nagai et al. |
| 2009/0233901 A1 | 9/2009 | Machinaga et al. |
| 2009/0318688 A1 | 12/2009 | Kataoka et al. |
| 2009/0325962 A1 | 12/2009 | Jackson et al. |
| 2010/0022783 A1 | 1/2010 | Ono et al. |
| 2010/0137593 A1 | 6/2010 | Takahashi et al. |
| 2010/0204505 A1 | 8/2010 | Kataoka et al. |
| 2010/0267754 A1 | 10/2010 | Wakabayashi et al. |
| 2011/0009434 A1 | 1/2011 | Fujita et al. |
| 2011/0065918 A1 | 3/2011 | Makino et al. |
| 2011/0313154 A1 | 12/2011 | Kataoka et al. |
| 2012/0157437 A1 | 6/2012 | Machinaga et al. |
| 2012/0253041 A1 | 10/2012 | Makino et al. |
| 2013/0030013 A1 | 1/2013 | Aburatani et al. |
| 2013/0065882 A1 | 3/2013 | Machinaga et al. |
| 2013/0066072 A1 | 3/2013 | Kataoka et al. |
| 2014/0206705 A1 | 7/2014 | Kataoka et al. |
| 2015/0045435 A1 | 2/2015 | Scott et al. |
| 2015/0051395 A1 | 2/2015 | Ueno et al. |
| 2016/0367517 A1 | 12/2016 | Thompson |
| 2017/0196870 A1 | 7/2017 | Kageyama et al. |
| 2018/0244648 A1 | 8/2018 | Harrison et al. |
| 2018/0312498 A1 | 11/2018 | Biediger et al. |
| 2020/0155538 A1 | 5/2020 | Blomgren et al. |
| 2020/0155563 A1 | 5/2020 | Blomgren et al. |
| 2020/0165248 A1 | 5/2020 | Blomgren et al. |
| 2021/0053967 A1 | 2/2021 | Blomgren et al. |

FOREIGN PATENT DOCUMENTS

| | | |
|---|---|---|
| EP | 1209147 A1 | 5/2002 |
| EP | 1323711 A1 | 7/2003 |
| EP | 1889827 B1 | 8/2010 |
| EP | 3064491 A1 | 9/2016 |
| EP | 2842945 B1 | 10/2016 |
| IN | 2966/DEL/2005 | 7/2009 |
| JP | 2001089368 A | 4/2001 |
| JP | 2003048889 A | 2/2003 |
| JP | 2003277340 A | 10/2003 |
| JP | 2003321358 A | 11/2003 |
| JP | 2004277338 A | 10/2004 |
| JP | 2015083970 A | 4/2015 |
| JP | 201637467 A | 3/2016 |
| JP | 201637468 A | 3/2016 |
| JP | 2019031449 A | 2/2019 |
| WO | WO-94/012181 A1 | 6/1994 |
| WO | WO-96/000581 A1 | 1/1996 |
| WO | WO-97/003094 A1 | 1/1997 |
| WO | WO-97/005865 A1 | 2/1997 |
| WO | WO-98/004247 A1 | 2/1998 |
| WO | WO-98/042656 A1 | 10/1998 |
| WO | WO-98/053814 A1 | 12/1998 |
| WO | WO-98/053817 A1 | 12/1998 |
| WO | WO-98/053818 A1 | 12/1998 |
| WO | WO-98/058902 A1 | 12/1998 |
| WO | WO-99/006431 A1 | 2/1999 |
| WO | WO-99/006434 A1 | 2/1999 |
| WO | WO-99/006436 A1 | 2/1999 |
| WO | WO-99/006437 A1 | 2/1999 |
| WO | WO-99/010312 A1 | 3/1999 |
| WO | WO-99/010313 A1 | 3/1999 |
| WO | WO-99/013898 A1 | 3/1999 |
| WO | WO-99/025731 A1 | 5/1999 |
| WO | WO-99/026615 A1 | 6/1999 |
| WO | WO-99/026921 A1 | 6/1999 |
| WO | WO-99/030713 A1 | 6/1999 |
| WO | WO-99/036393 A1 | 7/1999 |
| WO | WO-99/052898 A1 | 10/1999 |
| WO | WO-99/061421 A1 | 12/1999 |
| WO | WO-99/062901 A1 | 12/1999 |
| WO | WO-99/064395 A1 | 12/1999 |
| WO | WO-99/067230 A1 | 12/1999 |
| WO | WO-2000/002903 A1 | 1/2000 |
| WO | WO-2000/005223 A2 | 2/2000 |
| WO | WO-2000/015612 A1 | 3/2000 |
| WO | WO-2000/035855 A1 | 6/2000 |
| WO | WO-2000/037444 A1 | 6/2000 |
| WO | WO-2000/043354 A2 | 7/2000 |
| WO | WO-2000/043369 A1 | 7/2000 |
| WO | WO-2000/043371 A2 | 7/2000 |
| WO | WO-2000/043372 A1 | 7/2000 |
| WO | WO-2000/043413 A2 | 7/2000 |
| WO | WO-2000/048994 A1 | 8/2000 |
| WO | WO-2000/051974 A1 | 9/2000 |
| WO | WO-2000/063234 A2 | 10/2000 |
| WO | WO-2000/064866 A1 | 11/2000 |
| WO | WO-2000/067746 A1 | 11/2000 |
| WO | WO-2000/071572 A1 | 11/2000 |
| WO | WO-2001/000206 A1 | 1/2001 |
| WO | WO-2001/007400 A1 | 2/2001 |
| WO | WO-2001/012183 A1 | 2/2001 |
| WO | WO-2001/012186 A1 | 2/2001 |
| WO | WO-2001/014328 A2 | 3/2001 |
| WO | WO-2001/021584 A1 | 3/2001 |
| WO | WO-2001/032610 A1 | 5/2001 |
| WO | WO-2001/042215 A1 | 6/2001 |
| WO | WO-2001/042225 A2 | 6/2001 |
| WO | WO-2001/043774 A1 | 6/2001 |
| WO | WO-2001/047868 A1 | 7/2001 |
| WO | WO-2001/047887 A1 | 7/2001 |
| WO | WO-2001/053279 A1 | 7/2001 |
| WO | WO-2001/053295 A1 | 7/2001 |

(56) References Cited

FOREIGN PATENT DOCUMENTS

| | | |
|---|---|---|
| WO | WO-2001/055121 A1 | 8/2001 |
| WO | WO-2001/056994 A1 | 8/2001 |
| WO | WO-2001/068586 A2 | 9/2001 |
| WO | WO-2001/070670 A1 | 9/2001 |
| WO | WO-2002/002556 A2 | 1/2002 |
| WO | WO-2002/008201 A2 | 1/2002 |
| WO | WO-2002/008203 A2 | 1/2002 |
| WO | WO-2002/008206 A1 | 1/2002 |
| WO | WO-2002/014262 A1 | 2/2002 |
| WO | WO-2002/016329 A1 | 2/2002 |
| WO | WO-2002/018320 A2 | 3/2002 |
| WO | WO-2002/022563 A1 | 3/2002 |
| WO | WO-2002/024697 A1 | 3/2002 |
| WO | WO-2002/028830 A1 | 4/2002 |
| WO | WO-2002/053534 A1 | 7/2002 |
| WO | WO-2002/057242 A2 | 7/2002 |
| WO | WO-2002/068393 A1 | 9/2002 |
| WO | WO-2003/008380 A1 | 1/2003 |
| WO | WO-2003/010135 A1 | 2/2003 |
| WO | WO-2003/011815 A1 | 2/2003 |
| WO | WO-2003/024933 A1 | 3/2003 |
| WO | WO-2003/048126 A1 | 6/2003 |
| WO | WO-2003/053926 A1 | 7/2003 |
| WO | WO-2003/070709 A1 | 8/2003 |
| WO | WO-2003/072536 A1 | 9/2003 |
| WO | WO-2003/080611 A1 | 10/2003 |
| WO | WO-2003/089410 A1 | 10/2003 |
| WO | WO-2003/093237 A1 | 11/2003 |
| WO | WO-2003/099231 A2 | 12/2003 |
| WO | WO-2003/099809 A1 | 12/2003 |
| WO | WO-2004/006918 A1 | 1/2004 |
| WO | WO-2004/007428 A1 | 1/2004 |
| WO | WO-2004/007494 A1 | 1/2004 |
| WO | WO-2004/014844 A2 | 2/2004 |
| WO | WO-2004/014859 A2 | 2/2004 |
| WO | WO-2004/062601 A2 | 7/2004 |
| WO | WO-2004/066931 A2 | 8/2004 |
| WO | WO-2004/066932 A2 | 8/2004 |
| WO | WO-2004/074264 A1 | 9/2004 |
| WO | WO-2004/099126 A1 | 11/2004 |
| WO | WO-2004/103967 A2 | 12/2004 |
| WO | WO-2005/000244 A2 | 1/2005 |
| WO | WO-2005/009992 A1 | 2/2005 |
| WO | WO-2005/014532 A1 | 2/2005 |
| WO | WO-2005/040135 A1 | 5/2005 |
| WO | WO-2005/042529 A1 | 5/2005 |
| WO | WO-2005/044817 A1 | 5/2005 |
| WO | WO-2005/061440 A1 | 7/2005 |
| WO | WO-2005/061466 A1 | 7/2005 |
| WO | WO-2005/063705 A1 | 7/2005 |
| WO | WO-2005/070921 A1 | 8/2005 |
| WO | WO-2005/077914 A1 | 8/2005 |
| WO | WO-2005/077915 A1 | 8/2005 |
| WO | WO-2005/087760 A1 | 9/2005 |
| WO | WO-2005/097162 A2 | 10/2005 |
| WO | WO-2005/107762 A2 | 11/2005 |
| WO | WO-2005/121135 A1 | 12/2005 |
| WO | WO-2006/010054 A2 | 1/2006 |
| WO | WO-2006/019632 A2 | 2/2006 |
| WO | WO-2006/023396 A2 | 3/2006 |
| WO | WO-2006/028393 A1 | 3/2006 |
| WO | WO-2006/052962 A2 | 5/2006 |
| WO | WO-2006/066780 A1 | 6/2006 |
| WO | WO-2006/068058 A1 | 6/2006 |
| WO | WO-2006/068213 A1 | 6/2006 |
| WO | WO-2006/081986 A1 | 8/2006 |
| WO | WO-2006/090234 A1 | 8/2006 |
| WO | WO-2006/096807 A1 | 9/2006 |
| WO | WO-2006/112738 A1 | 10/2006 |
| WO | WO-2006/113199 A1 | 10/2006 |
| WO | WO-2006/115918 A2 | 11/2006 |
| WO | WO-2006/126635 A1 | 11/2006 |
| WO | WO-2006/127584 A1 | 11/2006 |
| WO | WO-2006/131200 A1 | 12/2006 |
| WO | WO-2007/004958 A1 | 1/2007 |
| WO | WO-2007/069635 A1 | 6/2007 |
| WO | WO-2007/082809 A1 | 7/2007 |
| WO | WO-2007/100763 A2 | 9/2007 |
| WO | WO-2007/101165 A1 | 9/2007 |
| WO | WO-2008/062859 A1 | 5/2008 |
| WO | WO-2008/064830 A1 | 6/2008 |
| WO | WO-2008/125210 A1 | 10/2008 |
| WO | WO-2008/154642 A2 | 12/2008 |
| WO | WO-2009/075806 A1 | 6/2009 |
| WO | WO-2009/124755 A1 | 10/2009 |
| WO | WO-2009/140621 A2 | 11/2009 |
| WO | WO-2010/104306 A2 | 9/2010 |
| WO | WO-2010/105363 A1 | 9/2010 |
| WO | WO-2010/112865 A1 | 10/2010 |
| WO | WO-2010/126914 A1 | 11/2010 |
| WO | WO-2011/048091 A1 | 4/2011 |
| WO | WO-2011/094890 A1 | 8/2011 |
| WO | WO-2011/122619 A1 | 10/2011 |
| WO | WO-2011/143274 A1 | 11/2011 |
| WO | WO-2011/150499 A1 | 12/2011 |
| WO | WO-2011/159781 A2 | 12/2011 |
| WO | WO-2012/011123 A1 | 1/2012 |
| WO | WO-2012/068251 A2 | 5/2012 |
| WO | WO-2012/106343 A2 | 8/2012 |
| WO | WO-2013/070842 A1 | 5/2013 |
| WO | WO-2013/110680 A1 | 8/2013 |
| WO | WO-2013/110681 A1 | 8/2013 |
| WO | WO-2013/148978 A1 | 10/2013 |
| WO | WO-2013/161904 A1 | 10/2013 |
| WO | WO-2013/178816 A1 | 12/2013 |
| WO | WO-2014/051056 A1 | 4/2014 |
| WO | WO-2014/052605 A1 | 4/2014 |
| WO | WO-2015/064580 A1 | 5/2015 |
| WO | WO-2015/138882 A1 | 9/2015 |
| WO | WO-2015/172196 A1 | 11/2015 |
| WO | WO-2016/040505 A1 | 3/2016 |
| WO | WO-2016/051828 A1 | 4/2016 |
| WO | WO-2016/145258 A1 | 9/2016 |
| WO | WO-2017/006272 A1 | 1/2017 |
| WO | WO-2017/070518 A1 | 4/2017 |
| WO | WO-2017/126637 A1 | 7/2017 |
| WO | WO-2017/132620 A1 | 8/2017 |
| WO | WO-2017/135471 A1 | 8/2017 |
| WO | WO-2017/135472 A1 | 8/2017 |
| WO | WO-2018/049068 A1 | 3/2018 |
| WO | WO-2018/064119 A1 | 4/2018 |
| WO | WO-2018/085552 A1 | 5/2018 |
| WO | WO-2018/085574 A2 | 5/2018 |
| WO | WO-2018/089353 A1 | 5/2018 |
| WO | WO-2018/089355 A1 | 5/2018 |
| WO | WO-2018/089357 A1 | 5/2018 |
| WO | WO-2018/089358 A1 | 5/2018 |
| WO | WO-2018/089360 A1 | 5/2018 |
| WO | WO-2018/160522 A1 | 9/2018 |
| WO | WO-2018/200625 A1 | 11/2018 |
| WO | WO-2018/201167 A2 | 11/2018 |
| WO | WO-2019/085441 A1 | 5/2019 |
| WO | WO-2019/094319 A1 | 5/2019 |
| WO | WO-2019/173653 A1 | 9/2019 |
| WO | WO-2019/178248 A1 | 9/2019 |
| WO | WO-2019/200202 A1 | 10/2019 |
| WO | WO-2020/033724 A1 | 2/2020 |
| WO | WO-2020/043533 A1 | 3/2020 |
| WO | WO-2020/047207 A1 | 3/2020 |
| WO | WO-2020/047208 A1 | 3/2020 |
| WO | WO-2020/047239 A1 | 3/2020 |
| WO | WO-2020/092375 A1 | 5/2020 |
| WO | WO-2020/092383 A1 | 5/2020 |
| WO | WO-2020/092394 A1 | 5/2020 |
| WO | WO-2020/092401 A1 | 5/2020 |
| WO | WO-2021/030438 A1 | 2/2021 |

OTHER PUBLICATIONS

Hatley R J D et al. (2019), "The Design of Potent, Selective and Drug-Like RGD αvβ1 Small-Molecule Inhibitors Derived from non-RGD α4β1 Antagonists", Chem MedChem, 14, 1-7.

(56) References Cited

OTHER PUBLICATIONS

Intl. Search Report-Written Opinion dated Jan. 14, 2020 for Intl. Appl. No. PCT/US2019/058610.
Intl. Search Report-Written Opinion dated Jan. 21, 2020 for Intl. Appl. No. PCT/US2019/058573.
Intl. Search Report-Written Opinion dated Jan. 23, 2020 for Intl. Appl. No. PCT/US2019/058583.
Intl. Search Report-Written Opinion dated Jan. 28, 2020 for Intl. Appl. No. PCT/US2019/058599.
Li H et al. (2018), "$\alpha_4\beta_7$ integrin inhibitors: a patent review", Expert Opinion on Therapeutic Patents, 28:12, 903-917.
Sircar Ila et al. (2002), "Synthesis and SAR of N-Benzoyl-L-Biphenylalanine Derivatives: Discovery of TR-14035, A Dual $\alpha_4\beta_7$/$\alpha_4\beta_1$ Integrin Antagonist", Bioorganic & Medicinal Chemistry, vol. 10, No. 6, pp. 2051-2066.
Xu Y-Z et al. (2013), "Orally available and efficacious $\alpha_4\beta_1$/$\alpha_4\beta_7$ integrin inhibitors", Bioorganic & Medicinal Chemistry Letters 23:4370-4373.
Office Action dated Aug. 4, 2020 for Taiwanese Appl. No. 108139359.
Office Action dated Sep. 11, 2020 for Taiwanese Appl. No. 108139358.
Office Action dated Sep. 18, 2020 for Taiwanese Appl. No. 108139336.
Intl. Preliminary Report on Patentability dated May 4, 2021 for Intl. Appl. No. PCT/US2019/058573.
Intl. Preliminary Report on Patentability dated May 4, 2021 for Intl. Appl. No. PCT/US2019/058583.
Intl. Preliminary Report on Patentability dated May 4, 20214 for Intl. Appl. No. PCT/US2019/058599.
Intl. Preliminary Report on Patentability dated May 4, 2021 for Intl. Appl. No. PCT/US2019/058610.
Intl. Search Re port-Written Opinion dated Jan. 1, 2021 for Intl. Appl. No. PCT/US2020/045938.
Non-Final Office Action dated Mar. 19, 2021 for U.S. Appl. No. 16/667,532.
Notice of Allowance dated Mar. 26, 2021 for Taiwanese Appl. No. 108139358.
Notice of Allowance and Fees Due dated Feb. 24, 2021 for U.S. Appl. No. 16/667,306.
Notice of Allowance and Fees Due dated Mar. 12, 2021 for U.S. Appl. No. 16/667,373.
Notice of Allowance and Fees Due dated Mar. 19, 2021 for U.S. Appl. No. 16/667,572.
Notice of Allowance and Fees Due dated Jun. 14, 2021 for U.S. Appl. No. 16/667,306.

COMPOUNDS FOR INHIBITION OF α4β7 INTEGRIN

CROSS REFERENCE TO RELATED APPLICATION

This application claims priority to U.S. Provisional Application No. 62/752,854, filed Oct. 30, 2018, which is incorporated herein in its entirety for all purposes.

FIELD

The present disclosure relates generally to novel compounds that have α4β7 integrin inhibitory action, prodrugs of compounds having α4β7 integrin inhibitory action, and methods of use and manufacture thereof.

BACKGROUND

Integrins are heterodimeric cell surface proteins involved in numerous cellular processes including cell-cell and cell-extracellular matrix interactions. Upon binding of an extracellular ligand, integrins mediate signal transduction to the cell interior resulting in lymphocyte cell capture, adhesion, and infiltration into the tissue.

Integrins are heterodimeric proteins consisting of an alpha and a beta subunit. There are 18 known alpha subunits and 8 known beta subunits. The α4β7 integrin is expressed on the surface of lymphocytes and recognizes the extracellular ligand mucosal addressing cell adhesion molecule-1 (MAdCAM-1). α4β7 integrin governs lymphocyte trafficking to and retention in gut tissues through its interaction with MAdCAM-1, which is expressed on venules in the intestinal mucosa and high endothelial venules (HEV) in the gut-associated lymphoid tissues (GALT). Inhibiting the interactions of integrins with their respective ligands has been proposed as an effective method of treating a variety of autoimmune and inflammatory diseases, and blocking the α4β7-MAdCAM-1 interaction has shown therapeutic benefit in inflammatory bowel disease (Crohn's disease and ulcerative colitis).

There is a need to for improved α4β7 integrin antagonist molecules for the treatment of autoimmune and inflammatory diseases, including, but not limited to, inflammatory bowel disease.

SUMMARY

The present disclosure provides compounds that are inhibitors for α4β7 integrin. The disclosure also provides compositions, including pharmaceutical compositions, kits that include the compounds, and methods of using (or administering) and making the compounds. The compounds provided herein are useful in treating diseases, disorders, or conditions that are mediated, at least in part, by α4β7 integrin. The disclosure also provides compounds for use in therapy. The disclosure further provides compounds for use in a method of treating a disease, disorder, or condition that is mediated, at least in part, by α4β7 integrin. Moreover, the disclosure provides uses of the compounds in the manufacture of a medicament for the treatment of a disease, disorder or condition that is mediated, at least in part, by α4β7 integrin.

The present disclosure provides a compound of formula (I):

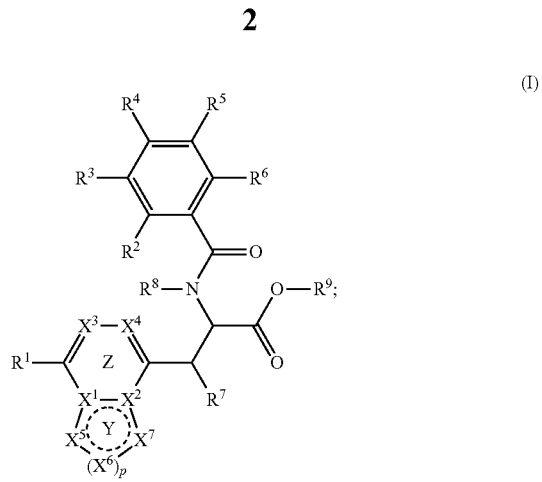

or a pharmaceutically acceptable salt thereof, wherein:
$X^1$ and $X^2$ are each independently selected from C, and N; wherein the bond between $X^1$ and $X^2$ is a single or a double bond;
$X^3$ and $X^4$ are each independently selected from $CR^{10}$, and N;
$X^5$ and $X^7$ are each independently selected from $CR^{10}R^{10}$, $CR^{10}$, S, S(O), S(O)$_2$, N, $NR^{11}$, C(O), and O;
each $X^6$ is independently selected from $CR^{10}R^{10}$, $CR^{10}$, S, S(O), S(O)$_2$, N, $NR^{11}$, C(O), and O; wherein the bond between $X^5$ and $X^6$, $X^6$ and $X^6$, or $X^6$ and $X^7$ is a single or a double, provided that at least one is a double bond;
$R^1$ is selected from -L-$A^1$, -L-$A^2$, -L-$A^3$, and -L-$A^4$;
L is selected from a bond, —O—, —O—C(O)—*, —NH—, —C(O)—N(H)—*, and —N(H)—C(O)—*; wherein * indicates a point of attachment of L to $A^1$, $A^2$, $A^3$, or $A^4$;
$A^1$ is $C_{6-10}$aryl optionally substituted with one to six $R^a$;
$A^2$ is 5-10 membered heteroaryl containing one to five heteroatoms independently selected from S, N, and O, and optionally one or two C(O); wherein $A^2$ is optionally substituted with one to six $R^a$;
$A^3$ is 5-10 membered cycloalkyl or 5-14 membered heterocyclyl; wherein $A^3$ is optionally substituted with one to six $R^a$; and
$A^4$ is —$NR^{a1}R^{a2}$;
wherein each $R^a$ is independently selected from halo, cyano, hydroxyl, —$NR^{a1}R^{a2}$, $C_{1-6}$alkyl, $C_{2-6}$alkenyl, $C_{2-6}$alkynyl, $C_{1-6}$alkoxyl, $C_{1-6}$haloalkyl, $C_{1-6}$haloalkoxyl, —S(O)$_m$—$C_{1-6}$alkyl, $C_{3-8}$cycloalkyl, 3-6 membered heterocyclyl, $C_{6-10}$aryl, 5-6 membered heteroaryl, —O-(3-6 membered heterocyclyl), —O—$C_{1-4}$alkylene-$C_{3-8}$cycloalkyl, —O-phenyl, and —O—$C_{3-8}$cycloalkyl;
each $C_{1-6}$alkyl, $C_{2-6}$alkenyl, $C_{2-6}$alkynyl, $C_{1-6}$alkoxyl, $C_{1-6}$haloalkyl, $C_{1-6}$haloalkoxyl, and —S(O)$_m$—$C_{1-6}$alkyl of $R^a$ are optionally substituted with one to three $R^{a3}$; wherein each $R^{a3}$ is independently selected from hydroxyl, cyano, —$NR^{a1}R^{a2}$, $C_{1-6}$alkoxyl, $C_{3-8}$cycloalkyl, phenyl, and 3-6 membered heterocyclyl; wherein each $C_{3-8}$cycloalkyl, phenyl, and 3-6 membered heterocyclyl of $R^{a3}$ is independently optionally substituted with one to three $R^{a4}$; wherein each $R^{a4}$ is independently selected from halo, cyano, hydroxyl, —$NR^{a1}R^{a2}$, $C_{1-6}$alkyl, $C_{1-6}$haloalkyl, $C_{1-6}$alkoxyl, $C_{1-6}$haloalkoxyl, $C_{3-8}$cycloalkyl, and 3-6 membered heterocyclyl; and each $C_{3-8}$cycloalkyl, 3-6 membered heteroaryl, $C_{6-10}$aryl, 5-6 membered heterocyclyl, —O—(3-6 membered heterocyclyl), —O—$C_{1-4}$alkylene-$C_{3-8}$cycloalkyl, —O— phenyl, and —O—$C_{3-8}$cycloalkyl of $R^a$ is independently optionally substituted with one to three groups independently selected from halo, cyano, hydroxyl, —$NR^{a1}R^{a2}$, $C_{1-6}$alkyl, $C_{1-6}$haloalkyl, $C_{1-6}$alkoxyl, and $C_{1-6}$haloalkoxyl;

each $R^2$, $R^3$, $R^4$, $R^5$, and $R^6$ is independently selected from H, halo, cyano, hydroxyl, $C_{1-6}$alkyl, $C_{2-6}$alkenyl, $C_{2-6}$alkynyl, $C_{1-6}$alkoxyl, $C_{1-8}$haloalkyl, $C_{1-8}$haloalkoxyl, —$NR^{b1}R^{b2}$, —$R^{b3}S(O)_mR^{b4}$, —$S(O)_mR^{b4}$, —$NR^{b1}S(O)_vR^{b4}$, —$COOR^{b1}$, —$CONR^{b1}R^{b2}$, —$NR^{b1}COOR^{b2}$, —$NR^{b1}COR^{b4}$, —$R^{b3}NR^{b1}R^{b2}$, —$S(O)_vNR^{b1}R^{b2}$, $C_{3-12}$cycloalkyl, $C_{6-10}$aryl, 5-6 membered heteroaryl, and 3-12 membered heterocyclyl;

each $C_{1-6}$alkyl, $C_{2-6}$alkenyl, $C_{2-6}$alkynyl, $C_{1-6}$alkoxyl, $C_{1-8}$haloalkyl, and $C_{1-8}$haloalkoxyl of $R^2$, $R^3$, $R^4$, $R^5$, and $R^6$ is independently optionally substituted with one to two $R^c$; wherein each $R^c$ is independently selected from azido, oxo, cyano, halo, hydroxyl, —$NR^{a1}R^{a2}$, $C_{1-4}$alkoxyl, $C_{3-8}$cycloalkyl, $C_{6-10}$aryl, 5-6 membered heteroaryl, and 4-6 membered heterocyclyl; wherein each $C_{3-8}$cycloalkyl, $C_{6-10}$aryl, 5-6 membered heteroaryl, and 4-6 membered heterocyclyl of $R^c$ is independently optionally substituted with one to three groups independently selected from halo, hydroxyl, cyano, —$NR^{a1}R^{a2}$, $C_{1-4}$alkyl, $C_{1-6}$haloalkyl, $C_{1-4}$alkoxyl, and $C_{3-6}$cycloalkyl;

each $C_{6-10}$aryl and 5-6 membered heteroaryl of $R^2$, $R^3$, $R^4$, $R^5$, and $R^6$ is independently optionally substituted with one to five $R^b$; and each $C_{3-12}$cycloalkyl and 3-12 membered heterocyclyl of $R^2$, $R^3$, $R^4$, $R^5$, and $R^6$ is independently optionally substituted with one to six groups independently selected from =$CR^{b1}R^{b2}$, and $R^b$;

wherein each $R^b$ is independently selected from azido, cyano, halo, hydroxyl, —$NR^{a1}R^{a2}$, $C_{1-6}$alkyl, $C_{1-8}$haloalkyl, $C_{1-6}$alkoxyl, $C_{3-6}$cycloalkyl, $C_{6-10}$aryl, 5-6 membered heteroaryl, and 4-6 membered heterocycyl; wherein each $C_{3-6}$cycloalkyl, $C_{6-10}$aryl, 5-6 membered heteroaryl, and 4-6 membered heterocyclyl of $R^b$ is independently optionally substituted with one to three groups independently selected from halo, hydroxyl, cyano, —$NR^{a1}R^{a2}$, $C_{1-4}$alkyl, $C_{1-4}$haloalkyl, and $C_{1-4}$alkoxyl;

each $R^{b1}$ and $R^{b2}$ is independently selected from H, $C_{1-8}$alkyl, $C_{1-8}$haloalkyl, $C_{3-8}$cycloalkyl, $C_{6-10}$aryl, 5-6 membered heteroaryl, and 3-8 membered heterocyclyl;

each $C_{1-8}$alkyl and $C_{1-6}$haloalkyl of $R^{b1}$ and $R^{b2}$ is optionally substituted with one to two $R^{b5}$; and each $C_{3-8}$cycloalkyl, $C_{6-10}$aryl, 5-6 membered heteroaryl, and 3-8 membered heterocyclyl of $R^{b1}$ and $R^{b2}$ is independently optionally substituted with one to three groups independently selected from halo, cyano, hydroxyl, —$NR^{a1}R^{a2}$, $C_{1-8}$alkyl, $C_{1-8}$haloalkyl, $C_{1-6}$alkoxyl, $C_{3-6}$cycloalkyl, $C_{6-10}$aryl, 5-6 membered heteroaryl, and 4-6 membered heterocyclyl;

$R^{b3}$ is $C_{1-4}$alkylene;

$R^{b4}$ is selected from $C_{1-4}$alkyl, $C_{1-4}$haloalkyl, $C_{3-6}$cycloalkyl, $C_{6-10}$aryl, 5-6 membered heteroaryl, and 4-6 membered heterocyclyl; wherein each $C_{1-4}$alkyl, $C_{1-4}$haloalkyl, $C_{3-8}$cycloalkyl, $C_{6-10}$aryl, 5-6 membered heteroaryl, and the 4-6 membered heterocyclyl of $R^{b4}$ is optionally substituted with one to three $R^{b6}$;

each $R^{b5}$ is independently selected from cyano, hydroxyl, $C_{1-4}$alkoxyl, $C_{3-8}$cycloalkyl, $C_{6-10}$aryl, 5-6 membered heteroaryl, and 4-6 membered heterocyclyl; wherein each $C_{3-8}$cycloalkyl, $C_{6-10}$aryl, 5-6 membered heteroaryl, and 4-6 membered heterocyclyl of $R^{b5}$ is optionally substituted with one to three groups independently selected from halo, cyano, hydroxyl, —$NR^{a1}R^{a2}$, $C_{1-4}$alkyl, $C_{1-4}$haloalkyl, $C_{1-4}$alkoxyl, and phenyl; and each $R^{b6}$ is independently selected from halo, cyano, $C_{1-4}$alkyl, $C_{1-4}$haloalkyl, $C_{1-4}$alkoxyl, $C_{3-6}$cycloalkyl, phenyl, 4-6 membered heterocyclyl, and 5-6 membered heteroaryl; wherein each $C_{3-6}$cycloalkyl, 4-6 membered heterocyclyl, and 5-6 membered heteroaryl of $R^{b6}$ is independently optionally substituted with one to three groups independently selected from halo, cyano, —$NR^{a1}R^{a2}$, $C_{1-4}$alkyl, $C_{1-4}$haloalkyl, and $C_{1-4}$alkoxyl;

or $R^2$ and $R^3$, $R^3$ and $R^4$, or $R^5$ and $R^6$ together with the atoms to which they are attached may form a $C_{6-10}$aryl, 5-6 membered heteroaryl, $C_{3-6}$cycloalkyl, or 5-6 membered heterocyclyl; wherein each $C_{6-10}$aryl, 5-6 membered heteroaryl, $C_{3-6}$cycloalkyl, or 5-6 membered heterocyclyl is optionally substituted with one to three groups independently selected from halo, cyano, —$NR^{a1}R^{a2}$, $C_{1-6}$alkyl, $C_{1-6}$alkoxyl, $C_{1-6}$haloalkyl, $C_{3-8}$cycloalkyl, 3-6 membered heterocyclyl, $C_{6-10}$aryl, 5-6 membered heteroaryl, $C_{1-4}$alkylene-$C_{3-8}$cycloalkyl, $C_{1-4}$alkylene-$C_{6-10}$aryl, and $C_{1-4}$alkylene-(5-6 membered heteroaryl);

$R^7$ is selected from H, $C_{1-4}$alkyl, and $C_{1-4}$haloalkyl;

$R^8$ is selected from H, $C_{1-4}$alkyl, and $C_{1-4}$haloalkyl;

$R^9$ is selected from H, $C_{1-6}$alkyl, —$C_{1-4}$alkylene-$NR^{a1}R^{a2}$, —$C_{1-4}$alkylene-$C(O)NR^{a1}R^{a2}$, —$C_{1-4}$alkylene-O—$C(O)$—$C_{1-4}$alkyl, —$C_{1-4}$alkylene-O—$C(O)$—O—$C_{1-4}$alkyl, —$C_{1-4}$alkylene-O—$C(O)$—$C_{1-4}$alkylene-$NR^{a1}R^{a2}$, —$C_{1-4}$alkylene-O—$C_{1-4}$alkyl, $C_{3-8}$cycloalkyl, —$C_{1-4}$alkylene-$C_{3-8}$cycloalkyl, 4-6 membered heterocyclyl, and —$C_{1-4}$alkylene-(4-6 membered heterocyclyl);

wherein each $C_{3-8}$cycloalkyl, —$C_{1-4}$alkylene-$C_{3-8}$cycloalkyl, and 4-6 membered heterocyclyl of $R^9$ is optionally substituted with one to three groups independently selected from halo, $C_{1-4}$alkyl, $C_{1-4}$alkoxyl, and $C_{1-4}$haloalkyl; or $R^9$ together with the N that attaches to $R^8$ forms a 5 membered heterocyclyl; wherein the 5 membered heterocyclyl is optionally substituted with one to two groups independently selected from halo, $C_{1-6}$alkyl, $C_{1-6}$alkoxyl, $C_{1-6}$haloalkyl, and $C_{6-10}$aryl; wherein $C_{6-10}$aryl is optionally substituted with one to three groups independently selected from halo, $C_{1-6}$alkyl, $C_{1-6}$alkoxyl, and $C_{1-6}$haloalkyl;

each $R^{10}$ is independently selected from H, halo, cyano, hydroxyl, —$C(O)R^{b1}$, —$NR^{a1}R^{a2}$, $C_{1-4}$alkyl, $C_{1-4}$alkoxyl, $C_{1-4}$haloalkyl, $C_{1-4}$haloalkoxyl, $C_{3-10}$cycloalkyl, 3-8 membered heterocyclyl, $C_{6-10}$aryl, and 5-6 membered heteroaryl; wherein each $C_{1-4}$alkyl, $C_{1-4}$alkoxyl, $C_{1-4}$haloalkyl, $C_{1-4}$haloalkoxyl, $C_{3-10}$cycloalkyl, 3-8 membered heterocyclyl, $C_{6-10}$aryl, and 5-6 membered heteroaryl is independently optionally substituted with one to three groups independently selected from halo, hydroxyl, cyano, —$NR^{a1}R^{a2}$, $C_{1-4}$alkyl, $C_{1-4}$haloalkyl, $C_{1-4}$alkoxyl, and $C_{3-6}$cycloalkyl;

or two $R^{10}$ either attached to the same or adjacent atoms form $C_{3-12}$cycloalkyl or 3-10 membered heterocyclyl; wherein each $C_{3-2}$cycloalkyl and 3-10 membered heterocyclyl is optionally substituted with one to three groups independently selected from H, halo, $C_{1-4}$alkyl, $C_{1-4}$alkoxyl, $C_{1-4}$haloalkyl, and $C_{1-4}$haloalkoxyl;

each $R^{11}$ is independently selected from H, $C_{1-4}$alkyl, and $C_{1-4}$haloalkyl; wherein each $C_{1-4}$alkyl, —C(O)$R^{b1}$, and $C_{1-4}$haloalkyl of $R^{11}$ is independently optionally substituted with one to three groups independently selected from halo, hydroxyl, cyano, —NR$^{a1}$R$^{a2}$, $C_{1-4}$alkyl, $C_{1-4}$haloalkyl, $C_{1-4}$alkoxyl, and $C_{3-6}$cycloalkyl;

or $R^{10}$ and $R^{11}$, or two $R^{11}$ together with the atoms to which they are attached to form 3-12 membered heterocyclyl; wherein 3-12 membered heterocyclyl is optionally substituted with one to three groups independently selected from H, halo, $C_{1-4}$alkyl, $C_{1-4}$alkoxyl, $C_{1-4}$haloalkyl, and $C_{1-4}$haloalkoxyl;

each $R^{a1}$ and $R^{a2}$ is independently selected from H, $C_{1-6}$alkyl, and $C_{1-6}$haloalkyl;

p is selected from 1, 2, and 3;

m is selected from 0, 1, and 2; and v is selected from 1 and 2.

Also provided herein is a pharmaceutical composition comprising a compound of formula (I), or any formula described herein, or a pharmaceutically acceptable salt, stereoisomer, mixture of stereoisomers, tautomer, or deuterated analog thereof, and at least one pharmaceutically acceptable carrier.

Also provided herein is a pharmaceutical composition comprising a compound of formula (I), or any formula described herein, or a pharmaceutically acceptable salt, stereoisomer, mixture of stereoisomers, tautomer, or deuterated analog thereof, and further comprising a second therapeutic agent.

In some embodiments, provided is a method for treating a disease or condition mediated, at least in part, by α4β7 integrin comprising administrating to a subject an effective amount of a pharmaceutical composition comprising a compound of formula (I), or any formula described herein, or a pharmaceutically acceptable salt, stereoisomer, mixture of stereoisomers, tautomer, or deuterated analog thereof, and at least one pharmaceutically acceptable carrier.

In some embodiments, provided is a method for treating a disease or condition mediated, at least in part, by α4β7 integrin comprising administrating to a subject an effective amount of a pharmaceutical composition comprising a compound of formula (I), or any formula described herein, or a pharmaceutically acceptable salt, stereoisomer, mixture of stereoisomers, tautomer, or deuterated analog thereof, and further comprising a second therapeutic agent.

Also provided herein is a pharmaceutical composition comprising a compound of formula (I), or any formula described herein, or a pharmaceutically acceptable salt, stereoisomer, mixture of stereoisomers, tautomer, or deuterated analog thereof, and at least one pharmaceutically acceptable carrier.

Also provided herein is a pharmaceutical composition comprising a compound of formula (I), or any formula described herein, or a pharmaceutically acceptable salt, stereoisomer, mixture of stereoisomers, tautomer, or deuterated analog thereof, and further comprising a second therapeutic agent.

In some embodiments, provided is a method for treating a disease or condition mediated, at least in part, by α4β7 integrin comprising administrating to a subject an effective amount of a pharmaceutical composition comprising a compound of formula (I), or any formula described herein, or a pharmaceutically acceptable salt, stereoisomer, mixture of stereoisomers, tautomer, or deuterated analog thereof, and at least one pharmaceutically acceptable carrier.

In some embodiments, provided is a method for treating a disease or condition mediated, at least in part, by α4β7 integrin comprising administrating to a subject an effective amount of a pharmaceutical composition comprising a compound of formula (I), or any formula described herein, or a pharmaceutically acceptable salt, stereoisomer, mixture of stereoisomers, tautomer, or deuterated analog thereof, and further comprising a second therapeutic agent.

In some embodiments, provided is a method for treating an inflammatory disease comprising administrating to a subject an effective amount of a pharmaceutical composition comprising a compound of formula (I), or any formula described herein, or a pharmaceutically acceptable salt, stereoisomer, mixture of stereoisomers, tautomer, or deuterated analog thereof.

DETAILED DESCRIPTION

Definitions and General Parameters

The following description sets forth exemplary methods, parameters and the like. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —CONH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

A squiggly line on a chemical group as shown below, for example,

indicates a point of attachment, i.e., it shows the broken bond by which the group is connected to another described group.

The prefix "$C_{u-v}$" indicates that the following group has from u to v carbon atoms. For example, "$C_{1-8}$ alkyl" indicates that the alkyl group has from 1 to 8 carbon atoms.

Reference to "about" a value or parameter herein includes (and describes) embodiments that are directed to that value or parameter per se. In some embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay"

includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e., —$(CH_2)_3CH_3$), sec-butyl (i.e., —$CH(CH_3)CH_2CH_3$), isobutyl (i.e., —$CH_2CH(CH_3)_2$) and tert-butyl (i.e., —$C(CH_3)_3$); and "propyl" includes n-propyl (i.e., —$(CH_2)_2CH_3$) and isopropyl (i.e., —$CH(CH_3)_2$).

"Alkenyl" refers to an aliphatic group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an aliphatic group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, iso-propoxy, n-butoxy, tert-butoxy, sec-butoxy, n-pentoxy, n-hexoxy, and 1,2-dimethylbutoxy.

"Alkylene" (including those which are part of other groups) refers to branched and unbranched divalent "alkyl" groups. As used herein, alkylene has 1 to 20 carbon atoms (i.e., $C_{1-20}$ alkylene), 1 to 8 carbon atoms (i.e., $C_{1-8}$ alkylene), 1 to 6 carbon atoms (i.e., $C_{1-6}$ alkylene), or 1 to 4 carbon atoms (i.e., $C_{1-4}$ alkylene). Examples include: methylene, ethylene, propylene, 1-methylethylene, butylene, 1-methylpropylene, 1,1-dimethylethylene or 1,2-dimethylethylene. Unless stated otherwise, the definitions propylene and butylene include all the possible isomeric forms of the groups in question with the same number of carbons. Thus, for example, propyl also includes 1-methylethylene and butylene includes 1-methylpropylene, 1,1-dimethylethylene, and 1,2-dimethylethylene.

"Acyl" refers to a group refers to a group —$C(O)R^y$, wherein $R^y$ is hydrogen, alkyl, alkenyl, alkynyl, cycloalkyl, heterocyclyl, aryl, heteroalkyl or heteroaryl; each of which may be optionally substituted, as defined herein. Examples of acyl include, e.g., formyl, acetyl, cyclohexylcarbonyl, cyclohexylmethyl-carbonyl and benzoyl.

"Amido" refers to both a "C-amido" group which refers to the group —$C(O)NR^yR^z$ and an "N-amido" group which refers to the group —$NR^yC(O)R^z$, wherein $R^y$ and $R^z$ are independently selected from the group consisting of hydrogen, alkyl, aryl, haloalkyl, or heteroaryl; each of which may be optionally substituted.

"Amino" refers to the group —$NR^yR^z$ wherein $R^y$ and $R^z$ are independently selected from the group consisting of hydrogen, alkyl, haloalkyl, aryl, or heteroaryl; each of which may be optionally substituted.

"Amidino" refers to —$C(NH)(NH_2)$.

"Carbamoyl" refers to both an "O-carbamoyl" group which refers to the group —$O$—$C(O)NR^yR^z$ and an "N-carbamoyl" group which refers to the group —$NR^yC(O)OR^z$, wherein $R^y$ and $R^z$ are independently selected from the group consisting of hydrogen, alkyl, aryl, haloalkyl, or heteroaryl; each of which may be optionally substituted.

"Carboxyl" refers to —$C(O)OH$.

"Carboxyl ester" refers to both —$OC(O)R$ and —$C(O)OR$, wherein R is alkyl, cycloalkyl, heterocyclyl, aryl, heteroalkyl, or heteroaryl; each of which may be optionally substituted, as defined herein.

"Guanidino" refers to —$NHC(NH)(NH_2)$.

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —$S(O)_2$—, and the like, where R is H, alkyl, aryl, cycloalkyl, heteroalkyl, heteroaryl or heterocyclyl, each of which may be optionally substituted. Examples of heteroalkyl groups include —$OCH_3$, —$CH_2OCH_3$, —$SCH_3$, —$CH_2SCH_3$, —$NRCH_3$, and —$CH_2NRCH_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Alkylsulfonyl" refers to the group —$S(O)_2R$, where R is alkyl.

"Alkylsulfinyl" refers to the group —$S(O)R$, where R is alkyl.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl ring, the resulting ring system is heteroaryl.

"Azido" refers to the group —$N_3$.

"Cyano" or "carbonitrile" refers to the group —CN.

"Cycloalkyl" refers to a saturated or partially saturated cyclic alkyl group having a single ring or multiple rings including fused, bridged, and spiro ring systems. The term "cycloalkyl" includes cycloalkenyl groups (e.g., the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include, but are not limited to, cyclopropyl, cyclobutyl, cyclopentyl, and cyclohexyl. Cycloalkyl groups also include partially unsaturated ring systems containing one or more double bonds, including fused ring systems with one aromatic ring and one non-aromatic ring, but not fully aromatic ring systems.

"Bridged" refers to a ring fusion wherein non-adjacent atoms on a ring are joined by a divalent substituent, such as an alkylenyl or heteroalkylenyl group or a single heteroatom. Quinuclidinyl and admantanyl are examples of bridged ring systems.

The term "fused" refers to a ring which is bound to an adjacent ring.

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents.

"Halogen" or "halo" includes fluoro, chloro, bromo, and iodo.

"Haloalkyl" refers to an unbranched or branched alkyl group as defined above, wherein one or more hydrogen atoms, up to the total number of possible hydrogen atoms in a group, are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—CHF$_2$) and trifluoromethyl (—CF$_3$).

"Haloalkoxyl" or "haloalkoxy" refers to an alkoxy group as defined above, wherein one or more hydrogen atoms, up to the total number of possible hydrogen atoms in a group, are replaced by a halogen. Examples of haloalkoxyl include, but are not limited to, difluoromethoxyl (—OCHF$_2$), and trifluoromethoxyl (—OCF$_3$).

The term "heterocyclyl" or "heterocycle" as used herein refers to a single saturated or partially unsaturated non-aromatic ring or a non-aromatic multiple ring system that has at least one heteroatom in the ring, i.e., at least one annular heteroatom selected from oxygen, nitrogen, and sulfur, wherein the nitrogen or sulfur may be oxidized. Thus, the term includes rings having one or more annular O, N, S, S(O), S(O)$_2$, and N-oxide groups. The term includes rings having one or more annular C(O) groups. Unless otherwise specified, a heterocyclyl group has from 5 to about 20 annular atoms, for example from 3 to 12 annular atoms, for example from 3 to 10 annular atoms, for example from 5 to 10 annular atoms or for example from 5 to 6 annular atoms. Thus, the term includes single saturated or partially unsaturated rings (e.g., 3, 4, 5, 6 or 7-membered rings) having from about 1 to 6 annular carbon atoms and from about 1 to 3 annular heteroatoms independently selected from the group consisting of oxygen, nitrogen and sulfur in the ring. The rings of the multiple condensed ring (e.g., bicyclic heterocyclyl) system can be connected to each other via fused, spiro and bridged bonds when allowed by valency requirements. Heterocycles include, but are not limited to, groups derived from azetidine, aziridine, imidazolidine, morpholine, oxirane (epoxide), oxetane, piperazine, piperidine, pyrazolidine, pyrrolidine, pyrrolidinone, tetrahydrofuran, tetrahydrothiophene, dihydropyridine, tetrahydropyridine, tetrahydro-2H-thiopyran 1,1-dioxide, quinuclidine, N-bromopyrrolidine, N-chloropiperidine, and the like. Heterocycles include spirocycles, such as, for example, aza or oxo-spiroheptanes. Heterocyclyl groups also include partially unsaturated ring systems containing one or more double bonds, including fused ring systems with one aromatic ring and one non-aromatic ring, but not fully aromatic ring systems. Examples include dihydroquinolines, e.g., 3,4-dihydroquinoline, dihydroisoquinolines, e.g., 1,2-dihydroisoquinoline, dihydroimidazole, tetrahydroimidazole etc., indoline, isoindoline, isoindolones (e.g., isoindolin-1-one), isatin, dihydrophthalazine, quinolinone, spiro[cyclopropane-1,1'-isoindolin]-3'-one, and the like. Additional examples of heterocycles include 3,8-diazabicyclo[3.2.1] octanyl, 2,5-diazabicyclo[2.2.1]heptanyl, 3,6-diazabicyclo [3.1.1]heptanyl, 3-oxa-7,9-diazabicyclo[3.3.1]nonanyl, and hexahydropyrazino[2,1-c][1,4]oxazinyl, for example.

"Hydroxyl" and "hydroxy" are used interchangeably and refer to —OH.

"Oxo" refers to the group (═O) or (O). Where tautomeric forms of the compound exist, hydroxyl and oxo groups may be interchangeable.

"Heteroaryl" refers to an aromatic group, including groups having an aromatic tautomer or resonance structure, having a single ring, multiple rings, or multiple fused rings, with at least one heteroatom in the ring, i.e., one or more ring heteroatoms independently selected from nitrogen, oxygen, and sulfur, wherein the nitrogen or sulfur may be oxidized. Thus, the term includes rings having one or more annular O, N, S, S(O), S(O)$_2$, and N-oxide groups. The term includes rings having one or more annular C(O) groups. As used herein, heteroaryl include 5 to 20 ring atoms (i.e., 5-20 membered heteroaryl), 5 to 12 ring atoms (i.e., 5-12 membered heteroaryl), or 5 to 10 ring atoms (i.e., 5-10 membered heteroaryl), and 1 to 5 heteroatoms independently selected from nitrogen, oxygen, and sulfur, and oxidized forms of the heteroatoms. Examples of heteroaryl groups include pyridin-2(1H)-one, pyridazin-3(2H)-one, pyrimidin-4(3H)-one, quinolin-2(1H)-one, pyrimidinyl, purinyl, pyridyl, pyridazinyl, benzothiazolyl, and pyrazolyl. Heteroaryl does not encompass or overlap with aryl as defined above.

"Sulfonyl" refers to the group —S(O)$_2$R, where R is alkyl, haloalkyl, heterocyclyl, cycloalkyl, heteroaryl, or aryl. Examples of sulfonyl are methylsulfonyl, ethylsulfonyl, phenylsulfonyl, and toluenesulfonyl.

Whenever the graphical representation of a group terminates in a singly bonded nitrogen atom, that group represents an —NH group unless otherwise indicated. Similarly, unless otherwise expressed, hydrogen atom(s) are implied and deemed present where necessary in view of the knowledge of one of skill in the art to complete valency or provide stability.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g., arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted.

In some embodiments, the term "substituted alkyl" refers to an alkyl group having one or more substituents including hydroxyl, halo, alkoxy, cycloalkyl, heterocyclyl, aryl, and heteroaryl. In additional embodiments, "substituted cycloalkyl" refers to a cycloalkyl group having one or more substituents including alkyl, haloalkyl, cycloalkyl, heterocyclyl, aryl, heteroaryl, alkoxy, halo, oxo, and hydroxyl; "substituted heterocyclyl" refers to a heterocyclyl group having one or more substituents including alkyl, haloalkyl, heterocyclyl, cycloalkyl, aryl, heteroaryl, alkoxy, halo, oxo, and hydroxyl; "substituted aryl" refers to an aryl group having one or more substituents including halo, alkyl, haloalkyl, cycloalkyl, heterocyclyl, heteroaryl, alkoxy, and cyano; "substituted heteroaryl" refers to an heteroaryl group having one or more substituents including halo, alkyl, haloalkyl, heterocyclyl, heteroaryl, alkoxy, and cyano and "substituted sulfonyl" refers to a group —S(O)$_2$R, in which R is substituted with one or more substituents including alkyl, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

Some of the compounds exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes compounds in which from 1 to n hydrogens attached to a carbon atom is/are replaced by deuterium, in which n is the number of hydrogens in the molecule. Such compounds exhibit increased resistance to metabolism and are thus useful for increasing the half-life of any compound provided herein when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, mono, di or tri cycloalkyl amines, mono, di or tri arylamines or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Provided are also compounds described herein or pharmaceutically acceptable salts, isomer, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts.

A "solvate" is formed by the interaction of a solvent and a compound. Solvates of salts of the compounds described herein are also provided. Hydrates of the compounds described herein are also provided.

A "prodrug" is a biologically inactive derivative of a drug that upon administration to the human body is converted to the biologically active parent drug according to some chemical or enzymatic pathway.

In some embodiments, provided are optical isomers, racemates, or other mixtures thereof of the compounds described herein or pharmaceutically acceptable salts or a mixture thereof. In those situations, the single enantiomer or diastereomer, i.e., optically active form, can be obtained by asymmetric synthesis or by resolution of the racemate. Resolution of racemates can be accomplished, for example, by conventional methods such as crystallization in the presence of a resolving agent, or chromatography, using, for example a chiral high pressure liquid chromatography (HPLC) column. In addition, provided are also Z- and E-forms (or cis- and trans-forms) of the hydroxyamidine compounds described herein. Specifically, Z- and E-forms are included even if only one designation is named for both carbon-carbon double bonds as well as the hydroxyamidine bond.

Where chirality is not specified but is present, it is understood that the embodiment is directed to either the specific diastereomerically or enantiomerically enriched form; or a racemic or scalemic mixture of such compound(s).

"Enantiomers" are a pair of stereoisomers that are non-superimposable mirror images of each other. A 1:1 mixture of a pair of enantiomers is a "racemic" mixture. A mixture of enantiomers at a ratio other than 1:1 is a "scalemic" mixture.

"Diastereoisomers" are stereoisomers that have at least two asymmetric atoms, but which are not mirror-images of each other.

"Atropisomers" are stereoisomers arising due to hindered rotation about a single bond, where the barrier to rotation about the bond is high enough to allow for isolation of individual stereoisomers.

Compositions provided herein that include a compound described herein or pharmaceutically acceptable salts, isomer, or a mixture thereof may include racemic mixtures, or mixtures containing an enantiomeric excess of one enantiomer or single diastereomers or diastereomeric mixtures. All such isomeric forms of these compounds are expressly included herein the same as if each and every isomeric form were specifically and individually listed.

In some embodiments, provided are also chelates, non-covalent complexes, and mixtures thereof, of the compounds described herein or pharmaceutically acceptable salts, isomer, or a mixture thereof. A "chelate" is formed by the coordination of a compound to a metal ion at two (or more) points. A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding).

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, "unit and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival).

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In some embodiments, the subject is a human.

The term "therapeutically effective amount" or "effective amount" of a compound described herein or pharmaceutically acceptable salts, isomer, or a mixture thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of α4β7 integrin activity. The therapeutically effective amount may vary depending on the subject, and disease or condition being treated, the weight and age of the subject, the severity of the disease or condition, and the manner of administering, which can readily be determined by one or ordinary skill in the art.

The term "inhibition" indicates a decrease in the baseline activity of a biological activity or process. "Inhibition of activity of α4β7 integrin" or variants thereof refers to a decrease in activity of α4β7 integrin as a direct or indirect response to the presence of a compound of the present application relative to the activity of α4β7 integrin in the absence of the compound of the present application. "Inhibition of α4β7 integrin" refers to a decrease in α4β7 integrin activity as a direct or indirect response to the presence of a compound described herein relative to the activity of α4β7 integrin in the absence of the compound described herein. In some embodiments, the inhibition of α4β7 integrin activity may be compared in the same subject prior to treatment, or other subjects not receiving the treatment.

Compounds

Provided herein are compounds that function as inhibitors of α4β7 integrin. In some embodiments, provided is a compound of formula (I):

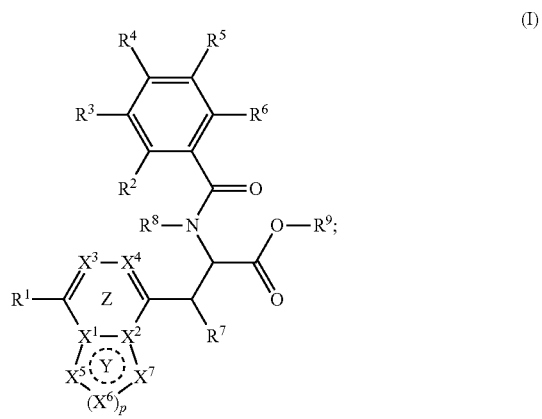

or a pharmaceutically acceptable salt thereof, wherein:
$X^1$ and $X^2$ are each independently selected from C, and N; wherein the bond between $X^1$ and $X^2$ is a single or a double bond;
$X^3$ and $X^4$ are each independently selected from $CR^{10}$, and N;
$X^5$ and $X^7$ are each independently selected from $CR^{10}R^{10}$, $CR^{10}$, S, S(O), S(O)$_2$, N, $NR^{11}$, C(O), and O;
each $X^6$ is independently selected from $CR^{10}R^{10}$, $CR^{10}$, S, S(O), S(O)$_2$, N, $NR^{11}$, C(O), and O; wherein the bond between $X^5$ and $X^6$, $X^6$ and $X^6$, or $X^6$ and $X^7$ is a single or a double, provided that at least one is a double bond;
$R^1$ is selected from -L-$A^1$, -L-$A^2$, -L-$A^3$, and -L-$A^4$;
L is selected from a bond, —O—, —O—C(O)—*, —NH—, —C(O)—N(H)—*, and —N(H)—C(O)—*; wherein * indicates a point of attachment of L to $A^1$, $A^2$, $A^3$, or $A^4$;
$A^1$ is $C_{6-10}$aryl optionally substituted with one to six $R^a$;
$A^2$ is 5-10 membered heteroaryl containing one to five heteroatoms independently selected from S, N, and O, and optionally one or two C(O); wherein $A^2$ is optionally substituted with one to six $R^a$;
$A^3$ is 5-10 membered cycloalkyl or 5-14 membered heterocyclyl; wherein $A^3$ is optionally substituted with one to six $R^a$; and
$A^4$ is —$NR^{a1}R^{a2}$;
wherein each $R^a$ is independently selected from halo, cyano, hydroxyl, —$NR^{a1}R^{a2}$, $C_{1-6}$alkyl, $C_{2-6}$alkenyl, $C_{2-6}$alkynyl, $C_{1-6}$alkoxyl, $C_{1-6}$haloalkyl, $C_{1-6}$haloalkoxyl, —S(O)$_m$—$C_{1-6}$alkyl, $C_{3-8}$cycloalkyl, 3-6 membered heterocyclyl, $C_{6-10}$aryl, 5-6 membered heteroaryl, —O-(3-6 membered heterocyclyl), —O—$C_{1-4}$alkylene-$C_{3-8}$cycloalkyl, —O-phenyl, and —O—$C_{3-8}$cycloalkyl;
each $C_{1-6}$alkyl, $C_{2-6}$alkenyl, $C_{2-6}$alkynyl, $C_{1-6}$alkoxyl, $C_{1-6}$haloalkyl, $C_{1-6}$haloalkoxyl, and —S(O)$_m$—$C_{1-6}$alkyl of $R^a$ are optionally substituted with one to three $R^{a3}$; wherein each $R^{a3}$ is independently selected from hydroxyl, cyano, —$NR^{a1}R^{a2}$, $C_{1-6}$alkoxyl, $C_{3-8}$cycloalkyl, phenyl, and 3-6 membered heterocyclyl; wherein each $C_{3-8}$cycloalkyl, phenyl, and 3-6 membered heterocyclyl of $R^{a3}$ is independently optionally substituted with one to three $R^{a4}$; wherein each $R^{a4}$ is independently selected from halo, cyano, hydroxyl, —$NR^{a1}R^{a2}$, $C_{1-6}$alkyl, $C_{1-6}$haloalkyl, $C_{1-6}$alkoxyl, $C_{1-6}$haloalkoxyl, $C_{3-8}$cycloalkyl, and 3-6 membered heterocyclyl; and each $C_{3-8}$cycloalkyl, 3-6 membered heteroaryl, $C_{6-10}$aryl, 5-6 membered heterocyclyl, —O—(3-6 membered heterocyclyl), —O—$C_{1-4}$alkylene-$C_{3-8}$cycloalkyl, —O— phenyl, and —O—$C_{3-8}$cycloalkyl of $R^a$ is independently optionally substituted with one to three groups independently selected from halo, cyano, hydroxyl, —$NR^{a1}R^{a2}$, $C_{1-6}$alkyl, $C_{1-6}$haloalkyl, $C_{1-6}$alkoxyl, and $C_{1-6}$haloalkoxyl;

each $R^2$, $R^3$, $R^4$, $R^5$, and $R^6$ is independently selected from H, halo, cyano, hydroxyl, $C_{1-6}$alkyl, $C_{2-6}$alkenyl, $C_{2-6}$alkynyl, $C_{1-6}$alkoxyl, $C_{1-8}$haloalkyl, $C_{1-8}$haloalkoxyl, —$NR^{b1}R^{b2}$, —$R^{b3}S(O)_mR^{b4}$, —$S(O)_mR^{b4}$, —$NR^{b1}S(O)_xR^{b4}$, —$COOR^{b1}$, —$CONR^{b1}R^{b2}$, —$NR^{b1}COOR^{b2}$, —$NR^{b1}COR^{b4}$, —$R^{b3}NR^{b1}R^{b2}$, —$S(O)_xNR^{b1}R^{b2}$, $C_{3-12}$cycloalkyl, $C_{6-10}$aryl, 5-6 membered heteroaryl, and 3-12 membered heterocyclyl;

each $C_{1-6}$alkyl, $C_{2-6}$alkenyl, $C_{2-6}$alkynyl, $C_{1-6}$alkoxyl, $C_{1-8}$haloalkyl, and $C_{1-8}$haloalkoxyl of $R^2$, $R^3$, $R^4$, $R^5$, and $R^6$ is independently optionally substituted with one to two $R^c$; wherein each $R^c$ is independently selected from azido, oxo, cyano, halo, hydroxyl, —$NR^{a1}R^{a2}$, $C_{1-4}$alkoxyl, $C_{3-8}$cycloalkyl, $C_{6-10}$aryl, 5-6 membered heteroaryl, and 4-6 membered heterocyclyl; wherein each $C_{3-8}$cycloalkyl, $C_{6-10}$aryl, 5-6 membered heteroaryl, and 4-6 membered heterocyclyl of $R^c$ is independently optionally substituted with one to three groups independently selected from halo, hydroxyl, cyano, —$NR^{a1}R^{a2}$, $C_{1-4}$alkyl, $C_{1-6}$haloalkyl, $C_{1-4}$alkoxyl, and $C_{3-6}$cycloalkyl;

each $C_{6-10}$aryl and 5-6 membered heteroaryl of $R^2$, $R^3$, $R^4$, $R^5$, and $R^6$ is independently optionally substituted with one to five $R^b$; and each $C_{3-12}$cycloalkyl and 3-12 membered heterocyclyl of $R^2$, $R^3$, $R^4$, $R^5$, and $R^6$ is independently optionally substituted with one to six groups independently selected from =$CR^{b1}R^{b2}$, and $R^b$;

wherein each $R^b$ is independently selected from azido, cyano, halo, hydroxyl, —$NR^{a1}R^{a2}$, $C_{1-6}$alkyl, $C_{1-8}$haloalkyl, $C_{1-6}$alkoxyl, $C_{3-6}$cycloalkyl, $C_{6-10}$aryl, 5-6 membered heteroaryl, and 4-6 membered heterocycly; wherein each $C_{3-6}$cycloalkyl, $C_{6-10}$aryl, 5-6 membered heteroaryl, and 4-6 membered heterocyclyl of $R^b$ is independently optionally substituted with one to three groups independently selected from halo, hydroxyl, cyano, —$NR^{a1}R^{a2}$, $C_{1-4}$alkyl, $C_{1-4}$haloalkyl, and $C_{1-4}$alkoxyl;

each $R^{b1}$ and $R^{b2}$ is independently selected from H, $C_{1-8}$alkyl, $C_{1-8}$haloalkyl, $C_{3-8}$cycloalkyl, $C_{6-10}$aryl, 5-6 membered heteroaryl, and 3-8 membered heterocyclyl;

each $C_{6-10}$alkyl and $C_{1-6}$haloalkyl of $R^{b1}$ and $R^{b2}$ is optionally substituted with one to two $R^{b5}$; and each $C_{3-8}$cycloalkyl, $C_{6-10}$aryl, 5-6 membered heteroaryl, and 3-8 membered heterocyclyl of $R^{b1}$ and $R^{b2}$ is independently optionally substituted with one to three groups independently selected from halo, cyano, hydroxyl, —$NR^{a1}R^{a2}$, $C_{1-8}$alkyl, $C_{1-8}$haloalkyl, $C_{1-6}$alkoxyl, $C_{3-6}$cycloalkyl, $C_{6-10}$aryl, 5-6 membered heteroaryl, and 4-6 membered heterocyclyl;

$R^{b3}$ is $C_{1-4}$alkylene;

$R^{b4}$ is selected from $C_{1-4}$alkyl, $C_{1-4}$haloalkyl, $C_{3-6}$cycloalkyl, $C_{6-10}$aryl, 5-6 membered heteroaryl, and 4-6 membered heterocyclyl; wherein each $C_{1-4}$alkyl, $C_{1-4}$haloalkyl, $C_{3-8}$cycloalkyl, $C_{6-10}$aryl, 5-6 membered heteroaryl, and the 4-6 membered heterocyclyl of $R^{b4}$ is optionally substituted with one to three $R^{b6}$;

each $R^{b5}$ is independently selected from cyano, hydroxyl, $C_{1-4}$alkoxyl, $C_{3-8}$cycloalkyl, $C_{6-10}$aryl, 5-6 membered heteroaryl, and 4-6 membered heterocyclyl; wherein each $C_{3-8}$cycloalkyl, $C_{6-10}$aryl, 5-6 membered heteroaryl, and 4-6 membered heterocyclyl of $R^{b5}$ is optionally substituted with one to three groups independently selected from halo, cyano, hydroxyl, —$NR^{a1}R^{a2}$, $C_{1-4}$alkyl, $C_{1-4}$haloalkyl, $C_{1-4}$alkoxyl, and phenyl; and each $R^{b6}$ is independently selected from halo, cyano, $C_{1-4}$alkyl, $C_{1-4}$haloalkyl, $C_{1-4}$alkoxyl, $C_{3-6}$cycloalkyl, phenyl, 4-6 membered heterocyclyl, and 5-6 membered heteroaryl; wherein each $C_{3-6}$cycloalkyl, 4-6 membered heterocyclyl, and 5-6 membered heteroaryl of $R^{b6}$ is independently optionally substituted with one to three groups independently selected from halo, cyano, —$NR^{a1}R^{a2}$, $C_{1-4}$alkyl, $C_{1-4}$haloalkyl, and $C_{1-4}$alkoxyl;

or $R^2$ and $R^3$, $R^3$ and $R^4$, or $R^5$ and $R^6$ together with the atoms to which they are attached may form a $C_{6-10}$aryl, 5-6 membered heteroaryl, $C_{3-6}$cycloalkyl, or 5-6 membered heterocyclyl; wherein each $C_{6-10}$aryl, 5-6 membered heteroaryl, $C_{3-6}$cycloalkyl, or 5-6 membered heterocyclyl is optionally substituted with one to three groups independently selected from halo, cyano, —$NR^{a1}R^{a2}$, $C_{1-6}$alkyl, $C_{1-6}$alkoxyl, $C_{1-6}$haloalkyl, $C_{3-8}$cycloalkyl, 3-6 membered heterocyclyl, $C_{6-10}$aryl, 5-6 membered heteroaryl, $C_{1-4}$alkylene-$C_{3-8}$cycloalkyl, $C_{1-4}$alkylene-$C_{6-10}$aryl, and $C_{1-4}$alkylene-(5-6 membered heteroaryl);

$R^7$ is selected from H, $C_{1-4}$alkyl, and $C_{1-4}$haloalkyl;

$R^8$ is selected from H, $C_{1-4}$alkyl, and $C_{1-4}$haloalkyl;

$R^9$ is selected from H, $C_{1-6}$alkyl, —$C_{1-4}$alkylene-$NR^{a1}R^{a2}$, —$C_{1-4}$alkylene-$C(O)NR^{a1}R^{a2}$, —$C_{1-4}$alkylene-O—C(O)—$C_{1-4}$alkyl, —$C_{1-4}$alkylene-O—C(O)—O—$C_{1-4}$alkyl, —$C_{1-4}$alkylene-O—C(O)—$C_{1-4}$alkylene-$NR^{a1}R^{a2}$, —$C_{1-4}$alkylene-O—$C_{1-4}$alkyl, $C_{3-8}$cycloalkyl, —$C_{1-4}$alkylene-$C_{3-8}$cycloalkyl, 4-6 membered heterocyclyl, and —$C_{1-4}$alkylene-(4-6 membered heterocyclyl);

wherein each $C_{3-8}$cycloalkyl, —$C_{1-4}$alkylene-$C_{3-8}$cycloalkyl, and 4-6 membered heterocyclyl of $R^9$ is optionally substituted with one to three groups independently selected from halo, $C_{1-4}$alkyl, $C_{1-4}$alkoxyl, and $C_{1-4}$haloalkyl; or $R^9$ together with the N that attaches to $R^8$ forms a 5 membered heterocyclyl; wherein the 5 membered heterocyclyl is optionally substituted with one to two groups independently selected from halo, $C_{1-6}$alkyl, $C_{1-6}$alkoxyl, $C_{1-6}$haloalkyl, and $C_{6-10}$aryl; wherein $C_{6-10}$aryl is optionally substituted with one to three groups independently selected from halo, $C_{1-6}$alkyl, $C_{1-6}$alkoxyl, and $C_{1-6}$haloalkyl;

each $R^{10}$ is independently selected from H, halo, cyano, hydroxyl, —$C(O)R^{b1}$, —$NR^{a1}R^{a2}$, $C_{1-4}$alkyl, $C_{1-4}$alkoxyl, $C_{1-4}$haloalkyl, $C_{1-4}$haloalkoxyl, $C_{3-10}$cycloalkyl, 3-8 membered heterocyclyl, $C_{6-10}$aryl, and 5-6 membered heteroaryl; wherein each $C_{1-4}$alkyl, $C_{1-4}$alkoxyl, $C_{1-4}$haloalkyl, $C_{1-4}$haloalkoxyl, $C_{3-10}$cycloalkyl, 3-8-membered heterocyclyl, $C_{6-10}$aryl, and 5-6 membered heteroaryl is independently optionally substituted with one to three groups independently selected from halo, hydroxyl, cyano, —$NR^{a1}R^{a2}$, $C_{1-4}$alkyl, $C_{1-4}$haloalkyl, $C_{1-4}$alkoxyl, and $C_{3-6}$cycloalkyl;

or two $R^{10}$ either attached to the same or adjacent atoms form $C_{3-12}$cycloalkyl or 3-10 membered heterocyclyl; wherein each $C_{3-12}$cycloalkyl and 3-10 membered heterocyclyl is optionally substituted with one to three groups independently selected from H, halo, $C_{1-4}$alkyl, $C_{1-4}$alkoxyl, $C_{1-4}$haloalkyl, and $C_{1-4}$haloalkoxyl;

each $R^{11}$ is independently selected from H, $C_{1-4}$alkyl, and $C_{1-4}$haloalkyl; wherein each $C_{1-4}$alkyl, —C(O)$R^{b1}$, and $C_{1-4}$haloalkyl of $R^{11}$ is independently optionally substituted with one to three groups independently selected from halo, hydroxyl, cyano, —NR$^{a1}$R$^{a2}$, $C_{1-4}$alkyl, $C_{1-4}$haloalkyl, $C_{1-4}$alkoxyl, and $C_{3-6}$cycloalkyl;

or $R^{10}$ and $R^{11}$, or two $R^{11}$ together with the atoms to which they are attached to form 3-12 membered heterocyclyl; wherein 3-12 membered heterocyclyl is optionally substituted with one to three groups independently selected from H, halo, $C_{1-4}$alkyl, $C_{1-4}$alkoxyl, $C_{1-4}$haloalkyl, and $C_{1-4}$haloalkoxyl;

each $R^{a1}$ and $R^{a2}$ is independently selected from H, $C_{1-6}$alkyl, and $C_{1-6}$haloalkyl;

p is selected from 1, 2, and 3;

m is selected from 0, 1, and 2; and v is selected from 1 and 2.

In some embodiments, provided is a compound of formula (I), or a pharmaceutically acceptable salt thereof, wherein:

$X^1$ and $X^2$ are each independently selected from C, and N; wherein the bond between $X^1$ and $X^2$ is a single or a double bond;

$X^3$ and $X^4$ are each independently selected from CR$^{10}$, and N;

$X^5$ and $X^7$ are each independently selected from CR$^{10}$R$^{10}$, CR$^{10}$, S, S(O), S(O)$_2$, N, NR$^{11}$, C(O), and O;

each $X^6$ is independently selected from CR$^{10}$R$^{10}$, CR$^{10}$, S, S(O), S(O)$_2$, N, NR$^{11}$, C(O), and O; wherein the bond between $X^5$ and $X^6$, $X^6$ and $X^6$, or $X^6$ and $X^7$ is a single or a double, provided that at least one is a double bond;

$R^1$ is selected from $A^1$, $A^2$, and $A^3$;

$A^1$ is $C_{6-10}$aryl optionally substituted with one to six $R^a$;

$A^2$ is 5-10 membered heteroaryl containing one to five heteroatoms independently selected from S, N, and O, and optionally one or two C(O); wherein $A^2$ is optionally substituted with one to six $R^a$; and $A^3$ is 5-10 membered cycloalkyl or 5-14 membered heterocyclyl; wherein $A^3$ is optionally substituted with one to four $R^a$;

wherein each $R^a$ is independently selected from halo, cyano, hydroxyl, $C_{1-6}$alkyl, $C_{2-6}$alkenyl, $C_{2-6}$alkynyl, $C_{1-6}$alkoxyl, $C_{1-6}$haloalkyl, $C_{1-6}$haloalkoxyl, $C_{3-8}$cycloalkyl, and —O—$C_{3-8}$cycloalkyl;

each $C_{1-6}$alkyl, $C_{2-6}$alkenyl, $C_{2-6}$alkynyl, $C_{1-6}$alkoxyl, $C_{1-6}$haloalkyl, $C_{1-6}$haloalkoxyl, $C_{3-8}$cycloalkyl, and —O—$C_{3-8}$cycloalkyl of $R^a$ is optionally substituted with one to three $R^{a3}$; wherein each $R^{a3}$ is independently selected from hydroxyl, $C_{1-6}$alkoxyl, $C_{1-6}$haloalkyl, and $C_{1-6}$haloalkoxyl;

each $R^2$ and $R^6$ is independently selected from H, halo, $C_{1-6}$alkyl, and $C_{1-6}$haloalkyl;

each $R^3$ and $R^5$ is H;

$R^4$ is selected from H, halo, $C_{1-6}$alkyl, $C_{1-6}$alkoxyl, $C_{1-6}$haloalkyl, $C_{1-6}$haloalkoxyl, —NR$^{b1}$R$^{b2}$, —R$^{b3}$S(O)$_m$R$^{b4}$, —S(O)$_m$R$^{b4}$, —NR$^{b1}$S(O)$_v$R$^{b4}$, —COOR$^{b1}$, —CONR$^{b1}$R$^{b2}$, —NR$^{b1}$COOR$^{b2}$—NR$^{b1}$COR$^{b4}$, —R$^{b3}$NR$^{b1}$R$^{b2}$, —S(O)$_v$NR$^{b1}$R$^{b2}$, $C_{6-10}$aryl, $C_{3-10}$cycloalkyl, 5-6 membered heteroaryl, and 4-10 membered heterocyclyl;

each $C_{1-6}$alkyl, $C_{1-6}$haloalkyl, $C_{1-6}$alkoxyl, and $C_{1-6}$haloalkoxyl of $R^4$ is independently optionally substituted with one to two $R^c$; wherein each $R^c$ is independently selected from cyano, azido, oxo, hydroxyl, —NR$^{a1}$R$^{a2}$, $C_{1-4}$alkoxyl, $C_{3-6}$cycloalkyl, and 4-6 membered heterocyclyl; and wherein each $C_{3-6}$cycloalkyl, and 4-6 membered heterocyclyl of $R^c$ is independently optionally substituted with one to three groups independently selected from halo, hydroxyl, cyano, —NR$^{a1}$R$^{a2}$, $C_{1-4}$alkyl, $C_{1-4}$haloalkyl, $C_{1-4}$alkoxyl, and $C_{3-6}$cycloalkyl;

each $C_{6-10}$aryl, $C_{3-10}$cycloalkyl, 5-6 membered heteroaryl, and 4-10 membered heterocyclyl of $R^4$ is independently optionally substituted with one to three $R^b$; wherein each $R^b$ is independently selected from halo, hydroxyl, cyano, —NR$^{a1}$R$^{a2}$, $C_{1-6}$alkyl, $C_{1-6}$haloalkyl, $C_{1-6}$alkoxyl, $C_{3-6}$cycloalkyl, phenyl, and 4-6 membered heterocyclyl; wherein each $C_{3-6}$cycloalkyl, phenyl, and 4-6 membered heterocyclyl of $R^b$ is optionally substituted with one to two groups independently selected from halo, hydroxyl, cyano, —NR$^{a1}$R$^{a2}$, $C_{1-4}$alkyl, $C_{1-4}$haloalkyl, and $C_{1-4}$alkoxyl;

each $R^{b1}$ and $R^{b2}$ is independently selected from H, $C_{1-8}$alkyl, $C_{1-8}$haloalkyl, $C_{3-6}$cycloalkyl, phenyl, and 4-6 membered heterocyclyl;

each $C_{1-8}$alkyl and $C_{1-6}$haloalkyl of $R^{b1}$ and $R^{b2}$ is independently optionally substituted with one to two $R^{b5}$; wherein each $R^{b5}$ is independently selected from hydroxyl, $C_{1-4}$alkoxyl, $C_{3-6}$cycloalkyl, phenyl, and 4-6 membered heterocyclyl; wherein each $C_{3-6}$cycloalkyl, phenyl, and 4-6 membered heterocyclyl of $R^{b5}$ is optionally substituted with one to three groups independently selected from halo, cyano, hydroxyl, —NR$^{a1}$R$^{a2}$, $C_{1-4}$alkyl, $C_{1-4}$haloalkyl, $C_{1-4}$alkoxyl, and phenyl; and each $C_{3-6}$cycloalkyl, phenyl, and 4-6 membered heterocyclyl of $R^{b1}$ and $R^{b2}$ is independently optionally substituted with one to three groups independently selected from halo, hydroxyl, cyano, —NR$^{a1}$R$^{a2}$, $C_{1-6}$alkyl, $C_{1-6}$haloalkyl, $C_{1-6}$alkoxyl, $C_{3-6}$cycloalkyl, phenyl, and 4-6 membered heterocyclyl;

$R^{b3}$ is $C_{1-4}$alkylene;

$R^{b4}$ is selected from $C_{1-4}$alkyl, $C_{1-4}$haloalkyl, $C_{3-6}$cycloalkyl, phenyl, and 4-6 membered heterocyclyl; wherein each $C_{3-6}$cycloalkyl, phenyl, and 4-6 membered heterocyclyl of $R^{b4}$ is optionally substituted with one to three $R^{b6}$; wherein each $R^{b6}$ is independently 4-6 membered heterocyclyl, and 5-6 membered heteroaryl; and wherein each $C_{3-6}$cycloalkyl, 4-6 membered heterocyclyl, and 5-6 membered heteroaryl of $R^{b6}$ is independently optionally substituted with one to three groups independently selected from halo, cyano, —NR$^{a1}$R$^{a2}$, $C_{1-4}$alkyl, $C_{1-4}$haloalkyl, and $C_{1-4}$alkoxyl;

each $R^{a1}$ and $R^{a2}$ is independently selected from H, $C_{1-6}$alkyl, and $C_{1-6}$haloalkyl;

$R^7$ is H;

$R^8$ is H;

$R^9$ is H;

each $R^{10}$ is independently selected from H, halo, $C_{1-4}$alkyl, $C_{1-4}$alkoxyl, $C_{1-4}$haloalkyl, and $C_{1-4}$haloalkoxyl;

or two $R^{10}$ either attached to the same or adjacent atoms form a $C_{3-10}$cycloalkyl; and each $R^{11}$ is independently selected from H, —C(O)$R^{b1}$, $C_{1-4}$alkyl, and $C_{1-4}$haloalkyl, wherein each $C_{1-4}$alkyl and $C_{1-4}$haloalkyl, is independently optionally substituted with one to three groups independently selected from halo, hydroxyl, $C_{1-4}$alkyl, $C_{1-4}$haloalkyl, $C_{1-4}$alkoxyl, and $C_{3-6}$cycloalkyl;

p is selected from 1 and 2;

m is selected from 0, 1, and 2;

v is selected from 1 and 2.

In some embodiments, provided is a compound of formula (I), or a pharmaceutically acceptable salt, $R^4$ is selected from H, $-NR^{b1}R^{b2}$, $-NR^{b1}S(O)_rR^{b4}$, and 4-10 membered heterocyclyl containing one to two heteroatoms independently selected from N and O;

the 4-10 membered heterocyclyl of $R^4$ is independently optionally substituted with one to three $R^b$; each $R^b$ is independently selected from halo, $C_{1-6}$alkyl, and $C_{1-8}$haloalkyl;

each of $R^{b1}$ and $R^{b2}$ is independently selected from H, $C_{1-8}$alkyl, and $C_{1-8}$haloalkyl;

each of the $C_{1-8}$alkyl and $C_{1-6}$haloalkyl of $R^{b1}$ and $R^{b2}$ is optionally substituted with one to two $R^{b5}$; each $R^{b5}$ is independently selected from $C_{1-4}$alkoxyl, $C_{3-6}$cycloalkyl, phenyl, and 4-6 membered heterocyclyl; and each the $C_{3-6}$cycloalkyl, phenyl, and 4-6 membered heterocyclyl of $R^{b5}$ is optionally substituted with one to three groups independently selected from halo, $C_{1-4}$alkyl, and $C_{1-4}$haloalkyl;

$R^{b4}$ is selected from $C_{1-4}$alkyl, $C_{1-4}$haloalkyl, $C_{3-6}$cycloalkyl, and phenyl; each the $C_{3-6}$cycloalkyl and phenyl of $R^{b4}$ is optionally substituted with one to three $R^{b6}$; each $R^{b6}$ is independently selected from halo, $C_{1-4}$alkyl, $C_{1-4}$haloalkyl, and 5-6 membered heteroaryl; and the 5-6 membered heteroaryl of $R^{b6}$ is independently optionally substituted with one to three groups independently selected from halo, $C_{1-4}$alkyl, and $C_{1-4}$haloalkyl.

In some embodiments, the ring formed by Y and Z does not form

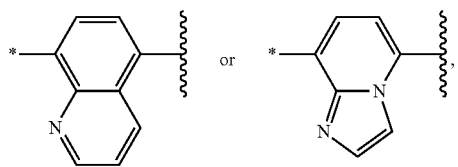 [SMILES: *c1ccc(*)c2ncccc12 ; *c1ccc(*)n2ccnc12]

wherein * indicates a point of attachment to $R^1$.

In some embodiments, ring Y is aromatic.

In some embodiments, the ring formed by Y and Z is selected from:

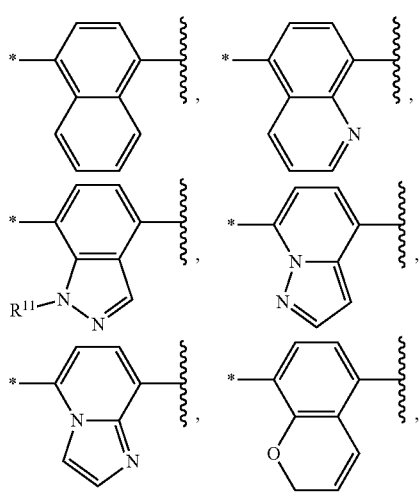

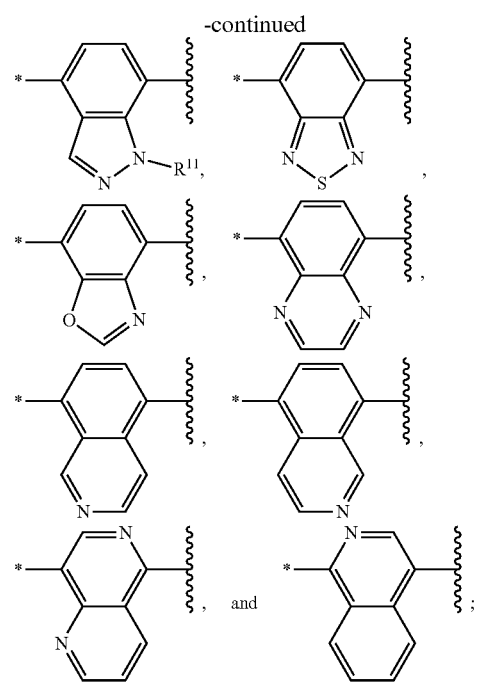

wherein * indicates a point of attachment to $R^1$; wherein each group is optionally substituted with 1 to 4 $R^{10}$; and wherein each $R^{10}$ is independently selected from halo, cyano, hydroxyl, $C_{1-4}$alkyl, $C_{1-4}$alkoxyl, $C_{1-4}$haloalkyl, $C_{1-4}$haloalkoxyl, $C_{3-10}$cycloalkyl, 3-8 membered heterocyclyl, $C_{6-10}$aryl, 5-6 membered heteroaryl, and $-NR^{a1}R^{a2}$; wherein each $C_{1-4}$alkyl, $C_{1-4}$alkoxyl, $C_{1-4}$haloalkyl, $C_{1-4}$haloalkoxyl, $C_{3-10}$cycloalkyl, 3-8 membered heterocyclyl, $C_{6-10}$aryl, 5-6 membered heteroaryl is independently optionally substituted with one to three groups independently selected from halo, hydroxyl, cyano, $-NR^{a1}R^{a2}$, $C_{1-4}$alkyl, $C_{1-4}$haloalkyl, $C_{1-4}$alkoxyl, and $C_{3-6}$cycloalkyl.

Also provided are compounds of formula (Ia):

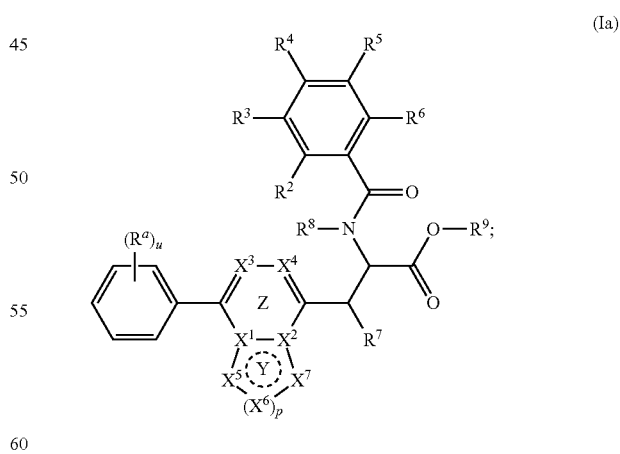

or a pharmaceutically acceptable salt thereof; wherein u is selected from 0, 1, 2, 3, 4, and 5. Y, Z, X, $X^2$, $X^3$, $X^4$, $X^5$, $X^6$, $X^7$, p, $R^a$, $R^2$, $R^3$, $R^4$, $R^5$, $R^6$, $R^7$, $R^8$, and $R^9$ are as defined above.

Also provided are compounds of formula (Ib):

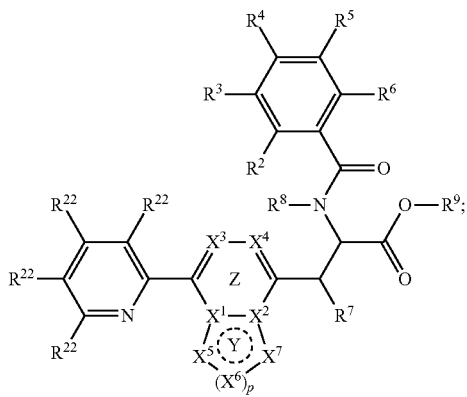

(Ib)

or a pharmaceutically acceptable salt; thereof; wherein each $R^{22}$ is independently selected from H and $R^a$. Y, Z, $X^1$, $X^2$, $X^3$, $X^4$, $X^5$, $X^6$, $X^7$, p, $R^a$, $R^2$, $R^3$, $R^4$, $R^5$, $R^6$, $R^7$, $R^8$, and $R^9$ are as defined above.

Also provided are compounds of formula (Ic):

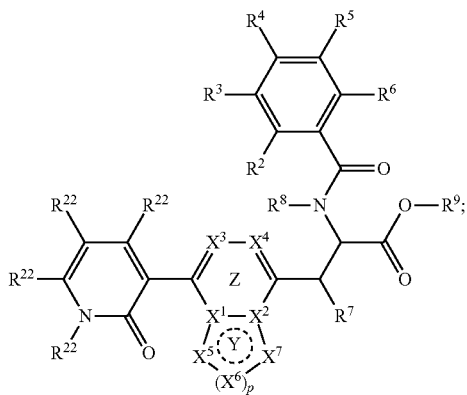

(Ic)

or a pharmaceutically acceptable salt thereof; wherein each $R^{22}$ is independently selected from H and $R^a$. Y, Z, $X^1$, $X^2$, $X^3$, $X^4$, $X^5$, $X^6$, $X^7$, p, $R^a$, $R^2$, $R^3$, $R^4$, $R^5$, $R^6$, $R^7$, $R^8$, and $R^9$ are as defined above.

Also provided are compounds of formula (Id)

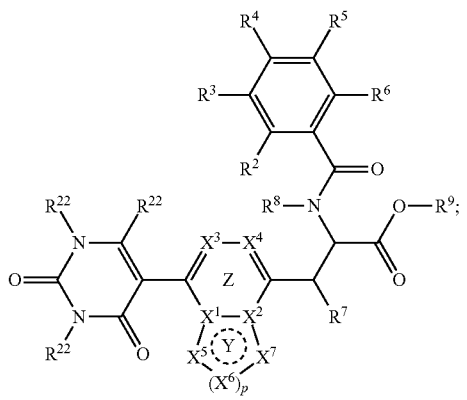

(Id)

or a pharmaceutically acceptable salt thereof; wherein each $R^{22}$ is independently selected from H and $R^a$. Y, Z, $X^1$, $X^2$, $X^3$, $X^4$, $X^5$, $X^6$, $X^7$, p, $R^a$, $R^2$, $R^3$, $R^4$, $R^5$, $R^6$, $R^7$, $R^8$, and $R^9$ are as defined above.

Also provided are compounds of formula (Ie):

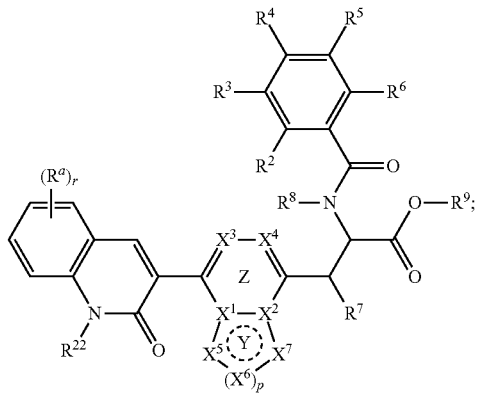

(Ie)

or a pharmaceutically acceptable salt thereof; wherein each $R^{22}$ is independently selected from H and $R^a$; and wherein r is selected from 0, 1, 2, 3, 4 and 5. Y, Z, $X^1$, $X^2$, $X^3$, $X^4$, $X^5$, $X^6$, $X^7$, p, $R^a$, $R^2$, $R^3$, $R^4$, $R^5$, $R^6$, $R^7$, $R^8$, and $R^9$ are as defined above.

Also provided are compounds of formula (If):

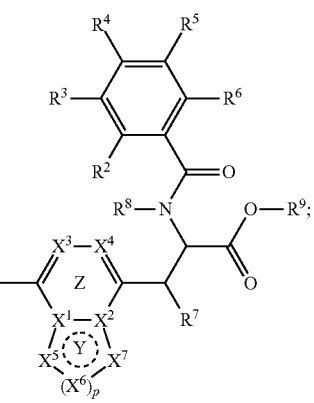

(If)

or a pharmaceutically acceptable salt thereof; wherein each $Y^1$, $Y^2$, $Y^3$, $Y^4$, and $Y^5$ is independently selected from $CR^{22}$ and N, provided that at least one of $Y^1$, $Y^2$, $Y^3$, $Y^4$, and $Y^5$ is $CR^{22}$; and wherein $R^{22}$ is selected from H and $R^a$. Y, Z, $X^1$, $X^2$, $X^3$, $X^4$, $X^5$, $X^6$, $X^7$, p, $R^a$, $R^2$, $R^3$, $R^4$, $R^5$, $R^6$, $R^7$, $R^8$, and $R^9$ are as defined above.

Also provided are compounds of formula (Ig):

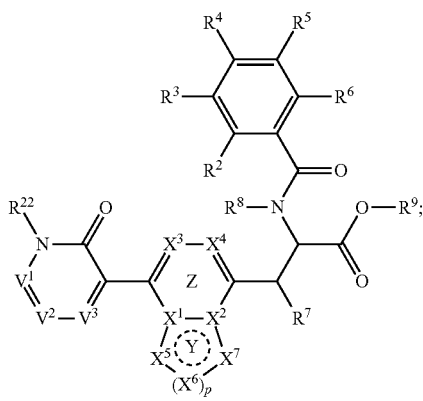

(Ig)

or a pharmaceutically acceptable salt thereof; each $V^1$, $V^2$, and $V^3$ is independently selected from $CR^{22}$ and N, provided that at least one of $V^1$, $V^2$, and $V^3$ is $CR^{22}$; and wherein $R^{22}$ is selected from H and $R^a$. Y, Z, $X^1$, $X^2$, $X^3$, $X^4$, $X^5$, $X^6$, $X^7$, p, $R^a$, $R^2$, $R^3$, $R^4$, $R^5$, $R^6$, $R^7$, $R^8$, and $R^9$ are as defined above.

Also provided are compounds of formula (Ih):

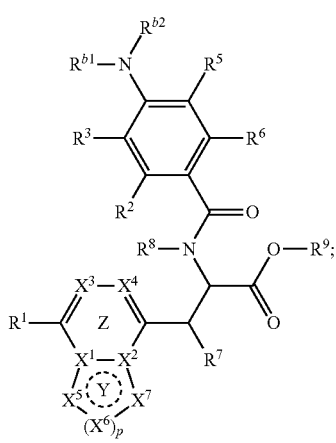

(Ih)

or a pharmaceutically acceptable salt thereof. $R^{b1}$, $R^{b2}$, Y, Z, $X^1$, $X^2$, $X^3$, $X^4$, $X^5$, $X^6$, $X^7$, p, $R^1$, $R^2$, $R^3$, $R^5$, $R^6$, $R^7$, $R^8$, and $R^9$ are as defined above.

Also provided are compounds of formula (Ii):

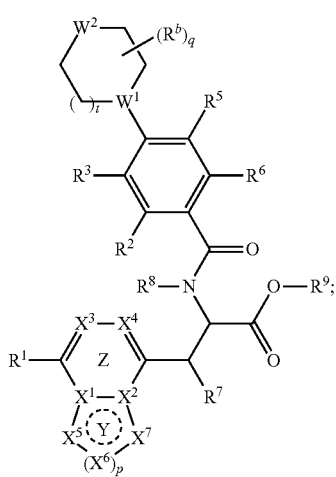

(Ii)

or a pharmaceutically acceptable salt thereof, wherein $W^1$ is selected from $CR^{31}$ and N; $W^2$ is selected from $CR^{31}R^{31}$, $NR^{32}$, O, and $S(O)_2$; each $R^{31}$ is independently selected from H and $R^b$; and $R^{32}$ is selected from H, $C_{1-4}$alkyl, and $C_{1-4}$haloalkyl; q is selected from 0, 1, 2, and 3; and t is 0 or 1. $R^b$, Y, Z, $X^1$, $X^2$, $X^3$, $X^4$, $X^5$, $X^6$, $X^7$, p, $R^1$, $R^2$, $R^3$, $R^5$, $R^6$, $R^7$, $R^8$, and $R^9$ are as defined above.

Also provided are compounds of formula (Ik):

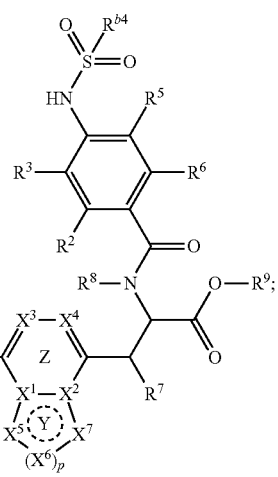

(Ik)

or a pharmaceutically acceptable salt thereof. $R^{b4}$, Y, Z, $X^1$, $X^2$, $X^3$, $X^4$, $X^5$, $X^6$, $X^7$, p, $R^1$, $R^2$, $R^3$, $R^5$, $R^6$, $R^7$, $R^8$, and $R^9$ are as defined above.

Also provided are compounds of formula (Im):

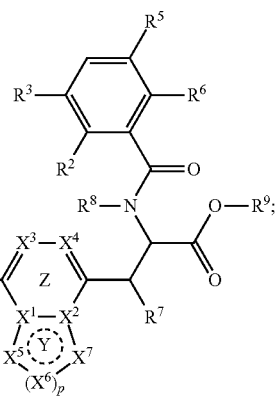

(Im)

or a pharmaceutically acceptable salt thereof. Y, Z, $X^1$, $X^2$, $X^3$, $X^4$, $X^5$, $X^6$, $X^7$, p, $R^1$, $R^2$, $R^3$, $R^5$, $R^6$, $R^7$, $R^8$, and $R^9$ are as defined above.

Also provided are compounds of formula (II):

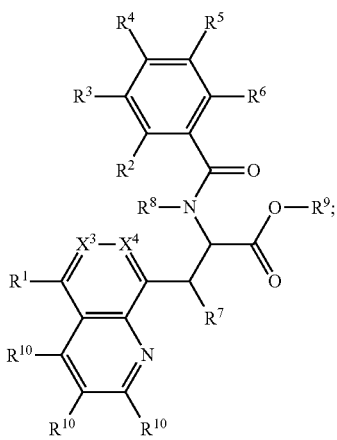
(II)

or a pharmaceutically acceptable salt thereof; wherein $X^3$, $X^4$, $R^1$, $R^2$, $R^3$, $R^4$, $R^5$, $R^6$, $R^7$, $R^8$, $R^9$, and $R^{10}$ are as defined above.

Also provided are compounds of formula (III):

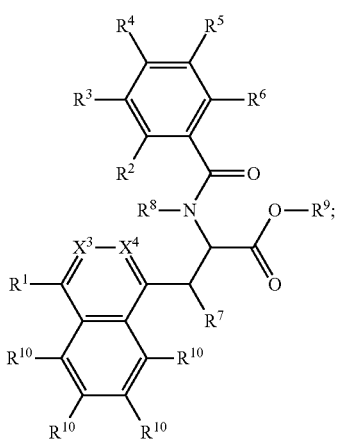
(III)

or a pharmaceutically acceptable salt thereof; wherein $X^3$, $X^4$, $R^1$, $R^2$, $R^3$, $R^4$, $R^5$, $R^6$, $R^7$, $R^8$, $R^9$, and $R^{10}$ are as defined above.

Also provided are compounds of formula (IV):

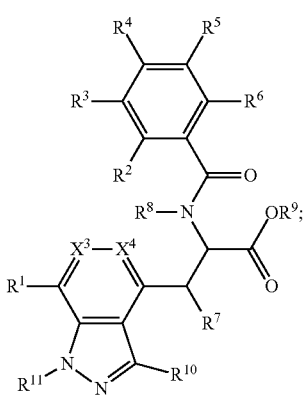
(IV)

or a pharmaceutically acceptable salt thereof; wherein $X^3$, $X^4$, $R^1$, $R^2$, $R^3$, $R^4$, $R^5$, $R^6$, $R^7$, $R^8$, $R^9$, $R^{10}$, and $R^{11}$ are as defined above.

Also provided are compounds of formula (V):

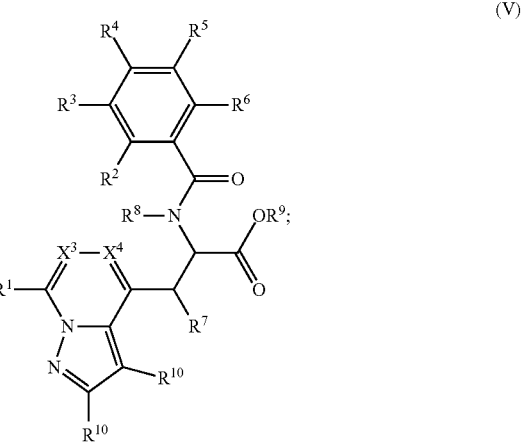
(V)

or a pharmaceutically acceptable salt thereof; wherein $X^3$, $X^4$, $R^1$, $R^2$, $R^3$, $R^4$, $R^5$, $R^6$, $R^7$, $R^8$, $R^9$, and $R^{10}$ are as defined above.

Also provided are compounds of formula (VI):

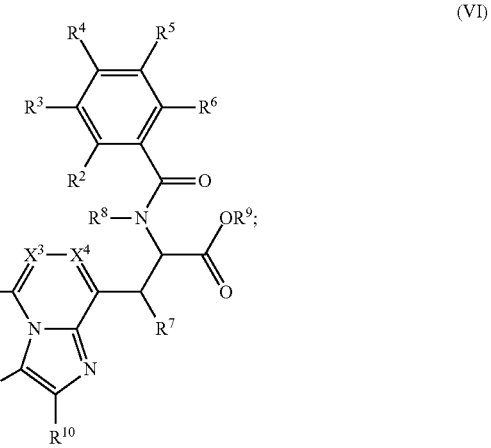
(VI)

or a pharmaceutically acceptable salt thereof; wherein $X^3$, $X^4$, $R^1$, $R^2$, $R^3$, $R^4$, $R^5$, $R^6$, $R^7$, $R^8$, $R^9$, and $R^{10}$ are as defined above.

Also provided are compounds of formula (VII):

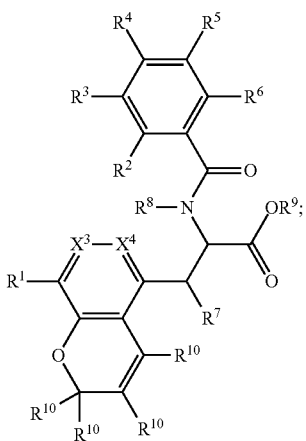

(VII)

or a pharmaceutically acceptable salt thereof; wherein $X^3$, $X^4$, $R^1$, $R^2$, $R^3$, $R^4$, $R^5$, $R^6$, $R^7$, $R^8$, $R^9$, and $R^{10}$ are as defined above.

Also provided are compounds of formula (VIII):

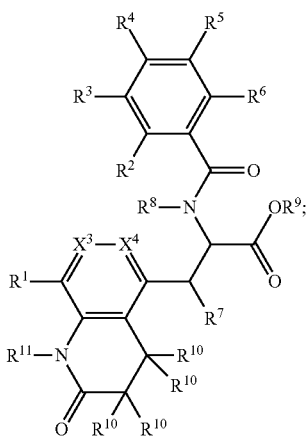

(VIII)

or a pharmaceutically acceptable salt thereof; wherein $X^3$, $X^4$, $R^1$, $R^2$, $R^3$, $R^4$, $R^5$, $R^6$, $R^7$, $R^8$, $R^9$, $R^{10}$, and $R^{11}$ are as defined above.

Also provided are compounds of formula (IX):

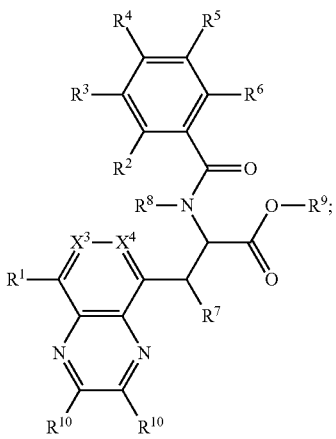

(IX)

or a pharmaceutically acceptable salt thereof; wherein $X^3$, $X^4$, $R^1$, $R^2$, $R^3$, $R^4$, $R^5$, $R^6$, $R^7$, $R^8$, $R^9$, and $R^{10}$ are as defined above.

Also provided are compounds of formula (X):

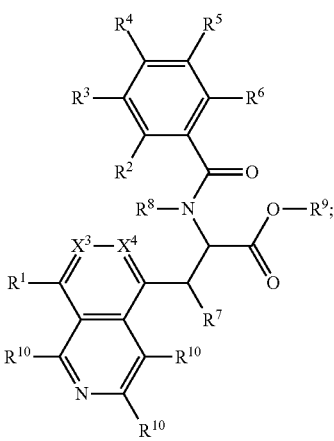

(X)

or a pharmaceutically acceptable salt thereof; wherein $X^3$, $X^4$, $R^1$, $R^2$, $R^3$, $R^4$, $R^5$, $R^6$, $R^7$, $R^8$, $R^9$, and $R^{10}$ are as defined above.

Also provided are compounds of formula (XI):

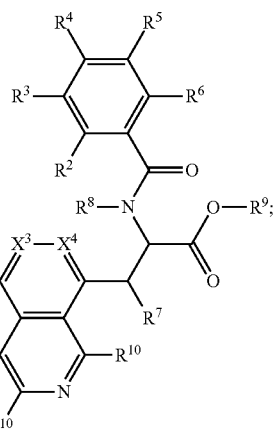

(XI)

or a pharmaceutically acceptable salt thereof; wherein $X^3$, $X^4$, $R^1$, $R^2$, $R^3$, $R^4$, $R^5$, $R^6$, $R^7$, $R^8$, $R^9$, and $R^{10}$ are as defined above.

Also provided are compounds of formula (XII):

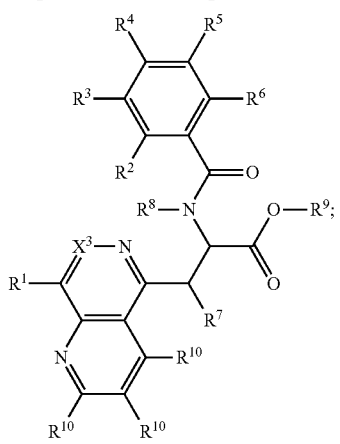

(XII)

or a pharmaceutically acceptable salt thereof; wherein $X^3$, $R^1$, $R^2$, $R^3$, $R^4$, $R^5$, $R^6$, $R^7$, $R^8$, $R^9$, and $R^{10}$ are as defined above.

Also provided are compounds of formula (XIII):

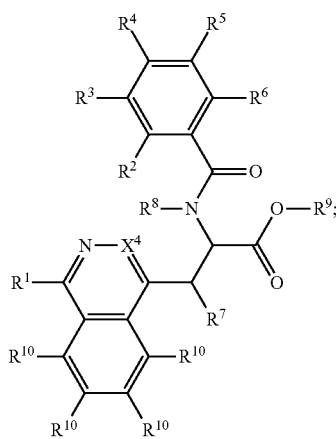

(XIII)

or a pharmaceutically acceptable salt thereof; wherein $X^4$, $R^1$, $R^2$, $R^3$, $R^4$, $R^5$, $R^6$, $R^7$, $R^8$, $R^9$, and $R^{10}$ are as defined above.

Also provided are compounds of formula (XIV):

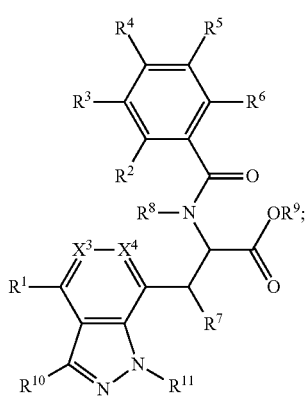

(XIV)

or a pharmaceutically acceptable salt thereof; wherein $X^3$, $X^4$, $R^1$, $R^2$, $R^3$, $R^4$, $R^5$, $R^6$, $R^7$, $R^8$, $R^9$, $R^{10}$, and $R^{11}$ are as defined above.

Also provided are compounds of formula (XV):

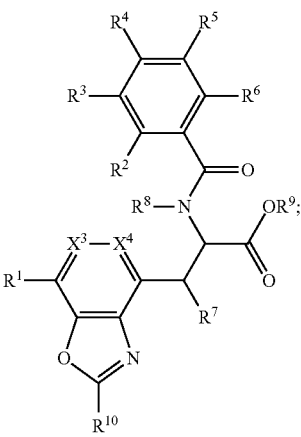

(XV)

or a pharmaceutically acceptable salt thereof; wherein $X^3$, $X^4$, $R^1$, $R^2$, $R^3$, $R^4$, $R^5$, $R^6$, $R^7$, $R^8$, $R^9$, and $R^{10}$ are as defined above.

Also provided are compounds of formula (XVI):

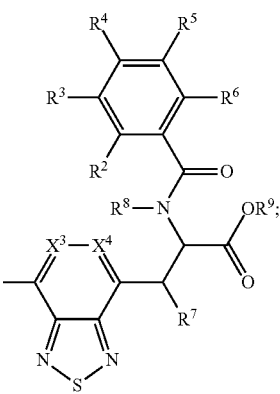

(XVI)

or a pharmaceutically acceptable salt thereof; wherein $X^3$, $X^4$, $R^1$, $R^2$, $R^3$, $R^4$, $R^5$, $R^6$, $R^7$, $R^8$, and $R^9$ are as defined above.

In some embodiments, each $X^3$ and $X^4$ is independently $CR^{10}$. In some embodiments, $X^3$ is $CR^{10}$ and $X^4$ is N. In some embodiments, $X^3$ is N and $X^4$ is $CR^{10}$. In some embodiments, each $X^3$ and $X^4$ is independently $CR^{10}$ and each $R^{10}$ is independently selected from H, halo, hydroxyl, $C_{1-4}$alkyl, $C_{1-4}$alkoxyl, $C_{1-4}$haloalkyl, and $C_{1-4}$haloalkoxyl, wherein each the $C_{1-4}$alkyl, $C_{1-4}$alkoxyl, $C_{1-4}$haloalkyl, $C_{1-4}$haloalkoxyl is independently optionally substituted with one to three groups independently selected from halo, hydroxyl, cyano, —$NR^{a1}R^{a2}$, $C_{1-4}$alkyl, $C_{1-4}$haloalkyl, $C_{1-4}$alkoxyl, and $C_{3-6}$cycloalkyl. In some embodiments, each $X^3$ and $X^4$ is independently $CR^{10}$ and each $R^{10}$ is independently selected from H, F, Cl, cyano, hydroxyl, —$CH_3$, —$CH_2F$, —$CHF_2$, —$CF_3$, —$OCH_3$, and —$OCF_3$.

In some embodiments, each $X^3$ and $X^4$ is CH.

In some embodiments, L is a bond, and $R^1$ is selected from -L-$A^1$, -L-$A^2$, and -L-$A^3$.

In some embodiments, $A^1$, $A^2$, or $A^3$ is selected from phenyl, naphthyl, pyridinyl, pyridazinyl, pyrazinyl, pyrimidinyl, quinolinyl, isoquinolinyl, isoxazolyl, triazolyl, pyrazolyl, benzothiazolyl, pyridinonyl, quinolinonyl, isoquinolinonyl, quinazolindionyl, pyrazinonyl, pyrimidinonyl, pyrimidinedionyl, pyridazinonyl, quinazolinonyl, benzofuranyl, tetrahydrocyclopenta[b]pyridinonyl, naphthyridinonyl, chromanyl, isochromanyl, and chromenonyl, and wherein each of which is independently optionally substituted with one to four $R^a$.

In some embodiments, $R^1$ is

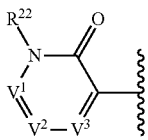

wherein each $V^1$, $V^2$, and $V^3$ is independently selected from $CR^{22}$ and N, provided that at least one of $V^1$, $V^2$, and $V^3$ is $CR^{22}$; and wherein $R^{22}$ is selected from H and $R^a$.

In some embodiments, $R^1$ is

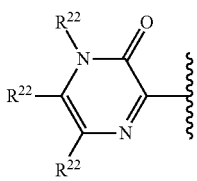

wherein $R^{22}$ is selected from H, and $R^a$.

In some embodiments, $R^1$ is

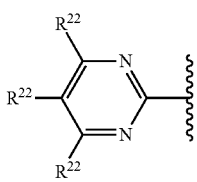

wherein $R^{22}$ is selected from H, and $R^a$.

In some embodiments, $R^1$ is

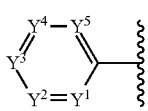

wherein each $Y^1$, $Y^2$, $Y^3$, $Y^4$, and $Y^5$ is independently selected from $CR^{22}$ and N, provided that at least one of $Y^1$, $Y^2$, $Y^3$, $Y^4$, and $Y^5$ is $CR^{22}$; and wherein $R^{22}$ is selected from H and $R^a$.

In some embodiments, $R^1$ is

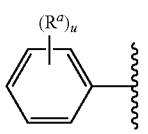

wherein u is selected from 0, 1, 2, 3, 4, and 5.

In some embodiments, $R^1$ is

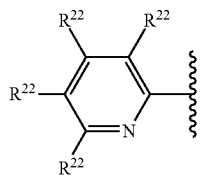

wherein $R^{22}$ is selected from H and $R^a$.

In some embodiments, $R^1$ is

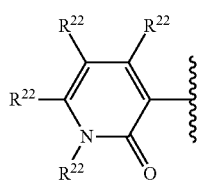

wherein $R^{22}$ is selected from H and $R^a$.

In some embodiments, $R^1$ is

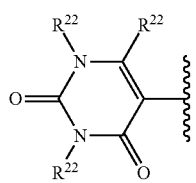

wherein $R^{22}$ is selected from H and $R^a$.

In some embodiments, $R^1$ is

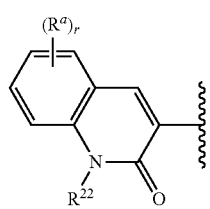

wherein r is selected from 0, 1, 2, 3, 4 and 5, and $R^{22}$ is selected from H and $R^a$.

In some embodiments, $R^1$ is selected from

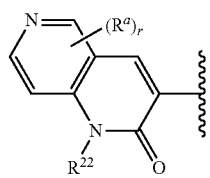

wherein r is selected from 0, 1, 2, 3, 4 and 5, and $R^{22}$ is selected from H, and $R^a$.

In some embodiments, R[1] is selected from
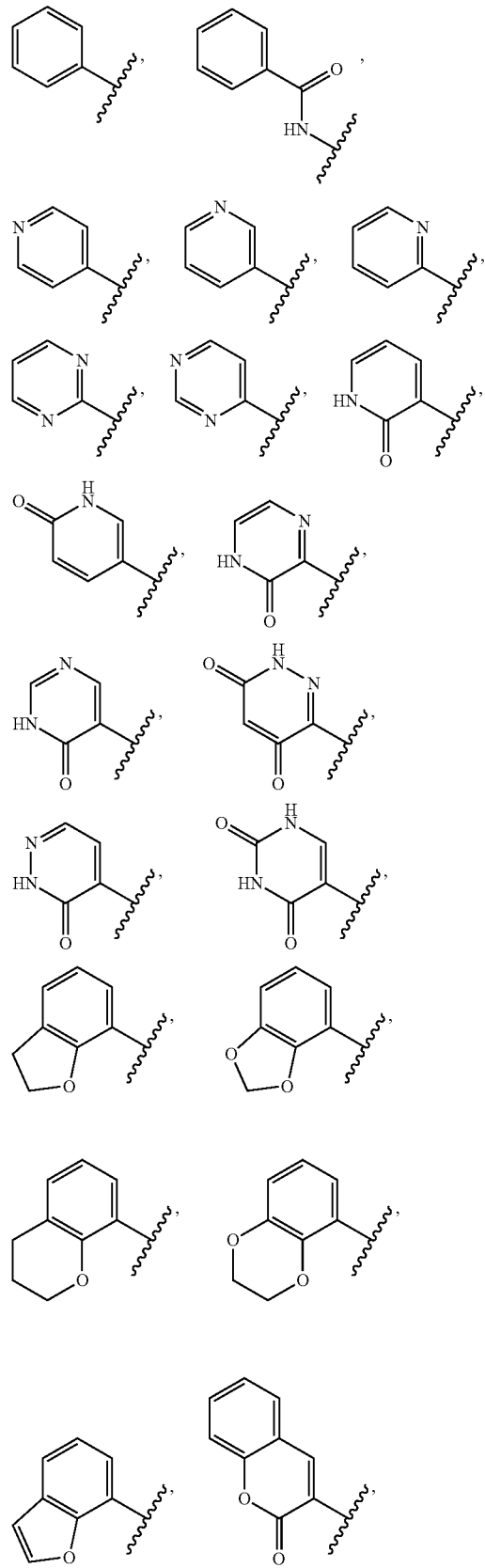
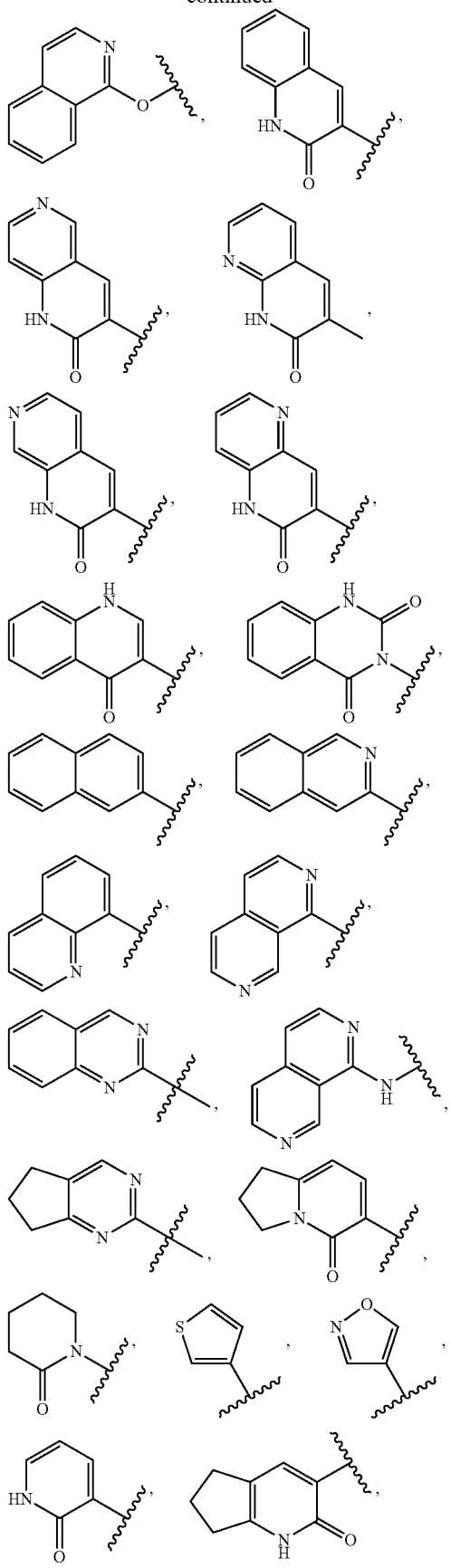

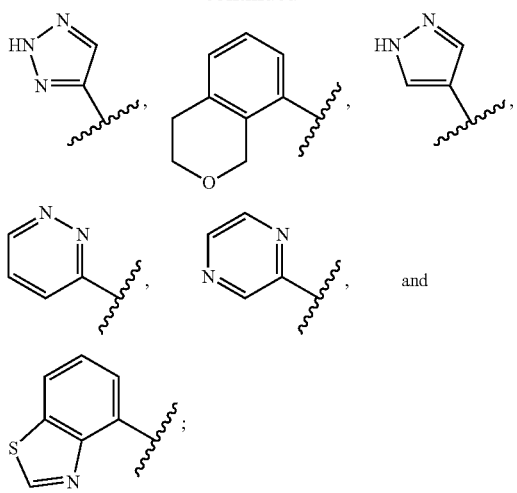

wherein each R¹ is optionally substituted with one to four R$^a$.

In some embodiments, R¹ is selected from

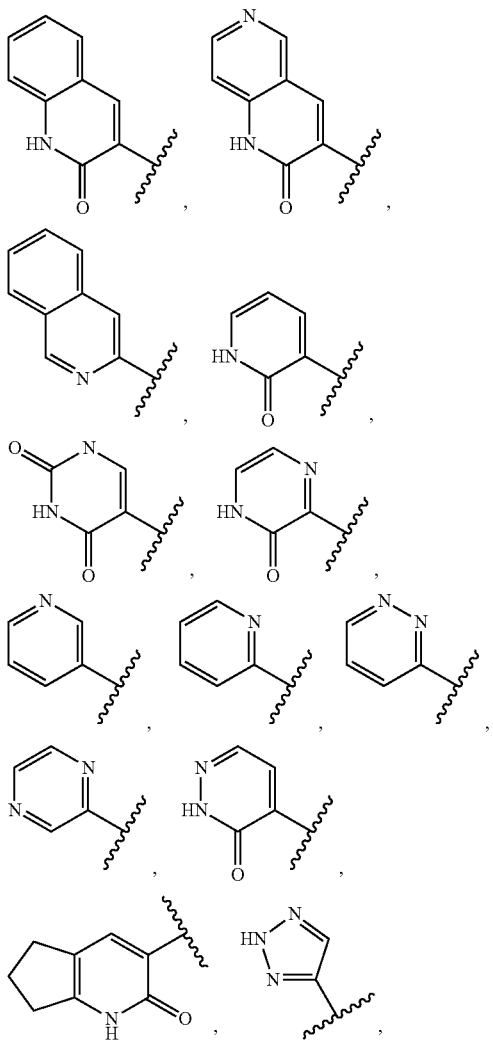

wherein each R¹ is optionally substituted with one to four R$^a$.

In some embodiments, R¹ is substituted with one to four R$^a$, and each R$^a$ is independently selected from halo, cyano, hydroxyl, —NR$^{a1}$R$^{a2}$, C$_{1-4}$alkyl, C$_{1-4}$alkoxyl, C$_{1-4}$haloalkyl, C$_{1-4}$haloalkoxyl, C$_{3-6}$cycloalkyl, phenyl, and —O—C$_{3-6}$cycloalkyl.

In some embodiments, R¹ is substituted with one to three R$^a$, and each R$^a$ is independently selected from F, Cl, Br, cyano, hydroxyl, —NH$_2$, —N(CH$_3$)$_2$, —CH$_3$, —CH$_2$CH$_3$, —CH(CH$_3$)$_2$, —C(CH$_3$)$_3$, —CH$_2$CN, —CH$_2$CH$_2$CN, —CH$_2$OH, —CH$_2$CH$_2$OH, —OCH$_3$, —OCD$_3$, —OCH$_2$CH$_3$, —OCH(CH$_3$)$_2$, —OC(CH$_3$)$_3$, —CH$_2$OCH$_3$, —CH$_2$OCH$_2$CH$_3$, —CH$_3$OCH(CH$_3$)$_2$, —CH$_2$F, —CHF$_2$, —CF$_3$, —CH$_2$CH$_2$F, —CH$_2$CHF$_2$, —CH$_2$CF$_3$, —OCH$_2$F, —OCHF$_2$, —OCF$_3$, —OCH$_2$CH$_2$F, —OCH$_2$CHF$_2$, —OCH$_2$CF$_3$, —SO$_2$CH$_3$, —SO$_2$CH$_2$CH$_3$,

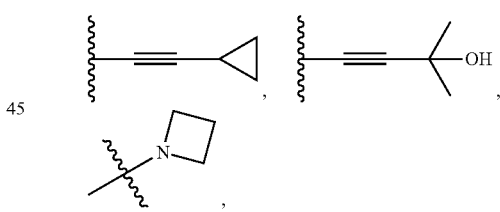

cyclopropyl, cyclobutyl, cyclopentyl, cyclohexyl, phenyl, —O-cyclopropyl, —O—CH$_2$-cyclopropyl, —O-cyclobutyl, —O—CH$_2$cyclobutyl, —O-cyclopentyl, —O—CH$_2$cyclopentyl, —O-cyclohexyl, —O—CH$_2$cyclohexyl, and —O-phenyl.

In some embodiments, R¹ is selected from

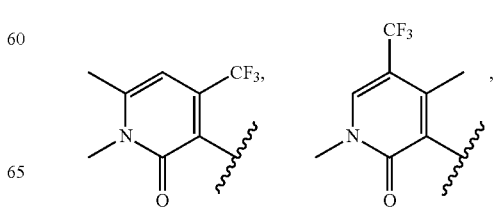

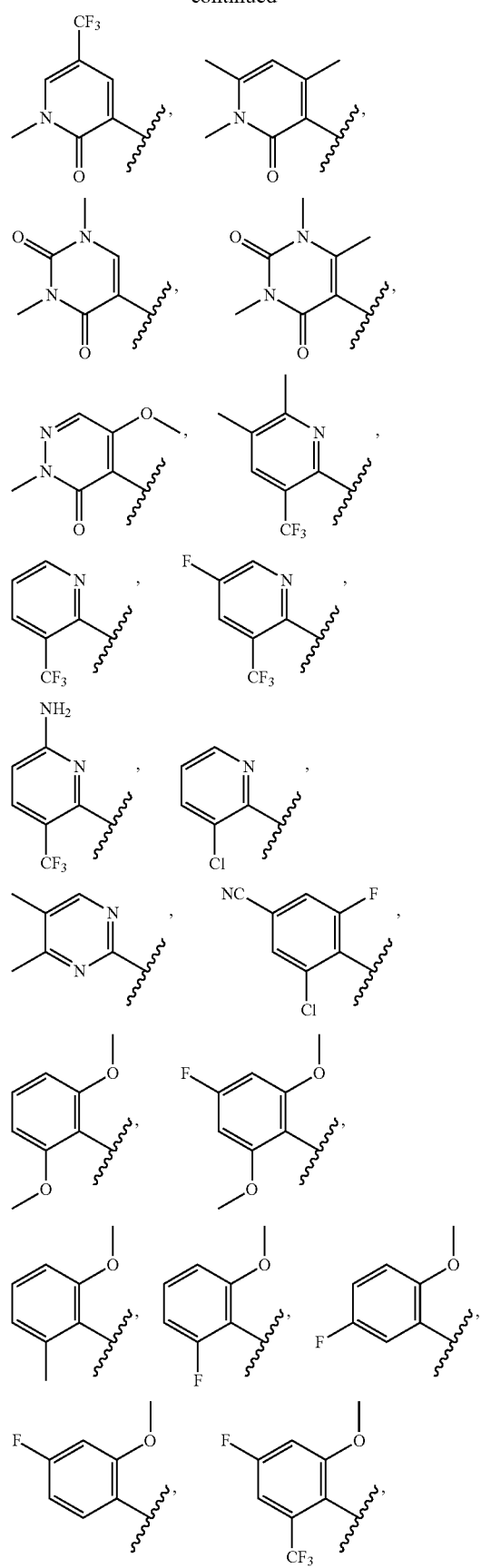
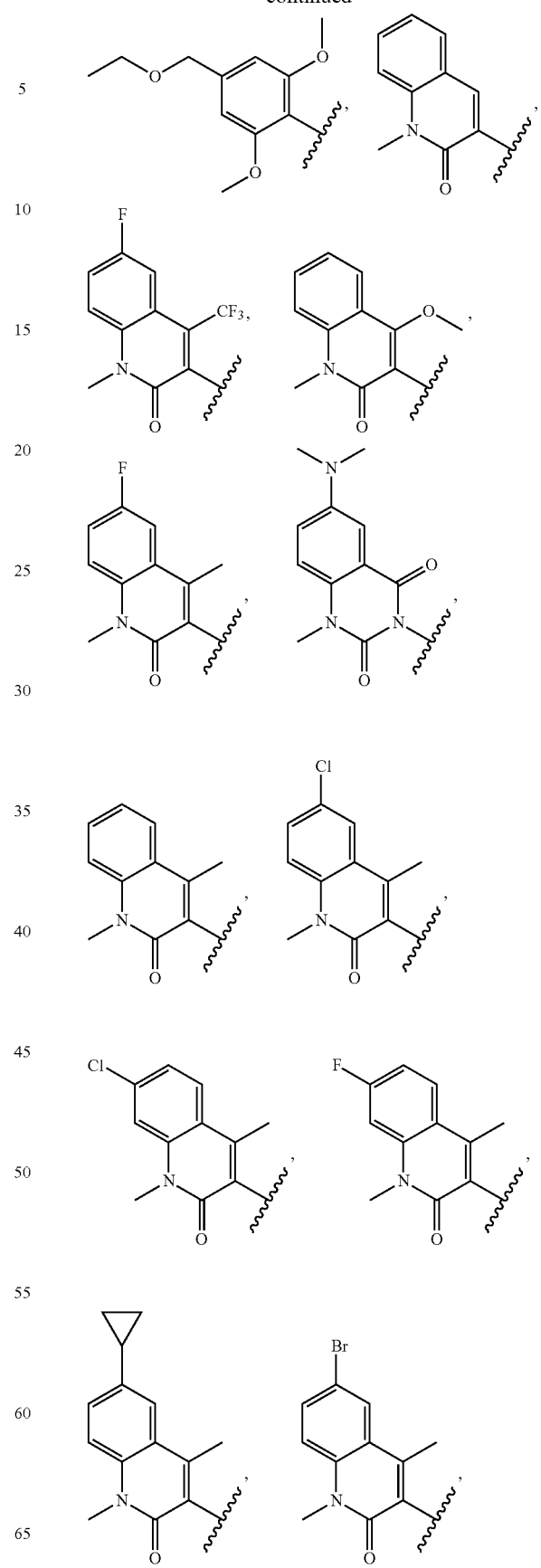

-continued
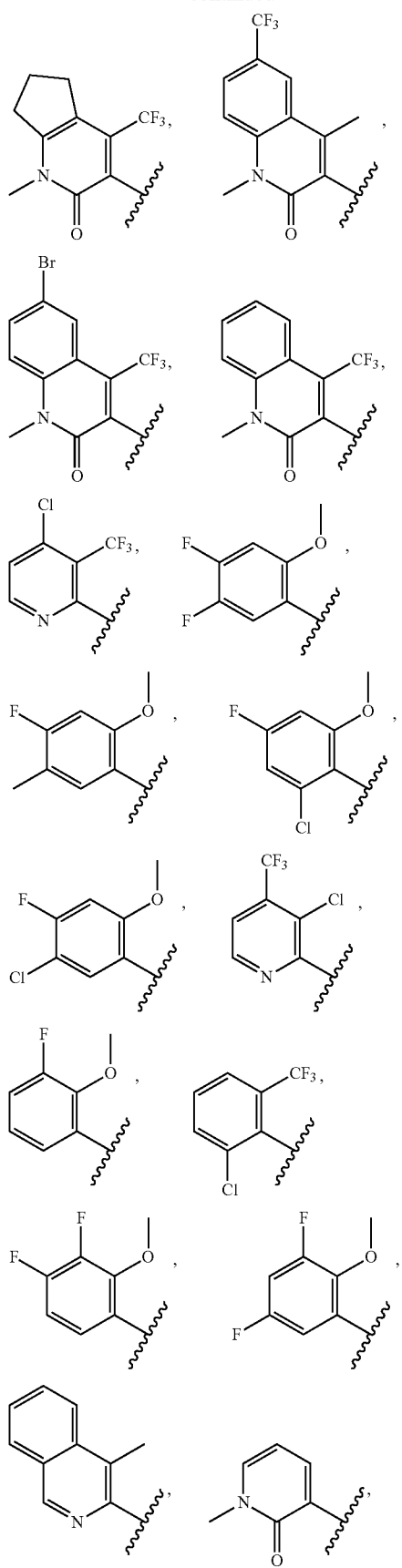
-continued
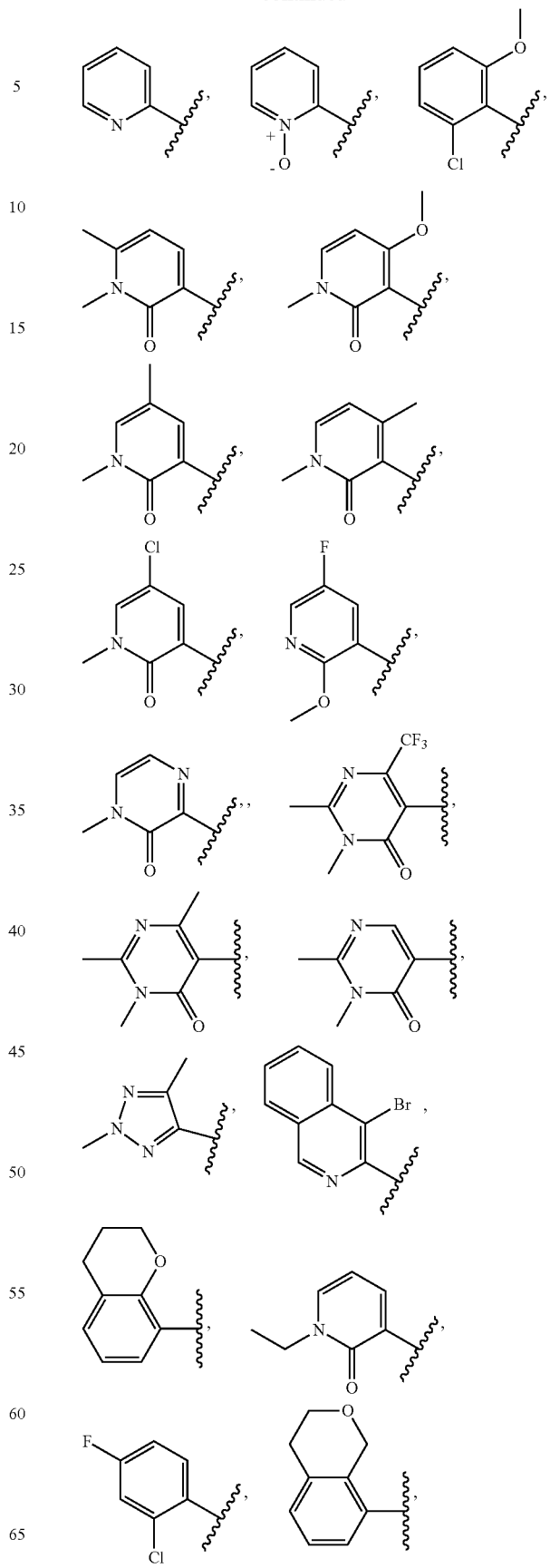

-continued
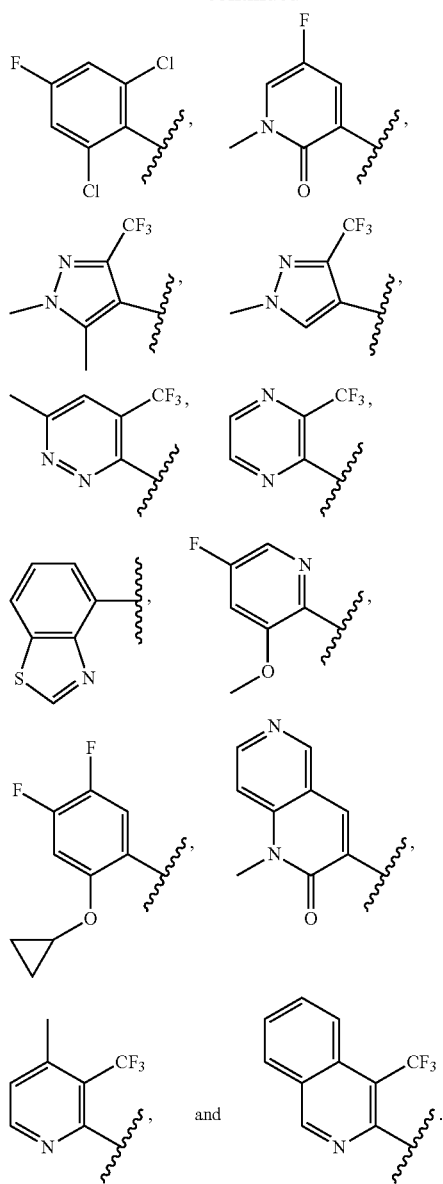
In some embodiments, R[1] is selected from
-continued
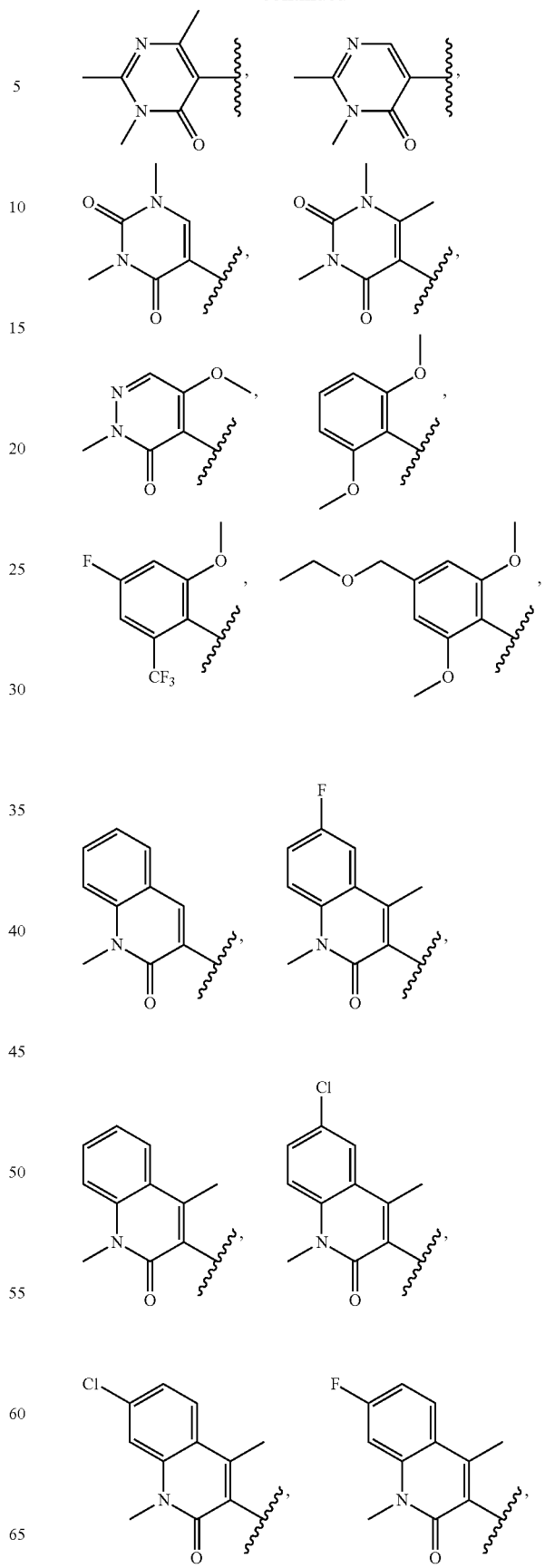

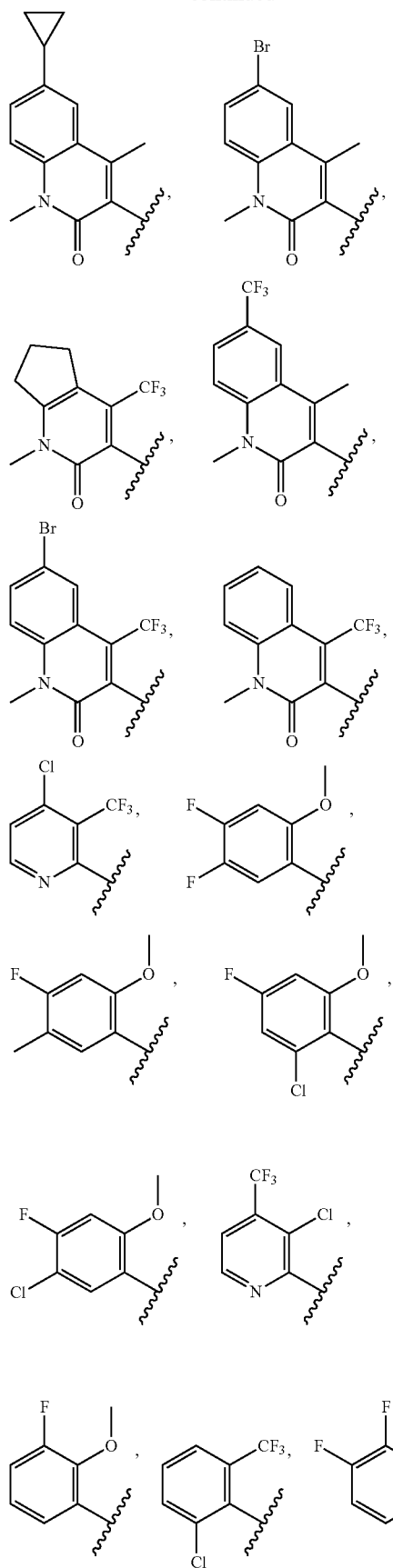
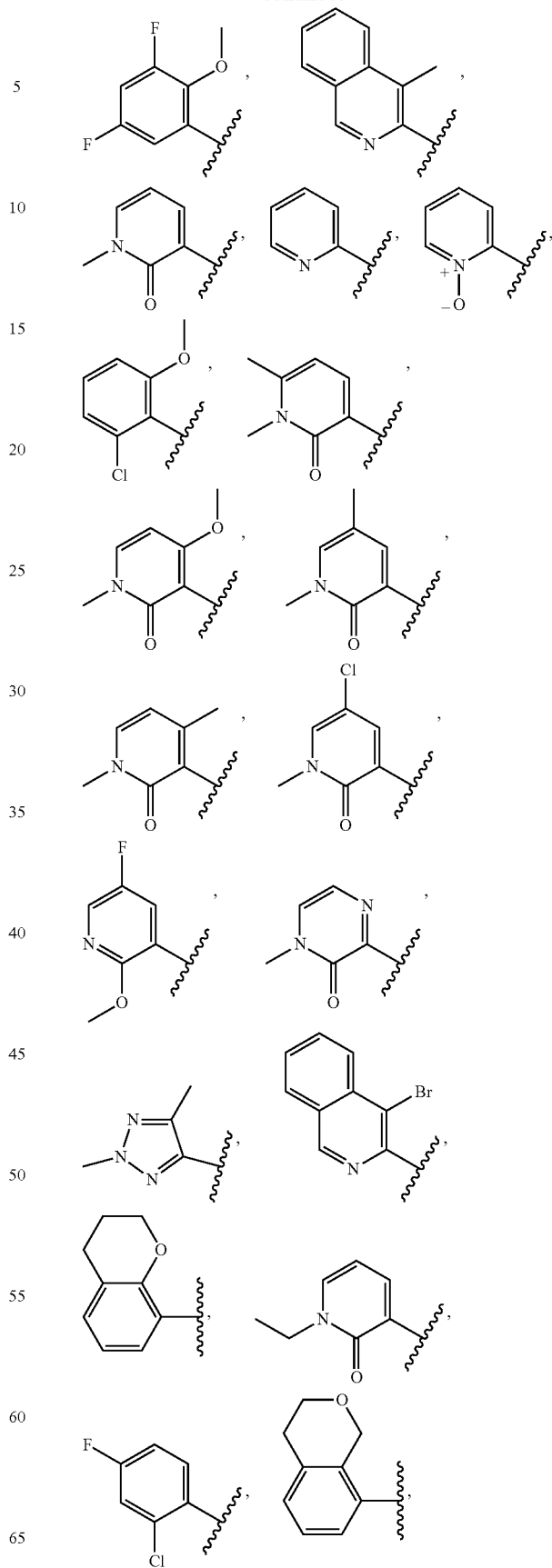

-continued

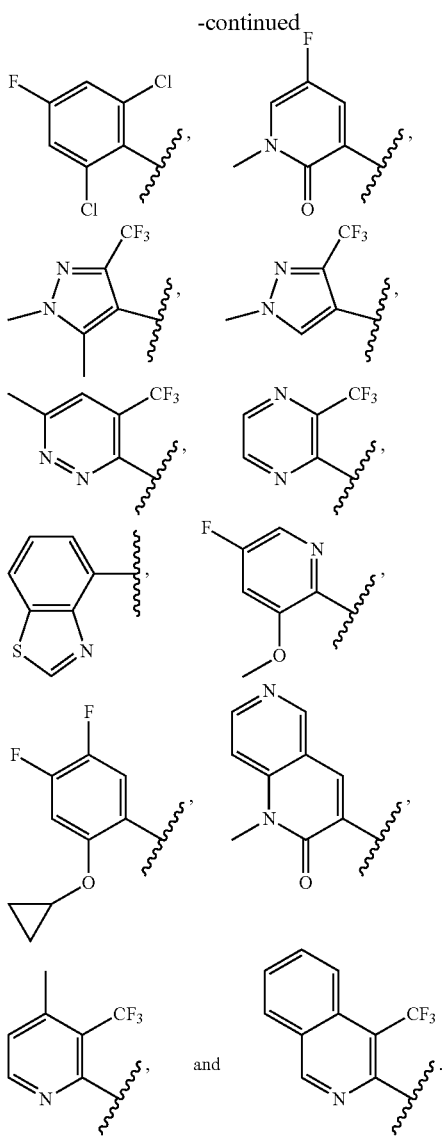

In some embodiments, $R^1$ is

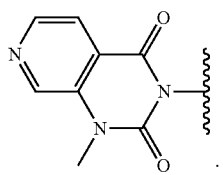 [SMILES: *n1c(=O)c2ccncc2n(C)c1=O]

In some embodiments, each $R^a$ is independently selected from halo, $C_{1-6}$alkyl, $C_{1-6}$alkoxyl, $C_{1-6}$haloalkyl, $C_3$cycloalkyl, and —O—$C_3$cycloalkyl. In some embodiments, each $R^a$ is independently selected from F, Cl, Br, —CH$_3$, —CH$_2$CH$_3$, —CH$_2$F, —CHF$_2$, —CF$_3$, —OCH$_3$, —OCD$_3$, —OCH$_2$CH$_3$, —CH$_2$OCH$_3$, —CH$_2$OCH$_2$CH$_3$, cyclopropyl, and —O-cyclopropyl.

In some embodiments, each $R^2$ and $R^6$ is independently selected from H, halo, cyano, hydroxyl, —NR$^{b1}$R$^{b2}$, $C_{1-4}$alkyl, $C_{1-4}$alkoxyl, $C_{1-4}$haloalkyl, and $C_{1-4}$haloalkoxyl. In some embodiments, each $R^2$ and $R^6$ is independently selected from F, Cl, cyano, hydroxyl, —NH$_2$, —N(CH$_3$)$_2$, —CH$_3$, —CD$_3$, —CH$_2$F, —CHF$_2$, —CF$_3$, —OCH$_3$, and —OCF$_3$.

In some embodiments, each $R^2$ and $R^6$ is independently F or Cl. In some embodiments, each $R^2$ and $R^6$ is F.

In some embodiments, each $R^3$ and $R^5$ is independently selected from H, $C_{1-4}$alkyl, $C_{1-4}$alkoxyl, $C_{1-4}$haloalkyl, and $C_{1-4}$haloalkoxyl. In some embodiments, each $R^3$ and $R^5$ is H.

In some embodiments, $R^4$ is selected from H, —NR$^{b1}$R$^{b2}$, —NR$^{b1}$S(O)$_v$R$^{b4}$, and 4-6 membered heterocyclyl containing one to two heteroatoms or groups independently selected from N, O, S, and S(O)$_2$.

In some embodiments, $R^4$ is —NR$^{b1}$R$^{b2}$. In some embodiments, $R^4$ is —NHR$^{b2}$, wherein R$^{b2}$ is selected from $C_{1-6}$alkyl, $C_{1-6}$haloalkyl, $C_{3-6}$cycloalkyl, and 4-6 membered heterocyclyl.

In some embodiments, each R$^{b1}$ and R$^{b2}$ is independently selected from H, $C_{1-8}$alkyl, $C_{1-6}$haloalkyl, $C_{3-6}$cycloalkyl, phenyl, and 4-6 membered heterocyclyl containing one to two atoms selected from N and O. In some embodiments, R$^{b1}$ is selected from H, and $C_{1-4}$alkyl. In some embodiments, R$^{b1}$ is selected from H, and CH$_3$. In some embodiments, R$^{b2}$ is selected from $C_{1-6}$alkyl, $C_{1-6}$haloalkyl, and 4-6 membered heterocyclyl. In some embodiments, R$^{b1}$ is H, and R$^{b2}$ is selected from $C_{1-6}$alkyl, $C_{1-6}$haloalkyl, and 5-6 membered heterocyclyl. In some embodiments, R$^{b1}$ is H, and R$^{b2}$ is $C_{1-6}$haloalkyl. In some embodiments, R$^{b2}$ is —$C_{1-5}$alkylene-CF$_3$. In some embodiments, R$^{b2}$ is selected from -methylene-CF$_3$, -ethylene-CF$_3$, -propylene-CF$_3$, -butylene-CF$_3$, and -pentylene-CF$_3$. In some embodiments, R$^{b2}$ is —$C_{1-5}$alkylene-CF$_3$ substituted with one or two R$^{b5}$. In some embodiments, each R$^b$s is independently selected from hydroxyl, $C_{1-4}$alkoxyl, $C_{3-6}$cycloalkyl, phenyl, and 4-6 membered heterocyclyl. In some embodiments, each R$^b$s is independently selected from $C_{3-6}$cycloalkyl, 4-6 membered heterocyclyl, and phenyl. Each $C_{3-6}$cycloalkyl, 4-6 membered heterocyclyl, and phenyl of R$^b$s is independently optionally substituted with one or three groups independently selected from halo, hydroxyl, cyano, —NR$^{b1}$R$^{b2}$, $C_{1-4}$alkyl, $C_{1-4}$alkoxyl, and $C_{1-4}$haloalkyl. In some embodiments, R$^b$s is selected from phenyl, cyclobutyl, cylcopentyl, tetrahydropyanyl, and tetrahydrofuranyl; and each R$^b$s is optionally substituted with one group selected from F, Cl, CN, —CH$_3$, —CH$_2$F, —CHF$_2$, and —CF$_3$. In some embodiments, R$^b$s is phenyl. In some embodiments, R$^b$s is phenyl substituted with one or two groups independently selected from F, Cl, CN, —CH$_3$, —CH$_2$F, —CHF$_2$, and —CF$_3$. In some embodiments, R$^b$s is phenyl substituted with one or two groups independently selected from F, Cl, CN, and —CF$_3$. In some embodiments, R$^b$s is unsubstituted phenyl.

In some embodiments, $R^4$ is H.

In some embodiments, $R^4$ is selected from

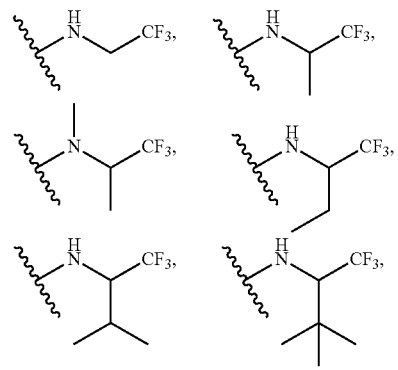

-continued
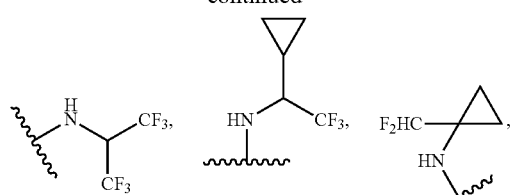
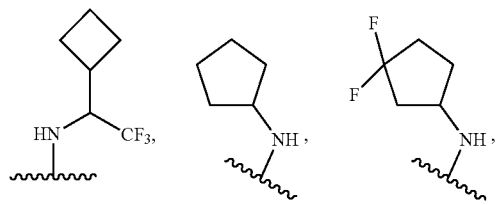
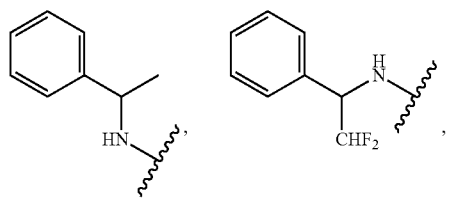
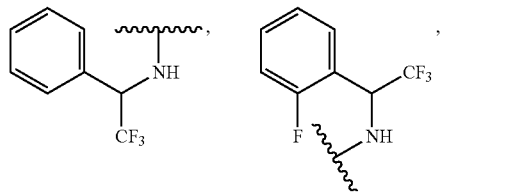
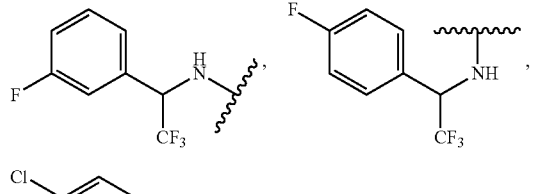
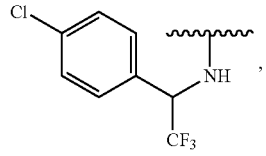
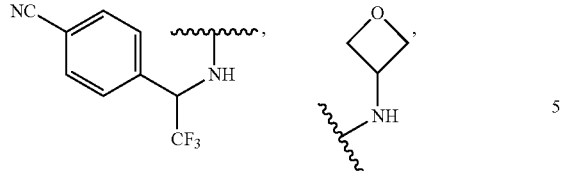
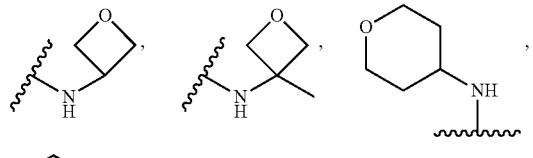
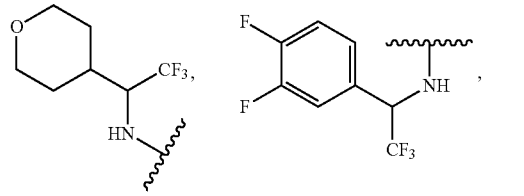
-continued
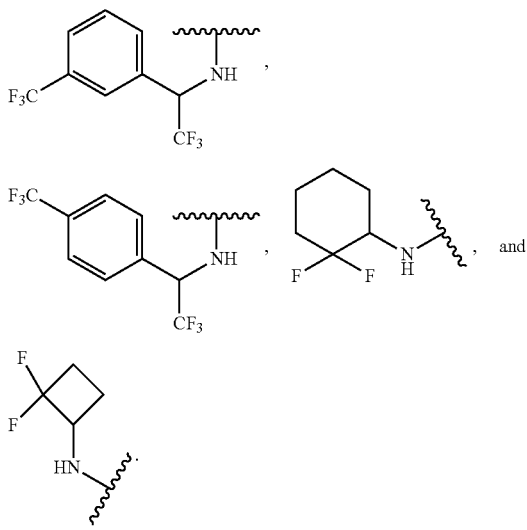
In some embodiments, $R^4$ is selected from
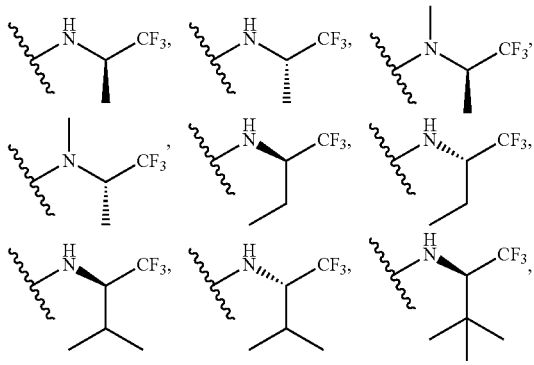
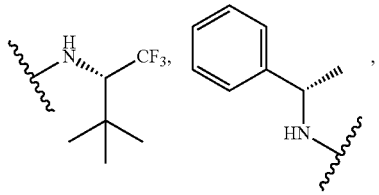
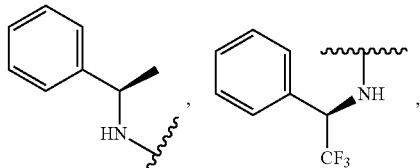
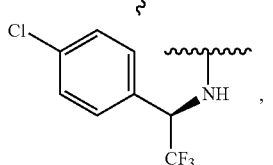
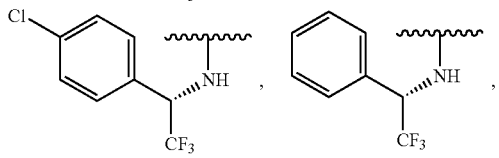

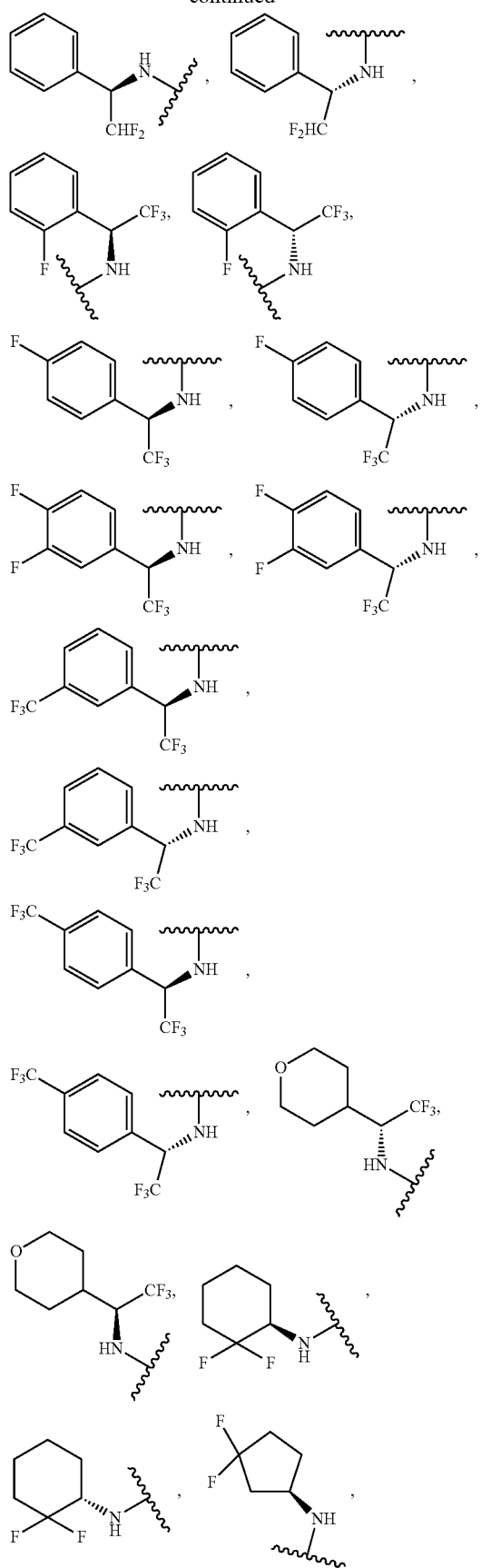

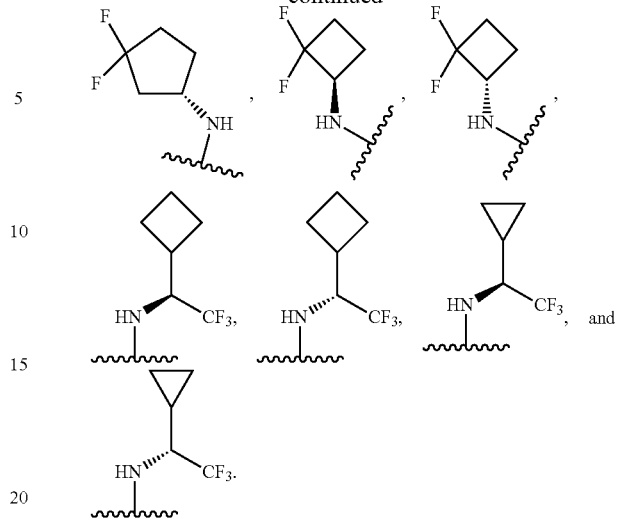

In some embodiments, R⁴ is selected from

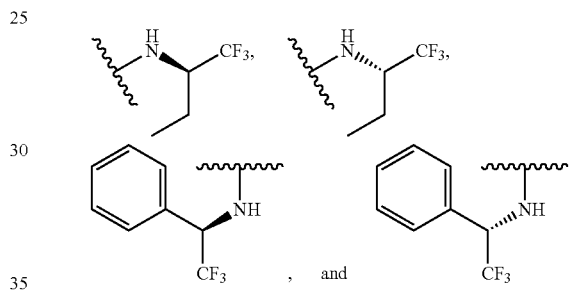

In some embodiments, R⁴ is 5-6 membered heterocyclyl optionally substituted with one to three $R^b$; and each $R^b$ is independently selected from halo, hydroxyl, cyano, —NR$^{a1}$R$^{a2}$, C$_{1-4}$alkyl, C$_{1-4}$alkoxyl, and C$_{1-4}$haloalkyl.

In some embodiments, R⁴ is 4-6 membered heterocyclyl containing one to two heteroatoms or groups independently selected from N, O, S, and S(O)₂. In some embodiments, R⁴ is a 4-10 membered saturated ring

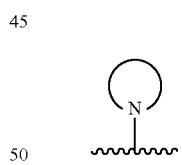

containing zero to two heteroatoms or groups independently selected from N, O, S, and S(O)₂.

In some embodiments, R⁴ is selected from morpholinyl, piperidinyl, tetrahydropyranyl, and pyrrolidinyl. In some embodiments, R⁴ is 5-6 membered heterocyclyl optionally substituted with one to two groups independently selected from F, Cl, CN, —OH, —CH₃, —CH(CH₃)₂, and —CF₃.

In some embodiments, R⁴ is selected from

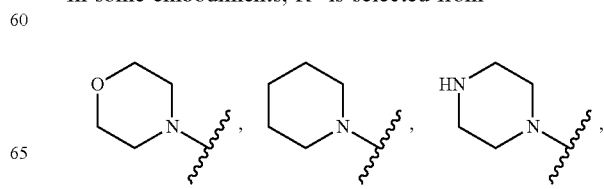

-continued
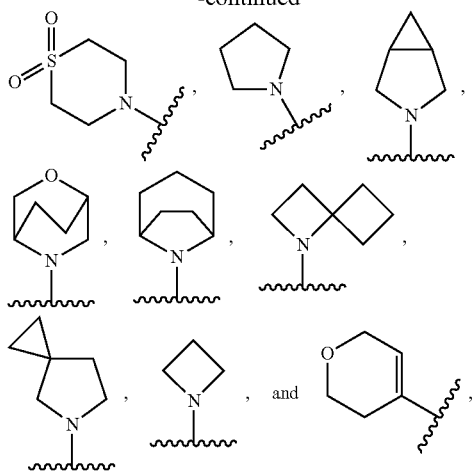
and each R⁴ is optionally substituted with one to two $R^b$ independently selected from halo, hydroxyl, cyano, —$NR^{a1}R^{a2}$, $C_{1-4}$alkyl, $C_{1-4}$alkoxyl, and $C_{1-4}$haloalkyl.
In some embodiments, R⁴ is selected from
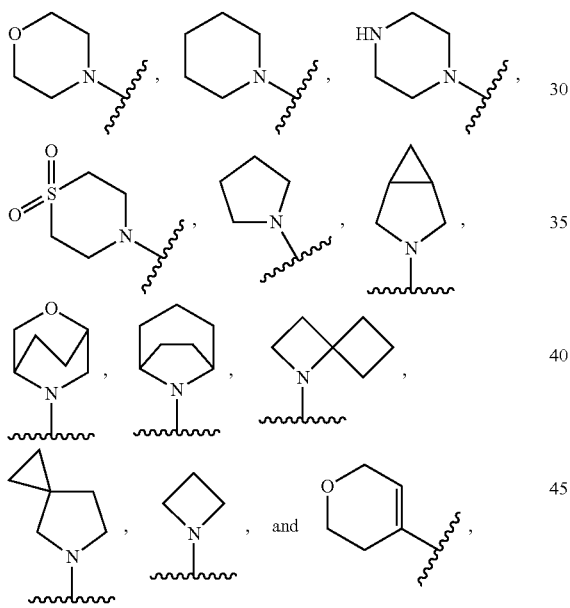
wherein each R⁴ is optionally substituted with one to two groups independently selected from F, Cl, hydroxyl, cyano, —$CH_3$, —$CH(CH_3)_2$, and —$CF_3$.
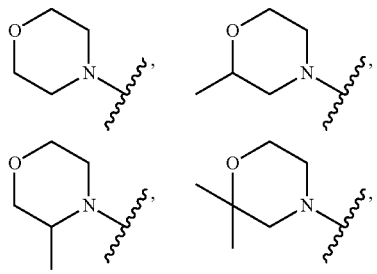
-continued
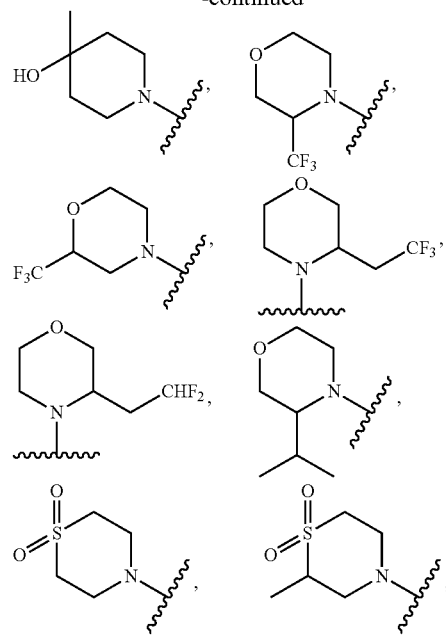
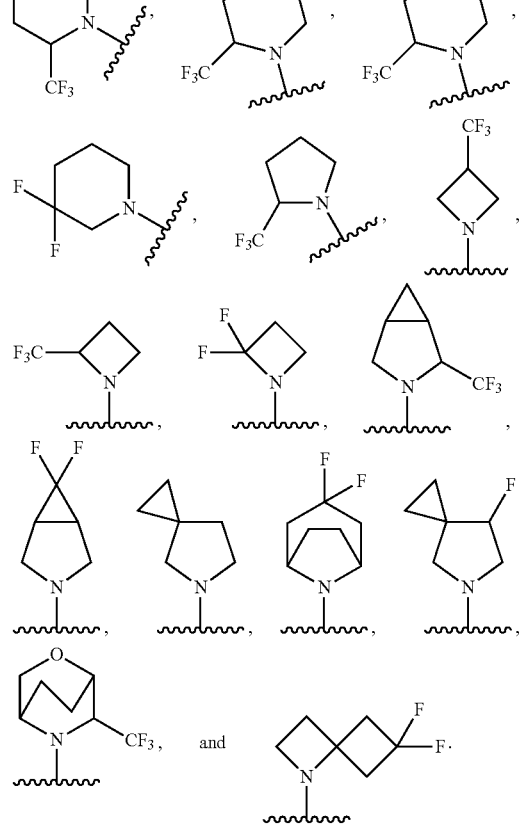

In some embodiments, $R^4$ is selected from

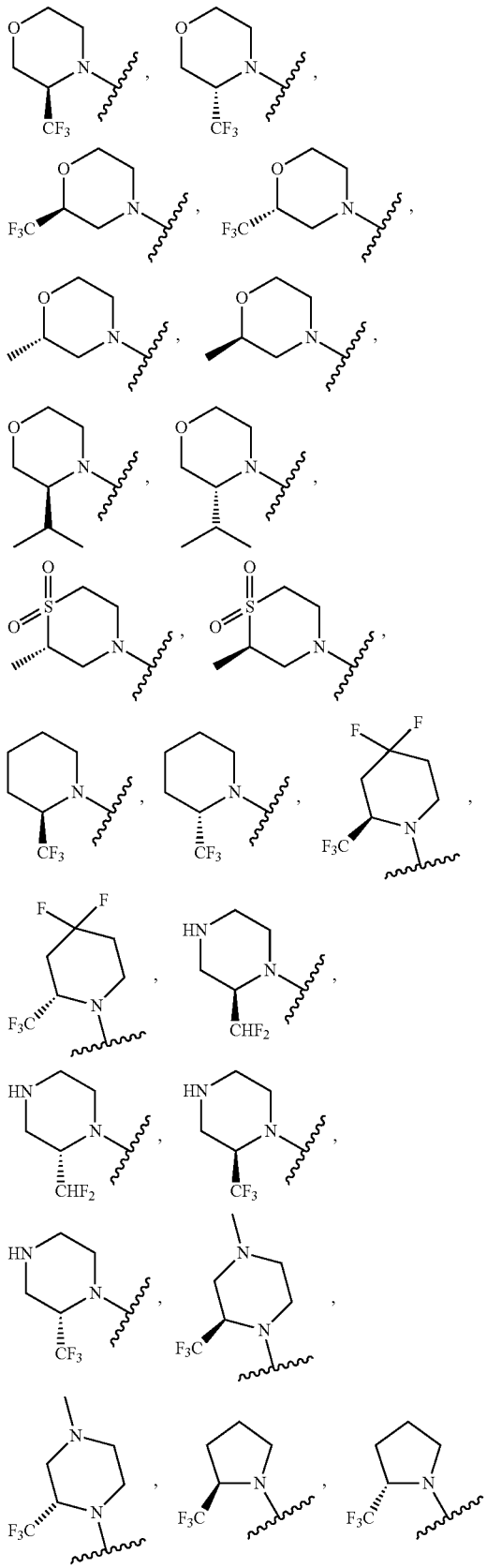

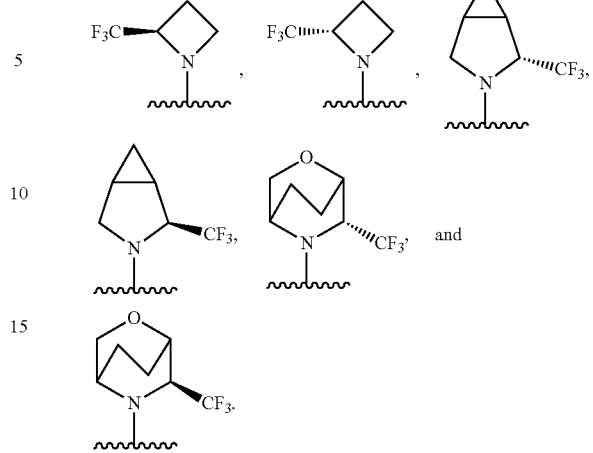

In some embodiments, $R^4$ is

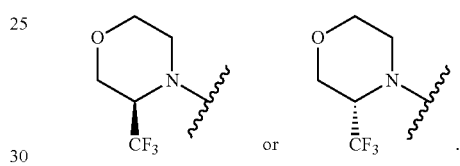

In some embodiments, $R^4$ is —$NR^{b1}S(O)_vR^{b4}$. In some embodiments $R^4$ is —$NHS(O)_2R^{b4}$, and $R^{b4}$ is selected from $C_{1-4}$alkyl, $C_{1-4}$haloalkyl, $C_{3-6}$cycloalkyl, and phenyl. In some embodiments, $R^{b4}$ is selected from —$CH_3$, —$CH_2F$, —$CHF_2$, —$CF_3$, and phenyl. The phenyl is optionally substituted with pyridinyl that is optionally substituted with one or two groups independently selected from halo, and $C_{1-4}$alkyl. In some embodiments, the pyridinyl is optionally substituted with one or two groups independently selected from F, and —$CH_3$. In some embodiments, $R^4$ is —$NHS(O)_2R^{b4}$, $R^{b4}$ is selected from —$CH_3$, —$CH_2F$, —$CHF_2$, —$CF_3$, and phenyl; and wherein the phenyl is optionally substituted with pyridinyl or triazolyl that is optionally substituted with one or two groups independently selected from halo, and $C_{1-4}$alkyl.

In some embodiments, $R^4$ is selected from

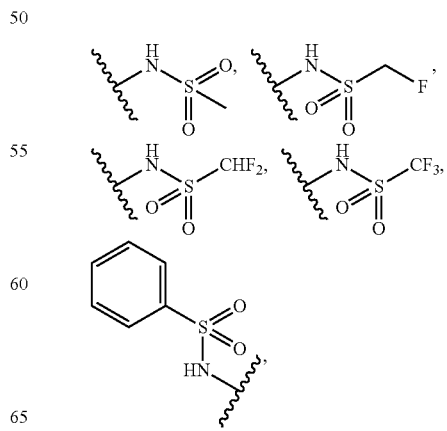

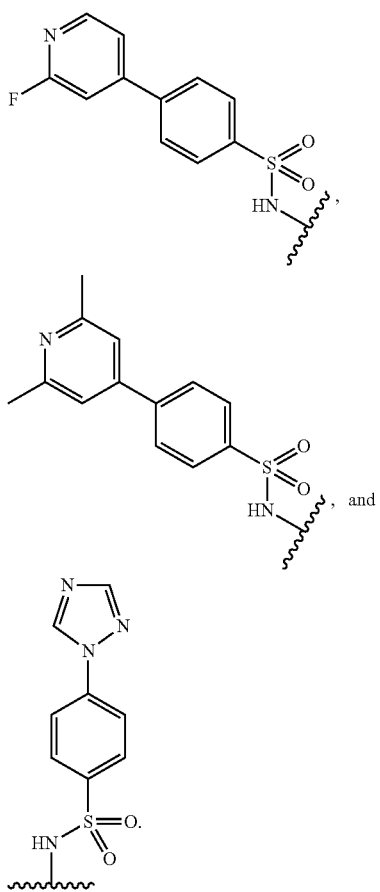

In some embodiments, R⁴ is selected from

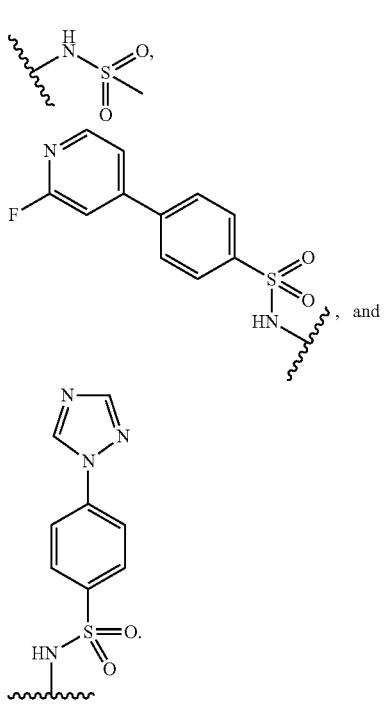

In some embodiments, R⁴ is selected from

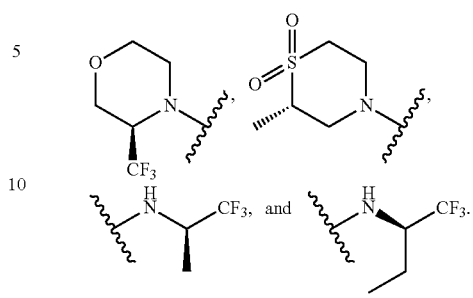

In some embodiments, each $R^7$ and $R^8$ is H. In some embodiments, each $R^7$, $R^8$, $R^{10}$ and $R^{11}$ is H.

In some embodiments, $R^9$ is selected from H, methyl, ethyl, propyl, butyl, —CH₂C(O)N(CH₃)₂, —(CH₂)₂N(CH₂CH₃)₂, —CH₂—O—C(O)CH₃, —(CH₂)₂—O—C(O)CH₃, —CH₂—O—C(O)C(CH)₃, —(CH₂)₂—O—C(O)C(CH)₃, —CH(CH₃)—O—C(O)—O—CH₃, —CH₂—O—C(O)—O—CH₃, —CH₂—O—C(O)—O—CH₂CH₃, —CH₂—O—C(O)—O—CH(CH₃)₂, —CH₂—O—C(O)—O—C(CH₃)₃, —(CH₂)₂C(O)CH₃,

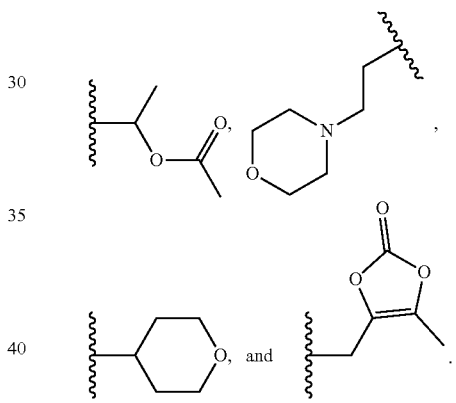

In some embodiments, $R^9$ is selected from H, —CH₂—O—C(O)C(CH)₃, —CH(CH₃)—O—C(O)—O—CH₃,

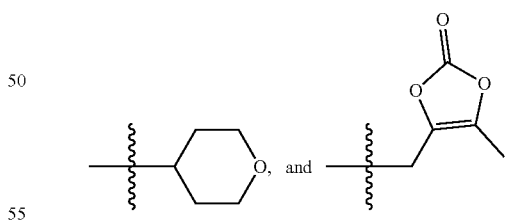

In some embodiments, $R^9$ is H.

In some embodiments, $R^9$ is methyl. In some embodiments, $R^9$ is ethyl. In some embodiments, $R^9$ is propyl.

In some embodiments, $R^9$ is H. In some embodiments, $R^9$ is selected from $C_{1-6}$alkyl, $C_{3-8}$cycloalkyl, and 4-6 membered heterocyclyl, wherein the $C_{1-6}$alkyl of $R^9$ is optionally substituted with one to three groups independently selected from halo, —NR$^{a1}$R$^{a2}$, —C(O)NR$^{a1}$R$^{a2}$, —O—C(O)—$C_{1-4}$alkyl, —O—C(O)—O—$C_{1-4}$alkyl, —O—C(O)—$C_{1-4}$alkylene-NR$^{a1}$R$^{a2}$, —O—$C_{1-4}$alkyl, $C_{3-8}$cycloalkyl, 4-6 membered heterocyclyl, and 4-6 membered heterocyclyl containing at least one heteroatom selected from N and O, and wherein the $C_{3-8}$cycloalkyl, and 4-6 membered heterocyclyl of $R^9$ is optionally substituted with one to three groups independently selected from halo, $C_{1-4}$alkyl, and $C_{1-4}$haloalkyl. In some embodiments, when administered to a patient, an $R^9$ ester generates a compound wherein $R^9$ is H, as a result of chemical reaction(s), enzyme catalyzed chemical reaction(s), and/or metabolic chemical reaction(s). In some embodiments, a compound in which $R^9$ is not H may be a prodrug.

In some embodiments, $R^9$ together with the N that attaches to $R^8$ forms a 5 membered heterocyclyl. In some embodiments, the 5 membered heterocyclyl is substituted with one to two groups independently selected from $C_{1-6}$alkyl, $C_{1-6}$alkoxyl, $C_{1-6}$haloalkyl, and $C_{6-10}$aryl. In some embodiments, the 5 membered heterocyclyl is substituted with one to two groups independently selected from $CH_3$, $CH_2CH_3$, —$OCH_3$, —$OCH_2CH_3$, and phenyl. In some embodiments, the 5 membered heterocyclyl is substituted with phenyl, and phenyl is optionally substituted with one to three groups independently selected from halo, $C_{1-6}$alkyl, $C_{1-6}$alkoxyl, and $C_{1-6}$haloalkyl.

In some embodiments, each $R^{10}$ is independently selected from H, halo, $C_{1-4}$alkyl, $C_{1-4}$haloalkyl, and $C_{1-4}$alkoxyl. In some embodiments, each $R^{10}$ is independently selected from H, F, Cl, —$CH_3$, —$CH_2F$, —$CHF_2$, —$CF_3$, —$OCH_3$, and —$OCF_3$. In some embodiments, each $R^{10}$ is H.

In some embodiments, each $R^{11}$ is independently selected from H, —$CH_3$, —$CH_2F$, —$CHF_2$, and —$CF_3$. In some embodiments, each $R^{11}$ is independently H or —$CH_3$.

In some embodiments, q is 1. In some embodiments, q is 2.

In some embodiments, r is selected from 1, 2, and 3. In some embodiments, r is 3.

In some embodiments, t is 0. In some embodiments, t is 1.

In some embodiments, u is selected from 1, 2, and 3. In some embodiments, u is 3.

In some embodiments, v is 2.

In some embodiments, each $V^1$, $V^2$ and $V^3$ is independently $CR^{22}$ or N, wherein $R^{22}$ is independently selected from H, halo, $C_{1-4}$alkyl, $C_{1-4}$haloalkyl, and $C_{1-4}$alkoxyl. In some embodiments, each $V^1$, $V^2$ and $V^3$ is independently $CR^{22}$ or N, wherein each $R^{22}$ is independently selected from H, F, Cl, —$CH_3$, —$CH_2F$, —$CHF_2$, —$CF_3$, —$OCH_3$, and —$OCF_3$. In some embodiments, $V^1$ is N, and each $V^2$ and $V^3$ is independently $CR^{22}$. In some embodiments, $V^1$ is N, and each $V^2$ and $V^3$ is independently $CR^{22}$, wherein each $R^{22}$ is independently selected from H, halo, $C_{1-4}$alkyl, $C_{1-4}$haloalkyl, and $C_{1-4}$alkoxyl. In some embodiments, $V^1$ is N, and each $V^2$ and $V^3$ is independently $CR^{22}$, wherein each $R^{22}$ is independently selected from H, F, Cl, —$CH_3$, —$CH_2F$, —$CHF_2$, —$CF_3$, —$OCH_3$, and —$OCF_3$.

In some embodiments, $W^1$ is N, and $W^2$ is O. In some embodiments, $W^1$ is N, and $W^2$ is $CH_2$. In some embodiments, $W^1$ is N, and $W^2$ is $S(O)_2$. In some embodiments, each $R^b$ is independently selected from F, OH, —$CH_3$, —$CH(CH_3)_2$, —$CH_2F$, —$CHF_2$, and —$CF_3$.

In some embodiments, at least one of $Y^1$, $Y^2$, $Y^3$, $Y^4$, and $Y^5$ is N. In some embodiments, $Y^1$ is N; and each $Y^2$, $Y^3$, $Y^4$, and $Y^5$ is independently $CR^{22}$. In some embodiments, $Y^2$ is N; and each $Y^1$, $Y^3$, $Y^4$, and $Y^5$ is independently $CR^{22}$. In some embodiments, $Y^3$ is N; and each $Y^1$, $Y^2$, $Y^4$, and $Y^5$ is independently $CR^{22}$. In some embodiments, $Y^4$ is N; and each $Y^1$, $Y^2$, $Y^3$, and $Y^5$ is independently $CR^{22}$. In some embodiments, $Y^1$ and $Y^5$ are N; and each $Y^1$, $Y^2$, and $Y^3$ is independently $CR^{22}$.

In some embodiments, the compound of the present disclosure is selected from examples 1-176.

In some embodiments, the compound of the present disclosure is selected from examples 177-180.

In some embodiments, provided is a compound of the present disclosure, or a pharmaceutically acceptable salt thereof.

One of skill in the art is aware that each and every embodiment of a group (e.g., $R^1$) disclosed herein may be combined with any other embodiment of each of the remaining groups (e.g., $R^4$, $R^9$, $X^3$, etc.) to generate a complete compound of formula (I), or any formula described herein or a pharmaceutically acceptable salt thereof, each of which is deemed within the ambit of the present disclosure.

LIST OF ABBREVIATIONS AND ACRONYMS

Abbreviation Meaning
% Percent
° C. Degree Celsius
Ac Acetyl
AcOH Acetic acid
ACN/$CH_3$CN/MeCN Acetonitrile
ADME Absorption, distribution, metabolism and excretion
AIBN 2,2'-Azobis(2-methylpropionitrile)
Aq. Aqueous
ASK Apoptosis signal-regulating kinase
Bicarb Bicarbonate
Bn Benzyl
BOC/Boc Tert-butyloxycarbonyl
Bpin Pinacolborane
br Broad
CAS Chemical Abstract Service
cataCXium A Di(1-adamantyl)-n-butylphosphine
CNS Central nervous system
COPD Chronic obstructive pulmonary disease
CREST Calcinosis, Raynaud's syndrome, esophageal dysmotility, sclerodactyly and telangiectasia
CVP Cyclophosphamide, vincristine, prednisone
d Doublet
D/d Deuterium
DAST Diethylaminosulfur trifluoride
DABCO® 1,4-Diazabicyclo[2.2.2]octane
DCC N,N'-Dicyclohexylcarbodiimide
DCE Dichloroethane
DCM Dichloromethane/methylene chloride
dd Doublet of doublets
DIEA N,N-Diisopropylethylamine
DIPEA N,N-Diisopropylethylamine
DMA N,N-Dimethylacetamide
DMAP 4-Dimethylaminopyridine
DME Dimethoxy ethane
DMF Dimethylformamide
DMPK Drug metabolism and pharmacokinetics
DMSO Dimethylsulfoxide
dppf 1,1'-Bis(diphenylphosphino)ferrocene
dppp 1,3-Bis(diphenylphosphino)propane
$EC_{50}$ The half maximal effective concentration
equiv/eq Equivalents
EA Ethyl acetate
Et Ethyl
$Et_2O$ Diethyl ether
EtOAc/AcOEt Ethyl acetate
EtOH Ethanol
F Fahrenheit
FBS Fetal bovine serum
g Grams Gp Glycoprotein
h/hr Hours
HATU (1-[Bis(dimethylamino)methylene]-1H-1,2,3-triazolo[4,5-b]pyridinium 3-oxid hexafluorophosphate)
hex Hexanes
HPLC High pressure liquid chromatography
Hz Hertz
IL Interleukin
IUPAC International Union of Pure and Applied Chemistry
J Coupling constant (MHz)
JAK Janus kinase
Kg/kg Kilogram
KOAc Potassium acetate
L Liter
LCMS/LC-MS Liquid chromatography-mass spectrometry
LHMDS Lithium hexamethyl disilazide
LiMg-TMP 2,2,6,6-Tetramethylpiperidinylmagnesium chloride lithium chloride complex
M Molar
m multiplet
M+ Mass peak
M+H Mass peak plus hydrogen
m-CPBA Meta-Chloroperbenzoic acid
Me Methyl
$Me_2N$ Dimethylamine
MeI Methyl Iodide
MeOH Methanol
MeOTs Methyl Tosylate
mg Milligram
MHz Megahertz
min/m Minute
ml/mL Milliliter
mM Millimolar
mmol Millimole
mol Mole
MS Mass spectroscopy
MS Multiple sclerosis
MsCl Methanesulfonyl chloride
MTBE Methyl tert-Butyl ether
M/Z Mass/Charge
N Normal
NADH Nicotinamide adenine dinucleotide in reduced form
NaOH Sodium hydroxide
NBS N-Bromosuccinimide
ng Nanograms
NIS N-Iodosuccinimide
nM Nanomolar
NMR Nuclear magnetic resonance
ON Overnight
PEG Polyethylene glycol
PET Positron emission tomography
Ph Phenyl
PhMe Toluene
$PhNO_2$ Nitrobenzene
$PhNTf_2$ N-Phenyl triflamide
pH Expressing the acidity or alkalinity of a solution
prep Preparative
RA Rheumatoid arthritis
Rf Retention factor
RPM Revolutions per minute
RT/r Room temperature
RuPhos 2-Dicyclohexylphosphino-2',6'-diisopropoxybiphenyl
s Second
s Singlet
sat. Saturated
SFC Super-critical fluid chromatography
SLE Systemic lupus erythematosus
SPECT Single-photon emission computed tomography
SPhos Pd G3 (2-Dicyclohexylphosphino-2',6'-dimethoxybiphenyl) [2-(2'-amino-1,1'-biphenyl)]palladium(II) methanesulfonate
SYK Spleen tyrosine kinase
t Triplet
TBACl Tetrabutylammonium chloride
TBS/TBDMS Tert-butyldimethylsilyl
tBuOH Tert-Butanol
tBuBrettPhos Pd G3 [(2-Di-tert-butylphosphino-3,6-dimethoxy-2',4',6'-triisopropyl-1,1'-biphenyl)-2-(2'-amino-1,1'-biphenyl)]palladium(II) methanesulfonate
TCA Trichloroacetic acid
TEA/$NEt_3$ Triethylamine
temp. Temperature
TES Triethylsilane
TFA Trifluoroacetic acid
TFAA Trifluoroacetic acid anhydride
THF Tetrahydrofuran
TLC Thin-layer chromatography
TMP Tetramethyl piperidine
TMS Trimethylsilyl
Tol Toluene
TPL2 Tumor Progression Locus 2 Kinase
Trityl Triphenylmethyl
Vac Vacuum
w/v Weight/volume
w/w Weight/weight
XPhos Pd G3 (2-Dicyclohexylphosphino-2',4',6'-triisopropyl-1,1'-biphenyl)[2-(2'-amino-1,1'-biphenyl)]palladium(II) methanesulfonate
δ Chemical shift (ppm)
μg Microgram
μL/μl Microliter
μM Micromolar
μm Micrometer
μmol Micromole Therapeutic Uses of the Compounds The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. Exemplary tissue samples include tumors and biopsies thereof. In this context, the compounds may be used for a variety of purposes, including therapeutic and experimental purposes. For example, the compounds may be used ex vivo to determine the optimal schedule and/or dosing of administration of an α4β7 integrin inhibitor for a given indication, cell type, individual, and other parameters. Information gleaned from such use may be used for experimental purposes or in the clinic to set protocols for in vivo treatment. Other ex vivo uses for which the compounds may be suited are described below or will become apparent to those skilled in the art. The selected compounds may be further characterized to examine the safety or tolerance dosage in human or non-human subjects. Such properties may be examined using commonly known methods to those skilled in the art.

In some embodiments, compounds described herein, for example, compounds of formula (I), formula (Ia), formula (Ib), formula (Ic), formula (Id), formula (Ie), formula (If), formula (Ig), formula (Ih), formula (Ii), formula (Ik), formula (Im), formula (II), formula (III), formula (IV), formula (V), formula (VI), formula (VII), formula (VIII), formula (IX), formula (X), formula (XI), formula (XII), formula (XIII), formula (XIV), formula (XV), or formula (XVI), or a pharmaceutically acceptable salt thereof, may be used to treat subjects who have or are suspected of having disease states, disorders, and conditions (also collectively referred to as "indications") responsive or believed to be responsive to the inhibition of $\alpha 4\beta 7$ integrin activity. In some embodiments, the compounds described herein may be used to inhibit the activity of $\alpha 4\beta 7$ integrin. In some embodiments, the compounds described herein may be used to inhibit excessive or destructive immune reactions or growth or a proliferation of a cell, such as a cancer cell, or inhibit immunosuppression.

Methods

In some embodiments, the present disclosure provides a compound described herein useful as an inhibitor of $\alpha 4\beta 7$ integrin. In some embodiments, the present disclosure provides a method of treating an inflammatory disease or condition mediated, at least in part, by $\alpha 4\beta 7$ integrin, comprising administering a compound described herein.

In some embodiments, the present disclosure provides a pharmaceutical composition comprising a compound described herein and a pharmaceutically acceptable carrier.

In some embodiments, the present disclosure provides a pharmaceutical composition comprising a compound described herein and at least one additional therapeutic agent and at least one pharmaceutically acceptable excipient.

The present disclosure provides a compound described herein for use in therapy.

In another embodiment, the present disclosure provides a compound described herein for use in the manufacture of a medicament for treating a disease or condition provided herein.

In some embodiments, provided is a compound described herein useful for the treatment of a disease or condition in a patient that is amenable to treatment by inhibiting $\alpha 4\beta 7$ integrin. Diseases or conditions that may be treated with the compounds described herein include a solid tumor, diabetes, an inflammatory disease, graft versus host disease, primary sclerosing cholangitis, HIV, an autoimmune disease, inflammatory bowel disease (IBD), alcoholic hepatitis, systemic lupus erythematosus (SLE), and lupus nephritis.

In some embodiments, provided is a compound described herein useful for the treatment of an inflammatory disease or condition in a patient that is mediated, at least in part, by $\alpha 4\beta 7$ integrin.

"Administering" or "administration" refers to the delivery of one or more therapeutic agents to a patient. In some embodiments, the administration is a monotherapy wherein a compound described herein is the only active ingredient administered to the patient in need of therapy. In another embodiment, the administration is co-administration such that two or more therapeutic agents are delivered together during the course of the treatment. In some embodiments, two or more therapeutic agents may be co-formulated into a single dosage form or "combined dosage unit", or formulated separately and subsequently combined into a combined dosage unit, as is typically for intravenous administration or oral administration as a mono or bilayer tablet or capsule.

In some embodiments, the compound described herein is administered to a human patient in need thereof in an effective amount, such as, from about 0.1 mg to about 1000 mg per dose of said compound. In some embodiments, the effective amount is from about 0.1 mg to about 200 mg per dose. In some embodiments, the effective amount is from about 1 mg to about 100 mg per dose. In other embodiments, the effective amount is about 1 mg, about 3 mg, about 5 mg, about 10 mg, about 15 mg, about 18 mg, about 20 mg, about 30 mg, about 40 mg, about 60 mg, about 80 mg, or about 100 mg per dose.

In some embodiments, the compound described herein and at least one additional therapeutic agent is administered to a human patient in need thereof in an effective amount of each agent, independently from about 0.1 mg to about 1000 mg per dose of a compound or formulation per dose per compound. In some embodiments, the effective amount of the combination treatment of a compound described herein and an additional compound is independently from about 0.1 mg to about 200 mg per compound per dose. In some embodiments, the effective amount of the combination treatment of a compound described herein and an additional compound is independently from about 1 mg to about 100 mg per compound per dose. In other embodiments, the effective amount of the combination treatment of a compound described herein and an additional compound is for each component, about 1 mg, about 3 mg, about 5 mg, about 10 mg, about 15 mg, about 18 mg, about 20 mg, about 30 mg, about 40 mg, about 60 mg, about 80 mg, about 100 mg, about 200 mg, or about 500 mg each per dose.

In some embodiments, the dose of a compound described herein and/or a combination of the dose of the compound described herein and/or the dose of an additional therapeutic agent is administered once per day, twice per day, or thrice per day. In yet another embodiment, the dose of a compound described herein and/or the dose of an additional therapeutic agent is administered as a loading dose of from about 0.1 mg to about 1000 mg per compound on the first day and each day or on alternate days or weekly for up to a month followed by a regular regimen of a compound described herein and/or one or more additional therapeutic agents or therapies. The maintenance dose may be about 0.1 mg to about 1000 mg once per day, twice per day, thrice per day, or weekly, for each component of a multi component drug regimen. A qualified care giver or treating physician is aware of what dose regimen is best for a particular patient or particular presenting conditions and will make appropriate treating regimen decisions for that patient. Thus, in another embodiment, the qualified caregiver is able to tailor a dose regimen of the compound described herein and/or an additional therapeutic agent(s) as disclosed herein to fit with the particular needs of the patient. Thus, it will be understood that the amount of the dose of a compound described herein and the amount of the dose of an additional therapeutic agent actually administered will usually be determined by a physician, in light of the relevant circumstances, including the condition(s) to be treated, the chosen route of administration, the actual compound (e.g., salt or free base) administered and its relative activity, the age, weight, and response of the individual patient, the severity of the patient's symptoms, and the like.

Co-administration may also include administering a dose of component drugs, e.g., a dose of one or more compounds described herein and a dose of one or more additional (e.g., a second, third, fourth or fifth) therapeutic agent(s). Such combination of a dose of one on more compounds described herein and a dose of one or more additional therapeutic agent(s) may be administered simultaneously or in sequence (one after the other) within a reasonable period of time of each administration (e.g., about 1 minute to 24 hours) depending on the pharmacokinetic and/or pharmacodynamics properties of each agent or the combination. Co-administration may also involve treatment with a fixed combination wherein agents of the treatment regimen are combinable in a fixed dosage or combined dosage medium, e.g., solid, liquid or aerosol. In some embodiments, a kit may be used to prepare and/or administer the drug or drug components.

Thus, some embodiments of the present disclosure is a method of treating a disease or condition mediated, at least in part, by α4β7 integrin, comprising administering therapeutically effective amounts of formulations of one on more compounds described herein and one or more additional therapeutic agents, including for example, via a kit to a patient in need thereof. It will be understood that a qualified care giver will administer or direct the administration of a therapeutically effective amount of any of the compound(s) or combinations of compounds of the present disclosure.

"Intravenous administration" is the administration of substances directly into a vein, or "intravenously." Compared with other routes of administration, the intravenous (IV) route is a faster way to deliver fluids and medications throughout the body. An infusion pump can allow precise control over the flow rate and total amount of medication delivered. However, in cases where a change in the flow rate would not have serious consequences, or if pumps are not available, the drip is often left to flow simply by placing the bag above the level of the patient and using the clamp to regulate the rate. Alternatively, a rapid infuser can be used if the patient requires a high flow rate and the IV access device is of a large enough diameter to accommodate it. This is either an inflatable cuff placed around the fluid bag to force the fluid into the patient or a similar electrical device that may also heat the fluid being infused. When a patient requires medications only at certain times, intermittent infusion is used which does not require additional fluid. It can use the same techniques as an intravenous drip (pump or gravity drip), but after the complete dose of medication has been given, the tubing is disconnected from the IV access device. Some medications are also given by IV push or bolus, meaning that a syringe is connected to the IV access device and the medication is injected directly (slowly, if it might irritate the vein or cause a too-rapid effect). Once a medicine has been injected into the fluid stream of the IV tubing there must be some means of ensuring that it gets from the tubing to the patient. Usually this is accomplished by allowing the fluid stream to flow normally and thereby carry the medicine into the bloodstream; however, a second fluid injection is sometimes used, as a "flush", following the injection to push the medicine into the bloodstream more quickly. Thus in some embodiments, compound(s) or combination of compounds described herein may be administered by IV administration alone or in combination with administration of certain components of the treatment regimen by oral or parenteral routes.

"Oral administration" is a route of administration where a substance is taken through the mouth, and includes buccal, sub labial, and sublingual administration, as well as enteral administration and that through the respiratory tract, unless made through, e.g., tubing so the medication is not in direct contact with any of the oral mucosa. Typical form for the oral administration of therapeutic agents includes the use of tablets or capsules. Thus in some embodiments, compound(s) or combination of compounds described herein may be administered by oral route alone or in combination with administration of certain components of the treatment regimen by IV or parenteral routes.

The compounds disclosed herein are useful for the treatment of diseases or conditions mediated, at least in part, by α4β7 integrin. Non-limiting examples of diseases or conditions mediated, at least in part, by α4β7 integrin include, without limitation, acne, acid-induced lung injury, Addison's disease, adrenal hyperplasia, adrenocortical insufficiency, adult-onset Still's disease, adult respiratory distress syndrome (ARDS), age-related macular degeneration, aging, alcoholic hepatitis, alcoholic liver disease, allergen-induced asthma, allergic bronchopulmonary, allergic conjunctivitis, allergic contact dermatitis, allergies, allergic encephalomyelitis, allergic neuritis, allograft rejection, alopecia, alopecia areata, Alzheimer's disease, amyloidosis, amyotrophic lateral sclerosis, angina pectoris, angioedema, angiofibroma, anhidrotic ectodermal dysplasia-ill, anti-glomerular basement membrane disease, antigen-antibody complex mediated diseases, ankylosing spondylitis, antiphospholipid syndrome, aphthous stomatitis, appendicitis, arthritis, ascites, aspergillosis, asthma, atherosclerosis, atherosclerotic plaques, atopic dermatitis, atrophic thyroiditis, autoimmune diseases, autoimmune hemolytic anemia (immune pancytopenia, paroxysmal nocturnal hemoglobinuria), autoimmune polyendocrinopathies, autoimmune thrombocytopenia (idiopathic thrombocytopenic purpura, immune-mediated thrombocytopenia), autoimmune hepatitis, autoimmune thyroid disorders, autoinflammatory diseases, back pain, *Bacillus anthracis* infection, Bechet's disease, bee sting-induced inflammation, Behget's syndrome, Bell's palsy, berylliosis, Blau syndrome, bone pain, bronchiolitis, bullous pemphigoid (BP) asthma, burns, bursitis, cardiac hypertrophy, carpal tunnel syndrome, Castleman's disease, catabolic disorders, cataracts, Celiac disease, cerebral aneurysm, chemical irritant-induced inflammation, chorioretinitis, chronic atypical neutrophilic dermatosis with lipodystrophy and elevated temperature (CANDLE) syndrome, chronic heart failure, chronic lung disease of prematurity, chronic obstructive pulmonary disease (COPD), chronic pancreatitis, chronic prostatitis, chronic recurrent multifocal osteomyelitis, cicatricial alopecia, colitis, complex regional pain syndrome, complications of organ transplantation, conjunctivitis, connective tissue disease, contact dermatitis, corneal graft neovascularization, corneal ulcer, Crohn's disease, cryopyrin-associated periodic syndromes, cutaneous lupus erythematosus (CLE), cryptococcosis, cystic fibrosis, deficiency of the interleukin-1 receptor antagonist (DIRA), dermatitis, dermatitis endotoxemia, dermatomyositis, diabetic macular edema, diverticulitis, eczema, encephalitis, endometriosis, endotoxemia, eosinophilic pneumonias, epicondylitis, epidermolysis bullosa, erythema multiforme, erythroblastopenia, esophagitis, familial amyloidotic polyneuropathy, familial cold urticarial, familial Mediterranean fever, fetal growth retardation, fibromyalgia, fistulizing Crohn's disease, food allergies, giant cell arteritis, glaucoma, glioblastoma, glomerular disease, glomerular nephritis, glomerulonephritis, gluten-sensitive enteropathy, gout, gouty arthritis, graft-versus-host disease (GVHD), granulomatous hepatitis, Graves' disease, growth plate injuries, Guillain-Barre syndrome, gut diseases, hair loss, Hashimoto's thyroiditis, head injury, headache, hearing loss, heart disease, hemangioma, hemolytic anemia, hemophilic joints, Henoch-Scholein purpura, hepatitis, hereditary periodic fever syndrome, heritable disorders of connective tissue, herpes zoster and simplex, hidradenitis suppurativa (HS), hip replacement, Hodgkin's disease, Huntington's disease, hyaline membrane disease, hyperactive inflammatory response, hyperammonemia, hypercalcemia, hypercholesterolemia, hypereosinophilic syndrome (HES), hyperimmunoglobulinemia D with recurrent fever (HIDS), hypersensitivity pneumonitis, hypertropic bone formation, hypoplastic and other anemias, hypoplastic anemia, ichthyosis, idiopathic demyelinating polyneuropathy, Idiopathic inflammatory myopathies (dermatomyositis, polymyositis), idiopathic pulmonary fibrosis, idiopathic thrombocytopenic purpura, immunoglobulin nephropathies, immune complex nephritis, immune thrombocytopenic purpura (ITP), incontinentia pigmenti (IP, Bloch-Siemens syndrome), infectious mononucleosis, infectious diseases including viral diseases such as AIDS (HIV infection), hepatitis A, B, C, D, and E, herpes; inflammation, inflammation of the CNS, inflammatory bowel disease (IBD), inflammatory disease of the lower respiratory tract including bronchitis or chronic obstructive pulmonary diseases, inflammatory disease of the upper respiratory tract including the nose and sinuses such as rhinitis or sinusitis, inflammatory diseases of the respiratory tract, inflammatory ischemic event such as stroke or cardiac arrest, inflammatory lung disease, inflammatory myopathy such as myocarditis, inflammatory liver disease, inflammatory neuropathy, inflammatory pain, insect bite-induced inflammation, interstitial cystitis, interstitial lung disease, iritis, irritant-induced inflammation, ischemia/reperfusion, joint replacement, juvenile arthritis, juvenile rheumatoid arthritis, keratitis, kidney injury caused by parasitic infections, kidney transplant rejection, leptospirosis, leukocyte adhesion deficiency, lichen sclerosus (LS), Lambert-Eaton myasthenic syndrome, Loeffler's syndrome, lupus, lupus nephritis, Lyme disease, Marfan syndrome (MFS), mast cell activation syndrome, mastocytosis, meningitis, meningioma, mesothelioma, mixed connective tissue disease, Muckle-Wells syndrome (urticaria deafness amyloidosis), mucositis, multiple organ injury syndrome, multiple sclerosis, muscle wasting, muscular dystrophy, myasthenia gravis (MG), myelodysplastic syndrome, myocarditis, myositis, nasal sinusitis, necrotizing enterocolitis, neonatal onset multisystem inflammatory disease (NOMID), neovascular glaucoma, nephrotic syndrome, neuritis, neuropathological diseases, non-allergen induced asthma, obesity, ocular allergy, optic neuritis, organ transplant rejection, Osier-Weber syndrome, osteoarthritis, osteogenesis imperfecta, osteonecrosis, osteoporosis, osterarthritis, otitis, pachyonychia congenita, Paget's disease, Paget's disease of bone, pancreatitis, Parkinson's disease, pediatric rheumatology, pelvic inflammatory disease, pemphigus, pemphigus vulgaris (PV), bullous pemphigoid (BP), pericarditis, periodic fever, periodontitis, peritoneal endometriosis, pernicious anemia (Addison's disease), pertussis, PFAPA (periodic fever aphthous pharyngitis and cervical adenopathy), pharyngitis and adenitis (PFAPA syndrome), plant irritant-induced inflammation, pneumocystis infection, pneumonia, pneumonitis, poison ivy/urushiol oil-induced inflammation, polyarthritis nodosa, polychondritis, polycystic kidney disease, polymyalgia rheumatic, giant cell arteritis, polymyositis, pouchitis, reperfusion injury and transplant rejection, primary biliary cirrhosis, primary pulmonary hypertension, primary sclerosing cholangitis (PSC), proctitis, psoriasis, psoriasis vulgaris, psoriatic arthritis, psoriatic epidermis, psychosocial stress diseases, pulmonary disease, pulmonary fibrosis, pulmonary hypertension, pyoderma gangrenosum, pyogenic granuloma retrolental fibroplasias, pyogenic sterile arthritis, Raynaud's syndrome, Reiter's disease, reactive arthritis, renal disease, renal graft rejection, reperfusion injury, respiratory distress syndrome, retinal disease, retrolental fibroplasia, Reynaud's syndrome, rheumatic carditis, rheumatic diseases, rheumatic fever, rheumatoid arthritis, rhinitis, rhinitis psoriasis, rosacea, sarcoidosis, Schnitzler syndrome, scleritis, sclerosis, scleroderma, scoliosis, seborrhea, sepsis, septic shock, severe pain, Sézary syndrome, sickle cell anemia, silica-induced disease (Silicosis), Sjogren's syndrome, skin diseases, skin irritation, skin rash, skin sensitization (contact dermatitis or allergic contact dermatitis), sleep apnea, spinal cord injury, spinal stenosis, spondyloarthropathies, sports injuries, sprains and strains, Stevens-Johnson syndrome (SJS), stroke, subarachnoid hemorrhage, sunburn, synovial inflammation, systemic inflammatory response syndrome (SIRS), systemic lupus erythematosus, systemic mast cell disease (SMCD), systemic vasculitis, systemic-onset juvenile idiopathic arthritis, temporal arteritis, tendinitis, tenosynovitis, thrombocytopenia, thyroditis, thyroiditis, tissue transplant, toxoplasmosis, trachoma, transplantation rejection, traumatic brain injury, tuberculosis, tubulointerstitial nephritis, tumor necrosis factor (TNF) receptor associated periodic syndrome (TRAPS), type 1 diabetes, type 2 diabetes, complications from type 1 or type 2 diabetes, ulcerative colitis, urticaria, uterine fibroids, uveitis, uveoretinitis, vascular restenosis, vasculitis, vasculitis (NHLBI), vitiligo, Wegener's granulomatosis, and Whipple's disease.

In further embodiments, the methods are provided for alleviating a symptom of a disease or disorder mediated, at least in part, by α4β7 integrin. In some embodiments, the methods include identifying a mammal having a symptom of a disease or disorder mediated, at least in part, by α4β7 integrin, and providing to the mammal an amount of a compound as described herein effective to ameliorate (i.e., lessen the severity of) the symptom.

In some embodiments, the disease or condition mediated, at least in part, by α4β7 integrin is an inflammatory disease or LPS induced endotoxin shock. In some embodiments, the disease is an autoimmune disease. In particular embodiments, the autoimmune disease is systemic lupus erythematosus (SLE), myestenia gravis, rheumatoid arthritis (RA), acute disseminated encephalomyelitis, idiopathic thrombocytopenic purpura, multiple sclerosis (MS), inflammatory bowel disease (IBD), sepsis, psoriasis, Sjoegren's syndrome, autoimmune hemolytic anemia, asthma, or chronic obstructive pulmonary disease (COPD), ankylosing spondylitis, acute gout and ankylosing spondylitis, reactive arthritis, monoarticular arthritis, osteoarthritis, gouty arthritis, juvenile arthritis, juvenile onset rheumatoid arthritis, juvenile rheumatoid arthritis or psoriatic arthritis. In other embodiments, the disease is inflammation. In yet other embodiments, the disease is excessive or destructive immune reactions, such as asthma, rheumatoid arthritis, multiple sclerosis, chronic obstructive pulmonary disease (COPD), and lupus.

In some embodiments, the disease or condition mediated, at least in part, by α4β7 integrin is inflammatory bowel disease (IBD). The term "inflammatory bowel disease" or "IBD" as used herein is a collective term describing inflammatory disorders of the gastrointestinal tract, the most common forms of which are ulcerative colitis and Crohn's disease. Other forms of IBD that can be treated with the presently disclosed compounds, compositions and methods include diversion colitis, ischemic colitis, infectious colitis, chemical colitis, microscopic colitis (including collagenous colitis and lymphocytic colitis), atypical colitis, pseudomembranous colitis, fulminant colitis, autistic enterocolitis, indeterminate colitis, Behget's disease, gastroduodenal CD, jejunoileitis, ileitis, ileocolitis, Crohn's (granulomatous) colitis, irritable bowel syndrome, mucositis, radiation induced enteritis, short bowel syndrome, celiac disease, stomach ulcers, diverticulitis, pouchitis, proctitis, and chronic diarrhea.

Treating or preventing IBD also includes ameliorating or reducing one or more symptoms of IBD. As used herein, the term "symptoms of IBD" refers to detected symptoms such as abdominal pain, diarrhea, rectal bleeding, weight loss, fever, loss of appetite, and other more serious complications, such as dehydration, anemia and malnutrition. A number of such symptoms are subject to quantitative analysis (e.g., weight loss, fever, anemia, etc.). Some symptoms are readily determined from a blood test (e.g., anemia) or a test that detects the presence of blood (e.g., rectal bleeding). The term "wherein said symptoms are reduced" refers to a qualitative or quantitative reduction in detectable symptoms, including but not limited to a detectable impact on the rate of recovery from disease (e.g., rate of weight gain). The diagnosis is typically determined by way of an endoscopic observation of the mucosa, and pathologic examination of endoscopic biopsy specimens.

The course of IBD varies, and is often associated with intermittent periods of disease remission and disease exacerbation. Various methods have been described for characterizing disease activity and severity of IBD as well as response to treatment in subjects having IBD. Treatment according to the present methods is generally applicable to a subject having IBD of any level or degree of disease activity.

In some embodiments, the disease or condition treated by the administration of a compound of composition described herein includes acute gout and ankylosing spondylitis, allergic disorders, Alzheimer's disease, Amyotrophic lateral sclerosis (ALS), Amyotrophic lateral sclerosis and multiple sclerosis, atherosclerosis, bacterial infections, bone cancer pain and pain due to endometriosis, BRAF resistant melanoma, brain stem glioma or pituitary adenomas, burns, bursitis, cancer of the anal region, cancer of the endocrine system, cancer of the kidney or ureter (e.g., renal cell carcinoma, and carcinoma of the renal pelvis), cancer of the penis, cancer of the small intestine, cancer of the thyroid, cancer of the urethra, cancers of the blood such as acute myeloid leukemia, cancers of the tongue, carcinoma of the cervix, carcinoma of the endometrium, carcinoma of the fallopian tubes, carcinoma of the renal pelvis, carcinoma of the vagina or carcinoma of the vulva, chronic myeloid leukemia, chronic or acute leukemia, chronic pain, classic Bartter syndrome, common cold conjunctivitis, coronary heart disease, cutaneous or intraocular melanoma, dermatitis, dysmenorrhea, eczema, endometriosis, familial adenomatous polyposis, fibromyalgia, fungal infections, gout, gynecologic tumors, uterine sarcomas, carcinoma of the fallopian tubes, headache, hemophilic arthropathy, Parkinson's disease, AIDS, herpes zoster, Hodgkin's disease, Huntington's, hyperprostaglandin E syndrome, influenza, iritis, juvenile arthritis, juvenile onset rheumatoid arthritis, juvenile rheumatoid arthritis, low back and neck pain, lymphocytic lymphomas, myofascial disorders, myositis, neuralgia, neurodegenerative disorders such as Alzheimer's disease, neuroinflammatory disorders, neuropathic pain, carcinoma of the vulva, Parkinson's disease, pediatric malignancy, pulmonary fibrosis rectal cancer, rhinitis, sarcoidosis, sarcomas of soft tissues, scleritis, skin cancer, solid tumors of childhood, spinal axis tumors, sprains and strains, stomach cancer, stroke, subacute and chronic musculoskeletal pain syndromes such as bursitis, surgical or dental procedures, symptoms associated with influenza or other viral infections, synovitis, toothache, ulcers, uterine cancer, uterine sarcomas, uveitis, vasculitis, viral infections, viral infections (e.g., influenza) and wound healing.

Criteria useful for assessment of disease activity in subjects with ulcerative colitis can be found in, e.g., Truelove et al. (1955) Br Med J 2:1041-1048.) Using these criteria, disease activity can be characterized in a subject having IBD as mild disease activity or severe disease activity. Subjects who do not meet all the criteria for severe disease activity, and who exceed the criteria for mild disease activity are classified as having moderate disease activity.

The presently disclosed treatment methods can also be applied at any point in the course of the disease. In some embodiments, the methods are applied to a subject having IBD during a time period of remission (i.e., inactive disease). In such embodiments, the present methods provide benefit by extending the time period of remission (e.g., extending the period of inactive disease) or by preventing, reducing, or delaying the onset of active disease. In other embodiments, methods may be applied to a subject having IBD during a period of active disease. Such methods provide benefit by reducing the duration of the period of active disease, reducing or ameliorating one or more symptoms of IBD, or treating IBD.

Measures for determining efficacy of treatment of IBD in clinical practice have been described and include, for example, the following: symptom control; fistula closure; extent of corticosteroid therapy required; and, improvement in quality of life. Heath-related quality of life (HRQL) can be assessed using the Inflammatory Bowel Disease Questionnaire (IBDQ), which is extensively used in clinical practice to assess quality of life in a subject with IBD. (See Guyatt et al. (1989) Gastroenterology 96:804-810.) In some embodiments, the disease or condition is immune-mediated liver injury, disease or condition.

In some embodiments, the disease or condition mediated, at least in part, by $\alpha 4\beta 7$ integrin is alcoholic hepatitis. Alcoholic hepatitis is a clinical syndrome characterized by jaundice and liver failure that develops in subjects with chronic and active alcohol abuse. (See Akriviadis E. et. al, Ann Gastroenterol. 2016 April-June; 29(2): 236-237). Alcoholic hepatitis can cause cirrhosis and fibrosis of the liver cells. Glucocorticoids, (e.g., prednisolone) and phosphodiesterase inhibitors (e.g., pentoxifylline) can be used to treat alcoholic hepatitis. The compounds herein can be used as stand-alone treatments or in combination with the current treatments for alcoholic hepatitis.

In one aspect, the present disclosure provides methods of treating or preventing a human immunodeficiency virus (HIV) infection in a subject in need thereof, comprising administering to the subject a therapeutically effective amount of a compound provided herein, or a pharmaceutically acceptable salt thereof, or a pharmaceutical composition provided herein.

In some embodiments, the disease or condition mediated, at least in part, by $\alpha 4\beta 7$ integrin is systemic lupus erythematosus (SLE), lupus nephritis, lupus-related, or other autoimmune disorders or a symptom of SLE. Symptoms of systemic lupus erythematosus include joint pain, joint swelling, arthritis, fatigue, hair loss, mouth sores, swollen lymph nodes, sensitivity to sunlight, skin rash, headaches, numbness, tingling, seizures, vision problems, personality changes, abdominal pain, nausea, vomiting, abnormal heart rhythms, coughing up blood and difficulty breathing, patchy skin color and Raynaud's phenomenon.

Combination Therapy

Also provided are methods of treatment in which a compound described herein is given to a patient in combination with one or more additional active agents or therapy.

Thus in some embodiments, a method of treating diseases or conditions mediated, at least in part, by α4β7 integrin and/or diseases or symptoms that co-present or are exacerbated or triggered by the diseases or conditions mediated, at least in part, by α4β7 integrin, e.g., an allergic disorder and/or an autoimmune and/or inflammatory disease, and/or an acute inflammatory reaction, comprises administering to a patient in need thereof an effective amount of a compound described herein optionally in combination with an additional agent (e.g., a second, third, fourth or fifth active agent) which can be useful for treating diseases or conditions mediated, at least in part, by α4β7, an allergic disorder and/or an autoimmune and/or inflammatory disease, and/or an acute inflammatory reaction incident to or co-presenting with diseases or conditions mediated, at least in part, by α4β7 integrin. Treatment with the second, third, fourth or fifth active agent may be prior to, concomitant with, or following treatment with a compound described herein. In some embodiments, a compound described herein is combined with another active agent in a single dosage form. Suitable therapeutics that may be used in combination with a compound described herein include, but are not limited to, therapeutic agents provided herein, or a combination comprising at least one therapeutic agent provided herein.

Included herein are methods of treatment in which a compound described herein is administered in combination with an agent for treatment of an inflammatory disease or condition. Examples of agents for treatment of an inflammatory disease or condition that can be used in combination with compounds described herein, include alpha-fetoprotein modulators; adenosine A3 receptor antagonist; adrenomedullin ligands; AKT1 gene inhibitors; antibiotics; antifungals; ASK1 inhibitors; ATPase inhibitors; beta adrenoceptor antagonists; BTK inhibitors; calcineurin inhibitors; carbohydrate metabolism modulators; cathepsin S inhibitors; CCR9 chemokine antagonists; CD233 modulators; CD29 modulators; CD3 antagonists; CD40 ligand inhibitors; CD40 ligand receptor antagonists; chemokine CXC ligand inhibitors; CHST15 gene inhibitors; collagen modulators; CSF-1 antagonists; CX3CR1 chemokine modulators; ecobiotics; eotaxin ligand inhibitors; EP4 prostanoid receptor agonists; F1F0 ATP synthase modulators; farnesoid X receptor (FXR and NR1H4) agonists or modulators; fecal microbiota transplantation (FMT); fractalkine ligand inhibitors; free fatty acid receptor 2 antagonists; GATA 3 transcription factor inhibitors; glucagon-like peptide 2 agonists; glucocorticoid agonists; Glucocorticoid receptor modulators; guanylate cyclase receptor agonists; HIF prolyl hydroxylase inhibitors; histone deacetylase inhibitors; HLA class II antigen modulators; hypoxia inducible factor-1 stimulator; ICAM1 gene inhibitors; IL-1 beta ligand modulators; IL-12 antagonists; IL-13 antagonists; IL-18 antagonists; IL-22 agonists; IL-23 antagonists; IL-23A inhibitors; IL-6 antagonists; IL-7 receptor antagonists; IL-8 receptor antagonists; integrin alpha-4/beta-1 antagonists; integrin alpha-4/beta-7 antagonists; integrin antagonists; interleukin ligand inhibitors; interleukin receptor 17A antagonists; interleukin-1 beta ligands; interleukin 1 like receptor 2 inhibitors; IL-6 receptor modulators; JAK tyrosine kinase inhibitors; Jak1 tyrosine kinase inhibitors; Jak3 tyrosine kinase inhibitors; lactoferrin stimulators; LanC like protein 2 modulators; leukocyte elastate inhibitors; leukocyte proteinase-3 inhibitors; MAdCAM inhibitors; melanin concentrating hormone (MCH-1) antagonist; melanocortin agonists; metalloprotease-9 inhibitors; microbiome-targeting therapeutics; natriuretic peptide receptor C agonists; neuregulin-4 ligands; NLPR3 inhibitors; NKG2 D activating NK receptor antagonists; nuclear factor kappa B inhibitors; opioid receptor antagonists; OX40 ligand inhibitors; oxidoreductase inhibitors; P2X7 purinoceptor modulators; PDE 4 inhibitors; Pellino homolog 1 inhibitors; PPAR alpha/delta agonists; PPAR gamma agonists; protein fimH inhibitors; P-selectin glycoprotein ligand-1 inhibitors; Ret tyrosine kinase receptor inhibitors; RIP-1 kinase inhibitors; RIP-2 kinase inhibitors; RNA polymerase inhibitors; sphingosine 1 phosphate phosphatase 1 stimulators; sphingosine-1-phosphate receptor-1 agonists; sphingosine-1-phosphate receptor-5 agonists; sphingosine-1-phosphate receptor-1 antagonists; sphingosine-1-phosphate receptor-1 modulators; stem cell antigen-1 inhibitors; superoxide dismutase modulators; SYK inhibitors; tissue transglutaminase inhibitor; TLR-3 antagonists; TLR-4 antagonists; Toll-like receptor 8 (TLR8) inhibitors; TLR-9 agonists; TNF alpha ligand inhibitors; TNF ligand inhibitors; TNF alpha ligand modulators; TNF antagonists; TPL-2 inhibitors; tumor necrosis factor 14 ligand modulators; tumor necrosis factor 15 ligand inhibitors; Tyk2 tyrosine kinase inhibitors; type I IL-1 receptor antagonists; vanilloid VR1 agonists; and zonulin inhibitors, and combinations thereof.

Adenosine A3 receptor antagonists include PBF-677.

Adrenomedullin ligands include adrenomedullin.

Antibiotics include ciprofloxacin, clarithromycin, metronidazole, vancomycin, rifamycin, rifaximin, and tosufloxacin.

ASK1 inhibitors include GS-4997.

Alpha-fetoprotein modulators include ACT-101.

Anti-CD28 inhibitors include JNJ-3133 and abatacept.

Beta adrenoceptor antagonists include NM-001.

BTK inhibitors include GS-4059.

Calcineurin inhibitors: include tacrolimus, and ciclosporin.

Carbohydrate metabolism modulators include ASD-003.

Cathepsin S inhibitors include VBY-129.

CCR9 chemokine antagonists include CCX-507.

CD233 modulators include GSK-2831781.

CD29 modulators include PF-06687234.

CD3 antagonists include NI-0401.

CD4 antagonists include IT-1208.

CD40 ligand inhibitors include SAR-441344, and letolizumab.

CD40 gene inhibitors include NJA-730.

CD40 ligand receptor antagonists include FFP-104, BI-655064.

Chaperonin binding immunoglobulin protein includes IRL-201805.

Chemokine CXC ligand inhibitors include LY-3041658.

CHST15 gene inhibitors include STNM-01.

Collagen modulators include ECCS-50 (DCCT-10).

COT protein kinase inhibitors include GS-4875.

CSF-1 antagonists include JNJ-40346527 (PRV-6527), and SNDX-6352.

CX3CR1 chemokine modulators include E-6130.

Ecobiotics include SER-287.

Eotaxin ligand inhibitors include bertilimumab.

EP4 prostanoid receptor agonists include KAG-308.

F1F0 ATP synthase modulators include LYC-30937 EC.

Fractalkine ligand inhibitors include quetmolimab (E-6011).

Free fatty acid receptor 2 antagonists include GLPG-0974.

GATA 3 transcription factor inhibitors include SB-012.

Glucagon-like peptide 2 agonists include teduglutide, and apraglutide.

Glucocorticoid receptor agonists include budesonide, beclomethasone dipropionate, and dexamethasone sodium phosphate.

Glucocorticoid receptor modulators/TNF ligand inhibitors include ABBV-3373.

Guanylate cyclase receptor agonists include dolcanatide.

HIF prolyl hydroxylase inhibitors include DS-1093, and AKB-4924.

HIF prolyl hydroxylase-2 inhibitors/hypoxia inducible factor-1 stimulators include GB-004.

Histone deacetylase inhibitors include givinostat.

Histone deacetylase-6 inhibitors include CKD-506.

HLA class II antigen modulators include HLA class II protein modulators.

ICAM1 gene inhibitors include alicaforsen.

IL-12 antagonists include ustekinumab (IL12/IL23).

IL-13 antagonists include tralokinumab.

IL-18 antagonists include GSK-1070806.

IL-22 agonists include RG-7880.

IL-23 antagonists include tildrakizumab, risankizumab (BI-655066), mirikizumab (LY-3074828), brazikumab (AMG-139), and PTG-200.

IL-23A inhibitors include guselkumab.

IL-6 antagonists include olokizumab.

IL-7 receptor antagonists include OSE-127.

IL-8 receptor antagonists include clotrimazole.

Integrin alpha-4/beta-1 antagonists include natalizumab.

Integrin alpha-4/beta-7 antagonists include etrolizumab (a4b7/aEb7), vedolizumab, carotegast methyl, TRK-170 (a4b7/a4b1), PN-10943, and PTG-100.

Integrin antagonists include E-6007.

Interleukin ligand inhibitors include bimekizumab (IL-17A/IL-17F).

Interleukin receptor 17A antagonists include brodalumab.

Interleukin-1 beta ligands include K(D)PT.

Interleukin 1 like receptor 2 inhibitors include BI-655130.

IL-6 receptor modulators include olamkicept.

JAK tyrosine kinase inhibitors include tofacitinib (⅓), peficitinib (⅓), TD-3504, an TD-1473. Jak1 tyrosine kinase inhibitors include a compound disclosed in WO2008/109943. Examples of other JAK inhibitors include, but are not limited to, AT9283, AZD1480, baricitinib, BMS-911543, fedratinib, filgotinib (GLPG0634), gandotinib (LY2784544), INCB039110, lestaurtinib, momelotinib (CYT0387), NS-018, pacritinib (SB1518), peficitinib (ASP015K), ruxolitinib, tofacitinib (formerly tasocitinib), XL019, upadacitinib (ABT-494), filgotinib, GLPG-0555, SHR-0302, and brepocitinib (PF-06700841) (JAK1/Tyk2).

Jak3 tyrosine kinase inhibitors include PF-06651600.

Lactoferrin stimulators include recombinant human lactoferrin (VEN-100).

LanC like protein 2 modulators include BT-11.

Leukocyte elastase inhibitors/Leukocyte proteinase-3 inhibitors include tiprelestat.

MAdCAM inhibitors include SHP-647 (PF-547659).

Melanin concentrating hormone (MCH-1) antagonists include CSTI-100.

Melanocortin MC1 receptor agonists include ASP-3291, and PL-8177.

Metalloprotease-9 inhibitors include GS-5745.

Microbiome modulator include ABI-M201.

Natriuretic peptide receptor C agonists include plecanatide.

Neuregulin-4 ligands include NRG-4.

NKG2 D activating NK receptor antagonists include JNJ-4500.

NLPR3 inhibitors include dapansutrile, BMS-986299, SB-414, MCC-950, IFM-514, JT-194, PELA-167, and NBC-6.

Farnesoid X receptor (FXR and NR1H4) agonists or modulators include AGN-242266, cilofexor tromethamine (GS-9674), EDP-305, EYP-001, GNF-5120, MET-409, nidufexor (LMB-763), obeticholic acid, TERN-101, and tropifexor.

Nuclear factor kappa B inhibitors include Thetanix.

Opioid receptor antagonists include naltrexone, and IRT-103.

OX40 ligand inhibitors include KHK-4083.

Oxidoreductase inhibitors include olsalazine.

Pellino homolog 1 inhibitors include BBT-401.

P2X7 purinoceptor modulators include SGM-1019.

PDE 4 inhibitors include apremilast.

PPAR alpha/delta agonists include elafibranor (GFT-1007).

PPAR gamma agonists include GED-0507-34-Levo.

Protein fimH inhibitors include sibofimloc (EB-8018).

P-selectin glycoprotein ligand-1 inhibitors include SEL-K2, AbGn-168H, and neihulizumab.

Ret tyrosine kinase receptor inhibitors include GSK-3179106.

RIP-1 kinase inhibitors include GSK-2982772.

RIP-2 kinase inhibitors include GSK-2983559.

Sphingosine 1 phosphate phosphatase 1 stimulators include etrasimod.

Sphingosine-1-phosphate receptor-1 agonists include ozanimod, mocravimod (KRP-203), and BMS-986166.

Sphingosine-1-phosphate receptor-1 agonists/Sphingosine-1-phosphate receptor-5 agonists include ozanimod.

Sphingosine-1-phosphate receptor-1 antagonists include amiselimod (MT-1303).

Sphingosine-1-phosphate receptor-1 modulators include OPL-002.

Stem cell antigen-1 inhibitors include Ampion (DMI-9523).

Superoxide dismutase modulators include midismase.

Syk inhibitors include GS-9876.

Tissue transglutaminase inhibitor includes zampilimab.

TLR-3 antagonists include PRV-300.

TLR-4 antagonists include JKB-122.

Toll-like receptor 8 (TLR8) inhibitors include E-6887, IMO-4200, IMO-8400, IMO-9200, MCT-465, MEDI-9197, motolimod, resiquimod, VTX-1463, and VTX-763.

TLR-9 agonists include cobitolimod, IMO-2055, IMO-2125, lefitolimod, litenimod, MGN-1601, and PUL-042.

TNF alpha ligand inhibitors include adalimumab, certolizumab pegol, infliximab, golimumab, DLX-105, Debio-0512, HMPL-004, CYT-020-TNFQb, Hemay-007, and V-565.

TNF antagonists include AVX-470, tulinercept, and etanercept.

TPL-2 inhibitors include GS-4875.

Tumor necrosis factor 14 ligand modulators include AEVI-002.

Tumor necrosis factor 15 ligand inhibitors include PF-06480605.

Tyk2 tyrosine kinase inhibitors include PF-06826647, and BMS-986165.

TrkA receptor antagonist includes SNA-125.

Type I IL-1 receptor antagonists include anakinra.

Zonulin inhibitors include larazotide acetate.

Included herein are methods of treatment in which a compound described herein is administered in combination with an anti-inflammatory agent. Anti-inflammatory agents include but are not limited to NSAIDs, non-specific and COX-2 specific cyclooxgenase enzyme inhibitors, gold compounds, corticosteroids, methotrexate, tumor necrosis factor receptor (TNF) receptors antagonists, immunosuppressants and methotrexate.

Examples of NSAIDs include, but are not limited to ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an $IC_{50}$ that is at least 50-fold lower than the $IC_{50}$ for COX-1) such as celecoxib, valdecoxib, lumiracoxib, etoricoxib and/or rofecoxib.

In a further embodiment, the anti-inflammatory agent is a salicylate. Salicylates include but are not limited to acetylsalicylic acid or aspirin, sodium salicylate, and choline and magnesium salicylates.

The anti-inflammatory agent may also be a corticosteroid. For example, the corticosteroid may be chosen from cortisone, dexamethasone, methylprednisolone, prednisolone, prednisolone sodium phosphate, and prednisone.

In some embodiments, the anti-inflammatory therapeutic agent is a gold compound such as gold sodium thiomalate or auranofin.

In some embodiments, the anti-inflammatory agent is a metabolic inhibitor such as a dihydrofolate reductase inhibitor, such as methotrexate or a dihydroorotate dehydrogenase inhibitor, such as leflunomide.

In some embodiments, the anti-inflammatory compound is an anti-C5 monoclonal antibody (such as eculizumab or pexelizumab), a TNF antagonist, such as entanercept, or infliximab, which is an anti-TNF alpha monoclonal antibody.

Included herein are methods of treatment in which a compound described herein, is administered in combination with an immunosuppressant. In some embodiments, the immunosuppressant is methotrexate, leflunomide, cyclosporine, tacrolimus, azathioprine, or mycophenolate mofetil.

Included herein are methods of treatment in which a compound described herein, is administered in combination with a class of agent for treatment of IBD. Examples of classes of agents for treatment of IBD that can be used in combination with a compound described herein include ASK1 inhibitors, beta adrenoceptor antagonists, BTK inhibitors, beta-glucuronidase inhibitors, bradykinin receptor modulators, calcineurin inhibitors, calcium channel inhibitors, cathepsin S inhibitors, CCR3 chemokine antagonists, CD40 ligand receptor antagonists, chemokine CXC ligand inhibitors, CHST15 gene inhibitors, collagen modulators, CSF-1 antagonists, cyclooxygenase inhibitors, cytochrome P450 3A4 inhibitors, eotaxin ligand inhibitors, EP4 prostanoid receptor agonists, erythropoietin receptor agonists, fractalkine ligand inhibitors, free fatty acid receptor 2 antagonists, GATA 3 transcription factor inhibitors, glucagon-like peptide 2 agonists, glucocorticoid agonists, guanylate cyclase receptor agonists, histone deacetylase inhibitors, HLA class II antigen modulators, IL-12 antagonists, IL-13 antagonists, IL-23 antagonists, IL-6 antagonists, IL-6 receptor modulators, interleukin-7 receptor modulators, IL-7 antagonists, IL-8 antagonists, integrin alpha-4/beta-1 antagonists, integrin alpha-4/beta-7 antagonists, integrin alpha-E antagonists, integrin antagonists, integrin beta-7 antagonists, interleukin ligand inhibitors, interleukin-2 ligand, interleukin receptor 17A antagonists, interleukin-1 beta ligands, interleukin-1 beta ligand modulators, IRAK4 inhibitors, JAK tyrosine kinase inhibitors, Jak1 tyrosine kinase inhibitors, Jak3 tyrosine kinase inhibitors, LanC like protein 2 modulators, lipoxygenase modulators, MAdCAM inhibitors, matrix metalloprotease inhibitors, melanocortin agonists, metalloprotease-9 inhibitors, natriuretic peptide receptor C agonists, neuregulin-4 ligands, NKG2 D activating NK receptor antagonists, opioid receptor antagonists, opioid receptor delta antagonists, oxidoreductase inhibitors, P2X7 purinoceptor agonists, PDE 4 inhibitors, phagocytosis stimulating peptide modulators, potassium channel inhibitors, PPAR alpha agonists, PPAR delta agonists, PPAR gamma agonists, protein fimH inhibitors, P-selectin glycoprotein ligand-1 inhibitors, RNA polymerase inhibitors, sphingosine 1 phosphate phosphatase 1 stimulators, sphingosine 1 phosphate phosphatase modulators, sphingosine-1-phosphate receptor-1 agonists, sphingosine-1-phosphate receptor-1 antagonists, sphingosine-1-phosphate receptor-1 modulators, sphingosine-1-phosphate receptor-5 modulators, STAT3 gene inhibitors, stem cell antigen-1 inhibitors, superoxide dismutase modulators, superoxide dismutase stimulators, SYK inhibitors, TGF beta 1 ligand inhibitors, thymulin agonists, TLR antagonists, TLR agonists, TNF alpha ligand inhibitors, TNF antagonists, tumor necrosis factor 14 ligand modulators, type II TNF receptor modulators, Tpl 2 inhibitors, and Zonulin inhibitors.

Included herein are methods of treatment in which a compound described herein is administered in combination with an agent for treatment of IBD. Examples of agents for treatment of IBD that can be used in combination with a compound described herein, or a pharmaceutically acceptable salt, stereoisomer, mixture of stereoisomers, tautomer, or deuterated analog thereof, include those provided herein for the treatment of an inflammatory disease or condition, and ABX-464, adalimumab; alicaforsen, ALLO-ASC-CD, AMG-966, anakinra, apremilast; Alequel; AMG-139; amiselimod, ASD-003, ASP-3291, AX-1505, BBT-401, balsalazide; beclomethasone dipropionate; BI-655130, BMS-986184; budesonide; CEQ-508; certolizumab; ChAdOx2-HAV, dexamethasone sodium phosphate, DNVX-078, etanercept; cibinetide; *Clostridium butyricum*; ETX-201, golimumab; GS-4997, GS-9876, GS-4875, GS-4059, infliximab; mesalazine, HLD-400, LYC-30937 EC; IONIS-JBI1-2.5Rx, JNJ-64304500, JNJ-4447, naltrexone; natalizumab; neihulizumab, olsalazine; PH-46-A, propionyl-L-carnitine; PTG-100; remestemcel-L; tacrolimus; teduglutide; tofacitinib; ASP-1002; ustekinumab; vedolizumab; AVX-470; INN-108; SGM-1019; PF-06480605; PF-06651600; PF-06687234; RBX-8225, SER-287; Thetanix; TOP-1288; VBY-129; 99mTc-annexin V-128; bertilimumab; DLX-105; dolcanatide; FFP-104; filgotinib; foralumab; GED-0507-34-Levo; givinostat; GLPG-0974; iberogast; JNJ-40346527; K(D)PT; KAG-308; KHK-4083; KRP-203; larazotide acetate; LY-3074828, midismase; olokizumab; OvaSave; P-28-GST; PF-547659; prednisolone; QBECO; RBX-2660, RG-7835; JKB-122; SB-012; STNM-01; Debio-0512; TRK-170; zucapsaicin; ABT-494; Ampion; BI-655066; carotegast methyl; cobitolimod; elafibranor; etrolizumab; GS-5745; HMPL-004; LP-02, ozanimod; peficitinib; quetmolimab (E-6011); RHB-104; rifaximin; tildrakizumab; tralokinumab; brodalumab; laquinimod, plecanatide; vidofludimus; and AZD-058.

Included herein are methods of treatment in which a compound described herein is administered in combination with an agent for treatment of graft versus host disease. Examples of agents for treatment of graft versus host disease that can be used in combination with a compound described herein include those provided herein for the treatment of an inflammatory disease or condition, and [18F]F-AraG, AM-01, Alpha 1 antitrypsin stimulator: AAT-IV and CSL-964; Allocetra, efavaleukin alfa (AMG-592), arsenic trioxide, ATIR-101, belatacept, belimumab, beta lactamase modulator: ribaxamase, bortezomib, brentuximab vedotin, brimonidine, brimonidine tartrate, cannabidiol, ciclosporin, CYP-001, um, dilanubicel, dornase alfa, DSM-9843, eculizumab, EDP-1066, everolimus, Furestem, GL-101, ibrutinib, IMSUT-CORD, IRX-4204, itolizumab, KD-025, MaaT-013, milatuzumab, mizoribine, mycophenolate mofetil, MSCTC-0010, nalotimagene carmaleucel, MET-2, nilotinib, narsoplimab (OMS-721), pacritinib, PF-05285401, ProTmune, QPI-1002, remestemcel-L, RGI-2001, saratin, SCM-CGH, sirolimus, T-allo10, telmisartan, TOP-1288, TZ-101, voclosporin; CCR5 chemokine antagonist: leronlimab (PRO-140); CD40 ligand receptor antagonist: iscalimab; Complement C1s subcomponent inhibitor: CE-1145, sutimlimab, Cinryze, BIVV-009; B-lymphocyte antigen CD20 inhibitor: obinutuzumab, rituximab; CASP9 gene stimulator: rivogenlecleucel; CD3 antagonist or CD7 inhibitor: T-Guard; Complement C5a factor inhibitor: olendalizumab; Dipeptidyl peptidase IV inhibitor: begelomab; JAK1/2 tyrosine kinase inhibitor: ruxolitinib; Jak1 tyrosine kinase inhibitor: itacitinib; Interleukin-2 ligand: aldesleukin; Interleukin 22 ligand: F-652; IL-2 receptor alpha subunit inhibitor: basiliximab and inolimomab; IL-6 receptor agonist: PLX-1; IL-6 receptor antagonist: clazakizumab; OX40 ligand inhibitor: KY-1005; An example of such OX40 inhibitor is a compound disclosed in U.S. Pat. No. 8,450,460, the entire contents of which are incorporated herein by reference; Signal transducer CD24 modulator: CD24-IgFc; Somatostatin receptor agonist: Thymoglobulin; and sphingosine-1-phosphate receptor-1 agonist: ponesimod.

Included herein are methods of treatment in which a compound described herein is administered in combination with an agent for treatment of primary sclerosing cholangitis. Examples of agents for treatment of primary sclerosing cholangitis that can be used in combination with compounds described herein include those provided herein for the treatment of an inflammatory disease or condition, and BTT-1023, CM-101, Doconexent, GRI-0124, HTD-1801, HTD-2802, hymecromone, IDN-7314, NGM-282, norursodeoxycholic acid, ORBCEL-C, integrin alpha-V/beta-1 and beta-6 antagonist: PLN-74809; PPAR delta agonist: seladelpar lysine; SCT-5-27, PTGS2 gene and TGF beta 1 gene inhibitor: SCT-5-27, and STP-705; Farnesoid X receptor (FXR, NR1H4) agonists or modulators: AGN-242266, cilofexor tromethamine (GS-9674), EDP-305, EYP-001, GNF-5120, MET-409, nidufexor (LMB-763), obeticholic acid, TERN-101, tropifexor; liver X receptor antagonist: DUR-928; and CCR5/CCR2 chemokine antagonist: cenicriviroc.

In some embodiments, the one or more additional therapeutic agents is selected from the group consisting of: combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or a pharmaceutically acceptable salt of any of the foregoing, or any combinations thereof.

In some embodiments, the one or more additional therapeutic agents is selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, or a pharmaceutically acceptable salt of any of the foregoing, or any combinations thereof.

In some embodiments, the one or more additional therapeutic agent is an immune modulating agent, e.g., an immunostimulant or an immunosuppressant. In certain other embodiments, an immune modulating agent is an agent capable of altering the function of immune checkpoints, including the CTLA-4, LAG-3, B7-H3, B7-H4, Tim3, BTLA, KIR, A2aR, CD200 and/or PD-1 pathways. In other embodiments, the immune modulating agent is immune checkpoint modulating agents. Exemplary immune checkpoint modulating agents include anti-CTLA-4 antibody (e.g., ipilimumab), anti-LAG-3 antibody, anti-B7-H3 antibody, anti-B7-H4 antibody, anti-Tim3 antibody, anti-BTLA antibody, anti-KIR antibody, anti-A2aR antibody, anti CD200 antibody, anti-PD-1 antibody, anti-PD-L1 antibody, anti-CD28 antibody, anti-CD80 or -CD86 antibody, anti-B7RP1 antibody, anti-B7-H3 antibody, anti-HVEM antibody, anti-CD137 or -CD137L antibody, anti-OX40 or -OX40L antibody, anti-CD40 or -CD40L antibody, anti-GAL9 antibody, anti-IL-10 antibody and A2aR drug. For certain such immune pathway gene products, the use of either antagonists or agonists of such gene products is contemplated, as are small molecule modulators of such gene products. In some embodiments, immune modulating agents include those agents capable of altering the function of mediators in cytokine mediated signaling pathways.

In some embodiments, a compound as disclosed herein may be combined with one or more (e.g., one, two, three, four, one or two, one to three, or one to four) additional therapeutic agents in any dosage amount of the compound described herein (e.g., from 10 mg to 1000 mg of compound).

A compound described herein may be combined with the agents provided herein in any dosage amount of the compound (e.g., from 50 mg to 500 mg of compound) the same as if each combination of dosages were specifically and individually listed.

In some embodiments, provided are kits comprising a pharmaceutical composition comprising a compound described herein or a compound described herein and at least one additional therapeutic agent, or a pharmaceutically acceptable salt thereof, and at least one pharmaceutically acceptable carrier. In some embodiments, kits comprising a compound disclosed herein, or a pharmaceutically acceptable salt, stereoisomer, mixture of stereoisomers, tautomer, or deuterated analog thereof, in combination with one or more (e.g., one, two, three, four, one or two, or one to three, or one to four) additional therapeutic agents are provided. Any pharmaceutical composition provided in the present disclosure may be used in the kits, the same as if each and every composition were specifically and individually listed for use in a kit. In some embodiments, the kit comprises instructions for use in the treatment of an inflammatory disease or condition. In some embodiments, the instructions in the kit are directed to use of the pharmaceutical composition for the treatment of IBD.

Articles of Manufacture

Articles of manufacture comprising a container in which a compound described herein and at least one pharmaceutically acceptable carrier are contained are provided. The article of manufacture may be a bottle, vial, ampoule, single-use disposable applicator, or the like, containing the pharmaceutical composition provided in the present disclosure. The container may be formed from a variety of materials, such as glass or plastic and in one aspect also contains a label on, or associated with, the container which indicates directions for use in the treatment of cancer or inflammatory conditions.

It should be understood that the active ingredient may be packaged in any material capable of providing reasonable chemical and physical stability, such as an aluminum foil bag.

Unit dosage forms of the pharmaceutical composition comprising a compound described herein and at least one pharmaceutically acceptable carrier are also provided.

Any pharmaceutical composition provided in the present disclosure may be used in the articles of manufacture, the same as if each and every composition were specifically and individually listed for use an article of manufacture.

Also provided is a kit that includes a compound described herein; a label, and/or instructions for use of the compound in the treatment of a disease or condition mediated, at least in part, by α4β7 integrin.

Also provided is an article of manufacture which includes a compound described herein; and a container. In some embodiments, the container may be a vial, jar, ampoule, preloaded syringe, or an intravenous bag.

Formulations of compound(s) of the present disclosure, i.e., a compound described herein or the combination of a compound described herein and an additional agent may be accomplished by admixing said compounds or salt thereof with one or more non-toxic, pharmaceutically acceptable vehicles, carriers and/or diluents and/or adjuvants collectively referred to herein as excipients or carrier materials. The compounds of the disclosure may be administered by any suitable route, preferably in the form of a pharmaceutical composition adapted to such route, and in a therapeutically effective dose. The compounds or the combination of compounds for the disclosure may be delivered orally, mucosally, parenterally, including intravascularly, intravenously, intraperitoneally, subcutaneously, intramuscularly, and intranasally in dosage formulations containing conventional pharmaceutical excipients.

In some embodiments, the combination of a compound described herein, and an additional therapeutic agent may be formulated in a fixed dose or combined dose formulation in a tablet, capsule or premixed IV solution. In another embodiment, the fixed dose combination preferably comprises of a compound described herein, and an additional anti-inflammatory agent. Other fixed dose formulations may include premixed liquids, suspensions, elixirs, aerosolized sprays or patch presentations. As used herein fixed dose or combined dose formulations are synonymous with simultaneous co-administration of the active ingredients of the compound described herein and at least one additional therapeutic agent.

Also provided herein are methods for treating a subject who is undergoing one or more standard therapies for treatment of an inflammatory disease or condition comprising administering or co-administering a compound described herein to said subject. Accordingly, one or more compounds described herein may be administered before, during, or after administration of another therapeutic agent for treatment of an inflammatory disease or condition, or combination thereof.

In some embodiments, the subject may be a human who is (i) substantially refractory to at least one treatment of an inflammatory disease or condition, or (ii) in relapse after treatment with treatment of an inflammatory disease or condition, or both (i) and (ii). In some of embodiments, the subject is refractory to at least two, at least three, or at least four treatment of an inflammatory disease or condition (including standard or experimental treatments of an inflammatory disease or condition).

The above therapeutic agents when employed in combination with a compound(s) disclosed herein, may be used, for example, in those amounts indicated in the referenced manuals, e.g., Physicians' Desk Reference or in amounts generally known to a qualified care giver, i.e., one of ordinary skill in the art. In the methods of the present disclosure, such other therapeutic agent(s) may be administered prior to, simultaneously with, or following the administration of the compound described herein. Certain other therapeutic agents may be combined into a single formulation or kit when amenable to such. For example, tablet, capsule or liquid formulations may be combined with other tablet, capsule or liquid formulations into one fixed or combined dose formulation or regimen. Other combinations may be given separately, contemporaneously or otherwise.

Improvements in any of the foregoing response criteria are specifically provided by the methods of the present disclosure.

Synthesis

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of typical compounds of formula (I), e.g., compounds having structures described by one or more of formula (I), or other formulas or compounds disclosed herein, or a pharmaceutically acceptable salt, stereoisomer, mixture of stereoisomers, tautomer, or deuterated analog thereof, may be accomplished as described in the following examples.

General Syntheses

Typical embodiments of compounds in accordance with the present disclosure may be synthesized using the general reaction schemes and/or examples described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Starting materials are typically obtained from commercial sources or synthesized using published methods for synthesizing compounds which are embodiments of the present disclosure, inspection of the structure of the compound to be synthesized will provide the identity of each substituent group. The identity of the final product will generally render apparent the identity of the necessary starting materials by a simple process of inspection, given the examples herein. Group labels (e.g., $R^1$, $R^a$) used in the reaction schemes herein are for illustrative purposes only and unless otherwise specified do not necessarily match by name or function the labels used elsewhere to describe compounds of formula (I), or any formula described herein, or aspects or fragments thereof.

Synthetic Reaction Parameters

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis,* 3rd Edition, Wiley, New York, and references cited therein.

Furthermore, the compounds of this disclosure may contain one or more asymmetric ("chiral") centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, $5^{th}$ Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

The term "q.s." means adding a quantity sufficient to achieve a stated function, e.g., to bring a solution to the desired volume (i.e., 100%).

Compounds as provided herein may be synthesized according to the general schemes provided below. In the Schemes below, it should be appreciated that each of the compounds shown therein may have protecting groups as required present at any step. Standard protecting groups are well within the pervue of one skilled in the art.

Scheme 1 shows an exemplary synthetic route for the synthesis of compounds provided herein (e.g., compounds of Formula I). The compounds of Formula I, or other formulas or compounds disclosed herein, are typically prepared by first providing the molecular core 503 and then attaching the desired $R^1$ substituents using suitable coupling conditions (e.g., Suzuki coupling) and the desired phenylamide substituents (substituted at the phenyl by $R^2$-$R^6$) using suitable amide coupling conditions. In Scheme 1, p, $R^1$, $R^2$, $R^3$, $R^4$, $R^5$, $R^6$, $R^7$, $R^8$, $R^9$, $X^1$, $X^2$, $X^3$, $X^4$, $X^5$, X6, and $X^7$ are as defined herein, $R^{51}$ is a leaving group (e.g., halo); $R^{52}$ is $C_{1-6}$ alkyl; $R^{53}$ is hydroxy or a leaving group (e.g., halo); $R^{54}$ is a moiety suitable for undergoing a coupling reaction (e.g., a boronic acid or halo); $R^{55}$ is O (i.e., oxo) or N, where if $R^{55}$ is N then $R^{55}$ is a constituent of optional ring to $E^1$; $E^1$ is a double bonded N-auxiliary that is optionally cyclized at $R^{55}$, or $E^1$ may be a single bonded N-protecting group and $R^8$; and $R^{56}$ is a moiety suitable for undergoing a metal-catalyzed coupling reaction (e.g., halo, or a boronic acid or an ester thereof).

In Scheme 1, compound 501 is reacted with compound 502 under standard nucleophilic displacement conditions (e.g., using a base) in a suitable solvent (e.g., THF etc.), optionally under an inert atmosphere, to provide compound 503. In general, compound 502 is deprotonated using a strong base, such as potassium hydroxide or butyllithium, and then contacted with compound 501. The reaction is carried out in an inert solvent, for example dichloromethane or THF. The reaction is typically conducted at a temperature of about −78 to 0° C., for about 5 minutes to about 1 hour, or at a temperature of about 0 to 50° C., for about 1 hour to about 12 hours. When the reaction is substantially complete, the product compound 503 is isolated by conventional means.

Compound 508 is reacted under acidic conditions sufficient to remove $E^1$. For example, compound 508 may be contacted with an acid in the presence of water or an alcohol, if $E^1$ is double bonded to N, such as when $E^1$ is a diphenylmethine. For example, compound 508 may be contacted with HCl in a suitable solvent, such as methanol/dioxane.

Alternatively, compound 508 may be contacted with an acid (e.g., HCl or trifluoroacetic acid) in an inert solvent (e.g., dioxane or dichloromethane), if $E^1$ is single bonded to N, such as when $E^1$ is a tert-butoxycarbonyl. Following removal of $E^1$, N—H derivative of compound 508 is reacted with compound 505 under standard amide coupling conditions in a suitable solvent (e.g., THF etc.), optionally under an inert atmosphere, to provide compound 510.

Scheme 1

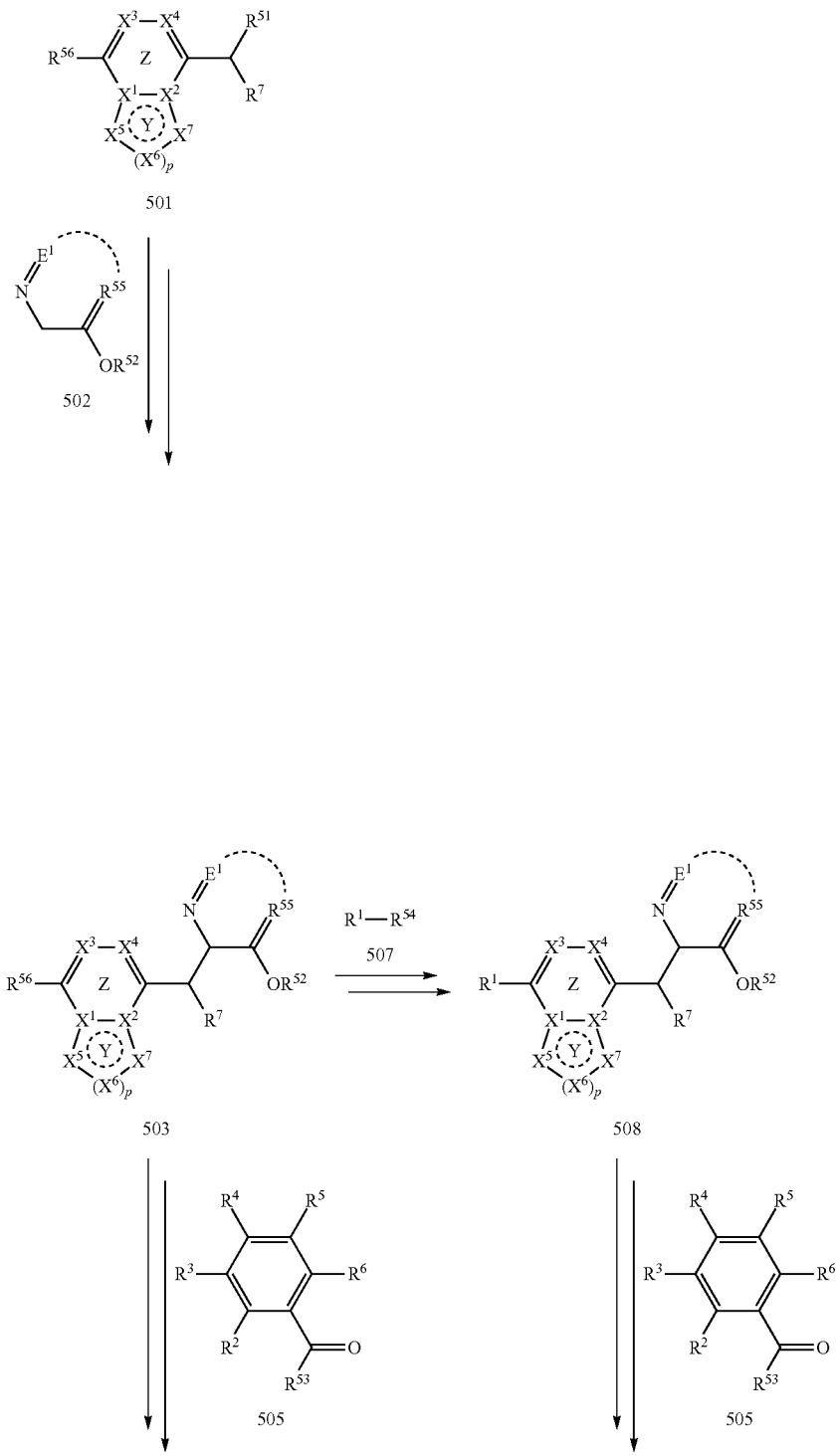

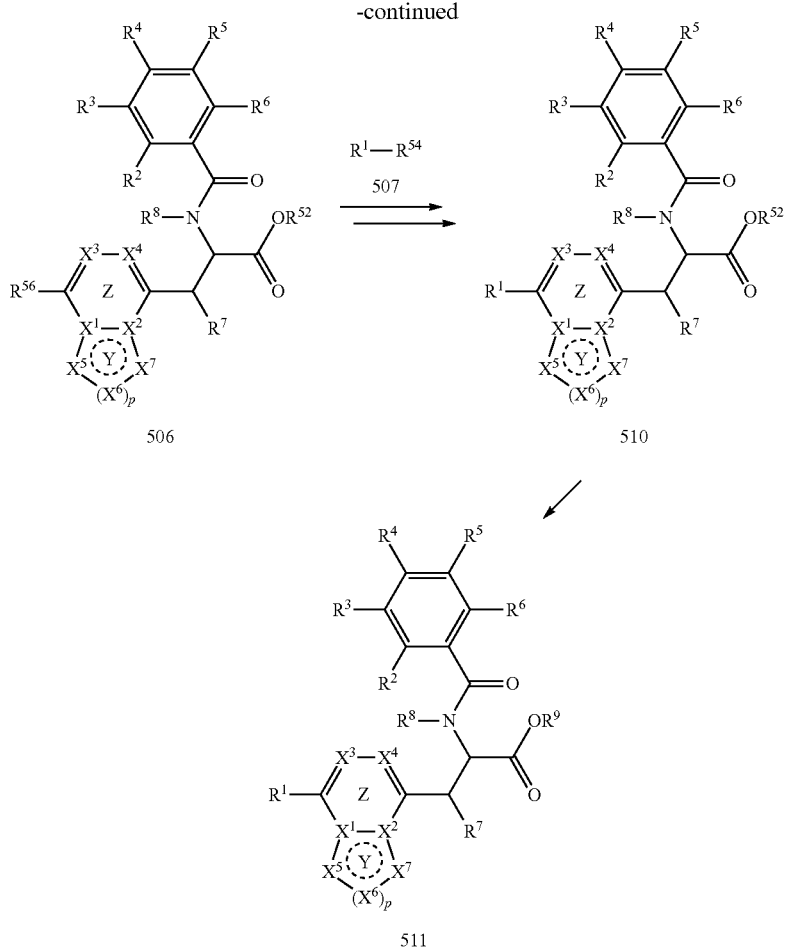

In compound 505, $R^{53}$ may be leaving group (e.g., halo), or —OH. Where $R^{53}$ is —OH, compound 505 is activated using a suitable agent, such as HATU, and contacted with compound 508 in the presence of a base (e.g., an organic base such as triethylamine or diisopropylethylamine). The reaction is carried out in an inert solvent, for example dichloromethane, DMF or THF. Where $R^{53}$ is a leaving group, compound 505 is contacted with compound 508 in the presence of a base (e.g., an organic base such as triethylamine or diisopropylethylamine) in an inert solvent, for example dichloromethane or THF. The reaction is typically conducted at a temperature of about 0 to 30° C., for about 5 minutes to about 12 hours. When the reaction is substantially complete, the product compound 510 is isolated by conventional means.

Alternatively, in Scheme 1, compound 503 is reacted under acidic conditions sufficient to remove $E^1$. For example, compound 503 may be contacted with an acid in the presence of water or an alcohol, if $E^1$ is double bonded to N, such as when $E^1$ is a diphenylmethine. For example, compound 503 may be contacted with HCl in a suitable solvent, such as methanol/dioxane. Alternatively, compound 503 may be contacted with an acid (e.g., HCl or trifluoroacetic acid) in an inert solvent (e.g., dioxane or dichloromethane), if $E^1$ is single bonded to N, such as when $E^1$ is a tert-butoxycarbonyl. Following removal of $E^1$, N—H derivative of compound 503 is reacted with compound 505 under standard amide coupling conditions in a suitable solvent (e.g., THF etc.), optionally under an inert atmosphere, to provide compound 506. In compound 505, $R^{53}$ may be a leaving group (e.g., halo), or —OH. Where $R^{53}$ is —OH, compound 505 is activated using a suitable agent, such as HATU, and contacted with compound 503 in the presence of a base (e.g., an organic base such as triethylamine or diisopropylethylamine). The reaction is carried out in an inert solvent, for example dichloromethane, DMF or THF. Where $R^{53}$ is a leaving group, compound 505 is contacted with compound 503 in the presence of a base (e.g., an organic base such as triethylamine or diisopropylethylamine) in an inert solvent, for example dichloromethane or THF. The reaction is typically conducted at a temperature of about 0 to 30° C., for about 5 minutes to about 24 hours. When the reaction is substantially complete, the product compound 506 is isolated by conventional means.

Compound 506 is coupled with compound 507 under standard metal-catalyzed coupling conditions (e.g., using a palladium catalyst) in a suitable solvent (e.g., dioxane, water, etc.), optionally under an inert atmosphere, to provide compound 510. Compound 507 is an appropriate derivative of formula $R^1$-$R^{54}$. If $R^{54}$ is a boronic acid —B(OH)$_2$, or an ester thereof, compound 507 is coupled to compound 506 where $R^{56}$ is a halogen (e.g., Br). If $R^{54}$ is a halogen, compound 506 may first be coupled with a suitable source of boron, e.g., bis(pinacolato)diboron, to provide a boronic acid, or an ester thereof, at $R^{56}$. The coupling reaction is carried out in an inert solvent, for example aqueous N,N- dimethylformamide, in the presence of a mild base, for example potassium acetate, potassium carbonate, or sodium bicarbonate. The reaction is typically conducted in the presence of a metal catalyst with an appropriate ligand, for example dichlorobis(triphenylphosphine) palladium(II) or dichloro 1,1'-bis(diphenylphosphino)ferrocene palladium (II), at a temperature of about 60 to 150° C., for about 10 minutes to about 12 hours. When the reaction is substantially complete, the product compound 510 is isolated by conventional means.

In general, compound 510 is hydrolyzed at $R^{52}$ under standard aqueous hydrolysis conditions (e.g., using a base or acid) in a suitable aqueous medium (e.g., THF and water, ethanol and water, etc.), optionally under an inert atmosphere, to provide compound 511. The reaction is typically conducted at a temperature of about 0 to 30° C., for about 10 minutes to about 1 hour or at a higher temperature, i.e., 30 to 100° C. for about 10 minutes to about 1 hour. When the reaction is substantially complete, the product of Formula I is isolated by conventional means.

It will be appreciated that the $R^1$ substituent can be added either before (as shown in Scheme 1) or after the removal of the $E^1$ moiety. Thus, the $R^1$ moiety may be coupled to the core-$E^1$ compound 503 under coupling reaction conditions with an appropriate reagent of formula $R^1$-$R^{54}$ as shown in Scheme 1. Alternatively, the $R^1$ moiety may be coupled to the core compound 506 with an appropriate reagent of formula $R^1$-$R^{54}$, following reaction with compound 505 as shown in Scheme 1.

Optional Synthesis

In some embodiments, compound 508 may be synthesized by routes illustrated in Scheme 2. For example, an alternative route for the synthesis of compound 508-1 is shown in Scheme 2, wherein the ring Y—Z forms an indazolyl or an isoquinolinyl. In the embodiment of scheme 2, $R^{55}$ is O, $E^1$ is a protecting group (e.g., tert-butoxycarbonyl), and the optional ring between $E^1$ and $R^{55}$ is absent. $R^{52}$ is as defined above. Compound 516 is an appropriate acrylate derivative. Compound 515 is coupled with compound 516 under Heck metal-catalyzed coupling conditions (e.g., using a palladium catalyst) in a suitable solvent (e.g., dioxane, water, etc.), optionally under an inert atmosphere, to provide compound 517. The coupling reaction is carried out in an inert solvent, for example aqueous N,N-dimethylformamide, in the presence of a mild base, for example triethylamine, potassium phosphate or sodium carbonate. The reaction is typically conducted in the presence of a metal catalyst, for example palladium(II) acetate, at a temperature of about 60 to 150° C., for about 10 minutes to about 12 hours. Compound 517 is reduced under suitable conditions including a reducing agent (e.g., sodium borohydride or hydrogen), and a metal catalyst, optionally in an inert solvent. For example, compound 517 is contacted with the reducing agent sodium borohydride and nickel(II) chloride in methanol. Alternatively, compound 517 is contacted with pressurized hydrogen gas (e.g., 20 to 5000 psi) and palladium on carbon (e.g., 10% Pd/C) in an inert solvent (e.g., ethanol). When the reaction is substantially complete, the product compound 508-1 is isolated by conventional means.

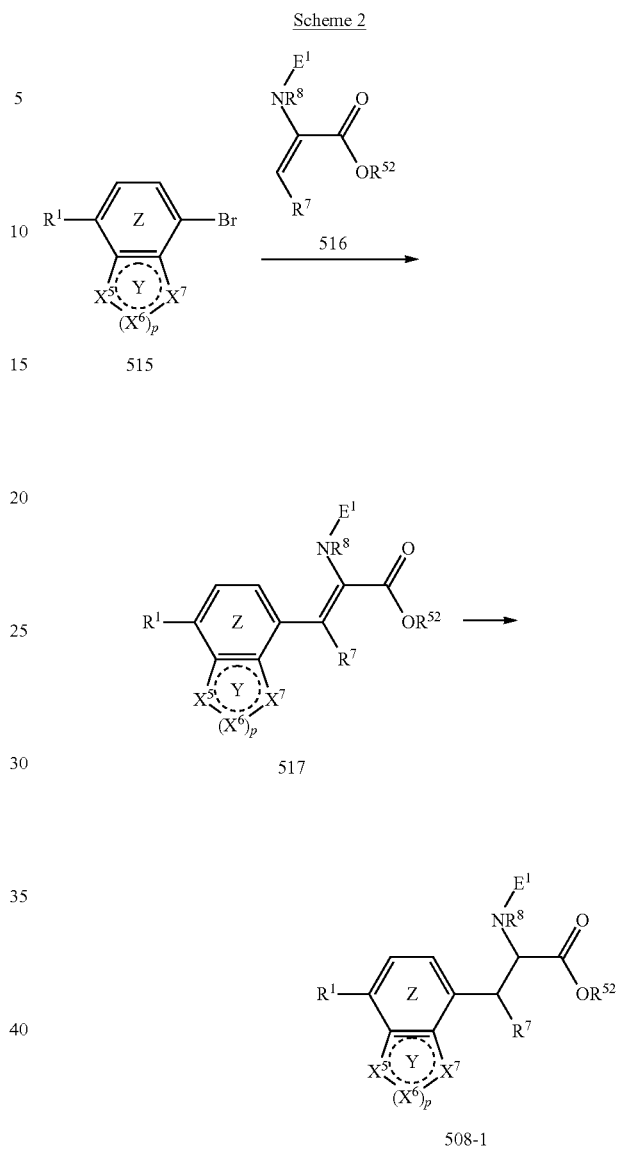

In some embodiments, compound 503 may be synthesized by routes illustrated in Scheme 3. For example, an alternative route for the synthesis of compound 503-1 is shown in Scheme 3, wherein the ring Y—Z forms a 1,6-naphthyridine. In the embodiment of scheme 3, $R^{55}$ is O, $E^1$ is tert-butoxycarbonyl, and the optional ring between $E^1$ and $R^{55}$ is absent. The reaction of compound 520 with compound 521 is conducted under Negishi metal-catalyzed coupling conditions (e.g., using a palladium catalyst) in a suitable solvent (e.g., DMF, etc.), optionally under an inert atmosphere, to provide compound 503-1. The coupling reaction is carried out in an inert solvent, for example N,N-dimethylformamide in which compound 520 is contacted with zinc dust, e.g., in the presence of a catalytic activator (e.g., $I_2$). The reaction is typically conducted in the presence of a metal catalyst with an appropriate ligand, for example dichlorobis(triphenylphosphine) palladium(II), at a temperature of about 20 to 100° C., for about 10 minutes to about 24 hours. When the reaction is substantially complete, the product compound 503-1 is isolated by conventional means.

Scheme 3

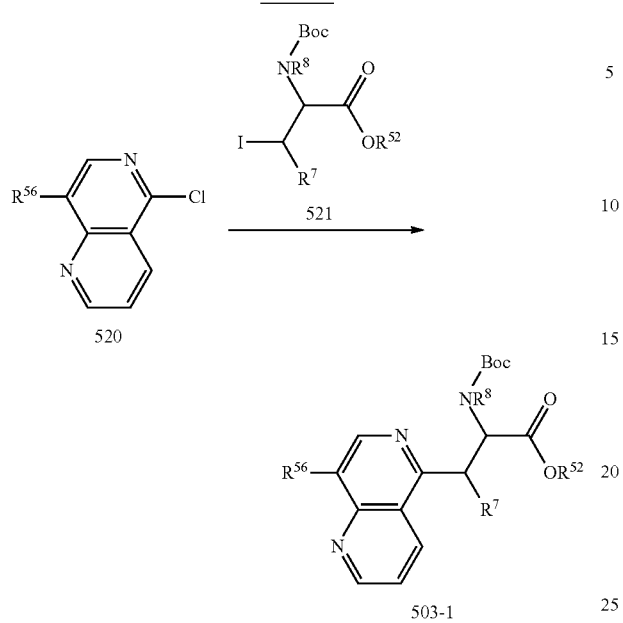

In some embodiments, compound 503 may be synthesized by routes illustrated in Scheme 4. For example, an alternative route for the synthesis of compound 503-2 is shown in Scheme 4, wherein the ring Y—Z forms a naphthyl. In Scheme 4, $E^2$ is a double bonded N-auxiliary such as diphenylmethine. $R^{51}$, $R^{52}$, and $R^{56}$ are as described above. The reaction of compound 501 with compound 525 is carried out under standard nucleophilic displacement conditions (e.g., using a base) in a suitable solvent (e.g., THF etc.), optionally under an inert atmosphere, to provide compound 526. Compound 525 is deprotonated using a strong base, such as potassium hydroxide or butyllithium, and then contacted with compound 501. The reaction is carried out in an inert solvent, for example dichloromethane or THF. The reaction is typically conducted at a temperature of about −78 to 0° C., for about 5 minutes to about 1 hour, or at a temperature of about 0 to 50° C., for about 1 hour to about 12 hours. When the reaction is substantially complete, the product compound 526 is isolated by conventional means. Compound 526 is converted to compound 503-2 by standard deprotection and protection steps, where $E^1$ is trityl or tert-butoxycarbonyl, $R^{55}$ is O, and the optional ring between $E^1$ and $R^{55}$ is absent. The product compound 503-2 is isolated by conventional means.

Scheme 4

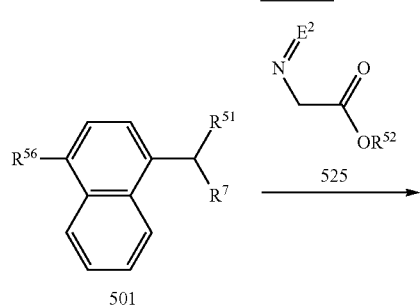

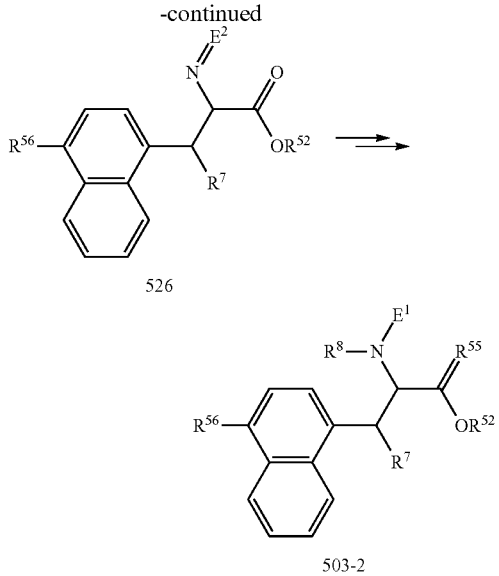

In some embodiments, compound 515 may be synthesized by routes illustrated in Scheme 5. For example, an alternative route for the synthesis of compounds 515-1 and 515-2 is shown in Scheme 5, wherein the ring Y—Z forms an indazolyl. In Scheme 5, $R^1$ and $R^{54}$ are as described above. The reaction of compound 530 to form compound 531 is carried out by contacting compound 530 with a strong base (e.g., sodium hydride) in an inert solvent (e.g., DMF) and then adding an electrophilic source of an alkylating agent (e.g., methyl iodide). The reaction is typically conducted at a temperature of about 0 to 50° C., for about 10 minutes to about 12 hours. When the reaction is substantially complete, the product compound 531 is isolated by conventional means. Compound 531 is then coupled with compound 507 under standard metal-catalyzed coupling conditions (e.g., using a palladium catalyst) in a suitable solvent (e.g., DMF, water, etc.), optionally under an inert atmosphere, to provide a mixture of compound 515-1 and compound 515-2. Compound 507 is an appropriate derivative of formula $R^1$-$R^{54}$ in which $R^{54}$ is a boronic acid —$B(OH)_2$, or an ester thereof. The coupling reaction is carried out in an inert solvent, for example aqueous N,N-dimethylformamide, in the presence of a mild base, for example sodium carbonate. The reaction is typically conducted in the presence of a metal catalyst with an appropriate ligand, for example tetrakis(triphenylphosphine) palladium(0), at a temperature of about 60 to 150° C., for about 10 minutes to about 12 hours. When the reaction is substantially complete, the product compounds 515-1 and 515-2 are isolated by conventional means. Compounds 515-1 and 515-2 may be separated by conventional means, e.g., by chromatography.

Scheme 5

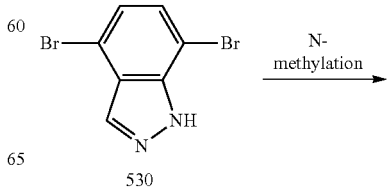

91

-continued

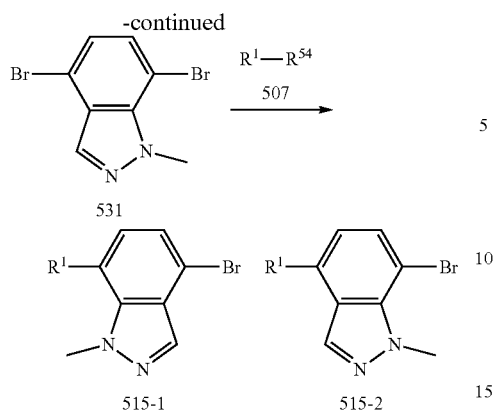

In some embodiments, an alternative route for the synthesis of compound 515 is illustrated in Scheme 6, wherein the ring Y—Z forms an isoquinoline. In Scheme 6, $R^1$ and $R^{54}$ are as described above. The reaction of compound 535 to form compound 515-3 and compound 515-4 is carried out by coupling with compound 507 under standard metal-catalyzed coupling conditions (e.g., using a palladium catalyst) in a suitable solvent (e.g., dioxane, water, etc.), optionally under an inert atmosphere, to provide a mixture of compound 515-3 and compound 515-4. Compound 507 is an appropriate derivative of formula $R^1$-$R^{54}$ in which $R^{54}$ is a boronic acid —$B(OH)_2$, or an ester thereof. The coupling reaction is carried out in an inert solvent, for example aqueous dioxane, in the presence of a mild base, for example sodium carbonate. The reaction is typically conducted in the presence of a metal catalyst with an appropriate ligand, for example dichlorobis(triphenylphosphine) palladium(II), at a temperature of about 60 to 150° C., for about 10 minutes to about 12 hours. When the reaction is substantially complete, the product compounds 515-3 and 515-4 are isolated by conventional means. Compounds 515-3 and 515-4 may be separated by conventional means, e.g., by chromatography.

Scheme 6

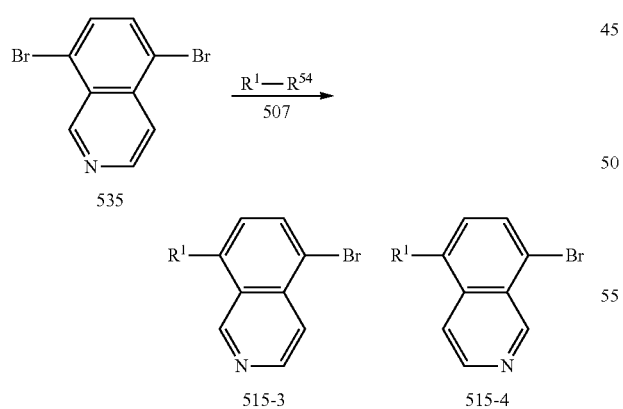

Suitably substituted compounds for use in the methods provided herein can be purchased from commercial sources or synthesized by known methods. Resolution of the isomers of compound 511 can be performed as needed using standard chiral separation/resolution conditions (e.g., chromatography, crystallization, etc.).

92

EXAMPLES

Methods for preparing the novel compounds described herein will be apparent to those of skill in the art with suitable procedures being described, for example, in the reaction schemes and examples below.

Synthetic Intermediates

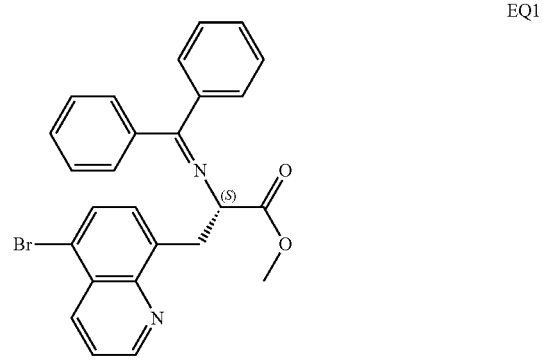

EQ1

Methyl (S)-3-(5-bromoquinolin-8-yl)-2-((diphenylmethylene)amino)propanoate (EQ1)

To a stirred solution of methyl 2-((diphenylmethylene)amino)acetate (98.0 g, 386.89 mmol) in dichloromethane (2.94 L) was added (−)-cinchonidine (11.38 g, 38.68 mmol) at room temperature. Then the reaction mixture was cooled to 0° C. 50% KOH solution (0.784 L) and 5-bromo-8-(bromomethyl)quinoline (139.82 g, 464.27 mmol) were added and the reaction mixture was allowed to warm to RT and stirred for 6 h. The progress of reaction was monitored by TLC (10% ethyl acetate in pet ether). The reaction mixture was diluted with water and stirred for 15 min, extracted with DCM and the organics were concentrated to provide the title compound.

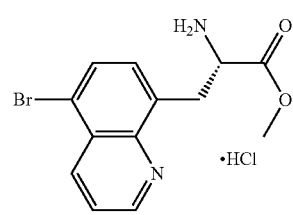

EQ2

Methyl (S)-2-amino-3-(5-bromoquinolin-8-yl)propanoate hydrochloride (EQ2)

(i) 4M HCl in 1,4-dioxane (1.26 L) was added to a stirred solution of methyl (S)-3-(5-bromoquinolin-8-yl)-2-((diphenylmethylene)amino)propanoate (EQ1) (180 g, 380.26 mmol) in methanol (0.90 L) at 0° C. and the reaction mixture was allowed to stir at room temperature for 16 h. The progress of reaction was monitored by TLC. The reaction mixture was concentrated under reduced pressure, dissolved in water and washed with ethyl acetate. The aqueous layer was separated and basified (pH~8) using Sat. NaHCO$_3$ and extracted with 10% methanol/DCM. The combined organic layers were dried over anhydrous Na$_2$SO$_4$ and concentrated under reduced pressure and purified by column chromatography by silica gel (100-200 mesh size) at 2% MeOH/DCM to obtain methyl (S)-2-amino-3-(5-bromoquinolin-8-yl)propanoate as a mixture of two isomers. (ii). The mixture was suspended in MTBE (400 mL) and heated to reflux for 1 h, cooled to room temperature (25-30° C.), the mixture was filtered, dried over sodium sulfate and concentrated. The above process was repeated twice to afford 19.5 g of methyl (S)-2-amino-3-(5-bromoquinolin-8-yl)propanoate. The material was dissolved in DCM and cooled to 0° C. and 4.0 M HCl in dioxane (60 mL) was added and resulting reaction mixture was evaporated under reduced pressure to obtain the title compound.

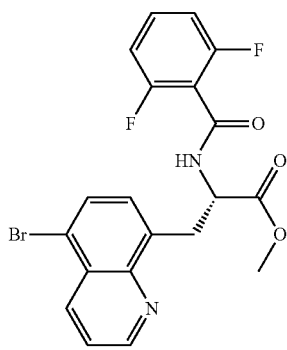

EQ3

Methyl (S)-3-(5-bromoquinolin-8-yl)-2-(2,6-difluorobenzamido)propanoate (EQ3)

To a stirred solution of EQ2 (230 mg, 0.74 mmol)) in DCM (5 mL) was added 2-fluoro-6-methylbenzoyl chloride (0.18 mL, 1.48 mmol) and TEA (0.31 mL, 2.22 mmol). The reaction mixture was allowed to stir at RT for 2 h, then concentrated. The material was taken up in MeOH and crashed out with water. The material was collected via filtration and dried on the high vacuum to afford the title compound.

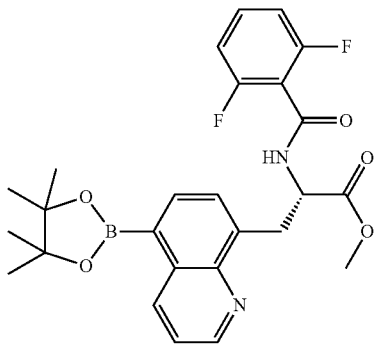

EQ4

Methyl (S)-2-(2,6-difluorobenzamido)-3-(5-(4,4,5,5-tetramethyl-1,3,2-dioxaborolan-2-yl)quinolin-8-yl)propanoate (EQ4)

To a stirred solution of EQ3 (750 mg, 1.55 mmol) in toluene (12 mL) was added bis(pinacolato)diboron (435 mg, 1.71 mmol), followed by potassium acetate (458 mg, 4.66 mmol) and dichloro 1,1'-bis(diphenylphosphino)ferrocene palladium (II) dichloromethane (64 mg, 0.08 mmol). The reaction vessel was flushed with nitrogen then heated to 100° C. overnight. It was cooled to RT and filtered. The reaction was concentrated and purified on silica gel eluting with EtOAc in hexanes (5-100%) to give the title compound.

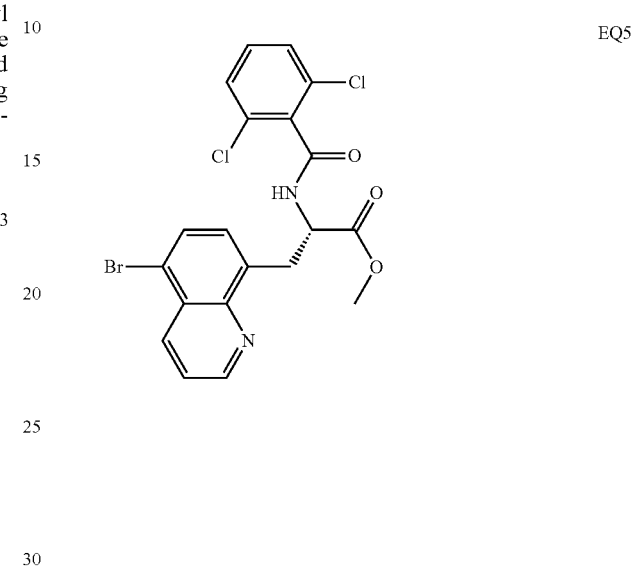

EQ5

Methyl (S)-3-(5-bromoquinolin-8-yl)-2-(2,6-dichlorobenzamido)propanoate (EQ5)

The title compound was prepared according to the method presented for the synthesis of compound EQ3, starting with EQ2 and 2,6-dichlorobenzoyl chloride.

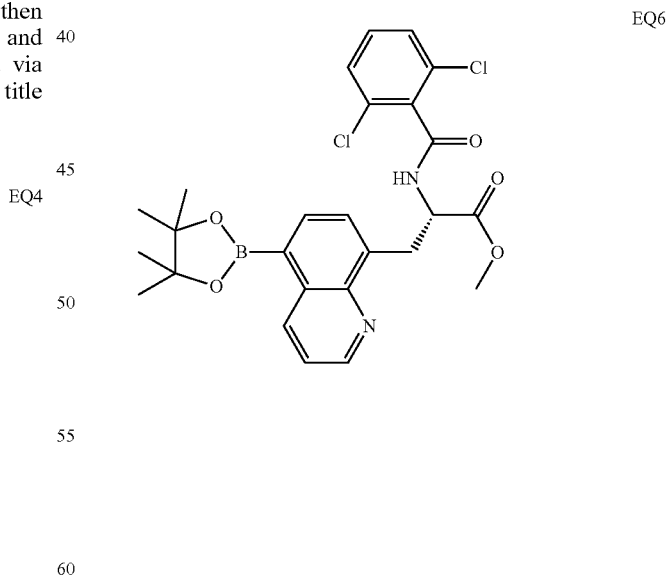

EQ6

Methyl (S)-2-(2,6-dichlorobenzamido)-3-(5-(4,4,5,5-tetramethyl-1,3,2-dioxaborolan-2-yl)quinolin-8-yl)propanoate (EQ6)

The title compound was prepared according to the method presented for the synthesis of compound EQ4 starting with EQ5.

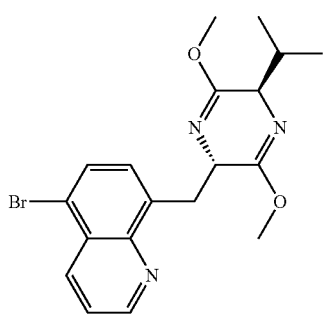 [SMILES: COC1=N[C@H](C(C)C)C(OC)=N[C@H]1Cc1ccc(Br)c2cccnc12]

5-Bromo-8-(((2S,5R)-5-isopropyl-3,6-dimethoxy-2,
5-dihydropyrazin-2-yl)methyl)quinolone To a stirring solution of (R)-2,5-dihydro-3,6-dimethoxy-2-isopropylpyrazine in THF (26 mL) at −78° C. was added BuLi (4.37 mL, 7.2 mmol, 1.6M) dropwise over 5 min. After 20 min at −78° C., 5-bromo-8-(bromomethyl)quinoline (1.55 g, 5.15 mmol) was added in THF (21 mL) dropwise over 15 min. After 15 min at −78° C. water and ethyl acetate were added and the mixture was allowed to warm to RT, extracted with ethyl acetate, dried over sodium sulfate, filtered, and concentrated. The residue was purified using ISCO chromatography eluting with ethyl acetate in hexanes to afford the title compound.

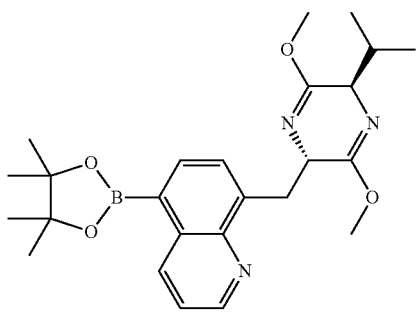 [SMILES: COC1=N[C@H](C(C)C)C(OC)=N[C@H]1Cc1ccc(B2OC(C)(C)C(C)(C)O2)c2cccnc12]

8-(((2S,5R)-5-isopropyl-3,6-dimethoxy-2,5-dihydropyrazin-2-yl)methyl)-5-(4,4,5,5-tetramethyl-1,3,2-dioxaborolan-2-yl)quinolone To a suspension of 5-bromo-8-(((2S,5R)-5-isopropyl-3,6-dimethoxy-2,5-dihydropyrazin-2-yl)methyl)quinoline (600 mg, 1.48 mmol), bis(pinacolato)diboron (754 mg, 2.97 mmol) and potassium acetate (437 mg, 4.45 mmol) in DMA (10 mL) was added cataCXium A Pd-G3 (54 mg, 0.074 mmol) and the reaction vial was degassed with nitrogen, sealed, and heated to 90° C. for 90 min. It was cooled to RT, and water was added and the mixture extracted 3× with EtOAc, dried over sodium sulfate, filtered, and concentrated under vacuum to afford the title compound which was used without further purification.

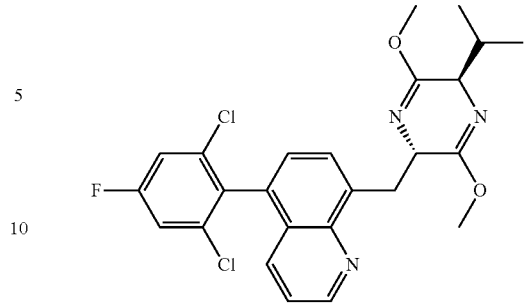

5-(2,6-Dichloro-4-fluorophenyl)-8-(((2S,5R)-5-isopropyl-3,6-dimethoxy-2,5-dihydropyrazin-2-yl)methyl)quinolone To a solution of 2-bromo-1,3-dichloro-5-fluorobenzene (225 mg, 0.93 mmol), 8-(((2S,5R)-5-isopropyl-3,6-dimethoxy-2,5-dihydropyrazin-2-yl)methyl)-5-(4,4,5,5-tetramethyl-1,3,2-dioxaborolan-2-yl)quinoline (278 mg, 0.616 mmol) in DME (4 mL) was added tetrakis(triphenylphosphine)palladium(0) (50 mg, 0.043 mmol) and potassium phosphate (2.1 mL, 2.1 mmol, 1N), and the reaction vial was degassed with nitrogen, sealed, and heated to 85° C. for 4 h. It was diluted with water and extracted with ethyl acetate, dried over sodium sulfate, filtered, concentrated and purified on silica gel eluting with hexanes and ethyl acetate to afford the title compound.

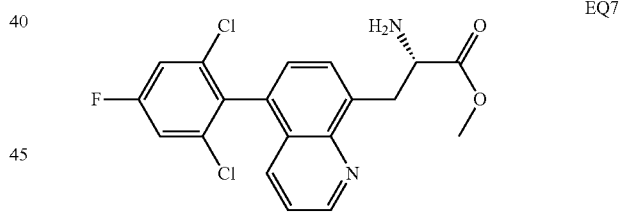

EQ7

Methyl (S)-2-amino-3-(5-(2,6-dichloro-4-fluorophenyl)quinolin-8-yl)propanoate (EQ7)

5-(2,6-dichloro-4-fluorophenyl)-8-(((2S,5R)-5-isopropyl-3,6-dimethoxy-2,5-dihydropyrazin-2-yl)methyl)quinoline (436 mg, 0.893 mmol) was dissolved in THF (3.6 mL) and added aqueous HCl (2.7 mL, 5.4 mmol, 2N). The mixture was stirred for 4.5 h and diluted with sat. NaHCO₃, then extracted with DCM, dried over sodium sulfate, concentrated under vacuum and the residue was purified by silica gel chromatography eluting with dichloromethane and methanol to afford the title compound.

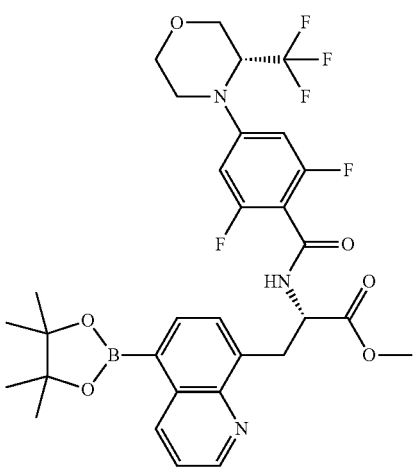

Methyl (S)-2-(2,6-difluoro-4-((R)-3-(trifluoromethyl)morpholino)benzamido)-3-(5-(4,4,5,5-tetramethyl-1,3,2-dioxaborolan-2-yl)quinolin-8-yl)propanoate (EQ8)

To a suspension of methyl (S)-3-(5-bromoquinolin-8-yl)-2-(2,6-difluoro-4-(((R)-1,1,1-trifluorobutan-2-yl)amino)benzamido)propanoate (550 mg, 0.958 mmol), Bis(pinacolato)diboron (292 mg, 1.15 mmol) and potassium acetate (282 mg, 2.87 mmol) in toluene (10 mL) was added [1,1'-bis(diphenylphosphino)ferrocene]dichloropalladium(II), complex with dichloromethane (39 mg, 0.048 mmol) and the reaction vial was degassed with nitrogen, sealed, and heated to 100° C. for 90 min. It was cooled to RT, and water was added and the mixture extracted 3× with EtOAc, dried over sodium sulfate, filtered, and concentrated under vacuum to afford the title compound which was used without further purification.

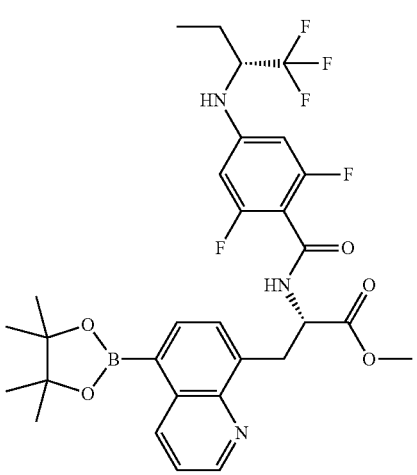

Methyl (S)-2-(2,6-difluoro-4-(((R)-1,1,1-trifluorobutan-2-yl)amino)benzamido)-3-(5-(4,4,5,5-tetramethyl-1,3,2-dioxaborolan-2-yl)quinolin-8-yl)propanoate (EQ9)

To a suspension of methyl (S)-3-(5-bromoquinolin-8-yl)-2-(2,6-difluoro-4-(((R)-1,1,1-trifluorobutan-2-yl)amino)benzamido)propanoate (550 mg, 0.958 mmol), bis(pinacolato)diboron (292 mg, 1.15 mmol) and potassium acetate (282 mg, 2.87 mmol) in toluene (10 mL) was added [1,1'-Bis(diphenylphosphino)ferrocene]dichloropalladium(II), complex with dichloromethane (39 mg, 0.048 mmol) and the reaction vial was degassed with nitrogen, sealed, and heated to 100° C. for 90 min. It was cooled to RT, and water was added and the mixture extracted 3× with EtOAc, dried over sodium sulfate, filtered, and concentrated under vacuum to afford the title compound which was used without further purification.

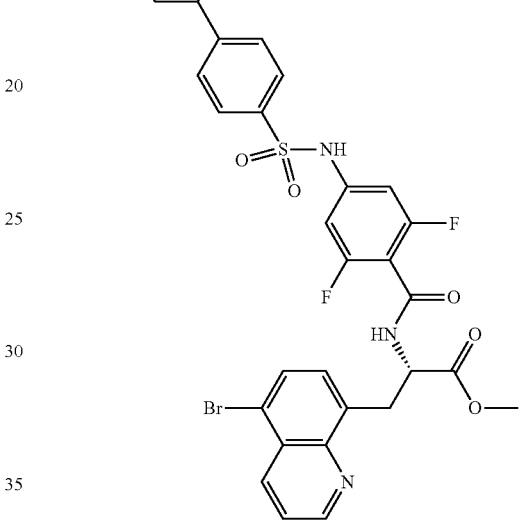

Methyl (S)-3-(8-bromoquinolin-5-yl)-2-(2,6-difluoro-4-((4-(2-fluoropyridin-4-yl)phenyl)sulfonamido)benzamido)propanoate (EQ10)

To a stirred solution of EQ2 (670 mg, 2 mmol) and N-ethyl-N-isopropylpropan-2-amine (840 mg, 2 mmol) in DCM (1.5 mL) HATU (0.83 g, 2 mmol) was added 2,6-difluoro-4-((4-(2-fluoropyridin-4-yl)phenyl)sulfonamido)benzoic acid (0.88 g, 2 mmol). The mixture was stirred overnight, diluted with water, concentrated, and chromatographed on silica gel eluting with methanol in dichloromethane to afford the title compound.

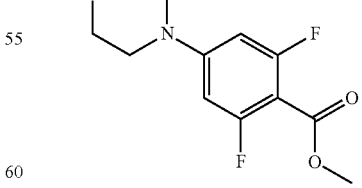

Methyl (R)-2,6-difluoro-4-(3-(trifluoromethyl)morpholino)benzoate

To methyl 4-bromo-2,6-difluorobenzoate (120 g, 478 mmol), 3-(trifluoromethyl)morpholine hydrochloride (109 g, 573 mmol), cesium carbonate (779 g, 2.39 mol), RuPhos (8.92 g, 19.1 mmol), and tBuBrettPhos-Pd-G3 (8.17 g, 9.56 mmol) was added 840 mL Toluene. The mixture was degassed by bubbling with $N_2$ for 10 min then heated to 120° C. for 16 h. Water (500 mL) was added and the mixture was filtered. The filtrate was washed with ethyl acetate (2×200 mL) and organics were washed with brine, dried over sodium sulfate, concentrated and chromatographed on silica gel eluting with petroleum ether, ethyl acetate, and methanol. The residue was stirred with 600 mL of a 15/1 mixture of petroleum ether and ethyl acetate for 12 and filtered to afford 78 g of the racemic title compound which was further resolved by SFC chromatography (column: DAICEL CHIRALPAK AS (250 mm*30 mm, 10 um); mobile phase: [Neu-ETOH]; B %: 14%-14%, 4.5 min) to provide the title compound.

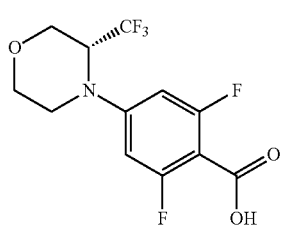

(R)-2,6-difluoro-4-(3-(trifluoromethyl)morpholino) benzoic acid (T1)

methyl (R)-2,6-difluoro-4-(3-(trifluoromethyl)morpholino)benzoate (35 g, 107.5 mmol, 1.00 eq) was added to a round bottom flask charged with THF (100.0 mL) and MeOH (100.0 mL) and $H_2O$ (120.0 mL). Lithium hydroxide (12.9 g, 537 mmol, 5 eq) was added and the mixture heated at 50° C. for 2 h. The mixture was concentrated on a rotary evaporator, extracted with ethyl acetate (3×20 mL) and the combined organic layers were dried over sodium sulfate, concentrated and triturated with petroleum ether/ethyl acetate (5/1, 50 mL×3) for 30 min to afford the title compound.

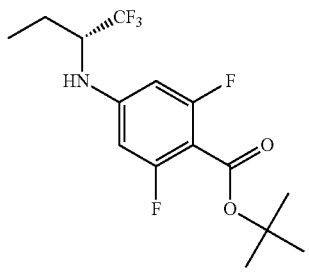 [SMILES: CC[C@@H](Nc1cc(F)c(C(=O)OC(C)(C)C)c(F)c1)C(F)(F)F]

tert-Butyl (R)-2,6-difluoro-4-((1,1,1-trifluorobutan-2-yl)amino)benzoate

To a stirred suspension of tert-butyl 4-bromo-2,6-difluorobenzoate (250 mg, 0.55 mmol), (R)-1,1,1-trifluorobutan-2-amine (85 mg, 0.67 mmol), cesium carbonate (904 mg, 2.8 mmol) and toluene (5 mL) was added XPhos Pd G3 (42 mg, 0.06 mmol). The reaction mixture was sparged with nitrogen and then heated to 90° C. for 12 h. The mixture was cooled to RT and diluted with ethyl acetate (50 mL). The resultant suspension was filtered through a pad of Celite®, and the filtrate was evaporated under reduced pressure to afford the title compound. MS (m/z) 284.1 $[M+H-C_4H_8]^+$.

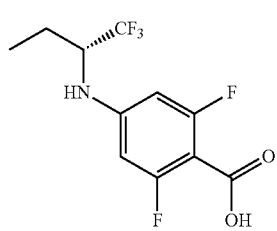

(R)-2,6-difluoro-4-((1,1,1-trifluorobutan-2-yl)amino) benzoic acid (T2)

To a stirred solution of tert-butyl (R)-2,6-difluoro-4-((1,1,1-trifluorobutan-2-yl)amino)benzoate (188 mg, 0.55 mmol) in dichloromethane (1 mL) was added trifluoroacetic acid (1 mL). The reaction mixture was allowed to stir at RT for 20 mins. The reaction mixture was concentrated under reduced pressure to afford crude material. This material was purified by silica gel column chromatography and eluted ethyl acetate in hexanes to afford the title compound. MS (m/z) 338.1 $[M+H]^+$.

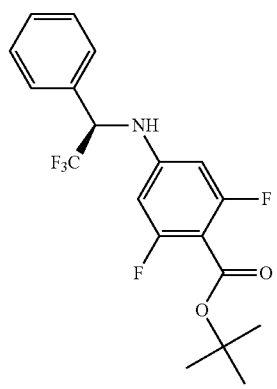 [SMILES: CC(C)(C)OC(=O)c1c(F)cc(N[C@H](c2ccccc2)C(F)(F)F)cc1F]

tert-Butyl (R)-2,6-difluoro-4-((2,2,2-trifluoro-1-phenylethyl)amino)benzoate

To a 500 mL pressure vessel was added tert-butyl 4-bromo-2,6-difluorobenzoate (3 g, 6.65 mmol), (R)-2,2,2-trifluoro-1-phenylethan-1-amine (1.39 g, 7.98 mmol), cesium carbonate, (10.84 g, 33.26 mmol), XPhos Pd G3 (0.5 g, 0.67 mmol), toluene (37 mL) and the mixture was sparged with $N_2$ for 15 min, sealed and stirred at 90° C. overnight. The mixture was cooled, filtered through celite, concentrated under vacuum to afford the title compound which was used without further purification.

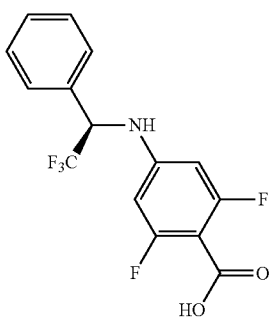

(R)-2,6-Difluoro-4-((2,2,2-trifluoro-1-phenylethyl)amino)benzoic acid (T3)

tert-butyl (R)-2,6-difluoro-4-((2,2,2-trifluoro-1-phenylethyl)amino)benzoate (3.88 g, 10 mmol), was dissolved in DCM (30 mL), then added TFA (30 mL). The solution was swirled and allowed to stand for 1 h. The mixture was concentrated under vacuum, then chromatographed on silica gel eluting with hexanes and ethyl acetate to afford the title compound.

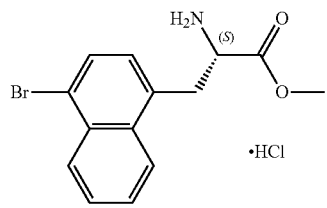

Methyl (S)-2-amino-3-(4-bromonaphthalen-1-yl)propanoate.HCl (N1)

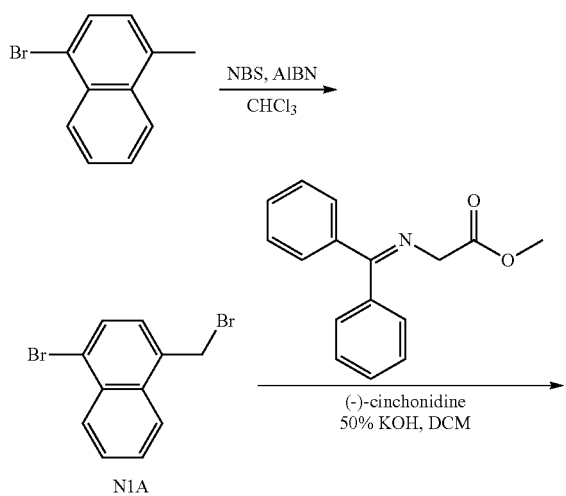

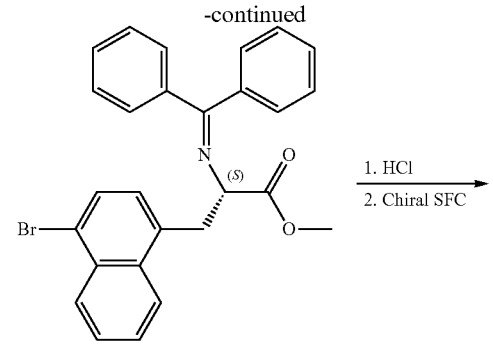

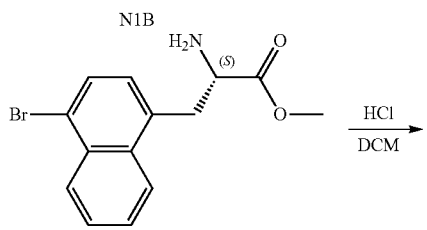

Synthesis of 1-bromo-4-(bromomethyl)naphthalene (N1A)

To a stirred solution of 1-bromo-4-methylnaphthalene (50.0 g, 0.226 mol) in chloroform (1.0 L) was added NBS (39.0 g, 0.226 mol) and AIBN (0.188 g, 1.13 mmol) at RT. The reaction mixture was heated to 70° C. for 16 h. After completion, the reaction was cooled to RT and diluted with DCM. The organic layer was washed with water, brine, and dried over anhydrous $Na_2SO_4$ before concentrating under reduced pressure to afford N1A.

Synthesis of methyl (S)-3-(4-bromonaphthalen-1-yl)-2-((diphenylmethylene) amino)propanoate (N1B)

To a stirred solution of methyl 2-((diphenylmethylene)amino)acetate (38.72 g, 0.153 mol) in dichloromethane (1.53 L) was added (−)-cinchonidine (5.0 g, 0.017 mol) at RT. The reaction mixture was cooled to 0° C. and KOH (0.408 L, 50% aq) was added followed by N1A (51.0 g, 0.17 mol). The reaction mixture was allowed to stir at RT for 6 h. The reaction mixture was diluted with water and stirred for 15 min. The aqueous layer was then extracted with DCM. The combined organic layer was washed with saturated $NaHCO_3$, brine, and dried over anhydrous $Na_2SO_4$. Volatiles were removed under reduced pressure to afford compound N1B. The crude compound was used without further purification for the next step.

Synthesis of methyl (S)-2-amino-3-(4-bromonaphthalen-1-yl)propanoate (N1C)

To a stirred solution of N1B (35.0 g, 0.138 mol) in methanol (0.175 L) was added HCl in 1,4-dioxane (0.35 L, 4M) at 0° C. The reaction mixture was allowed to stir at RT for 16 h. The reaction mixture was concentrated under reduced pressure, dissolved in water, and washed with ethyl acetate. The aqueous layer was adjusted to ~pH 8 using saturated NaHCO₃ and extracted with ethyl acetate. The combined organic layer was dried over anhydrous Na₂SO₄ and concentrated under reduced pressure to afford crude N1C. This material was purified by 100-200 mesh silica gel column chromatography and eluted with 2% methanol in DCM to afford compound N1C (mixture of isomers). The mixture of stereoisomers was then purified by chiral SFC (Chiralpak IC (30×250 mm), 5p; 0.5% isopropyl amine in IPA) to give N1C.

Synthesis of methyl (S)-2-amino-3-(4-bromonaphthalen-1-yl)propanoate HCl (N1)

To a stirred solution of N1C (5.5 g, 16.2 mmol) in dichloromethane (55.0 mL) was added HCl in 1,4-dioxane (16.5 mL, 4M) at 0° C. The reaction mixture was allowed to stir at RT for 30 m. The reaction mixture was concentrated under reduced pressure to obtain N1.

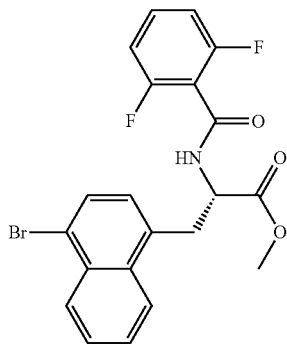

Methyl (S)-3-(4-bromonaphthalen-1-yl)-2-(2,6-difluorobenzamido)propanoate (N2)

To a stirred solution of N1 (172 mg, 0.5 mmol)) in DCM (5 mL) was added 2-fluoro-6-methylbenzoyl chloride (0.07 mL, 0.55 mmol) and TEA (0.35 mL, 2.5 mmol). The reaction mixture was allowed to stir for 1 h, then diluted with DCM and concentrated. The material was purified on silica gel eluting with EtOAc in hexanes (0-80%) to give the title compound.

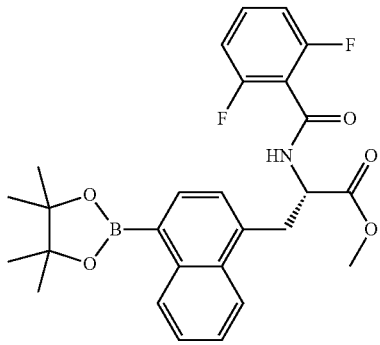

Methyl (S)-2-(2,6-difluorobenzamido)-3-(4-(4,4,5,5-tetramethyl-1,3,2-dioxaborolan-2-yl)naphthalen-1-yl)propanoate (N3)

To a stirred solution of N2 (152 mg, 0.34 mmol) in dioxane (3.5 mL) was added bis(pinacolato)diboron (172 mg, 0.68 mmol), followed by potassium acetate (100 mg, 1.0 mmol) and dichloro 1,1'-bis(diphenylphosphino)ferrocene palladium (II) dichloromethane (22.15 mg, 0.03 mmol). The reaction vessel was flushed with nitrogen then heated to 100° C. for 2 h. EtOAc was added then filtered through Celite and concentrated under reduced pressure to afford the title compound that was used without further purification.

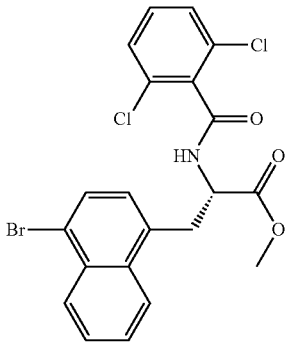

Methyl (S)-3-(4-bromonaphthalen-1-yl)-2-(2,6-dichlorobenzamido)propanoate (N4)

The title compound was prepared according to the method presented for the synthesis of compound N2 starting with N1 and 2,6-dichlorobenzoyl chloride.

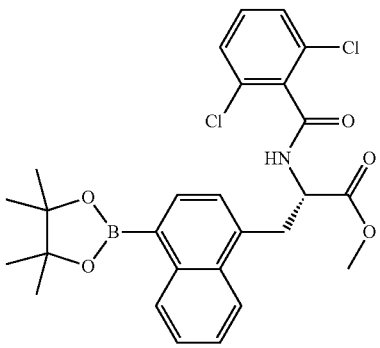

Methyl (S)-2-(2,6-dichlorobenzamido)-3-(4-(4,4,5,5-tetramethyl-1,3,2-dioxaborolan-2-yl)naphthalen-1-yl)propanoate (N5)

The title compound was prepared according to the method presented for the synthesis of compound N3 starting with N4.

N6

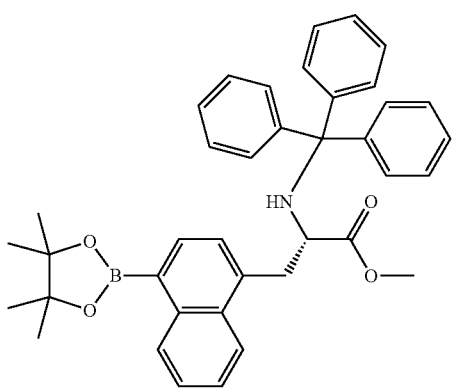

Methyl (S)-3-(4-(4,4,5,5-tetramethyl-1,3,2-dioxa-borolan-2-yl)naphthalen-1-yl)-2-(tritylamino)propanoate (N6)

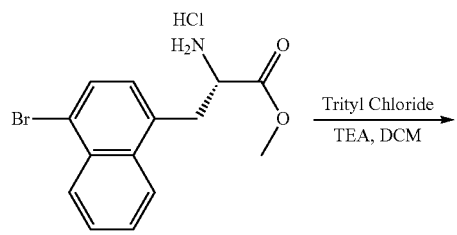

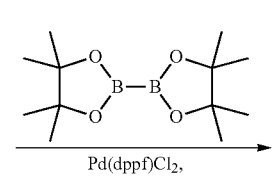

Synthesis of methyl (S)-3-(4-bromonaphthalen-1-yl)-2-(tritylamino)propanoate (N6A)

The title compound was prepared according to the method presented for the synthesis of compound N2 starting with N1 and trityl chloride.

Synthesis of methyl (S)-3-(4-(4,4,5,5-tetramethyl-1,3,2-dioxaborolan-2-yl)naphthalen-1-yl)-2-(tritylamino)propanoate (N6)

The title compound was prepared according to the method presented for the synthesis of compound N-3 starting with N6A.

N7

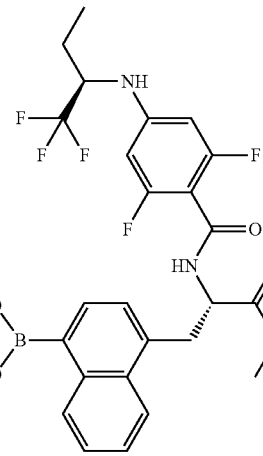

Methyl (S)-2-(2,6-difluoro-4-(((R)-1,1,1-trifluorobutan-2-yl)amino)benzamido)-3-(4-(4,4,5,5-tetramethyl-1,3,2-dioxaborolan-2-yl)naphthalen-1-yl)propanoate (N7)

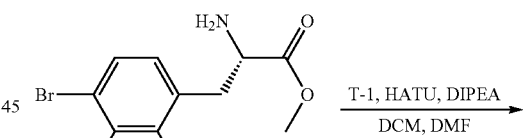

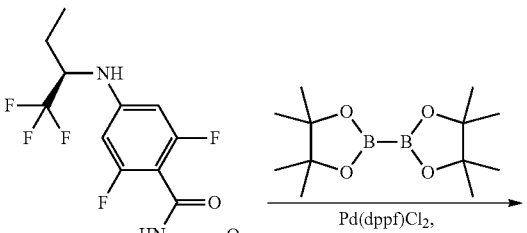

Methyl (S)-2-(2,6-difluoro-4-((R)-3-(trifluoromethyl)morpholino)benzamido)-3-(4-(4,4,5,5-tetramethyl-1,3,2-dioxaborolan-2-yl)naphthalen-1-yl)propanoate (N8)

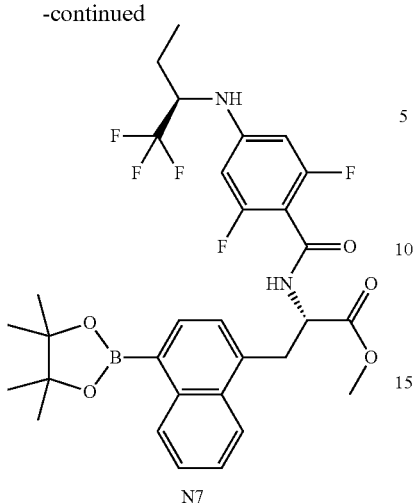

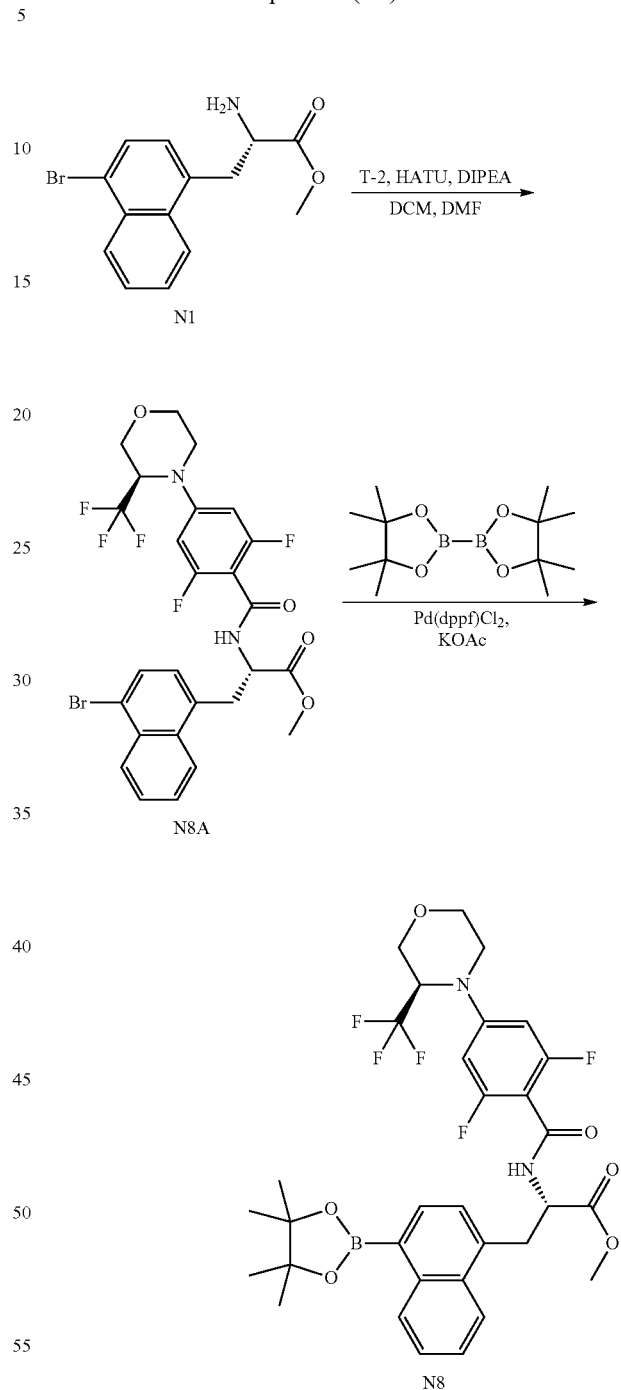

Synthesis of methyl (S)-3-(4-bromonaphthalen-1-yl)-2-(2,6-difluoro-4-(((R)-1,1,1-trifluorobutan-2-yl)amino)benzamido)propanoate (N7A)

To a stirred solution of N1 (100 mg, 0.29 mmol)) in DCM (1 mL) and DMF (1 mL) was added T1 (90 mg, 0.32 mmol), HATU (121 mg, 0.32 mmol) and DIPEA (0.25 mL, 1.5 mmol). The reaction mixture was allowed to stir for 1 h and concentrated. The material was purified on silica gel eluting with EtOAc in hexanes (0-50%) to give the title compound.

Synthesis of methyl (S)-2-(2,6-difluoro-4-(((R)-1,1,1-trifluorobutan-2-yl)amino)benzamido)-3-(4-(4,4,5,5-tetramethyl-1,3,2-dioxaborolan-2-yl)naphthalen-1-yl)propanoate (N7)

To a stirred solution of N7A (149 mg, 0.26 mmol) in dioxane (3 mL) was added bis(pinacolato)diboron (131 mg, 0.52 mmol), followed by potassium acetate (76 mg, 0.78 mmol) and dichloro 1,1'-bis(diphenylphosphino)ferrocene palladium (II) dichloromethane (17 mg, 0.02 mmol). The reaction vessel was flushed with nitrogen then heated to 100° C. overnight. EtOAc was added then filtered through Celite and concentrated under reduced pressure. The crude was purified on silica gel eluting with EtOAc in hexanes (0-60%) to give the title compound.

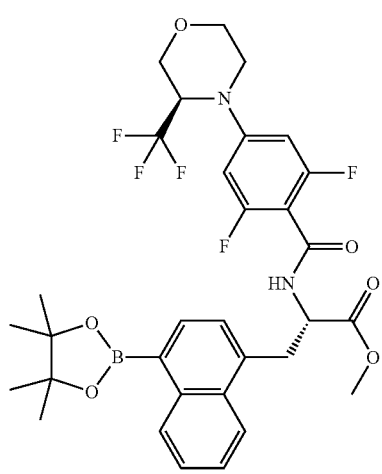

Synthesis of methyl (S)-3-(4-bromonaphthalen-1-yl)-2-(2,6-difluoro-4-((R)-3-(trifluoromethyl)morpholino)benzamido)propanoate (N8A)

The title compound was prepared according to the method presented for the synthesis of compound N7A starting with N1 and T2.

Synthesis of (S)-2-(2,6-difluoro-4-((R)-3-(trifluoromethyl)morpholino)benzamido)-3-(4-(4,4,5,5-tetramethyl-1,3,2-dioxaborolan-2-yl)naphthalen-1-yl)propanoate (N8)

The title compound was prepared according to the method presented for the synthesis of compound N3 starting with N8A.

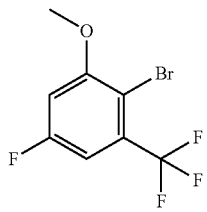

2-Bromo-5-fluoro-1-methoxy-3-(trifluoromethyl)benzene (H1)

To a stirred solution of 2-bromo-5-fluoro-3-(trifluoromethyl)phenol (0.21 g, 0.64 mmol) in DMF was added $K_2CO_3$ (133 mg, 0.96 mmol) and iodomethane (0.105 g, 0.74 mmol). The reaction mixture was allowed to stir ON at RT. EtOAc and water was added to the reaction mixture. The organic layer was washed with brine, dried over anhydrous $Na_2SO_4$, and concentrated under reduced pressure and purified by silica gel chromatography using hexanes/EtOAc as gradient.

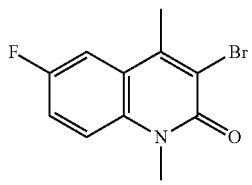

3-Bromo-6-fluoro-1,4-dimethylquinolin-2(1H)-one (H2)

To a solution of 6-fluoro-1,4-dimethylquinolin-2(1H)-one (210 mg, 1.1 mmol) in $CH_3CN$ (11 mL, 0.1 M) was added NBS (489 mg, 2.75 mmol) and the mixture was heated at 100° C. for 1.5 h in a MW reactor, and then filtered. The material was used directly in the next step.

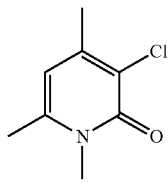

3-Chloro-1,4,6-trimethylpyridin-2(1H)-one (H3)

3-chloro-4,6-dimethylpyridin-2(1H)-one (0.950 g, 6 mmol), methyl iodide, (0.375 mL, 6 mmol), potassium carbonate (0.83 g, 6 mmol) and DME were combined and heated to 95° C. for 2 h. The reaction mixture was partitioned between ethyl acetate and water, layers were separated and the organics were dried over sodium sulfate, filtered and concentrated. The material was chromatographed on silica gel eluting with EA in hexanes 0-100% to afford the title compound.

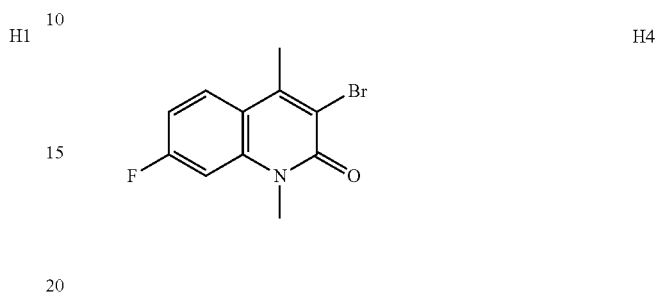

3-Bromo-7-fluoro-1,4-dimethylquinolin-2(1H)-one (H4)

a) 7-Fluoro-1,4-dimethylquinolin-2(1H)-one: To a stirred solution of 7-fluoro-4-methylquinolin-2-ol (1.0 g, 5.644 mmol) in DMF (56 mL) at 0° C. was added sodium hydride (0.293 g, 7.337 mmol) and methyl iodide (0.422 mL, 6.773 mmol). The reaction mixture was allowed to stir while warming to room temperature for 12 h. The reaction was quenched with NaOH (2 mL, 1 M) then water and EtOAc were added. The organic phase was separated and the aqueous phase was extracted with EtOAc (3×). The combined organic phases were dried over $Na_2SO_4$ and concentrated under reduced pressure. The crude mixture was purified via trituration from DCM to afford the title compound.

b) 3-Bromo-7-fluoro-1,4-dimethylquinolin-2(1H)-one: To a stirred solution of 7-fluoro-1,4-dimethylquinolin-2(1H)-one (414 mg, 2.165 mmol) in DMF (2 mL) was added N-bromosuccinimide (424 mg, 2.382 mmol) and the reaction mixture was allowed to stir under microwave irradiation at 110° C. for 30 min. The mixture was filtered to afford the title compound without further purification.

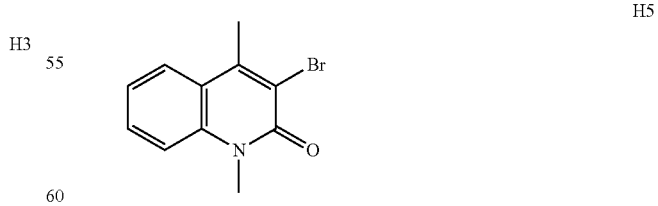

3-Bromo-1,4-dimethylquinolin-2(1H)-one (H5)

Prepared as described in Journal of Organic Chemistry (1961), 26, 4949-5.

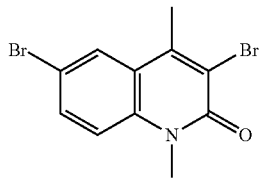

6-Bromo-3-iodo-1,4-dimethylquinolin-2(1H)-one (H6)

To a solution of (H5) (160 mg, 0.635 mmol) in DMF (6.00 mL, 0.1 M) was added NBS (124 mg, 0.698 mmol) and the mixture was stirred overnight. The mixture was filtered to afford the title compound.

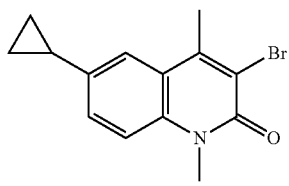

3-Bromo-6-cyclopropyl-1,4-dimethylquinolin-2(1H)-one (H7)

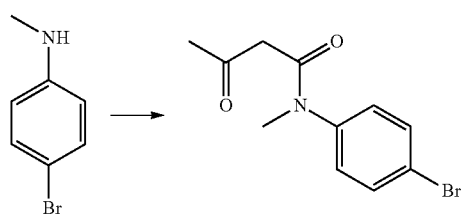

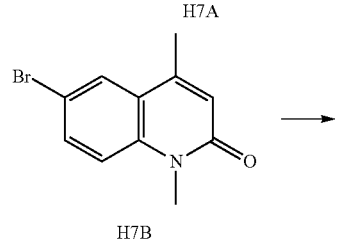

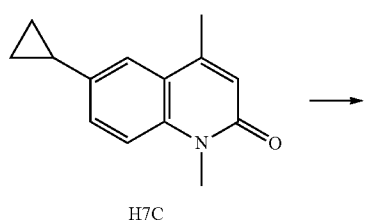

a) N-(4-Bromophenyl)-N-methyl-3-oxobutanamide (H7A): To a stirred solution of 4-bromo-N-methylaniline (1.0 g, 5.375 mmol) in toluene (5 mL) was added 2,2,6-trimethyl-4H-1,3-dioxin-4-one (0.79 ml, 5.91 mmol) and allowed to stir open to the atmosphere at 100° C. for 2 h. Upon completion (monitored with LCMS and TLC 50:50 EtOAc:hexanes), the reaction mixture was concentrated under reduced pressure and the crude product was purified via silica gel chromatography eluting hexanes/EtOAc 0-100% to afford the title compound.

b) 6-Bromo-1,4-dimethylquinolin-2(1H)-one (H7B): A stirred solution of H7A (1.78 g, 6.59 mmol) in conc. sulfuric acid (7.0 mL) was heated to 95° C. for 2 h. The reaction mixture was poured over ice and filtered to afford the title compound without further purification.

c) 3-Bromo-6-cyclopropyl-1,4-dimethylquinolin-2(1H)-one (H7C): To a solution of H7B (0.13 g, 0.52 mmol) in degassed toluene:water (4:1, 50 mL) was added $K_3PO_4$ (657 mg, 3.1 mmol), cyclopropyl boronic acid (133 mg, 1.55 mmol), and palladium tetrakistriphenylphosphine (60 mg, 0.052 mmol) in a sealed tube. The mixture was heated at 108° C. overnight. The mixture was diluted with EtOAc, washed with water, dried ($Na_2SO_4$), and concentrated under reduced pressure to provide the product. The material was purified using flash chromatography (EtOAc in hexanes 12-100%) to afford the title compound.

d) 3-Bromo-6-cyclopropyl-1,4-dimethylquinolin-2(1H)-one (H7): To a stirred solution of H7C (453 mg, 2.124 mmol) in DMF (21 mL) was added N-bromosuccinimide (416 mg, 2.336 mmol) and the reaction was allowed to stir at room temperature for 12 h. The crude product was purified via silica gel chromatography eluting hexanes/EtOAc 12-100% to afford the title compound.

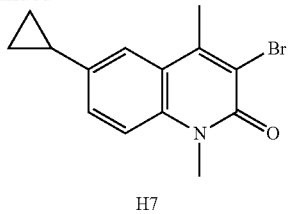

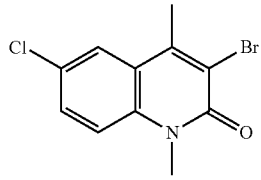

6-Chloro-3-bromo-1,4-dimethylquinolin-2(1H)-one (H8)

Prepared analogously to the method to produce H6 employing 6-chloro-1,4-dimethylquinolin-2(1H)-one in place of 3-bromo-1,4-dimethylquinolin-2(1H)-one.

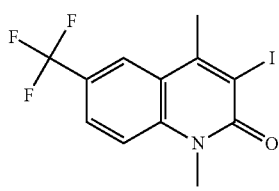

3-Iodo-1,4-dimethyl-6-(trifluoromethyl)quinolin-2(1H)-one (H9)

a) Synthesis of N-methyl-N-(4-(trifluoromethyl)phenyl)but-2-ynamide (H9A): To a solution of the N-methylaniline (1.5 g, 8.56 mmol) in CH$_2$Cl$_2$ (0.25 M) was added tetralic acid (0.79 g, 9.42 mmol) and DMAP (0.105 g, 0.856 mmol) at 0° C., followed by a solution of DCC (2.65 g, 12.85 mmol) in CH$_2$Cl$_2$. The reaction mixture was warmed to RT and stirred overnight. The mixture was filtrated, washed with CH$_2$Cl$_2$ and the filtrate was evaporated to provide the crude intermediate, which was purified using silica gel flash chromatography 10-100% EtOAc in hexanes to afford the product.

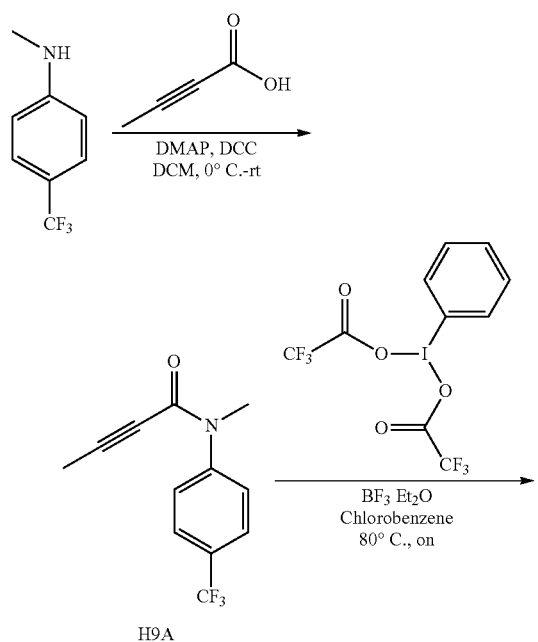

H9A

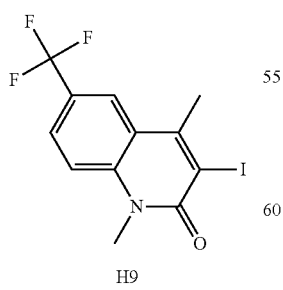

H9 b) Synthesis of 3-iodo-1,4-dimethyl-6-(trifluoromethyl)quinolin-2(1H)-one (H9): To a solution of H9A (0.234 g, 0.97 mmol) in chlorobenzene (0.1 M) was added a pre-mixed solution of PIFA (0.918 g, 2.134 mmol) and BF$_3$.OEt$_2$ (0.296 g, 0.97 mmol) in chlorobenzene (0.1 M) at RT under a N$_2$ atmosphere. The reaction was then heated at 80° C. overnight.

Upon completion, the solvent was removed under reduced pressure and the crude residue was dissolved in EtOAc, washed with Satd. NaHCO$_3$, dried (Na$_2$SO$_4$), and concentrated under reduced pressure. The crude was purified using silica gel flash chromatography 10-100% EtOAc in hexanes to afford the title compound.

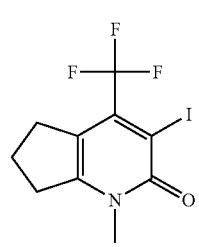

3-Iodo-1-methyl-4-(trifluoromethyl)-1,5,6,7-tetrahydro-2H-cyclopenta[b]pyridin-2-one (H10)

a) To a stirred solution of 4-(trifluoromethyl)-1,5,6,7-tetrahydro-2H-cyclopenta[b]pyridin-2-one (2.5 g, 12.31 mmol) and potassium carbonate (1.87 g, 0.01 mol) in DMF (20 mL) was added methyl iodide (1.92 g, 14 mmol). After stirring overnight the mixture was diluted with ethyl acetate, washed with brine and the organic layer was concentrated and the residue was purified by silica gel chromatography eluting with ethyl acetate in hexanes to afford 1-methyl-4-(trifluoromethyl)-1,5,6,7-tetrahydro-2H-cyclopenta[b]pyridin-2-one. $^1$H NMR (400 MHz, DMSO-d6) δ 6.54 (q, J=1.1 Hz, 1H), 3.43 (s, 3H), 3.07-2.91 (m, 2H), 2.79 (t, J=7.2 Hz, 2H), 2.12 (q, J=7.7 Hz, 2H).

b) To a stirred suspension of 1-methyl-4-(trifluoromethyl)-1,5,6,7-tetrahydro-2H-cyclopenta[b]pyridin-2-one (158 mg, 0.73 mmol) in THF (7 mL) at −78° C. was dropwise added 1 M 2,2,6,6-tetramethylpiperidinylmagnesium chloride, lithium chloride in THF (1.1 ml, 1N, 1.1 mmol). After 30 min solid iodine was added and the reaction mixture was removed from the dry ice bath and continued to stir for 1 h. The reaction mixture was adsorbed onto silica gel and chromatographed eluting with ethyl acetate in hexanes to afford the title compound.

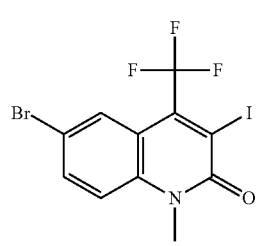

6-Bromo-3-iodo-1-methyl-4-(trifluoromethyl)quinolin-2(1H)-one (H11)

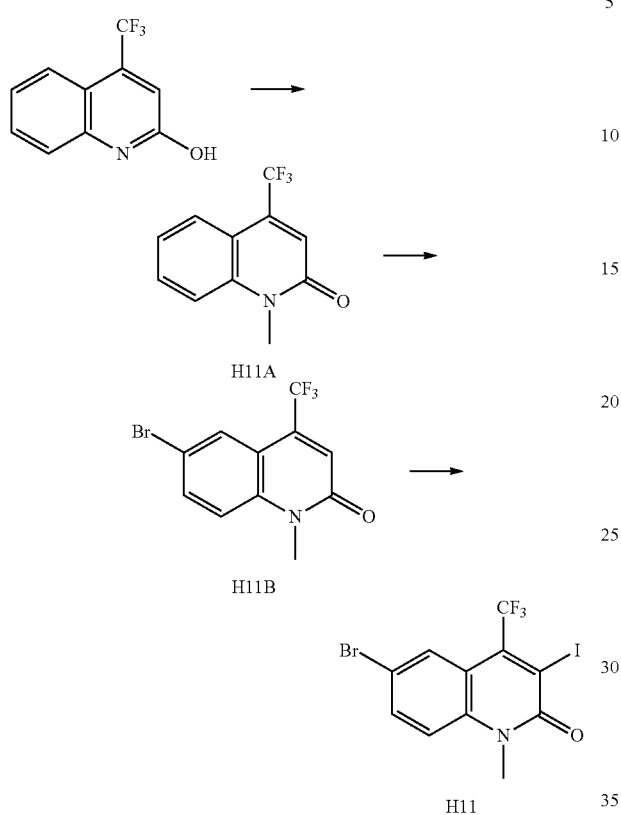

a) 1-Methyl-4-(trifluoromethyl)quinolin-2(1H)-one: To a stirred solution of 4-(trifluoromethyl)quinolin-2-ol (3.15 g, 0.015 mol) in DMF (10 mL) was added sodium hydride (0.711 g, 0.018 mol) and the reaction mixture was allowed to stir at room temperature for 20 min. Iodomethane (1.383 mL, 0.022 mol) was added and the reaction mixture was allowed to stir 14 h. The reaction was concentrated under reduced pressure and purified via silica gel chromatography eluting hexanes/EtOAc 0-100% to afford the title compound as a mixture of N-methyl and O-methyl.

b) 6-Bromo-1-methyl-4-(trifluoromethyl)quinolin-2(1H)-one: To a stirred solution of 1-methyl-4-(trifluoromethyl)quinolin-2(1H)-one (0.60 g, 0.003 mol) in acetonitrile was added N-bromosuccinimide (1.175 g, 0.007 mol) and the reaction was allowed to stir at 125° C. for 3 h. The reaction mixture was concentrated under reduced pressure and purified via silica gel chromatography to afford the title compound.

c) 6-Bromo-3-iodo-1-methyl-4-(trifluoromethyl)quinolin-2(1H)-one: To a stirred solution of 6-bromo-1-methyl-4-(trifluoromethyl)quinolin-2(1H)-one (641 mg, 2.094 mmol) in THF (15 mL) at –78° C. was added 2,2,6,6-tetramethylpiperidinylmagnesium chloride lithium chloride in THF (1 M, 2.51 mL, 2.513 mmol). The reaction mixture was allowed to stir at –78° C. for 30 min then iodine (1.329 g, 0.005 mol) in THF (5 mL) was added dropwise and the reaction was allowed to stir at –78° C. for an additional 10 min. The reaction mixture was purified via direct loading onto silica gel and subsequent normal phase chromatography eluting hexanes/EtOAc 0-60% to afford the title compound.

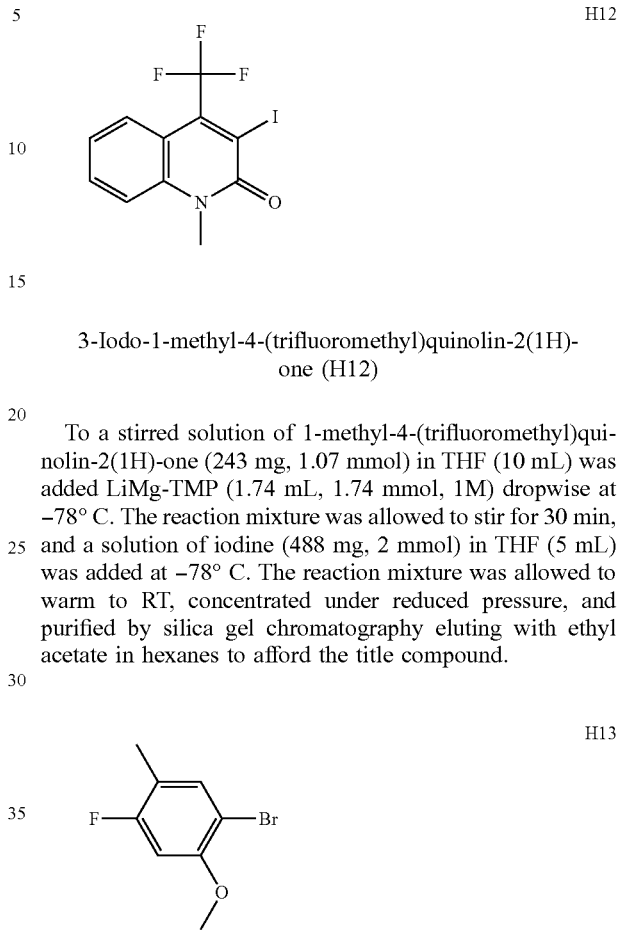

3-Iodo-1-methyl-4-(trifluoromethyl)quinolin-2(1H)-one (H12)

To a stirred solution of 1-methyl-4-(trifluoromethyl)quinolin-2(1H)-one (243 mg, 1.07 mmol) in THF (10 mL) was added LiMg-TMP (1.74 mL, 1.74 mmol, 1M) dropwise at –78° C. The reaction mixture was allowed to stir for 30 min, and a solution of iodine (488 mg, 2 mmol) in THF (5 mL) was added at –78° C. The reaction mixture was allowed to warm to RT, concentrated under reduced pressure, and purified by silica gel chromatography eluting with ethyl acetate in hexanes to afford the title compound.

H13

1-Bromo-4-fluoro-2-methoxy-5-methylbenzene (H13)

To a stirred solution of 5-fluoro-2-bromo-4-methylphenol (300 mg, 0.952 mmol) and K$_2$CO$_3$ (197 mg, 1.428 mmol) in DMF (2 mL) was added iodomethane (0.068 mL, 1.095 mmol) and the reaction mixture was allowed to stir at room temperature for 1 hr. The reaction mixture was diluted with EtOAc, filtered, concentrated under reduced pressure, and purified via silica gel chromatography eluting hexanes/EtOAc 0-50% to afford the title compound.

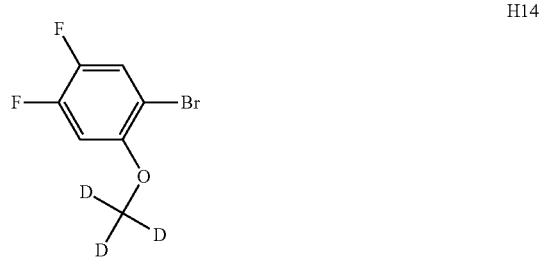 [SMILES: [2H]C([2H])([2H])Oc1cc(F)c(F)cc1Br]

1-Bromo-4,5-difluoro-2-(methoxy-d3)benzene (H14)

To a stirred solution of 2-bromo-4,5-difluorophenol (200 mg, 0.766 mmol) and K$_2$CO$_3$ (159 mg, 1.148 mmol) in DMF (1 mL) was added iodomethane-D$_3$ (128 mg, 0.880 mmol) and the reaction mixture was allowed to stir at room temperature for 1 hr. The reaction mixture was diluted with EtOAc, filtered, concentrated under reduced pressure, and purified via silica gel chromatography eluting hexanes/EtOAc 0-50% to afford the title compound.

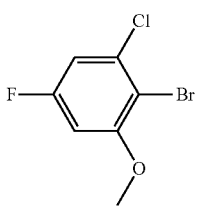

2-Bromo-1-chloro-5-fluoro-3-methoxybenzene (H15)

To a stirred solution of 2-bromo-3-chloro-5-fluorophenol (250 mg, 0.887 mmol) and K$_2$CO$_3$ (184 mg, 1.331 mmol) in DMF (1.5 mL) was added iodomethane (0.064 mL, 1.020 mmol) and the reaction mixture was allowed to stir at room temperature for 1 hr. The reaction mixture was diluted with EtOAc, filtered, concentrated under reduced pressure, and purified via silica gel chromatography eluting hexanes/EtOAc 0-50% to afford the title compound.

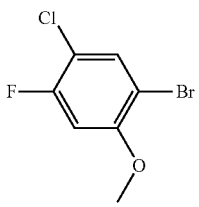

1-Bromo-5-chloro-4-fluoro-2-methoxybenzene (H16)

To a stirred solution of 2-bromo-4-chloro-5-fluorophenol (200 mg, 0.710 mmol) and K$_2$CO$_3$ (147 mg, 1.06 mmol) in DMF (1 mL) was added iodomethane (0.051 mL, 0.816 mmol) and the reaction mixture was allowed to stir at room temperature for 1 hr. The reaction mixture was diluted with EtOAc, filtered, concentrated under reduced pressure, and purified via silica gel chromatography eluting hexanes/EtOAc 0-50% to afford the title compound.

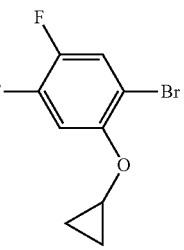

1-Bromo-2-cyclopropoxy-4,5-difluorobenzene (H17)

To a stirred solution of 2-bromo-4,5-difluorophenol (500 mg, 2.4 mmol) in DMF was added KI (397 mg, 2.4 mmol), Cs$_2$CO$_3$ (445 mg, 7 mmol) and bromocyclopropane (0.575 mL, 7 mmol). The reaction mixture was heated at 180° C. for 2 h in a microwave reactor. The reaction mixture was diluted with EtOAc and water. The aqueous layer was adjusted to pH 2 with 2M NaOH, extracted with EtOAc (2×), and the organic layer was washed with brine and concentrated. The crude product was purified via silica gel chromatography eluting hexanes/EtOAc 0-10% to afford the title compound.

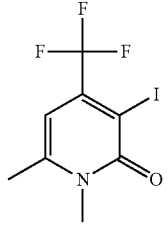

3-Iodo-1,6-dimethyl-4-(trifluoromethyl)pyridin-2 (1H)-one (H18)

Prepared according to the procedure for H10 employing 6-methyl-4-(trifluoromethyl)pyridin-2(1H)-one as starting material.

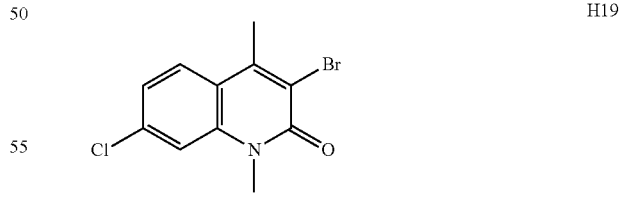

3-Bromo-7-chloro-1,4-dimethylquinolin-2(1H)-one (H19)

a) 7-Chloro-1,4-dimethylquinolin-2(1H)-one: To a stirred solution of N-(3-chlorophenyl)-N-methyl-3-oxobutanamide was added H$_2$SO$_4$ (5 mL) and the mixture was heated to 95° C. for 2 h, poured over ice, filtered and used in the next step without further purification.

b) 3-Bromo-7-chloro-1,4-dimethylquinolin-2(1H)-one: To a solution of 7-chloro-1,4-dimethylquinolin-2(1H)-one (0.54 g, 2.6 mmol) in DMF (26 mL) was added NBS (0.51 g, 2.86 mmol) and the mixture was stirred at overnight. The reaction was added to silica gel and chromatographed eluting with ethyl acetate in hexanes to afford 0.54 g of the title compound.

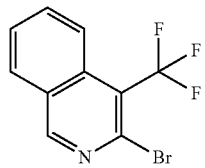

3-Bromo-4-(trifluoromethyl)isoquinoline (H20)

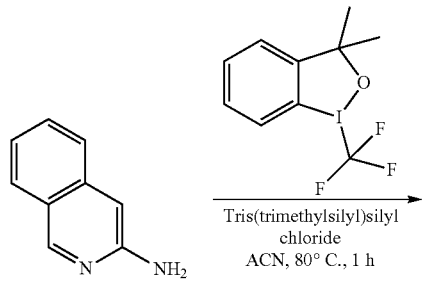

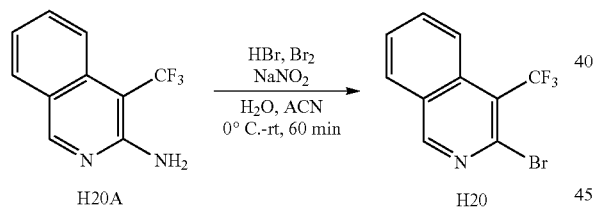

a) Synthesis of 4-(trifluoromethyl)isoquinolin-3-amine (H20A): To a sealed tube, tris(trimethylsilyl)silyl chloride (0.35 ml, 1.25 mmol), 3-aminoisoquinoline (150 mg, 1.04 mmol), and Togni's reagent (412 mg, 1.25 mmol) were dissolved in ACN and was heated to 80° C. for 1 hour. Then the reaction mixture was concentrated and purified on silica gel eluting with EtOAc/hexanes 0-100%.

b) Synthesis of 3-bromo-4-(trifluoromethyl)isoquinoline (H20): H20A (221 mg, 1.04 mmol) was added to HBr solution (16.8 mL, 148 mmol) at 0° C. (ice bath), then Br₂ (0.32 mL, 6.25 mmol) was added slowly at 0° C., stir for 10 min and NaNO₂ (360 mg, 5.21 mmol) in water was added dropwise over 5 min. The reaction mixture was stirred at 0° C. for 30 min then allowed to warm to RT for 60 min. Quench with satd. NaHCO₃ and extracted with DCM (3×). Organic layers were combined, concentrated and purified using silica gel eluting with 0-15% EtOAc in hexanes.

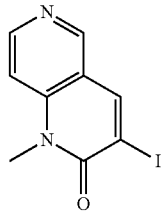

3-Iodo-1-methyl-1,6-naphthyridin-2(1H)-one (H21)

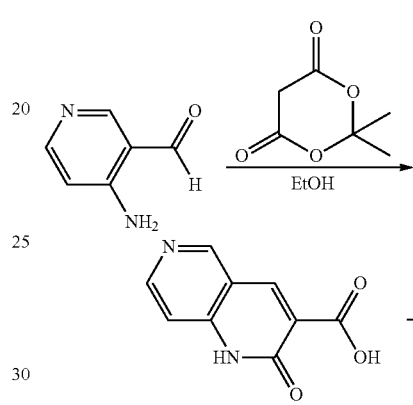

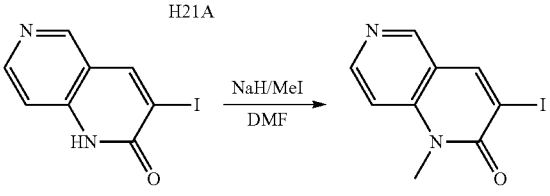

a) Synthesis of 2-oxo-1,2-dihydro-1,6-naphthyridine-3-carboxylic acid (H21A): To a stirred solution of 4-aminonicotinaldehyde (0.15 g, 1.2 mmol) in EtOH (2 mL) was added Meldrum's acid (0.17 g, 1.2 mmol), piperidine (10 µL, 0.13 mmol), and acetic acid (20 µL, 0.36 mmol). The reaction mixture was stirred at room temperature for 20 min and then heated at 100° C. for 2 h. After cooling to room temperature, the mixture was filtered, washed with EtOH, and dried in vacuum to give the title compounds without further purification.

b) Synthesis of 3-iodo-1,6-naphthyridin-2(1H)-one (H21B): In a microwave vial (10 mL) that contained a solution of compound H21A (80 mg, 0.42 mmol) in a mixture of DMF/water (9:1, 5 mL) were added NIS (331 mg, 1.47 mmol) and LiOAc (42 mg, 0.63 mmol). The vial was sealed and then heated under microwave heating at 120° C. for 30 min. After cooling, water was added, and the mixture was extracted with DCM. The organic layer was washed with brine, dried with Na₂SO₄, filtered, and concentrated under reduced pressure to give the title compound which was used without further purification.

c) Synthesis of 3-iodo-1-methyl-1,6-naphthyridin-2-one (H21): To a stirred solution of compound H21B (114 mg, 0.42 mmol) in DMF (4 mL) at 0° C. was added sodium hydride (60%, 20 mg, 0.5 mmol) and the mixture was stirred for 10 min at 0° C., followed by the addition of MeI (31 μL, 0.5 mmol). Ice bath was removed, and the reaction mixture was stirred at RT for 30 min. EA and water was added to the reaction mixture. The organic layer was washed with brine, dried over anhydrous $Na_2SO_4$, and concentrated under reduced pressure. The material was purified by silica gel chromatography using MeOH in DCM as eluent to afford the title compound.

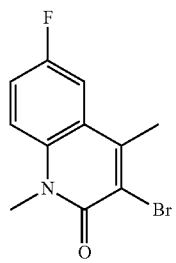

3-Bromo-6-fluoro-1,4-dimethylquinolin-2(1H)-one (H22)

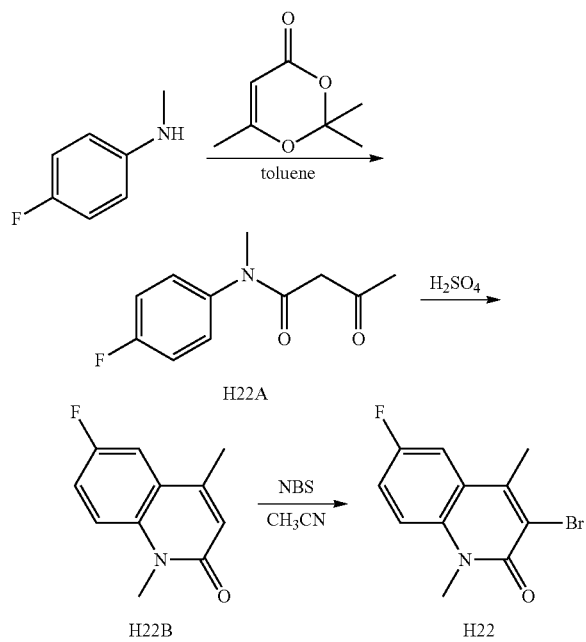

a) Synthesis of N-(4-fluorophenyl)-N-methyl-3-oxobutanamide (H22A): To a solution of N-methylaniline (0.500 g, 4.00 mmol) in toluene (4.0 mL) at 110° C. in an open vial (to evaporate off acetone-byproduct) was added 2,2,6-trimethyl-4H-1,3-dioxin-4-one (0.568 g, 4.00 mmol) and the mixture was heated at 110° C. for 3 h. Upon completion, the solvent was evaporated off under reduced pressure. The material was purified by flash chromatography using EA in hexanes to afford the product (mixture of keto and enol form).

b) Synthesis of 6-fluoro-1,4-dimethylquinolin-2(1H)-one (H22B): A mixture of H22A (0.250 g, 1.20 mmol) and concentrated $H_2SO_4$ (5.53 g, 56.4 mmol) was heated at 95° C. for 2 h. Upon completion, the reaction mixture was poured over ice. The precipitate was filtered off to afford the product that was used without further purification.

c) Synthesis of 3-bromo-6-fluoro-1,4-dimethylquinolin-2(1H)-one (H22): To a microwave vial was added H22B (0.210 g, 1.10 mmol), NBS (0.489 g, 2.75 mmol) and $CH_3CN$ (11 mL), and the mixture was heated at 100° C. for 1 h. The precipitate was filtered off to afford the title compound and used without further purification.

Compounds and Synthesis

Example 1

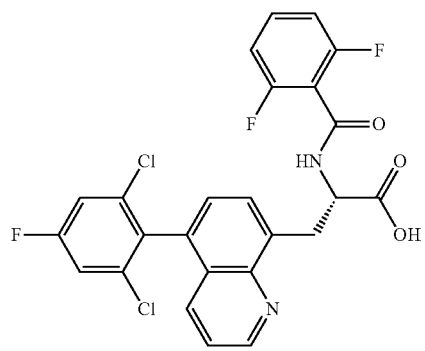

Methyl (S)-3-(5-(2,6-dichloro-4-fluorophenyl)quinolin-8-yl)-2-(2,6-difluoro benzamido)propanoate To a stirred solution of methyl (S)-2-amino-3-(5-(2,6-dichloro-4-fluorophenyl)quinolin-8-yl)propanoate (EQ7) (75 mg, 0.191 mmol) in DCM (2 mL) was added N,N-diisopropylethylamine (0.066 mL) and 2,6-difluorobenzoyl chloride (0.03 mL, 0.229 mmol) was then added. After stirring for 30 min the mixture was directly loaded onto silica gel and chromatographed on silica gel eluting with hexanes and ethyl acetate (0-100%) to afford the title compound.

Example 1: (S)-3-(5-(2,6-dichloro-4-fluorophenyl)quinolin-8-yl)-2-(2,6-difluorobenzamido)propanoic acid Methyl (S)-3-(5-(2,6-dichloro-4-fluorophenyl)quinolin-8-yl)-2-(2,6-difluorobenzamido)propanoate (100 mg, 0.188 mmol) was dissolved in THF (2 mL) added 2N NaOH (0.75 mL, 2 mmol) and stirred for 90 min. The mixture was acidified with TFA, diluted with DMSO and chromatographed on C18 eluting with acetonitrile and water containing 0.4% TFA to afford the title compound. MS (m/z) 519.1 $[M+H]^+$. 1H NMR (400 MHz, DMSO-d6) δ 9.20 (d, J=8.1 Hz, 1H), 9.00 (dd, J=4.1, 1.7 Hz, 1H), 7.79 (d, J=7.3 Hz, 1H), 7.76 (d, J=8.6 Hz, 2H), 7.71 (dd, J=8.5, 1.7 Hz, 1H), 7.54 (dd, J=8.5, 4.1 Hz, 1H), 7.47 (tt, J=8.4, 6.5 Hz, 1H), 7.43 (d, J=7.3 Hz, 1H), 7.14-7.03 (m, 2H), 5.01 (ddd, J=10.5, 8.1, 4.8 Hz, 1H), 4.01 (dd, J=13.5, 4.8 Hz, 1H), 3.41 (dd, J=13.6, 10.5 Hz, 1H).

Example 2

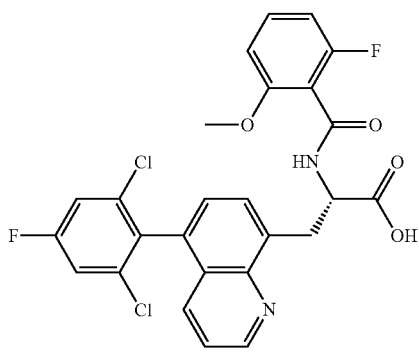

(S)-3-(5-(2,6-dichloro-4-fluorophenyl)quinolin-8-yl)-2-(2-fluoro-6-methoxybenzamido)propanoic acid The title compound was prepared according to the method presented for the synthesis of Example 1 replacing 2-fluoro-6-methoxybenzoyl chloride for 2,6-difluorobenzoyl chloride. MS (m/z) 531.1 [M+H]$^+$. 1H NMR (400 MHz, DMSO-d6) δ 8.99 (dd, J=4.2, 1.7 Hz, 1H), 8.89 (d, J=7.9 Hz, 1H), 7.82 (d, J=7.4 Hz, 1H), 7.79-7.75 (m, 2H), 7.72 (dd, J=8.5, 1.7 Hz, 1H), 7.55 (dd, J=8.5, 4.1 Hz, 1H), 7.48 (d, J=7.3 Hz, 1H), 7.35 (td, J=8.4, 6.8 Hz, 1H), 6.85 (dd, J=8.5, 0.8 Hz, 1H), 6.77 (ddd, J=9.1, 8.4, 0.8 Hz, 1H), 4.91 (ddd, J=10.4, 7.8, 4.6 Hz, 1H), 3.92 (dd, J=13.9, 4.6 Hz, 1H), 3.65 (s, 3H), 3.47 (dd, J=14.0, 10.4 Hz, 1H).

Example 3

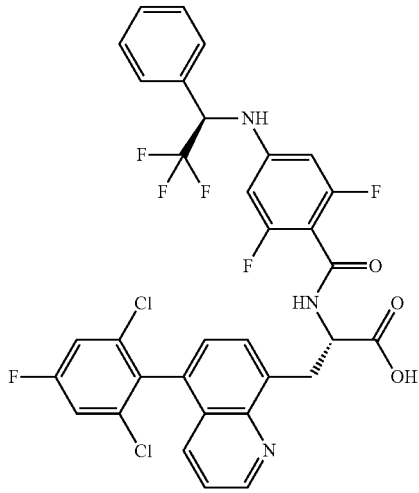 [SMILES: O=C(N[C@@H](Cc1ccc(-c2c(Cl)cc(F)cc2Cl)c2cccnc12)C(=O)O)c1c(F)cc(N[C@H](c2ccccc2)C(F)(F)F)cc1F]

Methyl (S)-3-(5-(2,6-dichloro-4-fluorophenyl)quinolin-8-yl)-2-(2,6-difluoro-4-(((R)-2,2,2-trifluoro-1-phenylethyl)amino)benzamido)propanoate To a stirred solution of methyl (S)-2-amino-3-(5-(2,6-dichloro-4-fluorophenyl)quinolin-8-yl)propanoate (EQ7) (30 mg, 0.076 mmol) in DCM (1 mL) was added N,N-diisopropylethylamine (0.04 mL), 1-[bis (dimethylamino) methylene]-1H-1,2,3-triazolo[4,5-b]pyridinium 3-oxide hexafluorophosphate (HATU) (44 mg, 0.11 mmol) and (R)-2,6-difluoro-4-((2,2,2-trifluoro-1-phenylethyl)amino)benzoic acid (T3) (30 mg, 0.09 mmol) was then added. After stirring for 30 min the mixture was directly loaded onto silica gel and chromatographed on silica gel eluting with hexanes and ethyl acetate (0-100%) to afford the title compound.

(S)-3-(5-(2,6-dichloro-4-fluorophenyl)quinolin-8-yl)-2-(2,6-difluoro-4-(((R)-2,2,2-trifluoro-1-phenylethyl)amino)benzamido)propanoic acid methyl (S)-3-(5-(2,6-dichloro-4-fluorophenyl)quinolin-8-yl)-2-(2,6-difluoro-4-(((R)-2,2,2-trifluoro-1-phenylethyl) amino) benzamido)propanoate (39 mg, 0.069 mmol) was dissolved in THF (2 mL), added 2N NaOH (0.75 mL, 2 mmol) and stirred for 90 min. The mixture was acidified with TFA, diluted with DMSO and chromatographed on C18 eluting with acetonitrile and water containing 0.4% TFA to afford the title compound. MS (m/z) 692.1 [M+H]$^+$. 1H NMR (400 MHz, DMSO-d6) δ 8.98-8.95 (m, 1H), 8.77 (d, J=7.9 Hz, 1H), 7.78-7.74 (m, 3H), 7.69 (dd, J=8.5, 1.7 Hz, 1H), 7.57 (d, J=7.2 Hz, 2H), 7.54-7.48 (m, 2H), 7.45-7.35 (m, 4H), 6.52 (d, J=11.3 Hz, 2H), 5.70 (p, J=8.4, 7.9 Hz, 1H), 4.92-4.84 (m, 1H), 3.94 (dd, J=13.5, 4.7 Hz, 1H), 3.38 (ddd, J=12.9, 10.2, 1.9 Hz, 1H).

Example 4

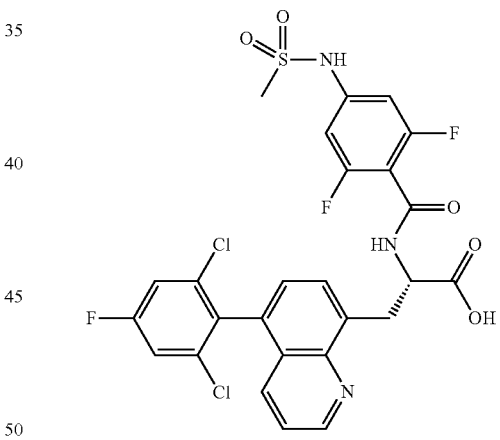

(S)-3-(5-(2,6-dichloro-4-fluorophenyl)quinolin-8-yl)-2-(2,6-difluoro-4-(methylsulfonamido)benzamido)propanoic acid The title compound was prepared according to the method presented for the synthesis of Example 3 replacing T3 with 2,6-difluoro-4-(methylsulfonamido)benzoic acid. MS (m/z) 612.0 [M+H]$^+$. 1H NMR (400 MHz, DMSO-d6) δ 10.43 (s, 1H), 9.08 (d, J=8.0 Hz, 1H), 9.00 (dd, J=4.1, 1.7 Hz, 1H), 7.77 (d, J=7.4 Hz, 1H), 7.76 (d, J=8.6 Hz, 2H), 7.71 (dd, J=8.5, 1.7 Hz, 1H), 7.54 (dd, J=8.5, 4.2 Hz, 1H), 7.43 (d, J=7.3 Hz, 1H), 6.83-6.77 (m, 2H), 4.96 (ddd, J=10.5, 8.1, 4.8 Hz, 1H), 4.00 (dd, J=13.5, 4.8 Hz, 1H), 3.40 (dd, J=13.5, 10.4 Hz, 1H), 3.13 (s, 3H).

Examples 5 and 6

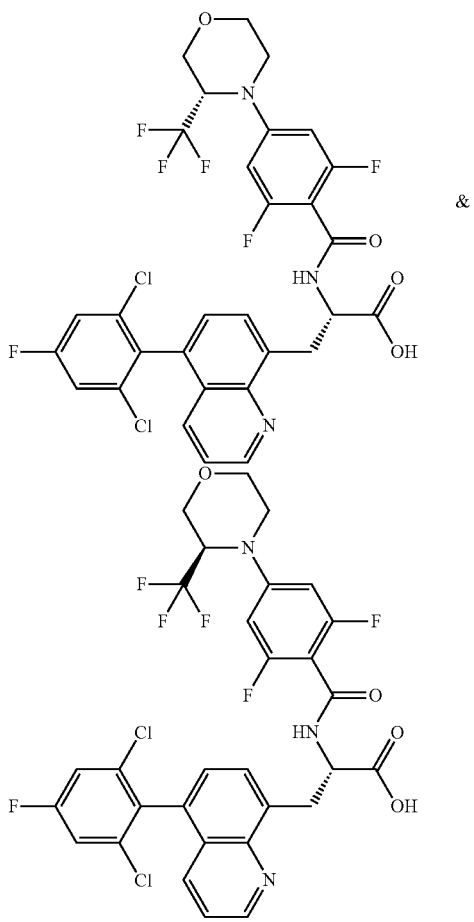

(2S)-3-(5-(2,6-dichloro-4-fluorophenyl)quinolin-8-yl)-2-(2,6-difluoro-4-(3-(trifluoromethyl)morpholino)benzamido)propanoic acid The title compound was prepared according to the method presented for the synthesis of Example 3 replacing T3 with 2,6-difluoro-4-(3-(trifluoromethyl)morpholino)benzoic acid. Enantiomers were arbitrarily assigned after separation by supercritical fluid chromatography eluting with 20% MeOH/DEA co-solvent on an IC SFC column.

Example 5: (S)-3-(5-(2,6-dichloro-4-fluorophenyl)quinolin-8-yl)-2-(2,6-difluoro-4-((S)-3-(trifluoromethyl)morpholino)benzamido)propanoic acid MS (m/z) 672.1 [M+H]+; 1H NMR (400 MHz, DMSO-d6) δ 8.97 (dd, J=4.2, 1.7 Hz, 1H), 8.90 (d, J=7.8 Hz, 1H), 7.81-7.72 (m, 3H), 7.68 (dd, J=8.5, 1.7 Hz, 1H), 7.52 (dd, J=8.4, 4.1 Hz, 1H), 7.40 (dd, J=7.3, 2.7 Hz, 1H), 6.71 (d, J=11.6 Hz, 2H), 4.90 (s, 2H), 4.13 (d, J=12.9 Hz, 1H), 3.93 (d, J=13.2 Hz, 2H), 3.72 (s, 1H), 3.53 (t, J=11.0 Hz, 1H), 3.39 (d, J=9.8 Hz, 1H), 3.21 (t, J=12.0 Hz, 1H).

Example 6: (S)-3-(5-(2,6-dichloro-4-fluorophenyl)quinolin-8-yl)-2-(2,6-difluoro-4-((R)-3-(trifluoromethyl)morpholino)benzamido)propanoic acid MS (m/z) 672.1 [M+H]+; 1H NMR (400 MHz, DMSO-d6) δ 12.69 (s, 1H), 8.97 (dd, J=4.2, 1.7 Hz, 1H), 8.91 (d, J=7.9 Hz, 1H), 7.80-7.72 (m, 3H), 7.68 (dd, J=8.5, 1.7 Hz, 1H), 7.52 (dd, J=8.5, 4.2 Hz, 1H), 7.40 (dd, J=7.3, 2.7 Hz, 1H), 6.72 (d, J=11.6 Hz, 2H), 4.89 (d, J=9.3 Hz, 3H), 4.13 (d, J=12.7 Hz, 1H), 4.02-3.86 (m, 2H), 3.71 (d, J=13.2 Hz, 1H), 3.53 (t, J=11.0 Hz, 1H), 3.39 (d, J=9.8 Hz, 1H), 3.21 (t, J=12.0 Hz, 1H).

Example 7

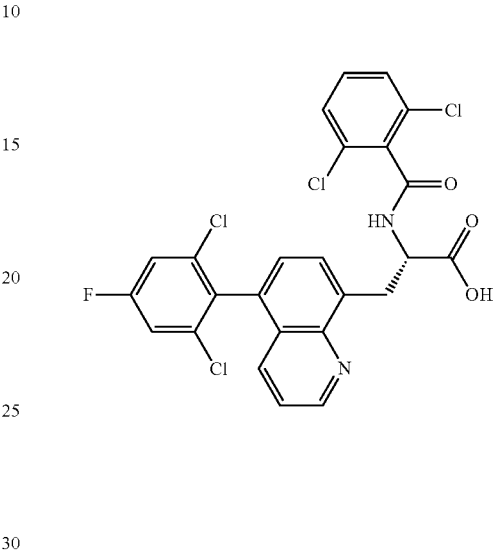

(S)-3-(5-(2,6-dichloro-4-fluorophenyl)quinolin-8-yl)-2-(2,6-dichloro benzamido)propanoic acid The title compound was prepared according to the method presented for the synthesis of Example 1 replacing 2,6-difluorobenzoyl chloride with 2,6-dichlorobenzoyl chloride. MS (m/z) 550.8 [M+H]+. 1H NMR (400 MHz, DMSO-d6) δ 12.75 (s, 1H), 9.15 (d, J=8.5 Hz, 1H), 9.00 (dd, J=4.1, 1.7 Hz, 1H), 7.85 (d, J=7.4 Hz, 1H), 7.81-7.73 (m, 2H), 7.70 (dd, J=8.4, 1.7 Hz, 1H), 7.54 (dd, J=8.5, 4.1 Hz, 1H), 7.45-7.33 (m, 4H), 5.08 (ddd, J=11.2, 8.5, 3.9 Hz, 1H), 4.04 (dd, J=13.5, 4.0 Hz, 1H), 3.35 (m, 1H).

Examples 8 and 9

Methyl (S)-2-(2,6-difluoro-4-(((R)-1,1,1-trifluorobutan-2-yl)amino)benzamido)-3-(5-(1,3,6-trimethyl-2,4-dioxo-1,2,3,4-tetrahydropyrimidin-5-yl)quinolin-8-yl)propanoate To a stirred solution of 5-bromo-1,3,6-trimethylpyrimidine-2,4(1H,3H)-dione (51 mg, 0.22 mmol), methyl (S)-2-(2,6-difluoro-4-(((R)-1,1,1-trifluorobutan-2-yl)amino)benzamido)-3-(5-(4,4,5,5-tetramethyl-1,3,2-dioxaborolan-2-yl)quinolin-8-yl)propanoate (EQ9) (125 mg, 0.20 mmol) in DME (2 mL) was added XPhos Pd G3 (9 mg, 0.012 mmol) and potassium phosphate (0.7 mL, 0.7 mmol, 1N), and the reaction vial was degassed with nitrogen, sealed, and heated to 120° C. in a microwave reactor for 30 min. It was diluted with water and extracted with ethyl acetate dried over sodium sulfate, filtered, concentrated and purified on silica gel eluting with hexanes and ethyl acetate to afford the title compound.

Example 8 atropisomer 1

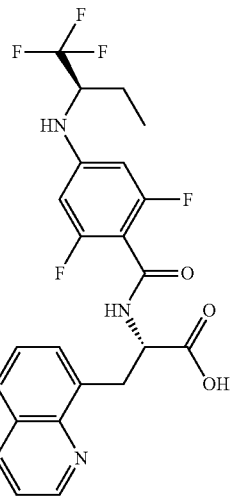

Example 9 atropisomer 2

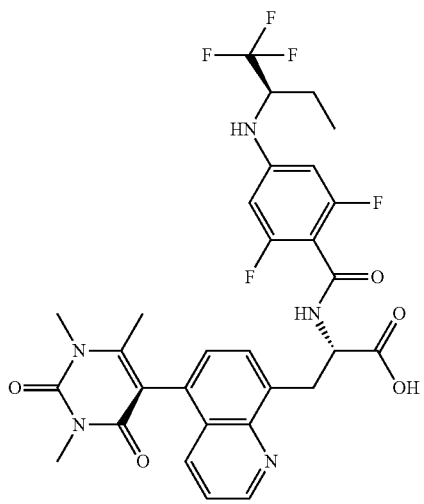

Example 8: (S)-2-(2,6-difluoro-4-(((R)-1,1,1-trifluorobutan-2-yl)amino) benzamido)-3-(5-(1,3,6-trimethyl-2,4-dioxo-1,2,3,4-tetrahydropyrimidin-5-yl) quinolin-8-yl)propanoic acid (Atropisomer 1)

To a stirred solution of methyl (S)-2-(2,6-difluoro-4-(((R)-1,1,1-trifluorobutan-2-yl)amino)benzamido)-3-(5-(1,3,6-trimethyl-2,4-dioxo-1,2,3,4-tetrahydropyrimidin-5-yl) quinolin-8-yl)propanoate (83 mg, 0.128 mmol) in THF (2 mL) and methanol (2 mL) was added lithium hydroxide (0.6 mL, 1.2 mmol, 2 mL) and the mixture as stirred for 4 h. The mixture was acidified with TFA, diluted with DMSO and the more volatile components were removed on a rotary evaporator. The residue was chromatographed on C-18 modified silica gel eluting with acetonitrile in water (0.4% TFA) to afford example 8 and example 9. Example 8 was the first eluting isomer. MS (m/z) 634.72 [M+H]+. 1H NMR (400 MHz, DMSO-d6) δ 8.94 (dd, J=4.2, 1.7 Hz, 1H), 8.72 (d, J=8.1 Hz, 1H), 8.12 (dd, J=8.5, 1.7 Hz, 1H), 7.66 (d, J=7.3 Hz, 1H), 7.49 (dd, J=8.5, 4.2 Hz, 1H), 7.28 (d, J=7.3 Hz, 1H), 6.73 (d, J=9.5 Hz, 1H), 6.39 (d, J=11.4 Hz, 2H), 4.87 (ddd, J=10.7, 8.1, 4.5 Hz, 1H), 4.28 (d, J=10.9 Hz, 1H), 4.00 (dd, J=13.2, 4.4 Hz, 1H), 3.43 (d, J=0.5 Hz, 3H), 3.22 (s, 3H), 1.93 (s, 3H), 1.75 (ddd, J=13.6, 7.3, 3.3 Hz, 1H), 1.50 (ddd, J=13.5, 10.4, 7.1 Hz, 1H), 0.95-0.85 (m, 3H).

Example 9: (S)-2-(2,6-difluoro-4-(((R)-1,1,1-trifluorobutan-2-yl)amino) benzamido)-3-(5-(1,3,6-trimethyl-2,4-dioxo-1,2,3,4-tetrahydropyrimidin-5-yl) quinolin-8-yl)propanoic acid (Atropisomer 2)

Prepared as describe above for example 8, example 9 was the second eluting peak from reversed phase chromatography. MS (m/z) 634.72 [M+H]+. 1H NMR (400 MHz, DMSO-d6) δ 8.94 (ddd, J=4.2, 2.7, 1.7 Hz, 1H), 8.78 (d, J=7.5 Hz, 1H), 8.13 (ddd, J=8.5, 4.8, 1.8 Hz, 1H), 7.67 (t, J=7.3 Hz, 1H), 7.53-7.45 (m, 1H), 7.29 (dd, J=10.8, 7.2 Hz, 1H), 6.74 (t, J=10.1 Hz, 1H), 6.42 (d, J=11.5 Hz, 1H), 4.76 (ddd, J=9.8, 7.5, 5.3 Hz, 1H), 4.29 (s, 1H), 3.79 (dd, J=13.6, 5.2 Hz, 1H), 3.50 (dd, J=13.6, 9.7 Hz, 1H), 3.43 (q, J=0.8 Hz, 2H), 3.22 (d, J=1.2 Hz, 3H), 1.92 (d, J=5.8 Hz, 3H), 1.75 (ddd, J=13.7, 7.2, 3.2 Hz, 1H), 1.51 (ddd, J=13.8, 10.4, 7.1 Hz, 1H), 0.95-0.86 (m, 3H).

Example 10

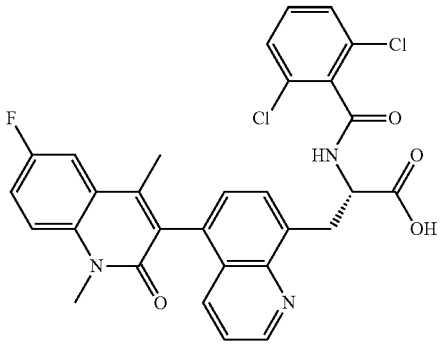 [SMILES: Cc1c(-c2ccc(C[C@H](NC(=O)c3c(Cl)cccc3Cl)C(=O)O)c3ncccc23)c(=O)n(C)c2ccc(F)cc12]

(S)-2-(2,6-dichlorobenzamido)-3-(6-fluoro-1,4-dimethyl-2-oxo-1,2-dihydro-[3,5'-biquinolin]-8'-yl)propanoic acid To a microwave vial were added (EQ6) (266 mg, 0.5 mmol), 3-bromo-6-fluoro-1,4-dimethylquinolin-2(1H)-one H2 (136 mg, 0.504 mmol), potassium phosphate (321 mg, 1.5 mmol), palladium tetrakistriphenylphoshine (29 mg, 0.025 mmol), dioxane (4 mL) and water (1 mL). The vial was purged with nitrogen, sealed and heated in a microwave reactor at 100° C. for 30 min. Sodium hydroxide (2 mL, 2N, 4 mmol) was added and the mixture stirred an additional 10 min. The mixture was acidified with TFA and volatile components were removed via rotary evaporator. The residue was dissolved in DMSO and chromatographed on C-18 modified silica gel eluting with acetonitrile in water (0.4% TFA) to afford the title compound. MS (m/z) 578.10 [M+H]+. 1H NMR (400 MHz, DMSO-d6) δ 9.14 (dd, J=8.5, 5.1 Hz, 1H), 8.95 (ddd, J=9.4, 4.1, 1.7 Hz, 1H), 7.86 (dd, J=8.5, 1.7 Hz, 1H), 7.74 (d, J=31.7 Hz, 1H), 7.66 (dd, J=9.4, 4.9 Hz, 1H), 7.58 (dd, J=11.5, 8.7 Hz, 1H), 7.47-7.42 (m, 1H), 7.42-7.35 (m, 2H), 7.31 (t, J=7.3 Hz, 1H), 5.05 (m, 1H), 4.08 (dd, J=13.6, 4.0 Hz, 1H), 3.88 (dd, J=13.5, 4.6 Hz, 1H), 3.66 (d, J=3.8 Hz, 3H), 3.24 (dd, J=13.5, 11.1 Hz, 1H), 2.09 (d, J=7.5 Hz, 3H).

Examples 11 and 12

Example 11: (S)-2-(2,6-dichlorobenzamido)-3-(6-fluoro-1,4-dimethyl-2-oxo-1,2-dihydro-[3,5'-biquinolin]-8'-yl)propanoic acid (Atropisomer 1)

Example 10 (S)-2-(2,6-dichlorobenzamido)-3-(6-fluoro-1,4-dimethyl-2-oxo-1,2-dihydro-[3,5'-biquinolin]-8'-yl)propanoic acid was chromatographed on an SFC-ADH column eluting with 30% methanol to afford example 11 as the first eluting isomer. MS (m/z) 578.1 [M+H]+. 1H NMR (400 MHz, DMSO-d6) δ 12.76 (s, 1H), 9.17 (d, J=8.5 Hz, 1H), 8.98 (dd, J=4.1, 1.7 Hz, 1H), 7.88 (dd, J=8.5, 1.6 Hz, 1H), 7.80-7.73 (m, 2H), 7.68 (dd, J=9.4, 4.9 Hz, 1H), 7.60 (td, J=9.4, 8.8, 2.9 Hz, 1H), 7.48-7.36 (m, 4H), 7.32 (d, J=7.2 Hz, 1H), 5.10 (ddd, J=12.0, 8.5, 3.9 Hz, 1H), 4.10 (dd, J=13.5, 4.1 Hz, 1H), 3.68 (s, 3H), 3.26 (dd, J=13.1, 11.3 Hz, 1H), 2.12 (s, 2H).

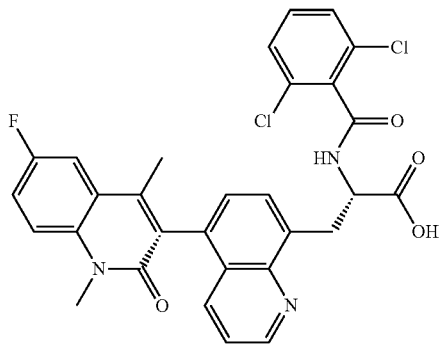

Example 11 Atropisomer 1

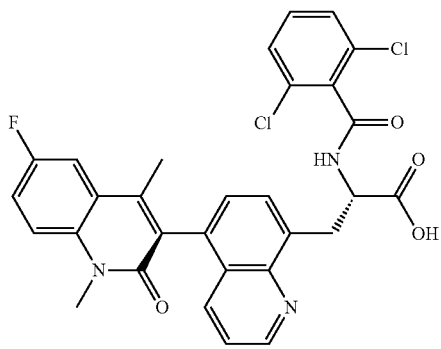

Example 12 Atropisomer 2

Example 12: (S)-2-(2,6-dichlorobenzamido)-3-(6-fluoro-1,4-dimethyl-2-oxo-1,2-dihydro-[3,5'-biquinolin]-8'-yl)propanoic acid Example 10 (S)-2-(2,6-dichlorobenzamido)-3-(6-fluoro-1,4-dimethyl-2-oxo-1,2-dihydro-[3,5'-biquinolin]-8'-yl)propanoic acid was chromatographed on an SFC-ADH column eluting with 30% methanol to afford example 12 as the second eluting isomer. MS (m/z) 578.10 [M+H]+. 1H NMR (400 MHz, DMSO-d6) δ 9.14 (dd, J=8.5, 5.1 Hz, 1H), 8.95 (ddd, J=9.4, 4.1, 1.7 Hz, 1H), 7.86 (dd, J=8.5, 1.7 Hz, 1H), 7.74 (d, J=31.7 Hz, 1H), 7.66 (dd, J=9.4, 4.9 Hz, 1H), 7.58 (dd, J=11.5, 8.7 Hz, 1H), 7.47-7.42 (m, 1H), 7.42-7.35 (m, 2H), 7.31 (t, J=7.3 Hz, 1H), 5.05 (m, 1H), 4.08 (dd, J=13.6, 4.0 Hz, 1H), 3.88 (dd, J=13.5, 4.6 Hz, 1H), 3.66 (d, J=3.8 Hz, 3H), 3.24 (dd, J=13.5, 11.1 Hz, 1H), 2.09 (d, J=7.5 Hz, 3H).

Example 13

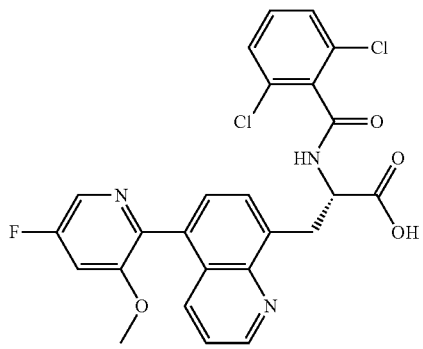 [SMILES: COc1cc(F)cnc1-c1ccc(C[C@H](NC(=O)c2c(Cl)cccc2Cl)C(=O)O)c2ncccc12]

(S)-2-(2,6-dichlorobenzamido)-3-(5-(5-fluoro-3-methoxypyridin-2-yl)quinolin-8-yl)propanoic acid Prepared according to the procedure described for example 10 employing 2-chloro-5-fluoro-3-methoxypyridine in place of H2. MS (m/z) 513.967 [M+H]+. 1H NMR (400 MHz, DMSO-d6) δ 9.09 (d, J=8.5 Hz, 1H), 8.95 (dd, J=4.1, 1.7 Hz, 1H), 8.32 (dd, J=2.4, 0.4 Hz, 1H), 7.91 (dd, J=8.5, 1.7 Hz, 1H), 7.75 (d, J=7.4 Hz, 1H), 7.70 (dd, J=11.1, 2.4 Hz, 1H), 7.55-7.43 (m, 3H), 7.41-7.32 (m, 3H), 5.08 (ddd, J=10.7, 8.4, 4.5 Hz, 1H), 3.98 (dd, J=13.5, 4.5 Hz, 1H), 3.74 (s, 3H), 3.36 (dd, J=13.6, 10.8 Hz, 1H).

Example 14

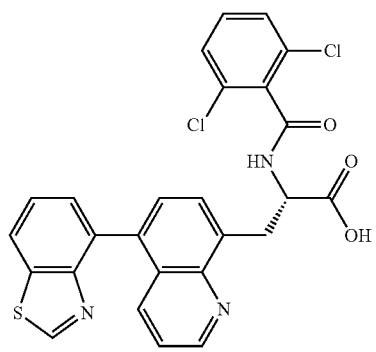 [SMILES: O=C(N[C@@H](Cc1ccc(-c2cccc3scnc23)c2cccnc12)C(=O)O)c1c(Cl)cccc1Cl]

(S)-3-(5-(benzo[d]thiazol-4-yl)quinolin-8-yl)-2-(2,6-dichloro benzamido) propanoic acid Prepared according to the procedure described for example 10 employing 4-bromobenzo[d]thiazole in place of H2. MS (m/z) 521.936 [M+H]+. 1H NMR (400 MHz, DMSO-d6) δ 9.26 (s, 1H), 9.12 (d, J=8.4 Hz, 1H), 8.95 (dd, J=4.2, 1.7 Hz, 1H), 8.30 (dd, J=8.1, 1.2 Hz, 1H), 7.86-7.72 (m, 3H), 7.65 (t, J=7.7 Hz, 1H), 7.53 (d, J=7.3 Hz, 3H), 7.47-7.24 (m, 6H), 5.11 (s, 1H), 4.02 (s, 1H), 3.39 (s, 1H)

Example 15

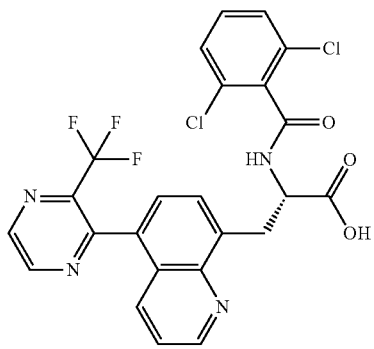 [SMILES: O=C(N[C@@H](Cc1ccc(-c2nccnc2C(F)(F)F)c2cccnc12)C(=O)O)c1c(Cl)cccc1Cl]

(S)-2-(2,6-dichlorobenzamido)-3-(5-(3-(trifluoromethyl)pyrazin-2-yl)quinolin-8-yl)propanoic acid Prepared according to the procedure described for example 10 employing 2-chloro-3-(trifluoromethyl)pyrazine in place of H2. MS (m/z) 535.1 [M+H]+. 1H NMR (400 MHz, DMSO-d6) δ 9.12 (d, J=2.4 Hz, 1H), 9.00 (dd, J=4.1, 1.7 Hz, 1H), 8.97 (dt, J=2.4, 0.5 Hz, 1H), 7.87 (dd, J=8.5, 1.7 Hz, 1H), 7.80 (d, J=7.4 Hz, 1H), 7.53-7.47 (m, 2H), 7.37 (dt, J=15.5, 8.3 Hz, 3H), 5.09 (s, 1H), 4.10-3.92 (m, 1H), 3.50-3.29 (m, 1H).

Example 16

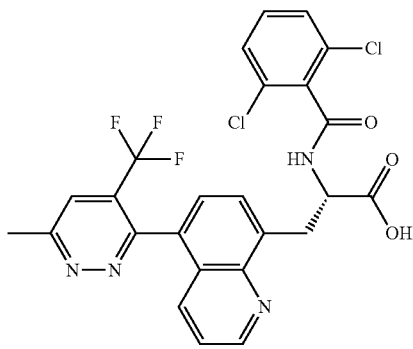 [SMILES: Cc1cc(C(F)(F)F)c(-c2ccc(C[C@H](NC(=O)c3c(Cl)cccc3Cl)C(=O)O)c3ncccc23)nn1]

(S)-2-(2,6-dichlorobenzamido)-3-(5-(6-methyl-4-(trifluoromethyl)pyridazin-3-yl)quinolin-8-yl)propanoic acid Prepared according to the procedure described for example 10 employing 3-bromo-6-methyl-4-(trifluoromethyl)pyridazine in place of H2. MS (m/z) 549.1 [M+H]+. 1H NMR (400 MHz, DMSO-d6) δ 9.14 (d, J=18.1 Hz, 1H), 9.00 (s, 1H), 8.25 (s, 1H), 8.21 (qd, J=0.8, 0.4 Hz, 1H), 7.82 (d, J=7.4 Hz, 1H), 7.71 (dd, J=8.5, 1.7 Hz, 1H), 7.56-7.47 (m, 2H), 7.38 (d, J=6.5 Hz, 4H), 5.10 (s, 1H), 4.01 (d, J=13.7 Hz, 1H), 3.41 (t, J=12.3 Hz, 1H), 2.86 (s, 3H).

Example 17

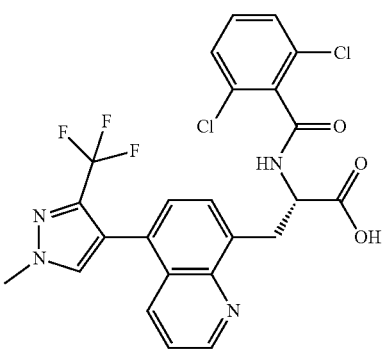 [SMILES: Cn1cc(-c2ccc(C[C@H](NC(=O)c3c(Cl)cccc3Cl)C(=O)O)c3ncccc23)c(C(F)(F)F)n1]

(S)-2-(2,6-dichlorobenzamido)-3-(5-(1-methyl-3-(trifluoromethyl)-1H-pyrazol-4-yl)quinolin-8-yl)propanoic acid Prepared according to the procedure described for example 10 employing 4-bromo-1-methyl-3-(trifluoromethyl)-1H-pyrazole in place of H2. MS (m/z) 536.957 [M+H]+. 1H NMR (400 MHz, DMSO-d6) δ 9.09 (d, J=8.5 Hz, 1H), 8.97 (dd, J=4.1, 1.7 Hz, 1H), 8.18-7.97 (m, 2H), 7.73 (d, J=7.3 Hz, 1H), 7.54 (dd, J=8.5, 4.1 Hz, 1H), 7.45-7.28 (m, 4H), 3.97 (dd, J=4.4 Hz, 2H), 3.34 (dd, J=13.7, 10.9 Hz, 1H).

Example 18

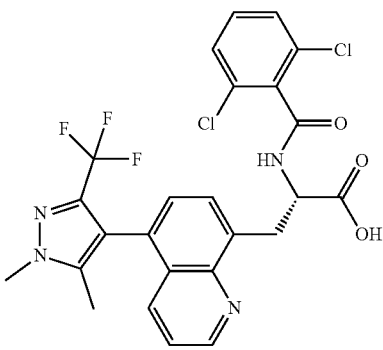 [SMILES: Cc1c(-c2ccc(C[C@H](NC(=O)c3c(Cl)cccc3Cl)C(=O)O)c3ncccc23)c(C(F)(F)F)nn1C]

(S)-2-(2,6-dichlorobenzamido)-3-(5-(1,5-dimethyl-3-(trifluoromethyl)-1H-pyrazol-4-yl)quinolin-8-yl)propanoic acid Prepared according to the procedure described for example 10 employing 4-bromo-1,5-dimethyl-3-(trifluoromethyl)-1H-pyrazole in place of H2. MS (m/z) 536.957 [M+H]+. 1H NMR (400 MHz, DMSO-d6) δ 9.09 (d, J=8.5 Hz, 1H), 8.97 (dd, J=4.1, 1.7 Hz, 1H), 8.18-7.97 (m, 2H), 7.73 (d, J=7.3 Hz, 1H), 7.54 (dd, J=8.5, 4.1 Hz, 1H), 7.45-7.28 (m, 4H), 3.97 (dd, J=4.4 Hz, 2H), 3.34 (dd, J=13.7, 10.9 Hz, 1H).

Example 19

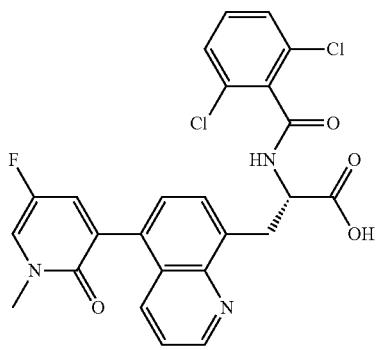 [SMILES: Cn1cc(F)cc(-c2ccc(C[C@H](NC(=O)c3c(Cl)cccc3Cl)C(=O)O)c3ncccc23)c1=O]

(S)-2-(2,6-dichlorobenzamido)-3-(5-(5-fluoro-1-methyl-2-oxo-1,2-dihydropyridin-3-yl)quinolin-8-yl)propanoic acid Prepared according to the procedure described for example 10 employing 3-bromo-5-fluoro-1-methylpyridin-2(1H)-one in place of H2. MS (m/z) 513.934 [M+H]+. 1H NMR (400 MHz, DMSO-d6) δ 9.10 (d, J=8.3 Hz, 1H), 8.94 (dd, J=4.1, 1.7 Hz, 1H), 8.11 (dd, J=4.7, 3.3 Hz, 1H), 8.01 (dd, J=8.5, 1.7 Hz, 1H), 7.71 (d, J=7.3 Hz, 1H), 7.60 (s, 1H), 7.49 (dd, J=8.5, 4.1 Hz, 1H), 7.44-7.29 (m, 4H), 5.03 (ddd, J=10.2, 8.3, 4.7 Hz, 1H), 3.49 (s, 3H), 3.36 (dd, J=13.7, 10.4 Hz, 1H), 2.65 (t, J=1.9 Hz, 1H), 2.52 (s, 1H), 2.31 (t, J=1.9 Hz, 1H).

Example 20

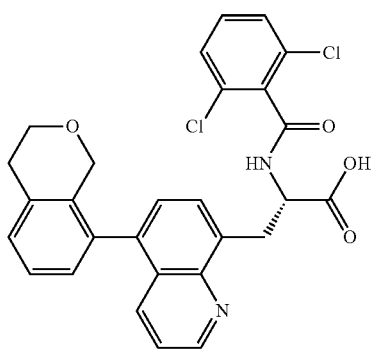 [SMILES: O=C(N[C@@H](Cc1ccc(-c2cccc3c2COCC3)c2cccnc12)C(=O)O)c1c(Cl)cccc1Cl]

(S)-2-(2,6-dichlorobenzamido)-3-(5-(isochroman-8-yl)quinolin-8-yl)propanoic acid Prepared according to the procedure described for example 10 employing 8-bromoisochromane in place of H2. MS (m/z) 521.1 [M+H]+. 1H NMR (400 MHz, DMSO-d6) δ 9.07 (dd, J=15.5, 8.5 Hz, 1H), 8.97 (ddd, J=5.9, 4.1, 1.8 Hz, 1H), 7.78-7.69 (m, 2H), 7.49 (ddd, J=8.5, 4.1, 1.9 Hz, 1H), 7.44-7.23 (m, 6H), 7.03-6.93 (m, 1H), 5.11 (ddt, J=11.0, 8.9, 4.6 Hz, 1H), 4.32 (dd, J=15.3, 2.7 Hz, 1H), 4.06-3.77 (m, 4H), 3.34 (ddd, J=28.9, 13.5, 11.1 Hz, 1H), 2.98-2.82 (m, 2H).

Example 21

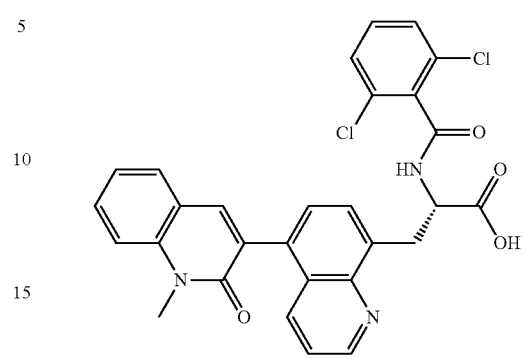

(S)-2-(2,6-dichlorobenzamido)-3-(1-methyl-2-oxo-1,2-dihydro-[3,5'-biquinolin]-8'-yl)propanoic acid Prepared according to the procedure described for example 10 employing 3-bromo-1-methylquinolin-2(1H)-one in place of H2. MS (m/z) 545.8 [M+H]+. 1H NMR (400 MHz, DMSO-d6) δ 9.13 (d, J=8.3 Hz, 1H), 8.96 (dd, J=4.1, 1.7 Hz, 1H), 8.08 (dt, J=8.5, 1.5 Hz, 1H), 7.99 (s, 1H), 7.83 (d, J=7.7 Hz, 1H), 7.79-7.60 (m, 3H), 7.55-7.45 (m, 2H), 7.45-7.29 (m, 4H), 5.13-5.00 (m, 1H), 4.01-3.91 (m, 1H), 3.73 (s, 3H), 3.41 (t, J=12.2 Hz, 1H).

Example 22

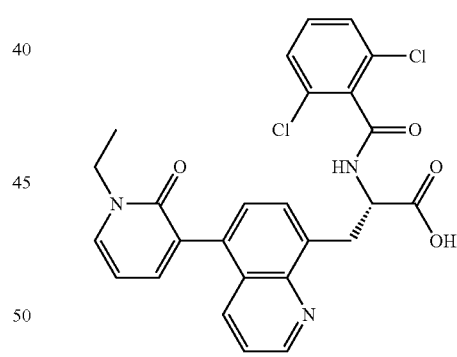

(S)-2-(2,6-dichlorobenzamido)-3-(5-(1-ethyl-2-oxo-1,2-dihydropyridin-3-yl)quinolin-8-yl)propanoic acid Prepared according to the procedure described for example 10 employing 3-bromo-1-ethylpyridin-2(1H)-one in place of H2. MS (m/z) 510.1 [M+H]+. 1H NMR (400 MHz, DMSO-d6) δ 9.09 (d, J=8.4 Hz, 1H), 8.93 (dd, J=4.2, 1.8 Hz, 1H), 7.96 (dd, J=8.5, 1.8 Hz, 1H), 7.86 (dd, J=6.8, 2.1 Hz, 1H), 7.70 (d, J=7.4 Hz, 1H), 7.49 (dd, J=8.5, 4.2 Hz, 1H), 7.46-7.31 (m, 4H), 6.40 (t, J=6.8 Hz, 1H), 5.11-4.95 (m, 1H), 3.99 (m, 3H), 3.36 (m, 1H), 1.27 (t, J=7.1 Hz, 3H).

Example 23

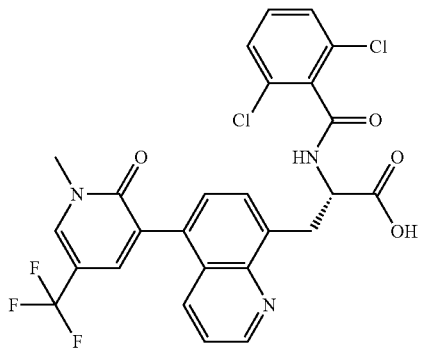 [SMILES: Cn1cc(C(F)(F)F)cc(-c2ccc(C[C@H](NC(=O)c3c(Cl)cccc3Cl)C(=O)O)c3ncccc23)c1=O]

(S)-2-(2,6-dichlorobenzamido)-3-(5-(1-methyl-2-oxo-5-(trifluoromethyl)-1,2-dihydropyridin-3-yl)quinolin-8-yl)propanoic acid Prepared according to the procedure described for example 10 employing 3-bromo-1-methyl-5-(trifluoromethyl)pyridin-2(1H)-one in place of H2. MS (m/z) 564.1 [M+H]+. 1H NMR (400 MHz, DMSO-d6) δ 9.09 (d, J=8.4 Hz, 1H), 8.94 (dd, J=4.1, 1.7 Hz, 1H), 8.56 (s, 1H), 8.01 (dd, J=8.5, 1.7 Hz, 1H), 7.72 (d, J=7.4 Hz, 1H), 7.50 (dd, J=8.5, 4.2 Hz, 1H), 7.45-7.31 (m, 4H), 5.10-4.99 (m, 1H), 3.95 (dd, J=13.6, 4.7 Hz, 1H), 3.58 (s, 3H), 3.36 (dd, J=13.6, 10.5 Hz, 1H).

Example 24

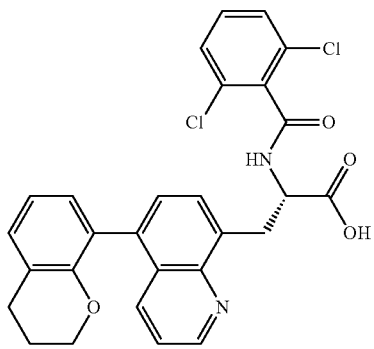 [SMILES: O=C(N[C@@H](Cc1ccc(-c2cccc3c2OCCC3)c2cccnc12)C(=O)O)c1c(Cl)cccc1Cl]

(S)-3-(5-(chroman-8-yl)quinolin-8-yl)-2-(2,6-dichlorobenzamido)propanoic acid

Prepared according to the procedure described for example 10 employing 8-bromochromane in place of H2. MS (m/z) 521.1 [M+H]+. 1H NMR (400 MHz, DMSO-d6) δ 9.11-9.02 (m, 1H), 8.92 (dd, J=4.2, 1.7 Hz, 1H), 7.89 (dt, J=8.5, 1.7 Hz, 1H), 7.71 (dd, J=7.3, 3.5 Hz, 1H), 7.65-7.57 (m, 4H), 7.57-7.50 (m, 3H), 7.48 (dd, J=8.5, 4.1 Hz, 1H), 7.44-7.29 (m, 4H), 7.18 (dd, J=6.8, 2.8 Hz, 1H), 7.02-6.90 (m, 2H), 5.08 (dtd, J=11.4, 7.5, 4.5 Hz, 1H), 3.97 (q, J=7.1, 5.4 Hz, 4H), 3.32 (q, J=12.2 Hz, 1H), 2.87 (dd, J=15.4, 8.3 Hz, 2H), 1.93-1.86 (m, 3H).

Example 25

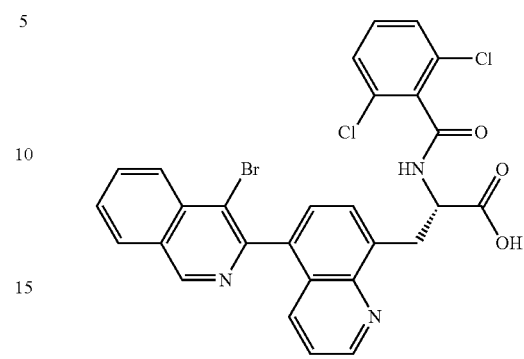

(S)-3-(5-(4-bromoisoquinolin-3-yl)quinolin-8-yl)-2-(2,6-dichloro benzamido)propanoic acid Prepared according to the procedure described for example 10 employing 3,4-dibromoisoquinoline in place of H2. MS (m/z) 594.0 [M+H]+. 1H NMR (400 MHz, DMSO-d6) δ 12.71 (s, 1H), 9.45 (s, 1H), 9.17 (t, J=11.7 Hz, 1H), 8.97 (s, 1H), 8.36-8.29 (m, 1H), 8.26 (d, J=8.5 Hz, 1H), 8.04 (ddd, J=8.4, 6.9, 1.3 Hz, 1H), 7.89 (ddd, J=8.1, 7.0, 1.1 Hz, 1H), 7.85-7.77 (m, 2H), 7.57 (d, J=7.2 Hz, 1H), 7.50-7.43 (m, 1H), 7.43-7.31 (m, 3H), 5.10 (d, J=9.2 Hz, 1H), 4.02 (d, J=13.4 Hz, 1H), 3.40 (q, J=14.3, 13.1 Hz, 1H).

Example 26

(S)-2-(2,6-dichlorobenzamido)-3-(5-(2,5-dimethyl-2H-1,2,3-triazol-4-yl)quinolin-8-yl)propanoic acid Prepared according to the procedure described for example 10 employing 4-bromo-2,5-dimethyl-2H-1,2,3-triazole in place of H2. MS (m/z) 483.880 [M+H]+. 1H NMR (400 MHz, DMSO-d6) δ 9.07 (d, J=8.5 Hz, 1H), 8.99 (dd, J=4.1, 1.7 Hz, 1H), 8.39 (d2, J=1.8 Hz, 1H), 7.77 (d, J=7.4 Hz, 1H), 7.61-7.52 (m, 2H), 7.41-7.30 (m, 3H), 5.10 (ddd, J=10.9, 8.6, 4.5 Hz, 1H), 4.19 (s, 3H), 4.06 (s, 1H), 3.99 (dd, J=13.5, 4.5 Hz, 1H), 3.35 (dd, J=13.6, 10.9 Hz, 1H), 2.21 (s, 3H), 2.16 (s, 1H).

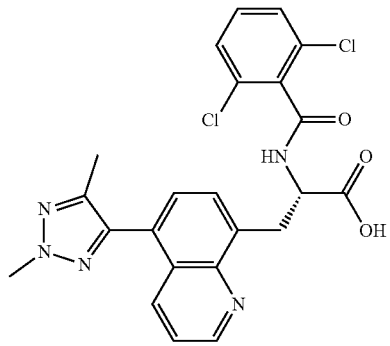 [SMILES: Cc1nn(C)nc1-c1ccc(C[C@H](NC(=O)c2c(Cl)cccc2Cl)C(=O)O)c2ncccc12]

Example 27

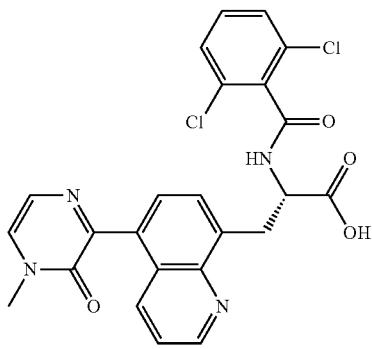 [SMILES: Cn1ccnc(-c2ccc(C[C@H](NC(=O)c3c(Cl)cccc3Cl)C(=O)O)c3ncccc23)c1=O]

(S)-2-(2,6-dichlorobenzamido)-3-(5-(4-methyl-3-oxo-3,4-dihydropyrazin-2-yl)quinolin-8-yl)propanoic acid Prepared according to the procedure described for example 10 employing 3-chloro-1-methylpyrazin-2(1H)-one in place of H2. MS (m/z) 496.898 [M+H]+. 1H NMR (400 MHz, DMSO-d6) δ 9.10 (d, J=8.3 Hz, 1H), 8.95 (dd, J=4.1, 1.7 Hz, 1H), 8.27 (dd, J=8.6, 1.7 Hz, 1H), 7.82 (d, J=4.2 Hz, 1H), 7.74 (d, J=7.4 Hz, 1H), 7.65 (d, J=7.4 Hz, 1H), 7.54-7.47 (m, 2H), 7.43-7.31 (m, 3H), 5.05 (ddd, J=10.4, 8.3, 4.8 Hz, 1H), 3.94 (dd, J=13.5, 4.8 Hz, 1H), 3.53 (s, 3H), 3.52-3.25 (m, 1H).

Example 28

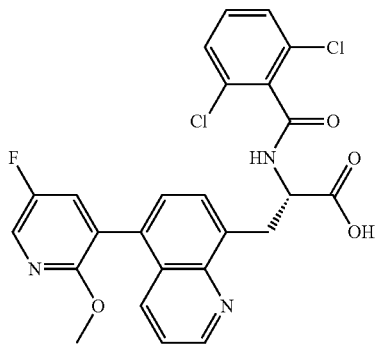 [SMILES: COc1ncc(F)cc1-c1ccc(C[C@H](NC(=O)c2c(Cl)cccc2Cl)C(=O)O)c2ncccc12]

(S)-2-(2,6-dichlorobenzamido)-3-(5-(5-fluoro-2-methoxypyridin-3-yl)quinolin-8-yl)propanoic acid Prepared according to the procedure described for example 10 employing 3-bromo-5-fluoro-2-methoxypyridine in place of H2. MS (m/z) 513.883 [M+H]+. 1H NMR (400 MHz, DMSO-d6) δ 9.08 (d, J=8.5 Hz, 1H), 8.96 (s, 1H), 8.30 (s, 1H), 7.87 (dd, J=8.5, 1.7 Hz, 1H), 7.74 (t, J=9.5 Hz, 1H), 7.62 (d, J=7.8 Hz, 1H), 7.51 (dd, J=8.5, 4.1 Hz, 1H), 7.41 (dt, J=24.6, 7.3 Hz, 4H), 5.08 (s, 1H), 3.74 (s, 3H), 3.36 (dd, J=51.4, 12.2 Hz, 1H).

Example 29

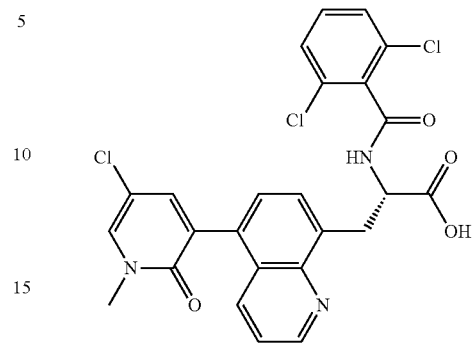

(S)-3-(5-(5-chloro-1-methyl-2-oxo-1,2-dihydropyridin-3-yl)quinolin-8-yl)-2-(2,6-dichlorobenzamido)propanoic acid Prepared according to the procedure described for example 10 employing 3-bromo-5-chloro-1-methylpyridin-2(1H)-one in place of H2. MS (m/z) 529.865 [M+H]+. 1H NMR (400 MHz, DMSO-d6) δ 9.09 (d, J=8.3 Hz, 1H), 8.94 (dd, J=4.2, 1.7 Hz, 1H), 8.16 (d, J=2.9 Hz, 1H), 8.05-7.98 (m, 1H), 7.71 (d, J=7.3 Hz, 1H), 7.50 (dd, J=8.5, 4.2 Hz, 1H), 7.45-7.29 (m, 3H), 5.04 (td, J=9.7, 9.1, 4.6 Hz, 1H), 3.94 (dd, J=13.6, 4.7 Hz, 1H), 3.50 (s, 3H), 3.36 (dd, J=13.7, 10.5 Hz, 1H).

Example 30

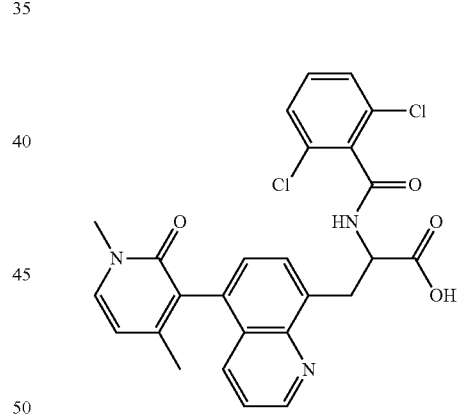

2-(2,6-Dichlorobenzamido)-3-(5-(1,4-dimethyl-2-oxo-1,2-dihydropyridin-3-yl)quinolin-8-yl)propanoic acid Prepared according to the procedure described for example 10 employing 3-chloro-1,4-dimethylpyridin-2(1H)-one in place of H2. MS (m/z) 510.1 [M+H]+. 1H NMR (400 MHz, DMSO-d6) δ 9.11 (dd, J=8.3, 6.1 Hz, 1H), 8.93 (ddd, J=10.2, 4.2, 1.8 Hz, 1H), 7.80 (dt, J=8.5, 2.0 Hz, 1H), 7.77-7.67 (m, 2H), 7.47 (ddd, J=8.5, 4.2, 0.8 Hz, 1H), 7.43-7.29 (m, 3H), 7.25 (dd, J=9.2, 7.2 Hz, 1H), 6.33-6.23 (m, 1H), 5.03 (dddd, J=23.3, 10.6, 8.3, 4.3 Hz, 1H), 3.94 (ddd, J=74.2, 13.7, 4.4 Hz, 1H), 3.49 (dd, J=13.9, 10.6 Hz, 1H), 3.44 (d, J=3.4 Hz, 3H), 3.25 (dd, J=13.5, 11.0 Hz, 1H), 1.78 (d, J=7.9 Hz, 3H).

Example 31

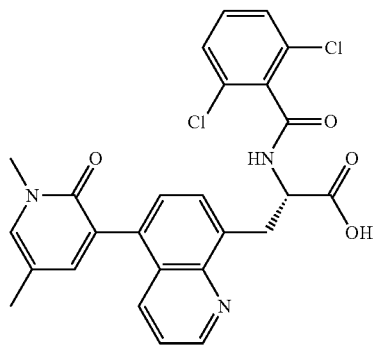

(S)-2-(2,6-Dichlorobenzamido)-3-(5-(1,5-dimethyl-2-oxo-1,2-dihydropyridin-3-yl)quinolin-8-yl)propanoic acid Prepared according to the procedure described for example 10 employing 3-chloro-1,5-dimethylpyridin-2(1H)-one in place of H2. MS (m/z) 510.1 [M+H]+. 1H NMR (400 MHz, DMSO-d6) δ 9.09 (d, J=8.3 Hz, 1H), 8.92 (dd, J=4.2, 1.8 Hz, 1H), 7.97 (dd, J=8.5, 1.7 Hz, 1H), 7.69 (d, J=7.3 Hz, 1H), 7.66 (dd, J=2.5, 1.1 Hz, 1H), 7.47 (dd, J=8.5, 4.1 Hz, 1H), 7.43-7.26 (m, 5H), 5.03 (t, J=11.7 Hz, 1H), 3.92 (d, J=13.4 Hz, 1H), 3.48 (s, 3H), 3.38 (d, J=16.4 Hz, 1H), 2.13-2.06 (m, 3H).

Example 32

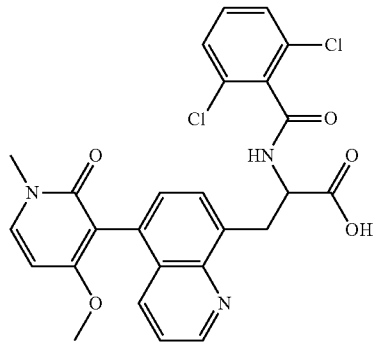 [SMILES: COc1ccn(C)c(=O)c1-c1ccc(CC(NC(=O)c2c(Cl)cccc2Cl)C(=O)O)c2ncccc12]

2-(2,6-Dichlorobenzamido)-3-(5-(4-methoxy-1-methyl-2-oxo-1,2-dihydropyridin-3-yl)quinolin-8-yl)propanoic acid Prepared according to the procedure described for example 10 employing 3-chloro-4-methoxy-1-methylpyridin-2(1H)-one in place of H2. MS (m/z) 526.1 [M+H]+. $^1$H NMR (400 MHz, DMSO-d$_6$) δ 9.10 (dd, J=8.4, 1.2 Hz, 1H), 8.91 (ddd, J=6.1, 4.2, 1.8 Hz, 1H), 7.94-7.81 (m, 2H), 7.71 (t, J=6.9 Hz, 1H), 7.46 (ddd, J=8.5, 4.2, 2.6 Hz, 1H), 7.43-7.32 (m, 3H), 7.26 (dd, J=12.7, 7.3 Hz, 1H), 6.44 (dd, J=7.8, 4.8 Hz, 1H), 5.03 (dddd, J=23.9, 10.6, 8.4, 4.5 Hz, 1H), 3.93 (ddd, J=53.0, 13.8, 4.5 Hz, 1H), 3.66 (d, J=9.1 Hz, 3H), 3.44 (d, J=2.3 Hz, 3H), 3.26 (dd, J=13.6, 10.9 Hz, 1H).

Example 33

(S)-2-(2,6-dichlorobenzamido)-3-(5-(1,6-dimethyl-2-oxo-1,2-dihydropyridin-3-yl)quinolin-8-yl)propanoic acid Prepared according to the procedure described for example 10 employing 3-chloro-1,6-dimethylpyridin-2(1H)-one in place of H2. MS (m/z) 510.1 [M+H]+. 1H NMR (400 MHz, DMSO-d6) δ 9.09 (d, J=8.3 Hz, 1H), 8.93 (dd, J=4.2, 1.8 Hz, 1H), 7.98 (dd, J=8.5, 1.8 Hz, 1H), 7.70 (d, J=7.3 Hz, 1H), 7.48 (dd, J=8.5, 4.2 Hz, 1H), 7.42-7.27 (m, 5H), 6.31 (dd, J=7.0, 0.9 Hz, 1H), 5.04 (td, J=9.5, 8.5, 4.7 Hz, 1H), 3.93 (d, J=13.4 Hz, 1H), 3.51 (s, 3H), 3.43-3.30 (m, 1H), 2.44 (d, J=0.8 Hz, 3H).

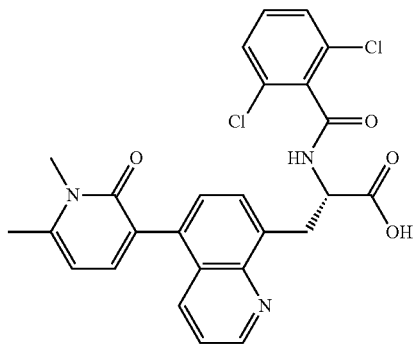 [SMILES: Cc1ccc(-c2ccc(C[C@H](NC(=O)c3c(Cl)cccc3Cl)C(=O)O)c3ncccc23)c(=O)n1C]

Example 34

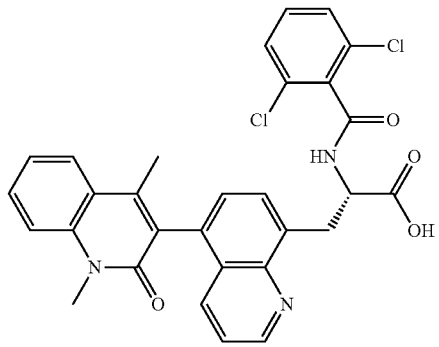

(S)-2-(2,6-dichlorobenzamido)-3-(1,4-dimethyl-2-oxo-1,2-dihydro-[3,5'-biquinolin]-8'-yl)propanoic acid Prepared according to the procedure described for example 10 employing H5 in place of H2. MS (m/z) 560.042 [M+H]+. 1H NMR (400 MHz, DMSO-d6) δ 9.14 (dd, J=8.4, 5.1 Hz, 1H), 8.95 (ddd, J=8.7, 4.2, 1.7 Hz, 1H), 7.96-7.85 (m, 2H), 7.78 (dd, J=7.2, 5.1 Hz, 1H), 7.70 (ddd, J=8.5, 7.0, 1.4 Hz, 1H), 7.63-7.60 (m, 1H), 7.46 (dd, J=8.5, 4.2 Hz, 1H), 7.43-7.27 (m, 5H), 5.35-4.91 (m, 1H), 4.07 (dd, J=13.4, 4.0 Hz, 1H), 3.88 (dd, J=13.8, 4.7 Hz, 1H), 3.67 (d, J=3.6 Hz, 3H), 3.52 (dd, J=13.8, 10.6 Hz, 1H), 3.27 (dd, J=13.5, 11.1 Hz, 1H), 2.12 (d, J=7.3 Hz, 3H).

Example 35

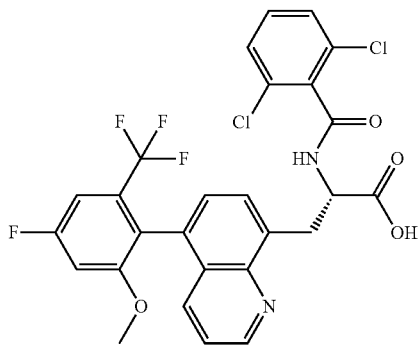 [SMILES: COc1cc(F)cc(C(F)(F)F)c1-c1ccc(C[C@H](NC(=O)c2c(Cl)cccc2Cl)C(=O)O)c2ncccc12]

(2S)-2-(2,6-dichlorobenzamido)-3-(5-(4-fluoro-2-methoxy-6-(trifluoromethyl) phenyl)quinolin-8-yl) propanoic acid Prepared according to the procedure described for example 10 employing H1 in place of H2. MS (m/z) 581.549 [M+H]+. 1H NMR (400 MHz, DMSO-d6) δ 9.12 (t, J=9.0 Hz, 1H), 8.93 (dd, J=4.2, 1.7 Hz, 1H), 7.76 (dd, J=7.3, 5.3 Hz, 1H), 7.60 (ddd, J=8.5, 2.7, 1.7 Hz, 1H), 7.45 (ddd, J=8.5, 4.1, 1.6 Hz, 2H), 7.42-7.31 (m, 4H), 7.31-7.25 (m, 1H), 5.16-4.94 (m, 1H), 3.97 (ddd, J=14.0, 10.3, 3.9 Hz, 1H), 3.61 (d, J=10.8 Hz, 3H), 3.35 (dt, J=14.0, 10.3 Hz, 1H).

Example 36

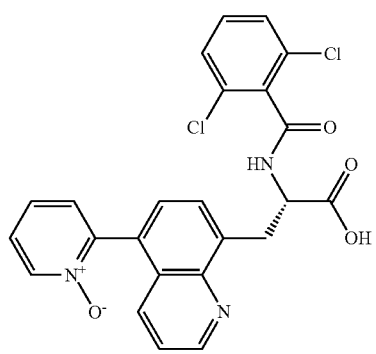 [SMILES: O=C(N[C@@H](Cc1ccc(-c2cccc[n+]2[O-])c2cccnc12)C(=O)O)c1c(Cl)cccc1Cl]

(2S)-3-(5-(2-chloro-4-fluoro-6-methoxyphenyl)quinolin-8-yl)-2-(2,6-dichloro benzamido)propanoic acid Prepared according to the procedure described for example 10 employing H15 in place of H2. MS (m/z) 547.061 [M+H]+. 1H NMR (400 MHz, DMSO-d6) δ 9.10 (t, J=8.5 Hz, 1H), 8.94 (dt, J=4.1, 2.0 Hz, 1H), 7.77 (dd, J=7.3, 3.7 Hz, 1H), 7.65 (ddd, J=8.4, 2.9, 1.8 Hz, 1H), 7.47 (ddd, J=8.5, 4.2, 1.7 Hz, 1H), 7.41-7.32 (m, 3H), 7.30 (dd, J=7.2, 1.5 Hz, 1H), 7.17 (dddd, J=21.1, 11.2, 4.1, 2.4 Hz, 2H), 5.16-4.96 (m, 1H), 4.06-3.94 (m, 1H), 3.62 (d, J=10.7 Hz, 3H), 3.40-3.21 (m, 1H).

Example 37

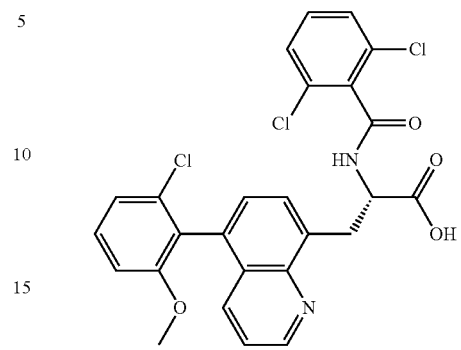

(2S)-3-(5-(2-chloro-6-methoxyphenyl)quinolin-8-yl)-2-(2,6-dichloro benzamido) propanoic acid Prepared according to the procedure described for example 10 employing (2-chloro-6-methoxyphenyl)boronic acid in place of EQ6 and EQ5 in place of H2. MS (m/z) 530.0 [M+H]+. 1H NMR (400 MHz, DMSO-d6) δ 9.10 (t, J=8.2 Hz, 1H), 8.94 (ddd, J=4.2, 2.5, 1.8 Hz, 1H), 7.78 (dd, J=7.3, 3.4 Hz, 1H), 7.68-7.44 (m, 6H), 7.42-7.28 (m, 4H), 7.22 (ddd, J=8.1, 4.0, 0.9 Hz, 1H), 7.18 (ddd, J=8.6, 4.1, 0.9 Hz, 1H), 5.16-4.98 (m, 1H), 4.01 (ddd, J=13.6, 6.4, 4.1 Hz, 1H), 3.61 (d, J=10.7 Hz, 3H), 3.32 (ddd, J=13.5, 11.2, 8.2 Hz, 1H).

Example 38

(S)-2-(8-(2-carboxy-2-2,6-dichlorobenzamido)ethyl) quinolin-5-yl)pyridine 1-oxide Prepared according to the procedure described for example 10 employing 2-bromopyridine 1-oxide in place of H2. MS (m/z) 482.0 [M+H]+. 1H NMR (400 MHz, DMSO-d6) δ 9.10 (d, J=8.4 Hz, 1H), 9.05-8.91 (m, 1H), 8.47-8.35 (m, 1H), 7.84-7.69 (m, 2H), 7.65-7.46 (m, 4H), 7.46-7.29 (m, 3H), 5.21-4.98 (m, 1H), 3.99 (ddd, J=23.5, 13.6, 4.7 Hz, 1H), 3.49-3.23 (m, 1H).

Example 39

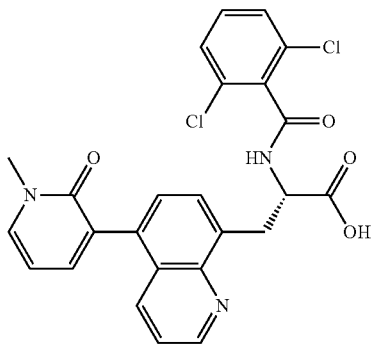 [SMILES: Cn1cccc(-c2ccc(C[C@H](NC(=O)c3c(Cl)cccc3Cl)C(=O)O)c3ncccc23)c1=O]

(S)-2-(2,6-dichlorobenzamido)-3-(5-(1-methyl-2-oxo-1,2-dihydropyridin-3-yl)quinolin-8-yl)propanoic acid Prepared according to the procedure described for example 10 employing 3-bromo-1-methylpyridin-2(1H)-one in place of H2. MS (m/z) 496.1 [M+H]+. 1H NMR (400 MHz, DMSO-d6) δ 9.09 (d, J=8.4 Hz, 1H), 8.94 (dd, J=4.2, 1.7 Hz, 1H), 8.00 (dd, J=8.5, 1.8 Hz, 1H), 7.86 (dd, J=6.8, 2.1 Hz, 1H), 7.71 (d, J=7.3 Hz, 1H), 7.50 (dd, J=8.5, 4.2 Hz, 1H), 7.46-7.30 (m, 5H), 6.38 (t, J=6.8 Hz, 1H), 5.13-4.99 (m, 1H), 3.94 (m, J=13.7 Hz, 1H), 3.52 (s, 3H), 3.34 (m, J=13.3 Hz, 1H).

Example 40

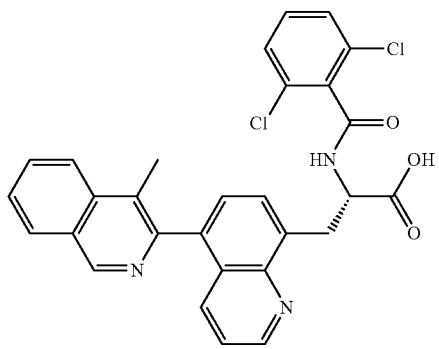 [SMILES: Cc1c(-c2ccc(C[C@H](NC(=O)c3c(Cl)cccc3Cl)C(=O)O)c3ncccc23)ncc2ccccc12]

(S)-2-(2,6-dichlorobenzamido)-3-(5-(4-methylisoquinolin-3-yl)quinolin-8-yl)propanoic acid Prepared according to the procedure described for example 10 employing 3-chloro-4-methylisoquinoline in place of H2. MS (m/z) 530.1 [M+H]+. 1H NMR (400 MHz, DMSO-d6) δ 9.52 (s, 1H), 9.16 (d, J=8.5 Hz, 1H), 9.01 (s, 1H), 8.37 (d, J=8.1 Hz, 1H), 8.28 (s, 1H), 8.06 (s, 2H), 7.88 (dt, J=15.4, 7.3 Hz, 3H), 7.60 (d, J=7.2 Hz, 1H), 7.50 (dd, J=8.5, 4.1 Hz, 1H), 7.47-7.32 (m, 3H), 5.11 (s, 1H), 4.14-3.91 (m, 1H), 3.61-3.27 (m, 1H), 2.40 (s, 3H).

Example 41

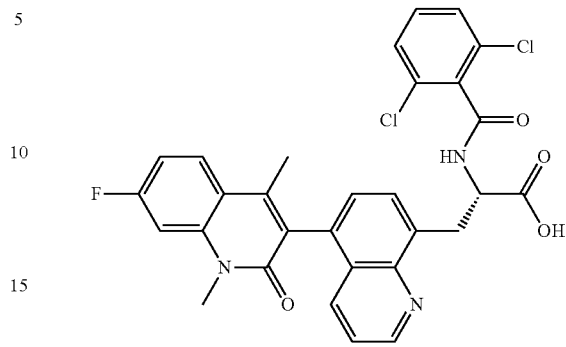

(S)-2-(2,6-dichlorobenzamido)-3-(7-fluoro-1,4-dimethyl-2-oxo-1,2-dihydro-[3,5'-biquinolin]-8'-yl)propanoic acid Prepared according to the procedure described for example 10 employing H4 in place of H2. MS (m/z) 578 [M+H]+. 1H NMR (400 MHz, DMSO-d6) δ 9.20-9.13 (m, 2H), 8.98 (d, J=12.6 Hz, 2H), 8.03-7.94 (m, 2H), 7.91 (d, J=8.5 Hz, 2H), 7.80 (dd, J=7.2, 4.7 Hz, 2H), 7.56-7.31 (m, 12H), 7.36 (d, J=36.1 Hz, 7H), 7.23 (td, J=8.6, 2.4 Hz, 2H), 5.13-5.02 (m, 2H), 4.10 (dd, J=13.9, 4.4 Hz, 1H), 3.90 (dd, J=13.5, 4.7 Hz, 1H), 3.65 (d, J=3.8 Hz, 5H), 3.52 (dd, J=13.7, 10.5 Hz, 2H), 3.27 (dd, J=14.0, 11.7 Hz, 1H), 2.12 (d, J=7.2 Hz, 5H).

Example 42

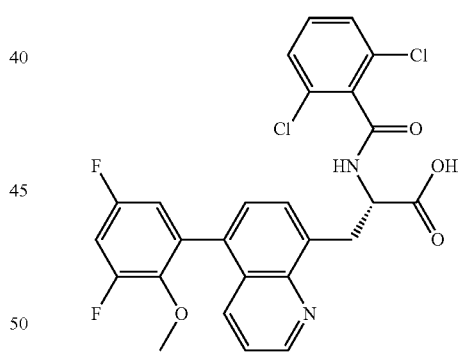

(S)-2-(2,6-dichlorobenzamido)-3-(5-(3,5-difluoro-2-methoxyphenyl)quinolin-8-yl)propanoic acid Prepared according to the procedure described for example 10 employing 1-bromo-3,5-difluoro-2-methoxybenzene in place of H2. MS (m/z) 560.042 [M+H]+. 1H NMR (400 MHz, DMSO-d6) δ 9.14 (dd, J=8.4, 5.1 Hz, 1H), 8.95 (ddd, J=8.7, 4.2, 1.7 Hz, 1H), 7.96-7.85 (m, 2H), 7.78 (dd, J=7.2, 5.1 Hz, 1H), 7.70 (ddd, J=8.5, 7.0, 1.4 Hz, 1H), 7.63-7.60 (m, 1H), 7.46 (dd, J=8.5, 4.2 Hz, 1H), 7.43-7.27 (m, 5H), 5.35-4.91 (m, 1H), 4.07 (dd, J=13.4, 4.0 Hz, 1H), 3.88 (dd, J=13.8, 4.7 Hz, 1H), 3.67 (d, J=3.6 Hz, 3H), 3.52 (dd, J=13.8, 10.6 Hz, 1H), 3.27 (dd, J=13.5, 11.1 Hz, 1H), 2.12 (d, J=7.3 Hz, 3H).

Example 43

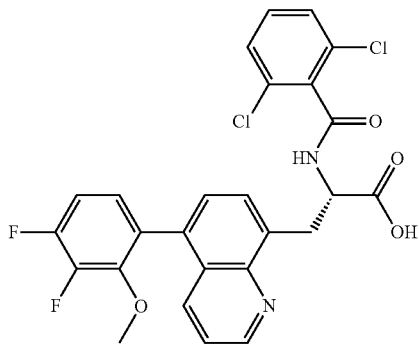 [SMILES: COc1c(-c2ccc(C[C@H](NC(=O)c3c(Cl)cccc3Cl)C(=O)O)c3ncccc23)ccc(F)c1F]

(S)-2-(2,6-dichlorobenzamido)-3-(5-(3,4-difluoro-2-methoxyphenyl)quinolin-8-yl)propanoic acid Prepared according to the procedure described for example 10 employing 1-bromo-3,4-difluoro-2-methoxybenzene in place of H2. MS (m/z) 530.940 [M+H]+. 1H NMR (400 MHz, DMSO-d6) δ 9.09 (dd, J=11.5, 8.5 Hz, 1H), 8.97 (dt, J=4.2, 1.7 Hz, 1H), 7.91 (dd, J=8.5, 1.7 Hz, 1H), 7.77 (dd, J=7.3, 3.3 Hz, 1H), 7.52 (dd, J=8.5, 4.2 Hz, 1H), 7.44-7.24 (m, 5H), 7.05 (dddd, J=16.8, 8.4, 6.0, 2.1 Hz, 1H), 5.74 (s, 1H), 5.24-4.99 (m, 1H), 4.12-3.88 (m, 1H), 3.57 (dd, J=12.3, 1.8 Hz, 3H), 3.52-3.23 (m, 1H).

Example 44

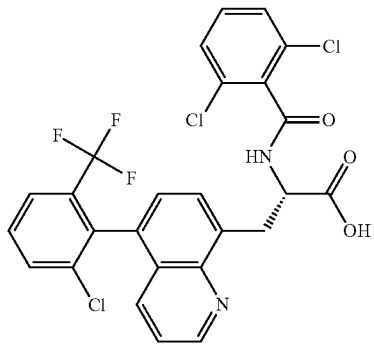 [SMILES: O=C(N[C@@H](Cc1ccc(-c2c(Cl)cccc2C(F)(F)F)c2cccnc12)C(=O)O)c1c(Cl)cccc1Cl]

(2S)-3-(5-(2-chloro-6-(trifluoromethyl)phenyl)quinolin-8-yl)-2-(2,6-dichloro benzamido)propanoic acid Prepared according to the procedure described for example 10 employing 2-bromo-1-chloro-3-(trifluoromethyl)benzene in place of H2. MS (m/z) 536.957 [M+H]+. 1H NMR (400 MHz, DMSO-d6) δ 9.16 (dd, J=8.4, 2.6 Hz, 1H), 8.97 (ddd, J=4.1, 1.8, 1.2 Hz, 1H), 8.11-7.90 (m, 2H), 7.82 (d, J=7.3 Hz, 1H), 7.61-7.43 (m, 2H), 7.44-7.20 (m, 4H), 5.04 (dtd, J=11.5, 8.1, 3.9 Hz, 1H), 4.00 (ddd, J=18.3, 13.8, 3.9 Hz, 1H), 3.44-3.23 (m, 1H).

Example 45

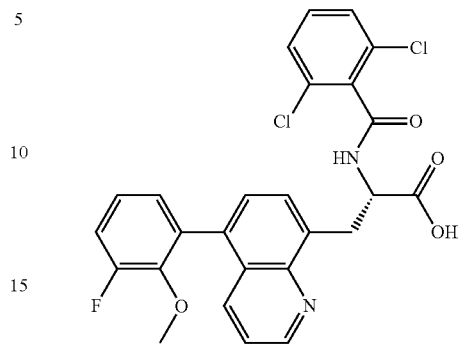

(S)-2-(2,6-dichlorobenzamido)-3-(5-(3-fluoro-2-methoxyphenyl)quinolin-8-yl)propanoic acid Prepared according to the procedure described for example 10 employing 1-bromo-3-fluoro-2-methoxybenzene in place of H2. MS (m/z) 512.892 [M+H]+. 1H NMR (400 MHz, Chloroform-d) δ 9.11 (dd, J=13.6, 8.5 Hz, 1H), 8.98 (dt, J=4.1, 1.7 Hz, 1H), 7.96-7.80 (m, 1H), 7.53 (dd, J=8.5, 4.2 Hz, 1H), 7.51-7.36 (m, 5H), 7.30-7.19 (m, 1H), 7.11-7.02 (m, 1H), 5.76 (s, 1H), 5.11 (s, 1H), 4.17-3.92 (m, 1H), 3.52 (dd, J=11.7, 1.5 Hz, 3H), 3.37 (dd, J=13.6, 11.0 Hz, 1H), 2.57-2.51 (m, 3H).

Example 46

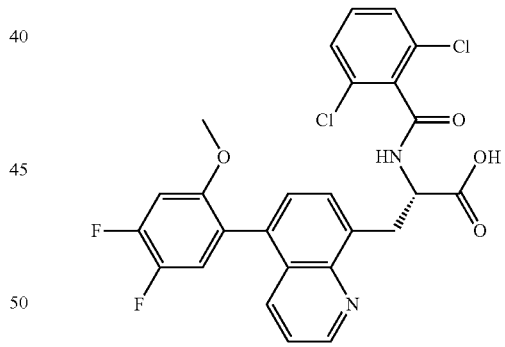

(S)-2-(2,6-dichlorobenzamido)-3-(5-(4,5-difluoro-2-methoxyphenyl)quinolin-8-yl)propanoic acid Prepared according to the procedure described for example 10 employing 1-bromo-4,5-difluoro-2-methoxybenzene in place of H2. MS (m/z) 533.6 [M+H]+. 1H NMR (400 MHz, DMSO-d6) δ 12.72 (s, 1H), 9.08 (dd, J=8.5, 2.2 Hz, 1H), 8.95 (td, J=4.2, 1.7 Hz, 1H), 7.84 (dd, J=8.5, 1.8 Hz, 1H), 7.74 (d, J=7.3 Hz, 1H), 7.56-7.46 (m, 1H), 7.46-7.29 (m, 6H), 5.10 (qd, J=9.6, 4.4 Hz, 1H), 4.00 (ddd, J=22.8, 13.5, 4.4 Hz, 1H), 3.65 (d, J=4.3 Hz, 4H), 3.39 (dd, J=13.7, 10.7 Hz, 1H).

Examples 47 and 48

Example 47: (S)-2-(2,6-dichlorobenzamido)-3-(1,4-dimethyl-2-oxo-1,2-dihydro-[3,5'-biquinolin]-8'-yl)propanoic acid Prepared according to the procedure described for example 11 employing H5 in place of H2. The title compound was identified as the first eluting peak from chiral separation. MS (m/z) 561.22 [M+H]+. 1H NMR (400 MHz, DMSO-d6) δ 9.13 (d, J=8.3 Hz, 1H), 8.93 (dd, J=4.2, 1.7 Hz, 1H), 7.96-7.83 (m, 2H), 7.78 (d, J=7.3 Hz, 1H), 7.75-7.66 (m, 1H), 7.62 (d, J=7.7 Hz, 1H), 7.48-7.24 (m, 5H), 3.97-3.83 (m, 1H), 3.67 (s, 3H), 2.65 (d, J=1.8 Hz, 1H), 2.11 (s, 3H).

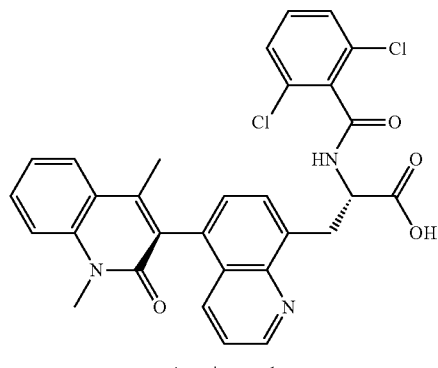

Example 47
Atropisomer 1

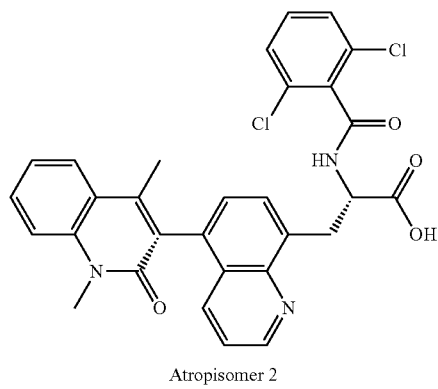

Example 48
Atropisomer 2

Example 48: (S)-2-(2,6-dichlorobenzamido)-3-(1,4-dimethyl-2-oxo-1,2-dihydro-[3,5'-biquinolin]-8'-yl)propanoic acid Prepared according to the procedure described for example 12 employing H5 in place of H2. The title compound was identified as the second eluting peak from chiral separation. MS (m/z) 561.23 [M+H]+. 1H NMR (400 MHz, DMSO-d6) δ9.14 (d, J=8.5 Hz, 1H), 8.96 (dd, J=4.2, 1.7 Hz, 1H), 8.00-7.83 (m, 2H), 7.77 (d, J=7.3 Hz, 1H), 7.73-7.67 (m, 1H), 7.62 (d, J=7.8 Hz, 1H), 7.51-7.21 (m, 7H), 5.18-4.97 (m, 1H), 4.08 (dd, J=13.3, 3.9 Hz, 1H), 3.66 (s, 3H), 3.37-3.13 (m, 1H), 2.12 (s, 3H).

Examples 49 and 50

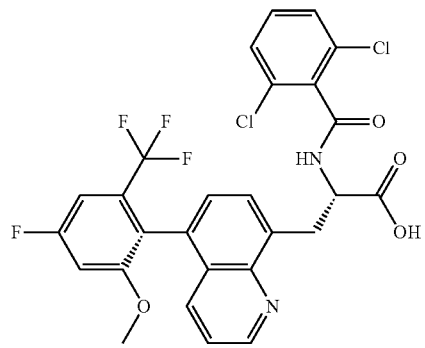

Example 49

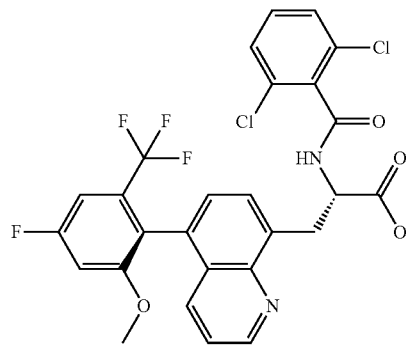

Example 50

Example 49: (S)-2-(2,6-dichlorobenzamido)-3-(5-((R)-4-fluoro-2-methoxy-6-(trifluoromethyl)phenyl)quinolin-8-yl)propanoic acid Prepared according to the procedure described for example 11 employing H1 in place of H2. The title compound was identified as the first eluting peak. MS (m/z) 581.074 [M+H]+. 1H NMR (400 MHz, Chloroform-d) M 9.39 (s, 1H), 8.19 (d, J=27.8 Hz, 2H), 7.71 (d, J=46.0 Hz, 3H), 7.35 (dtd, J=6.7, 4.8, 2.4 Hz, 7H), 7.05 (s, 1H), 5.22 (s, 1H), 4.20 (s, 1H), 3.80-3.60 (m, 3H), 1.35 (s, 1H).

Example 50: (S)-2-(2,6-dichlorobenzamido)-3-(5-((S)-4-fluoro-2-methoxy-6-(trifluoromethyl)phenyl)quinolin-8-yl)propanoic acid Prepared according to the procedure described for example 12 employing H1 in place of H2. The title compound was identified as the second eluting peak. MS (m/z) 581.089 [M+H]+. 1H NMR (400 MHz, Chloroform-d) δ 9.39 (s, 1H), 8.15 (d, J=8.7 Hz, 1H), 8.02 (d, J=7.4 Hz, 1H), 7.70 (dd, J=8.5, 4.9 Hz, 1H), 7.54 (d, J=7.4 Hz, 1H), 7.41 (d, J=6.0 Hz, 1H), 7.31-7.26 (m, 3H), 7.20 (dd, J=8.6, 2.3 Hz, 1H), 6.97 (dd, J=9.9, 2.5 Hz, 1H), 5.17 (d, J=5.4 Hz, 1H), 4.23 (dd, J=15.0, 4.1 Hz, 1H), 3.63 (d, J=1.9 Hz, 3H), 3.43 (dd, J=15.0, 7.2 Hz, 1H).

Example 51

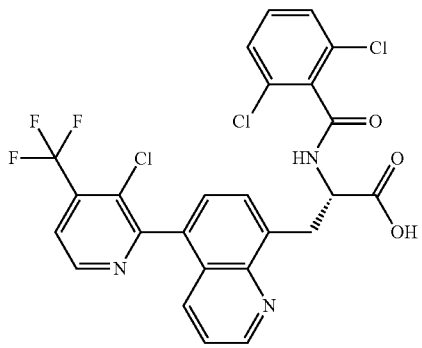 [SMILES: O=C(N[C@@H](Cc1ccc(-c2nccc(C(F)(F)F)c2Cl)c2cccnc12)C(=O)O)c1c(Cl)cccc1Cl]

(S)-3-(5-(3-chloro-4-(trifluoromethyl)pyridin-2-yl)quinolin-8-yl)-2-(2,6-dichlorobenzamido)propanoic acid Prepared according to the procedure described for example 10 employing 2-bromo-3-chloro-4-(trifluoromethyl)pyridine in place of H2. MS (m/z) 568.070 [M+H]+. 1H NMR (400 MHz, Chloroform-d) δ 9.36 (d, J=4.9 Hz, 1H), 8.87 (d, J=5.0 Hz, 1H), 8.33 (dd, J=8.6, 1.5 Hz, 1H), 8.12 (d, J=7.4 Hz, 1H), 7.85-7.73 (m, 3H), 7.53 (d, J=5.7 Hz, 1H), 7.31-7.26 (m, 2H), 5.12 (q, J=5.9 Hz, 1H), 4.23 (dd, J=15.0, 4.2 Hz, 1H), 3.53 (dd, J=15.0, 6.9 Hz, 1H), 1.25 (s, 1H).

Example 52

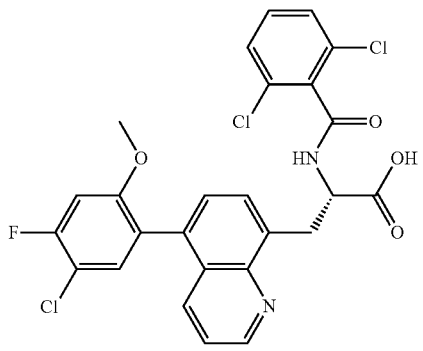 [SMILES: COc1cc(F)c(Cl)cc1-c1ccc(C[C@H](NC(=O)c2c(Cl)cccc2Cl)C(=O)O)c2ncccc12]

(S)-3-(5-(5-chloro-4-fluoro-2-methoxyphenyl)quinolin-8-yl)-2-(2,6-dichloro benzamido)propanoic acid Prepared according to the procedure described for example 10 employing 1-bromo-5-chloro-4-fluoro-2-methoxybenzene in place of H2. MS (m/z) 547.327 [M+H]+. 1H NMR (400 MHz, Chloroform-d) δ 9.56 (dd, J=39.5, 5.1 Hz, 1H), 8.55-8.46 (m, 1H), 8.12-8.00 (m, 1H), 7.84 (dt, J=9.3, 4.8 Hz, 1H), 7.65 (dd, J=10.3, 7.3 Hz, 1H), 7.44-7.27 (m, 2H), 6.90 (dd, J=10.6, 3.2 Hz, 1H), 5.24 (d, J=5.5 Hz, 1H), 4.23 (ddd, J=28.8, 14.8, 4.3 Hz, 1H), 3.68 (dd, J=2.7, 0.6 Hz, 3H), 3.48 (ddd, J=28.4, 14.9, 8.5 Hz, 1H).

Examples 53 and 54

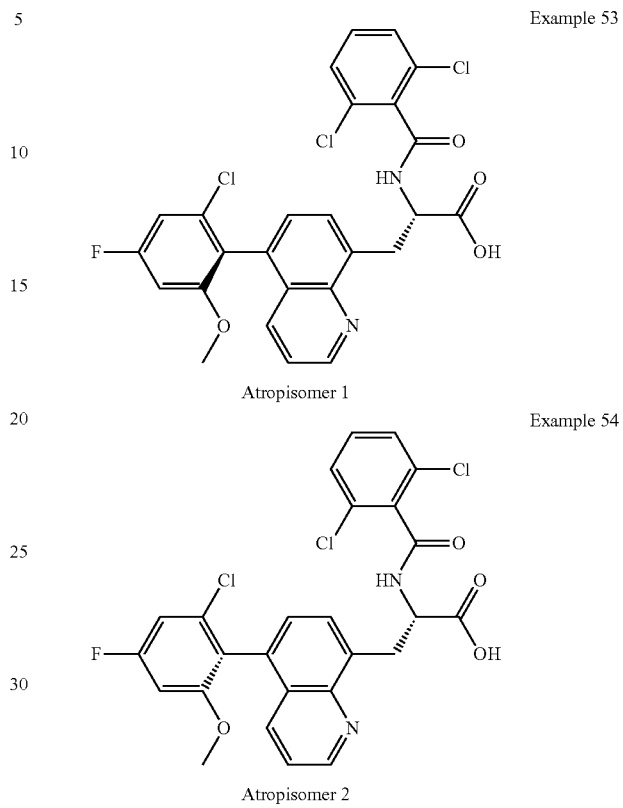

Atropisomer 1

Atropisomer 2

Example 53: (S)-3-(5-((R)-2-chloro-4-fluoro-6-methoxyphenyl)quinolin-8-yl)-2-(2,6-dichlorobenzamido)propanoic acid Prepared according to the procedure described for example 10 employing H15 in place of H2. The title compound was identified as the first eluting peak. MS (m/z) 547.535 [M+H]+. 1H NMR (400 MHz, Chloroform-d) δ 9.55 (d, J=5.1 Hz, 1H), 8.35 (dd, J=8.5, 1.5 Hz, 1H), 8.07 (d, J=7.4 Hz, 1H), 7.80 (dd, J=8.5, 5.1 Hz, 1H), 7.62 (d, J=7.3 Hz, 1H), 7.33 (d, J=6.3 Hz, 1H), 7.30-7.26 (m, 2H), 7.25-7.21 (m, 1H), 6.96 (dd, J=8.2, 2.4 Hz, 1H), 6.75 (dd, J=10.3, 2.4 Hz, 1H), 5.25 (s, 1H), 4.26 (dd, J=15.0, 4.1 Hz, 1H), 3.65 (s, 3H), 3.44 (dd, J=14.9, 8.4 Hz, 1H).

Example 54: (S)-3-(5-((S)-2-chloro-4-fluoro-6-methoxyphenyl)quinolin-8-yl)-2-(2,6-dichlorobenzamido)propanoic acid Prepared according to the procedure described for example 10 employing H15 in place of H2. The title compound was identified as the second eluting peak. MS (m/z) 547.343 [M+H]+. 1H NMR (400 MHz, Chloroform-d) δ 9.55 (d, J=5.1 Hz, 1H), 8.43-8.31 (m, 1H), 8.10 (dd, J=14.2, 7.4 Hz, 1H), 7.86-7.76 (m, 1H), 7.63 (t, J=6.9 Hz, 1H), 7.42-7.32 (m, 1H), 7.29-7.20 (m, 5H), 6.97 (ddd, J=8.4, 6.1, 2.4 Hz, 1H), 6.80-6.68 (m, 1H), 5.27 (d, J=8.9 Hz, 1H), 4.23 (td, J=15.9, 15.1, 4.2 Hz, 1H), 3.65 (d, J=4.2 Hz, 3H), 3.49 (ddd, J=24.1, 14.9, 8.6 Hz, 1H).

Example 55

(S)-2-(2,6-dichlorobenzamido)-3-(5-(4,5-difluoro-2-(methoxy-d3)phenyl)quinolin-8-yl)propanoic acid Prepared according to the procedure described for example 10 employing H14 in place of H2. MS (m/z) 534.042 [M+H]+. 1H NMR (400 MHz, DMSO-d6) δ 9.07 (dd, J=8.4, 2.1 Hz, 1H), 8.94 (td, J=3.9, 1.7 Hz, 1H), 7.83 (dt, J=8.5, 1.8 Hz, 1H), 7.73 (d, J=7.3 Hz, 1H), 7.64-7.58 (m, 4H), 7.58-7.57 (m, 1H), 7.56-7.52 (m, 2H), 7.51-7.46 (m, 1H), 7.42-7.34 (m, 4H), 5.15-5.00 (m, 1H), 4.04-3.91 (m, 1H), 3.33 (ddd, J=37.9, 13.5, 10.8 Hz, 1H).

Example 56

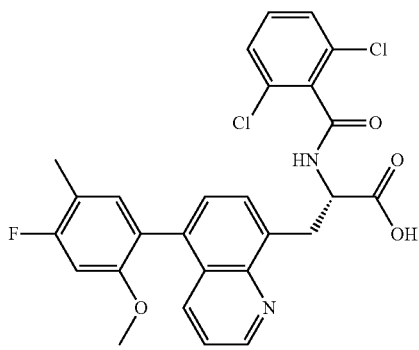 [SMILES: COc1cc(F)c(C)cc1-c1ccc(C[C@H](NC(=O)c2c(Cl)cccc2Cl)C(=O)O)c2ncccc12]

(S)-2-(2,6-dichlorobenzamido)-3-(5-(4-fluoro-2-methoxy-5-methylphenyl) quinolin-8-yl)propanoic acid Prepared according to the procedure described for example 10 employing H13 in place of H2. MS (m/z) 526.914 [M+H]+. 1H NMR (400 MHz, DMSO-d6) δ 9.08 (d, J=3.7 Hz, 1H), 9.06 (s, 1H), 8.92 (ddd, J=4.4, 2.8, 1.7 Hz, 1H), 7.81 (dd, J=8.5, 1.7 Hz, 1H), 7.71 (d, J=7.3 Hz, 1H), 7.47 (dd, J=8.5, 4.1 Hz, 1H), 7.42-7.35 (m, 3H), 7.32 (dd, J=7.3, 2.9 Hz, 1H), 7.12-7.00 (m, 2H), 5.08 (dt, J=5.4, 3.1 Hz, 1H), 4.01-3.91 (m, 1H), 3.61 (d, J=4.4 Hz, 3H), 3.28 (dd, J=7.4, 6.7 Hz, 2H), 2.23-2.19 (m, 3H), 2.18-2.12 (m, 1H), 1.94-1.82 (m, 1H).

Example 57

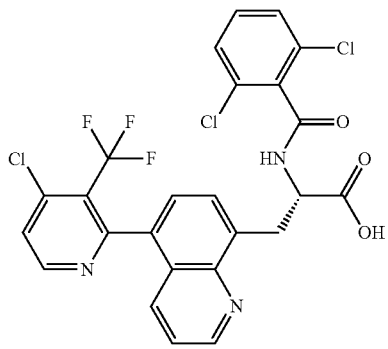 [SMILES: O=C(N[C@@H](Cc1ccc(-c2nccc(Cl)c2C(F)(F)F)c2cccnc12)C(=O)O)c1c(Cl)cccc1Cl]

(S)-3-(5-(4-chloro-3-(trifluoromethyl)pyridin-2-yl)quinolin-8-yl)-2-(2,6-dichlorobenzamido)propanoic acid Prepared according to the procedure described for example 10 employing 2-bromo-4-chloro-3-(trifluoromethyl)pyridine in place of H2. MS (m/z) 568.071 [M+H]+. 1H NMR (400 MHz, DMSO-d6) δ 9.13 (dd, J=23.8, 8.4 Hz, 1H), 8.98 (ddd, J=7.5, 4.1, 1.7 Hz, 1H), 8.87 (ddt, J=6.7, 5.3, 0.6 Hz, 1H), 7.96 (dq, J=5.3, 0.8 Hz, 1H), 7.85 (ddd, J=8.5, 2.7, 1.7 Hz, 1H), 7.76 (dd, J=7.3, 5.4 Hz, 1H), 7.64-7.57 (m, 1H), 7.56-7.54 (m, 1H), 7.51 (ddd, J=8.5, 4.2, 2.8 Hz, 1H), 7.44-7.35 (m, 3H), 5.74 (s, 1H), 5.05 (dddd, J=26.3, 10.7, 8.4, 4.4 Hz, 1H), 3.97 (dd, J=13.6, 4.4 Hz, 1H), 3.39 (ddd, J=15.8, 13.7, 10.7 Hz, 1H).

Example 58

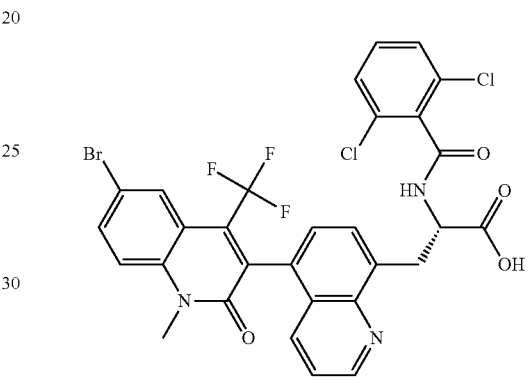

(S)-3-(6-bromo-1-methyl-2-oxo-4-(trifluoromethyl)-1,2-dihydro-[3,5'-biquinolin]-8'-yl)-2-(2,6-dichlorobenzamido)propanoic acid Prepared according to the procedure described for example 10 employing H11 in place of H2. MS (m/z) 694.049 [M+H]+. 1H NMR (400 MHz, DMSO-d6) δ 9.16 (dd, J=12.2, 8.3 Hz, 1H), 8.95 (ddd, J=7.7, 4.2, 1.7 Hz, 1H), 8.08-7.92 (m, 1H), 7.92-7.69 (m, 3H), 7.69-7.22 (m, 9H), 5.19-4.85 (m, 1H), 4.03 (dd, J=13.5, 4.0 Hz, 1H), 3.90 (d, J=13.7 Hz, 1H), 3.70 (d, J=5.6 Hz, 3H).

Example 59

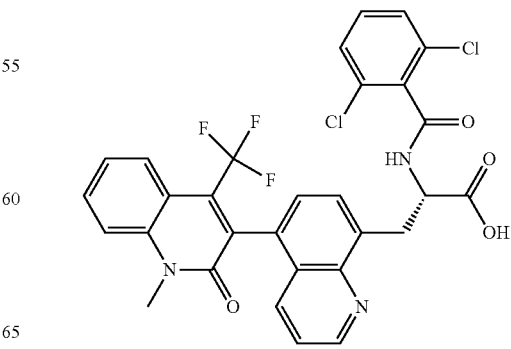

(S)-2-(2,6-dichlorobenzamido)-3-(1-methyl-2-oxo-4-(trifluoromethyl)-1,2-dihydro-[3,5'-biquinolin]-8'-yl)propanoic acid Prepared according to the procedure described for example 10 employing H12 in place of H2. MS (m/z) 614.049 [M+H]+. 1H NMR (400 MHz, DMSO-d6) δ 9.16 (dd, J=12.2, 8.3 Hz, 1H), 8.95 (ddd, J=7.7, 4.2, 1.7 Hz, 1H), 8.08-7.92 (m, 1H), 7.92-7.69 (m, 3H), 7.69-7.22 (m, 9H), 5.19-4.85 (m, 1H), 4.03 (dd, J=13.5, 4.0 Hz, 1H), 3.90 (d, J=13.7 Hz, 1H), 3.70 (d, J=5.6 Hz, 3H).

Examples 60 and 61

Example 60

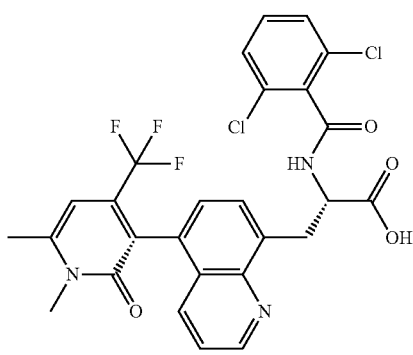

Atropisomer 1

Example 61

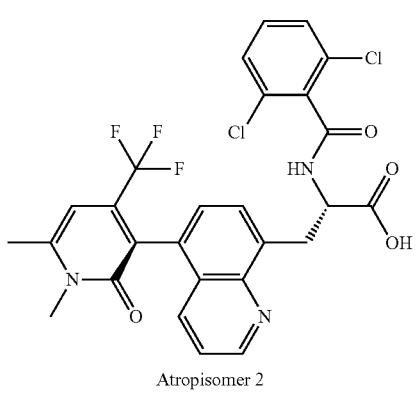

Atropisomer 2

Example 60: (S)-2-(2,6-dichlorobenzamido)-3-(5-(1,6-dimethyl-2-oxo-4-(trifluoromethyl)-1,2-dihydropyridin-3-yl)quinolin-8-yl)propanoic acid Prepared according to the procedure described for example 10 employing H18 in place of H2. The title compound was identified as the first eluting peak. MS (m/z) 577.8 [M+H]+. 1H NMR (400 MHz, Chloroform-d) δ 8.76 (d, J=4.3 Hz, 1H), 8.23-7.94 (m, 5H), 7.81-7.68 (m, 1H), 7.60-7.37 (m, 5H), 7.37-7.16 (m, 7H), 4.85 (d, J=4.6 Hz, 1H), 4.10-3.91 (m, 1H), 3.81 (s, 4H), 3.66 (dd, J=15.0, 4.8 Hz, 1H), 3.49 (s, 1H), 1.21 (d, J=6.1 Hz, 1H).

Example 61: (S)-2-(2,6-dichlorobenzamido)-3-(5-(1,6-dimethyl-2-oxo-4-(trifluoromethyl)-1,2-dihydropyridin-3-yl)quinolin-8-yl)propanoic acid Prepared according to the procedure described for example 11 employing H18 in place of H2. The title compound was identified as the second eluting peak. MS (m/z) 578.054 [M+H]+. 1H NMR (400 MHz, DMSO-d6) δ 9.09 (dd, J=11.3, 8.5 Hz, 1H), 8.97 (dd, J=4.1, 1.7 Hz, 1H), 7.89 (dt, J=8.5, 1.9 Hz, 1H), 7.82-7.72 (m, 1H), 7.52 (ddd, J=8.5, 4.1, 0.8 Hz, 1H), 7.45-7.28 (m, 4H), 5.21-4.96 (m, 1H), 3.99 (td, J=12.8, 4.1 Hz, 1H), 3.92 (s, 2H), 3.55-3.16 (m, 1H).

Examples 62 and 63

Example 62

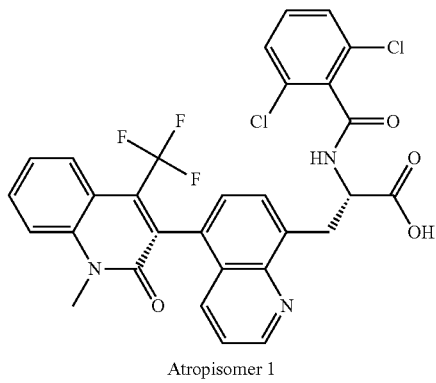

Atropisomer 1

Example 63

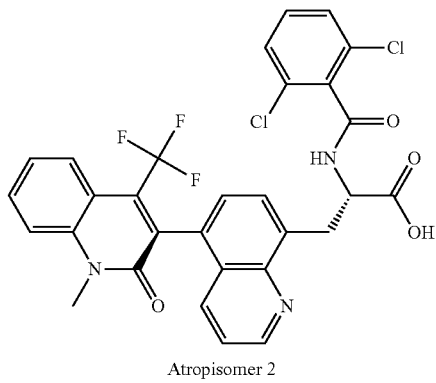

Atropisomer 2

Example 62: (S)-2-(2,6-dichlorobenzamido)-3-(1-methyl-2-oxo-4-(trifluoromethyl)-1,2-dihydro-[3,5'-biquinolin]-8'-yl)propanoic acid Prepared according to the procedure described for example 12 employing H12 in place of H2. The title compound was identified as the first eluting peak. MS (m/z) 614.049 [M+H]+. 1H NMR (400 MHz, Chloroform-d) δ 8.88 (dd, J=19.7, 5.0 Hz, 1H), 8.23-7.86 (m, 3H), 7.86-7.14 (m, 13H), 5.03-4.78 (m, 1H), 4.22-3.94 (m, 1H), 3.87-3.64 (m, 4H), 3.64-3.39 (m, 1H), 1.43-1.05 (m, 2H).

Example 63: (S)-2-(2,6-dichlorobenzamido)-3-(1-methyl-2-oxo-4-(trifluoromethyl)-1,2-dihydro-[3,5'-biquinolin]-8'-yl)propanoic acid Prepared according to the procedure described for example 11 employing H12 in place of H2. The title compound was identified as the second eluting peak. MS (m/z) 614.049 [M+H]+. 1H NMR (400 MHz, Chloroform-d) δ 8.88 (dd, J=19.7, 5.0 Hz, 1H), 8.23-7.86 (m, 3H), 7.86-

7.14 (m, 13H), 5.03-4.78 (m, 1H), 4.22-3.94 (m, 1H), 3.87-3.64 (m, 4H), 3.64-3.39 (m, 1H), 1.43-1.05 (m, 2H).

Examples 64 and 65

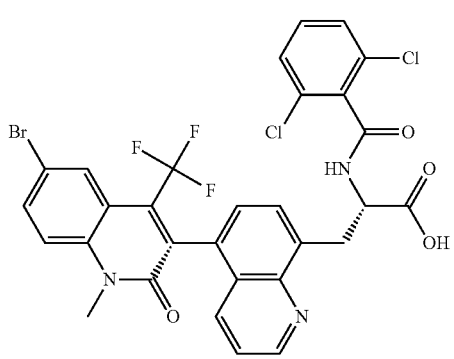 [SMILES: Cn1c(=O)c(-c2ccc(C[C@H](NC(=O)c3c(Cl)cccc3Cl)C(=O)O)c3ncccc23)c(C(F)(F)F)c2cc(Br)ccc21]

Example 64

Atropisomer 1

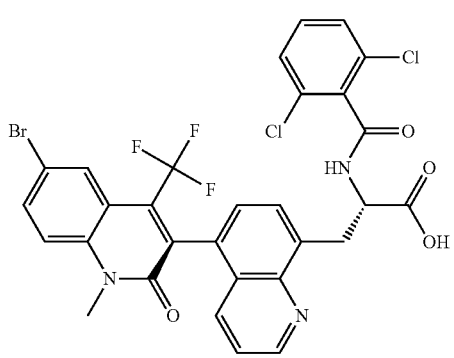

Example 65

Atropisomer 2

Example 64: (S)-3-(6-bromo-1-methyl-2-oxo-4-(trifluoromethyl)-1,2-dihydro-[3,5'-biquinolin]-8'-yl)-2-(2,6-dichlorobenzamido)propanoic acid Prepared according to the procedure described for example 12 employing H11 in place of H2. The title compound was identified as the first eluting peak. MS (m/z) 692.049 [M+H]+. 1H NMR (400 MHz, DMSO-d6) δ 7.93 (d, J=2.2 Hz, 1H), 7.90 (d, J=2.1 Hz, 1H), 7.88-7.84 (m, 2H), 7.65 (s, 1H), 7.63 (s, 1H), 7.29-7.21 (m, 1H), 7.20-7.11 (m, 1H), 4.32 (t, J=5.1 Hz, 1H), 3.72 (s, 7H), 3.42-3.33 (m, 1H), 2.59-2.51 (m, 1H), 2.48 (p, J=1.9 Hz, 11H), 1.65-1.49 (m, 1H), 1.48-1.34 (m, 1H), 1.33-1.21 (m, 1H).

Example 65: (S)-3-(6-bromo-1-methyl-2-oxo-4-(trifluoromethyl)-1,2-dihydro-[3,5'-biquinolin]-8'-yl)-2-(2,6-dichlorobenzamido)propanoic acid Prepared according to the procedure described for example 10 employing H11 in place of H2. The title compound was identified as the second eluting peak. MS (m/z) 692.049 [M+H]+. 1H NMR (400 MHz, DMSO-d6) δ 7.93 (d, J=2.2 Hz, 1H), 7.90 (d, J=2.1 Hz, 1H), 7.88-7.84 (m, 2H), 7.65 (s, 1H), 7.63 (s, 1H), 7.29-7.21 (m, 1H), 7.20-7.11 (m, 1H), 4.32 (t, J=5.1 Hz, 1H), 3.72 (s, 7H), 3.42-3.33 (m, 1H), 2.59-2.51 (m, 1H), 2.48 (p, J=1.9 Hz, 11H), 1.65-1.49 (m, 1H), 1.48-1.34 (m, 1H), 1.33-1.21 (m, 1H).

Example 66

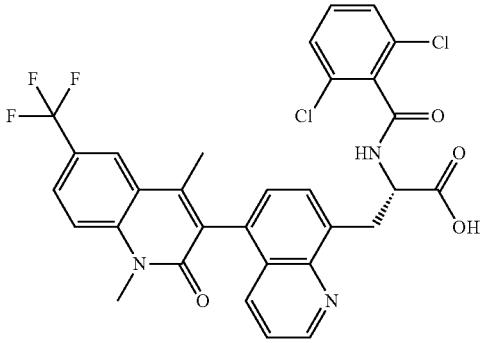 [SMILES: Cc1c(-c2ccc(C[C@H](NC(=O)c3c(Cl)cccc3Cl)C(=O)O)c3ncccc23)c(=O)n(C)c2ccc(C(F)(F)F)cc12]

(S)-2-(2,6-dichlorobenzamido)-3-(1,4-dimethyl-2-oxo-6-(trifluoromethyl)-1,2-dihydro-[3,5'-biquinolin]-8'-yl)propanoic acid Prepared according to the procedure described for example 10 employing H9 in place of H2. MS (m/z) 628.3 [M+H]+. 1H NMR (400 MHz, CDCl3-d) δ 9.17 (d, J=4.9 Hz, 1H), 8.44 (dd, J=8.5, 1.6 Hz, 1H), 8.38 (dd, J=8.6, 1.4 Hz, 2H), 8.17-8.06 (m, 5H), 7.92 (d, J=8.8 Hz, 2H), 7.77 (dd, J=8.4, 5.1 Hz, 1H), 7.73-7.67 (m, 2H), 7.64-7.57 (m, 4H), 5.18-5.09 (m, 2H), 4.32 (dd, J=14.9, 3.6 Hz, 1H), 4.08 (dd, J=14.9, 4.9 Hz, 1H), 3.83 (d, J=1.9 Hz, 6H), 3.72 (dd, J=15.0, 5.9 Hz, 1H), 3.37 (dd, J=14.9, 8.3 Hz, 1H), 2.29 (d, J=7.0 Hz, 6H).

Example 67

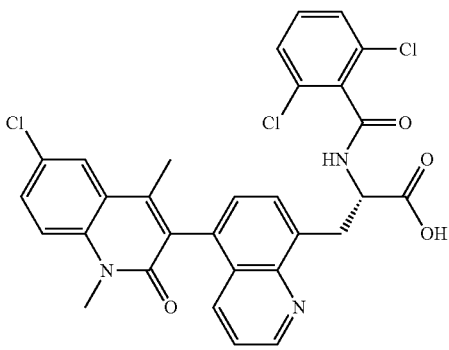

(S)-3-(6-chloro-1,4-dimethyl-2-oxo-1,2-dihydro-[3,5'-biquinolin]-8'-yl)-2-(2,6-dichlorobenzamido)propanoic acid Prepared according to the procedure described for example 10 employing H8 in place of H2. MS (m/z) 594.2 [M+H]+. 1H NMR (400 MHz, DMSO-d6) δ 9.16 (dd, J=8.3, 3.0 Hz, 1H), 8.97 (ddd, J=8.2, 4.1, 1.7 Hz, 1H), 7.94 (dd, J=7.9, 2.4 Hz, 1H), 7.89 (dd, J=8.5, 1.8 Hz, 1H), 7.80-7.77 (m, 1H), 7.75 (dd, J=9.0, 2.4 Hz, 1H), 7.66 (d, J=9.1 Hz, 1H), 7.64-7.58 (m, 1H), 7.58-7.53 (m, 1H), 7.48-7.44 (m, 1H), 7.43-7.37 (m, 3H), 7.33 (t, J=7.0 Hz, 1H), 5.07 (m, 2H), 4.09 (dd, J=13.5, 4.8 Hz, 1H), 3.90 (dd, J=13.5, 4.9 Hz, 2H), 3.67 (d, J=3.7 Hz, 6H), 3.25 (d, J=13.0 Hz, 2H), 2.12 (d, J=7.1 Hz, 2H), 1.38 (s, 1H).

Example 68

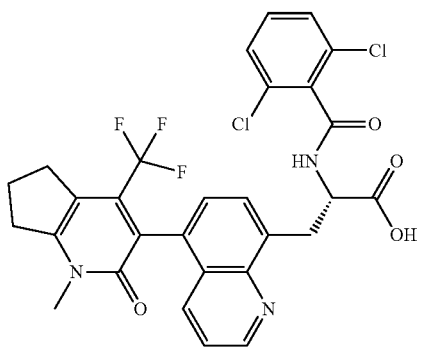 [SMILES: Cn1c2c(c(C(F)(F)F)c(-c3ccc(C[C@H](NC(=O)c4c(Cl)cccc4Cl)C(=O)O)c4ncccc34)c1=O)CCC2]

(S)-2-(2,6-dichlorobenzamido)-3-(5-(1-methyl-2-oxo-4-(trifluoromethyl)-2,5,6,7-tetrahydro-1H-cyclopenta[b]pyridin-3-yl)quinolin-8-yl)propanoic acid Prepared according to the procedure described for example 10 employing H10 in place of H2. MS (m/z) 604.142 [M+H]+. 1H NMR (400 MHz, DMSO-d6) δ 9.15 (dd, J=13.0, 8.4 Hz, 1H), 8.93 (ddd, J=8.8, 4.2, 1.8 Hz, 1H), 7.81 (d, J=8.5 Hz, 1H), 7.71 (d, J=7.4 Hz, 1H), 7.46 (dd, J=8.4, 4.2 Hz, 1H), 7.42-7.32 (m, 3H), 7.19 (dd, J=7.2, 5.2 Hz, 1H), 5.08-4.85 (m, 1H), 4.00 (dd, J=13.4, 4.0 Hz, 1H), 3.88 (dd, J=14.0, 4.4 Hz, 1H), 3.53-3.36 (m, 3H), 3.35-3.18 (m, 1H), 3.09 (t, J=7.8 Hz, 2H), 2.13 (q, J=7.9, 7.2 Hz, 2H).

Example 69

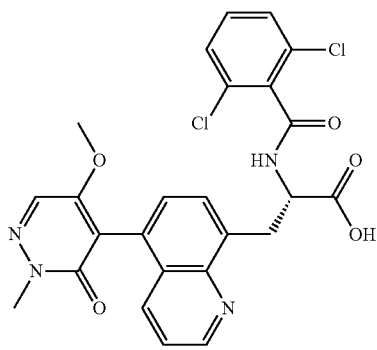 [SMILES: COc1cnn(C)c(=O)c1-c1ccc(C[C@H](NC(=O)c2c(Cl)cccc2Cl)C(=O)O)c2ncccc12]

(S)-2-(2,6-dichlorobenzamido)-3-(5-(5-methoxy-2-methyl-3-oxo-2,3-dihydro pyridazin-4-yl)quinolin-8-yl)propanoic acid Prepared according to the procedure described for example 10 employing 4-chloro-5-methoxy-2-methylpyridazin-3(2H)-one in place of H2. MS (m/z) 527.114 [M+H]+. 1H NMR (400 MHz, DMSO-d6) δ 9.10 (d, J=8.5 Hz, 1H), 8.94 (ddd, J=5.1, 4.2, 1.7 Hz, 1H), 8.30 (d, J=6.3 Hz, 1H), 7.92 (ddd, J=8.5, 5.9, 1.7 Hz, 1H), 7.73 (dd, J=7.4, 4.7 Hz, 1H), 7.48 (ddd, J=8.5, 4.2, 1.6 Hz, 1H), 7.44-7.23 (m, 4H), 5.04 (dddd, J=21.4, 10.7, 8.5, 4.4 Hz, 1H), 3.84 (s, 2H), 3.69 (d, J=2.4 Hz, 3H), 3.41 (dd, J=13.8, 10.6 Hz, 1H), 3.25 (dd, J=13.5, 11.0 Hz, 1H).

Example 70

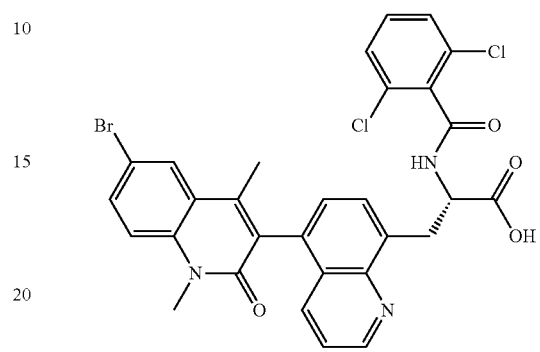

(S)-3-(6-bromo-1,4-dimethyl-2-oxo-1,2-dihydro-[3,5'-biquinolin]-8'-yl)-2-(2,6-dichlorobenzamido)propanoic acid Prepared according to the procedure described for example 10 employing H6 in place of H2. MS (m/z) 640 [M+H]+. 1H NMR (400 MHz, DMSO-d6) δ 9.12 (d, J=8.5 Hz, 1H), 9.01 (dd, J=4.1, 1.6 Hz, 1H), 8.25 (d, J=8.7 Hz, 1H), 7.95 (s, 1H), 7.81-7.75 (m, 3H), 7.60-7.54 (m, 3H), 7.43-7.34 (m, 4H), 5.12 (ddd, J=10.6, 9.2, 5.6 Hz, 2H), 4.02 (dd, J=13.3, 4.5 Hz, 2H), 3.81 (s, 3H), 3.66 (d, J=3.6 Hz, 1H), 3.38 (dd, J=13.6, 10.8 Hz, 2H), 2.73 (s, 3H).

Example 71

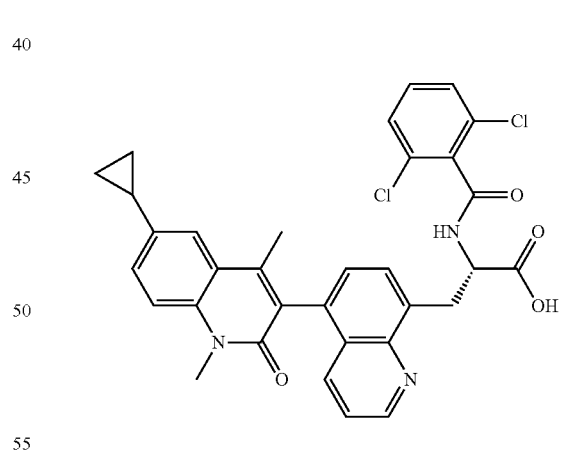

(S)-3-(6-cyclopropyl-1,4-dimethyl-2-oxo-1,2-dihydro-[3,5'-biquinolin]-8'-yl)-2-(2,6-dichlorobenzamido)propanoic acid Prepared according to the procedure described for example 10 employing H7 in place of H2. MS (m/z) 601.1 [M+H]+. 1H NMR (400 MHz, Chloroform-d) δ 9.23 (s, 1H), 8.92 (d, J=5.5 Hz, 1H), 8.29 (dd, J=28.0, 8.5 Hz, 1H), 8.07 (dd, J=22.7, 8.0 Hz, 1H), 7.89 (d, J=6.1 Hz, 1H), 7.69-7.61 (m, 2H), 7.60-7.52 (m, 4H), 7.52-7.44 (m, 2H), 7.38 (d, J=13.1 Hz, 3H), 7.35-7.27 (m, 3H), 5.07-4.95 (m, 2H), 4.28-4.20 (m, 1H), 4.03 (dd, J=14.9, 5.8 Hz, 1H), 3.78 (s, 3H), 3.71 (dd, J=14.8, 6.9 Hz, 1H), 3.42 (dd, J=16.1, 5.5 Hz, 1H), 2.23 (d, J=22.7 Hz, 3H), 2.09-2.00 (m, 2H), 1.06 (q, J=7.2 Hz, 2H), 0.76 (q, J=5.7, 5.2 Hz, 2H).

Examples 72 and 73

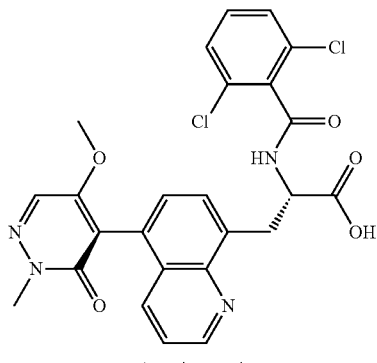

Example 72

Atropisomer 1

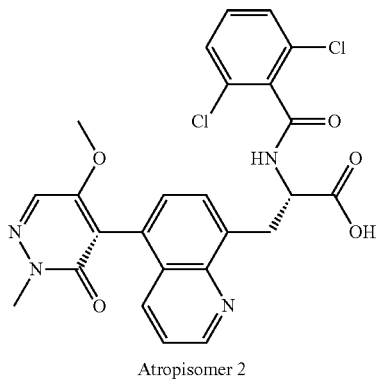

Example 73

Atropisomer 2

Example 72: (S)-2-(2,6-dichlorobenzamido)-3-(5-(5-methoxy-2-methyl-3-oxo-2,3-dihydropyridazin-4-yl)quinolin-8-yl)propanoic acid Prepared according to the procedure described for example 11 employing 4-chloro-5-methoxy-2-methylpyridazin-3(2H)-one in place of H2. The title compound was identified as the first eluting peak. MS (m/z) 527.082 [M+H]+. 1H NMR (400 MHz, DMSO-d6) δ 9.10 (d, J=8.5 Hz, 1H), 8.93 (ddd, J=5.7, 4.2, 1.8 Hz, 1H), 8.30 (d, J=6.4 Hz, 1H), 7.92-7.85 (m, 1H), 7.72 (dd, J=7.3, 3.5 Hz, 1H), 7.46 (dd, J=8.5, 4.1 Hz, 1H), 7.43-7.26 (m, 3H), 4.10-3.95 (m, 1H), 3.84 (s, 2H), 3.81 (s, 1H), 3.69 (d, J=2.4 Hz, 3H), 3.35-3.18 (m, 1H), 1.22 (s, 1H), 1.14 (t, J=7.2 Hz, 1H).

Example 73: (S)-2-(2,6-dichlorobenzamido)-3-(5-(5-methoxy-2-methyl-3-oxo-2,3-dihydropyridazin-4-yl)quinolin-8-yl)propanoic acid Prepared according to the procedure described for example 12 employing 4-chloro-5-methoxy-2-methylpyridazin-3(2H)-one in place of H2. The title compound was identified as the second eluting peak. MS (m/z) 527.082 [M+H]+. 1H NMR (400 MHz, DMSO-d6) δ 9.10 (d, J=8.5 Hz, 1H), 8.93 (ddd, J=5.7, 4.2, 1.8 Hz, 1H), 8.30 (d, J=6.4 Hz, 1H), 7.92-7.85 (m, 1H), 7.72 (dd, J=7.3, 3.5 Hz, 1H), 7.46 (dd, J=8.5, 4.1 Hz, 1H), 7.43-7.26 (m, 3H), 4.10-3.95 (m, 1H), 3.84 (s, 2H), 3.81 (s, 1H), 3.69 (d, J=2.4 Hz, 3H), 3.35-3.18 (m, 1H), 1.22 (s, 1H), 1.14 (t, J=7.2 Hz, 1H).

Example 74

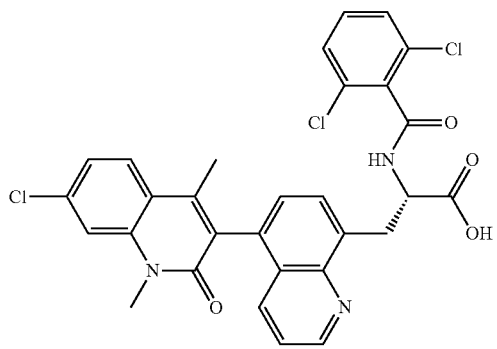

(S)-3-(7-chloro-1,4-dimethyl-2-oxo-1,2-dihydro-[3,5'-biquinolin]-8'-yl)-2-(2,6-dichlorobenzamido)propanoic acid Prepared according to the procedure described for example 10 employing H19 in place of H2. MS (m/z) 596 [M+H]+. 1H NMR (400 MHz, DMSO-d6) δ 9.16 (dd, J=8.3, 6.1 Hz, 1H), 9.00-8.95 (m, 1H), 7.97-7.89 (m, 2H), 7.80 (d, J=11.8 Hz, 1H), 7.72 (d, J=1.9 Hz, 1H), 7.66-7.54 (m, 1H), 7.48 (d, J=12.7 Hz, 1H), 7.44-7.36 (m, 4H), 7.33 (d, J=7.4 Hz, 1H), 5.16-4.99 (m, 3H), 4.10 (dd, J=13.6, 3.8 Hz, 1H), 3.91 (dd, J=14.2, 4.4 Hz, 1H), 3.67 (d, J=3.8 Hz, 3H), 3.52 (dd, J=14.1, 10.8 Hz, 1H), 3.27 (dd, J=13.1, 11.3 Hz, 1H), 2.12 (d, J=6.7 Hz, 3H).

Examples 75 and 76

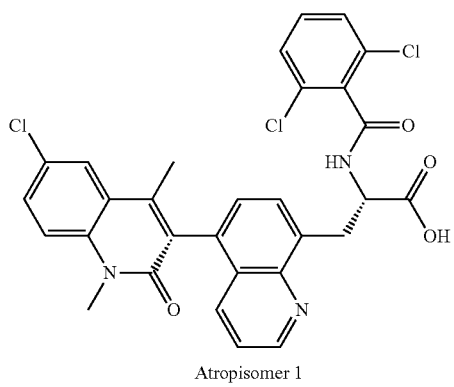

Example 75

Atropisomer 1

Example 76

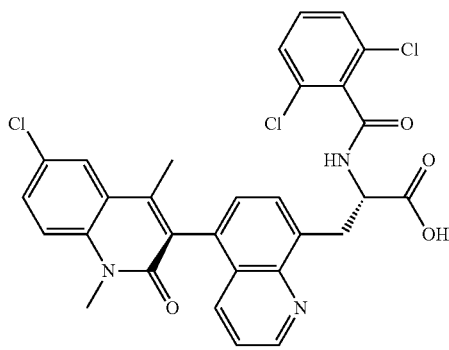

Atropisomer 2

Example 75: (S)-3-(6-chloro-1,4-dimethyl-2-oxo-1,2-dihydro-[3,5'-biquinolin]-8'-yl)-2-(2,6-dichlorobenzamido)propanoic acid Prepared according to the procedure described for example 11 employing H8 in place of H2. The title compound was identified as the first eluting peak. MS (m/z) 594.1 [M+H]+. 1H NMR (400 MHz, DMSO-d6) δ 12.74 (s, 1H), 9.16 (d, J=8.5 Hz, 1H), 8.98 (dd, J=4.1, 1.6 Hz, 1H), 7.96 (d, J=2.4 Hz, 1H), 7.88 (dd, J=8.5, 1.7 Hz, 1H), 7.78 (d, J=7.3 Hz, 1H), 7.75 (dd, J=9.1, 2.4 Hz, 1H), 7.67 (d, J=9.1 Hz, 1H), 7.49-7.38 (m, 4H), 7.31 (d, J=7.2 Hz, 1H), 5.10 (ddd, J=12.0, 8.5, 4.0 Hz, 1H), 4.10 (dd, J=13.5, 4.1 Hz, 1H), 3.67 (s, 3H), 3.27 (dd, J=13.2, 11.3 Hz, 1H), 2.13 (s, 3H).

Example 76: (S)-3-(6-chloro-1,4-dimethyl-2-oxo-1,2-dihydro-[3,5'-biquinolin]-8'-yl)-2-(2,6-dichlorobenzamido)propanoic acid Prepared according to the procedure described for example 12 employing H8 in place of H2. The title compound was identified as the second eluting peak. MS (m/z) 594.10 [M+H]+. 1H NMR (400 MHz, DMSO-d6) δ 12.74 (s, 1H), 9.16 (d, J=8.5 Hz, 1H), 8.98 (dd, J=4.1, 1.5 Hz, 1H), 7.95 (d, J=2.3 Hz, 1H), 7.88 (dd, J=8.4, 1.6 Hz, 1H), 7.78 (d, J=7.3 Hz, 1H), 7.75 (dd, J=9.1, 2.2 Hz, 1H), 7.67 (d, J=9.1 Hz, 1H), 7.48-7.37 (m, 4H), 7.31 (d, J=7.2 Hz, 1H), 5.13-5.06 (m, 1H), 4.13-4.06 (m, 2H), 3.67 (s, 3H), 3.30-3.22 (m, 2H), 2.13 (s, 3H).

Example 77

(S)-3-(7-chloro-1,4-dimethyl-2-oxo-1,2-dihydro-[3,5'-biquinolin]-8'-yl)-2-(2,6-dichlorobenzamido)propanoic acid Prepared according to the procedure described for example 11 employing H19 in place of H2. The title compound was identified as the first eluting peak. MS (m/z) 544.2 [M+H]+. 1H NMR (400 MHz, DMSO-d6) δ 9.30 (d, J=8.2 Hz, 1H), 8.89 (s, 1H), 8.79 (s, 1H), 7.98-7.93 (m, 1H), 7.76-7.61 (m, 5H), 7.54 (s, 1H), 7.36 (t, J=7.5 Hz, 1H), 7.16-7.09 (m, 2H), 4.80 (2H), 3.89 (dd, J=14.8, 3.9 Hz, 1H), 3.72 (d, J=12.2 Hz, 1H), 3.64 (s, 3H), 3.56 (dd, J=14.4, 9.8 Hz, 1H), 3.36 (dd, J=14.2, 10.7 Hz, 1H), 3.29 (s, 3H).

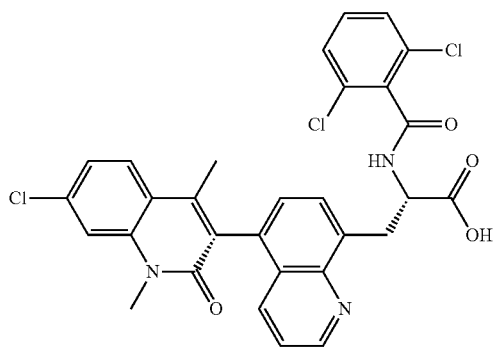

Example 78

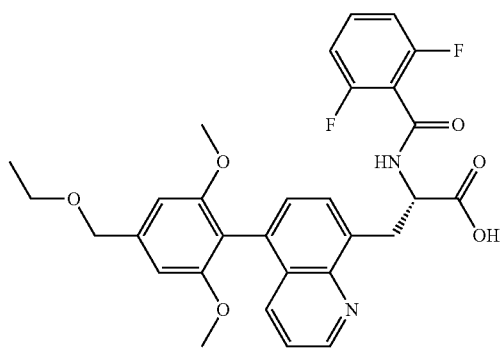 [SMILES: CCOCc1cc(OC)c(-c2ccc(C[C@H](NC(=O)c3c(F)cccc3F)C(=O)O)c3ncccc23)c(OC)c1]

(S)-2-(2,6-difluorobenzamido)-3-(5-(4-(ethoxymethyl)-2,6-dimethoxyphenyl) quinolin-8-yl)propanoic acid To a microwave vial was added EQ-2 (100 mg, 0.223 mmol), potassium phosphate (0.78 mL, 0.78 mmol, 1N), (4-(ethoxymethyl)-2,6-dimethoxyphenyl) boronic acid (59 mg, 0.245 mmol), and DME 2.4 mL. The vial was purged with nitrogen sealed and heated in a microwave reactor to 130° C. The reaction was diluted with DMSO, acidified with TFA and purified by HPLC and lyophilized to afford the title compound. MS (m/z) 551.2 [M+H]+. 1H NMR (400 MHz, DMSO-d6) δ 9.25 (d, J=7.8 Hz, 1H), 8.89 (dd, J=4.2, 1.7 Hz, 1H), 7.80-7.60 (m, 2H), 7.54-7.37 (m, 2H), 7.27 (d, J=7.3 Hz, 1H), 7.18-7.02 (m, 2H), 6.77 (d, J=1.1 Hz, 2H), 4.90 (ddd, J=10.0, 7.7, 4.8 Hz, 1H), 4.53 (s, 2H), 3.91 (dd, J=13.8, 4.8 Hz, 1H), 3.62-3.50 (m, 7H), 3.41 (dd, J=13.7, 10.0 Hz, 1H), 1.20 (t, J=7.0 Hz, 3H).

Example 79

(S)-3-(5-(4,5-difluoro-2-methoxyphenyl)quinolin-8-yl)-2-(2,6-difluorobenzamido) propanoic acid Prepared according to the procedure described for example 78 employing (4,5-difluoro-2-methoxyphenyl)boronic acid in place of (4-(ethoxymethyl)-2,6-dimethoxyphenyl) boronic acid. MS (m/z) 499.048 [M+H]+. 1H NMR (400 MHz, DMSO-d6) δ 9.22 (d, J=12.8, 8.0 Hz, 1H), 8.94 (ddd, J=4.2, 1.8, 0.7 Hz, 1H), 7.86 (ddd, J=8.5, 3.9, 1.8 Hz, 1H), 7.69 (dd, J=7.3, 5.7 Hz, 1H), 7.54-7.42 (m, 2H), 7.41-7.27 (m, 3H), 7.11 (ddd, J=8.6, 7.6, 1.6 Hz, 2H), 4.90 (dtd, J=10.0, 7.4, 4.8 Hz, 1H), 3.96 (ddd, J=19.0, 13.6, 4.9 Hz, 1H), 3.63 (d, J=4.4 Hz, 3H), 3.37 (ddd, J=18.4, 13.6, 10.1 Hz, 1H).

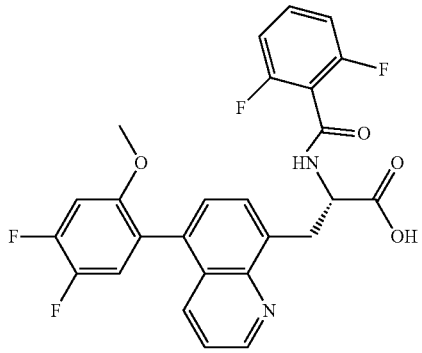 [SMILES: COc1cc(F)c(F)cc1-c1ccc(C[C@H](NC(=O)c2c(F)cccc2F)C(=O)O)c2ncccc12]

Example 80

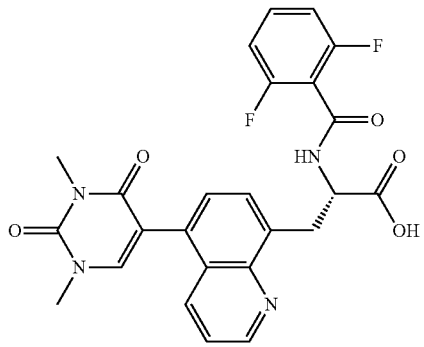 [SMILES: Cn1cc(-c2ccc(C[C@H](NC(=O)c3c(F)cccc3F)C(=O)O)c3ncccc23)c(=O)n(C)c1=O]

(S)-2-(2,6-difluorobenzamido)-3-(5-(1,3-dimethyl-2,4-dioxo-1,2,3,4-tetrahydropyrimidin-5-yl)quinolin-8-yl)propanoic acid Prepared according to the procedure described for example 78 employing EQ-4 in place of (4-(ethoxymethyl)-2,6-dimethoxyphenyl) boronic acid and 5-bromo-1,3-dimethylpyrimidine-2,4(1H,3H)-dione in place of EQ-3. MS (m/z) 495.2 [M+H]+. 1H NMR (400 MHz, DMSO-d6) δ 9.21 (d, J=7.9 Hz, 1H), 8.94 (dd, J=4.2, 1.7 Hz, 1H), 8.22 (dd, J=8.5, 1.7 Hz, 1H), 7.88 (s, 1H), 7.66 (d, J=7.3 Hz, 1H), 7.52 (dd, J=8.5, 4.2 Hz, 1H), 7.50-7.43 (m, 1H), 7.40 (d, J=7.3 Hz, 1H), 7.16-7.06 (m, 2H), 4.87 (td, J=8.9, 8.0, 4.9 Hz, 1H), 3.93 (d, J=13.4 Hz, 1H), 3.38 (m, 4H), 3.24 (s, 3H).

Examples 81 and 82

Example 81: (S)-2-(2,6-difluorobenzamido)-3-(5-(1,3,6-trimethyl-2,4-dioxo-1,2,3,4-tetrahydropyrimidin-5-yl)quinolin-8-yl)propanoic acid Prepared according to the procedure described for example 78 employing EQ-4 in place of (4-(ethoxymethyl)-2,6-dimethoxyphenyl)boronic acid and 5-bromo-1,3,6-trimethylpyrimidine-2,4(1H,3H)-dione in place of EQ-3. The first eluting isomer provided example 81. MS (m/z) 509.2 [M+H]+. 1H NMR (400 MHz, DMSO-d6) δ 9.13 (d, J=8.4 Hz, 1H), 8.95 (dd, J=4.2, 1.7 Hz, 1H), 8.13 (dd, J=8.5, 1.8 Hz, 1H), 7.66 (d, J=7.3 Hz, 1H), 7.52-7.40 (m, 2H), 7.29 (d, J=7.2 Hz, 1H), 7.06 (dd, J=8.5, 7.5 Hz, 2H), 5.00 (ddd, J=10.9, 8.4, 4.4 Hz, 1H), 4.07 (dd, J=13.3, 4.4 Hz, 1H), 3.43 (s, 3H), 3.22 (s, 4H), 1.94 (s, 3H); 1H NMR (400 MHz, DMSO-d6) δ 9.21 (d, J=7.7 Hz, 1H), 8.93 (dd, J=4.2, 1.8 Hz, 1H), 8.14 (dd, J=8.5, 1.8 Hz, 1H), 7.68 (d, J=7.3 Hz, 1H), 7.55-7.40 (m, 2H), 7.32 (d, J=7.3 Hz, 1H), 7.10 (dd, J=8.4, 7.5 Hz, 2H), 4.87 (ddd, J=9.8, 7.7, 5.3 Hz, 1H), 3.83 (dd, J=13.7, 5.3 Hz, 1H), 3.52 (dd, J=13.7, 9.8 Hz, 1H), 3.43 (s, 3H), 3.22 (s, 3H), 1.92 (s, 3H).

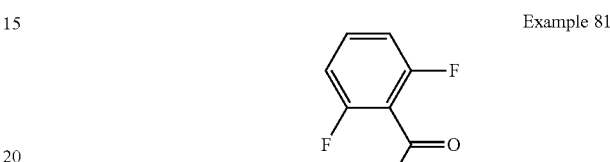

Example 81

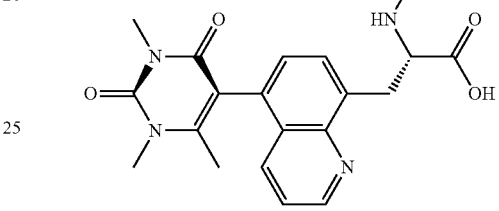

Atropisomer 1

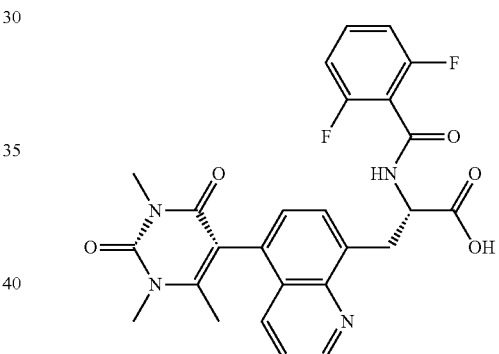

Example 82

Atropisomer 2

Example 82: (S)-2-(2,6-difluorobenzamido)-3-(5-(1,3,6-trimethyl-2,4-dioxo-1,2,3,4-tetrahydropyrimidin-5-yl)quinolin-8-yl)propanoic acid Prepared according to the procedure described for example 78 employing EQ-4 in place of (4-(ethoxymethyl)-2,6-dimethoxyphenyl)boronic acid and 5-bromo-1,3,6-trimethylpyrimidine-2,4(1H,3H)-dione in place of EQ-3. The second eluting isomer provided example 82. MS (m/z) 509.2 [M+H]+. 1H NMR (400 MHz, DMSO-d6) δ 9.13 (d, J=8.4 Hz, 1H), 8.95 (dd, J=4.2, 1.7 Hz, 1H), 8.13 (dd, J=8.5, 1.8 Hz, 1H), 7.66 (d, J=7.3 Hz, 1H), 7.52-7.40 (m, 2H), 7.29 (d, J=7.2 Hz, 1H), 7.06 (dd, J=8.5, 7.5 Hz, 2H), 5.00 (ddd, J=10.9, 8.4, 4.4 Hz, 1H), 4.07 (dd, J=13.3, 4.4 Hz, 1H), 3.43 (s, 3H), 3.22 (s, 4H), 1.94 (s, 3H); 1H NMR (400 MHz, DMSO-d6) δ 9.21 (d, J=7.7 Hz, 1H), 8.93 (dd, J=4.2, 1.8 Hz, 1H), 8.14 (dd, J=8.5, 1.8 Hz, 1H), 7.68 (d, J=7.3 Hz, 1H), 7.55-7.40 (m, 2H), 7.32 (d, J=7.3 Hz, 1H), 7.10 (dd, J=8.4, 7.5 Hz, 2H), 4.87 (ddd, J=9.8, 7.7, 5.3 Hz, 1H), 3.83 (dd, J=13.7, 5.3 Hz, 1H), 3.52 (dd, J=13.7, 9.8 Hz, 1H), 3.43 (s, 3H), 3.22 (s, 3H), 1.92 (s, 3H).

Example 83

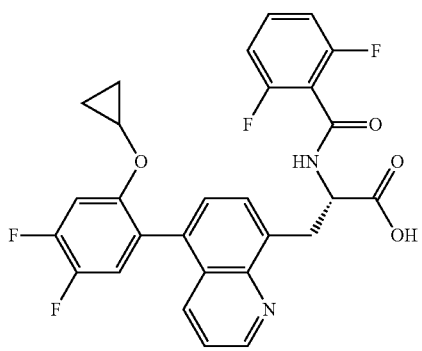 [SMILES: O=C(N[C@@H](Cc1ccc(-c2cc(F)c(F)cc2OC2CC2)c2cccnc12)C(=O)O)c1c(F)cccc1F]

Example 83: (S)-3-(5-(2-cyclopropoxy-4,5-difluoro-phenyl)quinolin-8-yl)-2-(2,6-difluorobenzamido) propanoic acid Prepared according to the procedure described for example 78 employing EQ-4 in place of (4-(ethoxymethyl)-2,6-dimethoxyphenyl)boronic acid and H17 in place of EQ-3. MS (m/z) 525.1 [M+H]+. 1H NMR (400 MHz, DMSO-d6) δ 9.18 (d, J=8.0 Hz, 1H), 8.93 (dt, J=3.9, 1.8 Hz, 1H), 7.83 (td, J=8.2, 1.7 Hz, 1H), 7.67 (d, J=7.3 Hz, 1H), 7.57-7.40 (m, 3H), 7.40-7.26 (m, 2H), 7.15-7.02 (m, 2H), 4.90 (ddd, J=12.7, 9.9, 4.9 Hz, 1H), 3.95 (ddd, J=24.7, 13.6, 4.8 Hz, 1H), 3.80 (tt, J=6.1, 2.9 Hz, 1H), 3.37 (ddd, J=17.0, 13.6, 10.2 Hz, 1H), 0.80-0.56 (m, 2H), 0.49 (dd, J=11.8, 3.1 Hz, 1H), 0.29 (ddd, J=17.8, 7.3, 4.3 Hz, 1H).

Example 84

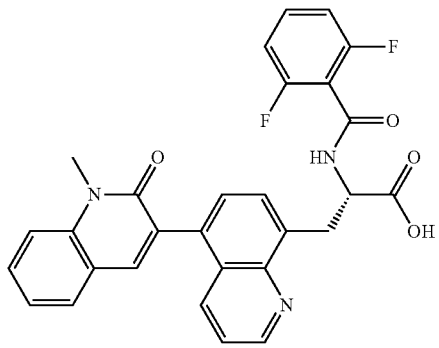 [SMILES: Cn1c(=O)c(-c2ccc(C[C@H](NC(=O)c3c(F)cccc3F)C(=O)O)c3ncccc23)cc2ccccc21]

(S)-2-(2,6-difluorobenzamido)-3-(1-methyl-2-oxo-1,2-dihydro-[3,5'-biquinolin]-8'-yl)propanoic acid Prepared according to the procedure described for example 78 employing EQ-4 in place of (4-(ethoxymethyl)-2,6-dimethoxyphenyl)boronic acid and 3-bromo-1-methylquinolin-2(1H)-one in place of EQ-3. MS (m/z) 514.2 [M+H]+. 1H NMR (400 MHz, DMSO-d6) δ 9.22 (d, J=7.8 Hz, 1H), 8.95 (dd, J=4.1, 1.7 Hz, 1H), 8.07 (dd, J=8.5, 1.7 Hz, 1H), 8.02 (s, 1H), 7.86-7.78 (m, 1H), 7.73-7.65 (m, 2H), 7.65-7.59 (m, 1H), 7.55-7.43 (m, 3H), 7.32 (ddd, J=7.7, 7.0, 1.1 Hz, 1H), 7.11 (dd, J=8.4, 7.5 Hz, 2H), 4.91 (s, 1H), 3.93 (d, J=35.0 Hz, 1H), 3.71 (s, 3H), 3.46 (d, J=54.5 Hz, 1H).

Examples 85 and 86

Methyl (S)-2-(2,6-difluoro-4-((R)-3-(trifluoromethyl)morpholino)benzamido)-3-(5-(1,6-dimethyl-2-oxo-4-(trifluoromethyl)-1,2-dihydropyridin-3-yl) quinolin-8-yl)propanoate To a solution of H18 (103 mg, 0.325 mmol), EQ8 (192 mg, 0.296 mmol) in DME (6 mL) was added XPhos Pd G3 (13 mg, 0.018 mmol) and potassium phosphate (1 mL, 1 mmol, 1N), and the reaction vial was degassed with nitrogen, sealed, and heated to 90° C. for 20 min. It was diluted with water and extracted with ethyl acetate dried over sodium sulfate, filtered, concentrated and purified on silica gel eluting with hexanes and ethyl acetate to afford the title compound.

Methyl (S)-2-(2,6-difluoro-4-((R)-3-(trifluoromethyl)morpholino)benzamido)-3-(5-(1,6-dimethyl-2-oxo-4-(trifluoromethyl)-1,2-dihydropyridin-3-yl) quinolin-8-yl)propanoate (Atropisomers 1 & 2) were isolated on a chiral SFC AD-H column eluting with 30% methanol and carried individually into the ensuing hydrolysis reactions.

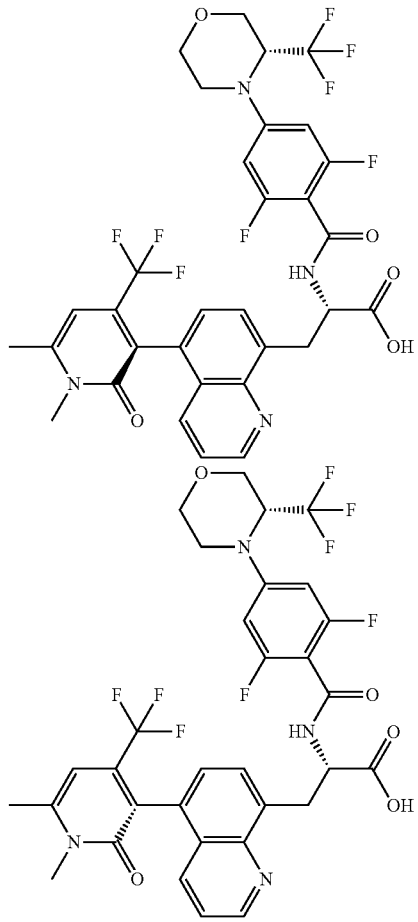

Example 85

(S)-2-(2,6-difluoro-4-((R)-3-(trifluoromethyl)morpholino) benzamido)-3-(5-(1,6-dimethyl-2-oxo-4-(trifluoromethyl)-1,2-dihydropyridin-3-yl)quinolin-8-yl)propanoic acid To a stirred solution of methyl (S)-2-(2,6-difluoro-4-((R)-3-(trifluoromethyl) morpholino)benzamido)-3-(5-(1,6-dimethyl-2-oxo-4-(trifluoromethyl)-1,2-dihydropyridin-3-yl) quinolin-8-yl)propanoate (Atropisomer 1, first eluting peak) (24 mg, 0.034 mmol) in THF (2 mL) and methanol (2 mL) was added sodium hydroxide (0.071 mL, 0.071 mmol, 1 N) and the mixture as stirred for 4 h, acidified with TFA, diluted with DMSO and the more volatile components were removed on a rotary evaporator. The residue was chromatographed on C-18 modified silica gel eluting with acetonitrile in water (0.4% TFA) to afford example 85. MS (m/z) 699.2 [M+H]+. 1H NMR (400 MHz, DMSO-d6) δ 8.95 (dd, J=11.7, 5.7 Hz, 2H), 7.83 (d, J=8.5 Hz, 1H), 7.70 (d, J=7.3 Hz, 1H), 7.49 (dd, J=8.6, 4.2 Hz, 1H), 7.26 (d, J=7.3 Hz, 1H), 6.75 (d, J=11.8 Hz, 2H), 6.64 (s, 1H), 4.91 (d, J=9.1 Hz, 1H), 4.81 (d, J=11.4 Hz, 1H), 4.16 (d, J=12.7 Hz, 1H), 3.95 (d, J=10.1 Hz, 1H), 3.88 (dd, J=13.9, 4.8 Hz, 1H), 3.74 (d, J=12.7 Hz, 1H), 3.57 (d, J=12.3 Hz, 1H), 3.52 (s, 3H), 3.48-3.36 (m, 2H), 3.24 (t, J=12.4 Hz, 1H), 2.55 (s, 3H).

Example 86: (S)-2-(2,6-difluoro-4-((R)-3-(trifluoromethyl)morpholino) benzamido)-3-(5-(1,6-dimethyl-2-oxo-4-(trifluoromethyl)-1,2-dihydropyridin-3-yl)quinolin-8-yl)propanoic acid To a stirred solution of methyl (S)-2-(2,6-difluoro-4-((R)-3-(trifluoromethyl) morpholino)benzamido)-3-(5-(1,6-dimethyl-2-oxo-4-(trifluoromethyl)-1,2-dihydropyridin-3-yl) quinolin-8-yl)propanoate (Atropisomer 2, second eluting peak) (26 mg, 0.035 mmol) in THF (2 mL) and Methanol (2 mL) was added sodium hydroxide (0.071 mL, 0.071 mmol, 1 N) and the mixture as stirred for 4 h, acidified with TFA, diluted with DMSO and the more volatile components were removed on a rotary evaporator. The residue was chromatographed on C-18 modified silica gel eluting with acetonitrile in water (0.4% TFA) to afford example 86. MS (m/z) 699.2 [M+H]+. 1H NMR (400 MHz, DMSO-d6) δ 8.99-8.81 (m, 2H), 7.82 (d, J=8.4 Hz, 1H), 7.69 (d, J=7.3 Hz, 1H), 7.48 (dd, J=8.6, 4.2 Hz, 1H), 7.24 (d, J=7.2 Hz, 1H), 6.73 (d, J=11.7 Hz, 2H), 6.64 (s, 1H), 4.97-4.81 (m, 2H), 4.15 (d, J=12.7 Hz, 1H), 3.94 (dd, J=11.5, 6.9 Hz, 2H), 3.74 (d, J=12.7 Hz, 1H), 3.57 (d, J=11.8 Hz, 1H), 3.51 (s, 3H), 3.47-3.33 (m, 2H), 3.24 (t, J=12.5 Hz, 1H), 2.55 (s, 3H).

Example 87

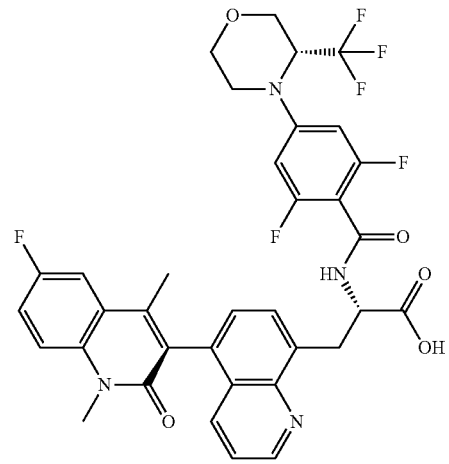

(S)-2-(2,6-difluoro-4-((R)-3-(trifluoromethyl)morpholino)benzamido)-3-(6-fluoro-1,4-dimethyl-2-oxo-1,2-dihydro-[3,5'-biquinolin]-8'-yl)propanoic acid Prepared according to the procedure described for example 85 employing H2 in place of H18. The title compound was identified as the first eluting peak. MS (m/z) 699.2 [M+H]+. 1H NMR (400 MHz, DMSO-d6) δ 8.96 (t, J=6.0 Hz, 2H), 7.91 (d, J=8.5 Hz, 1H), 7.78-7.65 (m, 3H), 7.64-7.56 (m, 1H), 7.47 (dd, J=8.6, 4.2 Hz, 1H), 7.34 (d, J=7.2 Hz, 1H), 6.76 (d, J=11.9 Hz, 2H), 4.98-4.79 (m, 2H), 4.16 (d, J=12.7 Hz, 1H), 3.95 (d, J=11.5 Hz, 1H), 3.84 (dd, J=13.5, 5.3 Hz, 1H), 3.74 (d, J=12.7 Hz, 1H), 3.69 (s, 3H), 3.57 (q, J=12.7 Hz, 2H), 3.43 (d, J=12.8 Hz, 1H), 3.24 (t, J=12.4 Hz, 1H), 2.09 (s, 3H).

Example 88

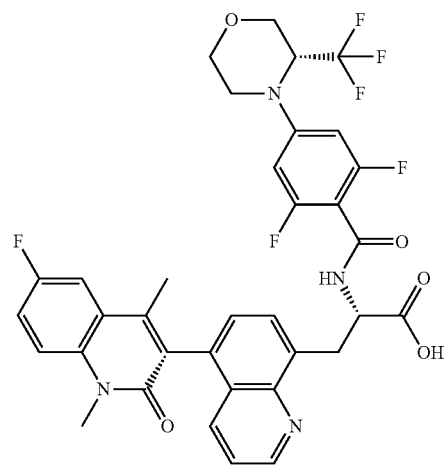

(S)-2-(2,6-difluoro-4-((R)-3-(trifluoromethyl)morpholino) benzamido)-3-(6-fluoro-1,4-dimethyl-2-oxo-1,2-dihydro-[3,5'-biquinolin]-8'-yl)propanoic acid Prepared according to the procedure described for example 86 employing H2 in place of H18. The title compound was identified as the second eluting peak. MS (m/z) 699.2 [M+H]+. 1H NMR (400 MHz, DMSO-d6) δ 8.96 (d, J=4.1 Hz, 1H), 8.90 (d, J=8.1 Hz, 1H), 7.89 (d, J=8.4 Hz, 1H), 7.79-7.64 (m, 3H), 7.60 (dd, J=10.4, 7.7 Hz, 1H), 7.46 (dd, J=8.5, 4.2 Hz, 1H), 7.31 (d, J=7.1 Hz, 1H), 6.73 (d, J=11.7 Hz, 2H), 5.01-4.84 (m, 2H), 4.16 (d, J=12.7 Hz, 1H), 4.07 (dd, J=13.3, 4.4 Hz, 1H), 3.95 (d, J=9.2 Hz, 1H), 3.73 (d, J=13.1 Hz, 1H), 3.68 (s, 3H), 3.55 (t, J=11.5 Hz, 1H), 3.42 (d, J=12.6 Hz, 1H), 3.27 (dt, J=26.4, 12.3 Hz, 2H), 2.10 (s, 3H).

Example 89

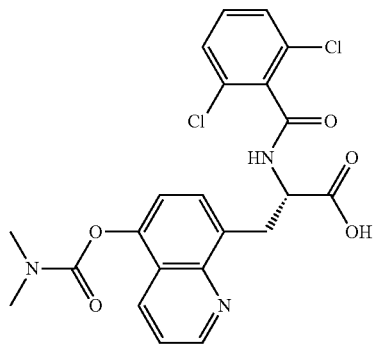 [SMILES: CN(C)C(=O)Oc1ccc(C[C@H](NC(=O)c2c(Cl)cccc2Cl)C(=O)O)c2ncccc12]

(S)-2-(2,6-dichlorobenzamido)-3-(5-((dimethylcarbamoyl)oxy)quinolin-8-yl)propanoic acid a) methyl (S)-2-(2,6-dichlorobenzamido)-3-(5-hydroxyquinolin-8-yl) propanoate: To a vial were added EQ-5 (200 mg, 0.415 mmol) cesium hydroxide (62 mg, 0.415 mmol) and TBuBrett Phos Pd G3 (354 mg, 0.415 mmol), dioxane (4 mL) and water (1 mL) and the vial was sealed and heated at 70° C. overnight. 1N HCl in methanol was added and the mixture was stirred an additional 24 h. The mixture was neutralized with NaHCO$_3$ and chromatographed on silica eluting with methanol in dichloromethane to afford the title compound. b) (S)-2-(2,6-dichlorobenzamido)-3-(5-((dimethylcarbamoyl)oxy)quinolin-8-yl)propanoic acid: To a stirred solution of methyl (S)-2-(2,6-dichlorobenzamido)-3-(5-hydroxyquinolin-8-yl)propanoate (25 mg, 0.059 mmol), trimethylamine (15 mg, 0.18 mmol), in dichloromethane (1 mL) was added dimethylcarbamic chloride (13 mg, 0.12 mmol) and let stir for 30 min. THF (1 mL) and lithium hydroxide (0.5 mL, 0.5 mmol, 1N) was then added the reaction stirred for an additional 2 h. The mixture was diluted with DMSO and neutralized with TFA, volatile components were removed on a rotary evaporator and the residue was chromatographed on C-18 functionalized silica gel eluting with acetonitrile in water (0.4% TFA) to afford the title compound after lyophilizing. MS (m/z) 475.967 [M+H]+. 1H NMR (400 MHz, DMSO-d6) δ 9.06 (d, J=8.4 Hz, 1H), 8.98 (dd, J=4.2, 1.7 Hz, 1H), 8.29 (dd, J=8.5, 1.8 Hz, 1H), 7.67 (d, J=7.9 Hz, 1H), 7.59 (dd, J=8.5, 4.2 Hz, 1H), 7.42-7.31 (m, 3H), 7.28 (d, J=7.8 Hz, 1H), 5.08-4.81 (m, 1H), 3.88 (dd, J=13.6, 4.6 Hz, 1H), 3.30 (dd, J=13.7, 10.6 Hz, 1H), 3.19 (s, 3H), 2.95 (s, 3H).

Example 90

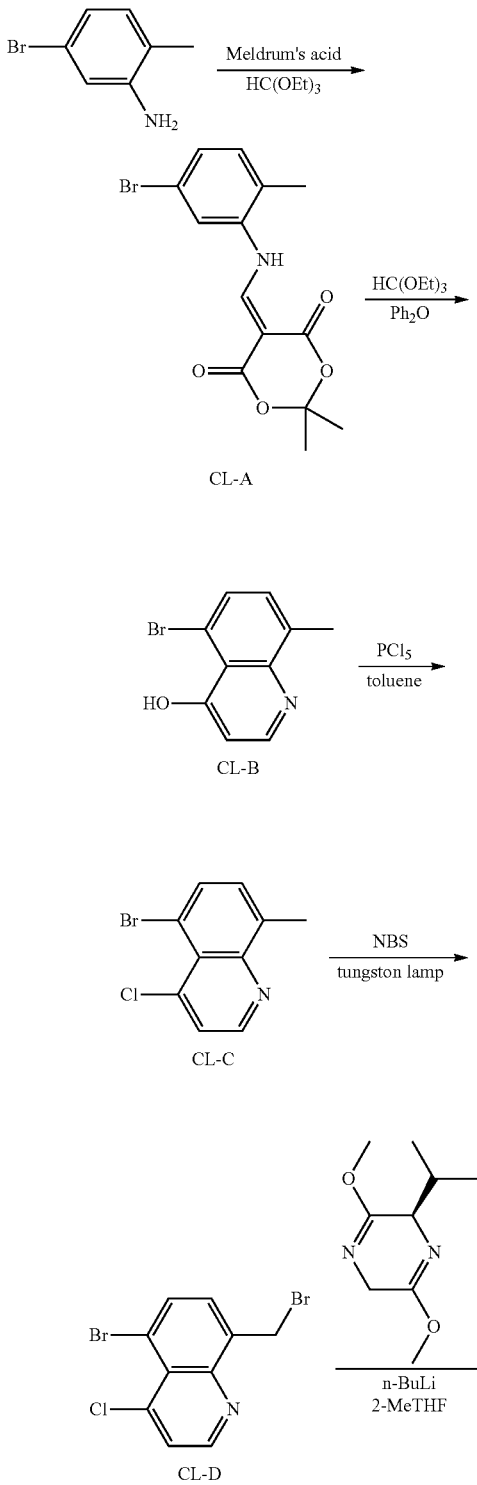

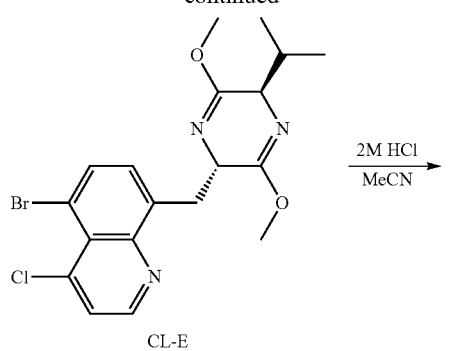

CL-E

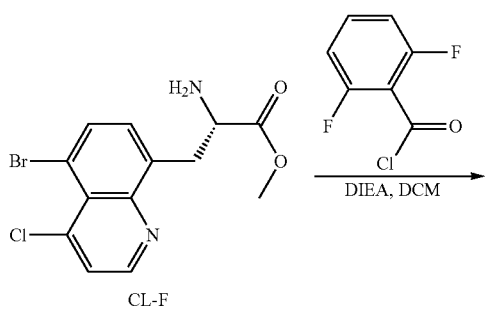

CL-F

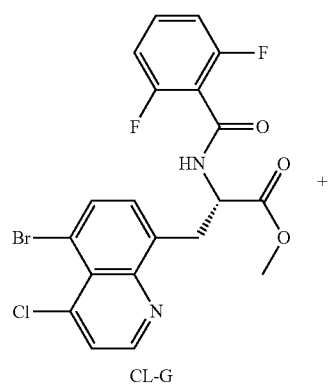

CL-G

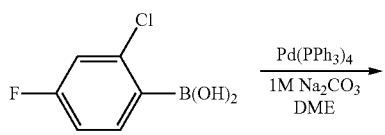

CL-H

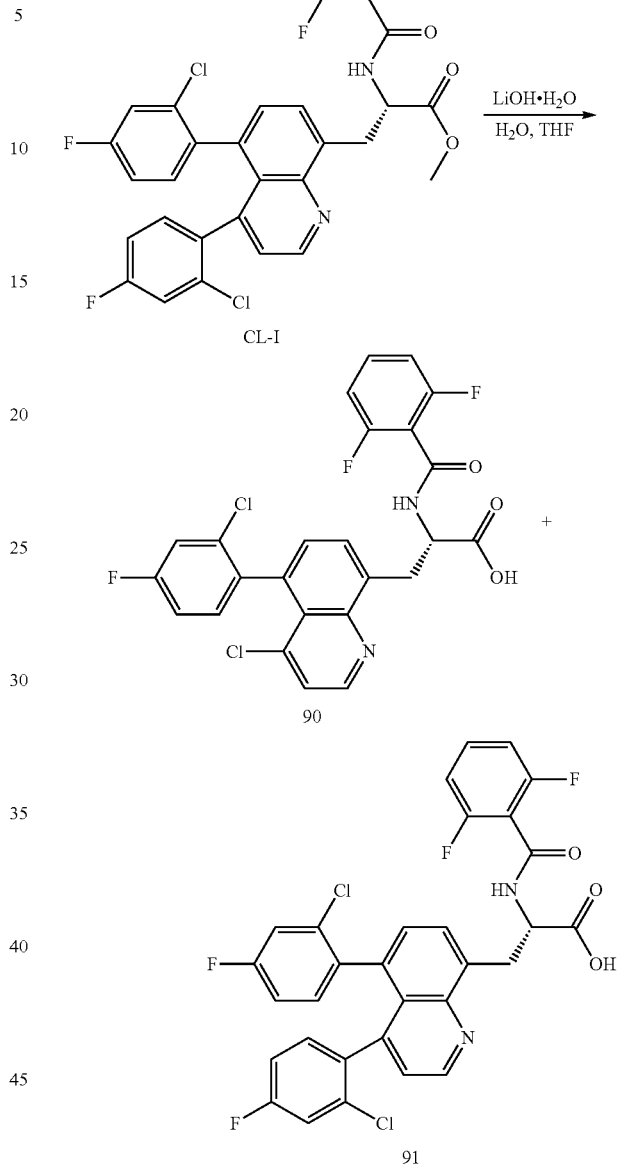

5-(((5-Bromo-2-methylphenyl)amino)methylene)-2,2-dimethyl-1,3-dioxane-4,6-dione (CL-A)

To a stirred mixture of 5-bromo-2-methylaniline (3.70 g, 20 mmol) and triethyl orthoformate (16.5 mL, 99 mmol) at RT was added 2,2-dimethyl-1,3-dioxane-4,6-dione (3.15 g, 21.9 mmol). The reaction mixture was heated to 100° C. and allowed to stir for 3 h. The reaction was then cooled to RT and MeOH (~5 mL) was added. After stirring for 5 min the solid was filtered and rinsed with MeOH. The solid was dried under reduced pressure and the resulting crude material of CL-A was used with no further purification.

5-Bromo-8-methylquinolin-4-ol (CL-B)

A stirred suspension of compound CL-A (1.04 g, 3.07 mmol) in diphenyl ether (8.8 mL) was heated at 200° C.

After 20 min, the reaction was cooled to RT and Et$_2$O was added. The solid was filtered, rinsed with Et$_2$O and dried under reduced pressure. The resulting crude material of CL-B was used with no further purification.

5-Bromo-4-chloro-8-methylquinoline (CL-C)

To a stirred solution of CL-B (1.0 g, 4.2 mmol) in toluene (21 mL) at RT was added PCl$_5$ (1.06 mL, 8.4 mmol). The reaction mixture was heated to 80° C. for 1 hr. The reaction mixture was then cooled to RT and water was carefully added. After stirring for 5 min, EtOAc was added to the reaction mixture. The aqueous layer was separated and extracted with EtOAc (2×). The combined organics were washed with brine, dried over anhydrous Na$_2$SO$_4$, and concentrated under reduced pressure. The material was purified on silica gel eluting with EtOAc in Hex (0-10%) to give the title compound.

5-Bromo-8-(bromomethyl)-4-chloroquinoline (CL-D)

To a stirred solution of CL-C (640 mg, 2.5 mmol) in benzene (7.1 mL) was added NBS (488 mg, 2.7 mmol) at RT. The reaction mixture was heated to reflux under tungsten light for 45 min. The reaction was cooled to RT, water added and extracted with ethyl acetate. The organic layer was separated, washed with brine, dried over anhydrous Na$_2$SO$_4$ and concentrated under reduced pressure to afford crude material. The material was purified on silica gel eluting with EtOAc in Hex (0-10%) to give the title compound.

Methyl 5-bromo-4-chloro-8-(((2S,5R)-5-isopropyl-3,6-dimethoxy-2,5-dihydropyrazin-2-yl)methyl)-7,8-quinoline (CL-E)

To a stirred solution of (R)-2,5-Dihydro-3,6-dimethoxy-2-isopropylpyrazine in 2-MeTHF (9.5 mL) was added nBuLi (1.6 mL, 1.6 M solution in hexanes) dropwise at −78° C. After stirring for 25 min, a solution of CL-D (640 mg, 1.9 mmol) in 2-MeTHF (11 mL) was added over a 3 min time frame. The reaction mixture was allowed to stir at −78° C. for 15 min. H$_2$O was added to the reaction mixture while allowing to warm to RT. The aqueous layer was separated and extracted with EtOAc (2×). The organic layer was washed with brine, dried over anhydrous Na$_2$SO$_4$, and concentrated under reduced pressure. The material was purified by silica gel chromatography using 0-30% EtOAc in hexanes to afford the title compound.

Methyl (S)-2-amino-3-(5-bromo-4-chloroquinolin-8-yl)propanoate (CL-F)

To a stirred solution of CL-E (726 mg, 1.7 mmol) in MeCN (17 mL) at RT was added aq HCl (4.1 mL, 2M). The reaction mixture was allowed to stir for 1 h and then carefully poured into sat aq NaHCO$_3$. EtOAc was then added to the mixture. The aqueous layer was separated and extracted with EtOAc (2×, ~10 mL) and 2-MeTHF (1×, ~10 mL). The organic layers were combined, dried over anhydrous Na$_2$SO$_4$, and concentrated under reduced pressure. The resulting crude material of the title compound was used with no further purification.

Methyl (S)-3-(5-bromo-4-chloroquinolin-8-yl)-2-(2,6-difluorobenzamido) propanoate (CL-G)

To a stirred solution of CL-F (2.0 g, 5.8 mmol) in DCM (57 mL) at RT was added 2-6-difluorobenzoyl chloride (0.82 mL, 5.8 mmol) and DIEA (5.0 mL, 129 mmol). The reaction mixture was allowed to stir for 10 min. DCM and water was added to the reaction mixture. The organic layer was washed with brine, dried over anhydrous Na$_2$SO$_4$, and concentrated under reduced pressure. The material was purified on silica gel eluting with EtOAc in hexanes (0-70%) to afford the title compound.

Methyl (S)-3-(4-chloro-5-(2-chloro-4-fluorophenyl)quinolin-8-yl)-2-(2,6-difluorobenzamido)propanoate (CL-H) and methyl (S)-3-(4,5-bis(2-chloro-4-fluorophenyl)quinolin-8-yl)-2-(2,6-difluorobenzamido) propanoate (CL-I)

To a pressure tube was added CL-G (149 mg, 0.29 mmol), 4,5-difluoro-2-methoxyphenylboronic acid (92 mg, 0.49 mmol), Pd(PPh$_3$)$_4$ (17 mg, 0.014 mmol), and aq Na$_2$CO$_3$ (0.87 mL, 1M) in DME (5.2 mL). The reaction mixture was allowed to stir at 100° C. for 20 min. EtOAc and water was added to the reaction mixture. The organic layer was washed with brine, dried over anhydrous Na$_2$SO$_4$, and concentrated under reduced pressure. The material was purified by silica gel chromatography using 0-50% EtOAc in hexanes to afford both the title compounds.

Example 90: (S)-3-(4-chloro-5-(2-chloro-4-fluorophenyl)quinolin-8-yl)-2-(2,6-difluorobenzamido) propanoic acid To a stirred solution of CL-H and CL-I (2:1 mixture, 60 mg, 0.11 mmol) in THF (1.1 mL) and H$_2$O (1.1 mL) was added LiOH*H$_2$O (24 mg, 0.56 mmol). The reaction mixture was allowed to stir for 30 min then concentrated under reduced pressure. The material was purified via reverse phase HPLC to afford the title compound. MS (m/z) 520.9 [M+H]$^+$. 1H NMR (400 MHz, DMSO-d6) δ 9.13 (d, J=8.3 Hz, 1H), 8.90 (dd, J=4.7, 2.1 Hz, 1H), 7.78 (dd, J=7.4, 2.3 Hz, 1H), 7.71 (dd, J=4.7, 1.0 Hz, 1H), 7.58-7.51 (m, 1H), 7.51-7.27 (m, 3H), 7.17-7.04 (m, 2H), 4.99 (dt, J=8.3, 5.1 Hz, 1H), 4.02 (ddd, J=40.7, 13.4, 4.9 Hz, 1H), 3.46-3.28 (m, 1H).

Example 91: (S)-3-(4,5-bis(2-chloro-4-fluorophenyl)quinolin-8-yl)-2-(2,6-difluorobenzamido)propanoic acid Prepared as mixture with example 90 and separated on reversed phase chromatography to afford the title compound. MS (m/z) 614.8 [M+H]$^+$. 1H NMR (400 MHz, DMSO-d6) δ 9.18 (dd, J=8.1, 3.4 Hz, 1H), 9.04 (dd, J=4.3, 0.9 Hz, 1H), 7.76 (dd, J=7.4, 4.7 Hz, 1H), 7.54-7.33 (m, 2H), 7.30 (dd, J=4.3, 1.4 Hz, 1H), 7.24 (d, J=7.3 Hz, 1H), 7.15-6.97 (m, 5H), 5.10-4.96 (m, 1H), 4.05 (d, J=13.4 Hz, 1H), 3.45 (dt, J=13.6, 9.7 Hz, 1H).

Example 92

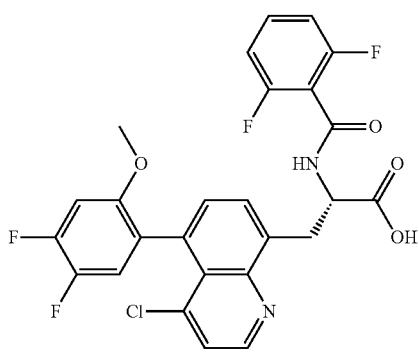 [SMILES: COc1cc(F)c(F)cc1-c1ccc(C[C@H](NC(=O)c2c(F)cccc2F)C(=O)O)c2nccc(Cl)c12]

(S)-3-(4-chloro-5-(4,5-difluoro-2-methoxyphenyl)
quinolin-8-yl)-2-(2,6-difluoro benzamido)propanoic
acid The title compound was prepared according to the method presented for the synthesis of Example 90 replacing (2-chloro-4-fluorophenyl) boronic acid with (4,5-difluoro-2-methoxyphenyl)boronic acid. MS (m/z) 533.9 [M+H]+. 1H NMR (400 MHz, DMSO-d6) δ 9.16 (dd, J=15.4, 8.1 Hz, 1H), 8.87 (dd, J=4.6, 0.6 Hz, 1H), 7.74 (dd, J=7.4, 6.0 Hz, 1H), 7.68 (d, J=4.6 Hz, 1H), 7.54-7.42 (m, 1H), 7.37 (dd, J=7.4, 1.4 Hz, 1H), 7.34-7.24 (m, 1H), 7.23-7.15 (m, 1H), 7.12 (ddd, J=8.5, 7.6, 1.9 Hz, 2H), 4.94 (ddd, J=10.6, 8.0, 4.7 Hz, 1H), 3.98 (ddd, J=41.4, 13.6, 4.9 Hz, 1H), 3.60 (d, J=3.2 Hz, 3H), 3.50-3.27 (m, 1H).

Example 93

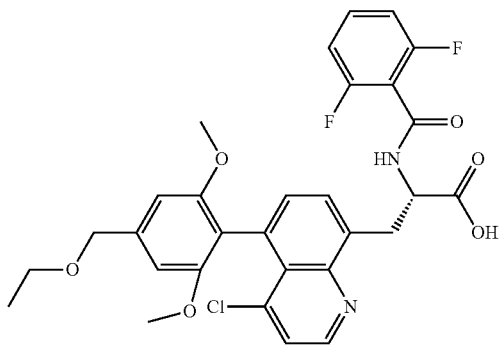 [SMILES: CCOCc1cc(OC)c(-c2ccc(C[C@H](NC(=O)c3c(F)cccc3F)C(=O)O)c3nccc(Cl)c23)c(OC)c1]

(S)-3-(4-chloro-5-(4-(ethoxymethyl)-2,6-dimethoxy-phenyl)quinolin-8-yl)-2-(2,6-difluorobenzamido)
propanoic acid The title compound was prepared according to the method presented for the synthesis of Example 90 replacing (2-chloro-4-fluorophenyl) boronic acid with (4-(ethoxymethyl)-2,6-dimethoxyphenyl)boronic acid. MS (m/z) 585.2 [M+H]+. 1H NMR (400 MHz, DMSO-d6) δ 9.18 (d, J=7.9 Hz, 1H), 8.81 (d, J=4.6 Hz, 1H), 7.72 (d, J=7.5 Hz, 1H), 7.59 (d, J=4.6 Hz, 1H), 7.55-7.42 (m, 1H), 7.24 (d, J=7.4 Hz, 1H), 7.12 (dd, J=8.4, 7.5 Hz, 2H), 6.68 (d, J=5.3 Hz, 2H), 4.94 (dd, J=8.0, 4.9 Hz, 1H), 4.52 (s, 2H), 3.94 (dd, J=13.6, 5.0 Hz, 1H), 3.64-3.50 (m, 8H), 3.41 (dd, J=13.7, 10.1 Hz, 1H), 1.21 (t, J=7.0 Hz, 3H).

Example 94

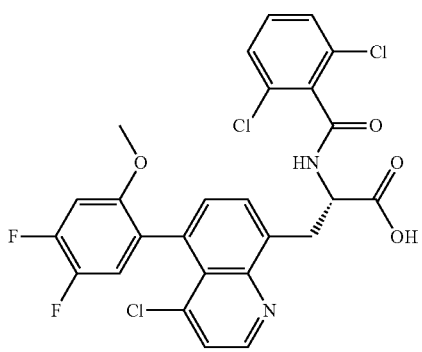 [SMILES: COc1cc(F)c(F)cc1-c1ccc(C[C@H](NC(=O)c2c(Cl)cccc2Cl)C(=O)O)c2nccc(Cl)c12]

(S)-3-(4-chloro-5-(4,5-difluoro-2-methoxyphenyl)
quinolin-8-yl)-2-(2,6-dichlorobenzamido)propanoic
acid The title compound was prepared according to the method presented for the synthesis of Example 90 replacing (2-chloro-4-fluorophenyl)boronic acid with (4,5-difluoro-2-methoxyphenyl)boronic acid. MS (m/z) 566.9 [M+H]+. 1H NMR (400 MHz, DMSO-d6) δ 9.06 (t, J=8.3 Hz, 1H), 8.93-8.82 (m, 1H), 7.79 (dd, J=7.4, 2.4 Hz, 1H), 7.67 (dd, J=4.7, 0.8 Hz, 1H), 7.49-7.25 (m, 4H), 7.20 (dd, J=12.5, 7.3 Hz, 1H), 5.20-4.99 (m, 1H), 4.00 (td, J=13.5, 4.4 Hz, 1H), 3.61 (d, J=5.0 Hz, 3H), 3.45-3.21 (m, 1H).

Example 95

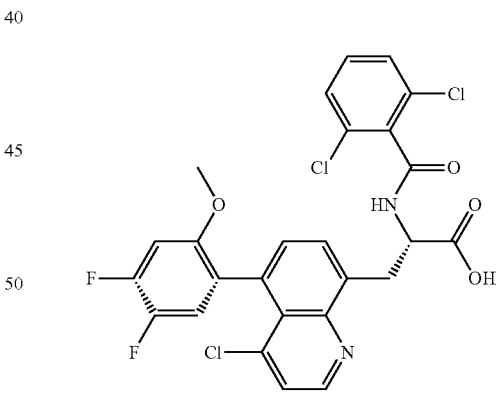

(S)-3-(4-chloro-5-(4,5-difluoro-2-methoxyphenyl)
quinolin-8-yl)-2-(2,6-dichlorobenzamido)propanoic
acid Atropisomers obtained in Example 94 were arbitrarily assigned after separation by supercritical fluid chromatography eluting with 20% MeOH/DEA co-solvent on an IC SFC column to give Example 95 and Example 96. The title compound was identified as the second eluting peak. MS (m/z) 565.0 [M+H]+. 1H NMR (400 MHz, DMSO-d6) δ 9.06 (t, J=8.3 Hz, 1H), 8.94-8.83 (m, 1H), 7.79 (dd, J=7.4, 2.4 Hz, 1H), 7.67 (dd, J=4.6, 0.8 Hz, 1H), 7.48-7.10 (m, 6H), 5.20-5.03 (m, 1H), 4.00 (td, J=13.5, 4.4 Hz, 1H), 3.61 (d, J=5.0 Hz, 3H), 3.43-3.22 (m, 1H).

Example 96

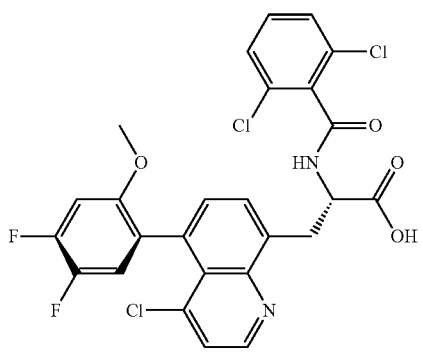

(S)-3-(4-chloro-5-(4,5-difluoro-2-methoxyphenyl)quinolin-8-yl)-2-(2,6-dichlorobenzamido)propanoic acid The title compound was identified as the third eluting peak. MS (m/z) 565.1 [M+H]+. 1H NMR (400 MHz, DMSO-d6) δ 9.06 (t, J=8.3 Hz, 1H), 8.87 (dd, J=5.3, 4.6 Hz, 1H), 7.79 (dd, J=7.4, 2.4 Hz, 1H), 7.67 (dd, J=4.7, 0.8 Hz, 1H), 7.51-7.10 (m, 5H), 5.21-4.99 (m, 1H), 4.00 (td, J=13.5, 4.4 Hz, 1H), 3.61 (d, J=5.0 Hz, 3H), 3.33 (ddd, J=34.2, 13.6, 11.0 Hz, 1H).

Example 97

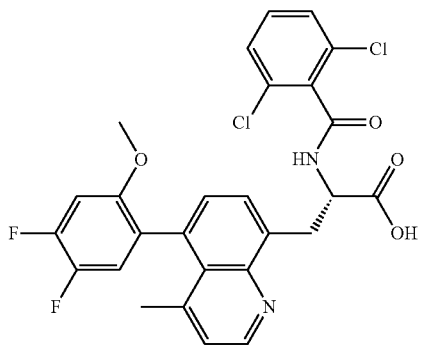 [SMILES: COc1cc(F)c(F)cc1-c1ccc(C[C@H](NC(=O)c2c(Cl)cccc2Cl)C(=O)O)c2nccc(C)c12]

(S)-2-(2,6-dichlorobenzamido)-3-(5-(4,5-difluoro-2-methoxyphenyl)-4-methylquinolin-8-yl)propanoic acid To a microwave vial was added methyl (S)-3-(4-chloro-5-(4,5-difluoro-2-methoxyphenyl)quinolin-8-yl)-2-(2,6-dichlorobenzamido)propanoate (104 mg, 0.18 mmol) (prepared according to the procedure described for CL-H replacing 2,6-difluoro benzoyl chloride with 2,6-dichlorobenzoyl chloride, and (2-chloro-4-fluorophenyl)boronic acid with (4,5-difluoro-2-methoxyphenyl)boronic acid). Trimethylboroxine (45 mg, 0.359 mmol), Tetrakis (triphenylphosphine) palladium(0) (10 mg, 0.01 mmol), sodium carbonate (0.9 mL, 1N, 0.9 mmol) and 1,2-dimethoxyethane were added to a microwave vial and heated to 130 C for 30 min. Trimethylboroxine (68 mg, 0.538 mmol) was added to the vial and the mixture was heated to 140° C. for 40 min. The mixture was diluted with ethyl acetate and water, the pH was adjusted to pH 4 and the organic layer was decanted, volatile components were removed on a rotary evaporator and the residue was loaded onto silica gel and chromatographed eluting with methanol in dichlormethane and diethyl ether to afford the title compound. MS (m/z) 546.7 [M+H]+. 1H NMR (400 MHz, DMSO-d6) δ 12.70 (s, 1H), 9.07 (dd, J=8.5, 2.3 Hz, 1H), 8.99-8.91 (m, 1H), 8.86 (s, 1H), 8.78 (dd, J=5.3, 4.3 Hz, 1H), 7.68 (d, J=7.3 Hz, 1H), 7.46-7.32 (m, 4H), 7.32-7.08 (m, 5H), 5.19-4.99 (m, 1H), 3.99 (td, J=12.6, 4.3 Hz, 1H), 3.64 (d, J=4.3 Hz, 4H), 2.06 (d, J=18.9 Hz, 5H).

Examples 98 and 99

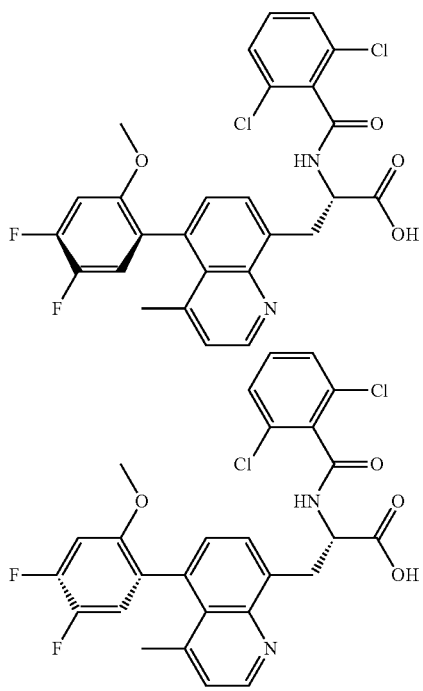

Atropisomers were arbitrarily assigned after separation by supercritical fluid chromatography eluting with 20% MeOH/DEA co-solvent on an IC SFC column.

Example 98

(S)-2-(2,6-dichlorobenzamido)-3-(5-(4,5-difluoro-2-methoxyphenyl)-4-methylquinolin-8-yl)propanoic acid: The title compound was identified as the first eluting isomer: MS (m/z) 546.7 [M+H]+. 1H NMR (400 MHz, DMSO-d6) δ 8.74 (t, J=4.8 Hz, 1H), 8.56 (s, 1H), 7.83-7.73 (m, 1H), 7.70 (d, J=7.3 Hz, 1H), 7.46 (s, 1H), 7.41-7.05 (m, 6H), 4.83 (s, 1H), 4.03-3.87 (m, 1H), 3.62 (t, J=4.3 Hz, 3H), 3.39 (d, J=14.3 Hz, 1H), 2.01 (s, 3H).

Example 99: (S)-2-(2,6-dichlorobenzamido)-3-(5-(4,5-difluoro-2-methoxyphenyl)-4-methylquinolin-8-yl)propanoic acid The title compound was identified as the second eluting isomer: MS (m/z) 546.4 [M+H]+. 1H NMR (400 MHz, DMSO-d6) δ 8.75 (dd, J=5.3, 4.3 Hz, 1H), 8.52 (d, J=28.5 Hz, 1H), 7.72 (d, J=7.3 Hz, 1H), 7.45-7.07 (m, 7H), 4.82 (d, J=13.6 Hz, 1H), 4.07-3.86 (m, 1H), 3.64 (d, J=4.8 Hz, 3H), 3.46-3.34 (m, 1H), 2.03 (s, 3H).

Example 100

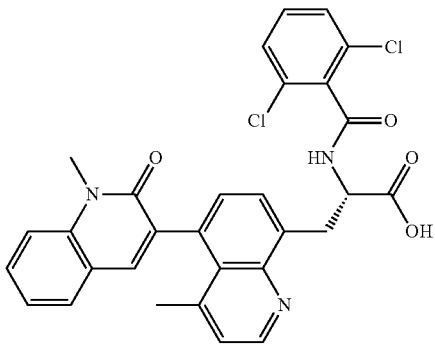 [SMILES: Cc1ccnc2c(C[C@H](NC(=O)c3c(Cl)cccc3Cl)C(=O)O)ccc(-c3cc4ccccc4n(C)c3=O)c12]

(S)-2-(2,6-dichlorobenzamido)-3-(1,4'-dimethyl-2-oxo-1,2-dihydro-[3,5'-biquinolin]-8'-yl)propanoic acid The title compound was prepared according to the method presented for the synthesis of Example 97 replacing (4,5-difluoro-2-methoxyphenyl)boronic acid with 1-methyl-3-(4,4,5,5-tetramethyl-1,3,2-dioxaborolan-2-yl)quinolin-2(1H)-one. MS (m/z) 561.8 [M+H]+. 1H NMR (400 MHz, DMSO-d6) δ 9.12 (d, J=8.4 Hz, 1H), 8.80 (d, J=4.3 Hz, 1H), 7.90 (d, J=27.6 Hz, 1H), 7.80 (ddd, J=9.5, 7.8, 1.5 Hz, 1H), 7.73-7.60 (m, 3H), 7.46-7.28 (m, 5H), 5.14-4.98 (m, 1H), 3.96 (ddd, J=34.5, 13.6, 4.8 Hz, 1H), 3.71 (d, J=0.9 Hz, 3H), 3.38 (ddd, J=29.5, 13.6, 10.3 Hz, 1H), 2.33 (d, J=2.5 Hz, 3H).

Example 101

(S)-2-(2,6-difluoro-4-((4-(2-fluoropyridin-4-yl)phenyl)sulfonamido)benzamido)-3-(5-(2,6-dimethoxyphenyl)quinolin-8-yl)propanoic acid Prepared according to the procedure described for example 10 employing EQ10 in place of EQ6, and (2,6-dimethoxyphenyl) boronic acid in place of H2. MS (m/z) 743.2 [M+H]+. 1H NMR (400 MHz, DMSO-d6) δ 11.20 (s, 1H), 9.10 (d, J=7.8 Hz, 1H), 8.85 (dd, J=4.2, 1.8 Hz, 1H), 8.33 (dt, J=5.4, 0.6 Hz, 1H), 8.11-8.02 (m, 2H), 8.02-7.91 (m, 2H), 7.76-7.70 (m, 1H), 7.67 (dd, J=8.4, 1.8 Hz, 1H), 7.64-7.50 (m, 3H), 7.46-7.38 (m, 2H), 7.25 (d, J=7.3 Hz, 1H), 6.80 (dd, J=8.8, 3.8 Hz, 4H), 4.84 (ddd, J=10.1, 7.8, 4.9 Hz, 1H), 3.92-3.81 (m, 1H), 3.54 (d, J=2.4 Hz, 6H), 3.35 (dd, J=13.8, 10.1 Hz, 1H).

Example 102

(S)-2-(2,6-difluoro-4-((4-(2-fluoropyridin-4-yl)phenyl)sulfonamido)benzamido)-3-(5-(4-(ethoxymethyl)-2,6-dimethoxyphenyl)quinolin-8-yl)propanoic acid Prepared according to the procedure described for example 10 employing EQ10 in place of EQ6, and (4-(ethoxymethyl)-2,6-dimethoxyphenyl)boronic acid in place of H2. MS (m/z) 801.2 [M+H]+. 1H NMR (400 MHz, DMSO-d6) δ 11.20 (s, 1H), 9.10 (d, J=7.8 Hz, 1H), 8.85 (dd, J=4.2, 1.8 Hz, 1H), 8.33 (dt, J=5.3, 0.6 Hz, 1H), 8.12-8.01 (m, 2H), 8.01-7.91 (m, 2H), 7.77-7.48 (m, 5H), 7.41 (dd, J=8.5, 4.2 Hz, 1H), 7.24 (d, J=7.3 Hz, 1H), 6.91-6.70 (m, 4H), 6.45 (dt, J=2.4, 0.6 Hz, 1H), 4.84 (ddd, J=10.1, 7.8, 4.9 Hz, 1H), 4.53 (s, 2H), 3.86 (dd, J=13.7, 4.7 Hz, 1H), 3.62-3.50 (m, 8H), 3.35 (dd, J=13.9, 10.0 Hz, 1H), 1.20 (t, J=7.0 Hz, 3H).

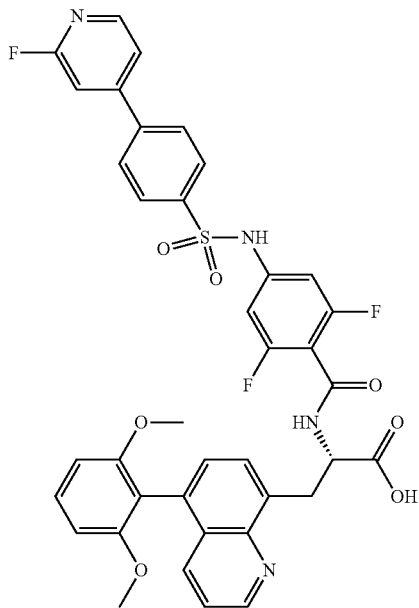 [SMILES: COc1cccc(OC)c1-c1ccc(C[C@H](NC(=O)c2c(F)cc(NS(=O)(=O)c3ccc(-c4ccnc(F)c4)cc3)cc2F)C(=O)O)c2ncccc12]

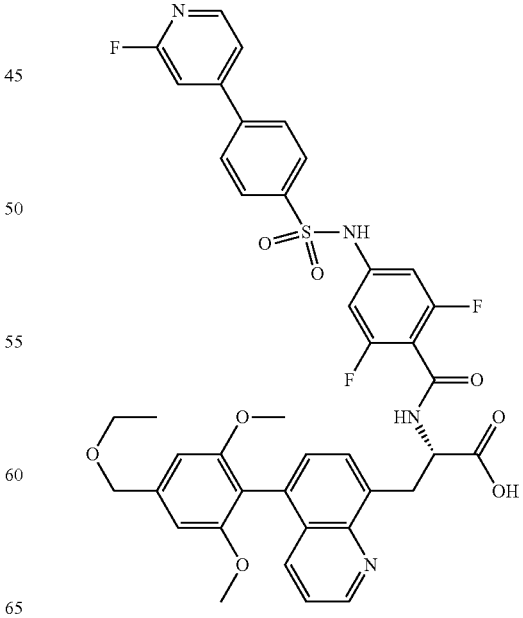

Example 103

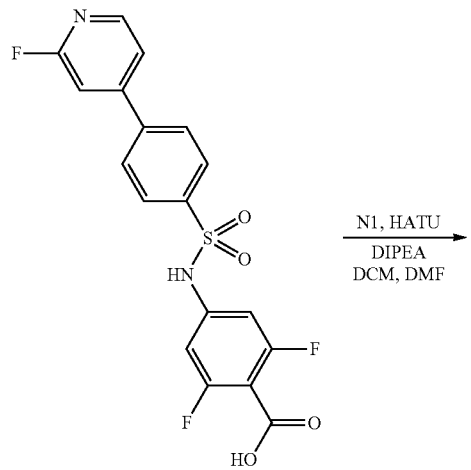

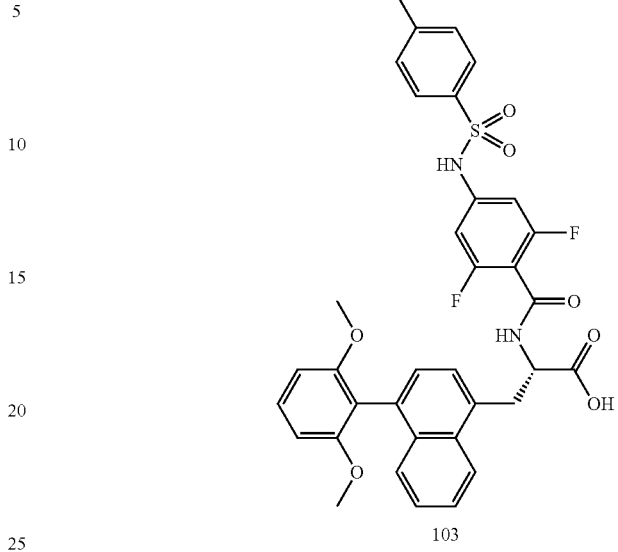

Synthesis of methyl (S)-3-(8-bromoquinolin-5-yl)-2-(2,6-difluoro-4-((4-(2-fluoropyridin-4-yl)phenyl)sulfonamido)benzamido)propanoate (103A)

The title compound was prepared according to the method presented for the synthesis of compound N7A starting with 2,6-difluoro-4-((4-(2-fluoropyridin-4-yl)phenyl)sulfonamido)benzoic acid and N1.

Synthesis of (S)-2-(2,6-difluoro-4-((4-(2-fluoropyridin-4-yl)phenyl)sulfonamido) benzamido)-3-(4-(2,6-dimethoxyphenyl)naphthalen-1-yl)propanoic acid (103)

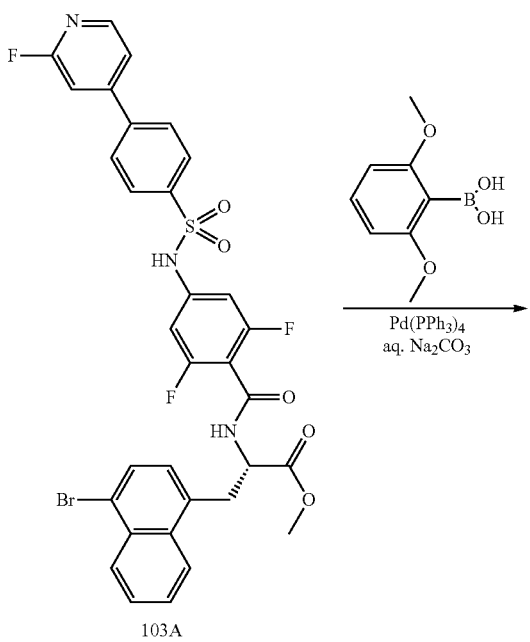

To a microwave vial was added 103A (170 mg, 0.25 mmol), (2,6-dimethoxyphenyl)boronic acid (54 mg, 0.29 mmol), Pd(PPh$_3$)$_4$(28 mg, 0.02 mmol), and aq Na$_2$CO$_3$ (0.37 mL, 2M) in DME (2 mL). The reaction mixture was allowed to stir at 135° C. for 30 min. EtOAc and water was added to the reaction mixture. The organic layer was washed with brine, dried over anhydrous Na$_2$SO$_4$, and concentrated under reduced pressure. The material was purified via reverse phase HPLC to afford the title compound. MS (m/z) 742.3 [M+H]$^+$. 1H NMR (400 MHz, DMSO-d6) δ 11.20 (s, 1H), 9.13 (d, J=7.9 Hz, 1H), 8.33 (d, J=5.3 Hz, 1H), 8.16-8.01 (m, 3H), 8.03-7.93 (m, 2H), 7.72 (dt, J=5.3, 1.8 Hz, 1H), 7.59 (d, J=1.3 Hz, 1H), 7.52 (ddd, J=8.4, 6.5, 1.6 Hz, 1H), 7.46-7.27 (m, 4H), 7.12 (d, J=7.2 Hz, 1H), 6.88-6.68 (m, 4H), 4.68 (ddd, J=9.9, 7.9, 4.3 Hz, 1H), 3.65 (dd, J=14.6, 4.3 Hz, 1H), 3.53 (d, J=1.8 Hz, 6H), 3.28 (dd, J=14.7, 9.9 Hz, 1H).

Example 104
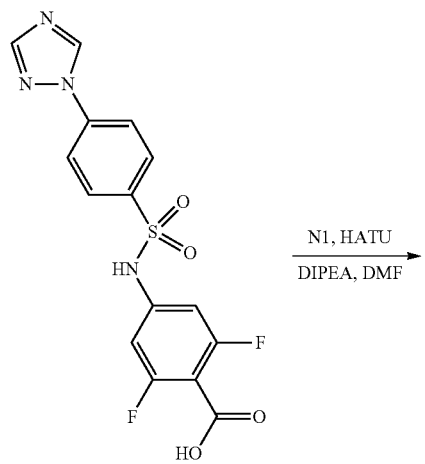
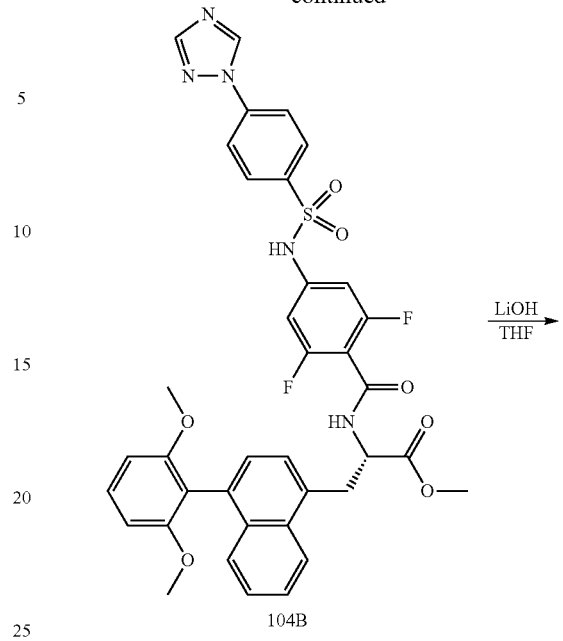
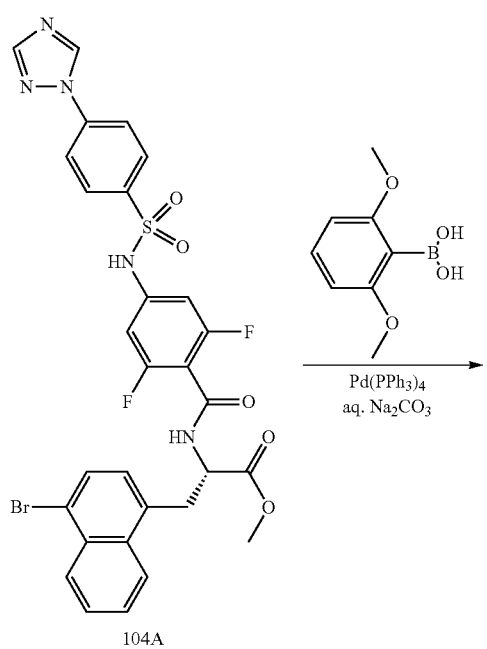
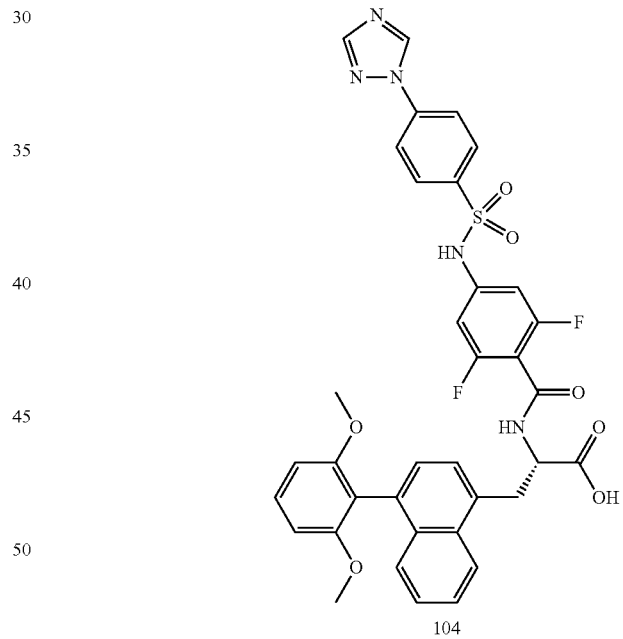
Synthesis methyl (S)-2-(4-((4-(1H-1,2,4-triazol-1-yl)phenyl)sulfonamido)-2,6-difluoro benzamido)-3-(4-bromonaphthalen-1-yl)propanoate (104A)
The title compound was prepared according to the method presented for the synthesis of compound N7A starting with 4-((4-(1H-1,2,4-triazol-1-yl)phenyl)sulfonamido)-2,6-difluorobenzoic acid and N1.

Synthesis of methyl (S)-2-(4-((4-(1H-1,2,4-triazol-1-yl)phenyl)sulfonamido)-2,6-difluorobenzamido)-3-(4-(2,6-dimethoxyphenyl)naphthalen-1-yl)propanoate (104B)

The title compound was prepared according to the method presented for the synthesis of compound 103 in example 103 starting with 104A and (2,6-dimethoxyphenyl)boronic acid.

Synthesis of (S)-2-(4-((4-(1H-1,2,4-triazol-1-yl)phenyl)sulfonamido)-2,6-difluoro benzamido)-3-(4-(2,6-dimethoxyphenyl)naphthalen-1-yl)propanoic acid (104)

To a stirred solution of 104B (50 mg, 0.07 mmol) in THF (1 mL) was added LiOH (0.21 mL, 1M). The reaction mixture was allowed to stir for 1 hour then concentrated under reduced pressure. The material was purified via reverse phase HPLC to afford the title compound. MS (m/z) 714.3 [M+H]$^+$. 1H NMR (400 MHz, DMSO-d6) δ 11.15 (s, 1H), 9.38 (s, 1H), 9.12 (d, J=7.9 Hz, 1H), 8.28 (s, 1H), 8.14-8.06 (m, 3H), 8.05-7.96 (m, 2H), 7.59-7.47 (m, 1H), 7.43-7.26 (m, 4H), 7.12 (d, J=7.2 Hz, 1H), 6.79 (dd, J=8.7, 6.2 Hz, 4H), 4.68 (ddd, J=9.9, 7.9, 4.2 Hz, 1H), 3.65 (dd, J=14.6, 4.3 Hz, 1H), 3.53 (d, J=1.3 Hz, 6H), 3.28 (dd, J=14.6, 9.8 Hz, 1H).

Example 105

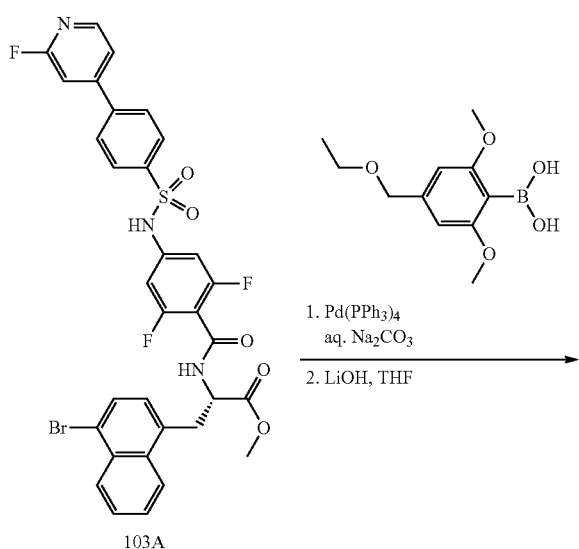

Synthesis of (S)-2-(2,6-difluoro-4-((4-(2-fluoropyridin-4-yl)phenyl)sulfonamido) benzamido)-3-(4-(4-(ethoxymethyl)-2,6-dimethoxyphenyl)naphthalen-1-yl)propanoic acid (105)

To a microwave vial was added 103A (64 mg, 0.09 mmol), (4-(ethoxymethyl)-2,6-dimethoxyphenyl)boronic acid (26 mg, 0.11 mmol), Pd(PPh$_3$)$_4$ (11 mg, 0.01 mmol), and aq Na$_2$CO$_3$ (0.14 mL, 2 M) in DME (1 mL). The reaction mixture was allowed to stir at 135° C. for 30 min. Then cool to RT and LiOH (0.25 mL, 1M) was added. The reaction mixture was allowed to stir for 1 hour then concentrated under reduced pressure. The material was purified via reverse phase HPLC to afford the title compound. MS (m/z) 800.45 [M+H]$^+$. 1H NMR (400 MHz, DMSO-d6) δ 11.22 (s, 1H), 9.15 (d, J=7.8 Hz, 1H), 8.33 (d, J=5.3 Hz, 1H), 8.13-8.01 (m, 3H), 8.02-7.93 (m, 2H), 7.73 (dt, J=5.3, 1.8 Hz, 1H), 7.59 (s, 1H), 7.56-7.48 (m, 1H), 7.43-7.26 (m, 3H), 7.11 (d, J=7.2 Hz, 1H), 6.81 (d, J=9.1 Hz, 2H), 6.74 (s, 2H), 4.74-4.59 (m, 1H), 4.53 (s, 2H), 3.63 (s, 1H), 3.60-3.54 (m, 2H), 3.53 (d, J=1.9 Hz, 6H), 3.31-3.20 (m, 1H), 1.20 (t, J=7.0 Hz, 3H).

Example 106

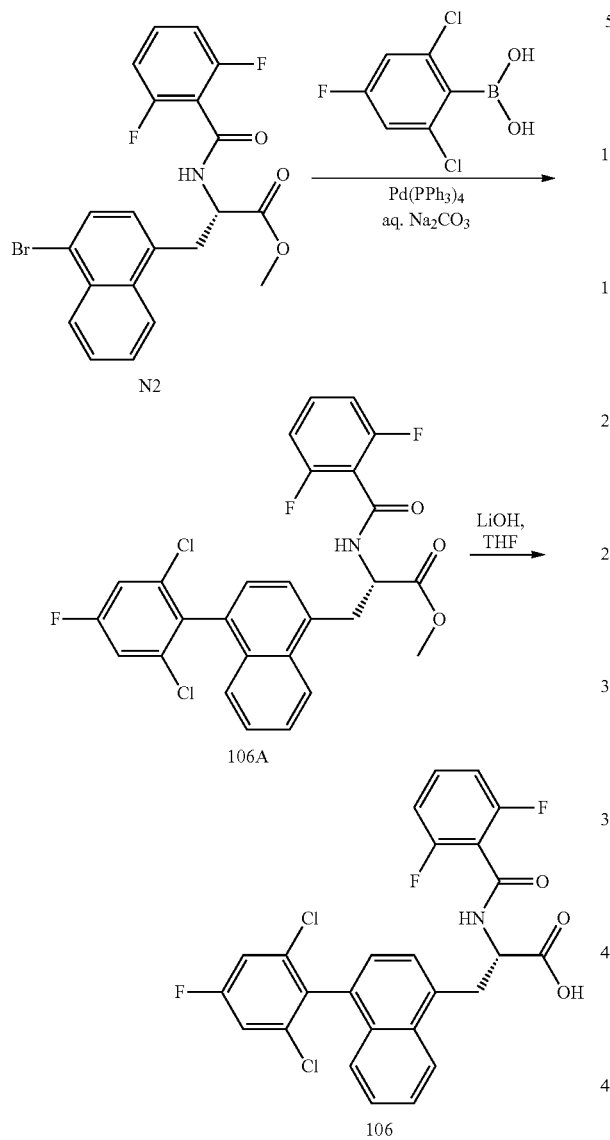

Example 107

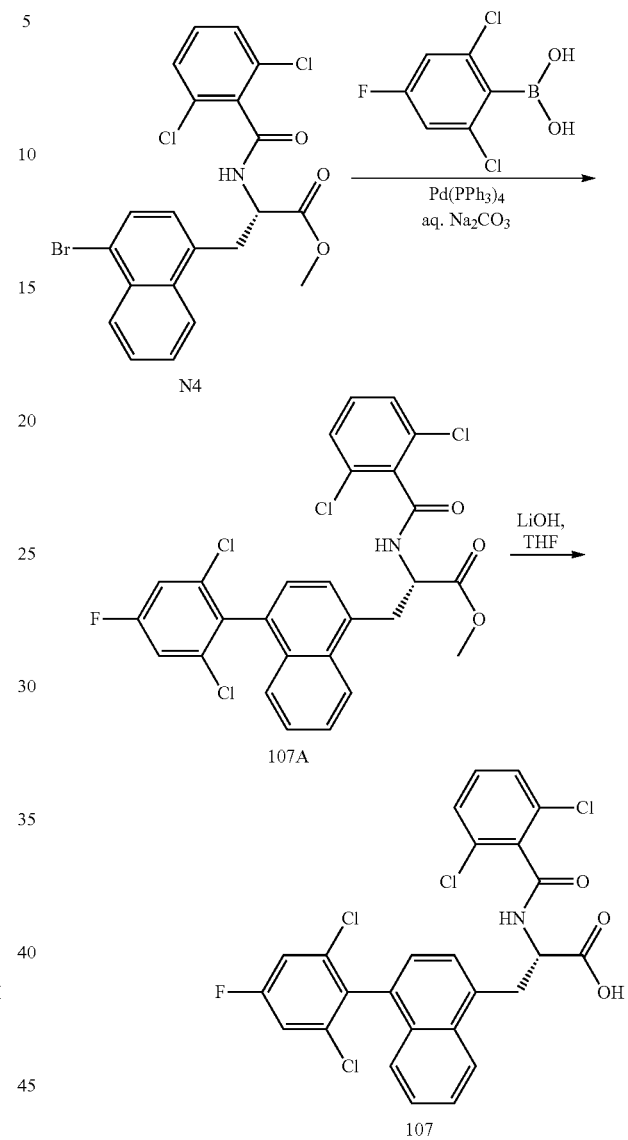

Synthesis of (S)-3-(4-(2,6-dichloro-4-fluorophenyl)naphthalen-1-yl)-2-(2,6-difluoro benzamido)propanoic acid (106)

The title compound was prepared according to the method presented for the synthesis of compound 104 in example 104 starting with N2 and (2,6-dichloro-4-fluorophenyl)boronic acid. MS (m/z) 519.5 [M+H]$^+$. 1H NMR (400 MHz, DMSO-d6) δ 9.27 (d, J=8.1 Hz, 1H), 8.22 (d, J=8.5 Hz, 1H), 7.72 (d, J=8.6 Hz, 2H), 7.64 (ddd, J=8.4, 6.8, 1.3 Hz, 1H), 7.56 (s, 1H), 7.53-7.41 (m, 2H), 7.32-7.21 (m, 2H), 7.10 (dd, J=8.5, 7.4 Hz, 2H), 4.79 (ddd, J=10.3, 8.0, 4.2 Hz, 1H), 3.76 (dd, J=14.5, 4.2 Hz, 1H), 3.32 (s, 1H).

Synthesis of (S)-3-(4-(2,6-dichloro-4-fluorophenyl)naphthalen-1-yl)-2-(2,6-dichloro benzamido)propanoic acid (107)

The title compound was prepared according to the method presented for the synthesis of compound 104 in example 104 starting with N4 and (2,6-dichloro-4-fluorophenyl)boronic acid. MS (m/z) 551.9 [M+H]$^+$. 1H NMR (400 MHz, DMSO-d6) δ 9.28 (d, J=8.4 Hz, 1H), 8.24 (d, J=8.5 Hz, 1H), 7.76-7.68 (m, 2H), 7.66 (ddd, J=8.4, 6.8, 1.3 Hz, 1H), 7.61 (d, J=7.3 Hz, 1H), 7.50 (ddd, J=8.1, 6.8, 1.1 Hz, 1H), 7.44-7.33 (m, 3H), 7.30-7.20 (m, 2H), 4.83 (ddd, J=10.7, 8.3, 3.5 Hz, 1H), 3.78 (dd, J=14.3, 3.5 Hz, 1H), 3.32 (dd, J=14.4, 10.8 Hz, 1H).

Example 108
Synthesis of (S)-2-(2,6-dichlorobenzamido)-3-(4-(1-methyl-2-oxo-1,2-dihydroquinolin-3-yl)naphthalen-1-yl)propanoic acid (108)
The title compound was prepared according to the method presented for the synthesis of compound 104 in example 104 starting with N5 and 3-bromo-1-methylquinolin-2(1H)-one. MS (m/z) 546.8 [M+H]$^+$. 1H NMR (400 MHz, DMSO-d6) δ 9.26 (d, J=8.2 Hz, 1H), 8.25-8.17 (m, 1H), 7.93 (d, J=16.9 Hz, 1H), 7.79 (d, J=7.8 Hz, 1H), 7.71-7.57 (m, 4H), 7.51 (d, J=7.3 Hz, 1H), 7.48-7.37 (m, 5H), 7.36-7.26 (m, 2H), 4.83 (td, J=8.8, 4.7 Hz, 1H), 3.71 (s, 3H), 3.37 (s, 1H).
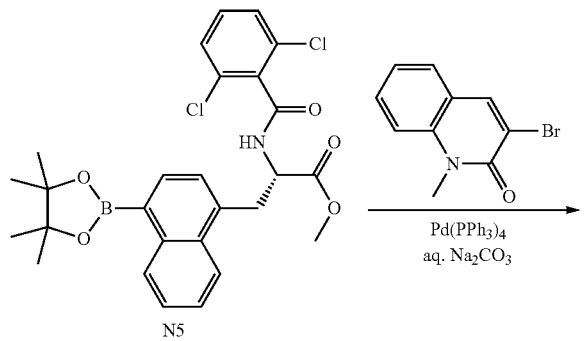
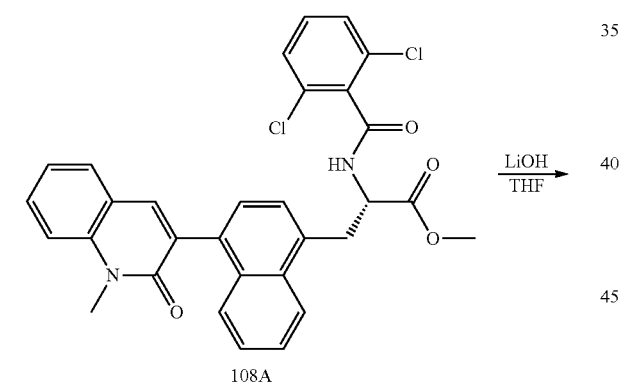
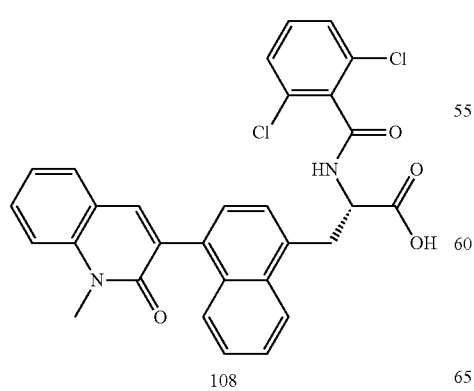
Examples 109 and 110
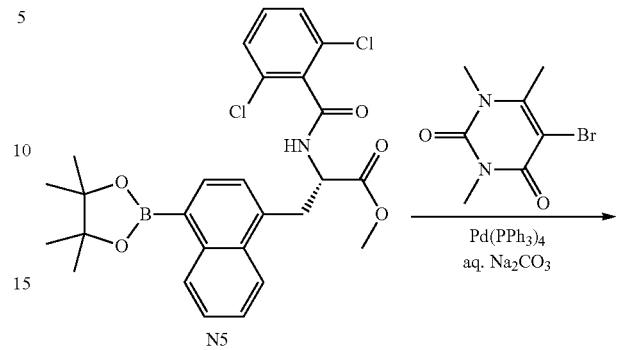
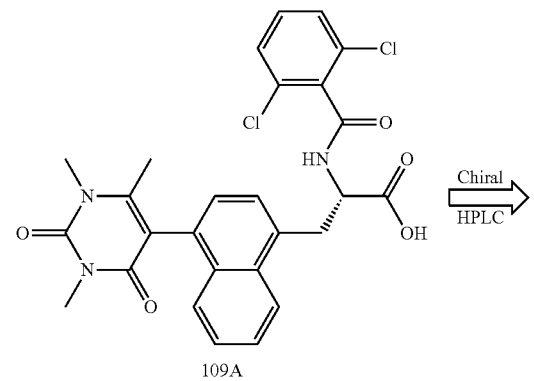
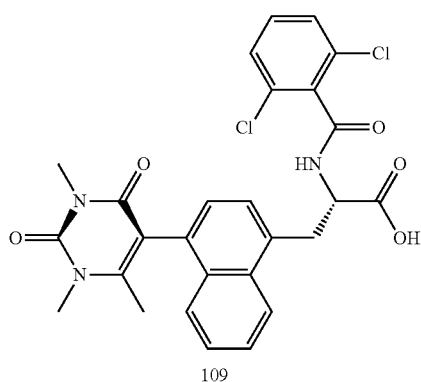

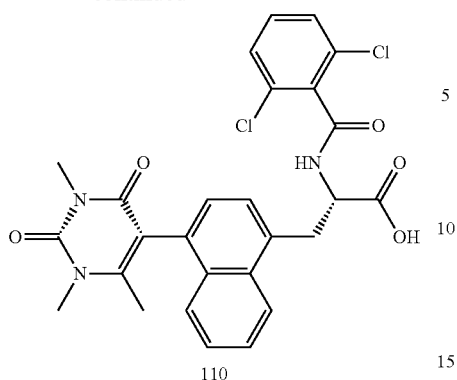

Synthesis of (S)-2-(2,6-dichlorobenzamido)-3-(4-(1,3,6-trimethyl-2,4-dioxo-1,2,3,4-tetrahydropyrimidin-5-yl)naphthalen-1-yl)propanoic acid Atropisomer 1 (109)

The title compound was prepared according to the method presented for the synthesis of compound 104 in example 104 starting with N5 and 5-bromo-1,3,6-trimethylpyrimidine-2,4(1H,3H)-dione. The acid product 109B was separated into its 2 diastereomeric atropisomers by reverse phase HPLC. The title compound was identified as the first eluting peak. MS (m/z) 541.6 [M+H]$^+$. 1H NMR (400 MHz, DMSO-d6) δ 9.23 (dd, J=12.0, 8.3 Hz, 1H), 8.19 (dd, J=8.6, 3.8 Hz, 1H), 7.71 (d, J=8.7 Hz, 1H), 7.68-7.54 (m, 1H), 7.49 (t, J=7.9 Hz, 2H), 7.46-7.33 (m, 4H), 7.25-7.10 (m, 1H), 4.90-4.73 (m, 1H), 3.81-3.59 (m, 1H), 3.48 (s, 3H), 3.22 (d, J=2.8 Hz, 3H), 1.91 (d, J=1.8 Hz, 3H).

Synthesis of (S)-2-(2,6-dichlorobenzamido)-3-(4-(1,3,6-trimethyl-2,4-dioxo-1,2,3,4-tetrahydropyrimidin-5-yl)naphthalen-1-yl)propanoic acid Atropisomer 2 (110)

The title compound was prepared according to the method presented for the synthesis of compound 104 in example 104 starting with N5 and 5-bromo-1,3,6-trimethylpyrimidine-2,4(1H,3H)-dione. The acid product 109B was separated into its 2 diastereomeric atropisomers by reverse phase HPLC. The title compound was identified as the second eluting peak. MS (m/z) 541.0 [M+H]$^+$. 1H NMR (400 MHz, DMSO-d6) δ 9.21 (d, J=8.3 Hz, 1H), 8.21 (d, J=8.5 Hz, 1H), 8.07-7.96 (m, 1H), 7.66 (ddd, J=8.4, 6.8, 1.2 Hz, 1H), 7.58 (ddd, J=8.2, 6.8, 1.2 Hz, 1H), 7.50-7.33 (m, 4H), 7.28 (d, J=7.3 Hz, 1H), 4.83 (s, 1H), 4.82-4.73 (m, 1H), 4.39 (d, J=4.6 Hz, 2H), 3.68 (dd, J=14.4, 4.2 Hz, 1H), 3.42 (s, 3H), 3.31-3.25 (m, 1H), 3.13 (s, 3H).

Example 111

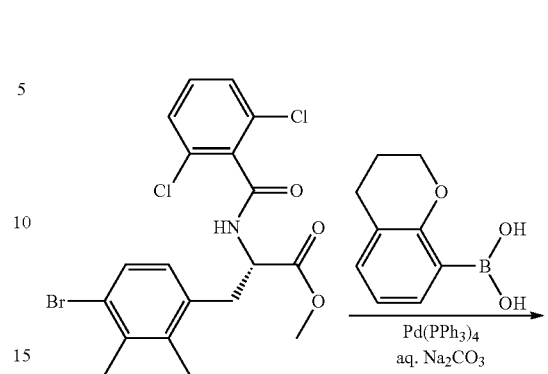

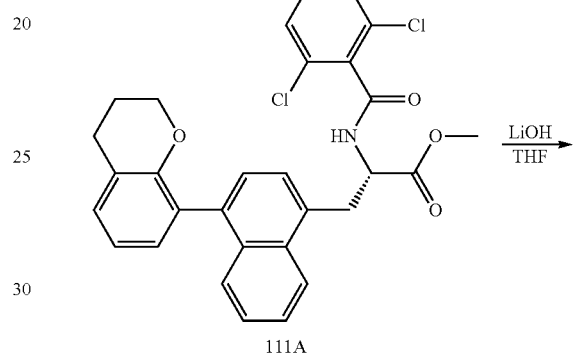

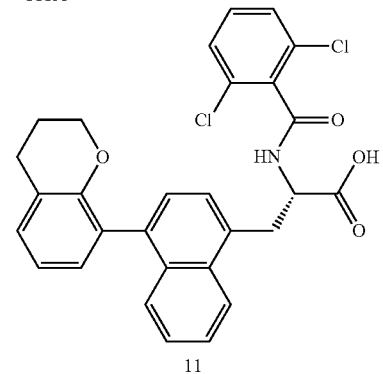

Synthesis of (S)-3-(4-(chroman-8-yl)naphthalen-1-yl)-2-(2,6-dichlorobenzamido) propanoic acid (111)

The title compound was prepared according to the method presented for the synthesis of compound 105 in example 105 starting with N4 and chroman-8-ylboronic acid heating at 120° C. for 20 min in a microwave reactor. MS (m/z) 520.1 [M+H]$^+$. 1H NMR (400 MHz, DMSO-d6) δ 9.24 (d, J=8.3 Hz, 1H), 8.17 (d, J=8.5 Hz, 1H), 7.58 (ddd, J=8.2, 6.5, 1.4 Hz, 1H), 7.54-7.44 (m, 3H), 7.44-7.35 (m, 3H), 7.20 (dd, J=7.2, 2.8 Hz, 1H), 7.15 (dt, J=7.0, 2.2 Hz, 1H), 6.97-6.88 (m, 2H), 4.92-4.75 (m, 1H), 3.94 (q, J=4.8, 4.3 Hz, 2H), 3.71 (ddd, J=14.7, 10.8, 4.3 Hz, 1H), 3.30 (d, J=10.0 Hz, 1H), 2.92-2.75 (m, 2H), 1.89 (p, J=5.3, 4.8 Hz, 2H).

Example 112

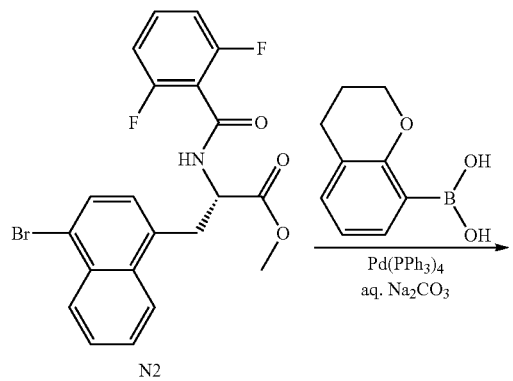

Synthesis of (S)-3-(4-(chroman-8-yl)naphthalen-1-yl)-2-(2,6-difluorobenzamido) propanoic acid (112)

The title compound was prepared according to the method presented for the synthesis of compound 105 in example 105 starting with N2 and chroman-8-ylboronic acid heat at 120° C. for 20 min in microwave. MS (m/z) 488.2 [M+H]⁺. 1H NMR (400 MHz, DMSO-d6) δ 9.28 (dd, J=10.5, 8.0 Hz, 1H), 8.25-8.05 (m, 1H), 7.65-7.34 (m, 5H), 7.23 (t, J=7.3 Hz, 1H), 7.18-7.07 (m, 3H), 6.99-6.88 (m, 2H), 4.73 (ddd, J=9.9, 8.0, 4.2 Hz, 1H), 4.18-3.86 (m, 2H), 3.71 (ddd, J=26.0, 14.4, 4.3 Hz, 1H), 3.33 (ddd, J=28.2, 14.5, 9.9 Hz, 1H), 2.95-2.76 (m, 2H), 1.89 (d, J=7.3 Hz, 2H).

Example 113

Synthesis of (S)-3-(4-(4-bromoisoquinolin-3-yl) naphthalen-1-yl)-2-(2,6-dichlorobenzamido) propanoic acid (113)

The title compound was prepared according to the method presented for the synthesis of compound 104 in example 104 starting with N5 and 3,4-dibromoisoquinoline heating at 120° C. for 20 min in microwave. MS (m/z) 595.0 [M+H]⁺. 1H NMR (400 MHz, DMSO-d6) δ 9.50-9.42 (m, 1H), 9.31 (dd, J=16.4, 8.3 Hz, 1H), 8.32 (d, J=8.2 Hz, 1H), 8.29-8.21 (m, 2H), 8.03 (ddt, J=8.6, 7.0, 1.6 Hz, 1H), 7.88 (ddt, J=8.0, 7.1, 1.0 Hz, 1H), 7.71-7.57 (m, 2H), 7.48-7.41 (m, 4H), 7.41-7.31 (m, 2H), 4.95-4.77 (m, 1H), 3.77 (ddd, J=14.1, 7.4, 4.2 Hz, 1H), 3.40-3.33 (m, 1H).

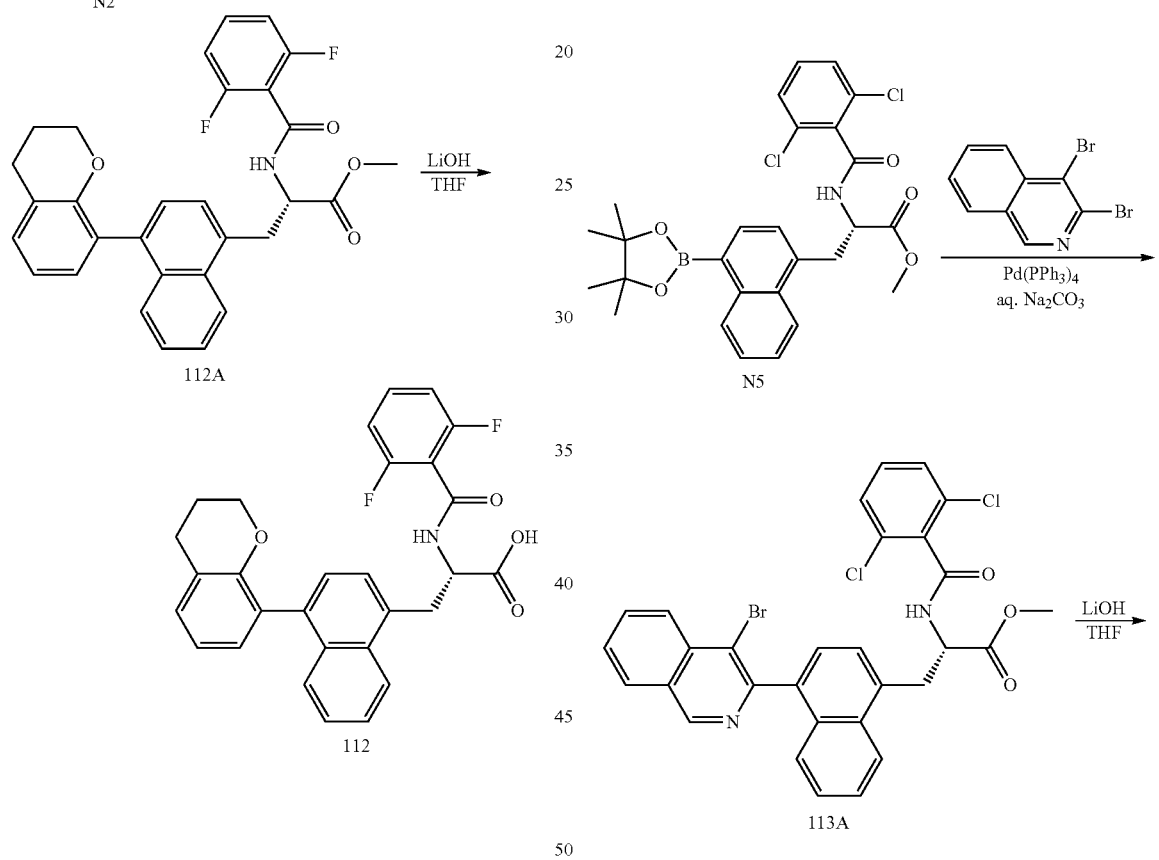

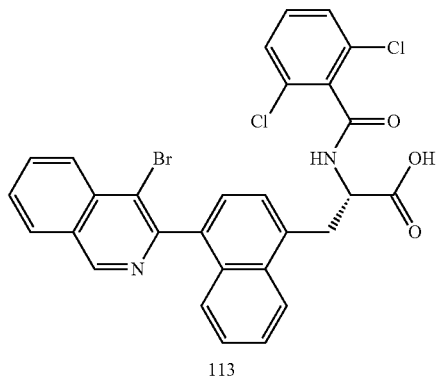

Example 114

Synthesis of (S)-3-(4-(4-bromoisoquinolin-3-yl) naphthalen-1-yl)-2-(2,6-difluoro benzamido)propanoic acid (114)

The title compound was prepared according to the method presented for the synthesis of compound 104 in example 104 starting with N3 and 3,4-dibromoisoquinoline heating at 120° C. for 20 min in microwave. MS (m/z) 563.1 [M+H]$^+$. 1H NMR (400 MHz, DMSO-d6) δ 9.45 (dd, J=2.7, 0.8 Hz, 1H), 9.32 (dd, J=8.0, 3.2 Hz, 1H), 8.33 (d, J=8.2 Hz, 1H), 8.29-8.22 (m, 2H), 8.03 (ddd, J=8.4, 7.0, 1.3 Hz, 1H), 7.88 (ddd, J=8.1, 7.0, 1.1 Hz, 1H), 7.68-7.60 (m, 1H), 7.60-7.52 (m, 1H), 7.47 (dddd, J=15.0, 7.9, 6.6, 3.7 Hz, 3H), 7.38-7.32 (m, 1H), 7.17-7.06 (m, 2H), 4.79 (ddd, J=18.7, 9.7, 4.0 Hz, 1H), 3.73 (dd, J=14.4, 4.8 Hz, 1H), 3.40 (ddd, J=41.1, 14.4, 10.0 Hz, 1H).

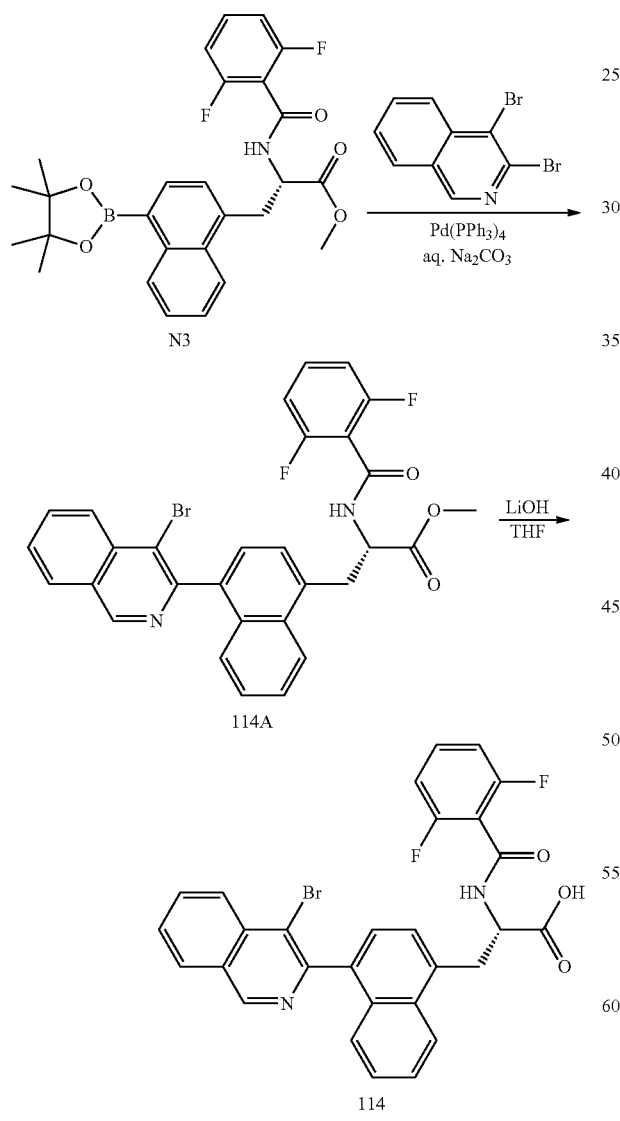

Example 115

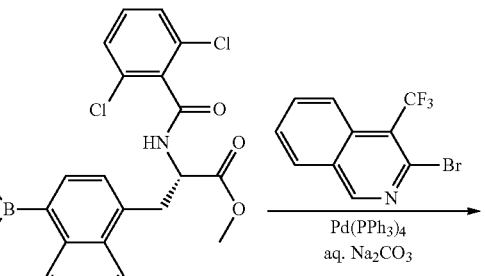

Synthesis of (S)-2-(2,6-dichlorobenzamido)-3-(4-(4-(trifluoromethyl)isoquinolin-3-yl)naphthalen-1-yl) propanoic acid (115)

The title compound was prepared according to the method presented for the synthesis of compound 104 in example 104 starting with N5 and 3-bromo-4-(trifluoromethyl)isoquinoline heating at 120° C. for 30 min in microwave. MS (m/z) 584.9 [M+H]$^+$. 1H NMR (400 MHz, DMSO-d6) δ 9.66 (d, J=5.0 Hz, 1H), 9.32 (dd, J=21.4, 8.3 Hz, 1H), 8.47-8.39 (m, 1H), 8.33-8.19 (m, 2H), 8.14-8.04 (m, 1H), 7.99-7.90 (m, 1H), 7.72-7.61 (m, 1H), 7.58 (dd, J=7.3, 2.1 Hz, 1H), 7.52-7.34 (m, 5H), 7.32 (d, J=7.2 Hz, 1H), 4.87 (dddd, J=26.8, 10.1, 8.3, 4.2 Hz, 1H), 3.77 (dt, J=14.2, 3.8 Hz, 1H), 3.40 (dt, J=14.3, 9.9 Hz, 1H).

Example 116

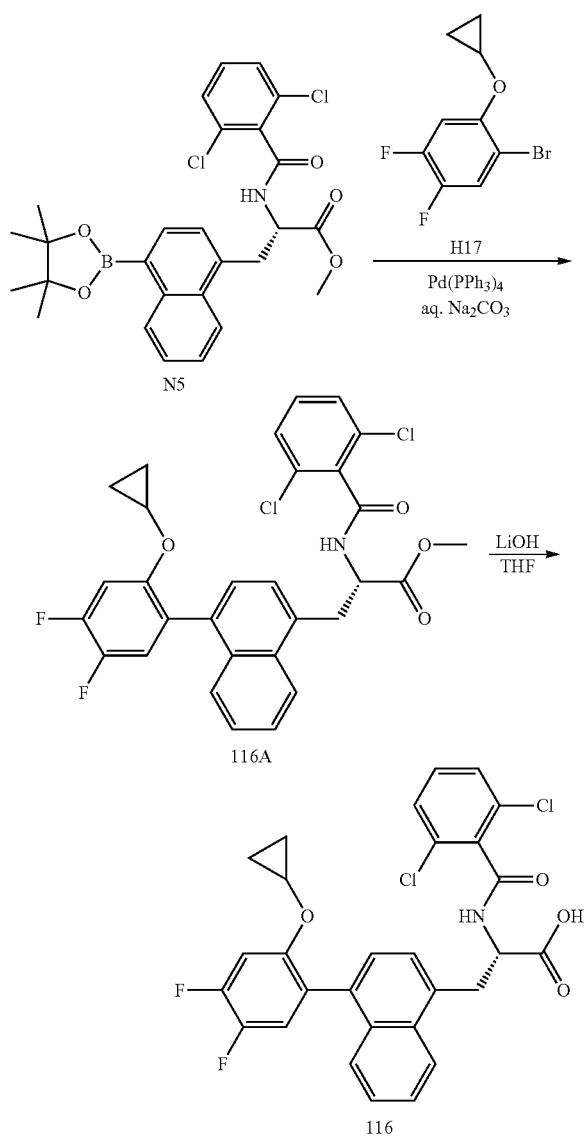

Synthesis of (S)-3-(4-(2-cyclopropoxy-4,5-difluoro-phenyl)naphthalen-1-yl)-2-(2,6-dichlorobenzamido) propanoic acid (116)

The title compound was prepared according to the method presented for the synthesis of compound 104 in example 104 starting with N5 and H17 heating at 130° C. for 30 min in microwave. MS (m/z) 556.1 [M+H]$^+$. 1H NMR (400 MHz, DMSO-d6) δ 9.27-9.14 (m, 1H), 8.18 (dd, J=8.6, 3.6 Hz, 1H), 7.60 (dddd, J=8.3, 6.1, 4.2, 1.6 Hz, 1H), 7.55-7.46 (m, 2H), 7.46-7.34 (m, 5H), 7.30-7.15 (m, 2H), 4.82 (ddq, J=8.1, 6.1, 2.2 Hz, 1H), 3.80 (dq, J=6.0, 3.0 Hz, 1H), 3.70 (ddd, J=14.2, 7.1, 4.3 Hz, 1H), 3.30 (d, J=14.5 Hz, 1H), 0.73-0.58 (m, 2H), 0.53-0.38 (m, 1H), 0.29 (dddd, J=9.8, 7.6, 4.8, 2.6 Hz, 1H).

Examples 117 and 118

Synthesis of (S)-2-(2,6-dichlorobenzamido)-3-(4-(1,4-dimethyl-2-oxo-1,2-dihydroquinolin-3-yl)naphthalen-1-yl)propanoic acid atropisomer 1 (117)

The title compound was prepared according to the method presented for the synthesis of compound 104 in example 104 starting with N5 and H5 heating at 130° C. for 35 min in microwave. The acid product 117B was then separated into its 2 diastereomeric atropisomers by supercritical fluid chromatography using 30% MeOH as co-solvent, at a flow rate of 3.0 mL/min, using an OJ-H 4.6×100 mm column. The title compound was identified as the first eluting peak. MS (m/z) 561.1 [M+H]$^+$. 1H NMR (400 MHz, DMSO-d6) δ 9.28 (dd, J=14.6, 8.3 Hz, 1H), 8.22 (dd, J=8.6, 4.0 Hz, 1H), 7.90 (ddd, J=7.9, 6.2, 1.5 Hz, 1H), 7.73-7.66 (m, 1H), 7.66-7.55 (m, 2H), 7.54 (d, J=7.3 Hz, 1H), 7.52-7.25 (m, 6H), 7.20 (t, J=7.1 Hz, 1H), 4.92-4.75 (m, 1H), 3.85-3.68 (m, 1H), 3.67 (d, J=2.4 Hz, 3H), 3.39-3.22 (m, 1H), 2.08 (d, J=0.7 Hz, 3H).

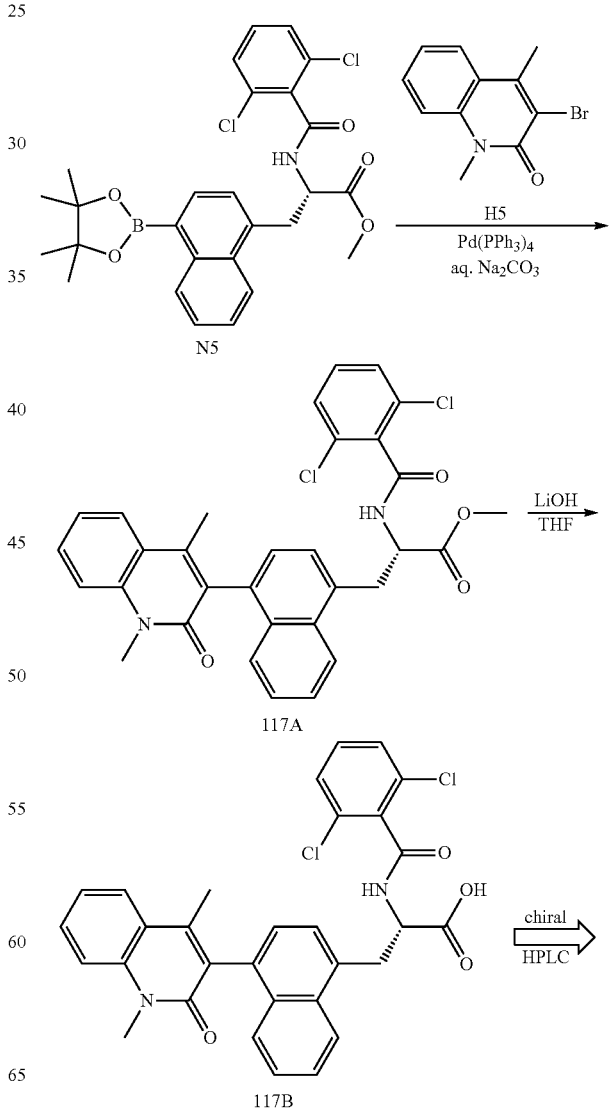

199

-continued

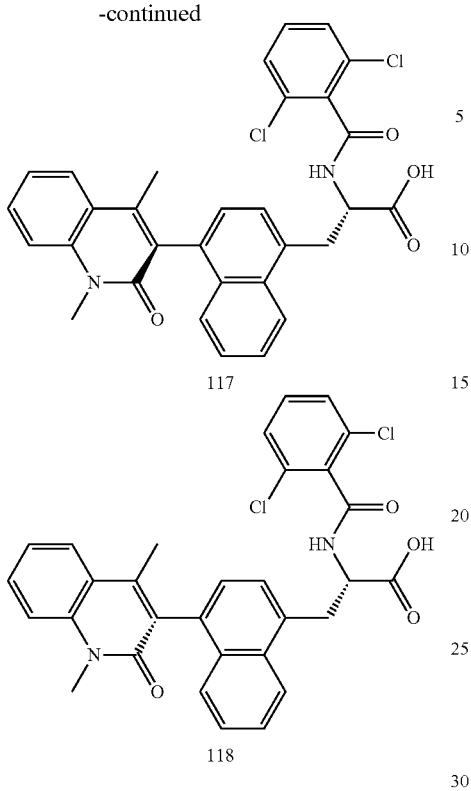

Preparation of (S)-2-(2,6-dichlorobenzamido)-3-(4-(1,4-dimethyl-2-oxo-1,2-dihydroquinolin-3-yl)naph-thalen-1-yl)propanoic acid Atropisomer 2 (118)

117B was separated into its 2 diastereomeric atropisomers by supercritical fluid chromatography using 30% MeOH a co-solvent, at a flow rate of 3.0 mL/min, using an OJ-H 4.6×100 mm column. The title compound was identified as the second eluting peak. MS (m/z) 561.0 [M+H]$^+$. 1H NMR (400 MHz, DMSO-d6) δ 9.30 (d, J=8.3 Hz, 1H), 8.22 (dd, J=8.7, 1.1 Hz, 1H), 7.91 (dd, J=8.1, 1.4 Hz, 1H), 7.69 (ddd, J=8.5, 7.0, 1.4 Hz, 1H), 7.63 (ddd, J=8.4, 6.8, 1.4 Hz, 2H), 7.55 (d, J=7.2 Hz, 1H), 7.51-7.30 (m, 6H), 7.20 (d, J=7.2 Hz, 1H), 4.82 (ddd, J=10.6, 8.3, 3.6 Hz, 1H), 3.79 (dd, J=14.2, 3.6 Hz, 1H), 3.67 (s, 3H), 3.28 (dd, J=14.3, 10.6 Hz, 1H), 2.08 (s, 3H).

Examples 119 and 120

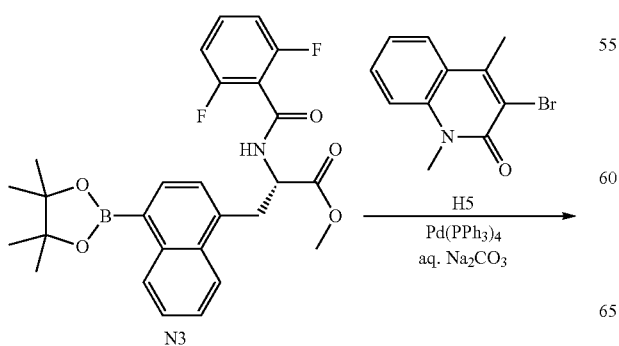

200

-continued

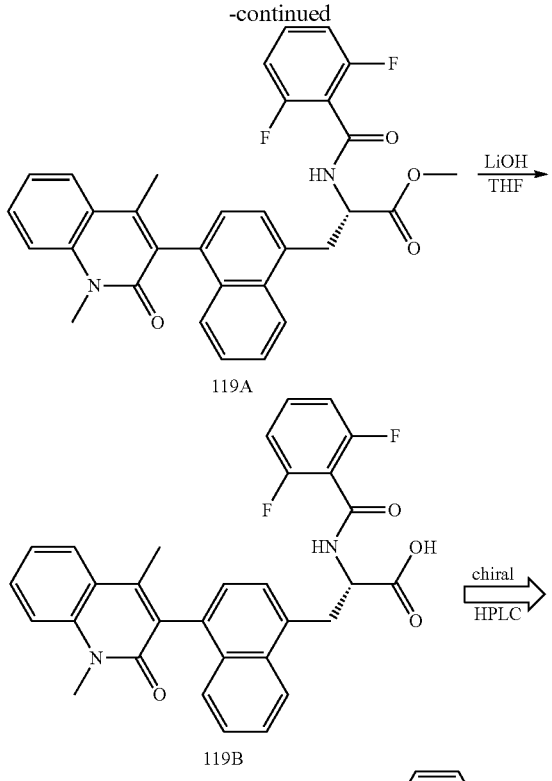

Synthesis of (S)-2-(2,6-difluorobenzamido)-3-(4-(1,4-dimethyl-2-oxo-1,2-dihydro quinolin-3-yl)naphthalen-1-yl)propanoic acid Atropisomer 1 (119)

The title compound was prepared according to the method presented for the synthesis of compound 104 in example 104 starting with N3 and H5 heating at 130° C. for 35 min in microwave. The acid product 119B was then separated into its 2 diastereomeric atropisomers by supercritical fluid chromatography using 30% MeOH as co-solvent, at a flow rate of 3.0 mL/min, using an OJ-H 4.6×100 mm column. The title compound was identified as the first eluting peak. MS (m/z) 527.2 [M+H]$^+$. 1H NMR (400 MHz, DMSO-d6) δ 9.16 (s, 1H), 8.23 (d, J=8.5 Hz, 1H), 7.90 (ddd, J=8.0, 4.5, 1.4 Hz, 1H), 7.69 (ddd, J=8.5, 7.0, 1.4 Hz, 1H), 7.64-7.55 (m, 2H), 7.54-7.43 (m, 3H), 7.43-7.37 (m, 1H), 7.34 (ddd, J=8.1, 7.0, 1.2 Hz, 1H), 7.20 (dd, J=10.7, 7.2 Hz, 1H), 7.15-7.06 (m, 2H), 4.72 (s, 1H), 3.88-3.70 (m, 1H), 3.67 (d, J=1.3 Hz, 3H), 3.43 (dd, J=14.5, 9.3 Hz, 1H), 2.08 (d, J=7.4 Hz, 3H).

Preparation of (S)-2-(2,6-difluorobenzamido)-3-(4-(1,4-dimethyl-2-oxo-1,2-dihydro quinolin-3-yl)naphthalen-1-yl)propanoic acid Atropisomer 2 (120)

119B was separated into its 2 diastereomeric atropisomers by supercritical fluid chromatography using 30% MeOH a co-solvent, at a flow rate of 3.0 mL/min, using an OJ-H 4.6×100 mm column. The title compound was identified as the second eluting peak. MS (m/z) 527.2 [M+H]$^+$. 1H NMR (400 MHz, DMSO-d6) δ9.24 (d, J=8.2 Hz, 1H), 8.20 (d, J=8.5 Hz, 1H), 8.01-7.84 (m, 1H), 7.69 (ddd, J=8.5, 7.0, 1.4 Hz, 1H), 7.64-7.57 (m, 2H), 7.52-7.44 (m, 3H), 7.44-7.39 (m, 1H), 7.35 (ddd, J=8.1, 7.0, 1.2 Hz, 1H), 7.20 (d, J=7.2 Hz, 1H), 7.10 (dd, J=8.4, 7.5 Hz, 2H), 4.86-4.72 (m, 1H), 3.82 (dd, J=14.2, 3.9 Hz, 1H), 3.67 (s, 3H), 3.30-3.23 (m, 1H), 2.09 (s, 3H).

Example 121

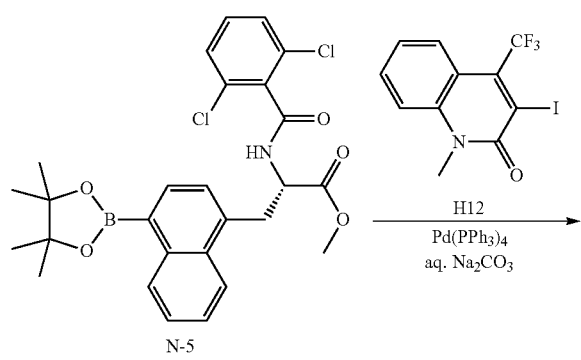

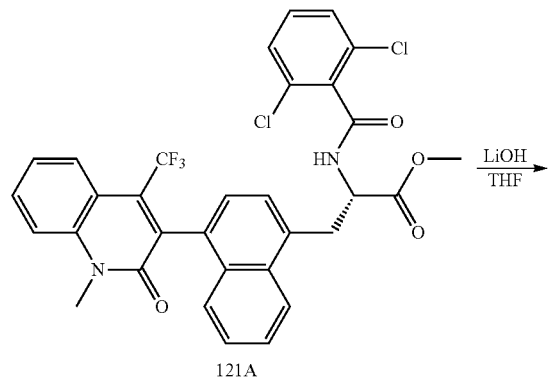

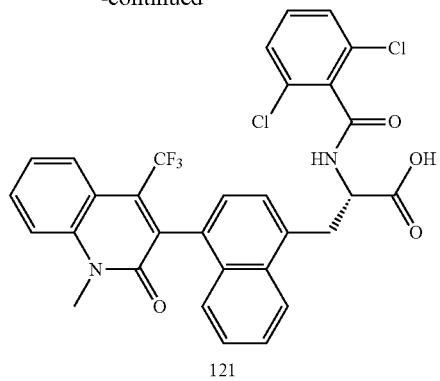

Preparation of (S)-2-(2,6-dichlorobenzamido)-3-(4-(1-methyl-2-oxo-4-(trifluoromethyl)-1,2-dihydroquinolin-3-yl)naphthalen-1-yl)propanoic acid (121)

The title compound was prepared according to the method presented for the synthesis of compound 104 in example 104 starting with N5 and H12 heating at 135° C. for 30 min in microwave. MS (m/z) 614.8 [M+H]$^+$. 1H NMR (400 MHz, DMSO-d6) δ 9.31 (dd, J=18.1, 8.3 Hz, 1H), 8.23 (t, J=7.8 Hz, 1H), 7.94 (d, J=8.1 Hz, 1H), 7.87-7.73 (m, 2H), 7.70-7.59 (m, 1H), 7.59-7.50 (m, 2H), 7.52-7.36 (m, 5H), 7.22 (dd, J=7.2, 5.2 Hz, 1H), 4.92-4.74 (m, 1H), 3.77 (dd, J=14.0, 3.5 Hz, 1H), 3.72 (d, J=4.4 Hz, 3H), 3.32 (dd, J=14.4, 10.3 Hz, 1H).

Example 122

Preparation of methyl (S)-3-(4-(4-methyl-3-(trifluoromethyl)pyridin-2-yl)naphthalen-1-yl)-2-(tritylamino)propanoate (122A)

To a solution of N6 (609.0 mg, 0.561 mmol) and 2-chloro-4-methyl-3-(trifluoromethyl)pyridine (132.0 mg, 0.673 mmol) in 1,2-dimethoxyethane (6.0 mL) was added XPhos Pd G3 (23.7 mg, 0.028 mmol) and a 1.0 M aqueous solution of K$_3$PO$_4$ (1.96 mL, 1.96 mmol). The reaction mixture was heated to 90° C. for 1 hr before concentrating under reduced pressure and purifying the crude product by silica gel chromatography eluting with EtOAc in hexanes (0-100%) to give 122A.

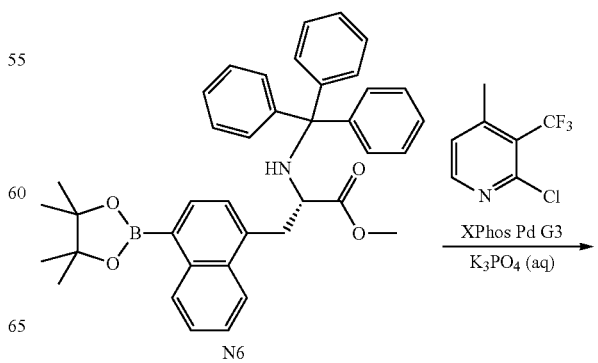

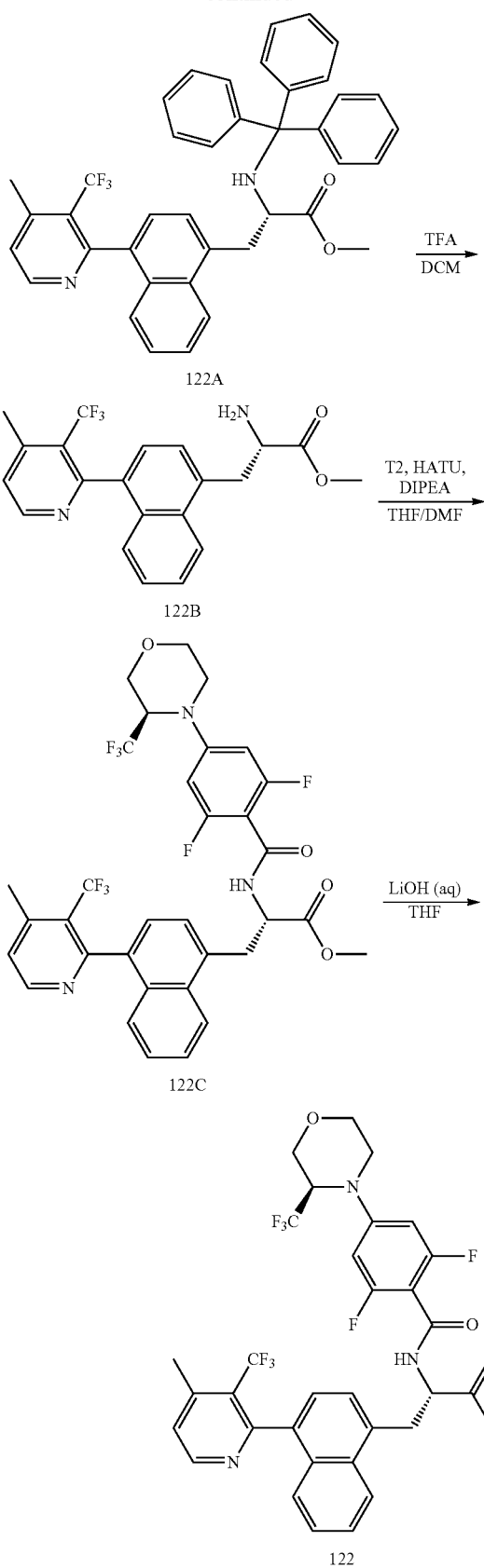

Preparation of methyl (S)-2-amino-3-(4-(4-methyl-3-(trifluoromethyl)pyridin-2-yl)naphthalen-1-yl)propanoate (122B)

To a stirring solution of 122A (243.0 mg, 0.385 mmol) in DCM (4.0 mL) was added TFA (0.072 mL, 0.963 mmol). The reaction mixture was allowed to stir for 1 hr before concentrating under reduced pressure and purifying the crude product by silica gel chromatography eluting with MeOH in DCM (0-20%) to afford 122B.

Preparation of methyl (S)-2-(2,6-difluoro-4-(((R)-1,1,1-trifluorobutan-2-yl)amino) benzamido)-3-(4-(4-methyl-3-(trifluoromethyl)pyridin-2-yl)naphthalen-1-yl)propanoate (122C)

To a stirring solution of 122B (24.0 mg, 0.062 mmol), T2 (21.2 mg, 0.068 mmol) and HATU (25.8 mg, 0.068 mmol) in THF (1.50 mL) and DMF (0.40 mL) was added DIPEA (0.043 mL, 0.25 mmol). The reaction mixture was stirred for 1 hr before concentrating under reduced pressure. The crude product was purified by silica gel chromatography eluting with EtOAc in hexanes (0-80%) to afford 122C.

Preparation of (S)-2-(2,6-difluoro-4-(((R)-1,1,1-trifluorobutan-2-yl)amino)benzamido)-3-(4-(4-methyl-3-(trifluoromethyl)pyridin-2-yl)naphthalen-1-yl)propanoic acid (122)

To a stirring solution of 122C (33.0 mg, 0.048 mmol) in THF (1.5 mL) was added an aqueous 1.0 M solution of LiOH (0.24 mL, 0.24 mmol). The reaction mixture was stirred for 1 hr before concentrating under reduced pressure. The material was purified via reverse phase HPLC to afford the title compound. MS (m/z) 668.8 [M+H]$^+$. 1H NMR (400 MHz, DMSO-d6) δ 8.98 (dd, J=8.0, 4.7 Hz, 1H), 8.76 (d, J=5.0 Hz, 1H), 8.23 (d, J=8.6 Hz, 1H), 7.68-7.58 (m, 2H), 7.55-7.42 (m, 2H), 7.28 (dd, J=8.4, 1.1 Hz, 1H), 7.23 (dd, J=7.2, 2.3 Hz, 1H), 6.76 (dd, J=11.5, 3.8 Hz, 2H), 4.98-4.85 (m, 1H), 4.80-4.65 (m, 1H), 4.16 (d, J=12.7 Hz, 1H), 3.95 (dd, J=11.5, 3.8 Hz, 1H), 3.83-3.66 (m, 2H), 3.55 (td, J=11.8, 3.3 Hz, 1H), 3.48-3.30 (m, 2H), 3.23 (t, J=12.7 Hz, 1H), 2.61 (q, J=2.6 Hz, 3H).

Example 123

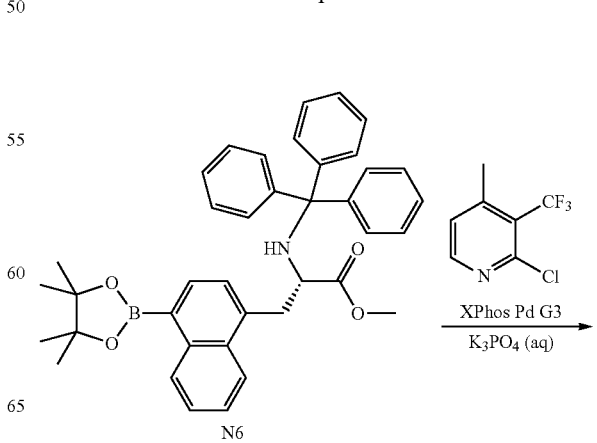

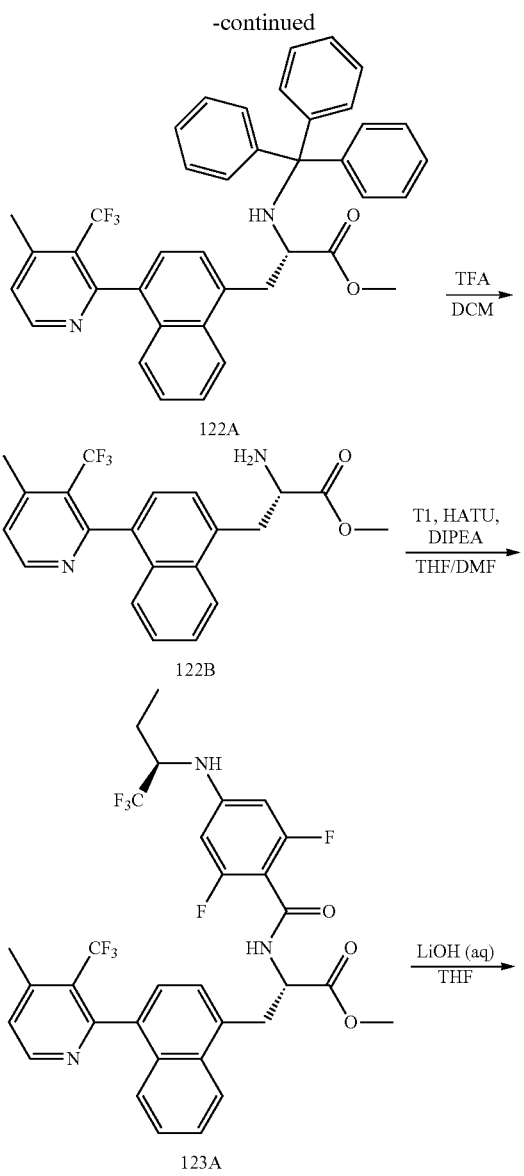

Preparation of methyl (S)-3-(4-(4-methyl-3-(trifluoromethyl)pyridin-2-yl)naphthalen-1-yl)-2-(tritylamino)propanoate (122A)

The title compound was prepared according to the method described in Example 122.

Preparation of methyl (S)-2-amino-3-(4-(4-methyl-3-(trifluoromethyl)pyridin-2-yl)naphthalen-1-yl)propanoate (122B)

The title compound was prepared according to the method described in Example 122.

Preparation of methyl (S)-3-(4-(4-methyl-3-(trifluoromethyl)pyridin-2-yl)naphthalen-1-yl)-2-(tritylamino)propanoate (123A)

The title compound was prepared according to the method presented for the synthesis of compound 122C starting with T1 and 122B.

Preparation of (S)-2-(2,6-difluoro-4-(((R)-1,1,1-trifluorobutan-2-yl)amino)benzamido)-3-(4-(4-methyl-3-(trifluoromethyl)pyridin-2-yl)naphthalen-1-yl)propanoic acid (123)

The title compound was prepared according to the method presented for the synthesis of compound 122 starting with 123A. MS (m/z) 640.2 [M+H]$^+$. 1H NMR (400 MHz, DMSO-d6) δ 8.82 (dd, J=7.9, 5.7 Hz, 1H), 8.75 (d, J=5.0 Hz, 1H), 8.22 (d, J=8.6 Hz, 1H), 7.67-7.58 (m, 2H), 7.54-7.41 (m, 2H), 7.28 (d, J=8.4 Hz, 1H), 7.23 (dd, J=7.2, 3.1 Hz, 1H), 6.77 (dd, J=9.4, 6.1 Hz, 1H), 6.49-6.41 (m, 2H), 4.77-4.62 (m, 1H), 4.31 (d, J=11.2 Hz, 1H), 3.73 (ddd, J=25.2, 14.3, 4.3 Hz, 1H), 3.36 (ddd, J=19.5, 14.3, 10.0 Hz, 1H), 2.61 (q, J=2.6 Hz, 3H), 1.84-1.70 (m, 1H), 1.61-1.44 (m, 1H), 0.93 (t, J=7.5, 1.6 Hz, 3H).

Example 124

Preparation of methyl (S)-3-(4-(4-methoxy-1,6-dimethyl-2-oxo-1,2-dihydropyridin-3-yl)naphthalen-1-yl)-2-(tritylamino)propanoate (124A)

The title compound was prepared according to the method presented for the synthesis of compound 122A starting with N6 and 3-bromo-4-methoxy-1,6-dimethylpyridin-2(1H)-one.

Preparation of methyl (S)-2-amino-3-(4-(4-methoxy-1,6-dimethyl-2-oxo-1,2-dihydropyridin-3-yl)naphthalen-1-yl)propanoate (124B)

The title compound was prepared according to the method presented for the synthesis of compound 122B starting with 124A.

Preparation of methyl (S)-2-(2,6-difluoro-4-((R)-3-(trifluoromethyl)morpholino) benzamido)-3-(4-(4-methoxy-1,6-dimethyl-2-oxo-1,2-dihydropyridin-3-yl)naphthalen-1-yl)propanoate (124C)

The title compound was prepared according to the method presented for the synthesis of compound 122C starting with 124B.

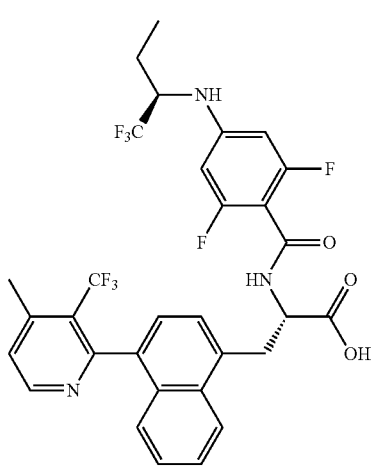

207

Preparation of methyl (S)-2-(2,6-difluoro-4-((R)-3-(trifluoromethyl)morpholino) benzamido)-3-(4-(4-methoxy-1,6-dimethyl-2-oxo-1,2-dihydropyridin-3-yl)naphthalen-1-yl)propanoate Atropisomer 1 (124D)

Ester 124C was separated into its 2 diastereomeric atropisomers by supercritical fluid chromatography using 40% MeOH as co-solvent, at a flow rate of 3.0 mL/min, using an OD-H 4.6×100 mm column. The title compound was identified as the first eluting peak.

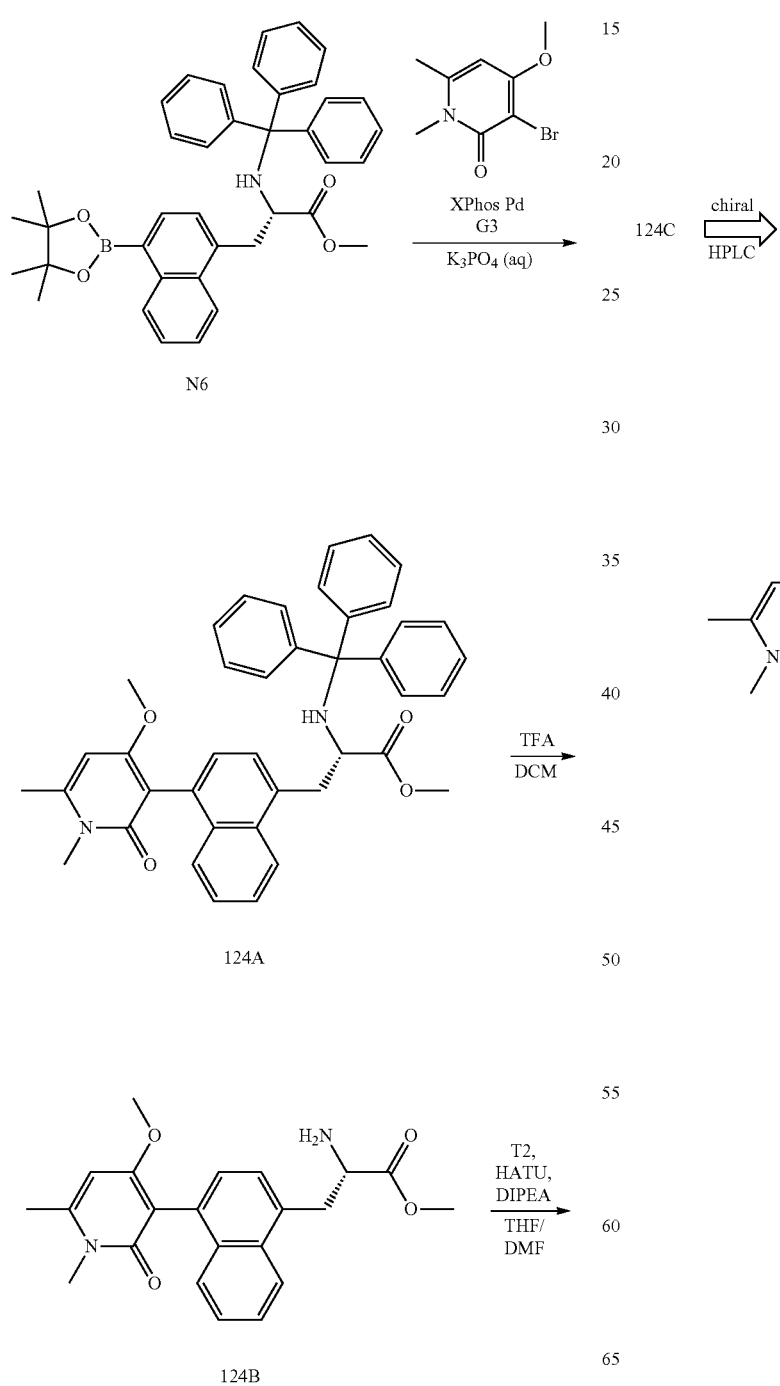

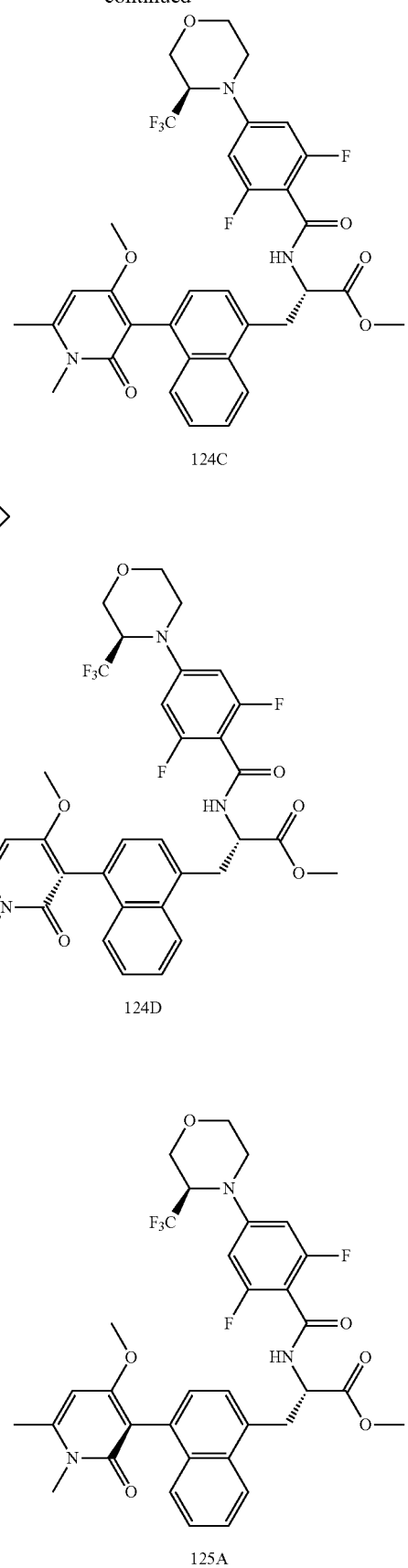

209

-continued

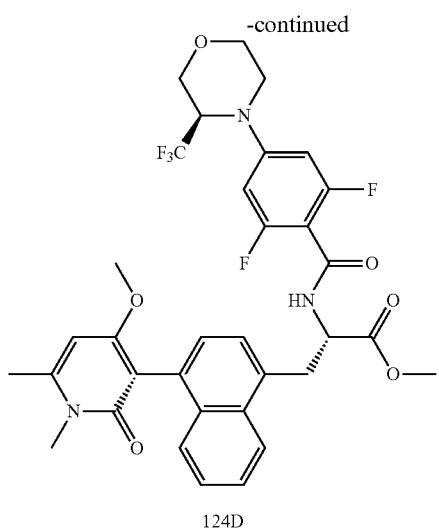

124D

↓ LiOH / THF

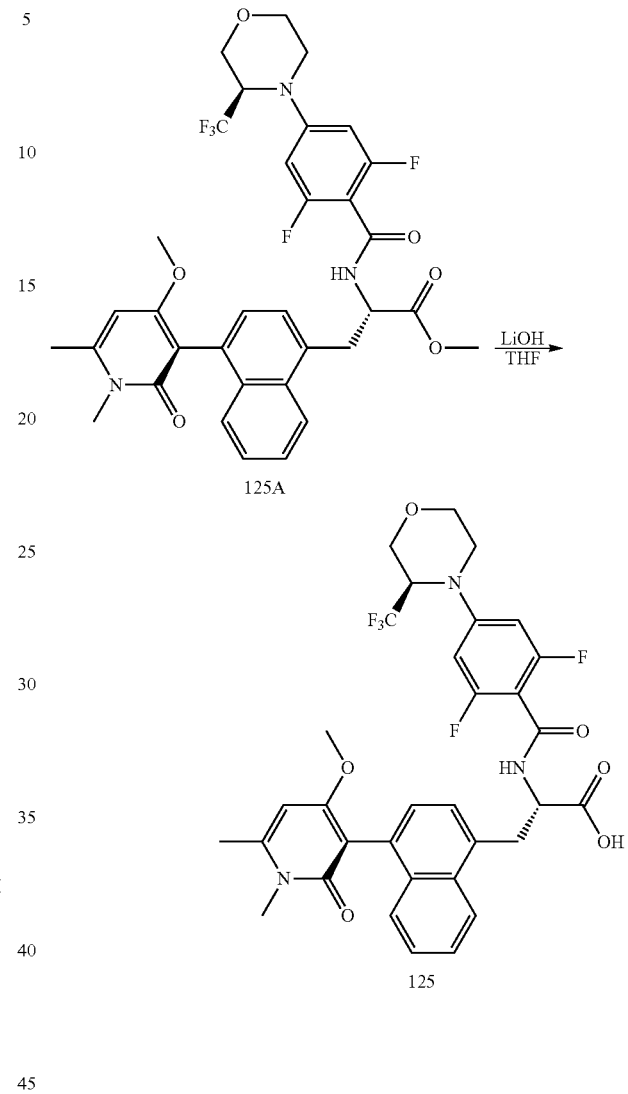

124

Preparation of (S)-2-(2,6-difluoro-4-((R)-3-(trifluoromethyl)morpholino)benzamido)-3-(4-(4-methoxy-1,6-dimethyl-2-oxo-1,2-dihydropyridin-3-yl)naphthalen-1-yl)propanoic acid (124)

The title compound was prepared according to the method presented for the synthesis of compound 122 starting with 124D. MS (m/z) 660.3 [M+H]$^+$. 1H NMR (400 MHz, DMSO-d6) δ 8.97 (d, J=7.7 Hz, 1H), 8.14 (d, J=8.5 Hz, 1H), 7.55 (t, J=7.6 Hz, 1H), 7.49 (d, J=8.4 Hz, 1H), 7.45-7.36 (m, 2H), 7.13 (d, J=7.2 Hz, 1H), 6.78 (d, J=11.8 Hz, 2H), 6.39 (s, 1H), 4.97-4.84 (m, 1H), 4.67 (td, J=8.7, 4.4 Hz, 1H), 4.16 (d, J=12.7 Hz, 1H), 3.97-3.93 (m, 1H), 3.75 (d, J=14.6 Hz, 2H), 3.63 (s, 3H), 3.59-3.52 (m, 1H), 3.45 (s, 4H), 3.39-3.31 (m, 1H), 3.24 (t, J=12.5 Hz, 1H), 2.48 (s, 3H).

210

Example 125

125A

↓ LiOH / THF

125

Preparation of (S)-2-(2,6-difluoro-4-((R)-3-(trifluoromethyl)morpholino)benzamido)-3-(4-(4-methoxy-1,6-dimethyl-2-oxo-1,2-dihydropyridin-3-yl)naphthalen-1-yl)propanoic acid Atropisomer 2 (125)

Ester 124C was separated into its 2 diastereomeric atropisomers by supercritical fluid chromatography using 40% MeOH as co-solvent, at a flow rate of 3.0 mL/min, using an OD-H 4.6×100 mm column. 125A was identified as the second eluting peak. The title compound was prepared according to the method presented for the synthesis of compound 122 starting with 125A. MS (m/z) 660.29 [M+H]$^+$. 1H NMR (400 MHz, DMSO-d6) δ 8.96 (d, J=7.8 Hz, 1H), 8.18 (d, J=8.5 Hz, 1H), 7.58 (ddd, J=8.4, 5.3, 2.9 Hz, 1H), 7.48 (d, J=7.3 Hz, 1H), 7.47-7.39 (m, 2H), 7.13 (d, J=7.2 Hz, 1H), 6.77 (d, J=11.6 Hz, 2H), 6.21 (s, 1H), 4.91 (dd, J=8.6, 3.6 Hz, 1H), 4.69 (td, J=8.7, 4.5 Hz, 1H), 4.16 (d, J=12.7 Hz, 1H), 3.99-3.91 (m, 1H), 3.79-3.69 (m, 2H), 3.68 (d, J=4.7 Hz, 1H), 3.45 (s, 5H), 3.28-3.18 (m, 1H), 2.41 (s, 3H), 1.71 (s, 3H).

Example 126
Preparation of methyl (S)-3-(4-(1,4,6-trimethyl-2-oxo-1,2-dihydropyridin-3-yl) naphthalen-1-yl)-2-(tritylamino)propanoate (126A)
The title compound was prepared according to the method presented for the synthesis of compound 122A starting with N6 and 3-bromo-1,4,6-trimethylpyridin-2(1H)-one.
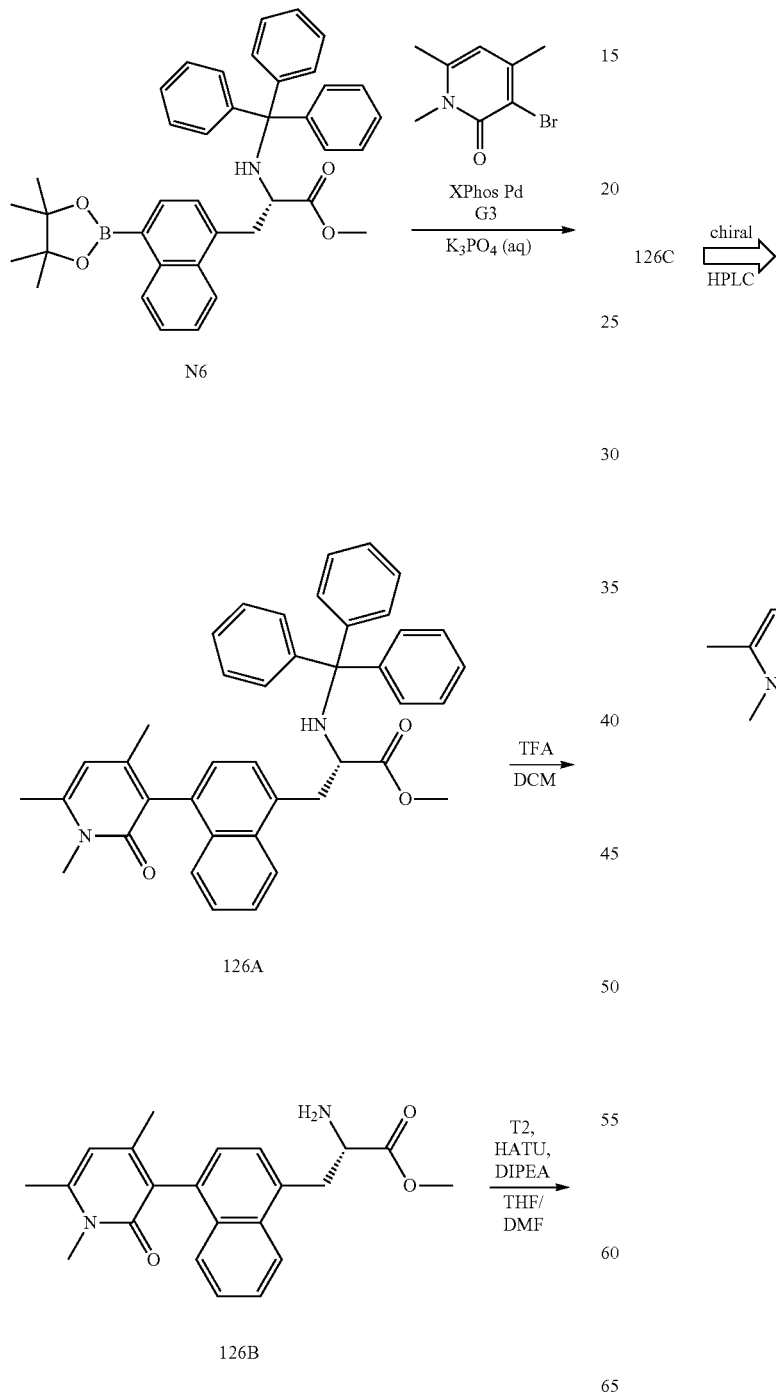
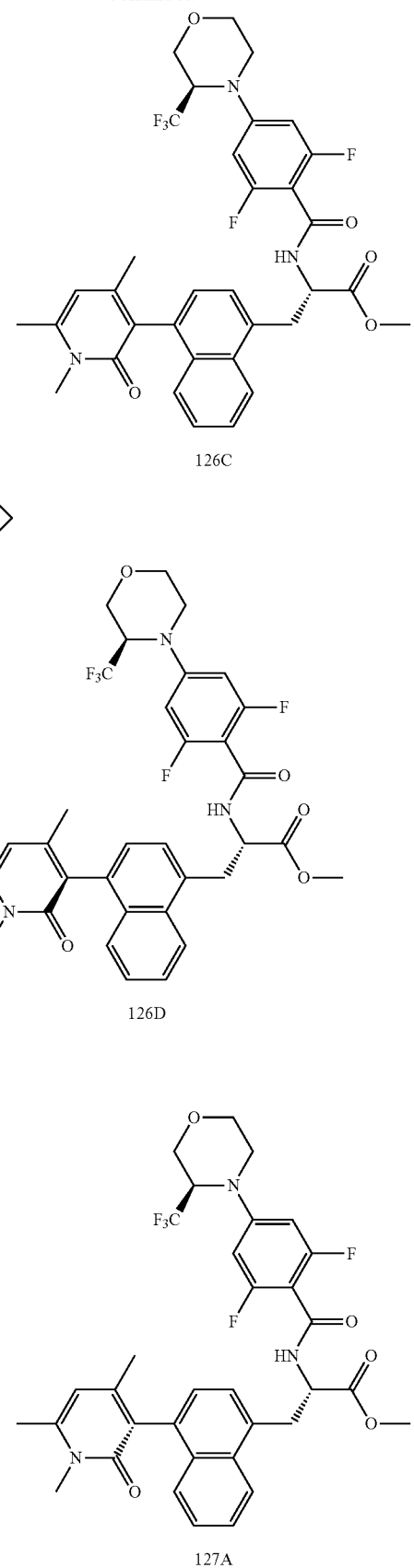

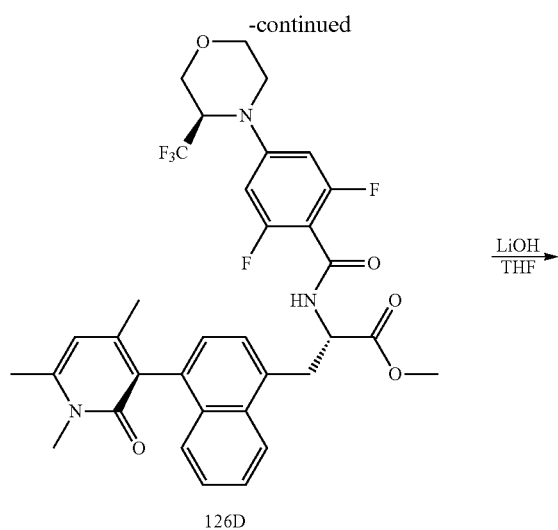

126D

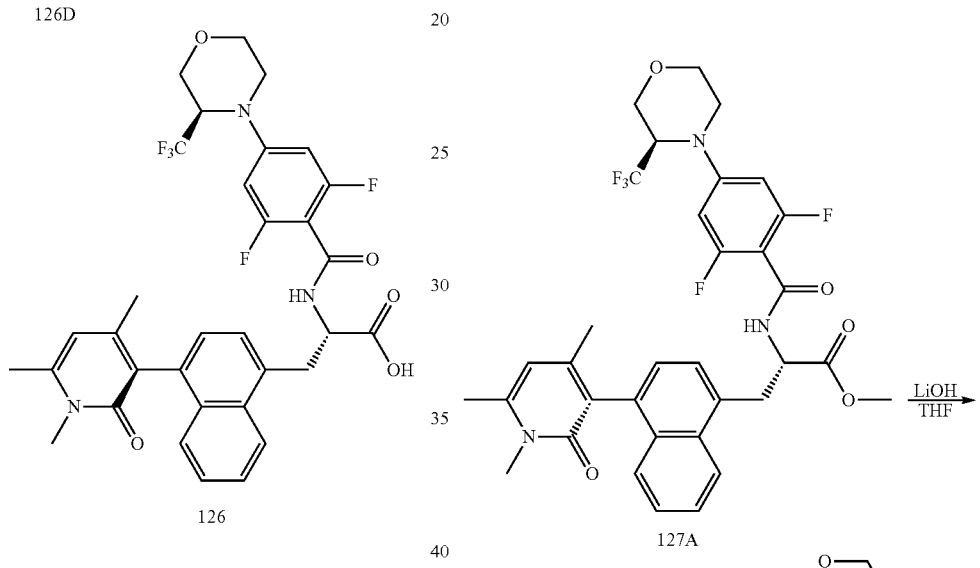

126

Preparation of methyl (S)-2-amino-3-(4-(1,4,6-trimethyl-2-oxo-1,2-dihydropyridin-3-yl) naphthalene 1-yl)propanoate (126B)

The title compound was prepared according to the method presented for the synthesis of compound 122B starting with 126A.

Preparation of methyl (S)-2-(2,6-difluoro-4-((R)-3-(trifluoromethyl) morpholino)benzamido)-3-(4-(1,4,6-trimethyl-2-oxo-1,2-dihydropyridin-3-yl)naphthalen-1-yl)propanoate (126C)

The title compound was prepared according to the method presented for the synthesis of compound 122C starting with 126B.

Preparation of methyl (S)-2-(2,6-difluoro-4-((R)-3-(trifluoromethyl) morpholino)benzamido)-3-(4-(1,4,6-trimethyl-2-oxo-1,2-dihydropyridin-3-yl)naphthalen-1-yl)propanoate Atropisomer 1 (126D)

Ester 126C was separated into its 2 diastereomeric atropisomers by supercritical fluid chromatography using 40% MeOH as co-solvent, at a flow rate of 3.0 mL/min, using an IC 4.6×100 mm 5 mic column. The title compound was identified as the first eluting peak.

Preparation of (S)-2-(2,6-difluoro-4-((R)-3-(trifluoromethyl)morpholino)benzamido)-3-(4-(1,4,6-trimethyl-2-oxo-1,2-dihydropyridin-3-yl)naphthalen-1-yl)propanoic acid (126)

The title compound was prepared according to the method presented for the synthesis of compound 122 starting with 126D. MS (m/z) 644.2 [M+H]$^+$. 1H NMR (400 MHz, DMSO-d6) δ 8.96 (d, J=7.8 Hz, 1H), 8.18 (d, J=8.5 Hz, 1H), 7.58 (ddd, J=8.4, 5.3, 2.9 Hz, 1H), 7.48 (d, J=7.3 Hz, 1H), 7.47-7.39 (m, 2H), 7.13 (d, J=7.2 Hz, 1H), 6.77 (d, J=11.6 Hz, 2H), 6.21 (s, 1H), 4.91 (dd, J=8.6, 3.6 Hz, 1H), 4.69 (td, J=8.7, 4.5 Hz, 1H), 4.16 (d, J=12.7 Hz, 1H), 3.99-3.91 (m, 1H), 3.79-3.69 (m, 2H), 3.68 (d, J=4.7 Hz, 1H), 3.45 (s, 5H), 3.28-3.18 (m, 1H), 2.41 (s, 3H), 1.71 (s, 3H).

Example 127

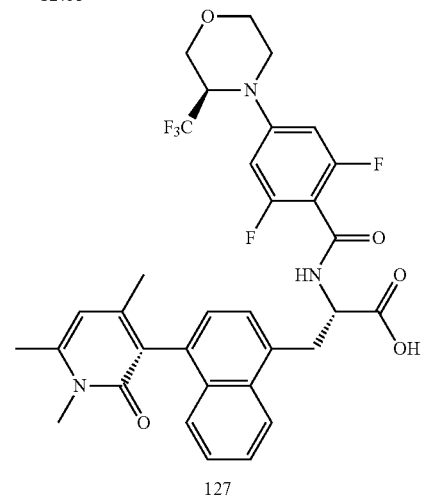

127

Preparation of (S)-2-(2,6-difluoro-4-((R)-3-(trifluoromethyl)morpholino)benzamido)-3-(4-(1,4,6-trimethyl-2-oxo-1,2-dihydropyridin-3-yl)naphthalen-1-yl)propanoic acid (127)

Ester 126C was separated into its 2 diastereomeric atropisomers by supercritical fluid chromatography using 40%

MeOH as co-solvent, at a flow rate of 3.0 mL/min, using an IC 4.6×100 mm 5 mic column. 127A was identified as the second eluting peak. The title compound was prepared according to the method presented for the synthesis of compound 122 starting with 127A. MS (m/z) 646.2 [M+H]⁺. 1H NMR (400 MHz, DMSO-d6) δ 8.93 (d, J=8.1 Hz, 1H), 8.17 (d, J=8.5 Hz, 1H), 7.59 (ddd, J=8.4, 5.4, 2.7 Hz, 1H), 7.50-7.39 (m, 3H), 7.10 (d, J=7.1 Hz, 1H), 6.75 (d, J=11.6 Hz, 2H), 6.21 (s, 1H), 4.89 (dt, J=12.3, 6.1 Hz, 1H), 4.79-4.68 (m, 1H), 4.16 (d, J=12.7 Hz, 1H), 3.94 (d, J=3.9 Hz, 1H), 3.80-3.69 (m, 2H), 3.59-3.49 (m, 1H), 3.45 (s, 4H), 3.26 (ddd, J=24.2, 13.7, 10.0 Hz, 2H), 2.41 (s, 3H), 1.72 (s, 3H).
Example 128
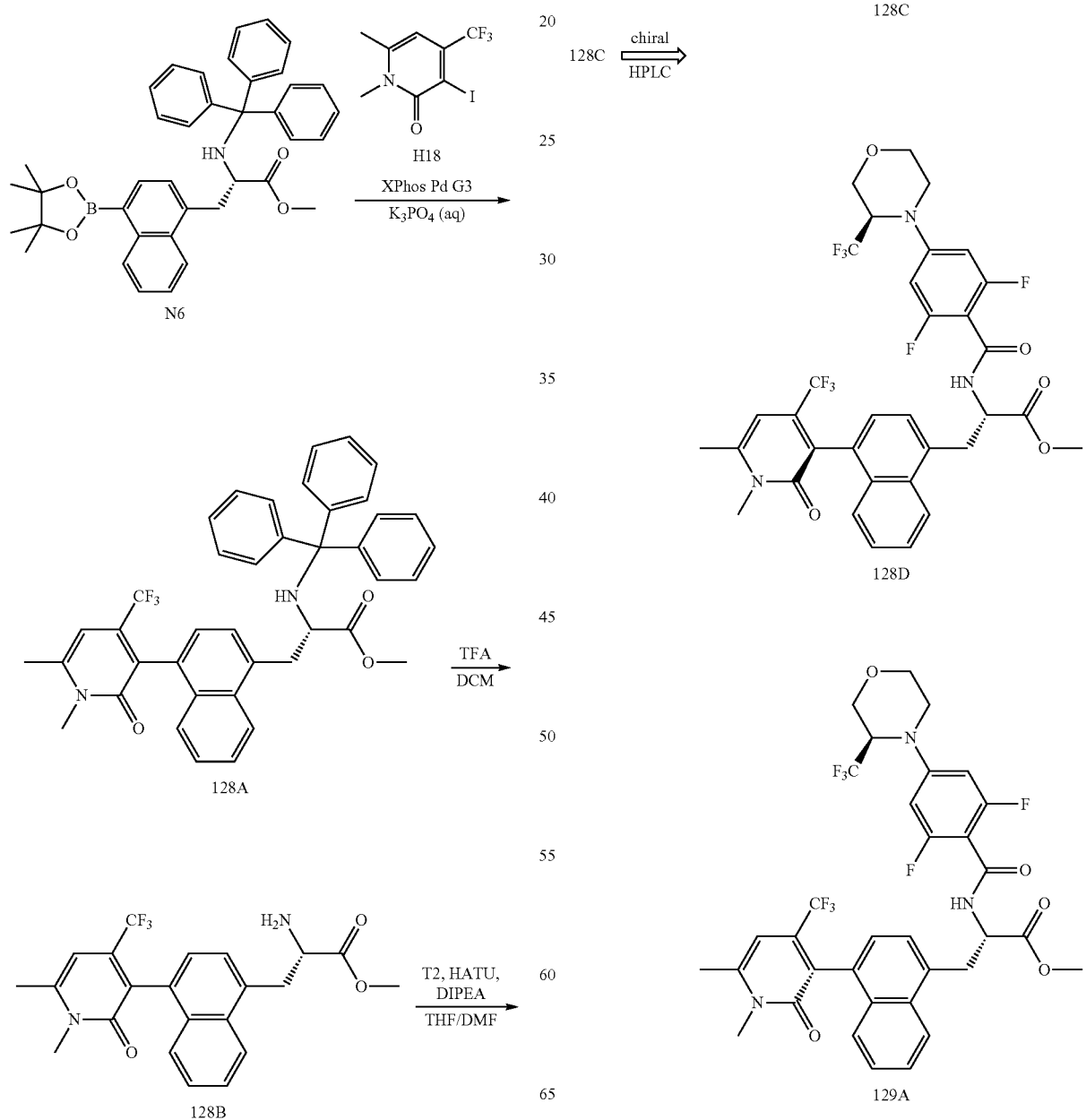

217

Preparation of methyl (S)-3-(4-(1,6-dimethyl-2-oxo-4-(trifluoromethyl)-1,2-dihydro pyridin-3-yl)naphthalen-1-yl)-2-(tritylamino)propanoate (128A)

The title compound was prepared according to the method presented for the synthesis of compound 122A starting with N6 and H18.

Preparation of methyl (S)-2-amino-3-(4-(1,6-dimethyl-2-oxo-4-(trifluoromethyl)-1,2-dihydropyridin-3-yl)naphthalen-1-yl)propanoate (128B)

The title compound was prepared according to the method presented for the synthesis of compound 122B starting with 128A.

Preparation of methyl (S)-2-(2,6-difluoro-4-((R)-3-(trifluoromethyl)morpholino) benzamido)-3-(4-(1,6-dimethyl-2-oxo-4-(trifluoromethyl)-1,2-dihydropyridin-3-yl)naphthalen-1-yl)propanoate (128C)

The title compound was prepared according to the method presented for the synthesis of compound 122C starting with 128B.

Preparation of methyl (S)-2-(2,6-difluoro-4-((R)-3-(trifluoromethyl)morpholino) benzamido)-3-(4-(1,6-dimethyl-2-oxo-4-(trifluoromethyl)-1,2-dihydropyridin-3-yl)naphthalen-1-yl)propanoate Atropisomer 1 (128D)

Ester 128C was separated into its 2 diastereomeric atropisomers by supercritical fluid chromatography using 30% MeOH as co-solvent, at a flow rate of 3.0 mL/min, using an OD-H 4.6×100 mm 5 mic column. The title compound was identified as the first eluting peak.

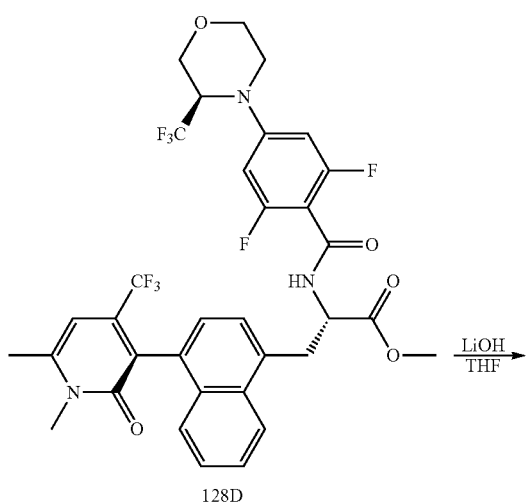

128D

218

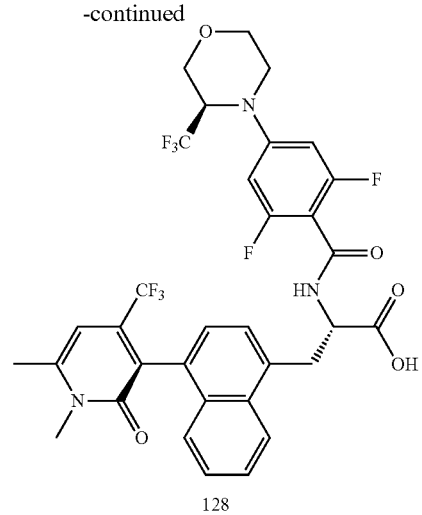

128

Preparation of (S)-2-(2,6-difluoro-4-((R)-3-(trifluoromethyl)morpholino)benzamido)-3-(4-(1,6-dimethyl-2-oxo-4-(trifluoromethyl)-1,2-dihydropyridin-3-yl)naphthalen-1-yl)propanoic acid (128)

The title compound was prepared according to the method presented for the synthesis of compound 122 starting with 128D. MS (m/z) 698.2 [M+H]$^+$. 1H NMR (400 MHz, DMSO-d6) δ 8.95 (d, J=7.9 Hz, 1H), 8.16 (d, J=8.5 Hz, 1H), 7.58 (ddd, J=8.4, 6.6, 1.5 Hz, 1H), 7.47-7.31 (m, 3H), 7.11 (d, J=7.3 Hz, 1H), 6.73 (d, J=11.6 Hz, 2H), 6.60 (d, J=0.8 Hz, 1H), 4.90 (dd, J=8.7, 3.6 Hz, 1H), 4.70 (ddd, J=10.1, 7.9, 4.3 Hz, 1H), 4.14 (d, J=12.7 Hz, 1H), 3.93 (dd, J=11.5, 3.8 Hz, 1H), 3.75-3.70 (m, 1H), 3.68 (d, J=4.3 Hz, 1H), 3.52 (m, 1H), 3.49 (s, 3H), 3.44-3.16 (m, 3H), 2.55-2.51 (m, 3H).

Example 129

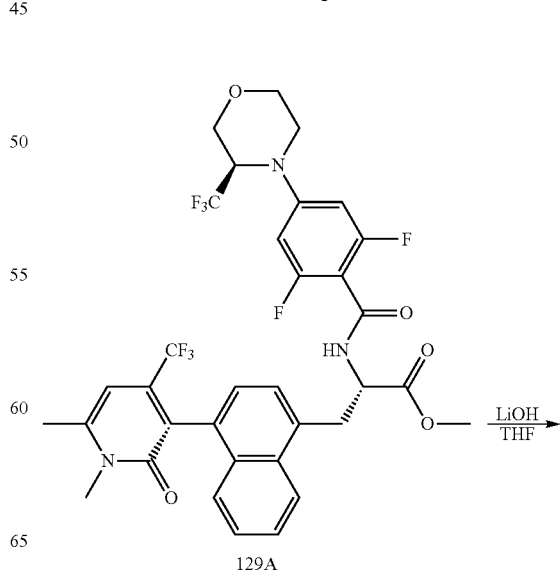

129A

219

-continued

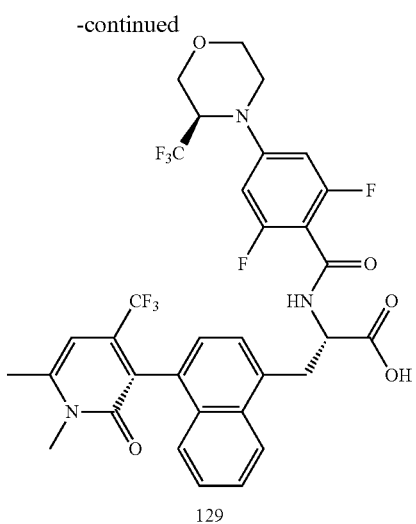

129

Preparation of (129)

Ester 128C was separated into its 2 diastereomeric atropisomers by supercritical fluid chromatography using 30% MeOH as co-solvent, at a flow rate of 3.0 mL/min, using an OD-H 4.6×100 mm 5 mic column. 129A was identified as the second eluting peak. The title compound was prepared according to the method presented for the synthesis of compound 122 starting with 129A. MS (m/z) 698.2 [M+H]⁺. 1H NMR (400 MHz, DMSO-d6) δ 8.97 (d, J=7.8 Hz, 1H), 8.16 (d, J=8.5 Hz, 1H), 7.58 (ddd, J=8.4, 6.5, 1.5 Hz, 1H), 7.49-7.34 (m, 3H), 7.12 (d, J=7.3 Hz, 1H), 6.75 (d, J=11.6 Hz, 2H), 6.59 (s, 1H), 4.89 (dt, J=8.8, 4.4 Hz, 1H), 4.68 (ddd, J=9.9, 7.8, 4.2 Hz, 1H), 4.14 (d, J=12.7 Hz, 1H), 3.93 (dd, J=11.5, 3.8 Hz, 1H), 3.75-3.64 (m, 2H), 3.49 (s, 3H), 3.43-3.35 (m, 2H), 3.34 (s, 1H), 3.28-3.14 (m, 1H), 2.52 (s, 3H).

Example 130

Preparation of methyl (S)-2-(2,6-difluoro-4-(((R)-1,1,1-trifluorobutan-2-yl)amino) benzamido)-3-(4-(4-methoxy-1,6-dimethyl-2-oxo-1,2-dihydropyridin-3-yl)naphthalen-1-yl) propanoate (130A)

The title compound was prepared according to the method presented for the synthesis of compound 123A starting with 124B.

Preparation of methyl (S)-2-(2,6-difluoro-4-(((R)-1,1,1-trifluorobutan-2-yl)amino) benzamido)-3-(4-(4-methoxy-1,6-dimethyl-2-oxo-1,2-dihydropyridin-3-yl)naphthalen-1-yl) propanoate Atropisomer 1 (130B)

Ester 130A was separated into its 2 diastereomeric atropisomers by supercritical fluid chromatography using 40% MeOH as co-solvent, at a flow rate of 3.0 mL/min, using an IC 4.6×100 mm 5 mic column. The title compound was identified as the first eluting peak.

Preparation of (S)-2-(2,6-difluoro-4-(((R)-1,1,1-trifluorobutan-2-yl)amino)benzamido)-3-(4-(4-methoxy-1,6-dimethyl-2-oxo-1,2-dihydropyridin-3-yl)naphthalen-1-yl)propanoic acid (130)

The title compound was prepared according to the method presented for the synthesis of compound 123 starting with

220

130B. MS (m/z) 632.2 [M+H]⁺. 1H NMR (400 MHz, DMSO-d6) δ 8.81 (d, J=7.5 Hz, 1H), 8.14 (d, J=8.5 Hz, 1H), 7.55 (t, J=7.6 Hz, 1H), 7.49 (d, J=8.4 Hz, 1H), 7.42 (dd, J=10.1, 7.3 Hz, 2H), 7.13 (d, J=7.2 Hz, 1H), 6.77 (d, J=9.4 Hz, 1H), 6.47 (d, J=11.6 Hz, 2H), 6.39 (s, 1H), 4.65 (td, J=8.6, 4.4 Hz, 1H), 4.31 (d, J=8.7 Hz, 1H), 3.66 (d, J=4.7 Hz, 1H), 3.63 (d, J=4.8 Hz, 3H), 3.45 (s, 3H), 3.35 (dd, J=14.6, 9.3 Hz, 1H), 2.48 (s, 3H), 1.78 (ddd, J=14.1, 7.3, 3.3 Hz, 1H), 1.53 (ddt, J=17.7, 14.4, 7.5 Hz, 1H), 0.93 (t, J=7.3 Hz, 3H).

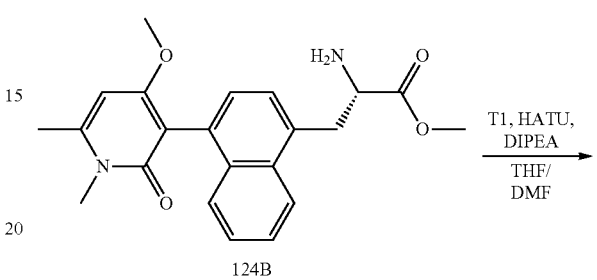

124B

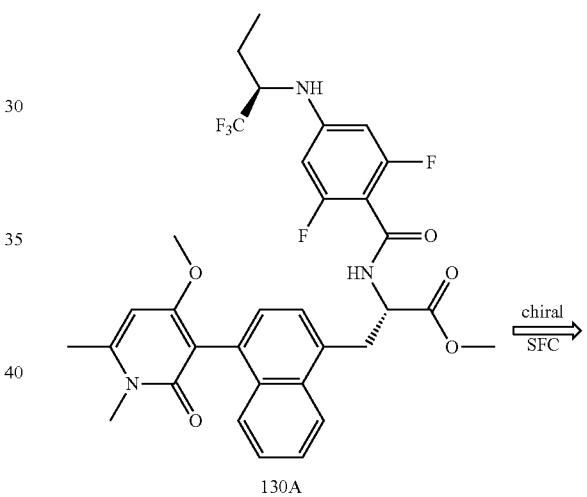

130A

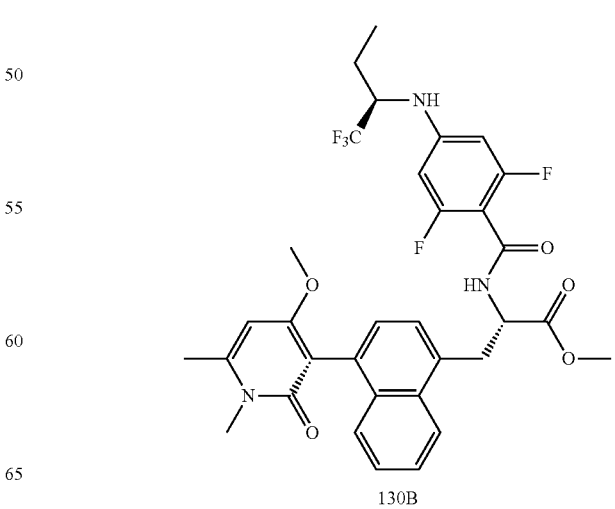

130B

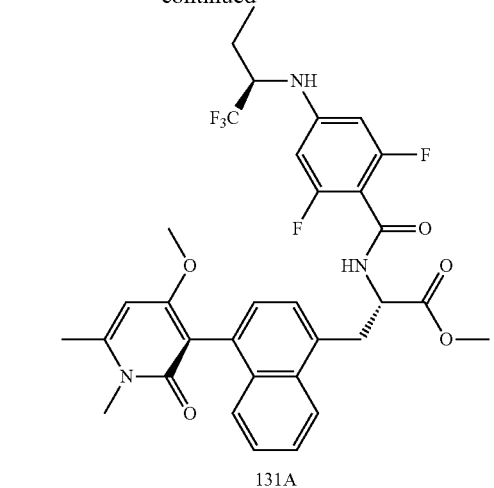

131A

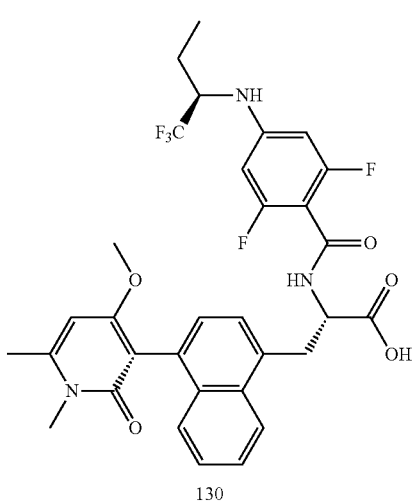

130

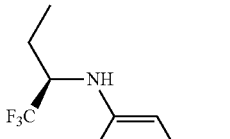

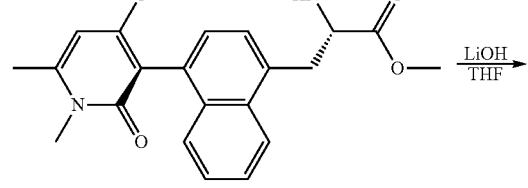

131A

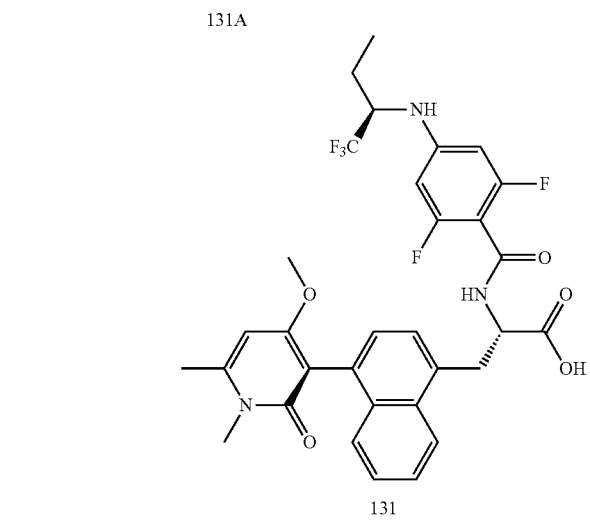

131

Preparation of (S)-2-(2,6-difluoro-4-(((R)-1,1,1-trifluorobutan-2-yl)amino)benzamido)-3-(4-(4-methoxy-1,6-dimethyl-2-oxo-1,2-dihydropyridin-3-yl)naphthalen-1-yl)propanoic acid (131)

Ester 130A was separated into its 2 diastereomeric atropisomers by supercritical fluid chromatography using 40% MeOH as co-solvent, at a flow rate of 3.0 mL/min, using an IC 4.6×100 mm 5 mic column. 131A was identified as the second eluting peak. The title compound was prepared according to the method presented for the synthesis of compound 123 starting with 131A. MS (m/z) 632.2 [M+H]$^+$. 1H NMR (400 MHz, DMSO-d6) δ 8.83 (d, J=7.6 Hz, 1H), 8.14 (d, J=8.5 Hz, 1H), 7.55 (t, J=7.7 Hz, 1H), 7.49 (d, J=8.4 Hz, 1H), 7.46-7.35 (m, 2H), 7.13 (d, J=7.2 Hz, 1H), 6.77 (d, J=9.4 Hz, 1H), 6.47 (d, J=11.7 Hz, 2H), 6.40 (s, 1H), 4.66 (td, J=8.7, 4.2 Hz, 1H), 4.31 (d, J=10.0 Hz, 1H), 3.68 (d, J=4.3 Hz, 1H), 3.63 (d, J=4.9 Hz, 3H), 3.44 (s, 3H), 3.33 (dd, J=14.5, 9.4 Hz, 1H), 2.48 (s, 3H), 1.78 (ddt, J=13.2, 9.0, 6.6 Hz, 1H), 1.53 (ddd, J=13.5, 10.2, 6.9 Hz, 1H), 0.93 (t, J=7.3 Hz, 3H).

Example 132

Preparation of methyl (S)-2-(2,6-difluoro-4-(((R)-1,1,1-trifluorobutan-2-yl)amino) benzamido)-3-(4-(1,4,6-trimethyl-2-oxo-1,2-dihydropyridin-3-yl)naphthalen-1-yl)propanoate (132A)

The title compound was prepared according to the method presented for the synthesis of compound 123A starting with 126B.

Preparation of methyl (S)-2-(2,6-difluoro-4-(((R)-1,1,1-trifluorobutan-2-yl)amino) benzamido)-3-(4-(1,4,6-trimethyl-2-oxo-1,2-dihydropyridin-3-yl)naphthalen-1-yl)propanoate Atropisomer 1 (132B)

Ester 132A was separated into its 2 diastereomeric atropisomers by supercritical fluid chromatography using 30% MeOH as co-solvent, at a flow rate of 3.0 mL/min, using an AZ-H 4.6×100 mm 5 mic column. The title compound was identified as the first eluting peak.

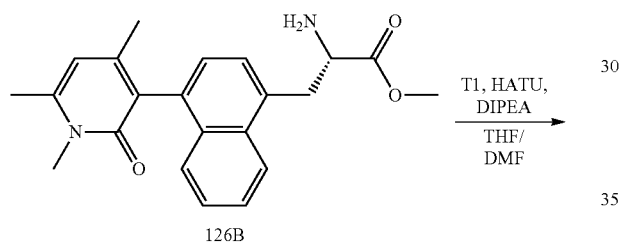

126B

T1, HATU, DIPEA
THF/DMF

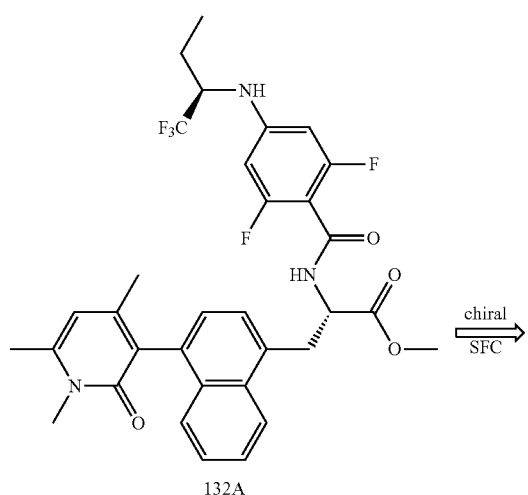

132A chiral SFC

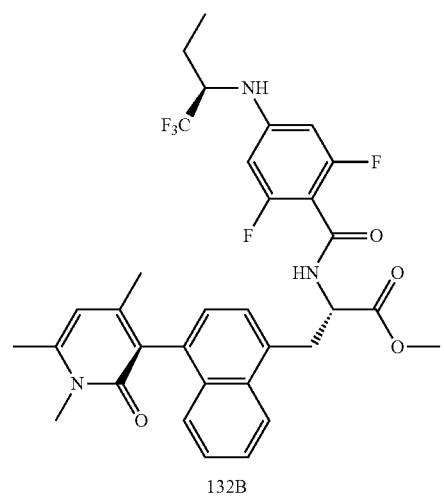

132B

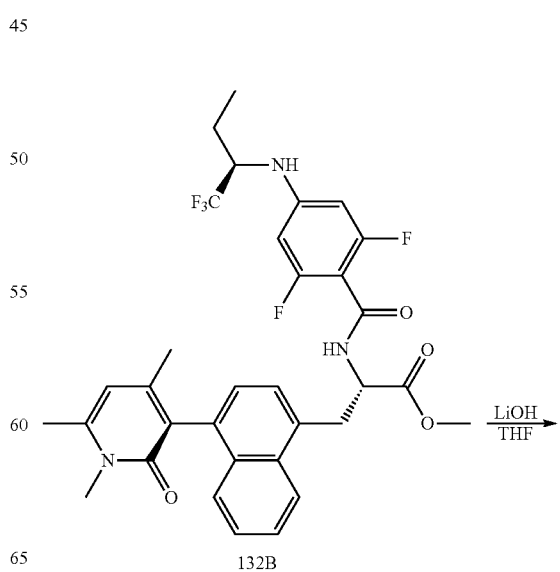

133A

132B

LiOH
THF

-continued

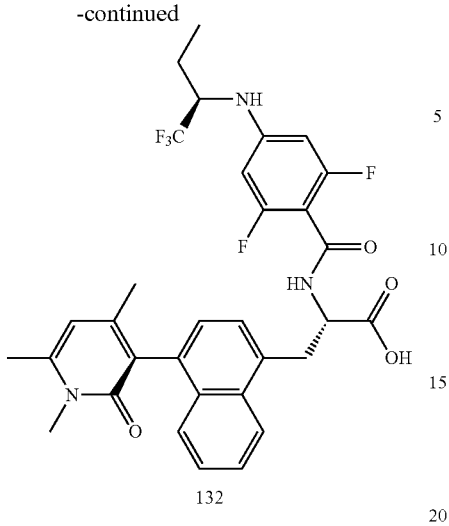

132

Preparation of (S)-2-(2,6-difluoro-4-(((R)-1,1,1-trifluorobutan-2-yl)amino)benzamido)-3-(4-(1,4,6-trimethyl-2-oxo-1,2-dihydropyridin-3-yl)naphthalen-1-yl)propanoic acid (132)

The title compound was prepared according to the method presented for the synthesis of compound 123 starting with 132B. MS (m/z) 616.3 [M+H]$^+$. 1H NMR (400 MHz, DMSO-d6) δ 8.80 (d, J=7.7 Hz, 1H), 8.17 (d, J=8.5 Hz, 1H), 7.58 (ddd, J=8.4, 5.3, 2.8 Hz, 1H), 7.50-7.38 (m, 3H), 7.13 (d, J=7.2 Hz, 1H), 6.77 (d, J=9.4 Hz, 1H), 6.46 (d, J=11.6 Hz, 2H), 6.21 (s, 1H), 4.67 (td, J=8.8, 4.7 Hz, 1H), 4.31 (d, J=10.2 Hz, 1H), 3.65 (dd, J=14.4, 4.5 Hz, 1H), 3.45 (s, 3H), 3.39 (dd, J=14.5, 9.7 Hz, 1H), 2.41 (s, 3H), 1.78 (ddd, J=13.7, 7.1, 3.1 Hz, 1H), 1.71 (s, 3H), 1.53 (ddt, J=17.8, 14.6, 7.5 Hz, 1H), 0.93 (t, J=7.3 Hz, 3H).

Example 133

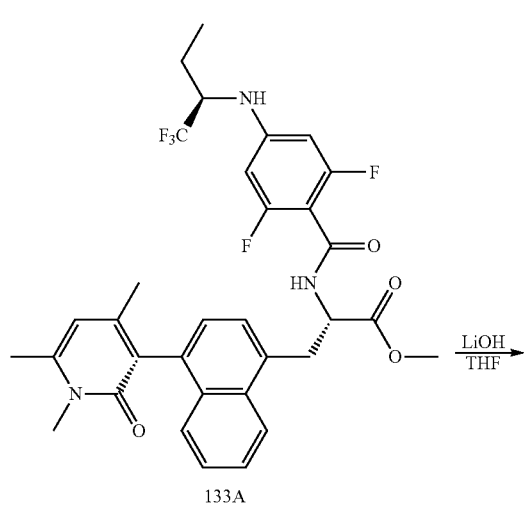

133A

-continued

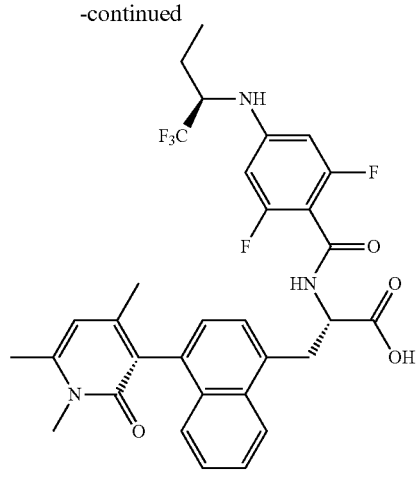

133

Preparation of (S)-2-(2,6-difluoro-4-(((R)-1,1,1-trifluorobutan-2-yl)amino)benzamido)-3-(4-(1,4,6-trimethyl-2-oxo-1,2-dihydropyridin-3-yl)naphthalen-1-yl)propanoic acid (133)

Ester 132A was separated into its 2 diastereomeric atropisomers by supercritical fluid chromatography using 30% MeOH as co-solvent, at a flow rate of 3.0 mL/min, using an AZ-H 4.6×100 mm 5 mic column. 133A was identified as the second eluting peak. The title compound was prepared according to the method presented for the synthesis of compound 123 starting with 133A. MS (m/z) 616.2 [M+H]$^+$. 1H NMR (400 MHz, DMSO-d6) δ 8.78 (d, J=8.0 Hz, 1H), 8.17 (d, J=8.5 Hz, 1H), 7.59 (ddd, J=8.3, 5.4, 2.7 Hz, 1H), 7.51-7.37 (m, 3H), 7.11 (d, J=7.1 Hz, 1H), 6.74 (d, J=9.4 Hz, 1H), 6.43 (d, J=11.6 Hz, 2H), 6.21 (s, 1H), 4.70 (td, J=9.4, 8.4, 4.1 Hz, 1H), 4.30 (d, J=9.5 Hz, 2H), 3.74 (dd, J=14.2, 4.2 Hz, 2H), 3.45 (s, 3H), 3.28 (dd, J=14.3, 10.2 Hz, 1H), 2.41 (s, 3H), 1.81-1.74 (m, 1H), 1.74 (s, 1H), 1.53 (ddd, J=13.7, 10.1, 6.9 Hz, 1H), 0.93 (t, J=7.3 Hz, 3H).

Example 134

Preparation of methyl (S)-2-(2,6-difluoro-4-(((R)-1,1,1-trifluorobutan-2-yl)amino) benzamido)-3-(4-(1,6-dimethyl-2-oxo-4-(trifluoromethyl)-1,2-dihydropyridin-3-yl)naphthalen-1-yl)propanoate (134A)

The title compound was prepared according to the method presented for the synthesis of compound 123A starting with 128B.

Preparation of methyl (S)-2-(2,6-difluoro-4-(((R)-1,1,1-trifluorobutan-2-yl)amino) benzamido)-3-(4-(1,6-dimethyl-2-oxo-4-(trifluoromethyl)-1,2-dihydropyridin-3-yl)naphthalen-1-yl)propanoatee Atropisomer 1 (134B)

Ester 134A was separated into its 2 diastereomeric atropisomers by supercritical fluid chromatography using 30% iPrOH as co-solvent, at a flow rate of 3.0 mL/min, using an OD-H 4.6×100 mm 5 mic column. The title compound was identified as the first eluting peak.

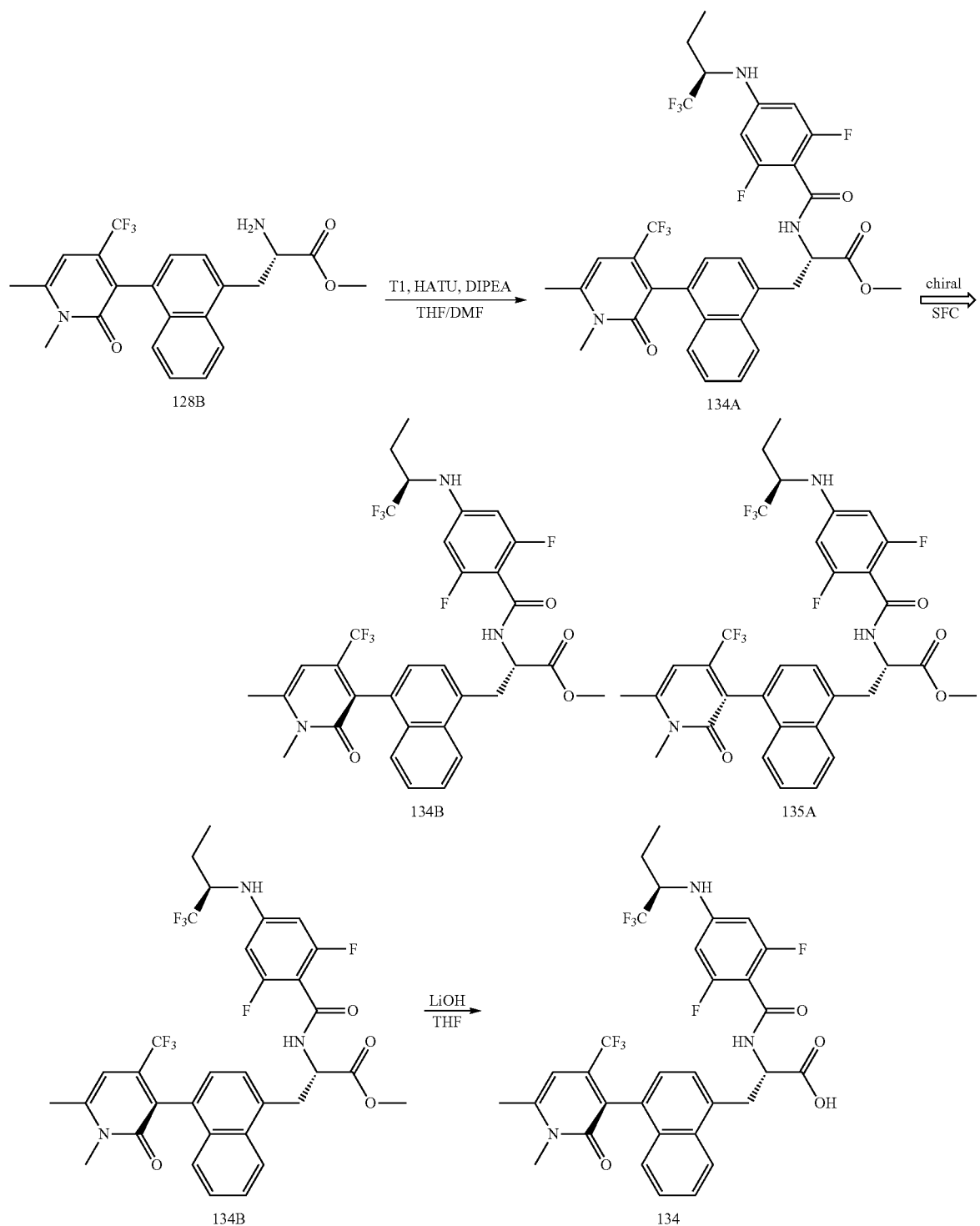

(S)-2-(2,6-difluoro-4-(((R)-1,1,1-trifluorobutan-2-yl)amino)benzamido)-3-(4-(1,6-dimethyl-2-oxo-4-(trifluoromethyl)-1,2-dihydropyridin-3-yl)naphthalen-1-yl)propanoic acid (134)

The title compound was prepared according to the method presented for the synthesis of compound 123 starting with 134B. MS (m/z) 670.2 [M+H]$^+$. 1H NMR (400 MHz, DMSO-d6) δ 8.81 (d, J=7.8 Hz, 1H), 8.15 (d, J=8.5 Hz, 1H), 7.58 (ddd, J=8.4, 6.6, 1.5 Hz, 1H), 7.50-7.31 (m, 3H), 7.12 (d, J=7.3 Hz, 1H), 6.76 (d, J=9.4 Hz, 1H), 6.59 (d, J=0.8 Hz, 1H), 6.44 (d, J=11.4 Hz, 2H), 4.65 (ddd, J=9.9, 7.8, 4.2 Hz, 1H), 4.38-4.19 (m, 1H), 3.66 (dd, J=14.6, 4.1 Hz, 1H), 3.50 (s, 3H), 3.35 (dd, J=14.7, 10.0 Hz, 1H), 2.52 (d, J=0.9 Hz, 3H), 1.75 (ddd, J=13.6, 7.3, 3.2 Hz, 1H), 1.51 (ddd, J=13.7, 10.4, 7.2 Hz, 1H), 0.91 (t, J=7.3 Hz, 3H).

Example 135

Preparation of (S)-2-(2,6-difluoro-4-(((R)-1,1,1-trifluorobutan-2-yl)amino)benzamido)-3-(4-(1,6-dimethyl-2-oxo-4-(trifluoromethyl)-1,2-dihydropyridin-3-yl)naphthalen-1-yl)propanoic acid (135)

Ester 134A was separated into its 2 diastereomeric atropisomers by supercritical fluid chromatography using 30% iPrOH as co-solvent, at a flow rate of 3.0 mL/min, using an OD-H 4.6×100 mm 5 mic column. 135A was identified as the second eluting peak. The title compound was prepared according to the method presented for the synthesis of compound 123 starting with 135A. MS (m/z) 670.2 [M+H]$^+$. 1H NMR (400 MHz, DMSO-d6) δ 8.80 (d, J=7.9 Hz, 1H), 8.23-8.05 (m, 1H), 7.58 (ddd, J=8.4, 6.6, 1.5 Hz, 1H), 7.49-7.32 (m, 3H), 7.11 (d, J=7.3 Hz, 1H), 6.74 (d, J=9.4 Hz, 1H), 6.60 (d, J=0.8 Hz, 1H), 6.42 (d, J=11.3 Hz, 2H), 4.68 (ddd, J=10.1, 7.9, 4.3 Hz, 1H), 4.31 (m, 1H), 3.68 (dd, J=14.4, 4.2 Hz, 1H), 3.49 (s, 3H), 3.31 (dd, J=14.4, 10.1 Hz, 1H), 2.56-2.50 (m, 3H), 1.75 (ddd, J=13.7, 7.3, 3.3 Hz, 1H), 1.51 (ddd, J=13.7, 10.4, 7.2 Hz, 1H), 0.91 (t, J=7.3 Hz, 3H).

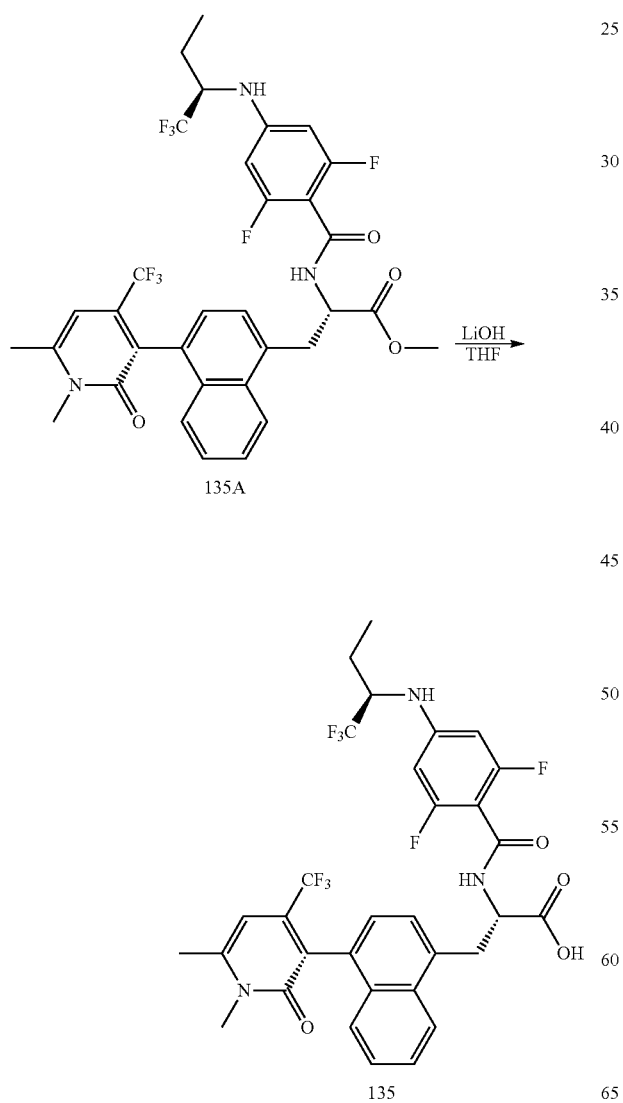

Example 136

Preparation of methyl (S)-3-(4-(5-methoxy-2-methyl-3-oxo-2,3-dihydropyridazin-4-yl)naphthalen-1-yl)-2-(tritylamino)propanoate (136A)

The title compound was prepared according to the method described in Example 129 starting with N6 and 4-chloro-5-methoxy-2-methylpyridazin-3(2H)-one.

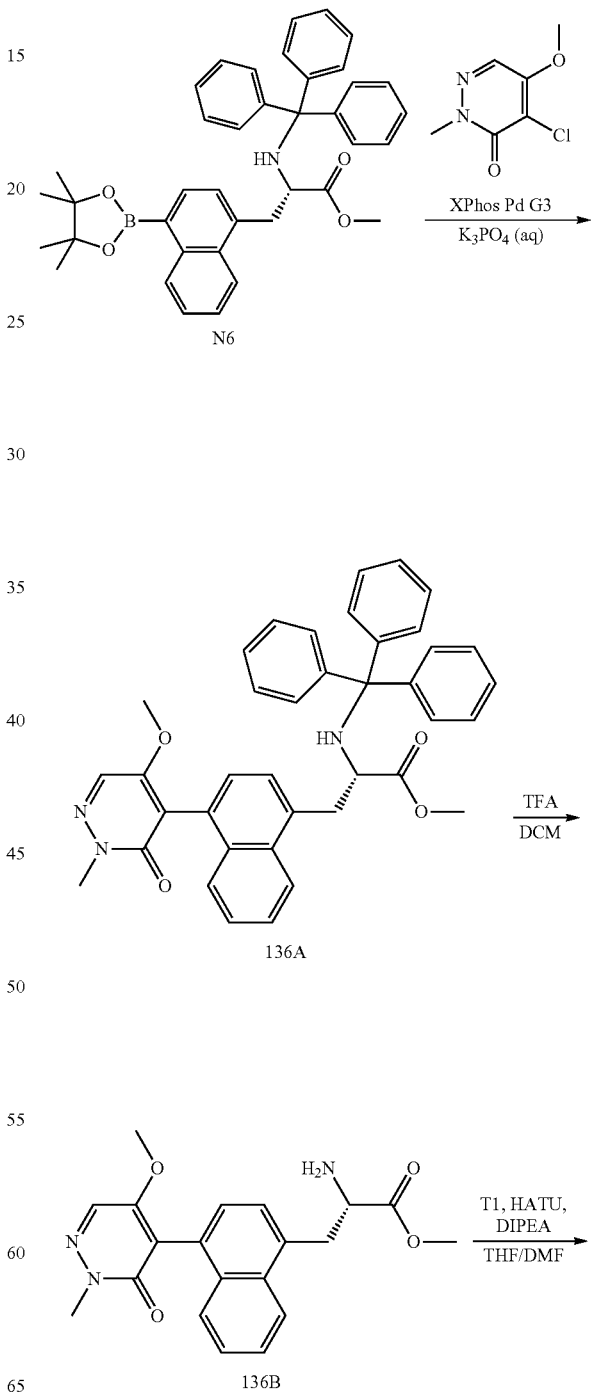

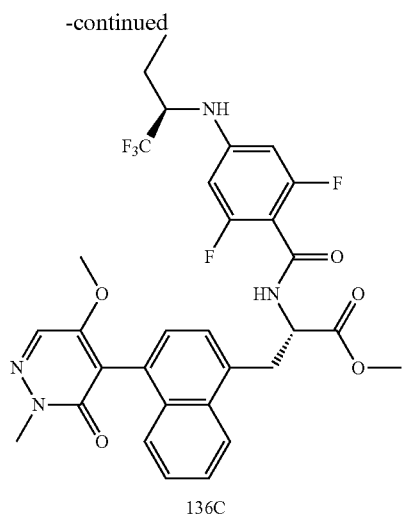

136C

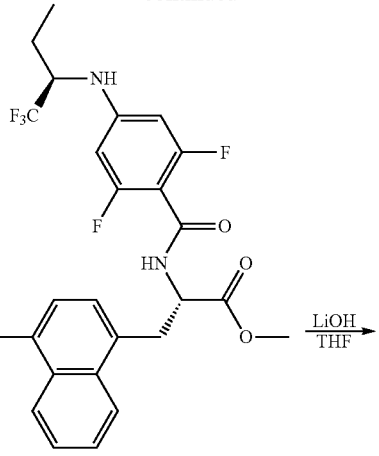

136D

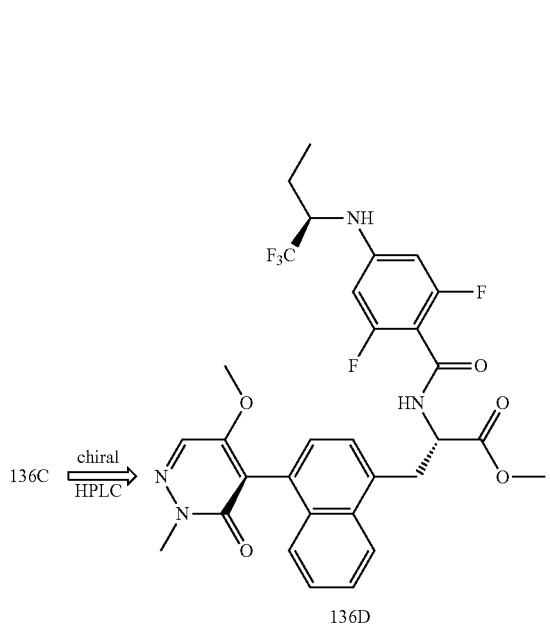

136C →(chiral HPLC) 136D

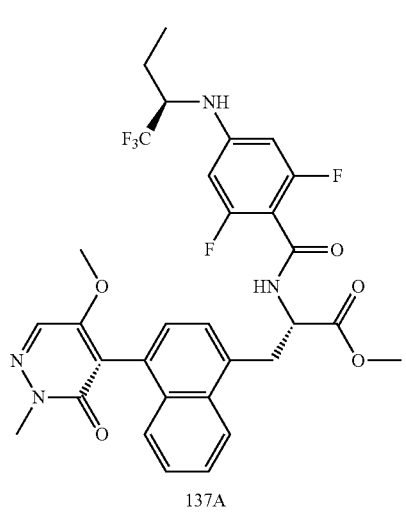

137A

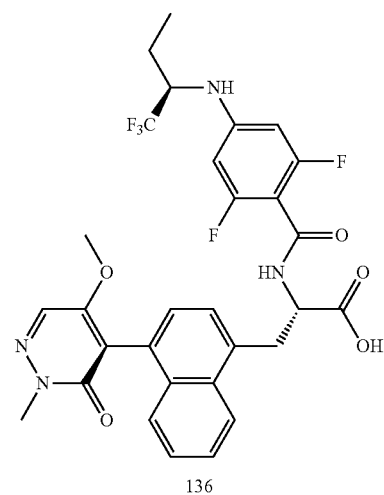

136

Preparation of methyl (S)-3-(4-(5-methoxy-2-methyl-3-oxo-2,3-dihydropyridazin-4-yl)naphthalen-1-yl)-2-(tritylamino)propanoate (136B)

The title compound was prepared according to the method described in Example 122 starting with 136A.

Preparation of methyl (S)-2-(2,6-difluoro-4-(((R)-1,1,1-trifluorobutan-2-yl)amino) benzamido)-3-(4-(5-methoxy-2-methyl-3-oxo-2,3-dihydropyridazin-4-yl)naphthalen-1-yl)propanoate (136C)

The title compound was prepared according to the method presented for the synthesis of compound 123A starting with 136B.

Preparation of methyl (S)-2-(2,6-difluoro-4-(((R)-1,1,1-trifluorobutan-2-yl)amino)benzamido)-3-(4-(5-methoxy-2-methyl-3-oxo-2,3-dihydropyridazin-4-yl)naphthalen-1-yl)propanoate Atropisomer 1 (136D)

Ester 136C was separated into its 2 diastereomeric atropisomers by supercritical fluid chromatography using 30% EtOH/TFA as co-solvent, at a flow rate of 3.0 mL/min, using an IG-H-5 μm-4.6×100 mm column. The title compound was identified as the first eluting peak.

(S)-2-(2,6-difluoro-4-(((R)-1,1,1-trifluorobutan-2-yl)amino)benzamido)-3-(4-(5-methoxy-2-methyl-3-oxo-2,3-dihydropyridazin-4-yl)naphthalen-1-yl)propanoic acid (136)

The title compound was prepared according to the method presented for the synthesis of compound 123 starting with 136D. MS (m/z) 619.2 [M+H]+. 1H NMR (400 MHz, DMSO-d6) δ 12.89 (s, 1H), 8.83 (dd, J=8.0, 3.7 Hz, 1H), 8.29 (s, 1H), 8.18 (d, J=8.5 Hz, 1H), 7.60 (t, 1H), 7.55-7.41 (m, 3H), 7.24 (d, J=7.1 Hz, 1H), 6.77 (d, J=9.3 Hz, 1H), 6.46 (d, J=11.8 Hz, 2H), 4.72-4.60 (m, 1H), 4.38-4.24 (m, 1H), 3.80 (s, 3H), 3.74-3.68 (m, 3H), 3.43-3.28 (m, 1H), 1.85-1.71 (m, 1H), 1.62-1.45 (m, 1H), 0.93 (t, J=7.3 Hz, 3H).

Example 137 an IG-H-5 μm-4.6×100 mm column. 137A was identified as the second eluting peak. The title compound was prepared according to the method presented for the synthesis of compound 123 starting with 137A. MS (m/z) 619.2 [M+H]+. 1H NMR (400 MHz, DMSO-d6) δ 8.87-8.78 (m, 1H), 8.29 (s, 1H), 8.18 (d, J=8.6 Hz, 1H), 7.60 (t, J=7.7 Hz, 1H), 7.54-7.41 (m, 3H), 7.24 (d, J=7.3 Hz, 1H), 6.77 (d, J=9.2 Hz, 1H), 6.46 (d, J=11.9 Hz, 2H), 4.73-4.63 (m, 1H), 4.34-4.27 (m, 1H), 3.80 (s, 3H), 3.72-3.69 (m, 4H), 3.35 (q, J=12.9 Hz, 1H), 1.83-1.73 (m, 1H), 1.60-1.47 (m, 1H), 0.93 (t, J=7.4 Hz, 3H).

Example 138

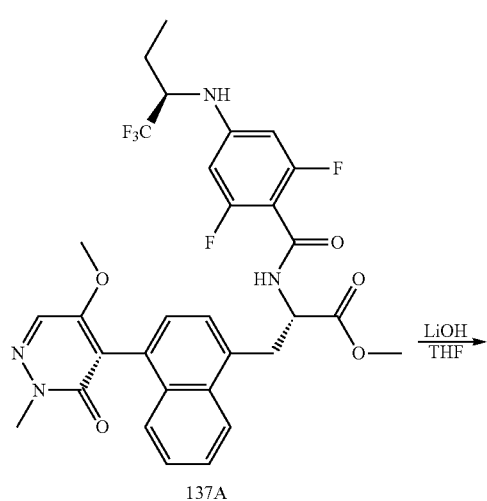

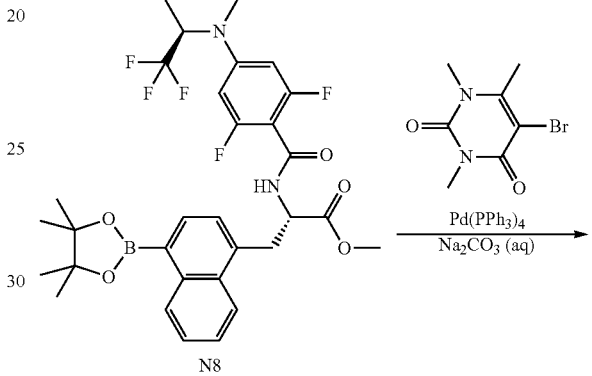

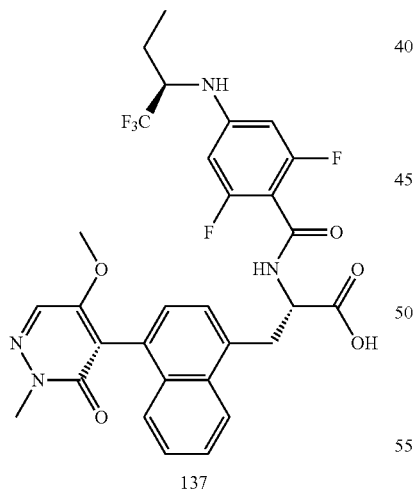

Preparation of (S)-2-(2,6-difluoro-4-(((R)-1,1,1-trifluorobutan-2-yl)amino)benzamido)-3-(4-(5-methoxy-2-methyl-3-oxo-2,3-dihydropyridazin-4-yl)naphthalen-1-yl)propanoic acid (137)

Ester 136C was separated into its 2 diastereomeric atropisomers by supercritical fluid chromatography using 30% EtOH/TFA as co-solvent, at a flow rate of 3.0 mL/min, using

Example 139

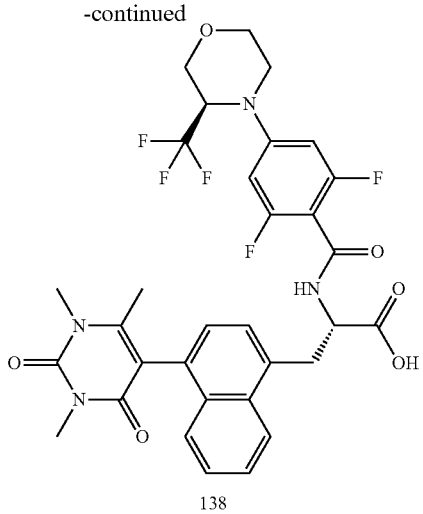

138

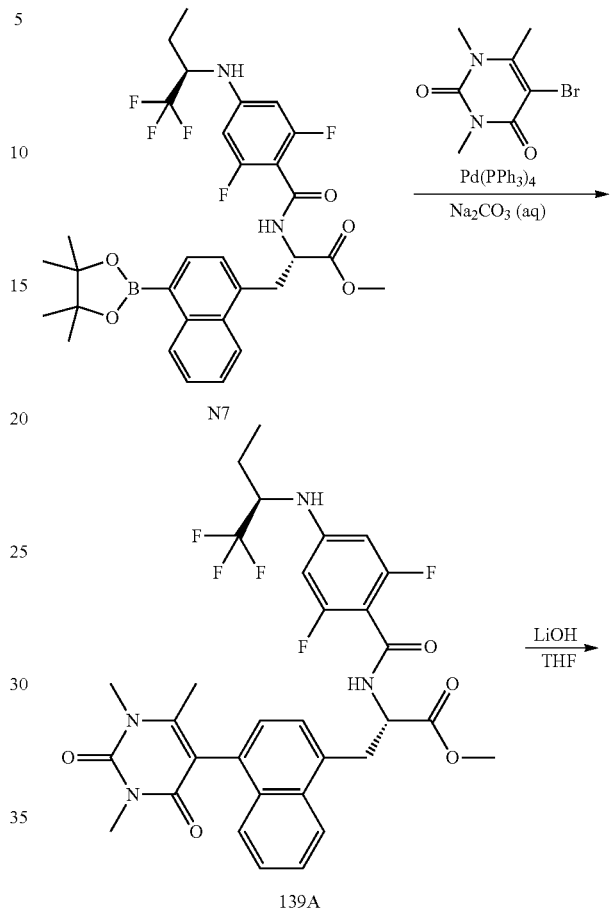

Preparation of methyl (S)-2-(2,6-difluoro-4-((R)-3-(trifluoromethyl)morpholino) benzamido)-3-(4-(1,3,6-trimethyl-2,4-dioxo-1,2,3,4-tetrahydropyrimidin-5-yl)naphthalen-1-yl)propanoate (138A)

To a microwave vial was added N8 (186.0 mg, 0.287 mmol), 5-bromo-1,3,6-trimethylpyrimidine-2,4(1H,3H)-dione (80.2 mg, 0.344 mmol), Pd(PPh$_3$)$_4$(33.2 mg, 0.029 mmol), and aq Na$_2$CO$_3$ (0.43 mL, 2M) in DME (3.0 mL). The reaction mixture was allowed to stir at 130° C. for 30 min. The reaction mixture was then filtered over a pad of Celite, washing with MeOH. Volatiles were removed under reduced pressure and the crude product was used as is, without further purification.

Preparation of (S)-2-(2,6-difluoro-4-((R)-3-(trifluoromethyl)morpholino)benzamido)-3-(4-(1,3,6-trimethyl-2,4-dioxo-1,2,3,4-tetrahydropyrimidin-5-yl)naphthalen-1-yl)propanoic acid (138)

To a stirring solution of the crude product 138A in THF (3.0 mL) was added an aqueous 1.0 M solution of LiOH (0.86 mL, 0.86 mmol). The reaction mixture was allowed to stir for 1 hr before concentrating under reduced pressure. The material was then purified via reverse phase HPLC to afford the title compound. MS (m/z) 661.2 [M+H]$^+$. 1H NMR (400 MHz, DMSO-d6) δ 8.99-8.89 (m, 1H), 8.16 (dd, J=8.5, 3.1 Hz, 1H), 7.70 (dd, J=8.3, 2.9 Hz, 1H), 7.64-7.54 (m, 1H), 7.46 (t, J=7.2 Hz, 2H), 7.18 (dd, J=10.7, 7.2 Hz, 1H), 6.74 (t, J=11.4 Hz, 2H), 4.96-4.82 (m, 1H), 4.77-4.64 (m, 1H), 4.14 (d, J=12.7 Hz, 1H), 3.93 (dd, J=11.4, 3.9 Hz, 2H), 3.76-3.67 (m, 1H), 3.69-3.59 (m, 1H), 3.53 (t, J=11.7 Hz, 1H), 3.47-3.32 (m, 4H), 3.22 (s, 4H), 1.90 (d, J=7.1 Hz, 3H).

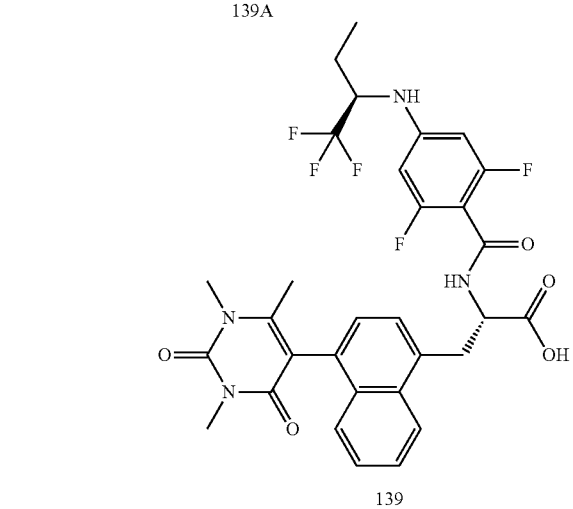

139

Preparation of methyl (S)-2-(2,6-difluoro-4-(((R)-1,1,1-trifluorobutan-2-yl)amino) benzamido)-3-(4-(1,3,6-trimethyl-2,4-dioxo-1,2,3,4-tetrahydropyrimidin-5-yl)naphthalen-1-yl)propanoate (139A)

The title compound was prepared according to the method described in Example 145 starting with N-7 and 5-bromo-1,3,6-trimethylpyrimidine-2,4(1H,3H)-dione.

Preparation of (S)-2-(2,6-difluoro-4-(((R)-1,1,1-trifluorobutan-2-yl)amino)benzamido)-3-(4-(1,3,6-trimethyl-2,4-dioxo-1,2,3,4-tetrahydropyrimidin-5-yl)naphthalen-1-yl)propanoic acid (139)

The title compound was prepared according to the method presented for the synthesis of compound 138 starting with 139A. MS (m/z) 633.2 [M+H]⁺. 1H NMR (400 MHz, DMSO-d6) δ 8.78 (q, J=10.1, 9.4 Hz, 1H), 8.18-8.12 (m, 1H), 7.70 (dd, J=8.5, 3.2 Hz, 1H), 7.65-7.51 (m, 2H), 7.48-7.42 (m, 1H), 7.18 (dd, J=9.7, 7.2 Hz, 1H), 6.75 (t, J=9.3 Hz, 1H), 6.42 (t, J=11.2 Hz, 2H), 4.75-4.59 (m, 1H), 4.29 (s, 1H), 3.74 (dd, J=14.3, 3.9 Hz, 1H), 3.46-3.32 (m, 3H), 3.26 (dd, J=14.4, 4.0 Hz, 1H), 3.22 (d, J=1.6 Hz, 3H), 1.90 (d, J=6.5 Hz, 3H), 1.74 (d, J=6.9 Hz, 1H), 1.59-1.42 (m, 1H), 0.91 (t, J=7.3 Hz, 3H).

Example 140

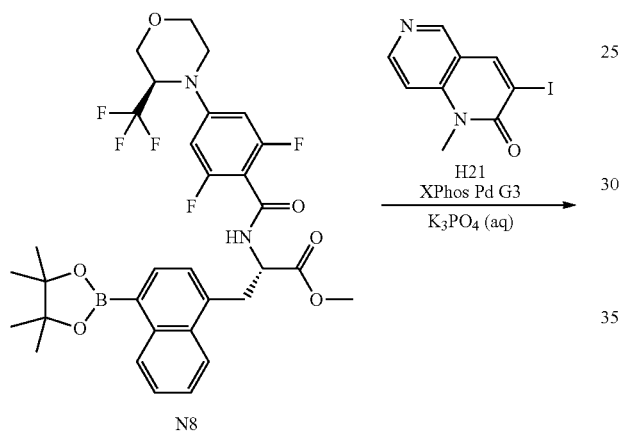

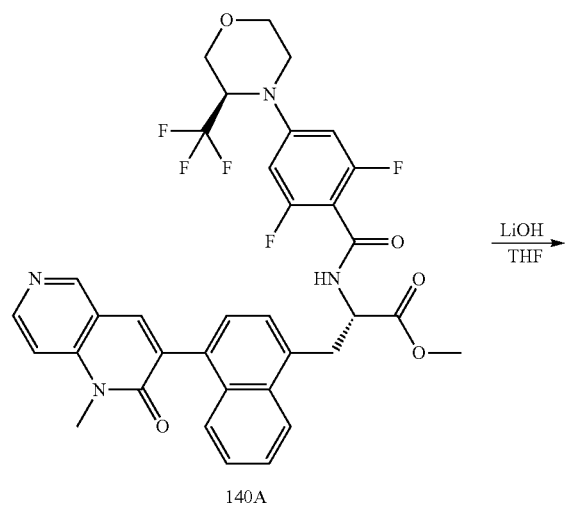

140A

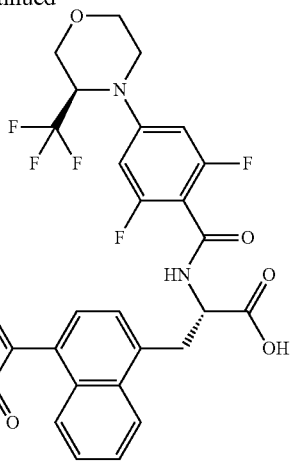

140

Preparation of methyl (S)-2-(2,6-difluoro-4-((R)-3-(trifluoromethyl)morpholino) benzamido)-3-(4-(1-methyl-2-oxo-1,2-dihydro-1,6-naphthyridin-3-yl) naphthalen-1-yl)propanoate (140A)

To a solution of N8 (394.0 mg, 0.273 mmol) and 3-iodo-1-methyl-1,6-naphthyridin-2(1H)-one (H21, 93.9 mg, 0.328 mmol) in 1,4-dioxane (4.0 mL) was added XPhos Pd G3 (11.6 mg, 0.014 mmol) and a 1.0 M aqueous solution of K₃PO₄ (0.96 mL, 0.96 mmol). The reaction mixture was degassed with N₂ before heating at 90° C. for 1 hr. Volatiles were then removed under reduced pressure and the crude product was purified by silica gel chromatography eluting with EtOAc in hexanes (0-100%) followed by MeOH in DCM (0-50%).

Preparation of (S)-2-(2,6-difluoro-4-((R)-3-(trifluoromethyl)morpholino)benzamido)-3-(4-(1-methyl-2-oxo-1,2-dihydro-1,6-naphthyridin-3-yl)naphthalen-1-yl)propanoic acid (140)

To a stirring solution of the 140A (58.0 mg, 0.060 mmol) in THF (1.0 mL) was added an aqueous 1.0 M solution of LiOH (0.24 mL, 0.24 mmol). The reaction mixture was allowed to stir for 1 hr before concentrating under reduced pressure. The material was then purified via reverse phase HPLC to afford the title compound. MS (m/z) 667.2 [M+H]⁺. 1H NMR (400 MHz, DMSO-d6) δ 9.12 (s, 1H), 8.99 (d, J=8.0 Hz, 1H), 8.77 (s, 1H), 8.23 (d, J=8.5 Hz, 1H), 8.18 (s, 1H), 7.83 (d, J=6.3 Hz, 1H), 7.71 (d, J=8.5 Hz, 1H), 7.65 (t, J=7.7 Hz, 1H), 7.56-7.45 (m, 2H), 7.39 (d, J=7.2 Hz, 1H), 6.78 (d, J=11.9 Hz, 2H), 4.97-4.85 (m, 1H), 4.71 (ddd, J=11.8, 8.7, 4.0 Hz, 1H), 4.17 (d, J=12.7 Hz, 1H), 3.96 (dd, J=11.4, 3.6 Hz, 1H), 3.73 (s, 5H), 3.63 (m, 2H), 3.25 (t, J=12.3 Hz, 2H).

Example 141

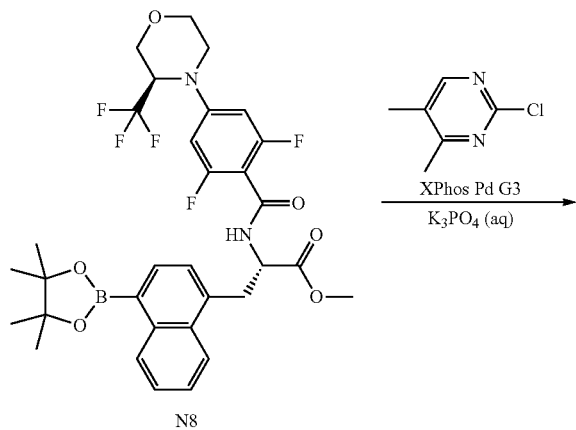

Preparation of methyl (S)-2-(2,6-difluoro-4-((R)-3-(trifluoromethyl)morpholino) benzamido)-3-(4-(4,5-dimethylpyrimidin-2-yl)naphthalen-1-yl)propanoate (141A)

The title compound was prepared according to the method described in Example 148 for the synthesis of 140A starting with N8 and 2-chloro-4,5-dimethylpyrimidine.

Preparation of (S)-2-(2,6-difluoro-4-((R)-3-(trifluoromethyl)morpholino)benzamido)-3-(4-(4,5-dimethylpyrimidin-2-yl)naphthalen-1-yl)propanoic acid (141)

The title compound was prepared according to the method described in Example 148 for the synthesis of 140 starting with 141A. MS (m/z) 615.2 [M+H]$^+$. 1H NMR (400 MHz, DMSO-d6) δ 8.95 (d, J=8.0 Hz, 1H), 8.68 (s, 1H), 8.59 (d, J=8.6 Hz, 1H), 8.24 (d, J=8.5 Hz, 1H), 7.83 (d, J=7.3 Hz, 1H), 7.65 (t, J=7.7 Hz, 1H), 7.56 (t, J=7.0 Hz, 2H), 6.77 (d, J=11.8 Hz, 2H), 4.90 (dt, J=11.4, 8.0 Hz, 1H), 4.71 (td, J=9.1, 4.1 Hz, 1H), 4.16 (d, J=12.8 Hz, 1H), 3.95 (dd, J=11.6, 3.7 Hz, 1H), 3.80-3.70 (m, 2H), 3.39 (d, J=10.3 Hz, 2H), 3.20 (d, J=25.9 Hz, 2H), 2.54 (s, 3H), 2.33 (s, 3H).

Example 142

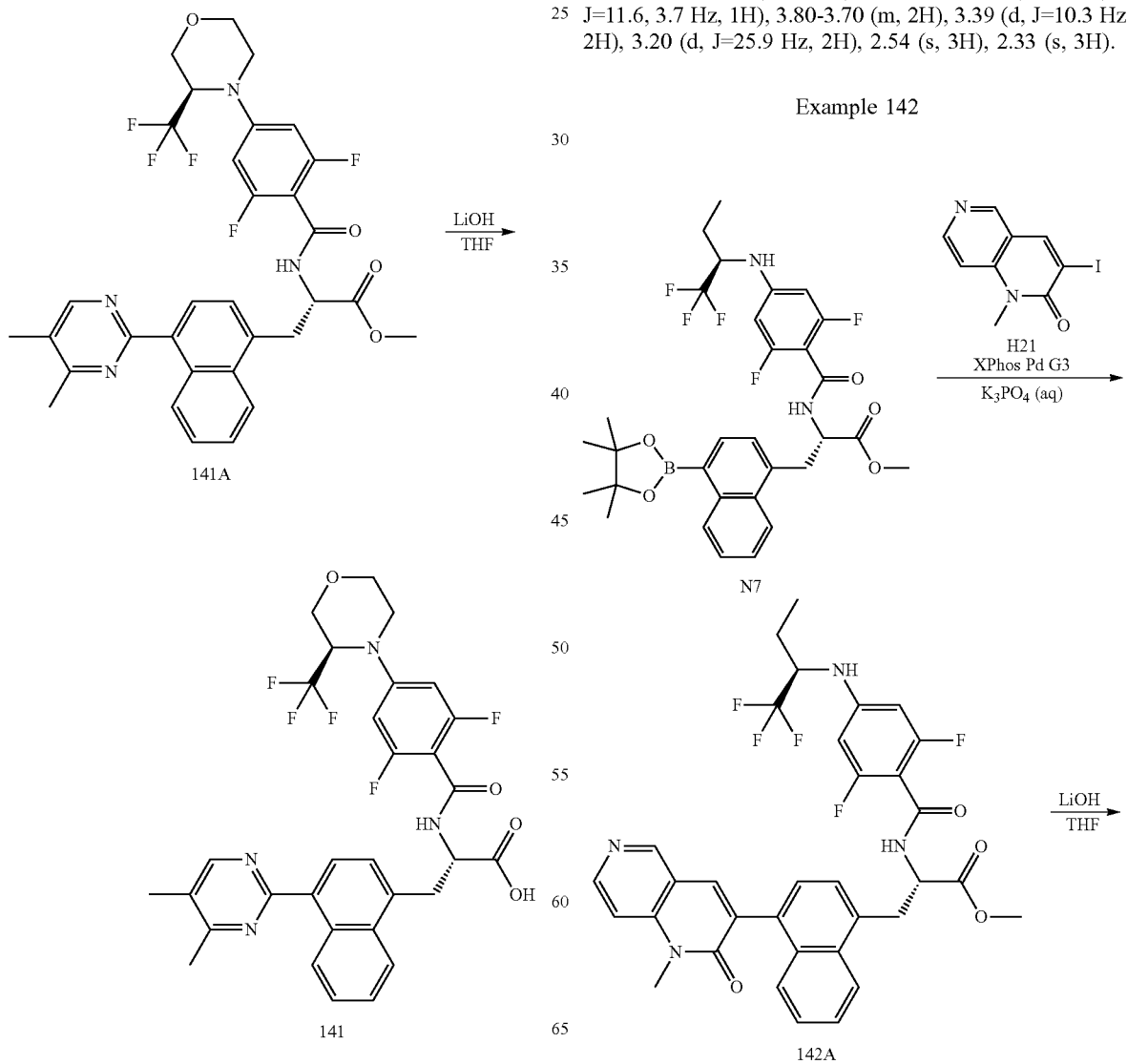

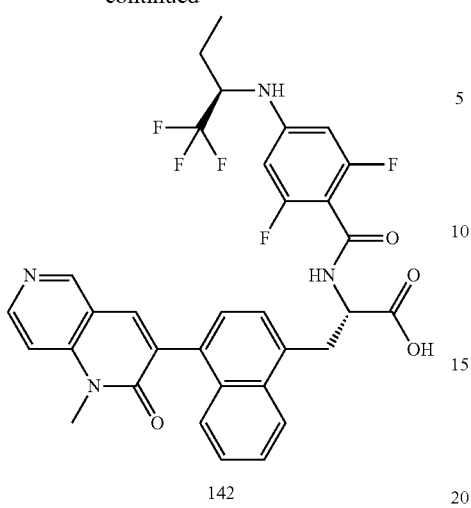

142

Preparation of methyl (S)-2-(2,6-difluoro-4-((R)-3-(trifluoromethyl)morpholino) benzamido)-3-(4-(1-methyl-2-oxo-1,2-dihydro-1,6-naphthyridin-3-yl) naphthalen-1-yl)propanoate (142A)

The title compound was prepared according to the method described in Example 148 for the synthesis of 140A starting with N7 and 3-iodo-1-methyl-1,6-naphthyridin-2(1H)-one (H21).

Preparation of (S)-2-(2,6-difluoro-4-((R)-3-(trifluoromethyl)morpholino)benzamido)-3-(4-(1-methyl-2-oxo-1,2-dihydro-1,6-naphthyridin-3-yl)naphthalen-1-yl)propanoic acid (142)

The title compound was prepared according to the method described in Example 148 for the synthesis of 140 starting with 142A. MS (m/z) 639.2 [M+H]⁺. 1H NMR (400 MHz, DMSO-d6) δ 9.13 (s, 1H), 8.83 (d, J=7.9 Hz, 1H), 8.77 (d, J=6.4 Hz, 1H), 8.26-8.14 (m, 2H), 7.84 (d, J=6.6 Hz, 1H), 7.71 (d, J=8.4 Hz, 1H), 7.65 (t, J=7.7 Hz, 1H), 7.57-7.46 (m, 2H), 7.39 (d, J=7.2 Hz, 1H), 6.78 (d, J=9.3 Hz, 1H), 6.47 (d, J=11.8 Hz, 2H), 4.68 (t, J=9.2 Hz, 1H), 4.31 (d, J=10.7 Hz, 1H), 3.79 (m, 1H), 3.73 (d, J=1.4 Hz, 3H), 3.36 (m, 1H), 1.77 (d, J=10.5 Hz, 1H), 1.54 (dt, J=19.8, 9.3 Hz, 1H), 0.93 (t, J=7.3 Hz, 3H).

Example 143

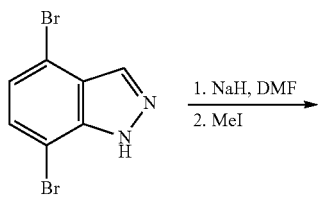

1. NaH, DMF
2. MeI

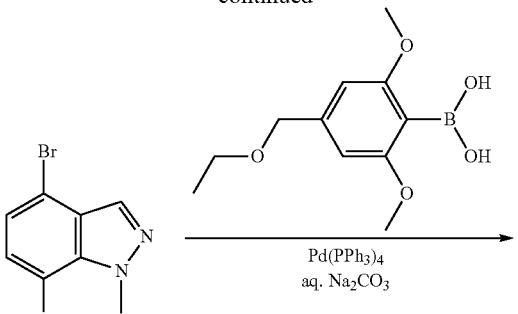

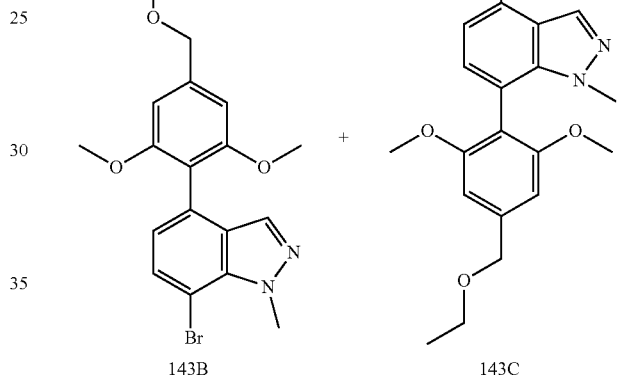

143B, 143C

Synthesis of 4,7-dibromo-1-methyl-1H-indazole (143A)

To a solution containing 4,7-dibromo-1H-indazole (600 mg, 2.29 mmol) in DMF (16 mL), sodium hydride was added in one portion at 0° C., and stir for 30 min. Then iodomethane (0.21 mL, 3.44 mmol) was added and the reaction mixture was stirred at RT for 30 min. Quench with water and extract with EtOAc (3×). Organic layers were combined, dried over sodium sulfate and filtered. The filtrate was concentrated under reduced pressure to give the crude product, which was purified on silica gel eluting with EtOAc in hexanes (0-30%-60%) to give the title compound.

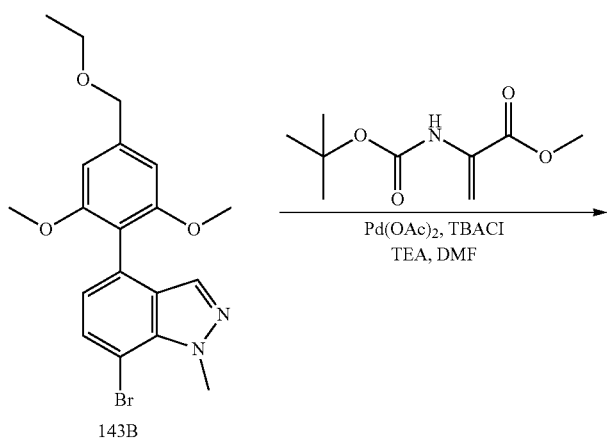
143B
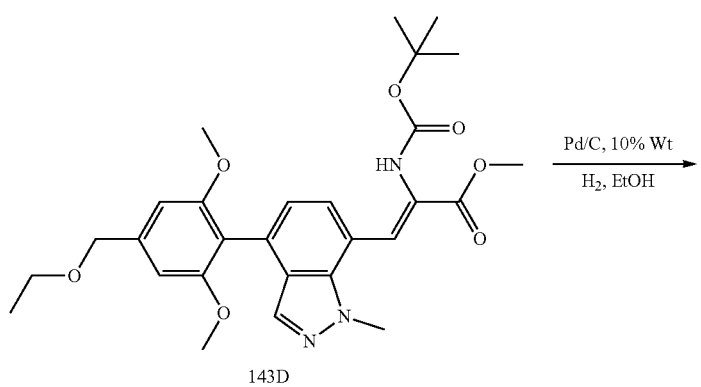
143D
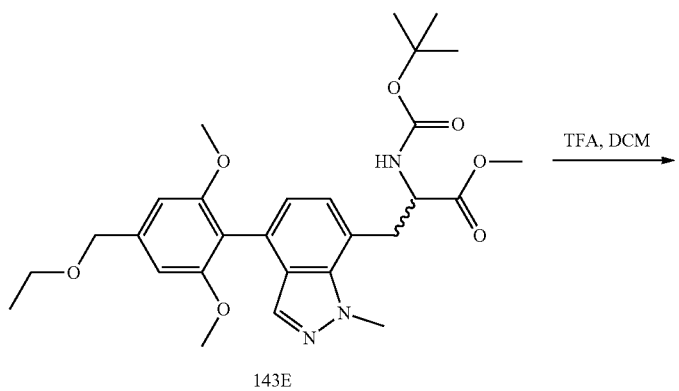
143E
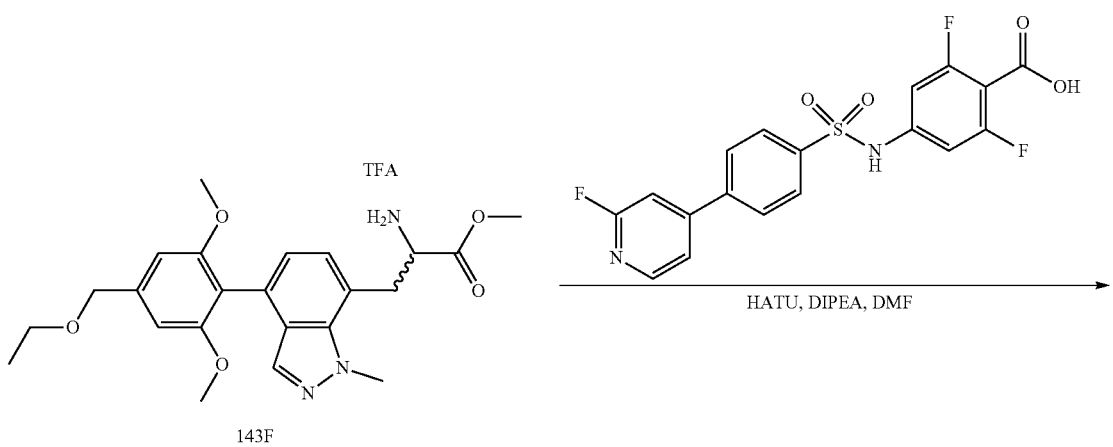
143F

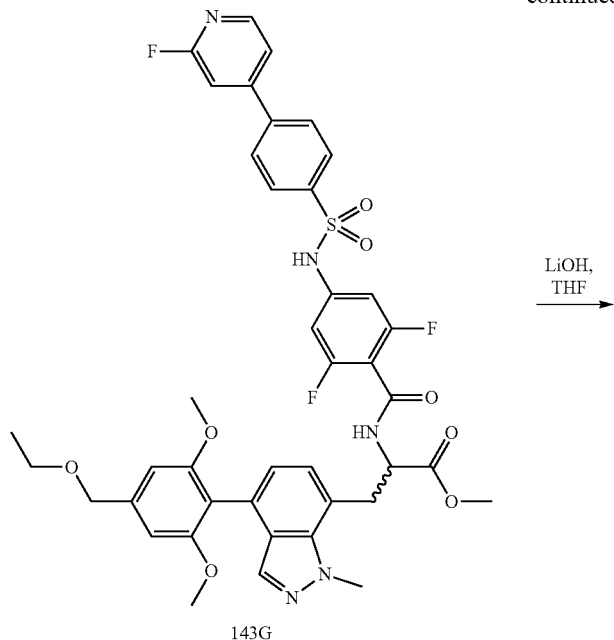

143G

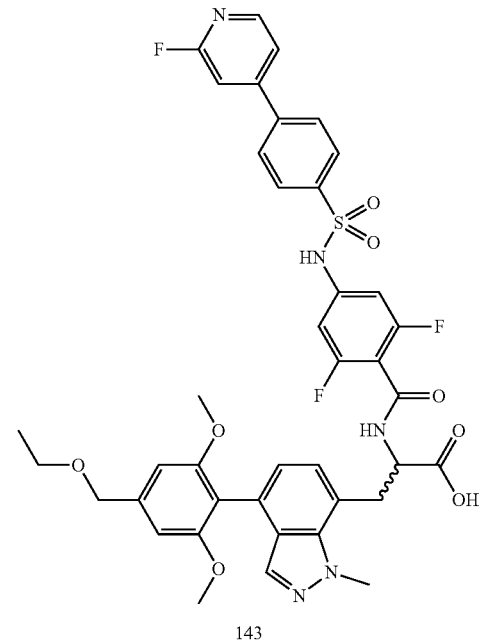

143

LiOH, THF

Synthesis of 7-bromo-4-(4-(ethoxymethyl)-2,6-dimethoxyphenyl)-1-methyl-1H-indazole (143B)

To a microwave vial was added 60A (890 mg, 3.07 mmol), (4-(ethoxymethyl)-2,6-dimethoxyphenyl)boronic acid (774 mg, 3.22 mmol), Pd(PPh$_3$)$_4$(355 mg, 0.31 mmol), and aq Na$_2$CO$_3$ (4.6 mL, 2M) in DME (30 mL). The reaction mixture was allowed to stir at 135° C. for 30 min. EtOAc and water was added to the reaction mixture. The organic layer was washed with brine, dried over anhydrous Na$_2$SO$_4$, and concentrated under reduced pressure. The material was purified by silica gel chromatography using 0-20%-40%-60% EtOAc in hexanes to afford the title compounds 60B as peak 1 and 60C as peak 2.

Synthesis of methyl (Z)-2-((tert-butoxycarbonyl)amino)-3-(4-(4-(ethoxymethyl)-2,6-dimethoxyphenyl)-1-methyl-1H-indazol-7-yl)acrylate (143D)

To a sealed tube was added 60B (127 mg, 0.31 mmol) and DMF (3 mL). This solution was degassed with nitrogen for 30 min. To this, methyl 2-((tert-butoxycarbonyl)amino)acrylate (189 mg, 0.94 mmol), tetrabutylammonium chloride (TBACl, 105 mg, 0.38 mmol), TEA (0.05 mL, 0.36 mmol) and palladium acetate (35 mg, 0.16 mmol) were added. The tube was sealed and heated to 90° C. for 6 h. Reaction mixture was cooled to RT and purified by silica gel chromatography using 0-100% EtOAc in hexanes to afford the title compound.

Synthesis of methyl 2-((tert-butoxycarbonyl)amino)-3-(4-(4-(ethoxymethyl)-2,6-dimethoxyphenyl)-1-methyl-1H-indazol-7-yl)propanoate (143E)

To a Parr shaker bottle was added 60D (94 mg, 0.18 mmol) and EtOH (30 mL). Pd on carbon (10% wt, 94 mg, 0.89 mmol) was added and the bottle was put on Parr shaker, shake under 45 psi Hydrogen gas for 12 h. Reaction mixture was filtered through Celite and concentrated to give the title compound that was used without further purification.

Synthesis of methyl 2-amino-3-(4-(4-(ethoxymethyl)-2,6-dimethoxyphenyl)-1-methyl-1H-indazol-7-yl)propanoate TFA salt (143F)

To a solution of 60E (94 mg, 0.18 mmol) in DCM (2 mL), TFA (0.34 mL, 4.5 mmol) was added and the reaction mixture was stirred at RT for 2 h. The reaction mixture was concentrated to give the title compound that was used without further purification.

Synthesis of methyl 2-(2,6-difluoro-4-((4-(2-fluoropyridin-4-yl)phenyl)sulfonamido) benzamido)-3-(4-(4-(ethoxymethyl)-2,6-dimethoxyphenyl)-1-methyl-1H-indazol-7-yl)propanoate (143G)

To a stirred solution of 60E (94 mg, 0.18 mmol) in DMF (1 mL) was added 2,6-difluoro-4-((4-(2-fluoropyridin-4-yl)phenyl)sulfonamido)benzoic acid (80 mg, 0.19 mmol), HATU (75 mg, 0.19 mmol) and DIPEA (0.09 mL, 0.53 mmol). The reaction mixture was allowed to stir for 2 hr at RT. The reaction mixture was concentrated under reduced pressure and purified by silica gel chromatography using 0-100% EtOAc in hexanes to afford the title compound.

Synthesis of 2-(2,6-difluoro-4-((4-(2-fluoropyridin-4-yl)phenyl)sulfonamido) benzamido)-3-(4-(4-(ethoxymethyl)-2,6-dimethoxyphenyl)-1-methyl-1H-indazol-7-yl)propanoic acid (143)

To a stirred solution of 60G (145 mg, 0.18 mmol) in THF (2 mL) was added LiOH (0.53 mL, 0.53 mmol). The reaction mixture was allowed to stir for 1 hour then concentrated under reduced pressure. The material was purified via reverse phase HPLC to afford the title compound. MS (m/z) 804.5 [M+H]+. 1H NMR (400 MHz, DMSO-d6) δ 11.22 (s, 1H), 9.15 (d, J=8.0 Hz, 1H), 8.33 (d, J=5.3 Hz, 1H), 8.12-8.03 (m, 2H), 8.02-7.93 (m, 2H), 7.72 (dt, J=5.3, 1.8 Hz, 1H), 7.59 (d, J=1.6 Hz, 1H), 7.40 (s, 1H), 7.14 (d, J=7.4 Hz, 1H), 6.79 (dd, J=14.8, 8.2 Hz, 3H), 6.70 (s, 2H), 4.66 (ddd, J=10.2, 8.0, 4.3 Hz, 1H), 4.49 (s, 2H), 4.26 (s, 3H), 3.75 (dd, J=15.0, 4.3 Hz, 1H), 3.57 (d, J=1.2 Hz, 6H), 3.53 (t, J=7.0 Hz, 2H), 3.29-3.21 (m, 1H), 1.19 (t, J=7.0 Hz, 3H).

Examples 144 and 145

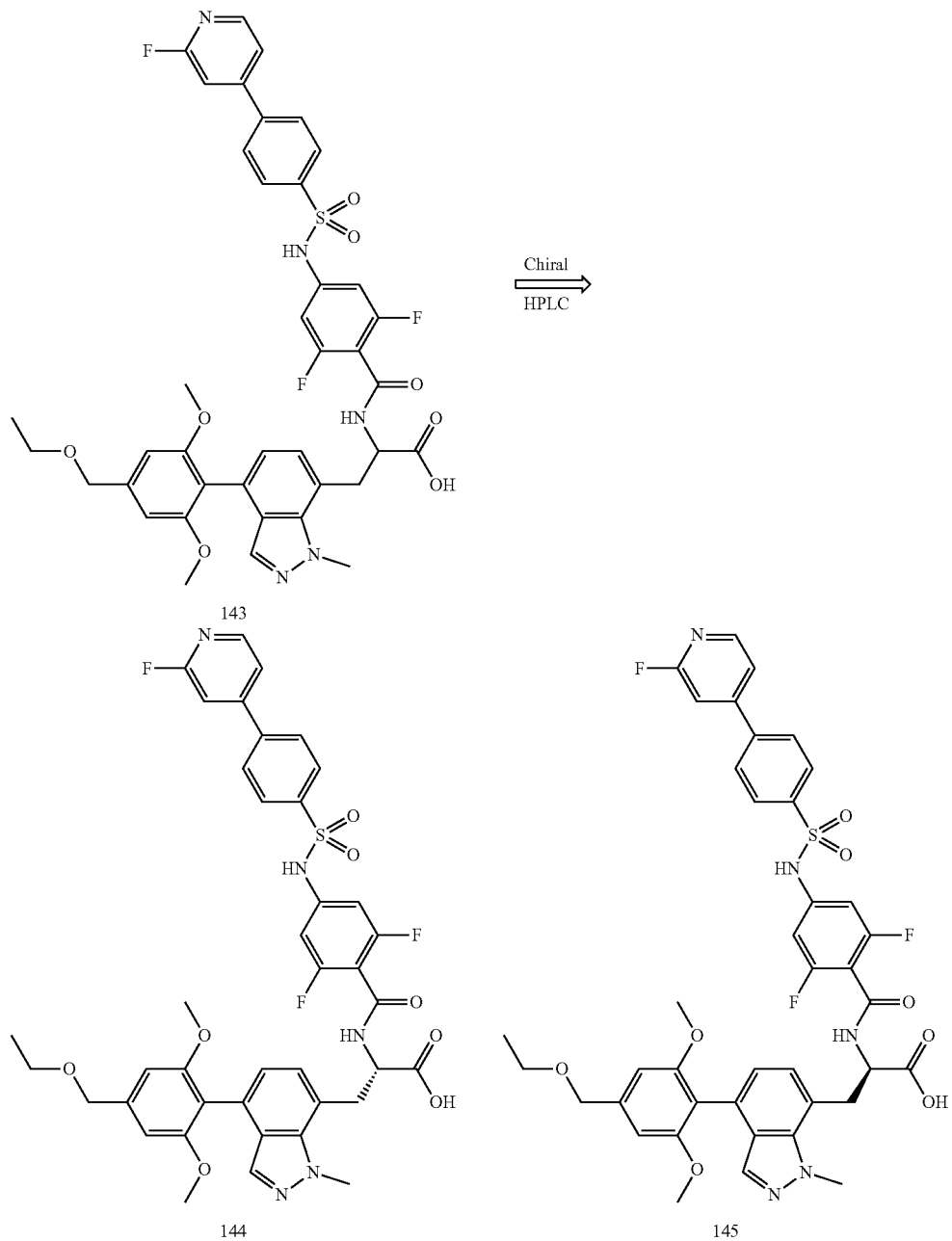

Preparation of (R)-2-(2,6-difluoro-4-((4-(2-fluoropyridin-4-yl)phenyl)sulfonamido) benzamido)-3-(4-(4-(ethoxymethyl)-2,6-dimethoxyphenyl)-1-methyl-1H-indazol-7-yl)propanoic acid (145)

143 was separated into its 2 enantiomers by supercritical fluid chromatography using 30% MeOH co-solvent, at a flow rate of 55 mL/min, using an AD-H 5 μm 21×250 mm column. The title compound was identified as the second eluting peak. MS (m/z) 804.5 [M+H]+.

Example 146

Synthesis of methyl (Z)-2-((tert-butoxycarbonyl)amino)-3-(7-(4-(ethoxymethyl)-2,6-dimethoxyphenyl)-1-methyl-1H-indazol-4-yl)acrylate (146A)

The title compound was prepared according to the method presented for the synthesis of compound 143D in example 143 starting with 143C.

249

Synthesis of methyl 2-((tert-butoxycarbonyl)amino)-3-(7-(4-(ethoxymethyl)-2,6-dimethoxyphenyl)-1-methyl-1H-indazol-4-yl)propanoate (146B)

The title compound was prepared according to the method presented for the synthesis of compound 143E in example 143 starting with 146A.

250

Synthesis of methyl 2-amino-3-(7-(4-(ethoxymethyl)-2,6-dimethoxyphenyl)-1-methyl-1H-indazol-4-yl)propanoate TFA salt (146C)

The title compound was prepared according to the method presented for the synthesis of compound 143F in example 143 starting with 146B.

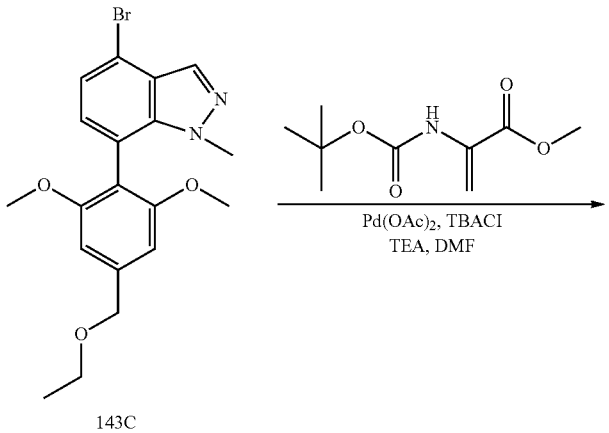

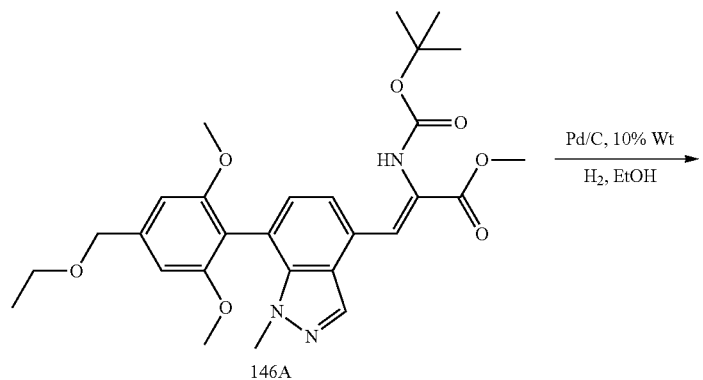

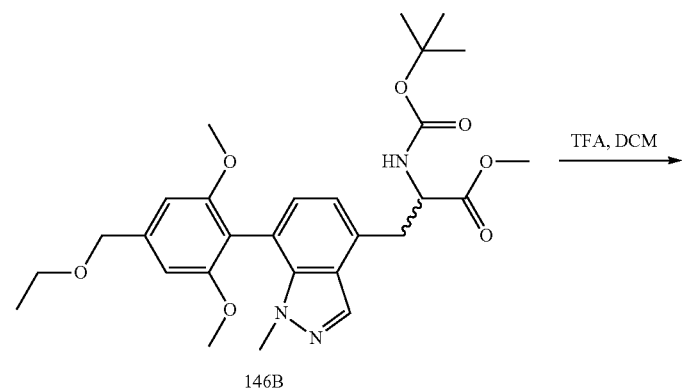

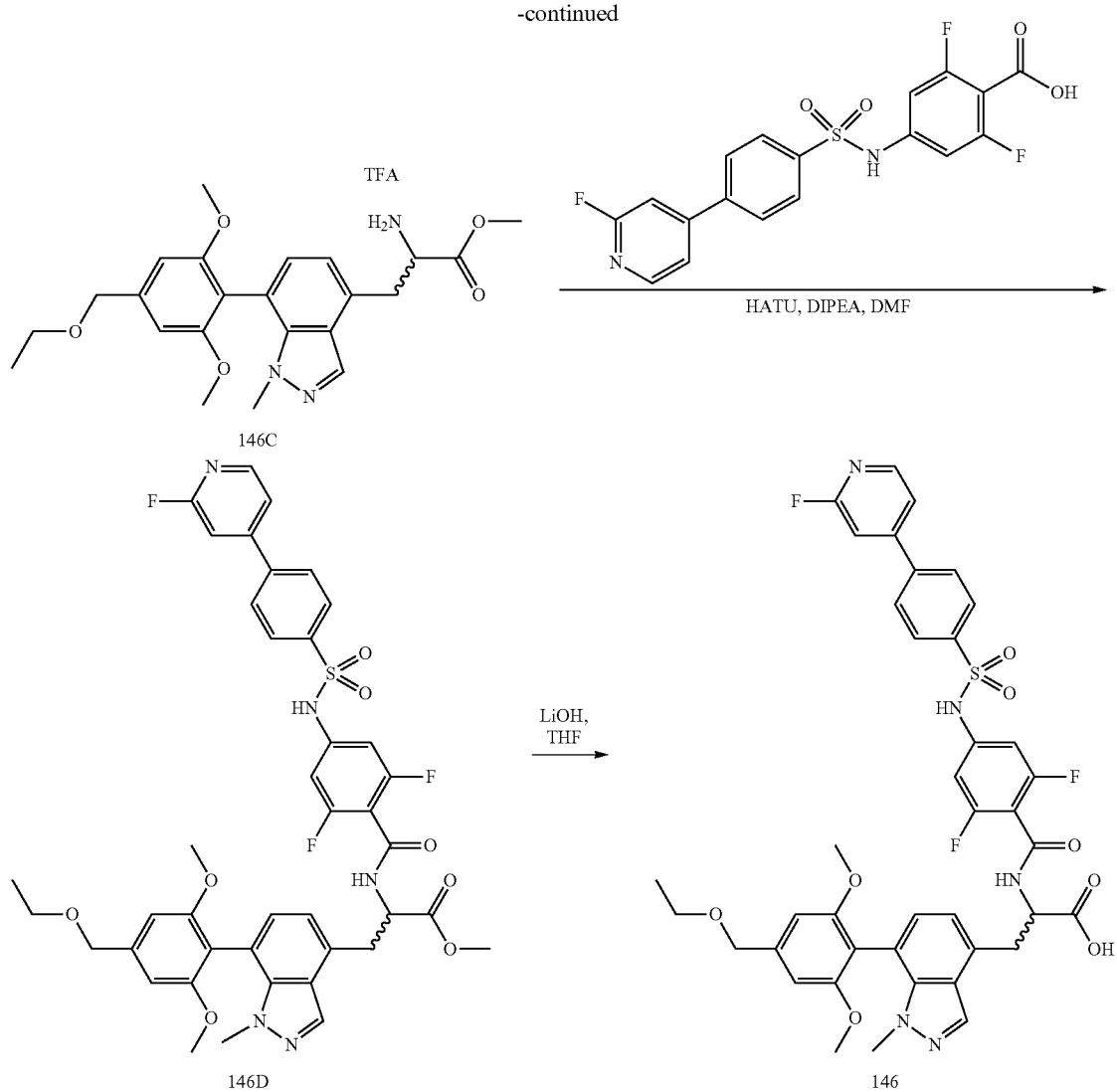

Synthesis of methyl 2-(2,6-difluoro-4-((4-(2-fluoro-pyridin-4-yl)phenyl)sulfonamido) benzamido)-3-(7-(4-(ethoxymethyl)-2,6-dimethoxyphenyl)-1-methyl-1H-indazol-4-yl)propanoate (146D)

The title compound was prepared according to the method presented for the synthesis of compound 143G in example 143 starting with 146C.

Synthesis of 2-(2,6-difluoro-4-((4-(2-fluoropyridin-4-yl)phenyl)sulfonamido) benzamido)-3-(7-(4-(ethoxymethyl)-2,6-dimethoxyphenyl)-1-methyl-1H-indazol-4-yl)propanoic acid (146)

The title compound was prepared according to the method presented for the synthesis of compound 143 in example 143 starting with 146D. MS (m/z) 804.4 [M+H]+. 1H NMR (400 MHz, DMSO-d6) δ 11.21 (s, 1H), 9.08 (d, J=7.8 Hz, 1H), 8.33 (d, J=5.3 Hz, 1H), 8.09-8.01 (m, 3H), 8.02-7.90 (m, 2H), 7.72 (dt, J=5.4, 1.8 Hz, 1H), 7.59 (d, J=1.5 Hz, 1H), 6.98-6.85 (m, 2H), 6.80 (d, J=9.1 Hz, 2H), 6.72 (s, 2H), 4.69 (ddd, J=9.5, 7.8, 4.7 Hz, 1H), 4.51 (s, 2H), 3.60 (d, J=1.6 Hz, 6H), 3.54 (m, 2H), 3.44 (s, 3H), 3.43-3.35 (m, 1H), 3.21 (dd, J=14.6, 9.4 Hz, 1H), 1.19 (t, J=7.0 Hz, 3H).

Example 147

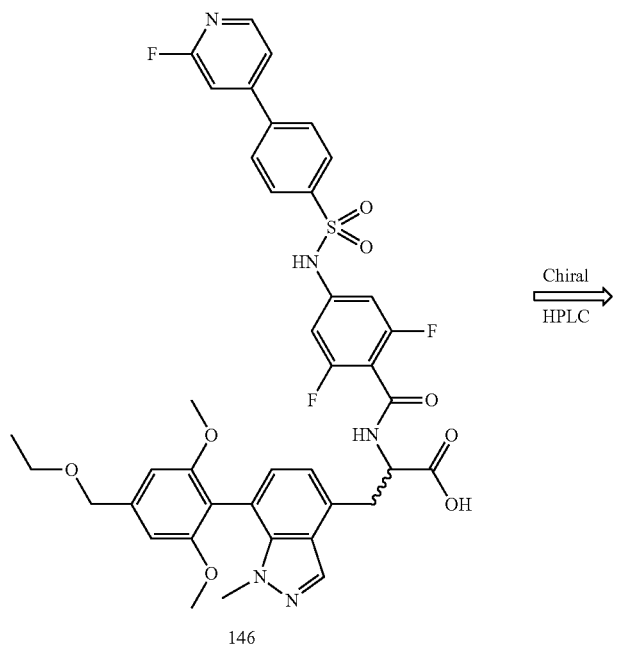

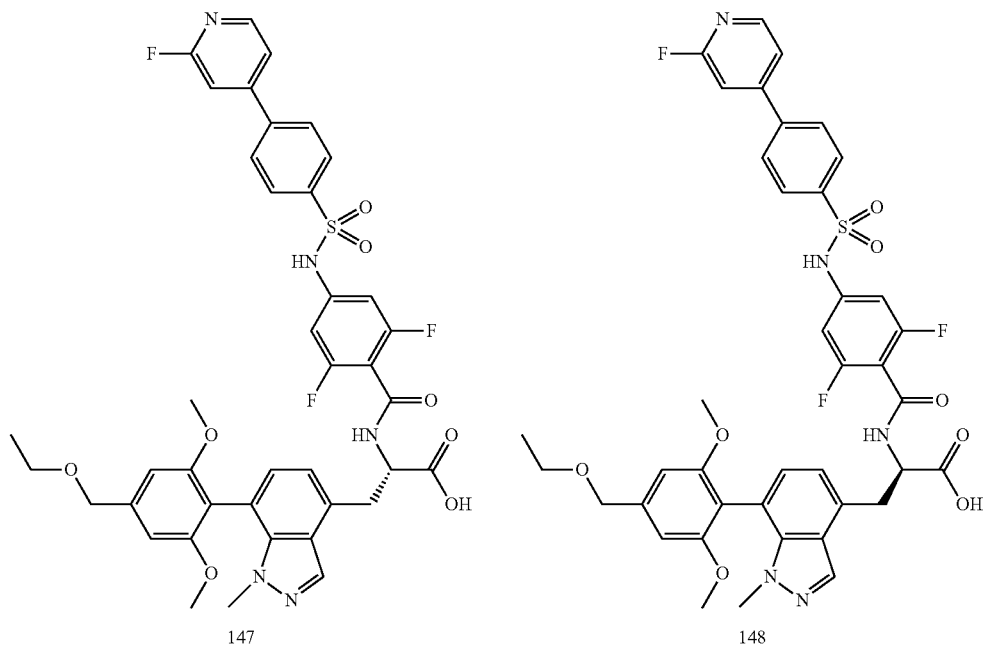

Preparation of (R)-2-(2,6-difluoro-4-((4-(2-fluoro-pyridin-4-yl)phenyl)sulfonamido) benzamido)-3-(7-(4-(ethoxymethyl)-2,6-dimethoxyphenyl)-1-methyl-1H-indazol-4-yl)propanoic acid (148)

146 was separated into its 2 enantiomers by supercritical fluid chromatography using 30% MeOH co-solvent, at a flow rate of 55 mL/min, using an AD-H 5 μm 21×250 mm column. The title compound was identified as the second eluting peak. MS (m/z) 804.5 [M+H]+.

Example 149

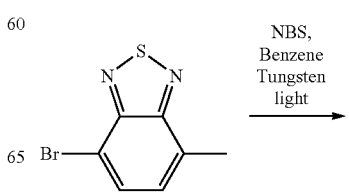

255
-continued

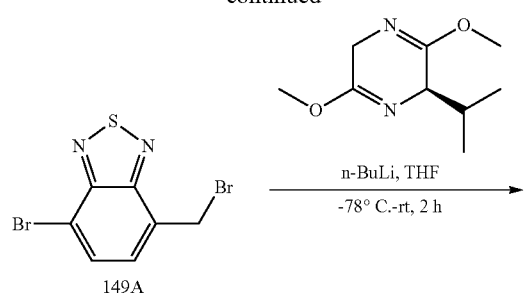
149A

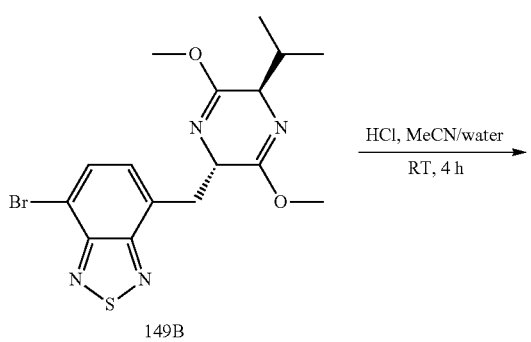
149B

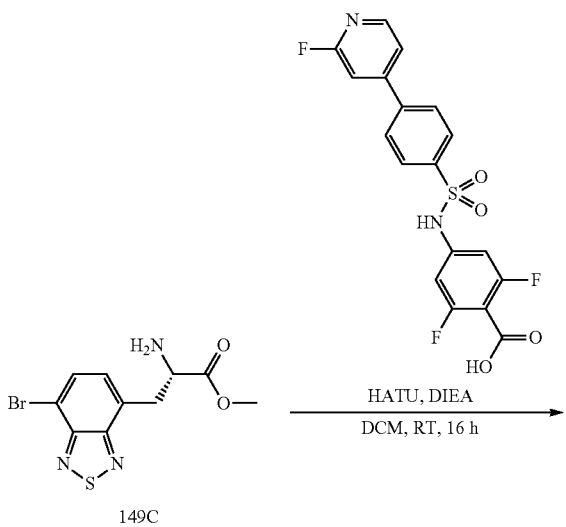
149C

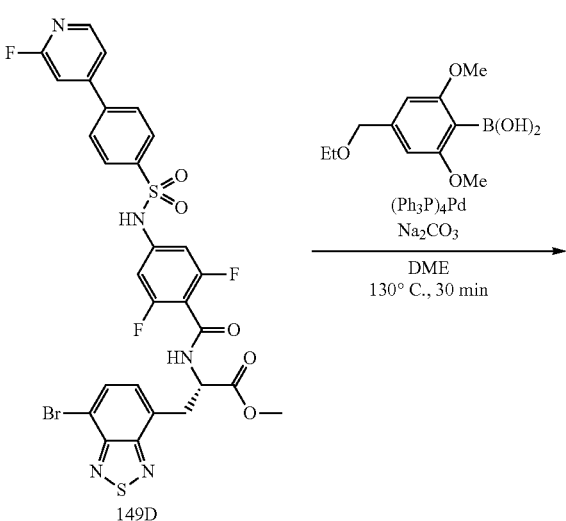
149D

256
-continued

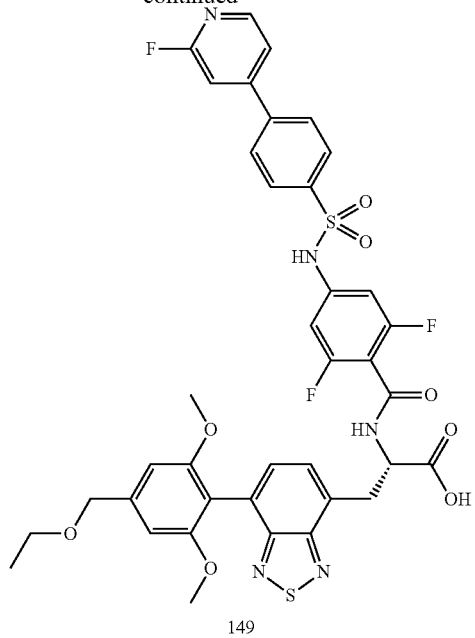
149

Synthesis of 4-bromo-7-(bromomethyl)benzo[c][1,2,5]thiadiazole (149A)

To a stirred solution of 4-bromo-7-methylbenzo[c][1,2,5]thiadiazole (1.00 g, 4.37 mmol) in benzene (11 mL) was added NBS (0.932 g, 5.24 mmol) at RT. The reaction mixture was heated to reflux under tungsten light for 16 h. The reaction was cooled to RT, filtered, and concentrated to yield 149A.

Synthesis of 4-bromo-7-(((2S,5R)-5-isopropyl-3,6-dimethoxy-2,5-dihydropyrazin-2-yl)methyl)benzo[c][1,2,5]thiadiazole (149B)

n-Butyllithium (1.6 M in hexanes, 0.93 mL, 1.5 mmol) was added dropwise to a stirred solution of (R)-2-isopropyl-3,6-dimethoxy-2,5-dihydropyrazine (250 mg, 1.36 mmol) in THF (14 mL) at −78° C. and the resulting reaction mixture was stirred for 30 min. Next, 149A (543 mg, 1.76 mmol) was added. The reaction mixture was stirred for 1 h, and then it was allowed to warm to room temperature over 1 h. The reaction mixture was quenched by the addition of a saturated ammonium chloride solution, the layers were separated, and the aqueous layer was extracted with ethyl acetate. The combined organics were washed with water and saturated sodium chloride, dried over sodium sulfate, and concentrated under reduced pressure to obtain crude compound. The crude compound was purified by flash chromatography on silica gel (eluent 1-30% EtOAc/hexanes linear gradient) to obtain 149B.

Synthesis of methyl (S)-2-amino-3-(7-bromobenzo[c][1,2,5]thiadiazol-4-yl)propanoate (149C)

To a stirred solution of 149B (158 mg, 0.384 mmol) in acetonitrile (7.6 mL) was added 3M hydrochloric acid (0.77 mL, 2.3 mmol), and the reaction was allowed to stir for 4 h at room temperature. It was concentrated, diluted with dimethylsulfoxide, and purified by preparatory HPLC (C18 column, water/MeCN with 0.1% TFA eluent). The fractions containing product were concentrated, treated with 2M aqueous sodium carbonate until a pH of 12 was reached, and were extracted twice with dichloromethane. The combined organics were dried over anhydrous sodium sulfate, filtered, and concentrated to yield 149C.

Synthesis of methyl (S)-3-(7-bromobenzo[c][1,2,5] thiadiazol-4-yl)-2-(2,6-difluoro-4-((4-(2-fluoropyridin-4-yl)phenyl)sulfonamido)benzamido)propanoate (149D)

To a stirred solution of 149C (31 mg, 0.098 mmol) and 2,6-difluoro-4-((4-(2-fluoropyridin-4-yl)phenyl)sulfonamido) benzoic acid (40 mg, 0.098 mmol) in dichloromethane (1 mL) was added diisopropylethylamine (38 mg, 0.29 mmol) and HATU (37 mg, 0.098 mmol), and the reaction was stirred for 16 h at RT. It was diluted with ethyl acetate and washed with 10% citric acid, sodium bicarbonate, and brine. It was dried over anhydrous sodium sulfate, filtered, and concentrated. It was purified on the by flash chromatography on silica gel (eluent: 5-100% EtOAc/hexanes linear gradient) to yield 149D.

Synthesis of (S)-2-(2,6-difluoro-4-((4-(2-fluoropyridin-4-yl)phenyl)sulfonamido) benzamido)-3-(7-(4-(ethoxymethyl)-2,6-dimethoxyphenyl)benzo[c]-[1,2,5]thiadiazol-4-yl)propanoic acid (149)

A microwave vial was charged with 149D (47 mg, 0.067 mmol), (4-(ethoxymethyl)-2,6-dimethoxyphenyl) boronic acid (18 mg, 0.073 mmol), and tetrakis(triphenylphosphine) palladium(0) (4 mg, 0.003 mmol). Next, 1,2-dimethoxyethane (1 mL) and 2M aqueous sodium carbonate (0.12 mL, 0.24 mmol) were added, and the reaction was degassed with nitrogen and sealed. It was heated to 130° C. for 30 min by microwave irradiation, and then was cooled to room temperature. It was diluted with DMSO, acidified with trifluoroacetic acid, and purified by preparatory HPLC to yield 149. MS (m/z) 808.0 [M+H]+. $^1$H NMR (400 MHz, DMSO-d$_6$) δ 12.88 (s, 1H), 11.19 (s, 1H), 9.06 (d, J=8.1 Hz, 1H), 8.35 (d, J=5.3 Hz, 1H), 8.07 (d, J=8.3 Hz, 2H), 7.98 (d, J=8.3 Hz, 2H), 7.74 (dd, J=5.6, 1.9 Hz, 1H), 7.60 (s, 1H), 7.50 (d, J=7.1 Hz, 1H), 7.36 (d, J=7.0 Hz, 1H), 6.80 (d, J=9.0 Hz, 2H), 6.74 (s, 2H), 4.94 (td, J=9.1, 8.1, 4.8 Hz, 1H), 4.52 (s, 2H), 3.81-3.65 (m, 1H), 3.61-3.52 (m, 8H), 3.33 (dd, J=14.4, 10.3 Hz, 1H), 1.21 (t, J=7.0 Hz, 3H).

Example 150

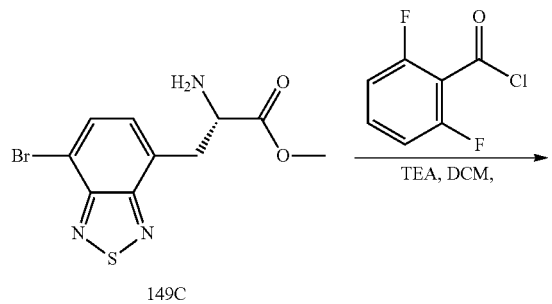

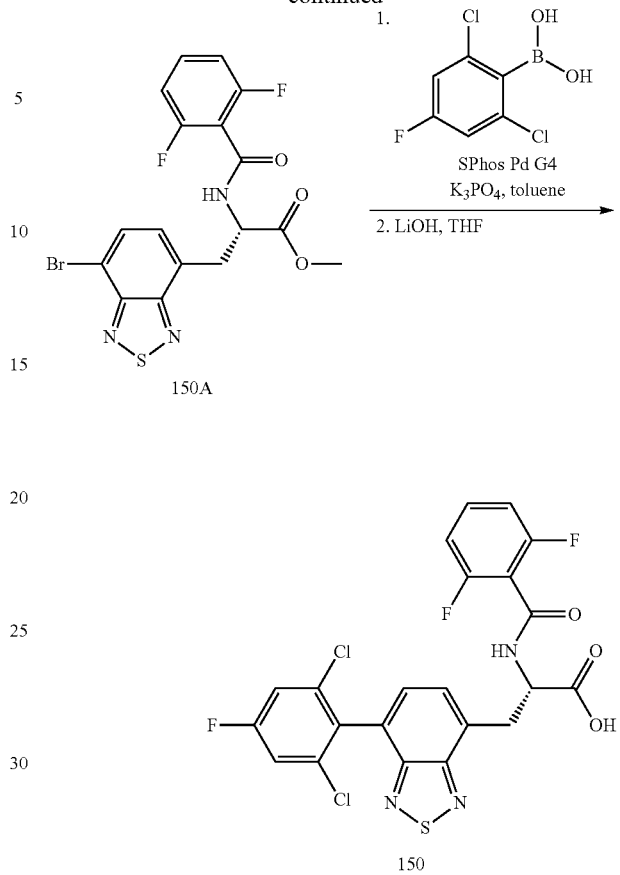

Synthesis of methyl (S)-3-(7-bromobenzo[c][1,2,5] thiadiazol-4-yl)-2-(2,6-difluoro benzamido)propanoate (150A)

The title compound was prepared according to the method presented for the synthesis of compound N2 starting with 149C and 2,6-difluorobenzoyl chloride.

Synthesis of (S)-3-(7-(2,6-dichloro-4-fluorophenyl) benzo[c][1,2,5]thiadiazol-4-yl)-2-(2,6-difluorobenzamido)propanoic acid (150)

To a sealed vial was added 150A (88 mg, 0.19 mmol), (2,6-dimethoxyphenyl)boronic acid (81 mg, 0.38 mmol), SPhos Pd G4 (34 mg, 0.04 mmol), and K$_3$PO$_4$ (127 mg, 0.6 mmol) in toluene. The reaction mixture was allowed to stir at 120° C. for 1 h. EtOAc and water was added to the reaction mixture. The organic layer was washed with brine, dried over anhydrous Na$_2$SO$_4$, and concentrated under reduced pressure. The material was purified on silica gel eluting with EtOAc in hexanes (0-100%) to give the ester product, which was then hydrolyzed to the acid using 1M LiOH and purified with prep HPLC to give the desired product. MS (m/z) 526.0 [M+H]$^+$. 1H NMR (400 MHz, DMSO-d6) δ 12.96 (s, 1H), 9.18 (d, J=8.3 Hz, 1H), 7.72 (d, J=8.6 Hz, 2H), 7.65 (d, J=7.1 Hz, 1H), 7.60 (d, J=7.0 Hz, 1H), 7.45 (tt, J=8.4, 6.5 Hz, 1H), 7.07 (dd, J=8.5, 7.5 Hz, 2H), 5.07 (ddd, J=10.8, 8.3, 4.8 Hz, 1H), 3.80 (dd, J=14.2, 4.7 Hz, 1H), 3.45-3.35 (m, 1H).

Example 151
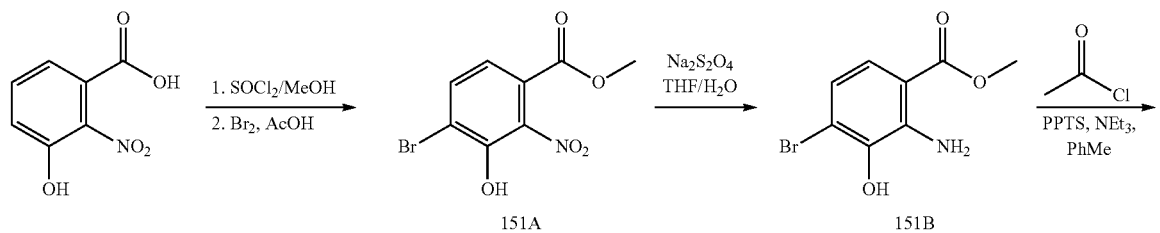
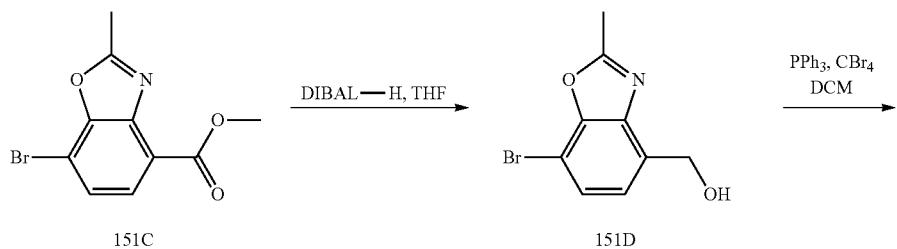
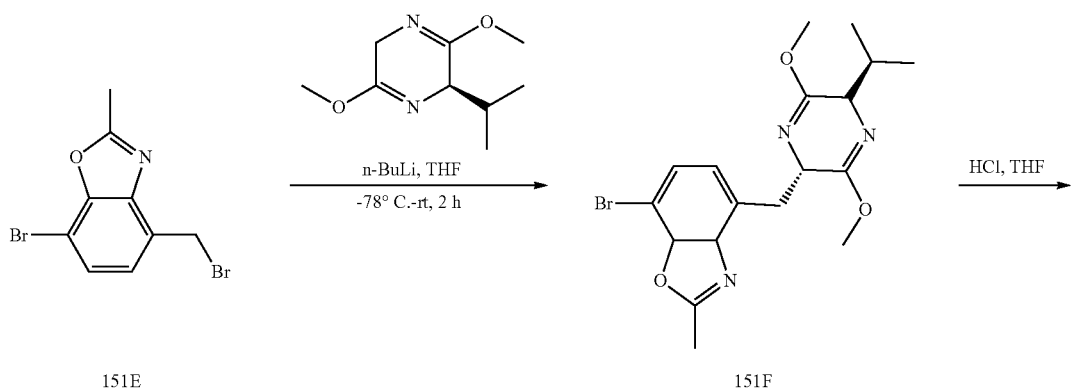
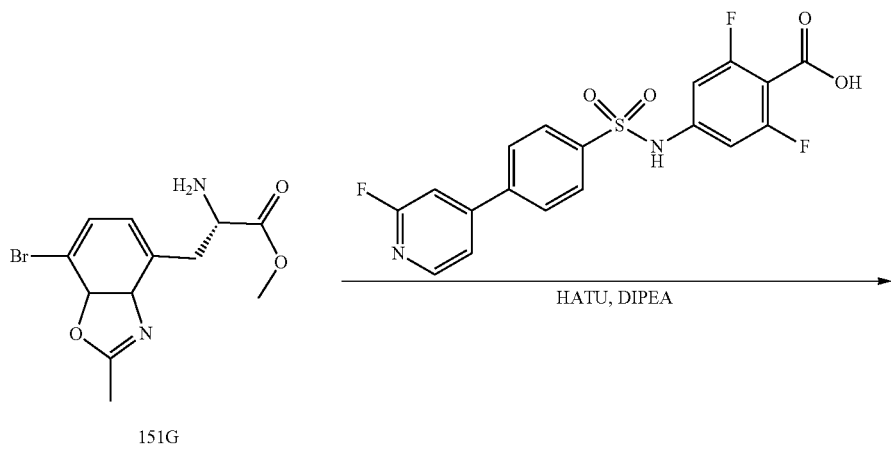

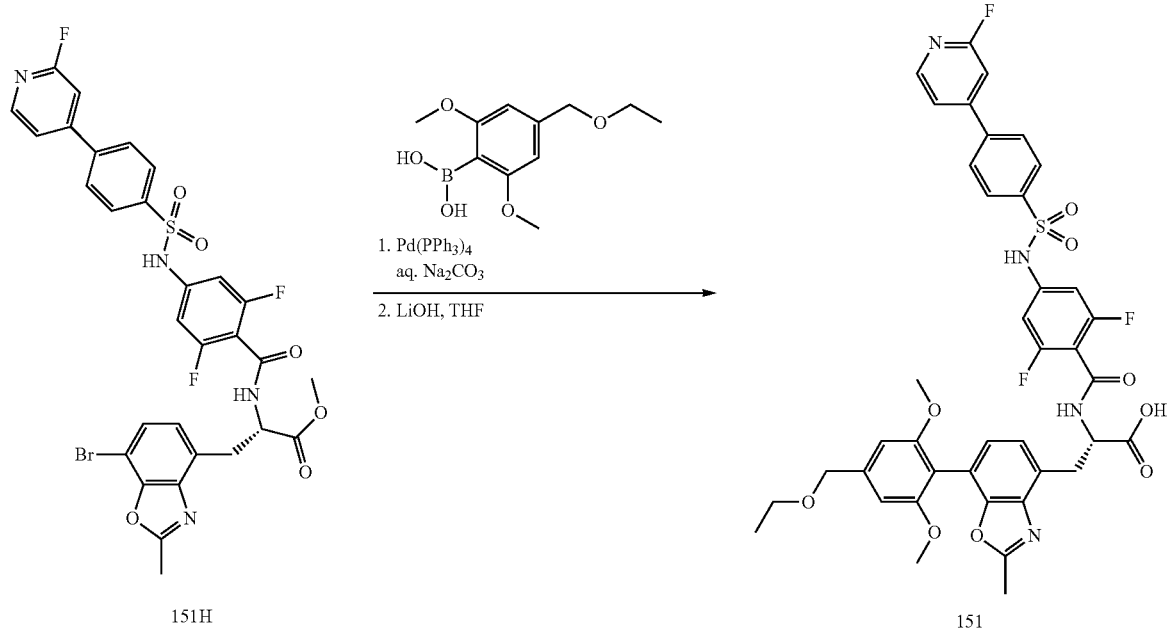 [SMILES: COC(=O)[C@H](Cc1ccc(Br)c2oc(C)nc12)NC(=O)c1c(F)cc(NS(=O)(=O)c2ccc(-c3ccnc(F)c3)cc2)cc1F ; CCOCc1cc(OC)c(B(O)O)c(OC)c1 ; CCOCc1cc(OC)c(-c2ccc(C[C@H](NC(=O)c3c(F)cc(NS(=O)(=O)c4ccc(-c5ccnc(F)c5)cc4)cc3F)C(=O)O)c3nc(C)oc23)c(OC)c1]

Synthesis of methyl 4-bromo-3-hydroxy-2-nitrobenzoate (151A)

SOCl$_2$ (23 mL, 314.00 mmol) was added slowly to the solution of 3-hydroxy-2-nitrobenzoic acid (23.00 g, 125.60 mmol) in MeOH (250 mL) at 0° C., and the resulting mixture was heated to reflux for overnight. TLC showed the SM was consumed, and the reaction mixture was concentrated. Then to the solution of this crude product in HOAc (500 mL) was added Br$_2$ (42.15 g, 263.76 mmol) drop wise, and the resulting suspension was stirred at 60° C. for overnight. The reaction mixture was quenched with sat. Na$_2$SO$_3$ (1.0 L), and the mixture was extracted with EtOAc (500 mL×2). The combined organic layer was washed with sat. NaHCO$_3$ (1.0 L), followed with brine (1.0 L), dried over Na$_2$SO$_4$, filtered and concentrated to give the crude product.

Synthesis of methyl 2-amino-4-bromo-3-hydroxybenzoate (151B)

To a solution of compound 151A (31 g, 112.3 mmol) in THF (300 mL) was added a solution of Na$_2$S$_2$O$_4$ (97.8 g, 561.51 mmol) in water (300 mL) drop wise, and the resulting mixture was stirred at RT for 0.5 h. TLC showed the SM was consumed. The reaction was diluted with 1 N HCl (500 mL), extracted with EtOAc (500 mL×2). The combined organic layer was washed with brine (500 mL), dried over Na$_2$SO$_4$, filtered and concentrated to give the crude product which was purified by column chromatography on silica gel (PE:EA=15:1) to afford the desired product.

Synthesis of methyl 7-bromo-2-methylbenzo[d]oxazole-4-carboxylate (151C)

A mixture of compound 151B (6.0 g, 24.38 mmol), acetyl chloride (2.1 g, 26.82 mmol), TEA (2.7 g, 26.82 mmol), PPTS (1.84 g, 7.31 mmol) in toluene (600 mL) was heated to reflux for overnight. TLC showed the most of SM was consumed. The reaction mixture was cooled to 0° C., washed with 1 N HCl (300 mL), and the organic layer was washed with brine (300 mL), dried over Na$_2$SO$_4$, filtered and concentrated to give the crude product which was triturated with MTBE to afford the crude product.

Synthesis of (7-bromo-2-methylbenzo[d]oxazol-4-yl)methanol (151D)

To a solution of compound 151C (5.0 g, 18.51 mmol) in THF (200 mL) was added DIBAL-H (1 M, 46 mmol) drop wise at −5~0° C., and the resulting mixture was stirred at 0° C. for 0.5 h. TLC showed the SM was consumed. The reaction was quenched with 5 mL H$_2$O slowly, and then diluted with sat. NaHCO$_3$ (300 mL). The mixture was extracted with EtOAc (200 mL×2), and the combined organic layer was washed with brine (300 mL), dried over Na$_2$SO$_4$, filtered and concentrated to give the crude product which was purified by column chromatography on Al$_2$O$_3$ to afford the product.

Synthesis of 7-bromo-4-(bromomethyl)-2-methyl-benzo[d]oxazole (151E)

To a solution of compound 151D (2.5 g, 10.33 mmol) in DCM (100 mL) was added PPh3 (5.42 g, 20.66 mmol), followed with CBr4 (6.85 g, 20.66 mmol) at 0° C., and the resulting suspension was stirred at 0° C.~RT for 1 h. TLC showed the SM was consumed. The reaction mixture was diluted with DCM (200 mL), washed with sat. Na$_2$SO$_3$ (200 mL), followed with brine (200 mL), dried over Na$_2$SO$_4$, filtered and concentrated to give the crude product which was purified by column chromatography on Al$_2$O$_3$(PE:EA=30:1) to afford the mixed product.

Synthesis of 7-bromo-4-(((2S,5S)-5-isopropyl-3,6-dimethoxy-2,5-dihydropyrazin-2-yl)methyl)-2-methyl-3a,7a-dihydrobenzo[d]oxazole (151F)

The title compound was prepared according to the method presented for the synthesis of compound 149B in Example 149 using 151D. MS (m/z) 410.1 [M+H]+.

Synthesis of methyl (S)-3-(7-bromo-2-methylbenzo[d]oxazol-4-yl)-2-(2,6-difluoro-4-((4-(2-fluoropyridin-4-yl)phenyl)sulfonamido)benzamido)propanoate (151G)

The title compound was prepared according to the method presented for the synthesis of compound 149C Example 149 starting with 151F. MS (m/z) 703.1 [M+H]+.

Synthesis of methyl (S)-3-(7-bromo-2-methylbenzo[d]oxazol-4-yl)-2-(2,6-difluoro-4-((4-(2-fluoropyridin-4-yl)phenyl)sulfonamido)benzamido)propanoate (151H)

The title compound was prepared according to the method presented for the synthesis of compound 149D Example 149 starting with 2,6-difluoro-4-((4-(2-fluoropyridin-4-yl)phenyl)sulfonamido)benzoic acid and 151G. MS (m/z) 703.1 [M+H]+.

Synthesis of (S)-2-(2,6-difluoro-4-((4-(2-fluoropyridin-4-yl)phenyl)sulfonamido) benzamido)-3-(7-(4-(ethoxymethyl)-2,6-dimethoxyphenyl)-2-methylbenzo[d]oxazol-4-yl) propanoic acid (151)

The title compound was prepared according to the method presented for the synthesis of compound 149 of Example 149 starting with 151H. MS (m/z) 805.2 [M+H]+. 1H NMR (400 MHz, DMSO-d6) δ 11.19 (s, 1H), 9.04 (d, J=7.9 Hz, 1H), 8.35-8.30 (m, 1H), 8.11-8.02 (m, 2H), 8.00-7.94 (m, 2H), 7.72 (dt, J=5.3, 1.8 Hz, 1H), 7.59 (d, J=1.6 Hz, 1H), 7.46 (dt, J=8.1, 0.9 Hz, 1H), 7.36 (ddd, J=8.2, 7.1, 1.2 Hz, 1H), 7.14-7.09 (m, 1H), 7.01 (d, J=7.7 Hz, 1H), 6.80 (d, J=9.1 Hz, 1H), 6.71 (s, 2H), 4.73 (ddd, J=10.0, 7.8, 5.1 Hz, 1H), 4.49 (s, 2H), 3.62 (s, 6H), 3.54 (q, J=7.0 Hz, 2H), 3.45 (dd, J=14.2, 5.0 Hz, 1H), 3.13 (dd, J=14.1, 9.8 Hz, 1H),), 2.47 (s, 2H), 1.19 (t, J=7.0 Hz, 3H).

Example 152

Synthesis of 7-(4-(ethoxymethyl)-2,6-dimethoxyphenyl)-4-(((2S,5S)-5-isopropyl-3,6-dimethoxy-2,5-dihydropyrazin-2-yl)methyl)-2-methylbenzo[d]oxazole (152A)

To a microwave vial was added 151F (350 mg, 0.853 mmol), (4-(ethoxymethyl)-2,6-dimethoxyphenyl)boronic acid (225 mg, 0.938 mmol), XPhos PD G2 (34 mg, 0.043 mmol), and aq Na2CO3 (1.5 mL, 2M) in DME (5 mL). The reaction mixture was allowed to stir at 130° C. for 30 min. Concentrated and DCM (50 mL) was added. The organic layer was washed with water (50 mL×2), dried over anhydrous Na2SO4, and concentrated under reduced pressure. The crude material was used for the next step.

Synthesis of methyl (S)-2-amino-3-(7-(4-(ethoxymethyl)-2,6-dimethoxyphenyl)-2-methylbenzo[d]oxazol-4-yl)propanoate (152B)

The title compound was prepared according to the method presented for the synthesis of compound 149C in Example 149 starting with 152A.

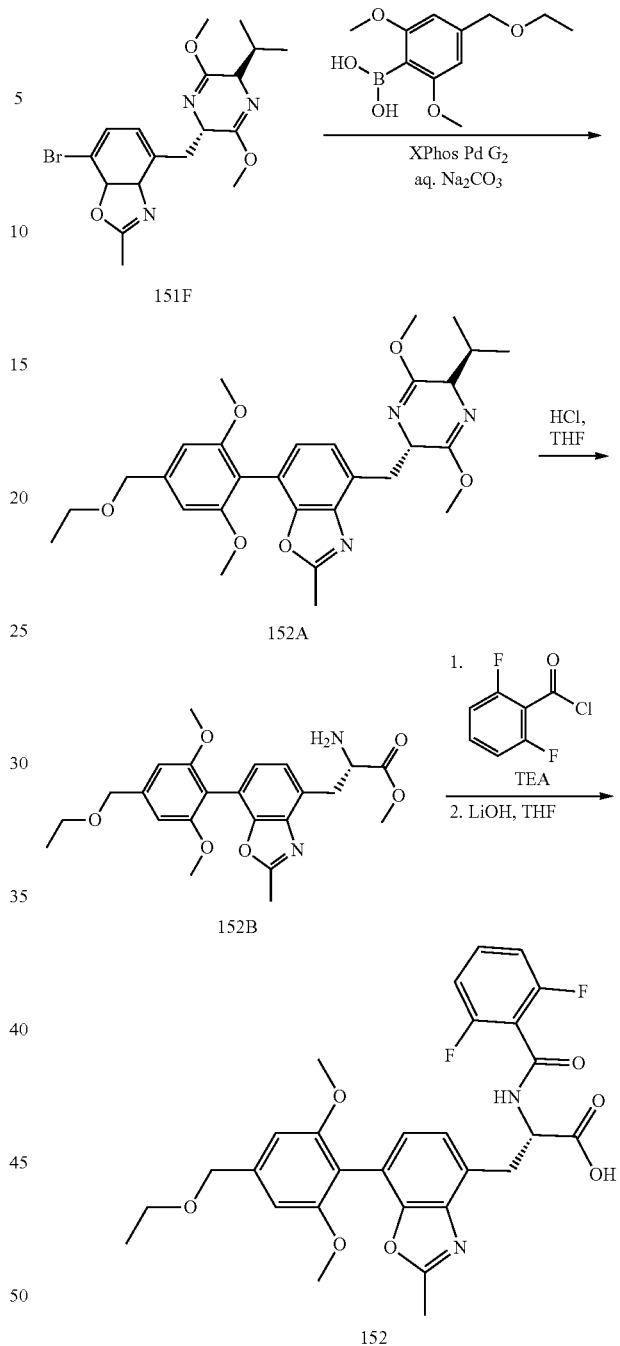

Synthesis of (S)-2-(2,6-difluorobenzamido)-3-(7-(4-(ethoxymethyl)-2,6-dimethoxy phenyl)-2-methylbenzo[d]oxazol-4-yl)propanoic acid (152)

The title compound was prepared according to the method presented for the synthesis of compound N2 starting with 152B and 2,6-difluorobenzoyl chloride to give the methyl ester product, then saponification according to the method for the synthesis of compound 104 in example 104. MS (m/z) 555.2 [M+H]+. 1H NMR (400 MHz, DMSO-d6) δ 9.20 (d, J=7.8 Hz, 1H), 7.49 (tt, J=8.5, 6.6 Hz, 1H), 7.18 (d, J=7.8 Hz, 1H), 7.12 (dd, J=8.4, 7.6 Hz, 2H), 7.04 (d, J=7.7 Hz, 1H), 6.72 (s, 2H), 4.80 (ddd, J=9.8, 7.8, 5.1 Hz, 1H), 4.49 (s, 2H), 3.64 (d, J=2.8 Hz, 6H), 3.54 (q, J=7.0 Hz, 2H), 3.19 (dd, J=14.1, 9.7 Hz, 1H), 2.52 (s, 3H), 1.19 (t, J=7.0 Hz, 3H).

Example 153

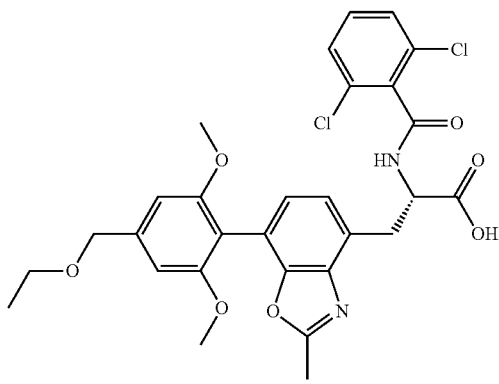

153

Synthesis of (S)-2-(2,6-dichlorobenzamido)-3-(7-(4-(ethoxymethyl)-2,6-dimethoxy phenyl)-2-methyl-benzo[d]oxazol-4-yl)propanoic acid (153)

The title compound was prepared according to the method presented for the synthesis of compound N2 starting with 152B and 2,6-dichlorobenzoyl chloride to give the methyl ester product, then saponification according to the method for the synthesis of compound 104 in example 104. MS (m/z) 587.2 [M+H]$^+$. 1H NMR (400 MHz, DMSO-d6) δ 9.07 (d, J=8.3 Hz, 1H), 7.43-7.33 (m, 3H), 7.21 (d, J=7.8 Hz, 1H), 7.00 (d, J=7.7 Hz, 1H), 6.72 (s, 2H), 4.95 (ddd, J=10.7, 8.3, 4.6 Hz, 1H), 4.50 (s, 2H), 3.65 (d, J=5.2 Hz, 6H), 3.58-3.48 (m, 3H), 3.14 (dd, J=14.1, 10.7 Hz, 1H), 2.53 (s, 3H), 1.19 (t, J=7.0 Hz, 3H).

Example 154

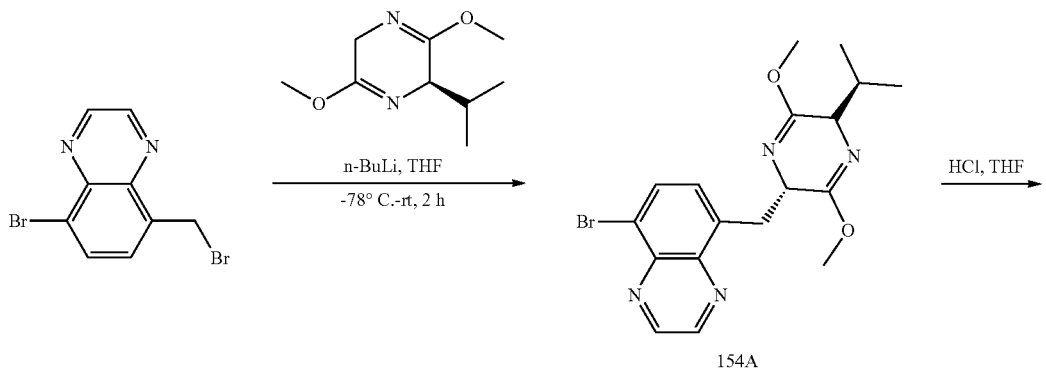

154A

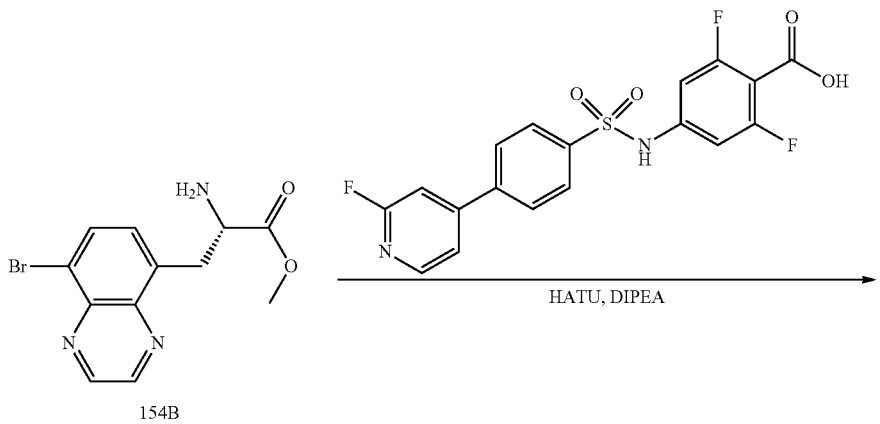

154B

267

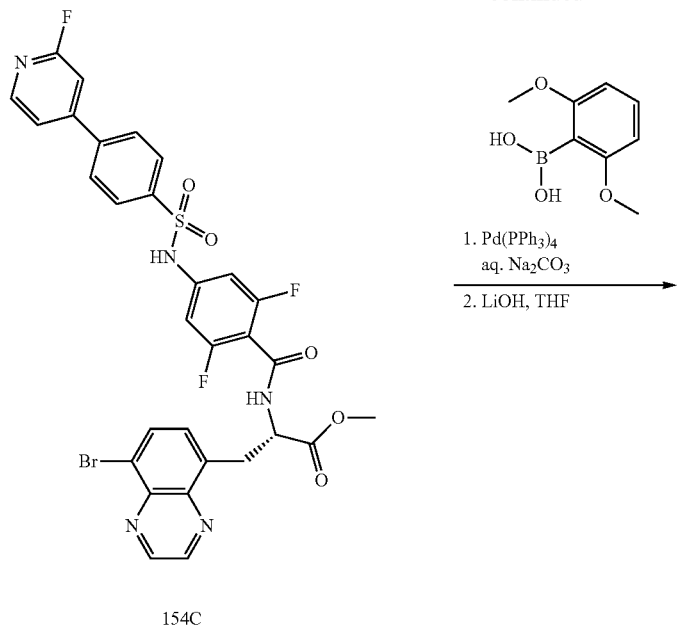 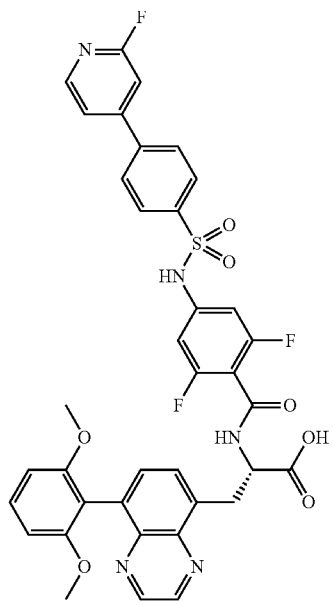

-continued

154C

1. Pd(PPh₃)₄
   aq. Na₂CO₃
2. LiOH, THF

268

154

Synthesis of 5-bromo-8-((((2S,5S)-5-isopropyl-3,6-dimethoxy-2,5-dihydropyrazin-2-yl)methyl)quinoxaline (154A)

The title compound was prepared according to the method presented for the synthesis of compound 149B in Example 149 starting with 5-bromo-8-(bromomethyl)quinoxaline.

Synthesis of methyl (S)-2-amino-3-(8-bromoquinoxalin-5-yl)propanoate (154B)

The title compound was prepared according to the method presented for the synthesis of compound 149C in Example 149 starting with 154A

Synthesis of methyl (S)-3-(8-bromoquinoxalin-5-yl)-2-(2,6-difluoro-4-((4-(2-fluoro pyridin-4-yl)phenyl)sulfonamido)benzamido)propanoate (154C)

The title compound was prepared according to the method presented for the synthesis of compound 149D in Example 149 starting with 154B.

Synthesis of (S)-2-(2,6-difluoro-4-((4-(2-fluoropyridin-4-yl)phenyl)sulfonamido) benzamido)-3-(8-(2,6-dimethoxyphenyl)quinoxalin-5-yl)propanoic acid (154)

The title compound was prepared according to the method presented for the synthesis of compound 149 in Example 66 starting with 154C and (2,6-dimethoxyphenyl)boronic acid. MS (m/z) 744.3 [M+H]⁺. 1H NMR (400 MHz, DMSO-d6) δ 11.20 (s, 1H), 9.04 (d, J=8.0 Hz, 1H), 8.89 (d, J=1.8 Hz, 1H), 8.79 (d, J=1.8 Hz, 1H), 8.33 (d, J=5.3 Hz, 1H), 8.10-8.00 (m, 2H), 8.00-7.91 (m, 2H), 7.72 (dt, J=5.4, 1.8 Hz, 1H), 7.68 (d, J=7.4 Hz, 1H), 7.59 (d, J=1.5 Hz, 1H), 7.47 (d, J=7.3 Hz, 1H), 7.34 (t, J=8.4 Hz, 1H), 6.78 (d, J=9.1 Hz, 2H), 6.73 (d, J=8.5 Hz, 2H), 4.84 (ddd, J=10.2, 8.0, 5.0 Hz, 1H), 3.88 (dd, J=13.8, 4.9 Hz, 1H), 3.50 (d, J=1.1 Hz, 6H), 3.36-3.28 (m, 1H).

Example 155

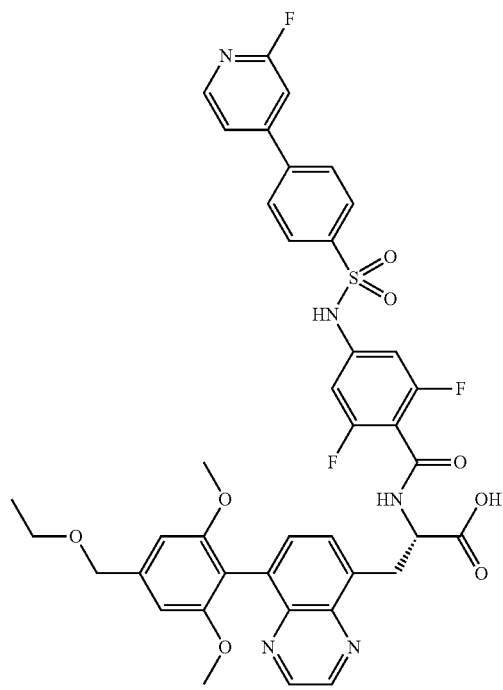

155

Synthesis of (S)-2-(2,6-difluoro-4-((4-(2-fluoropyridin-4-yl)phenyl)sulfonamido) benzamido)-3-(8-(4-(ethoxymethyl)-2,6-dimethoxyphenyl)quinoxalin-5-yl)propanoic acid (155)

The title compound was prepared according to the method presented for the synthesis of compound 149 in Example 149 starting with 154C and (4-(ethoxymethyl)-2,6-dimethoxyphenyl) boronic acid. MS (m/z) 802.1 [M+H]$^+$. 1H NMR (400 MHz, DMSO-d6) δ 11.19 (s, 1H), 9.04 (d, J=8.1 Hz, 1H), 8.89 (d, J=1.8 Hz, 1H), 8.79 (d, J=1.8 Hz, 1H), 8.33 (d, J=5.3 Hz, 1H), 8.11-8.00 (m, 2H), 8.02-7.92 (m, 2H), 7.72 (dt, J=5.4, 1.8 Hz, 1H), 7.67 (d, J=7.4 Hz, 1H), 7.59 (d, J=1.5 Hz, 1H), 7.47 (d, J=7.3 Hz, 1H), 6.78 (d, J=9.1 Hz, 2H), 6.69 (s, 2H), 4.84 (ddd, J=10.4, 8.1, 5.1 Hz, 1H), 4.50 (s, 2H), 3.88 (dd, J=13.7, 5.0 Hz, 1H), 3.59-3.51 (m, 2H), 3.50 (d, J=1.5 Hz, 6H), 3.34 (dd, J=13.8, 10.3 Hz, 1H), 1.20 (t, J=7.0 Hz, 3H).

Example 156

Synthesis of (S)-3-(8-(2,6-dichloro-4-fluorophenyl)quinoxalin-5-yl)-2-(2,6-difluorobenzamido)propanoic acid (156)

The title compound was prepared according to the method presented for the synthesis of compound 150 in Example 150 starting with 156A and (2,6-dichloro-4-fluorophenyl) boronic acid. MS (m/z) 521.8 [M+H]$^+$. 1H NMR (400 MHz, DMSO-d6) δ 9.17 (d, J=8.3 Hz, 1H), 9.03 (d, J=1.8 Hz, 1H), 8.90 (d, J=1.8 Hz, 1H), 7.85 (d, J=7.4 Hz, 1H), 7.73-7.62 (m, 3H), 7.45 (tt, J=8.4, 6.5 Hz, 1H), 7.07 (dd, J=8.5, 7.5 Hz, 2H), 4.99 (ddd, J=10.7, 8.3, 4.9 Hz, 1H), 4.00 (dd, J=13.6, 4.9 Hz, 1H), 3.40 (dd, J=13.7, 10.7 Hz, 1H).

Example 157

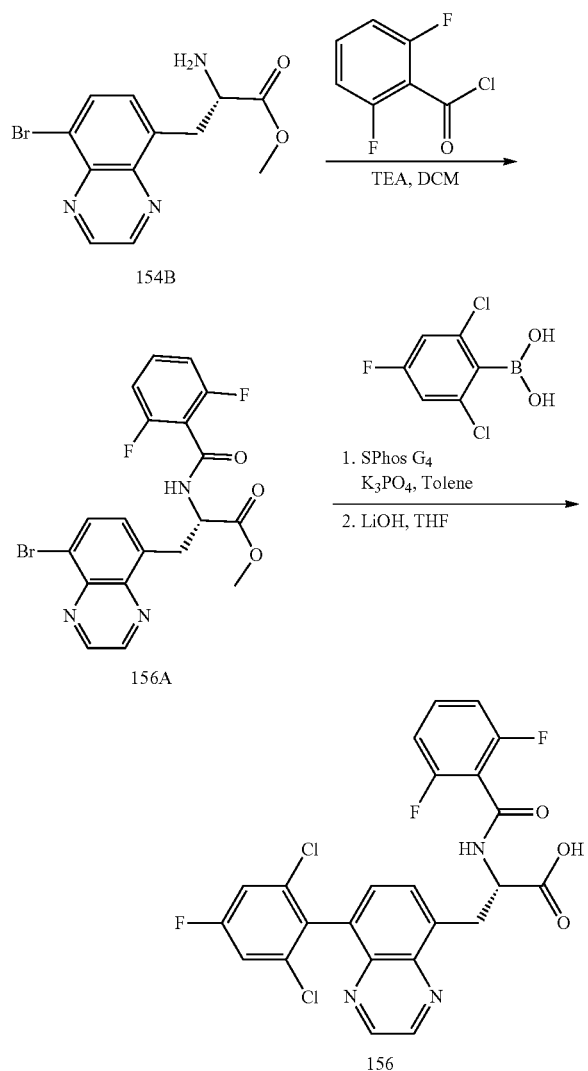

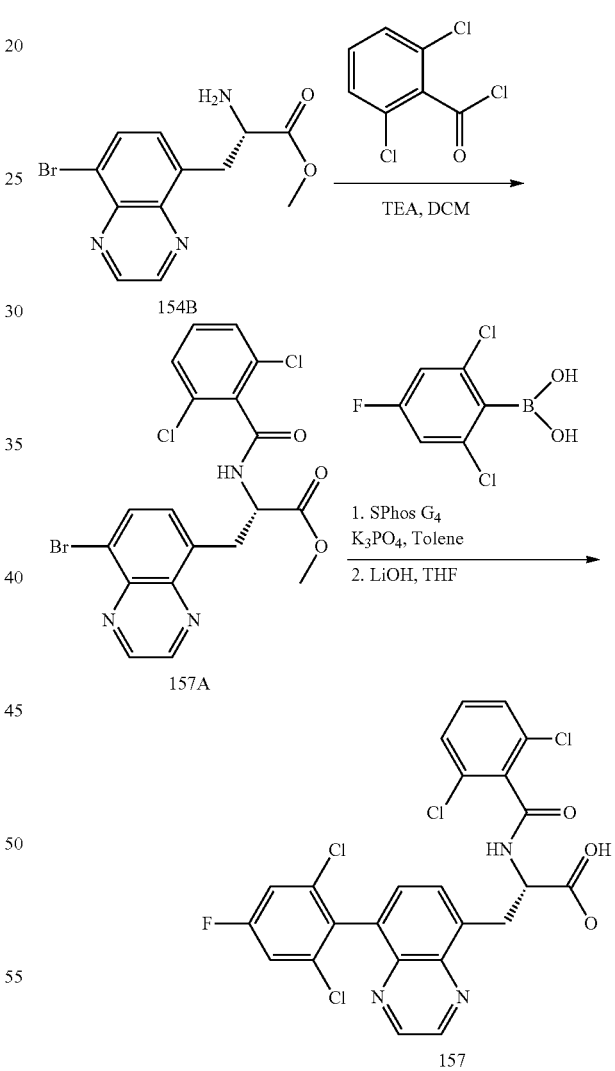

Synthesis of methyl (S)-3-(8-bromoquinoxalin-5-yl)-2-(2,6-difluorobenzamido) propanoate (156A)

The title compound was prepared according to the method presented for the synthesis of compound N2 starting with 154B and 2,6-difluorobenzoyl chloride.

Synthesis of methyl (S)-3-(8-bromoquinoxalin-5-yl)-2-(2,6-dichlorobenzamido) propanoate (157A)

The title compound was prepared according to the method presented for the synthesis of compound N2 starting with 154B and 2,6-dichlorobenzoyl chloride.

Synthesis of (S)-3-(8-(2,6-dichloro-4-fluorophenyl) quinoxalin-5-yl)-2-(2,6-dichloro benzamido)propanoic acid (157)

The title compound was prepared according to the method presented for the synthesis of compound 150 in Example 150 starting with 157A and (2,6-dichloro-4-fluorophenyl) boronic acid. MS (m/z) 553.5 [M+H]⁺. 1H NMR (400 MHz, DMSO-d6) δ 9.17 (d, J=8.7 Hz, 1H), 9.04 (d, J=1.8 Hz, 1H), 8.90 (d, J=1.8 Hz, 1H), 7.91 (d, J=7.4 Hz, 1H), 7.72-7.62 (m, 3H), 7.44-7.31 (m, 3H), 5.06 (ddd, J=11.4, 8.7, 4.0 Hz, 1H), 4.01 (dd, J=13.6, 4.0 Hz, 1H), 3.36 (dd, J=13.7, 11.4 Hz, 1H).

Example 158

Synthesis of tert-butyl (S)-3-(8-bromoquinoxalin-5-yl)-2-((diphenylmethylene)amino) propanoate (158A)

To a stirred solution of 5-bromo-8-(bromomethyl)quinoxaline (180 mg, 0.6 mmol), tert-butyl 2-((diphenylmethylene)amino)acetate (233 mg, 0.8 mmol) and (11bS)-(+)-4,4-dibutyl-4,5-dihydro-2,6-bis(3,4,5-trifluorophenyl)-3H-dinaphth[2,1-c:1',2'-e]azepinium bromide (33 mg, 0.04 mmol) in toluene (6 mL) at 0° C. was added 50% aq KOH solution (1.8 mL). The reaction mixture was allowed to stir for 6 h while warming to RT. EtOAc and water was added to the reaction mixture. The aqueous layer was purified on silica gel eluting with EtOAc in Hex (0-20%) to give the title compound.

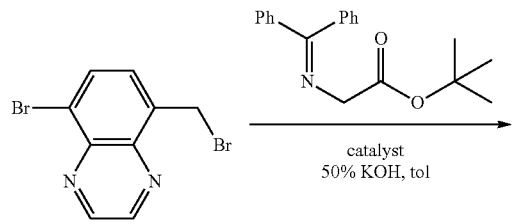

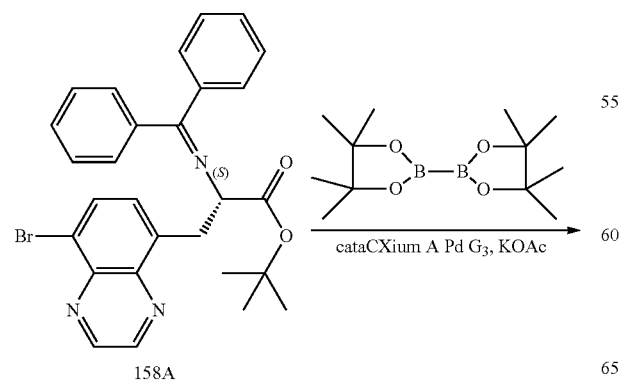

158A

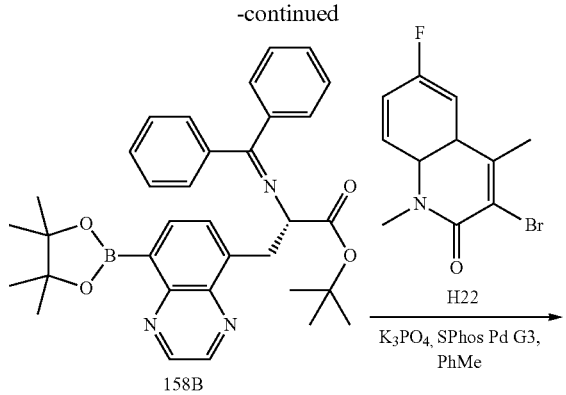

158B

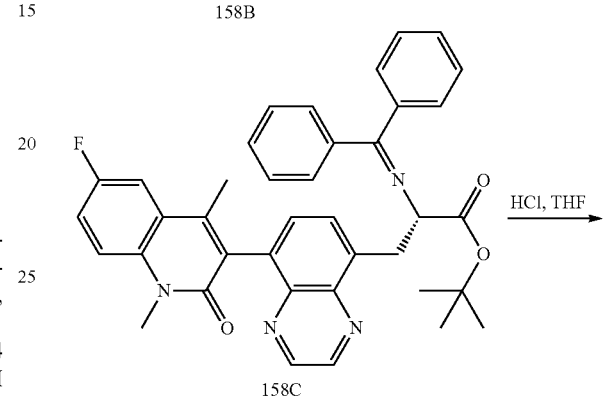

158C

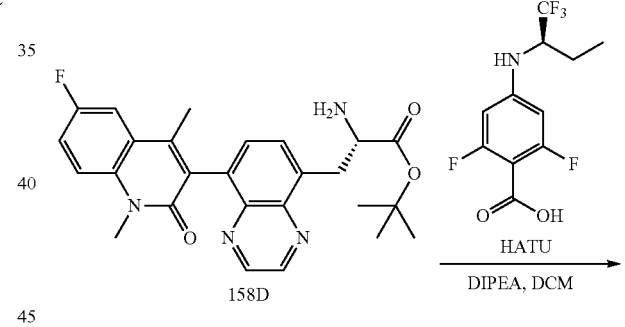

158D

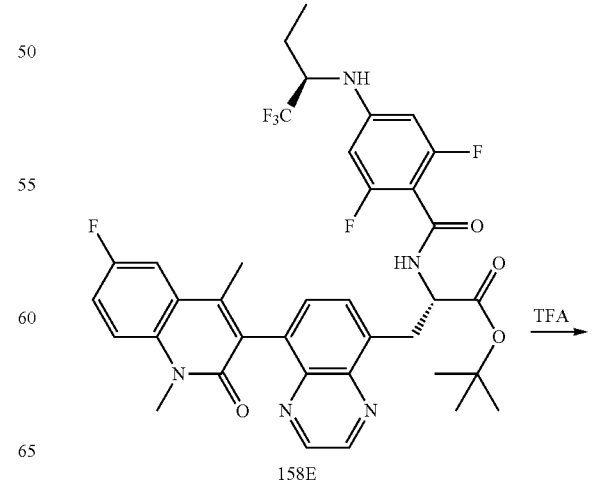

158E

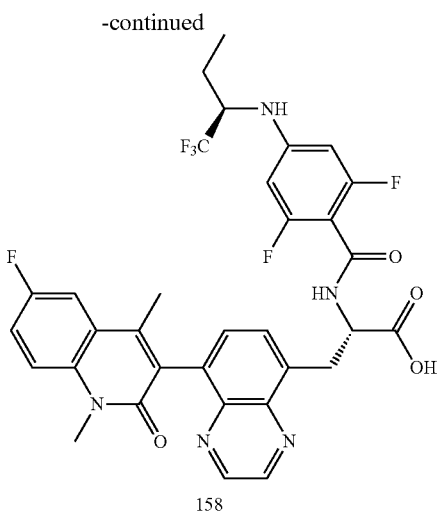

158

Synthesis of tert-butyl (S)-2-((diphenylmethylene)amino)-3-(8-(4,4,5,5-tetramethyl-1,3,2-dioxaborolan-2-yl)quinoxalin-5-yl)propanoate (158B)

To a stirred solution of 158A (718 mg, 1.4 mmol) in DMA (9.3 mL) was added bis(pinacolato)diboron (706 mg, 2.8 mmol), followed by KOAc (409 mg, 4.2 mmol) and cataCXium A Pd G3 (51 mg, 0.07 mmol). The reaction vessel was flushed with nitrogen then heated to 90° C. for 1 hr. EtOAc and water were added to the reaction mixture. The aqueous layer was separated and extracted with EtOAc (2×). The organic layer was washed with water (4×s) and brine, dried over anhydrous $Na_2SO_4$, and concentrated under reduced pressure. The material was purified on silica gel eluting with EtOAc in Hex (0-50%) to give the title compound.

Synthesis of tert-butyl (S)-2-((diphenylmethylene)amino)-3-(8-(6-fluoro-1,4-dimethyl-2-oxo-1,2-dihydroquinolin-3-yl)quinoxalin-5-yl)propanoate (158C)

To a stirred solution of 158B (783 mg, 1.4 mmol), 3-bromo-6-fluoro-1,4-dimethyl-4a,8a-dihydroquinolin-2(1H)-one (H22, 375 mg, 1.4 mmol), $K_3PO_4$ (1032 mg, 4.86 mmol), SPhos Pd G3 (108 mg, 0.14 mmol) were dissolved in toluene (11.6 mL) and heated to 100° C. for 2 h. After cooling to RT, EtOAc and water was added to the reaction mixture. The aqueous layer was separated and extracted with EtOAc (2×). The organic layer was washed with brine, dried over anhydrous $Na_2SO_4$, and concentrated under reduced pressure to give the title compound.

Synthesis of tert-butyl (S)-2-amino-3-(8-(6-fluoro-1,4-dimethyl-2-oxo-1,2-dihydro quinolin-3-yl)quinoxalin-5-yl)propanoate (158D)

To a stirred solution of 158C (1.1 g, 1.7 mmol) in THF (10 mL) was added aq. HCl (2.5 mL, 2N). The reaction mixture was allowed to stir at RT for 30 min. The reaction mixture was diluted with EtOAc and sat. aq. $NaHCO_3$ and then extracted with ethyl acetate. The combined organic layer was dried over anhydrous $Na_2SO_4$, and concentrated under reduced pressure to afford the crude material. The material was purified using 230-400 mesh silica gel column chromatography and eluted with 10% methanol in DCM to afford the title compound.

Synthesis of tert-butyl (S)-2-(2,6-difluoro-4-(((R)-1,1,1-trifluorobutan-2-yl)amino) benzamido)-3-(8-(6-fluoro-1,4-dimethyl-2-oxo-1,2-dihydroquinolin-3-yl)quinoxalin-5-yl) propanoate (158E)

To a stirred solution of 158D (77 mg, 0.17 mmol), (R)-2,6-difluoro-4-((1,1,1-trifluorobutan-2-yl)amino)benzoic acid (47 mg, 0.17 mmol), DIPEA (0.2 mL, 1.17 mmol) in DCM (1.7 mL) and DMF (1.7 mL) was added HATU (70 mg, 0.18 mmol). The reaction mixture was allowed to stir for 45 min and then concentrated. DCM and water was added and extracted with DCM. The organic layer was washed with brine, dried over anhydrous $Na_2SO_4$, and concentrated under reduced pressure. The material was purified by silica gel chromatography eluting with EtOAc in hexanes (0-100%) to give the title compound.

Synthesis of (S)-2-(2,6-difluoro-4-(((R)-1,1,1-trifluorobutan-2-yl)amino)benzamido)-3-(8-(6-fluoro-1,4-dimethyl-2-oxo-1,2-dihydroquinolin-3-yl)quinoxalin-5-yl)propanoic acid (158)

To a stirred solution of 158E (95 mg, 0.13 mmol) in DCM (0.5 mL) was added TFA (0.1 mL, 1.3 mmol). After stirring for 1 h additional TFA (0.1 mL, 1.3 mmol) was added. This was repeated two more times after 2 h and 3 h. After stirring for 5 h, the reaction mixture was concentrated under reduced pressure. The material was purified via reverse phase HPLC to afford the title compound. MS (m/z) 672.3 $[M+H]^+$. 1H NMR (400 MHz, DMSO-d6) δ 8.99 (t, J=2.1 Hz, 1H), 8.85 (d, J=1.9 Hz, 1H), 8.75 (dd, J=18.7, 8.1 Hz, 1H), 7.82 (dd, J=14.4, 7.4 Hz, 1H), 7.74-7.52 (m, 5H), 6.76 (t, J=9.4 Hz, 1H), 6.43 (t, J=11.6 Hz, 2H), 4.92 (ddd, J=12.6, 8.3, 4.5 Hz, 0.5H), 4.86-4.76 (m, 0.5H), 4.30 (s, 1H), 4.08 (dd, J=13.3, 4.5 Hz, 0.5H), 3.85 (dd, J=13.7, 5.3 Hz, 0.5H), 3.66 (d, J=1.4 Hz, 3H), 3.61-3.50 (m, 0.5H), 3.35-3.19 (m, 0.5H), 2.07 (d, J=7.1 Hz, 3H), 1.77 (s, 1H), 1.53 (d, J=10.3 Hz, 1H), 0.93 (t, J=7.3 Hz, 3H).

Example 159

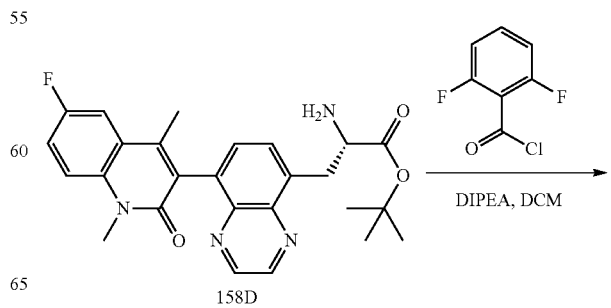

158D

275

-continued

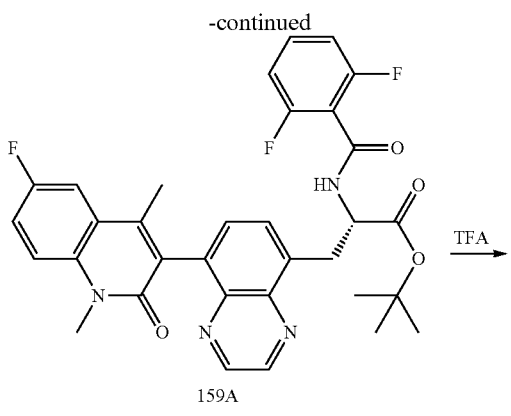
159A

↓ TFA

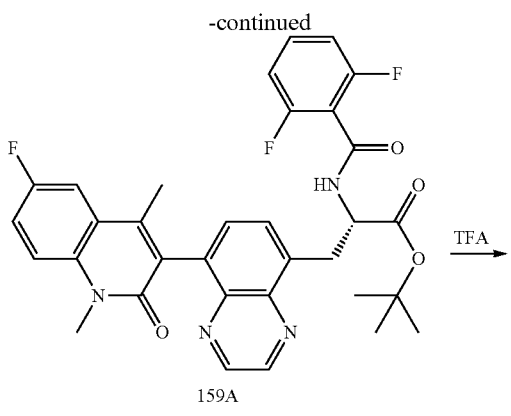
159

Synthesis of tert-butyl (S)-2-(2,6-difluorobenzamido)-3-(8-(6-fluoro-1,4-dimethyl-2-oxo-1,2-dihydroquinolin-3-yl)quinoxalin-5-yl)propanoate (159A)

The title compound was prepared according to the method presented for the synthesis of compound N2 starting with 158D and 2,6-difluorobenzoyl chloride.

(S)-2-(2,6-difluorobenzamido)-3-(8-(6-fluoro-1,4-dimethyl-2-oxo-1,2-dihydroquinolin-3-yl)quinoxalin-5-yl)propanoic acid (159)

The title compound was prepared according to the method presented for the synthesis of compound 158 in Example 158 starting with 159A. MS (m/z) 547.2 [M+H]⁺. 1H NMR (400 MHz, DMSO-d6) δ 9.24 (d, J=8.0 Hz, 1H), 9.17 (d, J=8.5 Hz, 1H), 9.00 (dd, J=4.6, 1.8 Hz, 1H), 8.86 (t, J=1.3 Hz, 1H), 7.82 (dd, J=18.6, 7.4 Hz, 1H), 7.72 (dt, J=10.1, 3.0 Hz, 1H), 7.69-7.54 (m, 3H), 7.47 (p, J=7.6 Hz, 1H), 7.11 (dt, J=12.0, 8.0 Hz, 2H), 5.10-4.97 (m, 1H), 4.98-4.87 (m, 1H), 4.13 (dd, J=13.3, 4.5 Hz, 1H), 3.88 (dd, J=13.7, 5.4 Hz, 1H), 3.66 (d, J=1.4 Hz, 3H), 3.59 (dd, J=13.8, 9.9 Hz, 1H), 3.35-3.20 (m, 1H), 2.08 (d, J=9.7 Hz, 3H).

276

Example 160

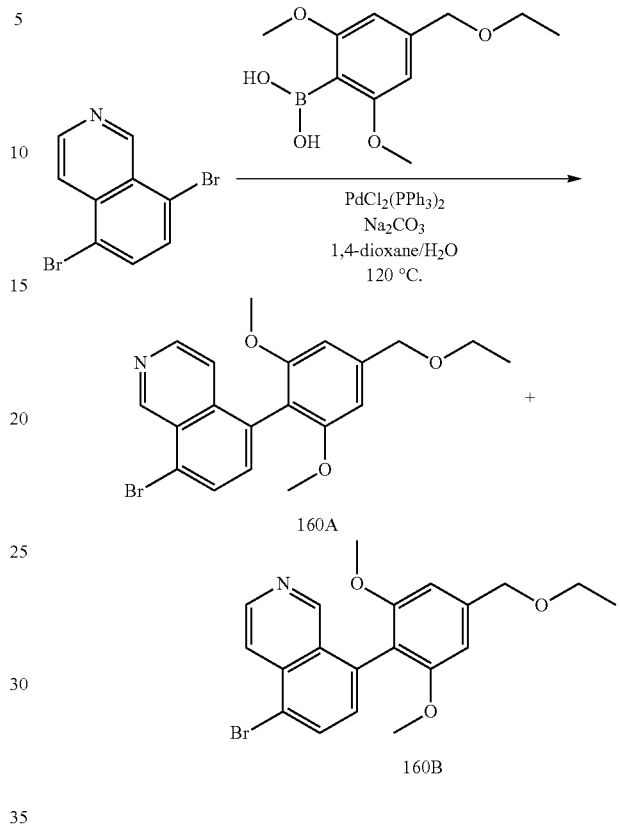

Synthesis of 5-bromo-8-(4-(ethoxymethyl)-2,6-dimethoxyphenyl)isoquinoline (160B)

A microwave vial equipped with a magnetic stir bar was charged with (4-(ethoxymethyl)-2,6-dimethoxyphenyl) boronic acid (800 mg, 3.33 mmol), 5,8-dibromoisoquinoline (3.83 g, 13.3 mmol), and bis(triphenylphosphine)palladium dichloride (234 mg, 333 umol), followed by 1,4-dioxane (16 mL) and aqueous 2.0 M sodium carbonate solution (3.89 mL, 7.78 mmol). The mixture was flashed with Ar for 1 min, then quickly sealed. The reaction mixture was stirred at 120° C. under microwave irradiation for 3 h, then cooled to room temperature, diluted with water, and extracted three times with DCM. The organic layer was combined, and the resulting solution was adsorbed onto silica gel for purification by silica gel chromatography using 20-40% EtOAc in hexanes. The second eluting peak was the title compound. MS (m/z) 402.1 [M+H]⁺.

Synthesis of methyl (Z)-2-((tert-butoxycarbonyl)amino)-3-(8-(4-(ethoxymethyl)-2,6-dimethoxyphenyl)isoquinolin-5-yl)acrylate (160C)

To a solution of 5-bromo-8-(4-(ethoxymethyl)-2,6-dimethoxyphenyl)isoquinoline (160B, 401 mg, 997 µmol) in DMF (10 mL) was added palladium acetate (11 mg, 50 µmol), and the mixture was flushed with N₂ for 30 min. To the resulting mixture were added methyl 2-((tert-butoxycarbonyl)amino)acrylate (501 mg, 2.49 mmol), tetrabutylammonium chloride (332 mg, 1.20 mmol), and triethylamine (161 uL, 1.16 mmol), and the mixture was flushed with N₂ for an additional 2 min. The reaction vial was then sealed and stirred at 90° C. overnight. The reaction mixture was then cooled to room temperature, diluted with EtOAc, and washed with 10% aqueous citric acid solution, sat. NaHCO₃, and brine. The organic layer was concentrated under reduced pressure. The resulting material was purified by silica gel chromatography using 0-100% EtOAc in hexanes to afford the title compound. MS (m/z) 523.3 [M+H]⁺.

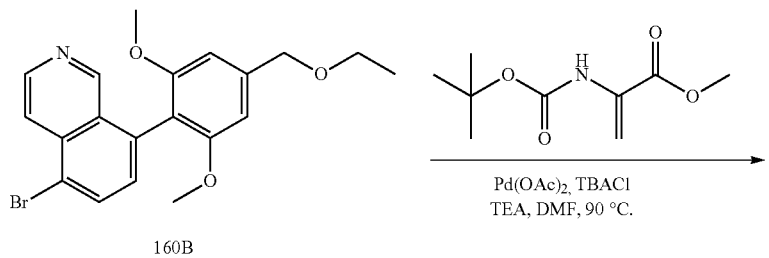

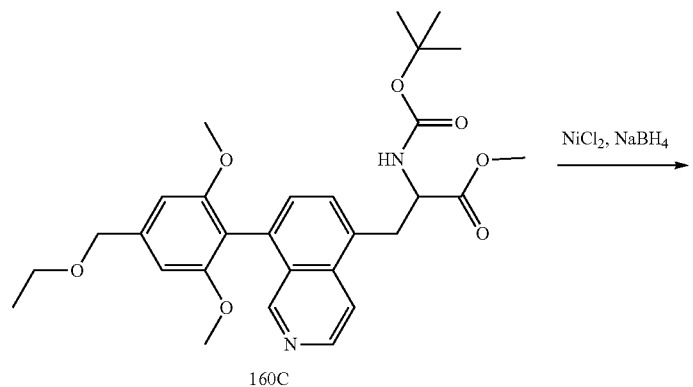

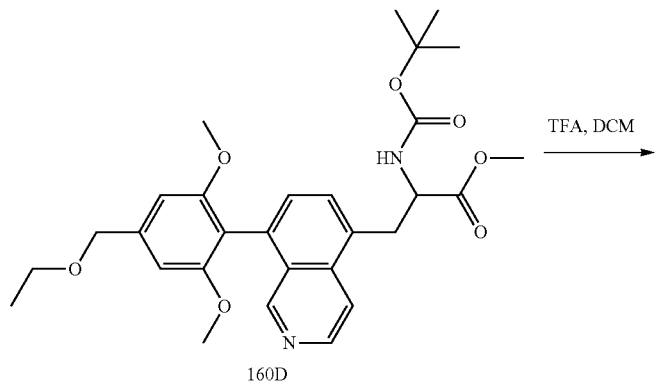

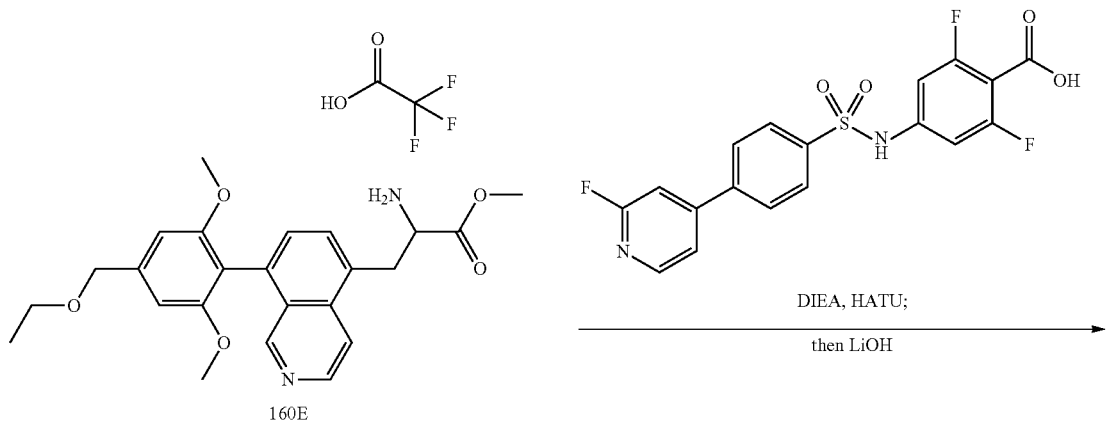

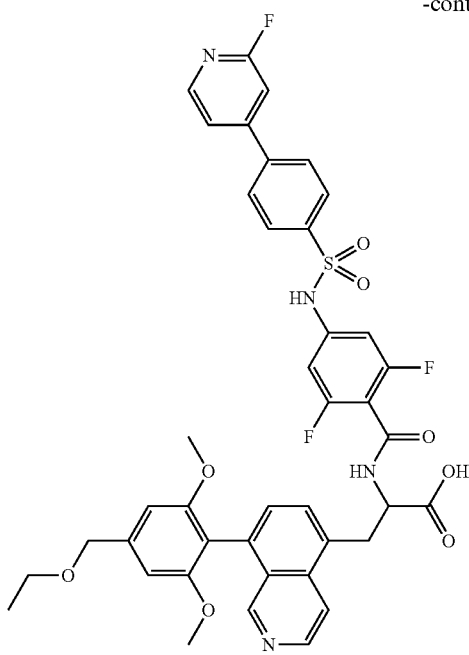

160

Synthesis of methyl 2-((tert-butoxycarbonyl)amino)-3-(8-(4-(ethoxymethyl)-2,6-dimethoxyphenyl)isoquinolin-5-yl)propanoate (160D)

A solution of methyl (Z)-2-((tert-butoxycarbonyl)amino)-3-(8-(4-(ethoxymethyl)-2,6-dimethoxyphenyl)isoquinolin-5-yl)acrylate (160° C., 176 mg, 337 µmol) and nickel(II) chloride (32 mg, 340 µmol) in MeOH (17 mL) was cooled in an ice bath with stirring, then treated a single portion of sodium borohydride (64 mg, 1.7 mmol). After 15 min, the reaction mixture was quenched with sat. aqueous ammonium chloride and extracted three times with DCM. The combined organic layers were concentrated under vacuum, and purified by silica gel chromatography using 0-100% EtOAc in hexanes to afford the title compound. MS (m/z) 525.3 [M+H]$^+$.

Synthesis of methyl 2-amino-3-(8-(4-(ethoxymethyl)-2,6-dimethoxyphenyl) isoquinolin-5-yl)propanoate TFA Salt (160E)

A solution of methyl 2-((tert-butoxycarbonyl)amino)-3-(8-(4-(ethoxymethyl)-2,6-dimethoxyphenyl)isoquinolin-5-yl)propanoate (160D, 140 mg, 267 µmol) in DCM (3 mL) was treated with trifluoroacetic acid (1 mL). The reaction mixture was allowed to stand for 90 min, then was concentrated under vacuum, and co-evaporated with DCM and PhMe to remove residual trifluoroacetic acid, affording the title compound, which was advanced without further purification. MS (m/z) 425.2 [M+H]$^+$.

Synthesis of 2-(2,6-difluoro-4-((4-(2-fluoropyridin-4-yl)phenyl)sulfonamido) benzamido)-3-(8-(4-(ethoxymethyl)-2,6-dimethoxyphenyl)isoquinolin-5-yl)propanoic acid (160)

The title compound was prepared according to the method presented for the synthesis of compound 143 in Example 143 starting with 160E and 2,6-difluoro-4-((4-(2-fluoropyridin-4-yl)phenyl)sulfonamido)benzoic acid. MS (m/z) 801.2 [M+H]$^+$. 1H NMR (400 MHz, DMSO-d6) δ 11.23 (s, 1H), 9.16 (d, J=8.1 Hz, 1H), 8.85 (s, 1H), 8.59 (d, J=6.3 Hz, 1H), 8.35 (d, J=5.3 Hz, 1H), 8.26 (d, J=6.2 Hz, 1H), 8.10-8.05 (m, 2H), 8.01-7.96 (m, 2H), 7.84 (d, J=7.4 Hz, 1H), 7.74 (dt, J=5.4, 1.8 Hz, 1H), 7.61 (s, 1H), 7.49 (d, J=7.4 Hz, 1H), 6.82 (s, 3H), 6.80 (s, 1H), 4.77-4.69 (m, 1H), 4.56 (s, 2H), 3.72 (dd, J=14.6, 4.5 Hz, 1H), 3.63-3.55 (m, 8H), 3.37 (dd, J=14.8, 10.3 Hz, 1H), 1.23 (t, J=7.0 Hz, 3H).

Examples 161 and 162

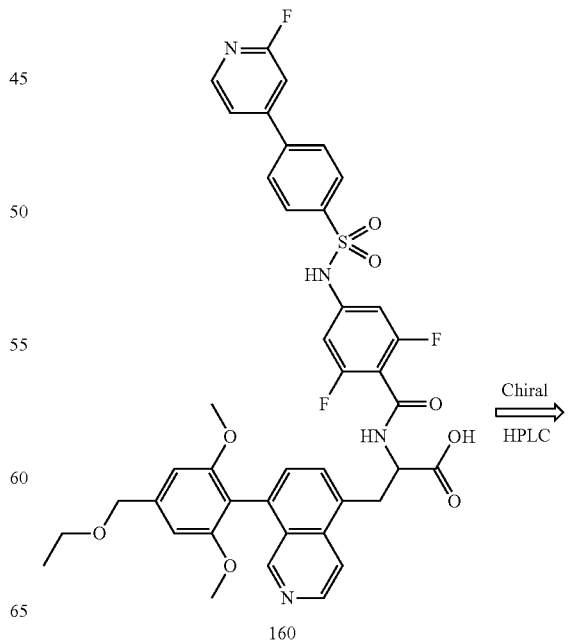

160

Chiral ⇒ HPLC

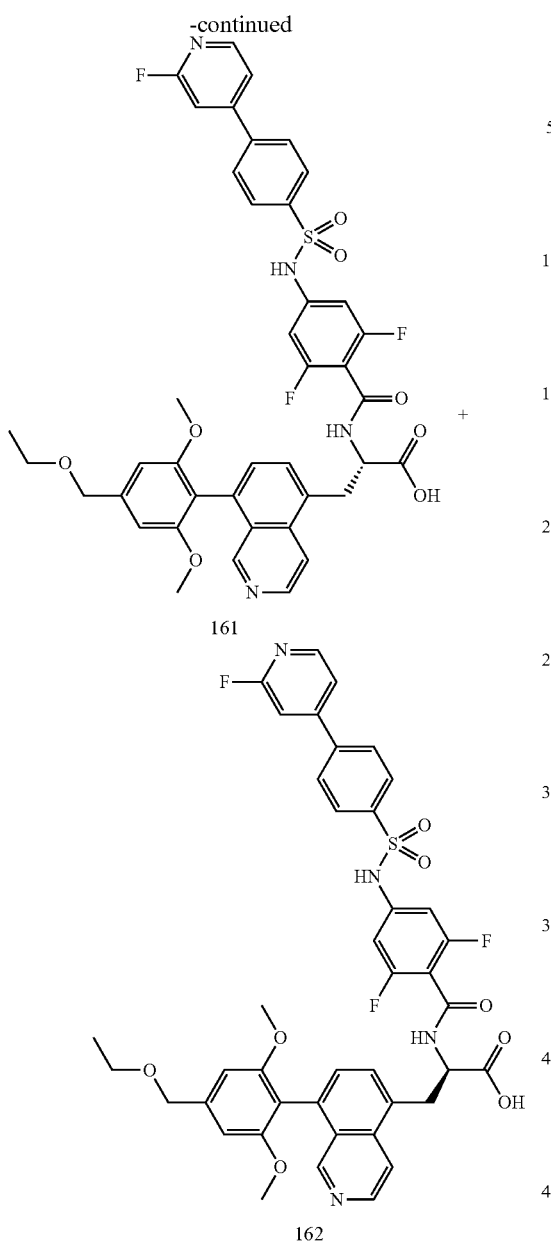

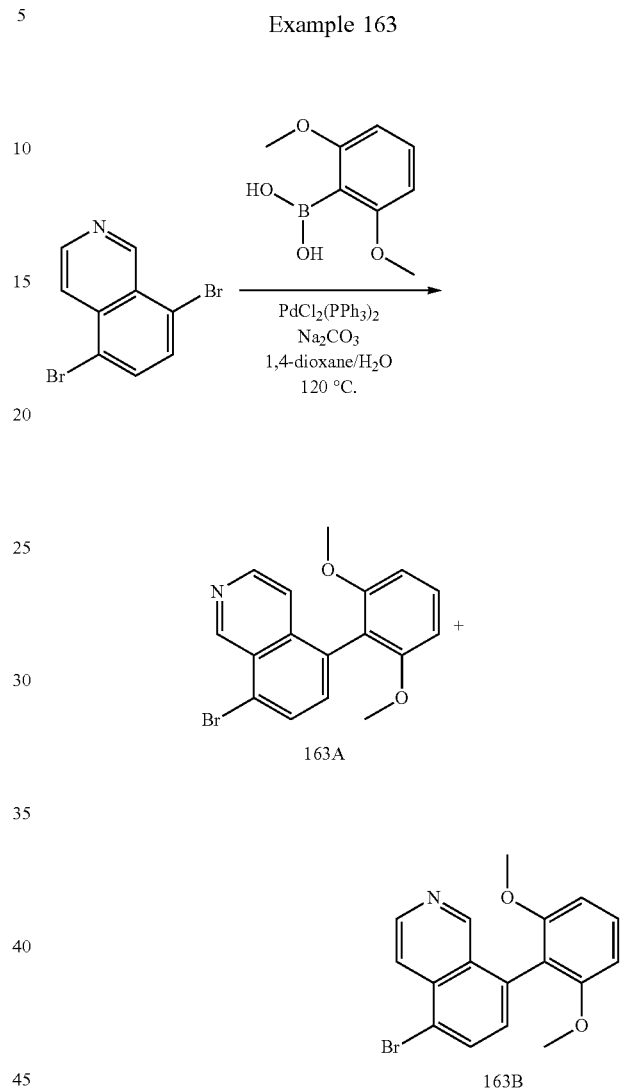

flow rate of 55 mL/min, using an AD-H 5 μm 21×250 mm column. The title compound was identified as the second eluting peak. MS (m/z) 801.2 [M+H]+.

Example 163

Synthesis of (S)-2-(2,6-difluoro-4-((4-(2-fluoropyridin-4-yl)phenyl)sulfonamido) benzamido)-3-(8-(4-(ethoxymethyl)-2,6-dimethoxyphenyl)isoquinolin-5-yl)propanoic acid (161)

160 was separated into its 2 enantiomers by supercritical fluid chromatography using 30% MeOH co-solvent, at a flow rate of 55 mL/min, using an AD-H 5 μm 21×250 mm column. The title compound was identified as the first eluting peak. MS (m/z) 801.2 [M+H]+.

Synthesis of (R)-2-(2,6-difluoro-4-((4-(2-fluoropyridin-4-yl)phenyl)sulfonamido) benzamido)-3-(8-(4-(ethoxymethyl)-2,6-dimethoxyphenyl)isoquinolin-5-yl)propanoic acid (162)

160 was separated into its 2 enantiomers by supercritical fluid chromatography using 30% MeOH co-solvent, at a Synthesis of 8-bromo-5-(2,6-dimethoxyphenyl)isoquinoline (163A)

The title compound was prepared according to the method presented for the synthesis of compound 160B in Example 160 starting with 5,8-dibromoisoquinoline and (2,6-dimethoxyphenyl)boronic acid. The first eluting peak was the title compound.

Synthesis of methyl (Z)-2-((tert-butoxycarbonyl)amino)-3-(5-(2,6-dimethoxyphenyl) isoquinolin-8-yl)acrylate (163C)

The title compound was prepared according to the method presented for the synthesis of compound 160C in Example 160 starting with 160B and methyl 2-((tert-butoxycarbonyl)amino)acrylate.

283

Synthesis of methyl 2-((tert-butoxycarbonyl)amino)-3-(5-(2,6-dimethoxyphenyl) isoquinolin-8-yl)propanoate (163D)

The title compound was prepared according to the method presented for the synthesis of compound 146B in Example 146 starting with 163C.

Synthesis of methyl 2-amino-3-(5-(2,6-dimethoxyphenyl)isoquinolin-8-yl)propanoate TFA Salt (163E)

The title compound was prepared according to the method presented for the synthesis of compound 160E in Example 160 starting with 80D.

284

Synthesis of 2-(4-((4-(1H-1,2,4-triazol-1-yl)phenyl) sulfonamido)-2,6-difluoro benzamido)-3-(5-(2,6-dimethoxyphenyl)isoquinolin-8-yl)propanoic acid (163)

The title compound was prepared according to the method presented for the synthesis of compound 160 in Example 160 starting with 163E and 4-((4-(1H-1,2,4-triazol-1-yl)phenyl)sulfonamido)-2,6-difluorobenzoic acid. MS (m/z) 715.3 [M+H]+. 1H NMR (400 MHz, DMSO-d6) δ 11.18 (s, 1H), 9.81 (s, 1H), 9.39 (s, 1H), 9.13 (d, J=8.2 Hz, 1H), 8.47 (s, 1H), 8.29 (s, 1H), 8.13-7.97 (m, 4H), 7.77 (s, 2H), 7.56 (d, J=6.2 Hz, 1H), 7.48 (t, J=8.4 Hz, 1H), 6.94-6.69 (m, 4H), 4.90-4.80 (m, 1H), 3.85 (dd, J=14.8, 4.6 Hz, 1H), 3.55 (d, J=0.9 Hz, 6H).

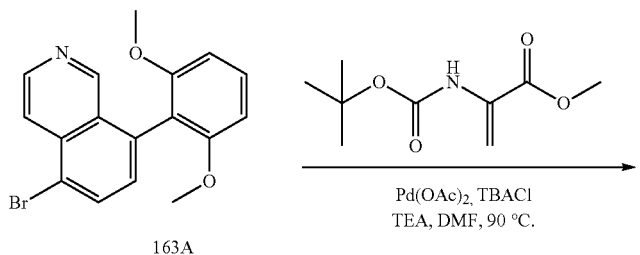

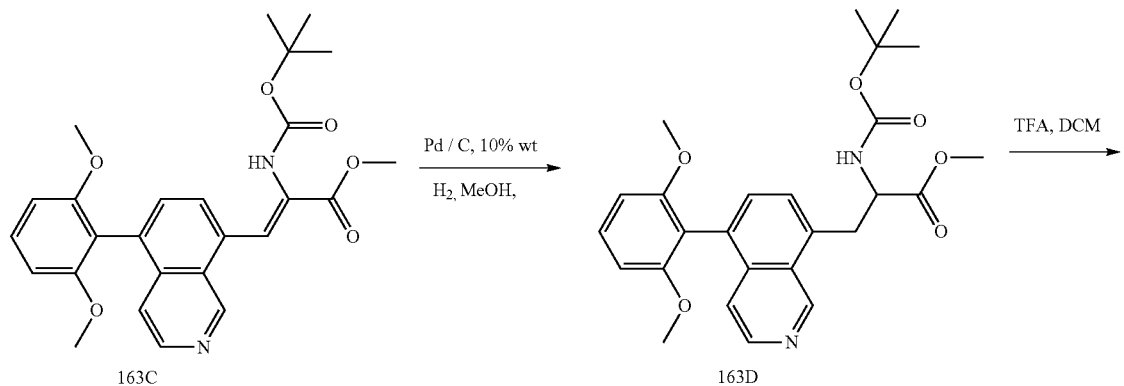

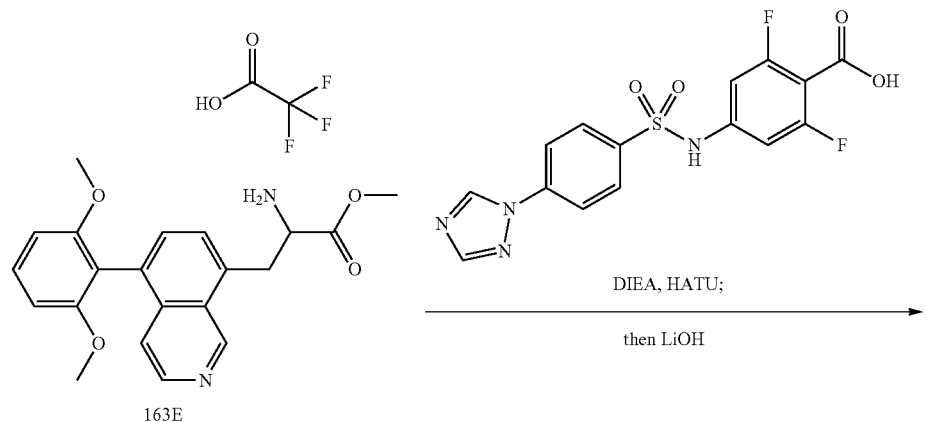

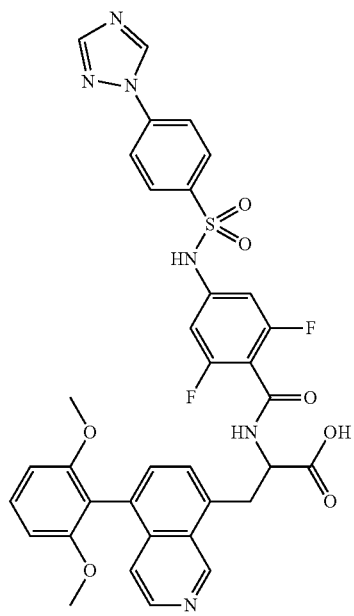
163
Examples 164 and 165
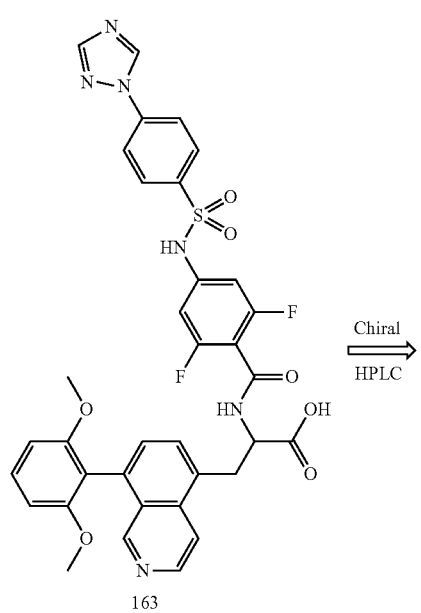
163
Chiral HPLC ⟹
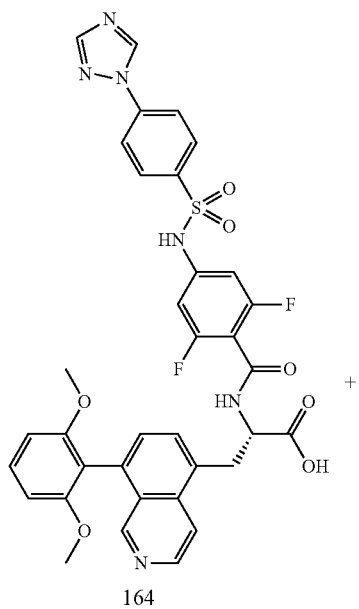
164
+

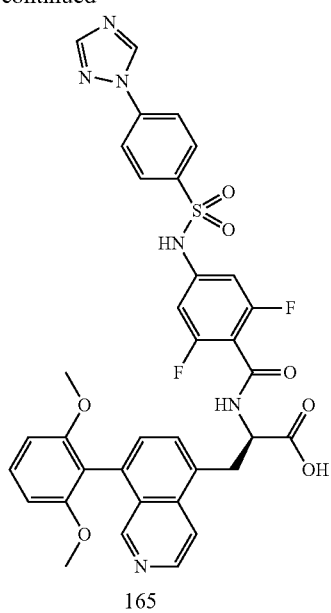

165

Synthesis of (S)-2-(4-((4-(1H-1,2,4-triazol-1-yl)
phenyl)sulfonamido)-2,6-difluoro benzamido)-3-(8-
(2,6-dimethoxyphenyl)isoquinolin-5-yl)propanoic
acid (164)

163 was separated into its 2 enantiomers by supercritical fluid chromatography using heptane:ethanol 8:2/0.1% IPA-TFA, using an AD-H 5 μm 21×250 mm column. The title compound was identified as the first eluting peak. MS (m/z) 715.2 [M+H]+.

Synthesis of (R)-2-(4-((4-(1H-1,2,4-triazol-1-yl)
phenyl)sulfonamido)-2,6-difluoro benzamido)-3-(8-
(2,6-dimethoxyphenyl)isoquinolin-5-yl)propanoic
acid (165)

163 was separated into its 2 enantiomers by supercritical fluid chromatography using heptane:ethanol 8:2/0.1% IPA-TFA, using an AD-H 5 μm 21×250 mm column. The title compound was identified as the second eluting peak. MS (m/z) 715.2 [M+H]+.

Example 166

Synthesis of methyl (S)-3-(8-bromo-1,6-naphthyri-
din-5-yl)-2-((tert-butoxycarbonyl) amino)propanoate
(166A)

A vial equipped with a magnetic stir bar was charged with Zn dust (376 mg, 5.75 mmol) and the head space was purged with $N_2$ for 10 min. DMF (2.6 mL, previously degassed by sparging with $N_2$ for 15 min) was added, followed by solid $I_2$ (21 mg, 82 μmol), and the reaction vial was quickly sealed. The mixture was stirred vigorously for 5 min, then cooled in an ice bath with stirring. Methyl (R)-2-((tert-butoxycarbonyl)amino)-3-iodopropanoate (1.49 g, 4.52 mmol) was added as a solution in degassed DMF (2.6 mL). After 30 min, the ice bath was removed and the reaction mixture was allowed to warm to room temperature. The vial was quickly opened and 8-bromo-5-chloro-1,6-naphthyridine (1.00 g, 4.11 mmol) and trans-dichlorobis(triphenylphosphine)palladium (130 mg, 205 μmol) were added. The vial was then sealed, and the reaction mixture stirred at 50° C. overnight. The reaction mixture was then cooled to room temperature, diluted with water and 10% aqueous citric acid solution, and extracted three times with EtOAc. The combined organics were concentrated under vacuum and purified by silica gel chromatography using 0-100% EtOAc in hexanes to afford the title compound. MS (m/z) 410.1 [M+H]+.

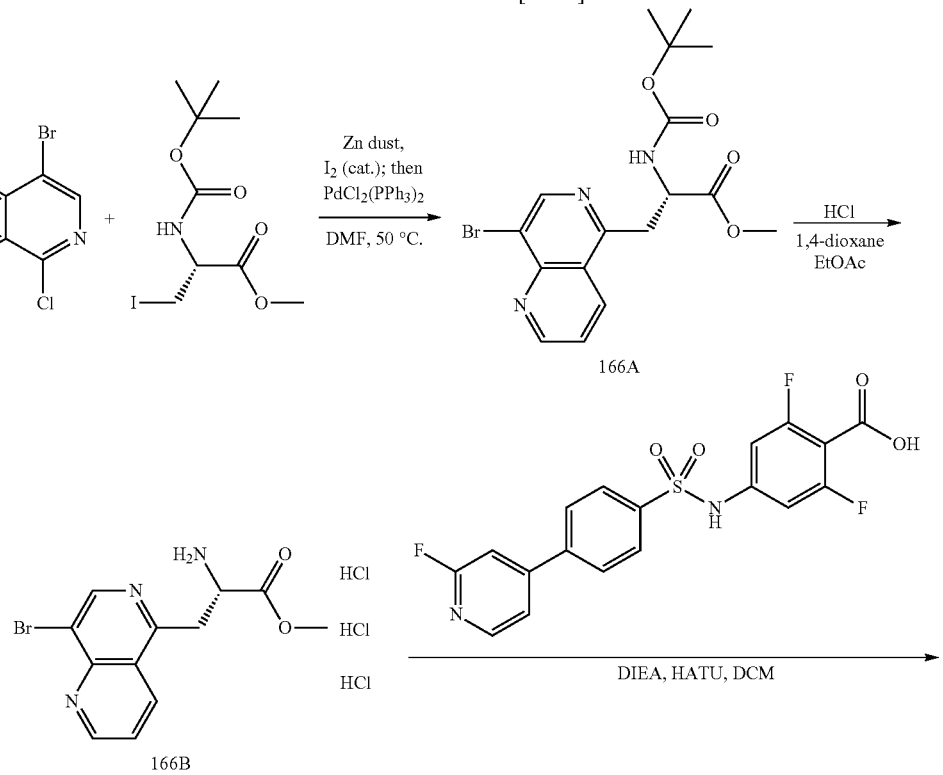

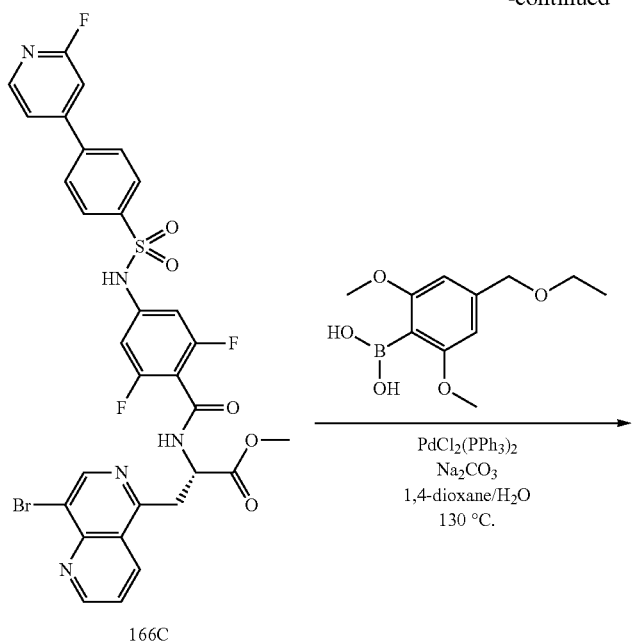

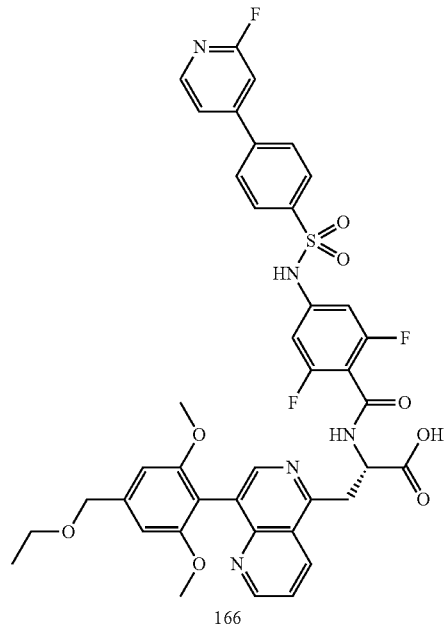

Synthesis of methyl (S)-2-amino-3-(8-bromo-1,6-naphthyridin-5-yl)propanoate trihydrochloride (166B)

A suspension of methyl (S)-3-(8-bromo-1,6-naphthyridin-5-yl)-2-((tert-butoxycarbonyl)amino)propanoate (166A), 691 mg, 1.68 mmol) in EtOAc (11 mL) was treated with 4.0 M hydrogen chloride in 1,4-dioxane (4.21 mL, 16.8 mmol), and the reaction mixture was stirred overnight at room temperature. The reaction mixture was diluted with EtOAc and then filtered. The material was thus dissolved in methanol and filtered. The resulting filtrate was concentrated under vacuum, co-evaporated with EtOAc to remove residual MeOH, and dried under vacuum to afford the title compound. MS (m/z) 310.0 [M+H]$^+$.

Synthesis of methyl (S)-3-(8-bromo-1,6-naphthyridin-5-yl)-2-(2,6-difluoro-4-((4-(2-fluoropyridin-4-yl)phenyl)sulfonamido)benzamido)propanoate (166C)

The title compound was prepared according to the method presented for the synthesis of compound 149D in Example 149 starting with 166B and 2,6-difluoro-4-((4-(2-fluoropyridin-4-yl)phenyl)sulfonamido)benzoic acid.

Synthesis of (S)-2-(2,6-difluoro-4-((4-(2-fluoropyridin-4-yl)phenyl)sulfonamido) benzamido)-3-(8-(4-(ethoxymethyl)-2,6-dimethoxyphenyl)-1,6-naphthyridin-5-yl)propanoic acid (166)

The title compound was prepared according to the method presented for the synthesis of compound 149 in Example 149 starting with 166C and (4-(ethoxymethyl)-2,6-dimethoxyphenyl) boronic acid. MS (m/z) 802.2 [M+H]+. 1H NMR (400 MHz, DMSO-d6) δ 11.20 (s, 1H), 9.02 (d, J=7.8 Hz, 1H), 8.98 (dd, J=4.2, 1.7 Hz, 1H), 8.70 (dd, J=8.6, 1.7 Hz, 1H), 8.37 (s, 1H), 8.36-8.33 (m, 1H), 8.09-8.03 (m, 2H), 8.00-7.94 (m, 2H), 7.76-7.71 (m, 1H), 7.64 (dd, J=8.6, 4.2 Hz, 1H), 7.60 (t, J=1.0 Hz, 1H), 6.82-6.75 (m, 2H), 6.73 (s, 2H), 5.21-5.13 (m, 1H), 4.53 (s, 2H), 3.78 (d, J=6.8 Hz, 2H), 3.61-3.52 (m, 8H), 1.21 (t, J=7.0 Hz, 3H).

Example 167

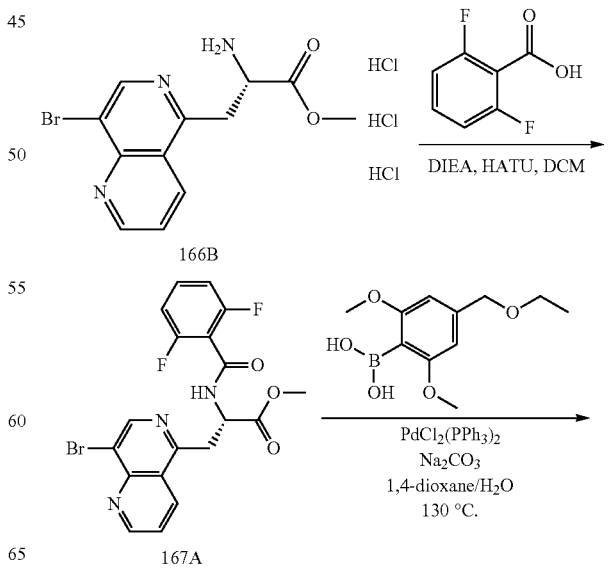

291

-continued

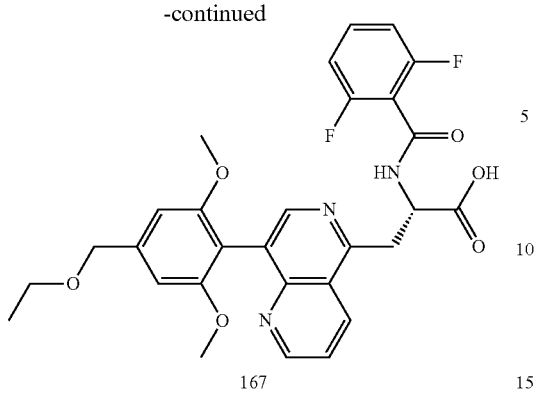
167

Synthesis of methyl (S)-3-(8-bromo-1,6-naphthyridin-5-yl)-2-(2,6-difluoro benzamido)propanoate (167A)

The title compound was prepared according to the method presented for the synthesis of compound 149D in Example 149 starting with 166B and 2,6-difluorobenzoic acid.

Synthesis of (S)-2-(2,6-difluorobenzamido)-3-(8-(4-(ethoxymethyl)-2,6-dimethoxy phenyl)-1,6-naphthyridin-5-yl)propanoic acid (167)

The title compound was prepared according to the method presented for the synthesis of compound 149 in Example 149 starting with 167A and (4-(ethoxymethyl)-2,6-dimethoxyphenyl)boronic acid. MS (m/z) 552.2 [M+H]+. 1H NMR (400 MHz, DMSO-d6) δ 9.19 (d, J=7.8 Hz, 1H), 9.01 (dd, J=4.2, 1.6 Hz, 1H), 8.76 (dd, J=8.6, 1.7 Hz, 1H), 8.43 (s, 1H), 7.69 (dd, J=8.5, 4.2 Hz, 1H), 7.48 (tt, J=8.4, 6.5 Hz, 1H), 7.14-7.05 (m, 2H), 6.74 (s, 2H), 5.30-5.20 (m, 1H), 4.53 (s, 2H), 3.84 (d, J=6.9 Hz, 2H), 3.61-3.54 (m, 8H), 1.22 (t, J=7.0 Hz, 3H).

Example 168

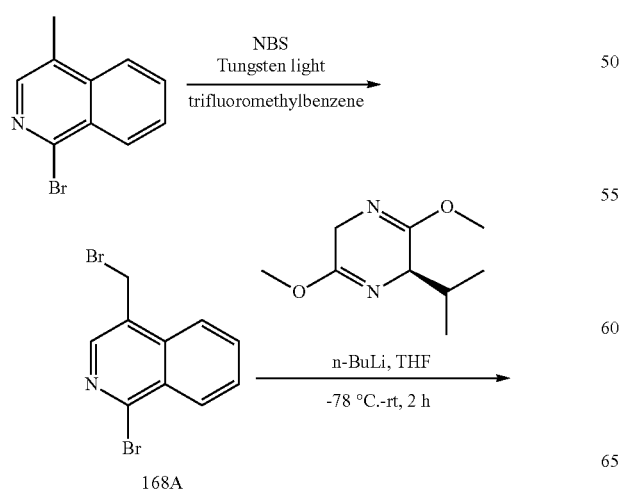
168A

292

-continued

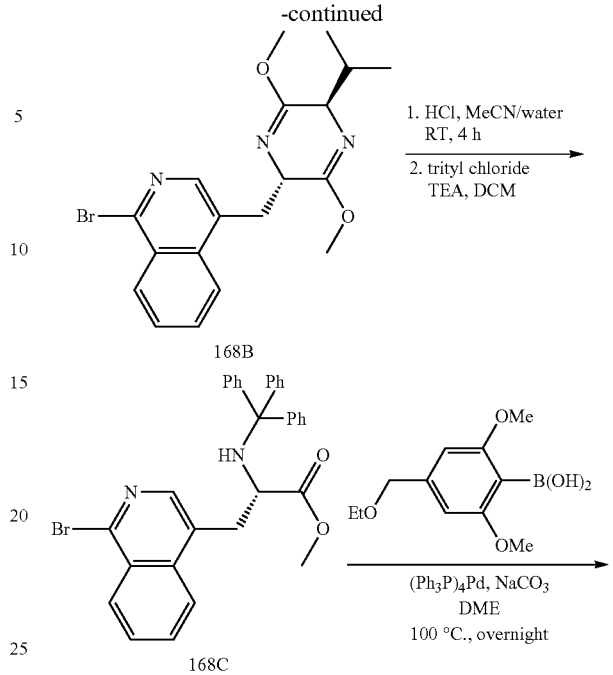
168B

168C

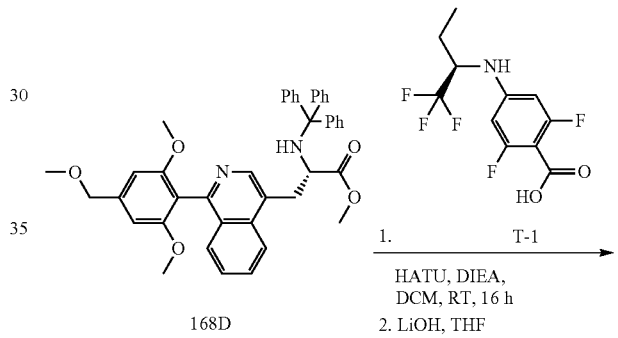
168D

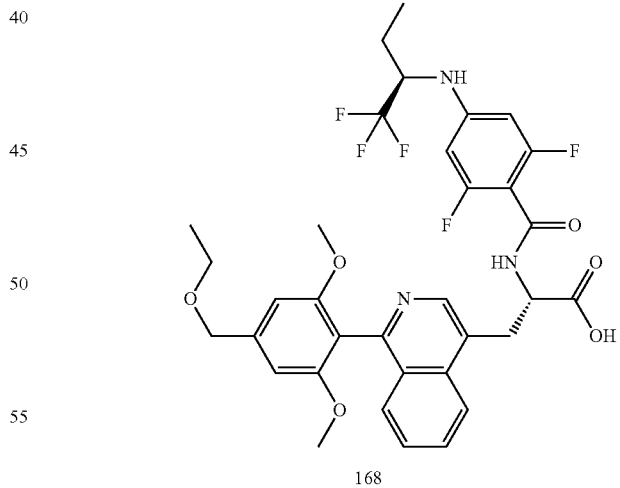
168

Synthesis of 1-bromo-4-(bromomethyl)isoquinoline (168A)

The title compound was prepared according to the method presented for the synthesis of compound 149A in Example 149 starting with 1-bromo-4-methylisoquinoline and NBS.

Synthesis of 1-bromo-4-(((2S,5R)-5-isopropyl-3,6-dimethoxy-2,5-dihydropyrazin-2-yl)methyl)isoquinoline (168B)

The title compound was prepared according to the method presented for the synthesis of compound 149B in Example 149 starting with 168A and (R)-2-isopropyl-3,6-dimethoxy-2,5-dihydropyrazine.

Synthesis of methyl (S)-3-(1-bromoisoquinolin-4-yl)-2-(tritylamino)propanoate (168C)

To a stirred solution of 168B (675 mg, 2 mmol) in acetonitrile was added 2 M hydrochloric acid (10 mL, 20 mmol), and the reaction was allowed to stir for 4 h at room temperature. It was concentrated, and the crude material was dissolved in DCM, trityl chloride (0.47 g, 2 mmol) was added. The reaction mixture was stirred at RT for 1 h, then purified with by silica gel chromatography using 0-100% EtOAc in hexanes to afford the title compound.

Synthesis of (S)-3-(1-(4-(ethoxymethyl)-2,6-dimethoxyphenyl)isoquinolin-4-yl)-2-(tritylamino)propanoic acid (168D)

The title compound was prepared according to the method presented for the synthesis of compound 143B in Example 143 starting with 168D and (4-(ethoxymethyl)-2,6-dimethoxyphenyl)boronic acid.

Synthesis of (S)-2-(2,6-difluoro-4-(((R)-1,1,1-trifluorobutan-2-yl)amino)benzamido)-3-(1-(4-(ethoxymethyl)-2,6-dimethoxyphenyl)isoquinolin-4-yl)propanoic acid (168)

The title compound was prepared according to the method presented for the synthesis of compound 160 in Example 160 starting with 168D and T1. MS (m/z) 676.4 [M+H]+. 1H NMR (400 MHz, DMSO-d6) δ 8.84 (d, J=8.1 Hz, 1H), 8.50 (s, 1H), 8.38 (s, 1H), 8.10 (s, 1H), 7.77 (s, 2H), 6.88 (d, J=3.1 Hz, 2H), 6.78 (d, J=9.4 Hz, 1H), 6.44 (d, J=11.7 Hz, 2H), 4.81 (s, 1H), 4.60 (s, 2H), 4.31 (d, J=9.3 Hz, 1H), 3.78 (s, 1H), 3.63 (s, 3H), 3.60 (d, J=7.0 Hz, 2H), 3.46 (d, J=12.3 Hz, 1H), 3.11 (ddd, J=12.1, 7.0, 4.2 Hz, 1H), 1.77 (ddd, J=13.8, 7.8, 3.4 Hz, 1H), 1.52 (ddd, J=13.7, 10.2, 7.0 Hz, 1H), 1.25 (dt, J=10.6, 6.6 Hz, 6H), 1.18 (t, J=7.3 Hz, 1H), 0.92 (t, J=7.3 Hz, 3H).

Example 169

Synthesis of 2-bromo-5-(((tert-butyldimethylsilyl)oxy)methyl)phenol (169A)

To a stirred solution of 2-bromo-5-(hydroxymethyl)phenol (4.9 g, 24 mmol) and imidazole (1.8 g, 27 mmol) in DCM (30 mL) and THF (10 mL) was added a solution of TBSCl (4.0 g, 27 mmol) in THF (5 mL) dropwise over 30 min at 0° C. The reaction mixture was stirred for 3 hrs. EtOAc and water was added to the reaction mixture. The aqueous layer was separated and extracted with EtOAc (2×). The combined organics were washed with brine, dried over anhydrous Na$_2$SO$_4$, and concentrated under reduced pressure. The material was purified on silica gel eluting with EtOAc in Hex (0-100%) to give the title compound.

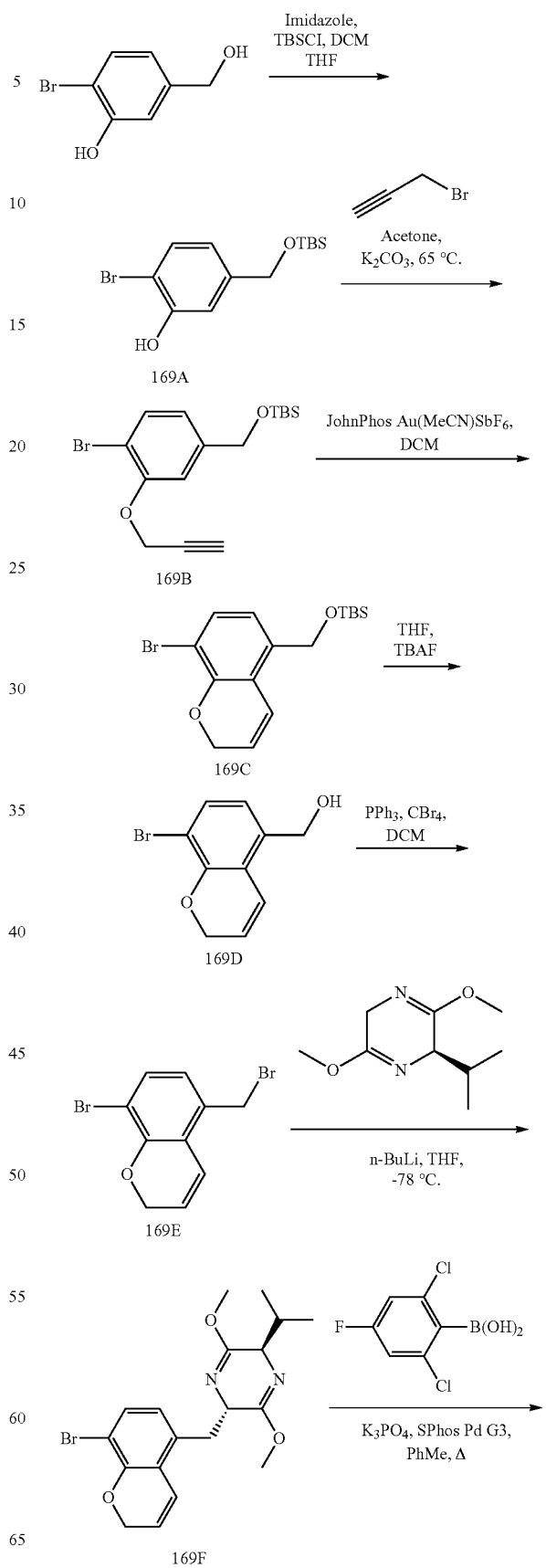

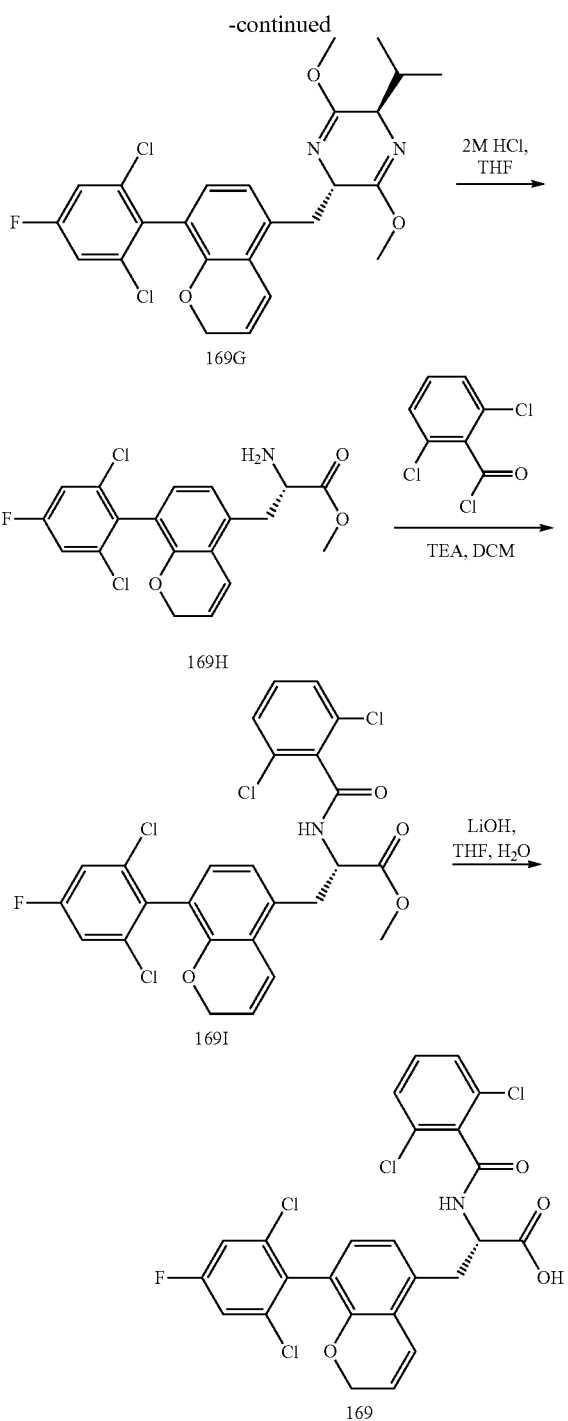

Synthesis of ((4-bromo-3-(prop-2-yn-1-yloxy)benzyl)oxy)(tert-butyl)dimethylsilane (169B)

To a stirred solution of 169A (200.2 mg, 0.63 mmol) in acetone (2.10 mL) was added potassium carbonate (174.4 mg, 1.26 mmol), followed by propargyl bromide (69 µL, 0.92 mmol). The reaction vessel was sealed and heated to 65° C. for 3 hours. After cooling to room temperature, the reaction was diluted with water and EtOAc. The aqueous layer was extracted and the organic layer was dried over anhydrous $MgSO_4$ and concentrated under reduced pressure.

The material was purified by silica gel chromatography using 0-10% EtOAc in hexanes to afford the title compound.

Synthesis of ((8-bromo-2H-chromen-5-yl)methoxy)(tert-butyl)dimethylsilane (169C)

A reaction vessel containing a solution of 169B (192.6 mg, 0.54 mmol) in dichloromethane (5.4 mL) was wrapped in aluminum foil to avoid decomposition from light. To this solution was added (acetonitrile)[(2-biphenyl)di-tert-butylphosphine]gold(I) hexafluoroantimonate (20.9 mg, 0.027 mmol) and the reaction was stirred at room temperature for 16 hours. The reaction was concentrated under reduced pressure and the resulting residue was purified by silica gel chromatography using 0-10% EtOAc in hexanes to afford the title compound.

Synthesis of (8-bromo-2H-chromen-5-yl)methanol (169D)

To a stirred solution of 169C (132.6 mg, 0.37 mmol) in THF (1.87 mL) was added tetrabutylammonium fluoride (1.0M in THF, 0.45 mL, 0.45 mmol) dropwise. The reaction was stirred at room temperature for 15 min and then quenched with water. The reaction was concentrated under reduced pressure and then diluted with water and EtOAc. The aqueous layer was extracted and the organic layer was dried over anhydrous $MgSO_4$ and concentrated under reduced pressure. The material was purified by silica gel chromatography using 0-50% EtOAc in hexanes to afford the title compound.

Synthesis of 8-bromo-5-(bromomethyl)-2H-chromene (169E)

To a solution of compound 169D (20.0 g, 87.30 mmol) in DCM (0.180 L) were added triphenylphosphine (34.31 g, 130.9 mmol) and carbon tetrabromide (43.4 g, 130.9 mmol) at room temperature. The reaction mixture was allowed to stir at RT for 1 hr. The reaction mixture was concentrated under reduced pressure and purified via 100-200 mesh silica gel chromatography eluting 2-6% EA in hexanes to afford the title compound.

Synthesis of (2S,5R)-2-((8-bromo-2H-chromen-5-yl)methyl)-5-isopropyl-3,6-dimethoxy-2,5-dihydropyrazine (169F)

To a stirred solution of (R)-2,5-Dihydro-3,6-dimethoxy-2-isopropylpyrazine (0.44 mL, 184 mmol) in 2-MeTHF (8.1 mL) was added nBuLi (1.6 mL, 1.6M solution in hexanes) dropwise at −78° C. After stirring for 25 min, a solution of 169E (500 mg, 1.6 mmol) in 2-MeTHF (13 mL) was added dropwise. The reaction mixture was allowed to stir at −78° C. for 45 min. $H_2O$ was added and the reaction mixture was warmed to RT. The aqueous layer was separated and extracted with EtOAc (2×). The organic layer was washed with brine, dried over anhydrous $Na_2SO_4$, and concentrated under reduced pressure. The material was purified by silica gel chromatography using 0-40% EtOAc in hexanes to give the title compound.

Synthesis of (2S,5R)-2-((8-(2,6-dichloro-4-fluorophenyl)-2H-chromen-5-yl)methyl)-5-isopropyl-3,6-dimethoxy-2,5-dihydropyrazine (169G)

To a stirred solution of 169F (303 mg, 0.74 mmol), (2,6-dichloro-4-fluorophenyl)boronic acid (308 mg, 1.47 mmol), K$_3$PO$_4$ (547 mg, 2.58 mmol), SPhos Pd G3 (575 mg, 0.74 mmol) were dissolved in toluene (5.8 mL) and heated to 100° C. for 2 hours. After cooling to RT, EtOAc and water were added to the reaction mixture. The aqueous layer was separated and extracted with EtOAc (2×). The organic layer was washed with brine, dried over anhydrous Na$_2$SO$_4$, and concentrated under reduced pressure. The material was purified on silica gel eluting with EtOAc in Hex (0-50%) to give the title compound.

Synthesis of methyl (S)-2-amino-3-(8-(2,6-dichloro-4-fluorophenyl)-2H-chromen-5-yl)propanoate (169H)

To a stirred solution of 169G (100 mg, 0.2 mmol) in MeCN (2 mL) at RT was added aq. HCl (0.5 mL, 2M). The reaction mixture was allowed to stir for 2 h and then carefully poured into sat aq. NaHCO$_3$. EtOAc was then added to the mixture. The aqueous layer was separated and extracted with EtOAc (2×, ~10 mL) and 2-MeTHF (1×, ~10 mL). The organic layers were combined, dried over anhydrous Na$_2$SO$_4$, and concentrated under reduced pressure. The material was purified on silica gel eluting with DCM in MeOH (0-5%) to give the title compound.

Synthesis of methyl (S)-3-(8-(2,6-dichloro-4-fluorophenyl)-2H-chromen-5-yl)-2-(2,6-dichlorobenzamido)propanoate (169I)

To a stirred solution of 169H (0.37 mmol) in DCM (3.7 mL) was added 2,6-dichlorobenzoyl chloride (0.44 mmol) and DIPEA (0.32 mL, 1.8 mmol). The reaction mixture was allowed to stir for 10 min, then DCM and water were added to the reaction mixture. The aqueous layer was separated and extracted with DCM (2×). The organic layer was washed with brine, dried over anhydrous Na$_2$SO$_4$, and concentrated under reduced pressure. The material was purified on silica gel eluting with EtOAc in Hex (0-50%) to give the title compound.

Synthesis of (S)-3-(8-(2,6-dichloro-4-fluorophenyl)-2H-chromen-5-yl)-2-(2,6-dichlorobenzamido)propanoic acid (169)

The title compound was prepared according to the method presented for the synthesis of compound 1 of Example 1 starting with 169I. MS (m/z) 554.0 [M+H]$^+$. 1H NMR (400 MHz, DMSO-d6) δ 12.90 (s, 1H), 9.17 (d, J=8.3 Hz, 1H), 7.60 (d, J=8.6 Hz, 2H), 7.47-7.36 (m, 3H), 6.98 (d, J=7.9 Hz, 1H), 6.87 (d, J=7.9 Hz, 1H), 6.82 (dt, J=10.1, 1.8 Hz, 1H), 6.03 (dt, J=10.1, 3.7 Hz, 1H), 4.66 (dt, J=4.0, 2.0 Hz, 2H), 4.61 (ddd, J=10.5, 8.3, 4.1 Hz, 1H), 3.25 (dd, J=14.3, 4.1 Hz, 1H), 2.95 (dd, J=14.3, 10.5 Hz, 1H).

Example 170

Synthesis of methyl 4-bromo-3-((2-methylbut-3-yn-2-yl)oxy)benzoate (170A)

To a flame dried flask containing methyl 4-bromo-3-hydroxybenzoate (2.3 g, 10 mmol) and ACN (100 mL) at 0° C. was added 1,8-Diazabicyclo[5.4.0]undec-7-ene (1.94 mL, 13 mmol) and copper(II) chloride (13 mg, 0.1 mmol). 3-Chloro-3-methylbut-1-yne (1.33 g, 13 mmol) was then added and the mixture was stirred for 16 h, concentrated and chromatographed on silica gel eluting with EtOAc in hexanes to afford the title compound.

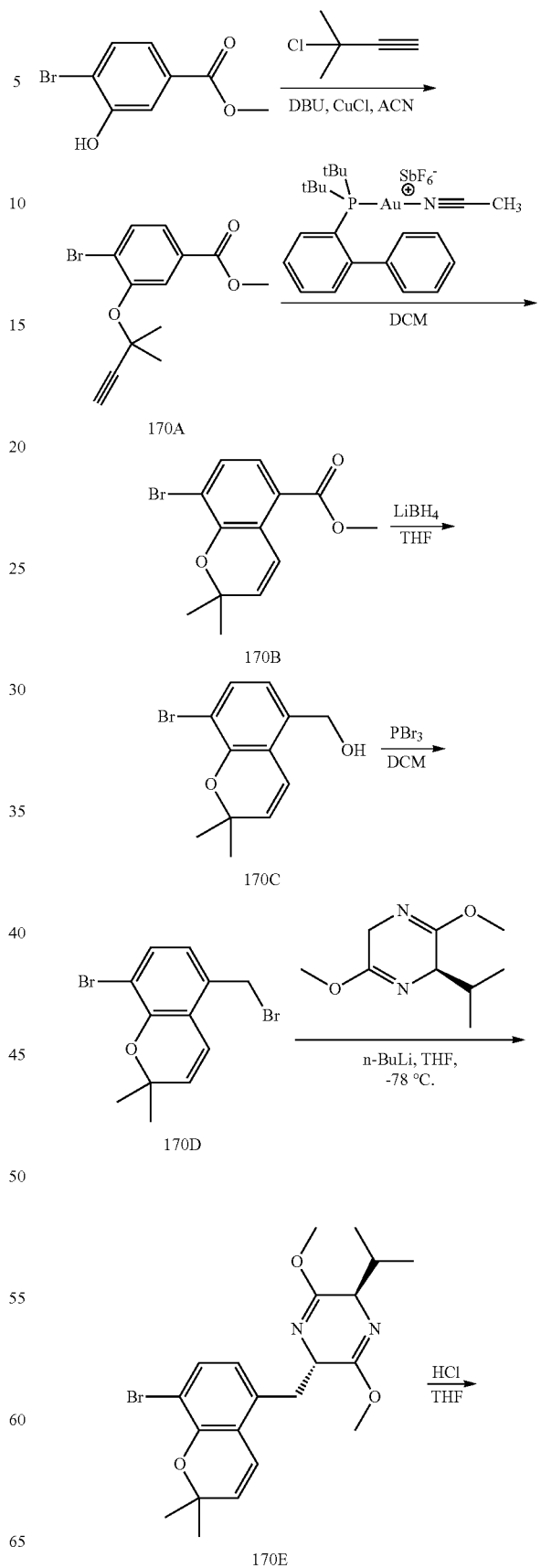

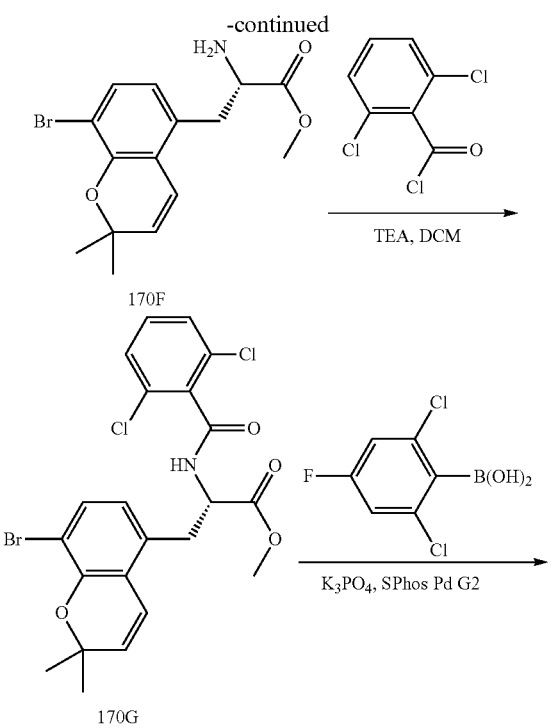

170F

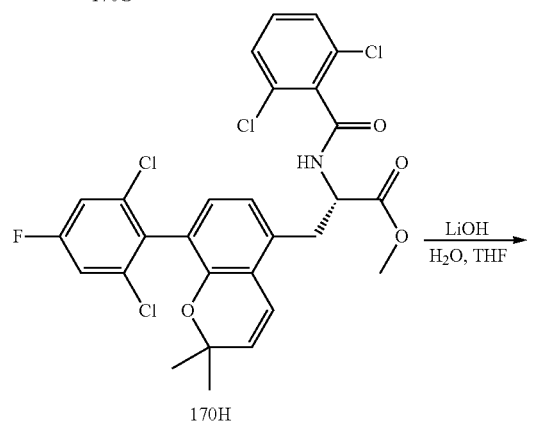

170G

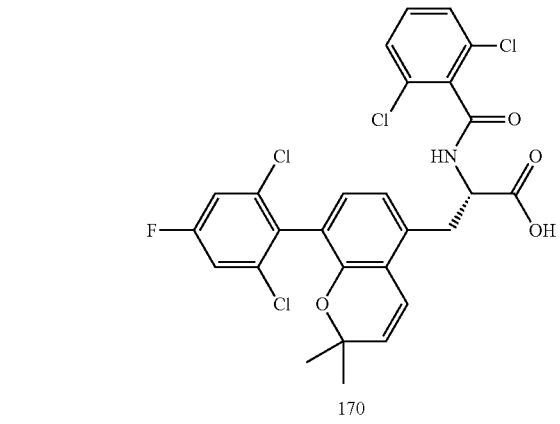

170H

170

Synthesis of methyl 8-bromo-2,2-dimethyl-2H-chromene-5-carboxylate (170B)

To a stirring solution of methyl 4-bromo-3-((2-methylbut-3-yn-2-yl)oxy)benzoate (3 g, 10.1 mmol) in DCM (50 mL) was added (Acetonitrile)[(2-biphenyl)di-tert-butylphosphine]gold(I) hexafluoro antimonate (0.39 g, 0.5 mmol). After 2 hours the mixture was concentrated and chromatographed on silica gel eluting with EtOAc in hexanes (0-40%) to afford the title compound.

Synthesis of (8-bromo-2,2-dimethyl-2H-chromen-5-yl)methanol (170C)

To a stirring solution of methyl 8-bromo-2,2-dimethyl-2H-chromene-5-carboxylate (600 mg, 2 mmol) and THF (5 mL) at 0° C. was added lithium borohydride (5 mL, 5 mmol, 1N) and the mixture was stirred ON. 1 mL of a concentrated Rochelle's salt solution was added and the mixture was stirred for an additional 1 h. The mixture was filtered washed with EtOAc and the eluent was concentrated and the residue was chromatographed on silica gel eluting with EtOAc in hexanes (0-60%) to afford the title compound.

Synthesis of 8-bromo-5-(bromomethyl)-2,2-dimethyl-2H-chromene (170D)

To a stirring solution of (8-bromo-2,2-dimethyl-2H-chromen-5-yl)methanol (527 mg, 1.96 mmol) in DCM (3 mL) was added phosphorous tribromide (1N in DCM, 1.96 mL, 1.96 mmol) and the mixture was stirred ON, loaded directly onto silica gel and chromatographed eluting with EtOAc in hexanes (0-20%) to afford the title compound.

Synthesis of (2S,5R)-2-((8-bromo-2,2-dimethyl-2H-chromen-5-yl)methyl)-5-isopropyl-3,6-dimethoxy-2,5-dihydropyrazine (170E)

To a flame dried vial containing (R)-2,5-dihydro-3,6-dimethoxy-2-isopropylpyrazine (1.01 ml, 5.66 mmol) and THF (28 mL) at −78° C. was added n-butyllithium 2.5 M in hexanes (2.26 ml, 5.66 mmol) dropwise. The reaction was stirred for 20 minutes when 8-bromo-5-(bromomethyl)-2,2-dimethyl-2H-chromene was added (1.044 g, 3.1 mmol) and the mixture was stirred for 1 h at −78° C. and ammonium chloride (sat) was added and the mixture was extracted with EtOAc, concentrated, and the residue was chromatographed on silica gel eluting with EtOAc in hexanes (0-10%) to afford the title compound.

Synthesis of methyl (S)-2-amino-3-(8-bromo-2,2-dimethyl-2H-chromen-5-yl) propanoate (170F)

To a stirred solution of (2S,5R)-2-((8-bromo-2,2-dimethyl-2H-chromen-5-yl)methyl)-5-isopropyl-3,6-dimethoxy-2,5-dihydropyrazine and THF (20 mL) was added 2N HCl (11.5 mL, 23 mmol) and the mixture was stirred for 2 h, diluted with EtOAc and treated with sodium bicarbonate (sat) until basic. The organic layer was concentrated and chromatographed on silica gel eluting with MeOH in dichloromethane (0-30%) to afford the title compound.

Synthesis of methyl (S)-3-(8-bromo-2,2-dimethyl-2H-chromen-5-yl)-2-(2,6-dichloro benzamido)propanoate (170G)

To a stirred solution methyl (S)-2-amino-3-(8-bromo-2,2-dimethyl-2H-chromen-5-yl)propanoate (360 mg, 1.06 mmol) and DCM (5 mL) at 0° C. was added N-ethyl-N-isopropylpropan-2-amine (0.37 mL, 2.12 mmol), and 2,6-dichlorobenzoyl chloride (0.15 mL, 1.06 mmol) dropwise. The mixture was stirred for 4 h and sodium bicarbonate (sat, 1 mL) was added and the organic layer was concentrated and chromatographed on silica gel eluting with EtOAc in hexanes (0-100%) to afford the title compound.

Synthesis of (S)-3-(8-(2,6-dichloro-4-fluorophenyl)-2,2-dimethyl-2H-chromen-5-yl)-2-(2,6-dichlorobenzamido)propanoic acid (170)

To a stirred solution of methyl (S)-3-(8-(2,6-dichloro-4-fluorophenyl)-2,2-dimethyl-2H-chromen-5-yl)-2-(2,6-dichlorobenzamido)propanoate (38 mg, 0.06 mmol) and THF (2 mL) was added lithium hydroxide (1N, 0.5 mL, 0.5 mmol) and stirred for 2 h. The mixture was concentrated, TFA was added and the mixture was again concentrated under reduced pressure and chromatographed on reversed phase eluting with ACN and water containing 0.4% TFA to afford the title compound. MS (m/z) 583.8 [M+H]$^+$. 1H NMR (400 MHz, DMSO-d6) δ 1H NMR (400 MHz, DMSO-d6) δ 9.13 (d, J=8.4 Hz, 1H), 7.62-7.52 (m, 2H), 7.49-7.28 (m, 3H), 6.90 (d, J=7.9 Hz, 1H), 6.80 (d, J=7.8 Hz, 1H), 6.69 (d, J=10.0 Hz, 1H), 5.87 (d, J=10.0 Hz, 1H), 4.66-4.53 (m, 1H), 3.26 (dd, J=14.2, 4.2 Hz, 1H), 2.92 (dd, J=14.3, 10.6 Hz, 1H), 1.23 (d, J=7.7 Hz, 7H).

The compounds in Table 1 were prepared by processes described herein.

Table 1

| Example | Structure | 1H-NMR | M/Z [M + H]+ |
|---|---|---|---|
| 171 | 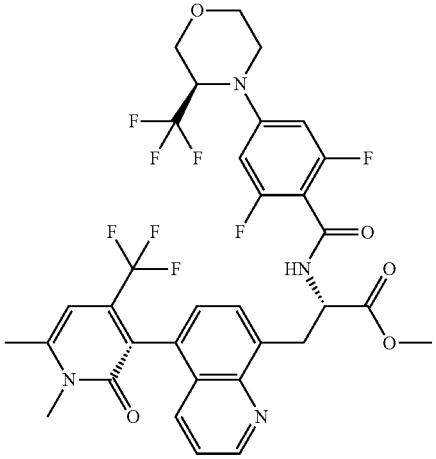 | 1H NMR (400 MHz, DMSO-d6) δ 9.12 (d, J = 7.1 Hz, 1H), 8.95 (dd, J = 4.2, 1.7 Hz, 1H), 7.82 (dd, J = 8 5, 1.7 Hz, 1H), 7.63 (d, J = 7.3 Hz, 1H), 7.49 (dd, J = 8.5, 4.2 Hz. 1H), 7.25 (d, J = 7.3 Hz, 1H), 6.78 (d, J = 11.7 Hz, 2H), 6.69-6.59 (m, 1H). 4.90 (ddd, J = 15.7, 11.1, 5.5 Hz, 2H), 4.17 (d, J = 12.7 Hz, 1H), 3.96 (dd, J = 11.4, 3.8 Hz, 2H), 3.80-3.66 (m, 2H), 3.52 (s, 3H), 3.49 (s, 3H), 3.44 (d, J = 13.2 Hz, 2H), 3.25 (t, J = 12.2 Hz, 1H), 2.55 (s, 3H). | 713.2 |
| 172 | 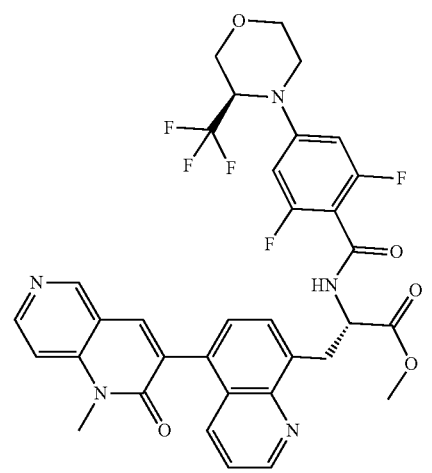 [SMILES: COC(=O)[C@H](Cc1ccc(-c2cc3cnccc3n(C)c2=O)c2cccnc12)NC(=O)c1c(F)cc(N2CCOC[C@@H]2C(F)(F)F)cc1F] | 1H NMR (400 MHz, DMSO-d6) δ 9.19-9.02 (m, 2H), 8.75 (d, J = 6.4 Hz, 1H), 8.26-8.11 (m, 2H), 7.80 (d, J = 6.5 Hz, 1H), 7.71 (d, J = 8.5 Hz, 1H), 7.65 (t, J = 7.7 Hz, 1H), 7.50 (dt. J = 11.2, 5.6 Hz, 2H), 7.39 (d, J = 7.2 Hz, 1H), 6.79 (d, J = 11.8 Hz, 2H), 4.99-4.85 (m, 1H), 4.77 (q, J = 7.7, 7.0 Hz, 1H), 4.17 (d, J = 12.7 Hz, 1H), 3.96 (dd, J = 11.4, 3.6 Hz, 1H), 3.72 (s, 5H), 3.68 (s, 3H), 3.57 (d, J = 12.2 Hz, 2H), 3.27 (d, J = 14.6 Hz, 2H). | 681.4 |

Table 1-continued

| Example | Structure | 1H-NMR | M/Z [M + H]+ |
|---|---|---|---|
| 173 | 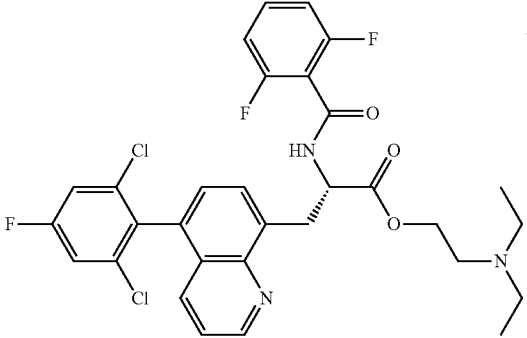 [SMILES: CCN(CC)CCOC(=O)[C@H](Cc1ccc(-c2c(Cl)cc(F)cc2Cl)c2cccnc12)NC(=O)c1c(F)cccc1F] | 1H NMR (400 MHz, DMSO-d6) δ 9.37 (d, J = 7.6 Hz, 1H), 9.25 (s, 1H), 8.97 (dd, J = 4.1, 1.7 Hz, 1H), 7.77 (dd, J = 8.0, 3.9 Hz, 3H), 7.71 (dd, J = 8.5, 1.7 Hz, 1H), 7.54 (dd, J = 8.5, 4.1 Hz, 1H), 7.52-7.46 (m, 1H), 7.44 (d, J = 7.3 Hz, 1H), 7.11 (dd, J = 8.5, 7.6 Hz, 2H), 5.13 (ddd, J = 10.0, 7.6, 5.3 Hz, 1H), 4.49-4.39 (m, 1H), 4.39-4.27 (m, 1H), 4.00 (dd, J = 13.5, 5.3 Hz, 1H), 3.49 (dd, J = 13.6, 10.0 Hz, 1H), 3.39 (d, J = 13.4 Hz, 2H), 3.25-3.14 (m, 4H), 1.18 (td, J = 7.3, 1.3 Hz, 6H). | 618.1 |
| 174 | 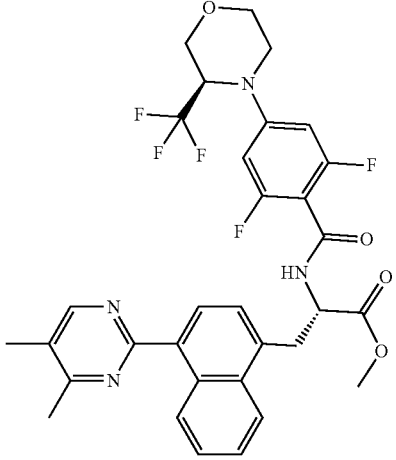 [SMILES: COC(=O)[C@H](Cc1ccc(-c2ncc(C)c(C)n2)c2ccccc12)NC(=O)c1c(F)cc(N2CCOC[C@@H]2C(F)(F)F)cc1F] | 1H NMR (400 MHz, DMSO-d6) δ 9.09 (d, J = 7.7 Hz, 1H), 8.68 (s, 1H), 8.59 (d, J = 8.6 Hz, 1H), 8.20 (d, J = 8.5 Hz, 1H), 7.84 (d, J = 7.4 Hz, 1H), 7.65 (t, J = 7.6 Hz, 1H), 7.56 (dd, J = 13.5, 7.4 Hz, 2H), 6.78 (d, J = 11.8 Hz, 2H), 4.91 (dd, J = 9.3, 3.2 Hz, 1H), 4.77 (td, J = 8.5, 4.7 Hz, 1H), 4.16 (d, J = 12.7 Hz, 1H), 3.95 (dd, J = 11.8, 3.7 Hz, 1H), 3.73 (dd, J = 14.3, 4.9 Hz, 2H), 3.68 (s, 3H), 3.56 (d, J = 12.5 Hz, 2H), 3.29-3.16 (m, 2H), 2.54 (s, 3H), 2.33 (s, 3H). | 629.2 |
| 175 | 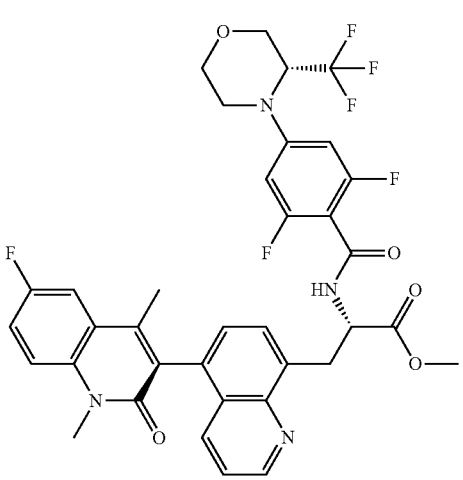 | 1H NMR (400 MHz, DMSO-d6) δ 9.03 (d, J = 7.8 Hz, 1H), 8.96 (dd, J = 4.1, 1.7 Hz, 1H), 7.88 (dd, J = 8.5, 1.7 Hz, 1H), 7.78-7.65 (m, 3H), 7.60 (td, J = 9.2, 8.6, 2.8 Hz, 1H), 7.46 (dd, J = 8.5, 4.1 Hz, 1H), 7.31 (d, J = 7.2 Hz, 1H), 6.75 (d, J = 11.7 Hz, 2H), 5.10-4.98 (m, 1H), 4.91 (s, 1H), 4.16 (d, J = 12.8 Hz, 1H), 4.02 (dd, J = 13.0, 5.1 Hz, 1H), 3.96 (dd, J = 11.5, 3.7 Hz, 1H), 3.74 (d, J = 12.6 Hz, 1H), 3.68 (s, 3H), 3.65 (s, 3H), 3.61-3.50 (m, 1H), 3.45-3.30 (m, 1H), 3.33-3.18 (m, 2H), 2.10 (s, 3H). | 713.2 |

| Example | Structure | 1H-NMR | M/Z [M + H]+ |
|---|---|---|---|
| 176 | 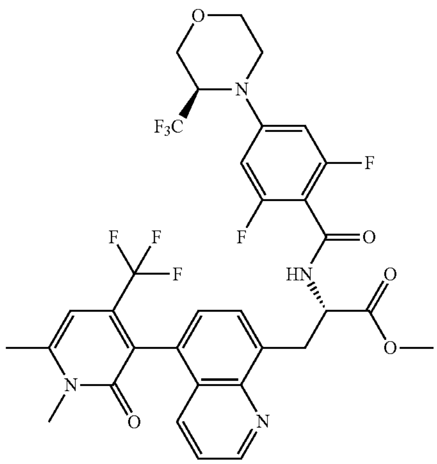 | 1H NMR (400 MHz, DMSO-d6) δ 9.05 (d, J = 7.4 Hz, 1H), 8.94 (dd, J = 4.2, 1.7 Hz, 1H), 7.81 (dd, J = 8.5, 1.7 Hz, 1H), 7.66 (d, J = 7.3 Hz, 1H), 7.48 (dd, J = 8.5, 4.1 Hz, 1H), 7.24 (d, J = 7.2 Hz, 1H), 6.75 (d, J = 11.6 Hz, 2H), 6.64 (s, 1H), 5.01-4.87 (m, 2H), 4.16 (d, J = 12.7 Hz, 1H), 3.95 (dd, J = 11.5, 3.8 Hz, 1H), 3.89 (dd, J = 13.2, 5.7 Hz, 1H), 3.74 (d, J = 12.9 Hz, 2H), 3.57 (s, 3H), 3.51 (s, 3H), 3.43 (m, 2H), 3.24 (t, J = 12.4 Hz, 1H), 2.55 (s, 3H). | 713.2 |
| 177 | 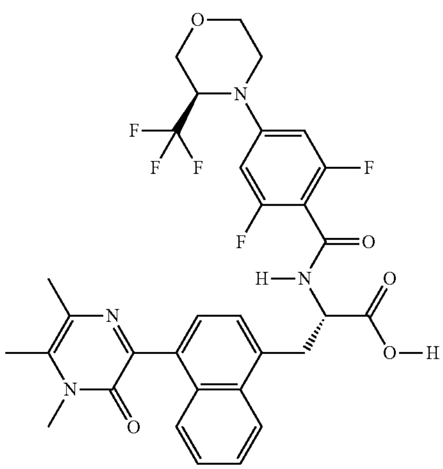 [SMILES: Cc1nc(-c2ccc(C[C@H](NC(=O)c3c(F)cc(N4CCOC[C@@H]4C(F)(F)F)cc3F)C(=O)O)c3ccccc23)c(=O)n(C)c1C] | 1H NMR (400 MHz, DMSO-d6) δ 8.96 (d, J = 7.9 Hz, 1H), 8.20 (d, J = 8.6 Hz, 1H), 7.72 (d, J = 8.5 Hz, 1H), 7.61 (t, J = 7.7 Hz, 1H), 7.52-7.40 (m, 3H), 6.78 (d, J = 11.9 Hz, 2H), 4.91 (p, J = 8.6, 8.2 Hz, 1H), 4.68 (td, J = 8.8, 4.2 Hz, 1H), 4.16 (d, J = 12.7 Hz, 1H), 3.96 (dd, J = 11.8, 3.6 Hz, 1H), 3.73 (t, J = 13.4 Hz, 2H), 3.56 (s, 3H), 3.36 (d, J = 13.5 Hz, 2H), 3.24 (t, J = 12.8 Hz, 2H), 2.42 (s, 3H), 2.34 (s, 3H). | 645.2 |
| 178 | 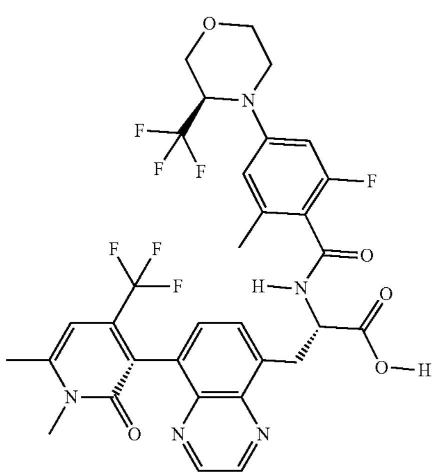 | 1H NMR (400 MHz, DMSO-d6) δ 9.00 (d, J = 1.8 Hz, 1H), 8.86 (d, J = 1.8 Hz, 1H), 8.74 (d, J = 8.3 Hz, 1H), 7.79 (d, J = 7.4 Hz, 1H), 7.52 (d, J = 7.3 Hz, 1H), 6.71-6.53 (m, 4H), 5.01-4.89 (m, 1H), 4.88-4.78 (m, 1H), 4.14 (d, J = 12.6 Hz, 1H), 4.05-3.91 (m, 2H), 3.72 (d, J = 12.7 Hz, 1H), 3.49 (s, 4H), 3.40-3.19 (m, 2H), 2.53 (s, 4H), 1.95 (s, 3H). | 696.2 |

TABLE 1-continued

| Example | Structure | 1H-NMR | M/Z [M + H]+ |
|---|---|---|---|
| 179 | 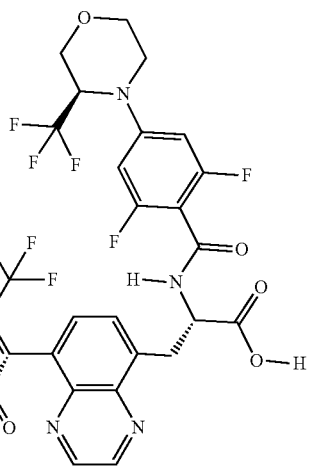 | 1H NMR (400 MHz, DMSO-d6) δ 8.98 (d, J = 1.8 Hz, 1H), 8.90-8.81 (m, 2H), 7.77 (d, J = 7.4 Hz, 1H), 7.51 (d, J = 7.3 Hz, 1H), 6.72 (d, J = 11.5 Hz, 2H), 6.57 (s, 1H), 4.89 (td, J = 9.3, 4.5 Hz, 2H), 4.15 (d, J = 12.7 Hz, 1H), 4.02-3.90 (m, 2H), 3.73 (d, J = 12.3 Hz, 1H), 3.54 (s, OH), 3.49 (s, 3H), 3.46-3.15 (m, 2H), 2.53 (s, 3H). | 700.2 |
| 180 | 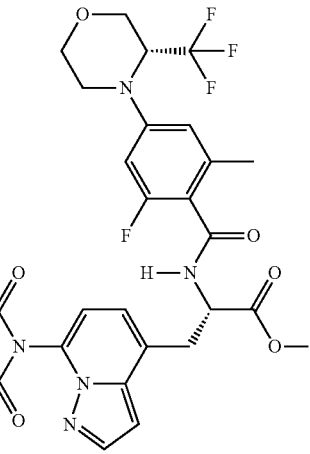 | 1H NMR (400 MHz, DMSO-d6) δ 9.06 (s, 1H), 8.83 (d, J = 8.1 Hz, 1H), 8.63 (d, J = 4.9 Hz, 1H), 7.94 (dd, J = 5.0, 2.5 Hz, 2H), 7.26 (d, J = 7.3 Hz, 1H), 7.11 (d, J = 7.3 Hz, 1H), 6.86 (d, J = 2.3 Hz, 1H), 6.80-6.61 (m, 4H), 4.87 (ddt, J = 12.1, 8.6, 3.7 Hz, 3H), 4.15 (dd, J = 12.7, 6.2 Hz, 2H), 3.95 (dt, J = 11.4, 4.4 Hz, 2H), 3.66 (d, J = 1.4 Hz, 3H), 3.55 (tt, J = 11.5, 3.8 Hz, 1H), 3.44 (dd, J = 14.8, 3.9 Hz, 2H), 3.35 (d, J = 11.4 Hz, 1H), 3.32-3.20 (m, 3H), 2.04 (d, J = 2.2 Hz, 3H). | 670.2 |

α4β7 Integrin Cell Capture Assay

The potency of inhibitors in preventing α4β7 integrin interaction with MadCAM-1 was measured by monitoring the capture of α4β7 integrin expressing cells on a recombinant MadCAM-1 extracellular domain-coated plate.

384-Well plates (Corning 3702) were coated with MadCAM-1 extracellular domain by dispensing 20 µL of MAdCAM-1 at 1.0 µg/mL per well and incubating overnight at 4° C. The plates were then washed with PBS and blocked with 3% BSA for 2 hours before being washed again.

RPMI8866 cells were spun down and re-suspended in assay medium (DMEM+0.5% FBS+0.5 mM $MnCl_2$) at a density of $0.5\times10^6$ cells/mL. The cells were then dispensed (60 µL/well) to a 384-well plate (Greiner 781280) that was previously spotted with 60 nL of test compound per well. The plates were incubated at 37° C. for 1 hour. 50 µL of cells were transferred to the blocked, MadCAM-1-coated plates and incubated for 30 minutes at 37° C. 10 µL of 12% glutaraldehyde containing Hoechst 33342 (0.06 mg/mL) was added to the cells (2% glutaraldehyde and 0.01 mg/mL final concentrations). The plates were incubated for 90 minutes at room temperature. The plates were then washed 3 times with 70 µL of PBS per well and imaged on a Cellomics ArrayScan instrument. The cells that were bound to the plate were counted and plotted against the compound concentration to determine the $EC_{50}$ of the test compounds. Results are presented in Table 2.

TABLE 2

α4β7 Integrin Cell Capture Assay Results

| Example # | $EC_{50}$ α4β7 (nM) |
|---|---|
| 1 | 210.3 |
| 2 | 416.7 |
| 3 | 392.6 |
| 4 | 26.0 |
| 5 | 702.0 |
| 6 | 139.0 |
| 7 | 522.2 |
| 8 | 0.8 |
| 9 | 4.1 |
| 10 | 1.1 |
| 11 | 0.5 |
| 12 | 19.5 |
| 13 | 66.9 |
| 14 | 57.7 |
| 15 | 85.0 |
| 16 | 144.0 |
| 17 | 356.2 |
| 18 | 416.5 |

TABLE 2-continued

α4β7 Integrin Cell Capture Assay Results

| Example # | EC$_{50}$ α4β7 (nM) |
|---|---|
| 19 | 26.3 |
| 20 | 373.7 |
| 21 | 5.8 |
| 22 | 123.2 |
| 23 | 18.5 |
| 24 | 49.5 |
| 25 | 20.0 |
| 26 | 290.5 |
| 27 | 57.7 |
| 28 | 193.6 |
| 29 | 16.7 |
| 30 | 46.4 |
| 31 | 23.2 |
| 32 | 6.0 |
| 33 | 12.2 |
| 34 | 4.0 |
| 35 | 53.5 |
| 36 | 115.3 |
| 37 | 65.6 |
| 38 | 211.8 |
| 39 | 74.0 |
| 40 | 32.7 |
| 41 | 7.5 |
| 42 | 152.5 |
| 43 | 160.5 |
| 44 | 538.3 |
| 45 | 243.0 |
| 46 | 32.2 |
| 47 | 28.6 |
| 48 | 2.1 |
| 49 | 46.2 |
| 50 | 151.7 |
| 51 | 45.1 |
| 52 | 43.8 |
| 53 | 149.6 |
| 54 | 38.8 |
| 55 | 63.1 |
| 56 | 68.5 |
| 57 | 23.6 |
| 58 | 19.2 |
| 59 | 10.7 |
| 60 | 2.7 |
| 61 | 15.1 |
| 62 | 3.2 |
| 63 | 33.8 |
| 64 | 4.4 |
| 65 | 26.8 |
| 66 | 6.2 |
| 67 | 2.5 |
| 68 | 2.7 |
| 69 | 9.2 |
| 70 | 55.1 |
| 71 | 15.4 |
| 72 | 11.2 |
| 73 | 8.4 |
| 74 | 130.8 |
| 75 | 23.0 |
| 76 | 55.7 |
| 77 | 60.4 |
| 78 | 12.4 |
| 79 | 45.7 |
| 80 | 17.0 |
| 81 | 6.6 |
| 82 | 39.0 |
| 83 | 109.3 |
| 84 | 10.9 |
| 85 | 3.0 |
| 86 | 0.3 |
| 87 | 2.9 |
| 88 | 0.1 |
| 89 | 172.7 |
| 90 | 4280.7 |
| 91 | 686.0 |
| 92 | 89.4 |
| 93 | 26.8 |
| 94 | 110.8 |
| 95 | 15.2 |
| 96 | 571.5 |
| 97 | 97.2 |
| 98 | 469.5 |
| 99 | 50.4 |
| 100 | 22.2 |
| 101 | 1.7 |
| 102 | 1.0 |
| 103 | 1.9 |
| 104 | 0.8 |
| 105 | 0.8 |
| 106 | 195.7 |
| 107 | 138.6 |
| 108 | 3.4 |
| 109 | 2.1 |
| 110 | 14.2 |
| 111 | 76.6 |
| 112 | 53.3 |
| 113 | 12.3 |
| 114 | 29.9 |
| 115 | 21.7 |
| 116 | 72.6 |
| 117 | 82.0 |
| 118 | 2.5 |
| 119 | 82.9 |
| 120 | 1.5 |
| 121 | 3.9 |
| 122 | 1.1 |
| 123 | 10.2 |
| 124 | 0.2 |
| 125 | 0.5 |
| 126 | 6.4 |
| 127 | 0.4 |
| 128 | 1.7 |
| 129 | 0.1 |
| 130 | 0.6 |
| 131 | 0.5 |
| 132 | 13.7 |
| 133 | 0.5 |
| 134 | 8.3 |
| 135 | 1.0 |
| 136 | 0.8 |
| 137 | 0.9 |
| 138 | 0.3 |
| 139 | 0.4 |
| 140 | 0.1 |
| 141 | 3.6 |
| 142 | 0.5 |
| 143 | 30.2 |
| 144 | 4.9 |
| 145 | 34.9 |
| 146 | 0.6 |
| 147 | 0.4 |
| 148 | 3.6 |
| 149 | 0.3 |
| 150 | 180.6 |
| 151 | 5.8 |
| 152 | 57.8 |
| 153 | 28.4 |
| 154 | 2.6 |
| 155 | 1.6 |
| 156 | 135.4 |
| 157 | 160.7 |
| 158 | 0.4 |
| 159 | 1.9 |
| 160 | 0.6 |
| 161 | 0.5 |
| 162 | 1.7 |
| 163 | 0.9 |
| 164 | 1.3 |
| 165 | 37.8 |
| 166 | 24.4 |
| 167 | 835.8 |
| 168 | 26.6 |
| 169 | 142.1 |
| 170 | 206.34 |

TABLE 2-continued

α4β7 Integrin Cell Capture Assay Results

| Example # | EC$_{50}$ α4β7 (nM) |
|---|---|
| 171 | N/A |
| 172 | N/A |
| 173 | N/A |
| 174 | N/A |
| 175 | N/A |
| 176 | N/A |
| 177 | 0.22 |
| 178 | 0.08 |
| 179 | 0.10 |
| 180 | 0.09 |

What is claimed is:

1. A compound of Formula (I):

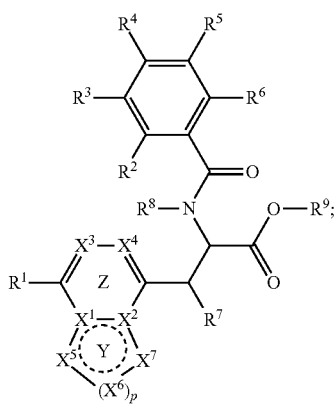

or a pharmaceutically acceptable salt thereof, wherein:
 $X^1$ and $X^2$ are each independently selected from C, and N; wherein the bond between $X^1$ and $X^2$ is a single or a double bond;
 $X^3$ and $X^4$ are each independently selected from $CR^{10}$, and N;
 $X^5$ and $X^7$ are each independently selected from $CR^{10}R^{10}$, $CR^{10}$, S, S(O), S(O)$_2$, N, $NR^{11}$, C(O), and O;
 each $X^6$ is independently selected from $CR^{10}R^{10}$, $CR^{10}$, S, S(O), S(O)$_2$, N, $NR^{11}$, C(O), and O; wherein the bond between $X^5$ and $X^6$, $X^6$ and $X^6$, or $X^6$ and $X^7$ is a single or a double, provided that at least one is a double bond;
 $R^1$ is selected from -L-$A^1$, -L-$A^2$, -L-$A^3$, and -L-$A^4$;
  L is selected from a bond, —O—, —O—C(O)—*, —NH—, —C(O)—N(H)—*, and —N(H)—C(O)—*; wherein * indicates a point of attachment of L to $A^1$, $A^2$, $A^3$, or $A^4$;
  $A^1$ is $C_{6-10}$aryl optionally substituted with one to six Ra;
  $A^2$ is 5-10 membered heteroaryl containing one to five heteroatoms independently selected from S, N, and O, and optionally one or two C(O); wherein $A^2$ is optionally substituted with one to six $R^a$;
  $A^3$ is 5-10 membered cycloalkyl or 5-14 membered heterocyclyl; wherein $A^3$ is optionally substituted with one to six $R^a$; and
  $A^4$ is —$NR^{a1}R^{a2}$;
  wherein each $R^a$ is independently selected from halo, cyano, hydroxyl, —$NR^{a1}R^{a2}$, $C_{1-6}$alkyl, $C_{2-6}$alkenyl, $C_{2-6}$alkynyl, $C_{1-6}$alkoxyl, $C_{1-6}$haloalkyl, $C_{1-6}$haloalkoxyl, —S(O)$_m$—$C_{1-6}$alkyl, $C_{3-8}$cycloalkyl, 3-6 membered heterocyclyl, $C_{6-10}$aryl, 5-6 membered heteroaryl, —O-(3-6 membered heterocyclyl), —O—$C_{1-4}$alkylene-$C_{3-8}$cycloalkyl, —O-phenyl, and —O—$C_{3-8}$cycloalkyl;
  each $C_{1-6}$alkyl, $C_{2-6}$alkenyl, $C_{2-6}$alkynyl, $C_{1-6}$alkoxyl, $C_{1-6}$haloalkyl, $C_{1-6}$haloalkoxyl, and —S(O)$_m$—$C_{1-6}$alkyl of $R^a$ are optionally substituted with one to three $R^{a3}$; wherein each $R^{a3}$ is independently selected from hydroxyl, cyano, —$NR^{a1}R^{a2}$, $C_{1-6}$alkoxyl, $C_{3-8}$cycloalkyl, phenyl, and 3-6 membered heterocyclyl; wherein each $C_{3-8}$cycloalkyl, phenyl, and 3-6 membered heterocyclyl of $R^{a3}$ is independently optionally substituted with one to three $R^{a4}$; wherein each $R^{a4}$ is independently selected from halo, cyano, hydroxyl, —$NR^{a1}R^{a2}$, $C_{1-6}$alkyl, $C_{1-6}$haloalkyl, $C_{1-6}$alkoxyl, $C_{1-6}$haloalkoxyl, $C_{3-8}$cycloalkyl, and 3-6 membered heterocyclyl; and
  each $C_{3-8}$cycloalkyl, 3-6 membered heterocyclyl, $C_{6-10}$aryl, 5-6 membered heteroaryl, —O-(3-6 membered heterocyclyl), —O—$C_{1-4}$alkylene-$C_{3-8}$cycloalkyl, —O— phenyl, and —O—$C_{3-8}$cycloalkyl of $R^a$ is independently optionally substituted with one to three groups independently selected from halo, cyano, hydroxyl, —$NR^{a1}R^{a2}$, $C_{1-6}$alkyl, $C_{1-6}$haloalkyl, $C_{1-6}$alkoxyl, and $C_{1-6}$haloalkoxyl;
 each $R^2$, $R^3$, $R^4$, $R^5$, and $R^6$ is independently selected from H, halo, cyano, hydroxyl, $C_{1-6}$alkyl, $C_{2-6}$alkenyl, $C_{2-6}$alkynyl, $C_{1-6}$alkoxyl, $C_{1-8}$haloalkoxyl, $C_{1-8}$haloalkoxy, —$NR^{b1}R^{b2}$, —$R^{b3}S(O)_mR^{b4}$, —S(O)$_mR^{b4}$, —$NR^{b1}S(O)_vR^{b4}$, —COO$R^{b1}$, —CON$R^{b1}R^{b2}$, —$NR^{b1}$COO$R^{b2}$, —$NR^{b1}$CO$R^{b4}$, —$R^{b3}NR^{b1}R^{b2}$, —S(O)$_v$N$R^{b1}R^{b2}$, $C_{3-12}$cycloalkyl, $C_{6-10}$aryl, 5-6 membered heteroaryl, and 3-12 membered heterocyclyl;
 each $C_{1-6}$alkyl, $C_{2-6}$alkenyl, $C_{2-6}$alkynyl, $C_{1-6}$alkoxyl, $C_{1-8}$haloalkyl, and $C_{1-8}$haloalkoxyl of $R^2$, $R^3$, $R^4$, $R^5$, and $R^6$ is independently optionally substituted with one to two $R^c$; wherein each $R^c$ is independently selected from azido, oxo, cyano, halo, hydroxyl, —$NR^{a1}R^{a2}$, $C_{1-4}$alkoxyl, $C_{3-8}$cycloalkyl, $C_{6-10}$aryl, 5-6 membered heteroaryl, and 4-6 membered heterocyclyl; wherein each $C_{3-8}$cycloalkyl, $C_{6-10}$aryl, 5-6 membered heteroaryl, and 4-6 membered heterocyclyl of $R^c$ is independently optionally substituted with one to three groups independently selected from halo, hydroxyl, cyano, —$NR^{a1}R^{a2}$, $C_{1-4}$alkyl, $C_{1-6}$haloalkyl, $C_{1-4}$alkoxyl, and $C_{3-6}$cycloalkyl;
 each $C_{6-10}$aryl and 5-6 membered heteroaryl of $R^2$, $R^3$, $R^4$, $R^5$, and $R^6$ is independently optionally substituted with one to five $R^b$; and
 each $C_{3-12}$cycloalkyl and 3-12 membered heterocyclyl of $R^2$, $R^3$, $R^4$, $R^5$, and $R^6$ is independently optionally substituted with one to six groups independently selected from =C$R^{b1}R^{b2}$, and $R^b$;
  wherein each $R^b$ is independently selected from azido, cyano, halo, hydroxyl, —$NR^{a1}R^{a2}$, $C_{1-6}$alkyl, $C_{1-8}$haloalkyl, $C_{1-6}$alkoxyl, $C_{3-6}$cycloalkyl, $C_{6-10}$aryl, 5-6 membered heteroaryl, and 4-6 membered heterocycly; wherein each $C_{3-6}$cycloalkyl, $C_{6-10}$aryl, 5-6 membered heteroaryl, and 4-6 membered heterocyclyl of $R^b$ is independently optionally substituted with one to three groups independently selected from halo, hydroxyl, cyano, —NR$^{a1}$R$^{a2}$, C$_{1-4}$haloalkyl, and C$_{1-4}$alkoxyl;

each R$^{b1}$ and R$^{b2}$ is independently selected from H, C$_{1-8}$alkyl, C$_{1-8}$haloalkyl, C$_{3-8}$cycloalkyl, C$_{6-10}$aryl, 5-6 membered heteroaryl, and 3-8 membered heterocyclyl;

each C$_{1-8}$alkyl and C$_{1-6}$haloalkyl of R$^{b1}$ and R$^{b2}$ is optionally substituted with one to two R$^{b5}$; and each C$_{3-8}$cycloalkyl, C$_{6-10}$aryl, 5-6 membered heteroaryl, and 3-8 membered heterocyclyl of R$^{b1}$ and R$^{b2}$ is independently optionally substituted with one to three groups independently selected from halo, cyano, hydroxyl, —NR$^{a1}$R$^{a2}$, C$_{1-8}$alkyl, C$_{1-8}$haloalkyl, C$_{1-6}$alkoxyl, C$_{3-6}$cycloalkyl, C$_{6-10}$aryl, 5-6 membered heteroaryl, and 4-6 membered heterocyclyl;

R$^{b3}$ is C$_{1-4}$alkylene;

R$^{b4}$ is selected from C$_{1-4}$alkyl, C$_{1-4}$haloalkyl, C$_{3-6}$cycloalkyl, C$_{6-10}$aryl, 5-6 membered heteroaryl, and 4-6 membered heterocyclyl; wherein each C$_{1-4}$alkyl, C$_{1-4}$haloalkyl, C$_{3-8}$cycloalkyl, C$_{6-10}$aryl, 5-6 membered heteroaryl, and the 4-6 membered heterocyclyl of R$^{b4}$ is optionally substituted with one to three R$^{b6}$;

each R$^{b5}$ is independently selected from cyano, hydroxyl, C$_{1-4}$alkoxyl, C$_{3-8}$cycloalkyl, C$_{6-10}$aryl, 5-6 membered heteroaryl, and 4-6 membered heterocyclyl; wherein each C$_{3-8}$cycloalkyl, C$_{6-10}$aryl, 5-6 membered heteroaryl, and 4-6 membered heterocyclyl of R$^{b5}$ is optionally substituted with one to three groups independently selected from halo, cyano, hydroxyl, —NR$^{a1}$R$^{a2}$, C$_{1-4}$alkyl, C$_{1-4}$haloalkyl, C$_{1-4}$alkoxyl, and phenyl; and each R$^{b6}$ is independently selected from halo, cyano, C$_{104}$alkyl, C$_{1-4}$haloalkyl, C$_{1-4}$alkoxyl, C$_{3-6}$cycloalkyl, phenyl, 4-6 membered heterocyclyl, and 5-6 membered heteroaryl; wherein each C$_{3-6}$cycloalkyl, 4-6 membered heterocyclyl, and 5-6 membered heteroaryl of R$^{b6}$ is independently optionally substituted with one to three groups independently selected from halo, cyano, —NR$^{a1}$R$^{a2}$, C$_{1-4}$alkyl, C$_{1-4}$haloalkyl, and C$_{1-4}$alkoxyl;

or R$^2$ and R$^3$, R$^3$ and R$^4$, or R$^5$ and R$^6$ together with the atoms to which they are attached may form a C$_{6-10}$aryl, 5-6 membered heteroaryl, C$_{3-6}$cycloalkyl, or 5-6 membered heterocyclyl; wherein each C$_{6-10}$aryl, 5-6 membered heteroaryl, C$_{3-6}$cycloalkyl, or 5-6 membered heterocyclyl is optionally substituted with one to three groups independently selected from halo, cyano, —NR$^{a1}$R$^{a2}$, C$_{1-6}$alkyl, C$_{1-6}$alkoxyl, C$_{1-6}$haloalkyl, C$_{3-8}$cycloalkyl, 3-6 membered heterocyclyl, C$_{6-10}$aryl, 5-6 membered heteroaryl, C$_{1-4}$alkylene-C$_{3-8}$cycloalkyl, C$_{1-4}$alkylene-C$_{6-10}$aryl, and C$_{1-4}$alkylene-(5-6 membered heteroaryl);

R$^7$ is selected from H, C$_{1-4}$alkyl, and C$_{1-4}$haloalkyl;
R$^8$ is selected from H, C$_{1-4}$alkyl, and C$_{1-4}$haloalkyl;
R$^9$ is selected from H, C$_{1-6}$alkyl, —C$_{1-4}$alkylene-NR$^{a1}$R$^{a2}$, —C$_{1-4}$alkylene-C(O)NR$^{a1}$R$^{a2}$, —C$_{1-4}$alkylene-O—C(O)—O—C$_{1-4}$alkyl, —C$_{1-4}$alkylene-O—C(O)—C$_{1-4}$alkylene-NR$^{a1}$R$^{a2}$, —C$_{1-4}$alkylene-O—C$_{1-4}$alkyl, C$_{3-8}$cycloalkyl, —C$_{1-4}$alkylene-C$_{3-8}$cycloalkyl, 4-6 membered heterocyclyl, and —C$_{1-4}$alkylene-(4-6 membered heterocyclyl);
wherein each C$_{3-8}$cycloalkyl, —C$_{1-4}$alkylene-C$_{3-8}$cycloalkyl, and 4-6 membered heterocyclyl of R$^9$ is optionally substituted with one to three groups independently selected from halo, C$_{1-4}$alkyl, C$_{1-4}$alkoxyl, and C$_{1-4}$haloalkyl; or R$^9$ together with the N that attaches to R$^8$ forms a 5 membered heterocyclyl; wherein the 5 membered heterocyclyl is optionally substituted with one to two groups independently selected from halo, C$_{1-6}$alkyl, C$_{1-6}$alkoxyl, C$_{1-6}$haloalkyl, and C$_{6-10}$aryl; wherein C$_{6-10}$aryl is optionally substituted with one to three groups independently selected from halo, C$_{1-6}$alkyl, C$_{1-6}$alkoxyl, and C$_{1-6}$haloalkyl;

each R$^{10}$ is independently selected from H, halo, cyano, hydroxyl, —C(O)R$^{b1}$, —NR$^{a1}$R$^{a2}$, C$_{1-4}$alkyl, C$_{1-4}$alkoxyl, C$_{1-4}$haloalkyl, C$_{1-4}$haloalkoxyl, C$_{3-10}$cycloalkyl, 3-8 membered heterocyclyl, C$_{6-10}$aryl, and 5-6 membered heteroaryl; wherein each C$_{1-4}$alkyl, C$_{1-4}$alkoxyl, C$_{1-4}$haloalkyl, C$_{1-4}$haloalkoxyl, C$_{3-10}$cycloalkyl, 3-8-membered heterocyclyl, C$_{6-10}$aryl, and 5-6 membered heteroaryl is independently optionally substituted with one to three groups independently selected from halo, hydroxyl, cyano, —NR$^{a1}$R$^{a2}$, C$_{1-4}$alkyl, C$_{1-4}$haloalkyl, C$_{1-4}$alkoxyl, and C$_{3-6}$cycloalkyl;

or two R$^{10}$ either attached to the same or adjacent atoms form C$_{3-12}$cycloalkyl or 3-10 membered heterocyclyl; wherein each C$_{3-12}$cycloalkyl and 3-10 membered heterocyclyl is optionally substituted with one to three groups independently selected from H, halo, C$_{1-4}$alkyl, C$_{1-4}$alkoxyl, C$_{1-4}$haloalkyl, and C$_{1-4}$haloalkoxyl;

each R$^{11}$ is independently selected from H, C$_{1-4}$alkyl, and C$_{1-4}$haloalkyl; wherein each C$_{1-4}$alkyl, —C(O)R$^{b1}$, and C$_{1-4}$haloalkyl of R$^{11}$ is independently optionally substituted with one to three groups independently selected from halo, hydroxyl, cyano, —NR$^{a1}$R$^{a2}$, C$_{1-4}$alkyl, C$_{1-4}$haloalkyl, C$_{1-4}$alkoxyl, and C$_{3-6}$cycloalkyl;

or R$^{10}$ and R$^{11}$, or two R$^{11}$ together with the atoms to which they are attached to form 3-12 membered heterocyclyl; wherein 3-12 membered heterocyclyl is optionally substituted with one to three groups independently selected from H, halo, C$_{1-4}$alkyl, C$_{1-4}$alkoxyl, C$_{1-4}$haloalkyl, and C$_{1-4}$haloalkoxyl;

each R$^{a1}$ and R$^{a2}$ is independently selected from H, C$_{1-6}$alkyl, and C$_{1-6}$haloalkyl;
p is selected from 1, 2, and 3;
m is selected from 0, 1, and 2; and
v is selected from 1 and 2; and
provided that the ring formed by Y and Z is not one of

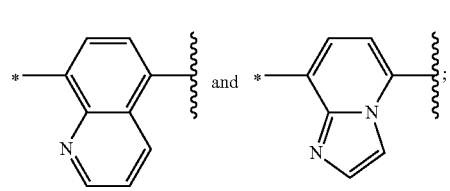 [SMILES: *c1ccc(C)c2ncccc12 ; *c1ccc(C)c2nccn12]

wherein * indicates a point of attachment to R$^1$.

2. The compound of claim 1, or a pharmaceutically acceptable salt thereof, wherein the ring formed by Y and Z is selected from:

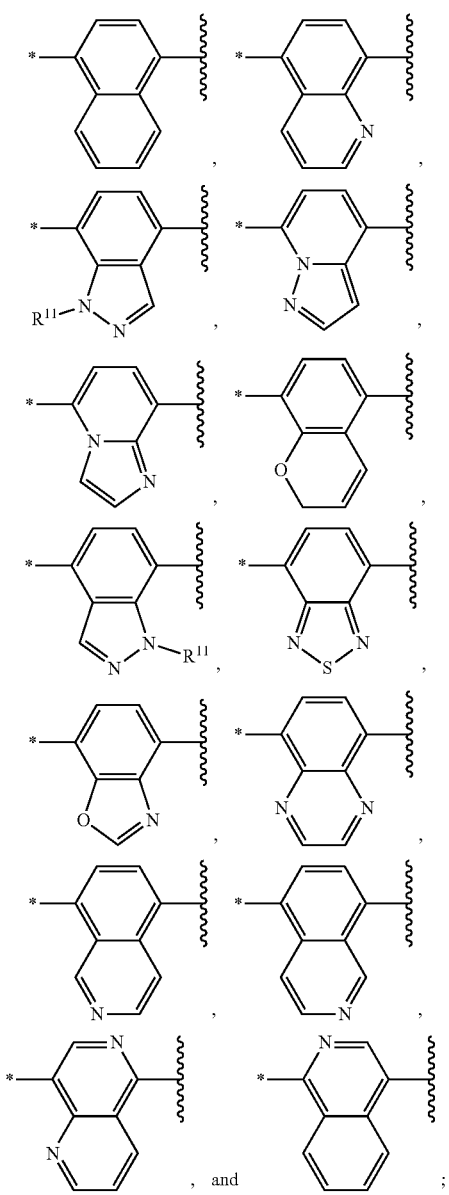

wherein * indicates a point of attachment to $R^1$;
wherein each group is optionally substituted with 1 to 4 $R^{10}$;
  wherein each $R^{10}$ is independently selected from halo, cyano, hydroxyl, $C_{1-4}$alkyl, $C_{1-4}$alkoxyl, $C_{1-4}$haloalkyl, $C_{1-4}$haloalkoxyl, $C_{3-10}$cycloalkyl, 3-8 membered heterocyclyl, $C_{6-10}$aryl, 5-6 membered heteroaryl, and $-NR^{a1}R^{a2}$; wherein each $C_{1-4}$alkyl, $C_{1-4}$haloalkyl, $C_{1-4}$haloalkoxyl, $C_{3-10}$cycloalkyl, 3-8 membered heterocyclyl, $C_{6-10}$aryl, 5-6 membered heteroaryl is independently optionally substituted with one to three groups independently selected from halo, hydroxyl, cyano, $-NR^{a1}R^{a2}$, $C_{1-4}$alkyl, $C_{1-4}$haloalkyl, $C_{1-4}$alkoxyl, and $C_{3-6}$cycloalkyl.

3. The compound of claim 1, of Formula (II)

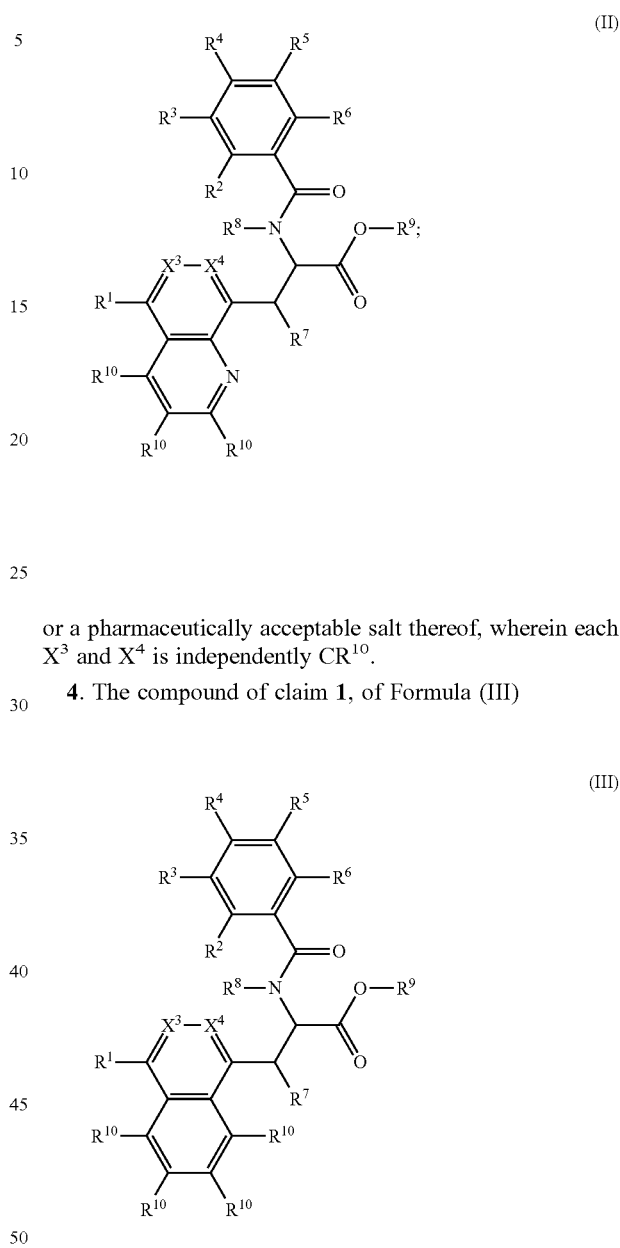

or a pharmaceutically acceptable salt thereof, wherein each $X^3$ and $X^4$ is independently $CR^{10}$.

4. The compound of claim 1, of Formula (III)

or a pharmaceutically acceptable salt thereof, wherein each $X^3$ and $X^4$ is independently $CR^{10}$.

5. The compound of claim 1, or a pharmaceutically acceptable salt thereof, where $A^1$, $A^2$, or $A^3$ is selected from phenyl, naphthyl, pyridinyl, pyridazinyl, pyrazinyl, pyrimidinyl, quinolinyl, isoquinolinyl, isoxazolyl, triazolyl, pyrazolyl, benzothiazolyl, pyridinonyl, quinolinonyl, isoquinolinonyl, quinazolindionyl, pyrazinonyl, pyrimidinonyl, pyrimidinedionyl, pyridazinonyl, quinazolinonyl, benzofuranyl, tetrahydrocyclopenta[b]pyridinonyl, naphthyridinonyl, chromanyl, isochromanyl, and chromenonyl, and wherein each $R^1$ which is independently optionally substituted with one to four $R^a$.

6. The compound of claim 1, or a pharmaceutically acceptable salt thereof, wherein $R^1$ is selected from:

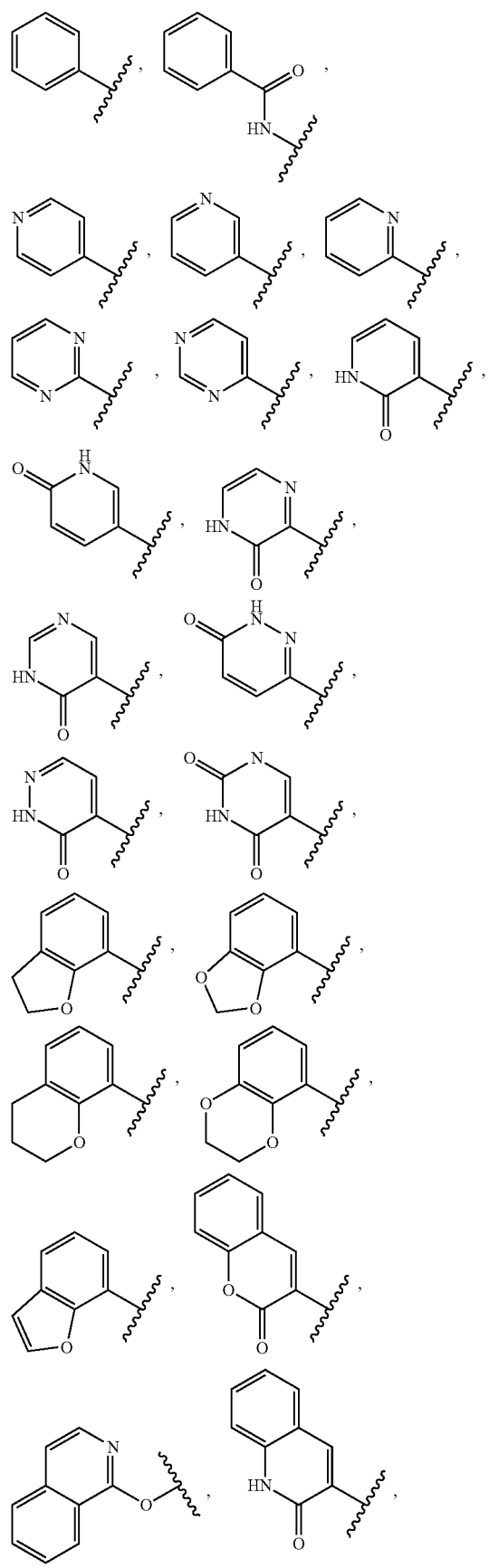
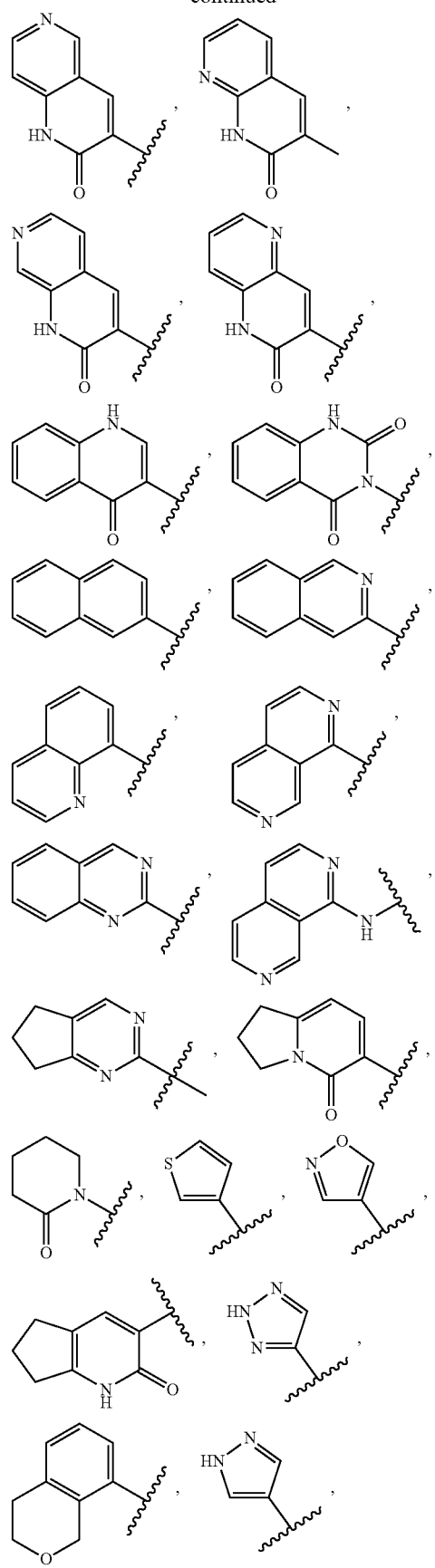

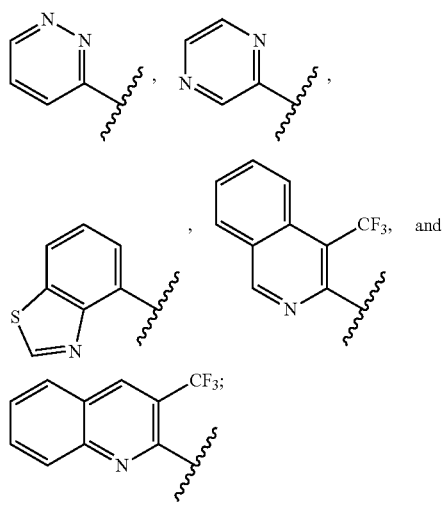

wherein each R¹ is optionally substituted with one to four Rᵃ.

7. The compound of claim 1, or a pharmaceutically acceptable salt or N-oxide thereof, wherein R¹ is substituted with one to three Rᵃ, and each Rᵃ is independently selected from F, Cl, Br, cyano, hydroxyl, —NH₂, —N(CH₃)₂, —CH₃, —CH₂CH₃, —CH(CH₃)₂, —C(CH₃)₃, —CH₂CN, —CH₂CH₂CN, —CH₂OH, —CH₂CH₂OH, —OCH₃, —OCD₃, —OCH₂CH₃, —OCH(CH₃)₂, —OC(CH₃)₃, —CH₂OCH₃, —CH₂OCH₂CH₃, —CH₃OCH(CH₃)₂, —CH₂F, —CHF₂, —CF₃, —CH₂CH₂F, —CH₂CHF₂, —CH₂CF₃, —OCH₂F, —OCHF₂, —OCF₃, —OCH₂CH₂F, —OCH₂CHF₂, —OCH₂CF₃, —SO₂CH₃, —SO₂CH₂CH₃,

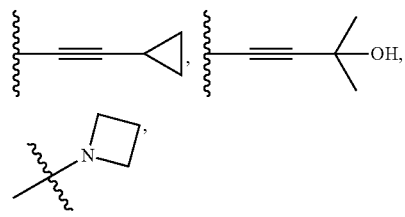

cyclopropyl, cyclobutyl, cyclopentyl, cyclohexyl, phenyl, —O-cyclopropyl, —O—CH₂-cyclopropyl, —O-cyclobutyl, —O—CH₂cyclobutyl, —O-cyclopentyl, —O—CH₂cyclopentyl, —O-cyclohexyl, —O—CH₂cyclohexyl, and —O— phenyl.

8. The compound of claim 1, or a pharmaceutically acceptable salt thereof wherein R¹ is selected from:

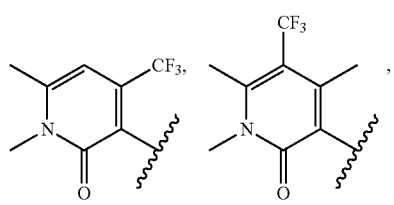

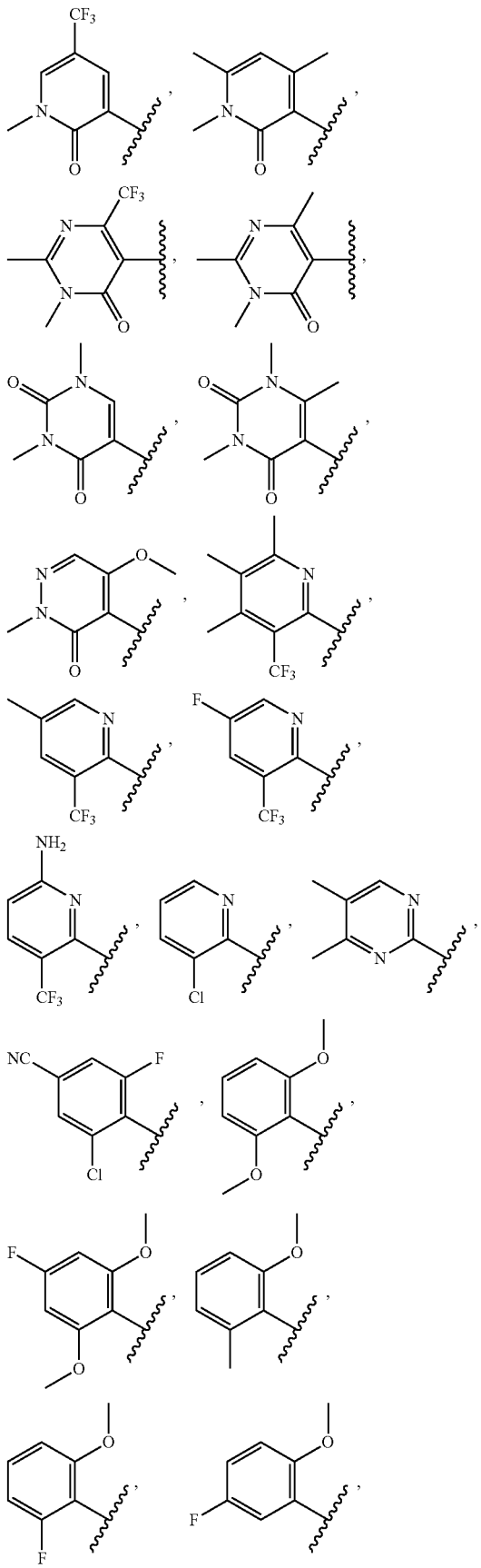

-continued
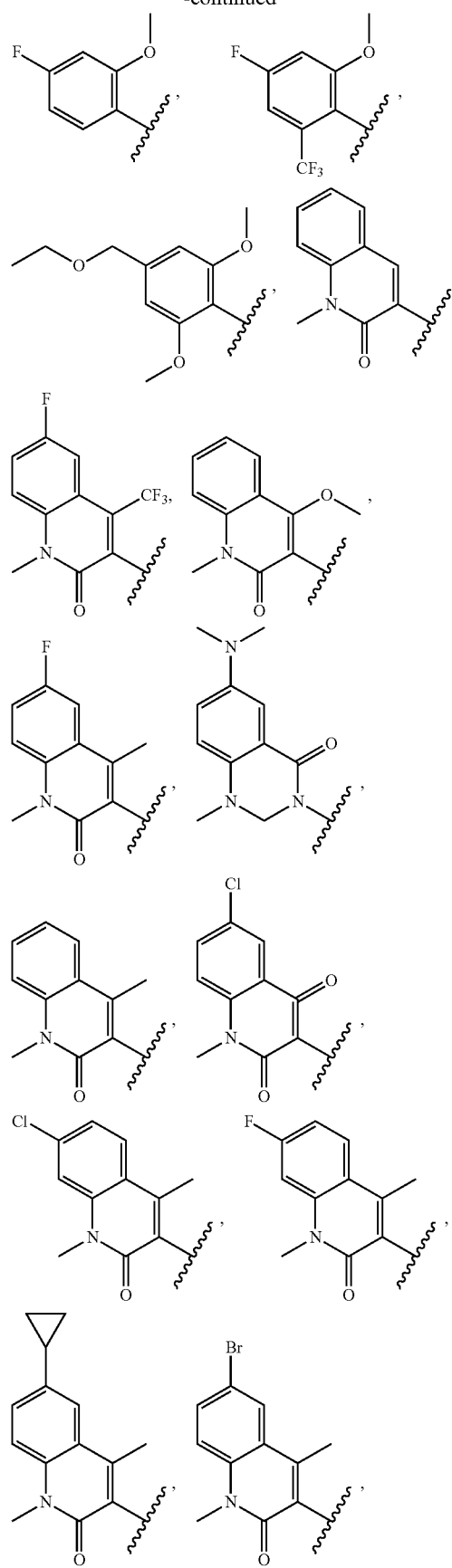
-continued
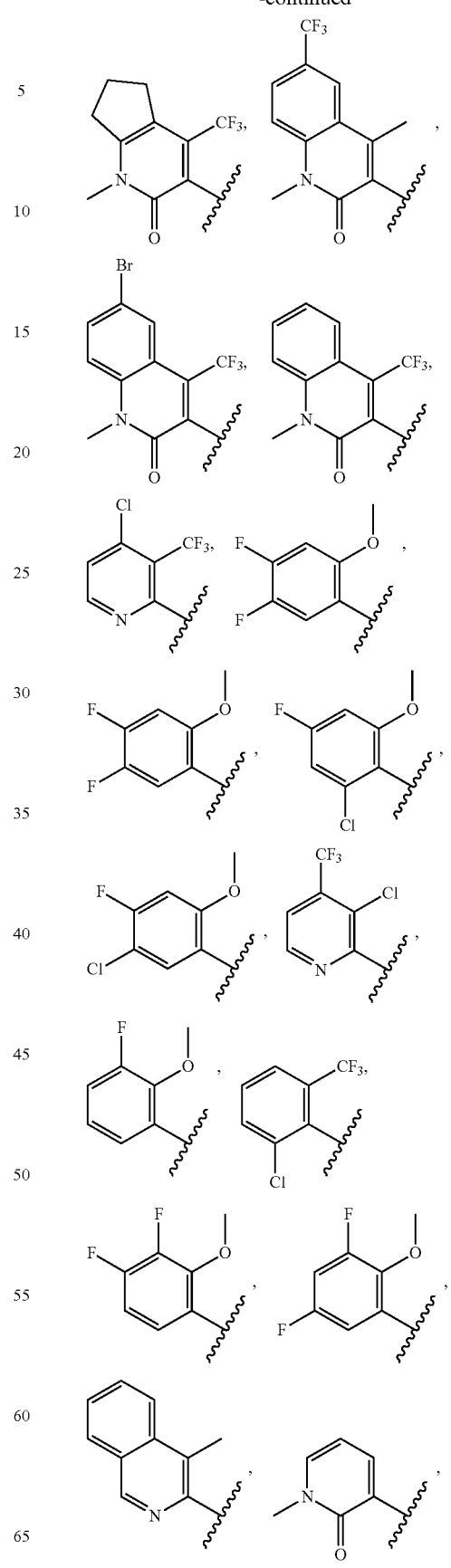

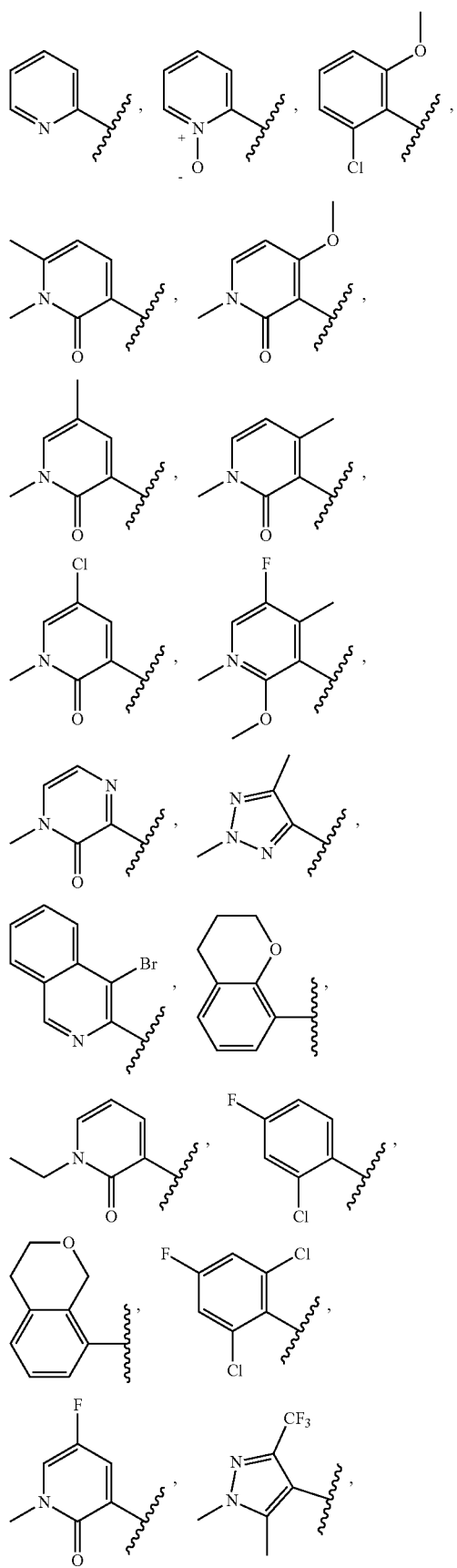

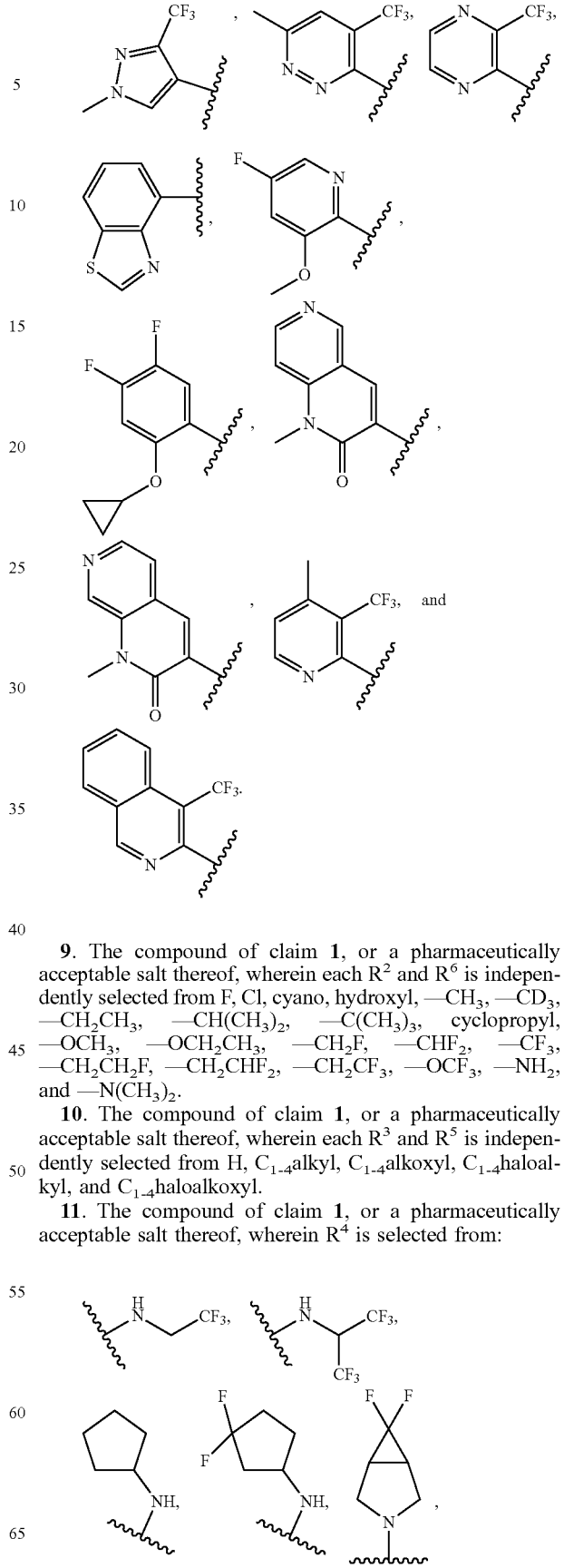

9. The compound of claim 1, or a pharmaceutically acceptable salt thereof, wherein each $R^2$ and $R^6$ is independently selected from F, Cl, cyano, hydroxyl, —$CH_3$, —$CD_3$, —$CH_2CH_3$, —$CH(CH_3)_2$, —$C(CH_3)_3$, cyclopropyl, —$OCH_3$, —$OCH_2CH_3$, —$CH_2F$, —$CHF_2$, —$CF_3$, —$CH_2CH_2F$, —$CH_2CHF_2$, —$CH_2CF_3$, —$OCF_3$, —$NH_2$, and —$N(CH_3)_2$.

10. The compound of claim 1, or a pharmaceutically acceptable salt thereof, wherein each $R^3$ and $R^5$ is independently selected from H, $C_{1-4}$alkyl, $C_{1-4}$alkoxyl, $C_{1-4}$haloalkyl, and $C_{1-4}$haloalkoxyl.

11. The compound of claim 1, or a pharmaceutically acceptable salt thereof, wherein $R^4$ is selected from:

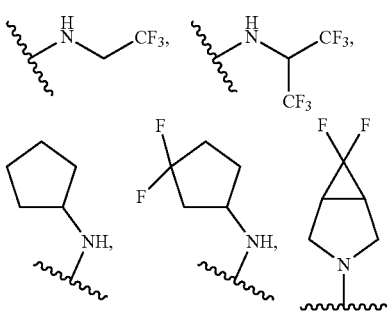

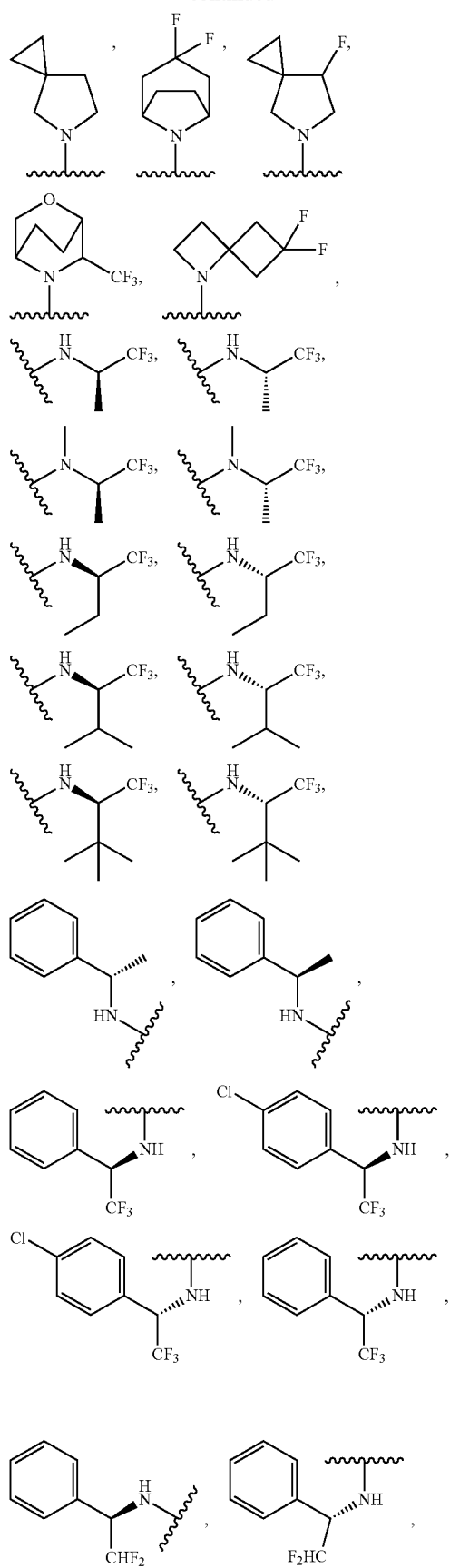
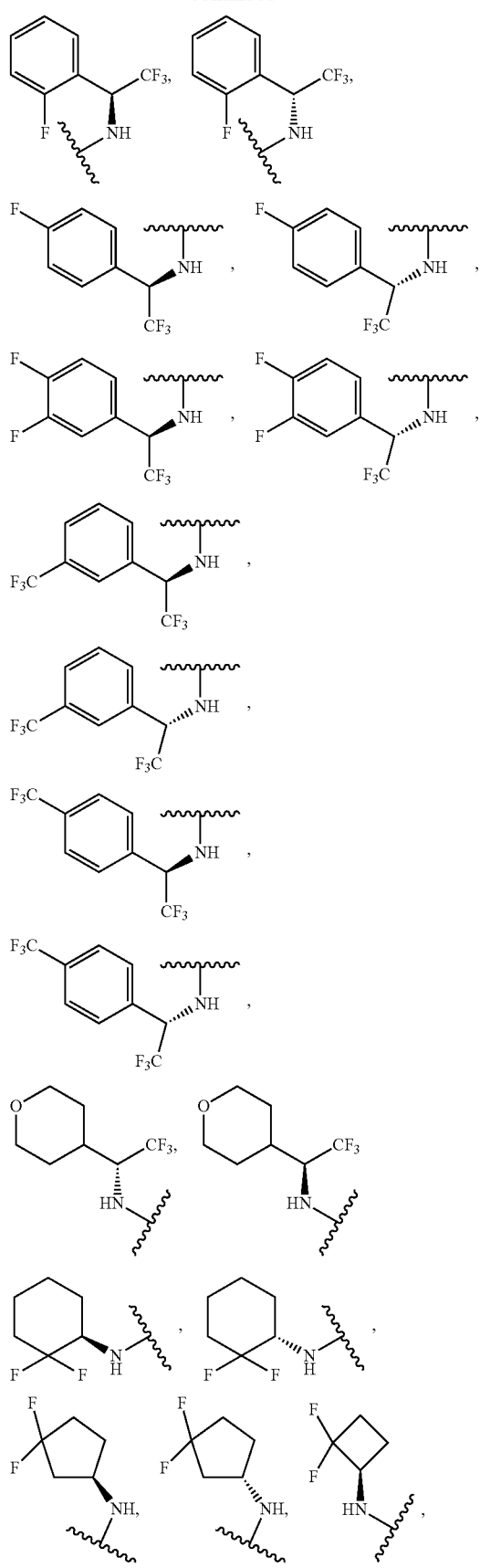

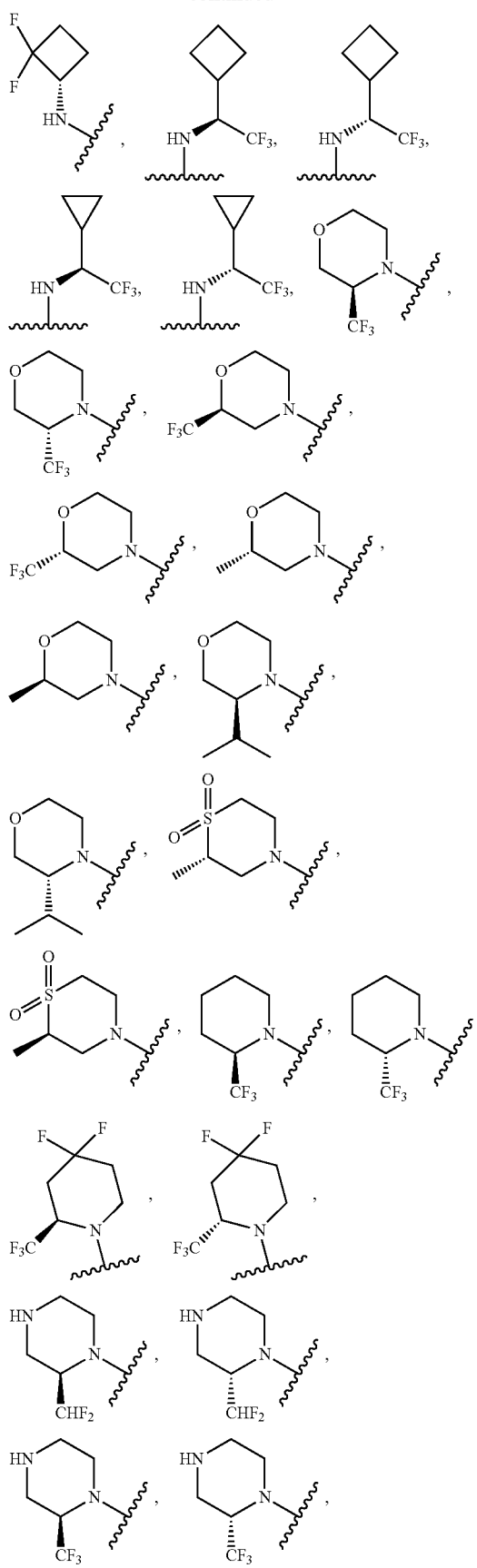

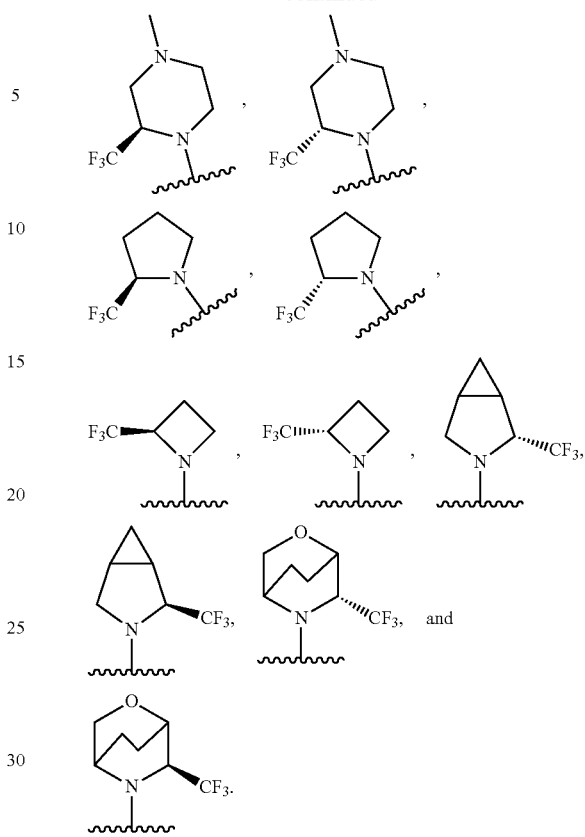

12. The compound of claim 1, or a pharmaceutically acceptable salt thereof, wherein $R^9$ is selected from H, methyl, ethyl, propyl, butyl, —$CH_2C(O)N(CH_3)_2$, —$(CH_2)_2N(CH_2CH_3)_2$, —$CH_2$—O—$C(O)CH_3$, —$(CH_2)_2$—O—$C(O)CH_3$, —$CH_2$—O—$C(O)C(CH_3)_3$, —$(CH_2)_2$—O—$C(O)C(CH)_3$, —$CH_2$—O—$C(O)$—O—$CH_3$, —$CH_2$—O—$C(O)$—O—$CH_2CH_3$, —$CH_2$—O—$C(O)$—O—$CH(CH_3)_2$, —$CH_2$—O—$C(O)$—O—$C(CH_3)_3$, —$(CH_2)_2C(O)CH_3$,

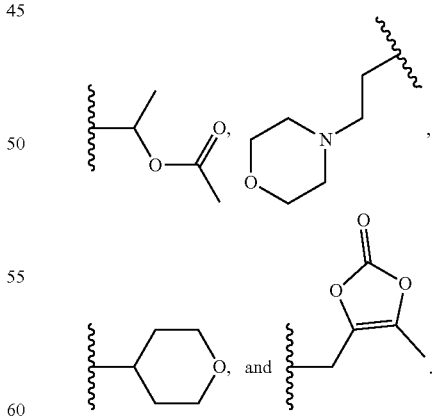

13. The compound of claim 1, or a pharmaceutically acceptable salt thereof, wherein $R^9$ is selected from H, methyl, and ethyl.

14. A compound or a pharmaceutically acceptable salt thereof, selected from:

329
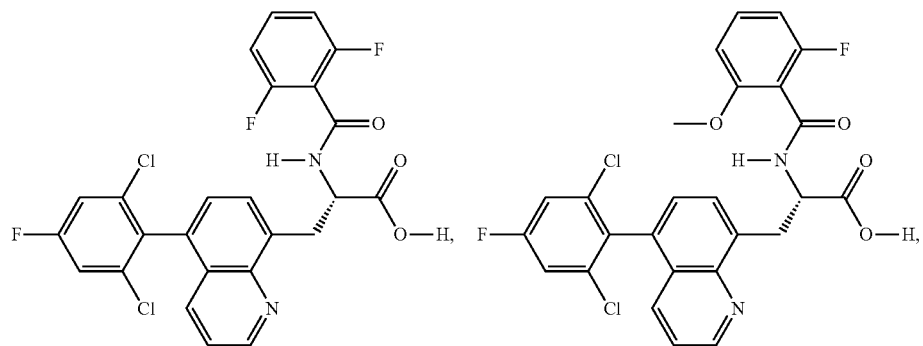
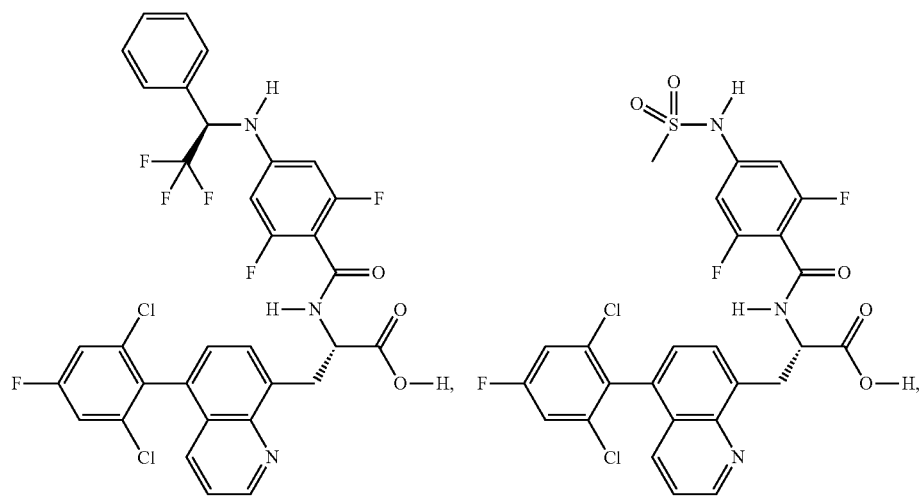
330
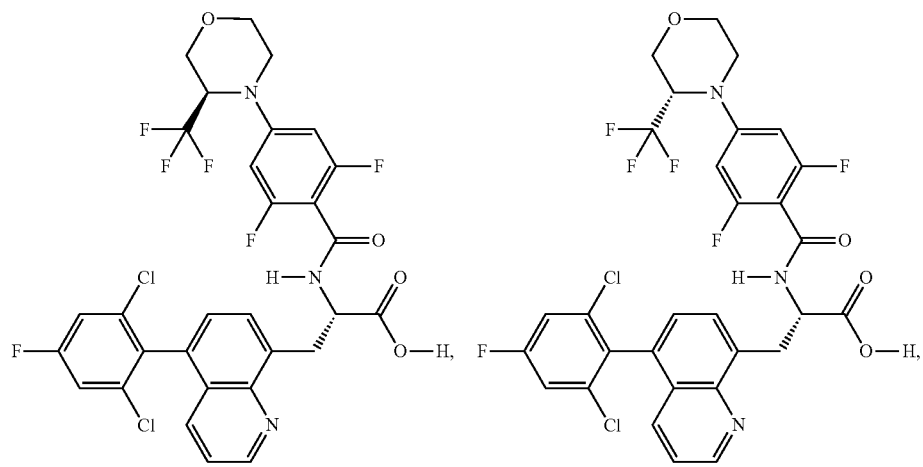

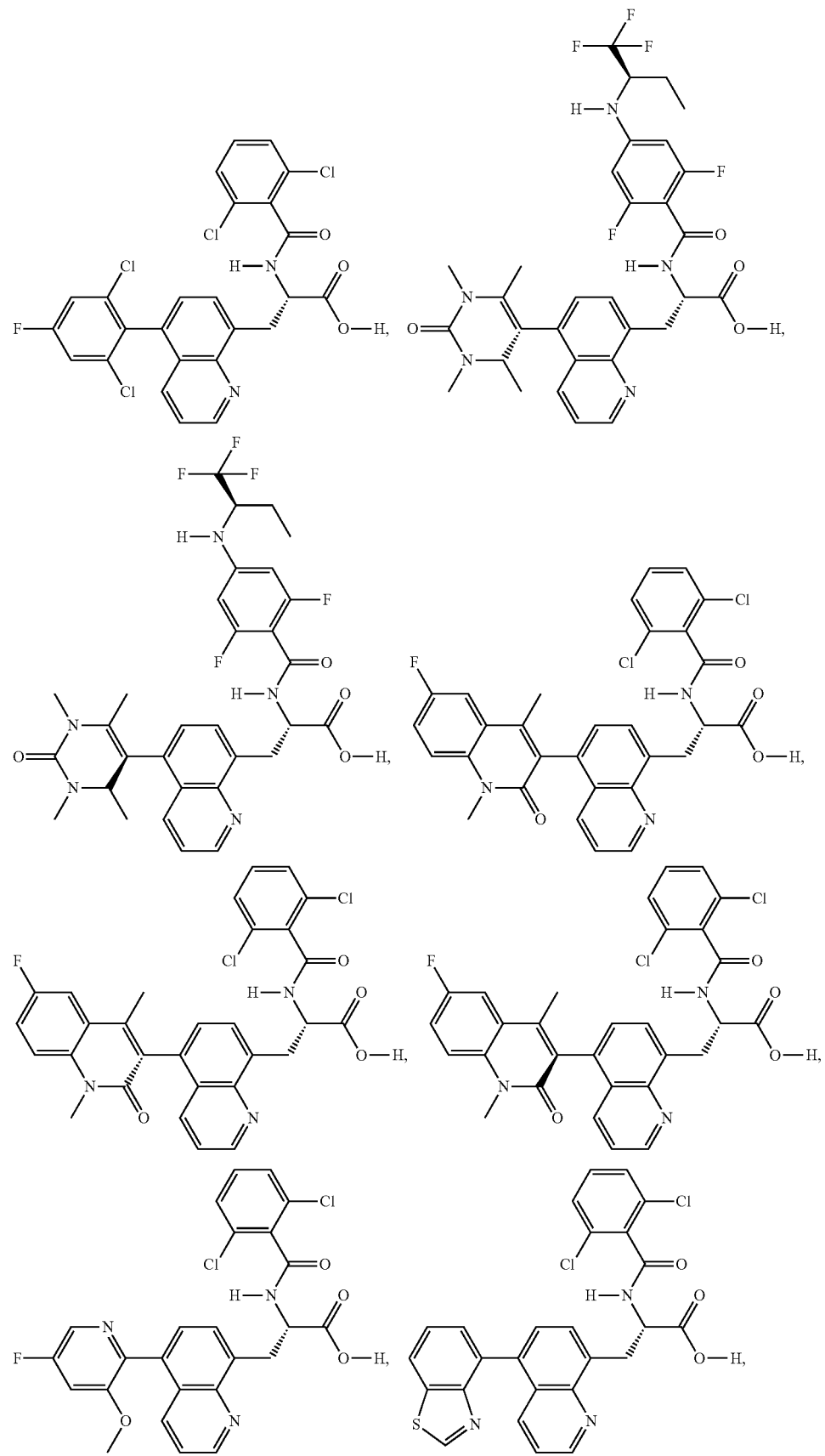

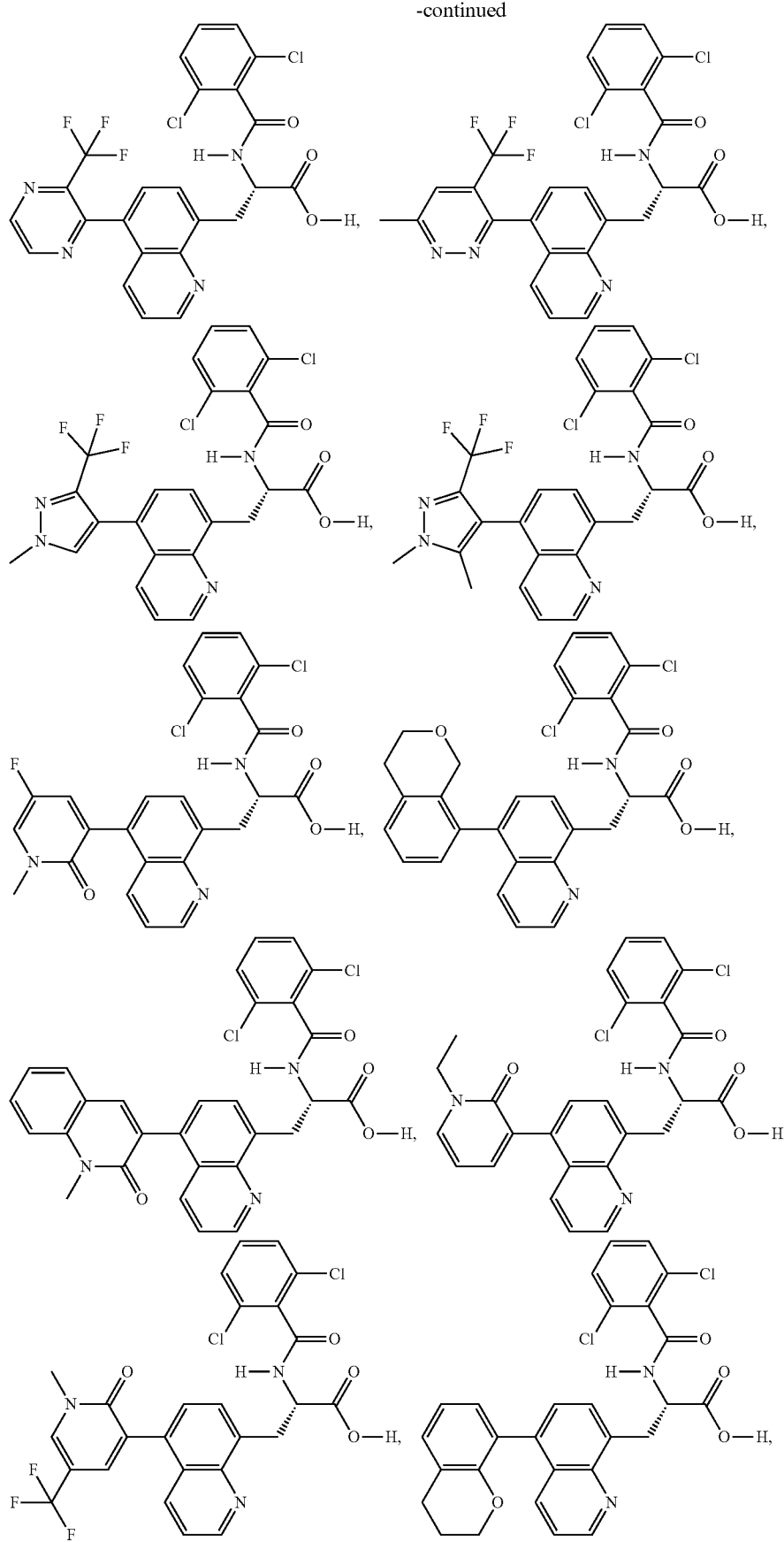

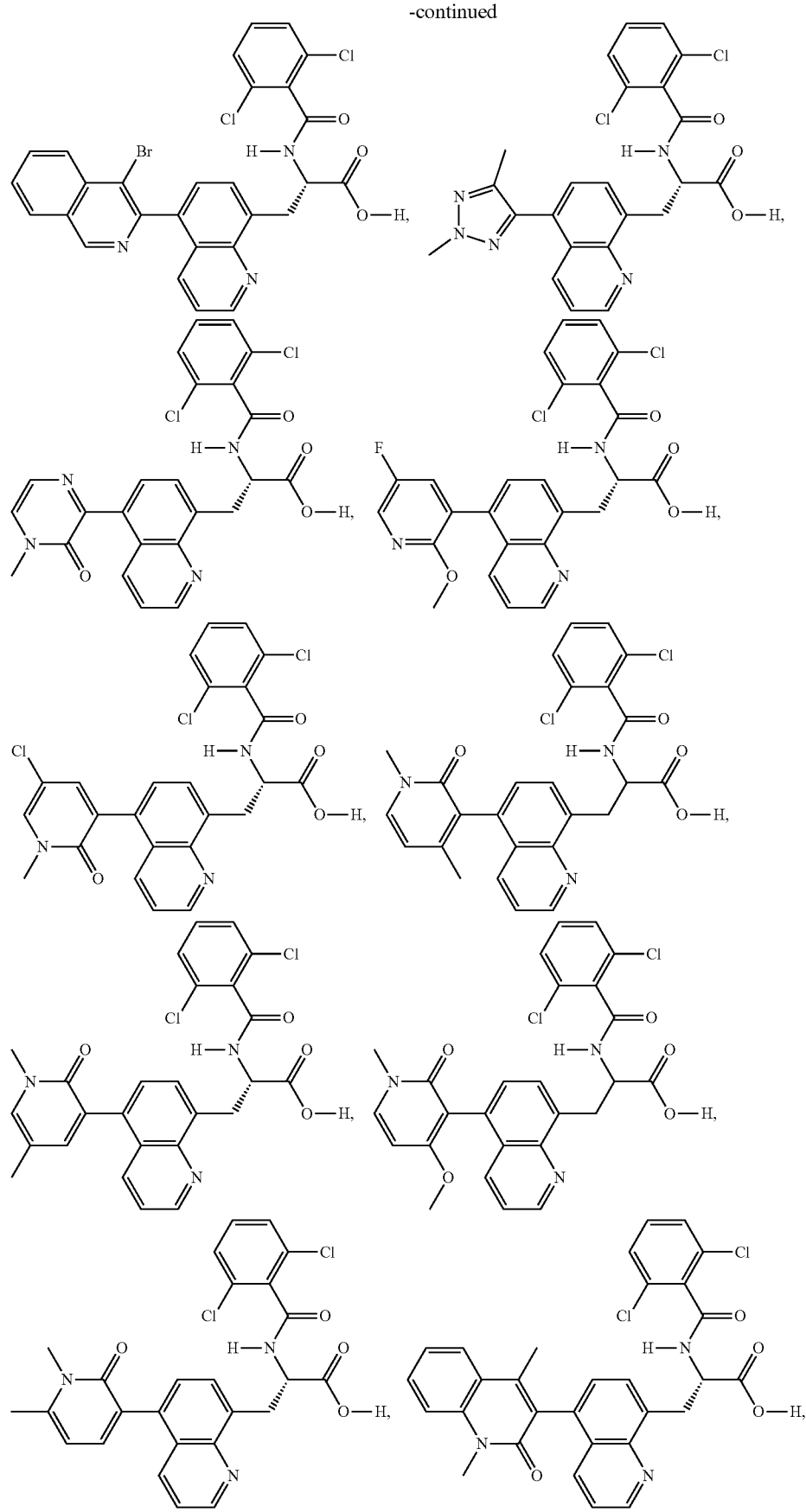

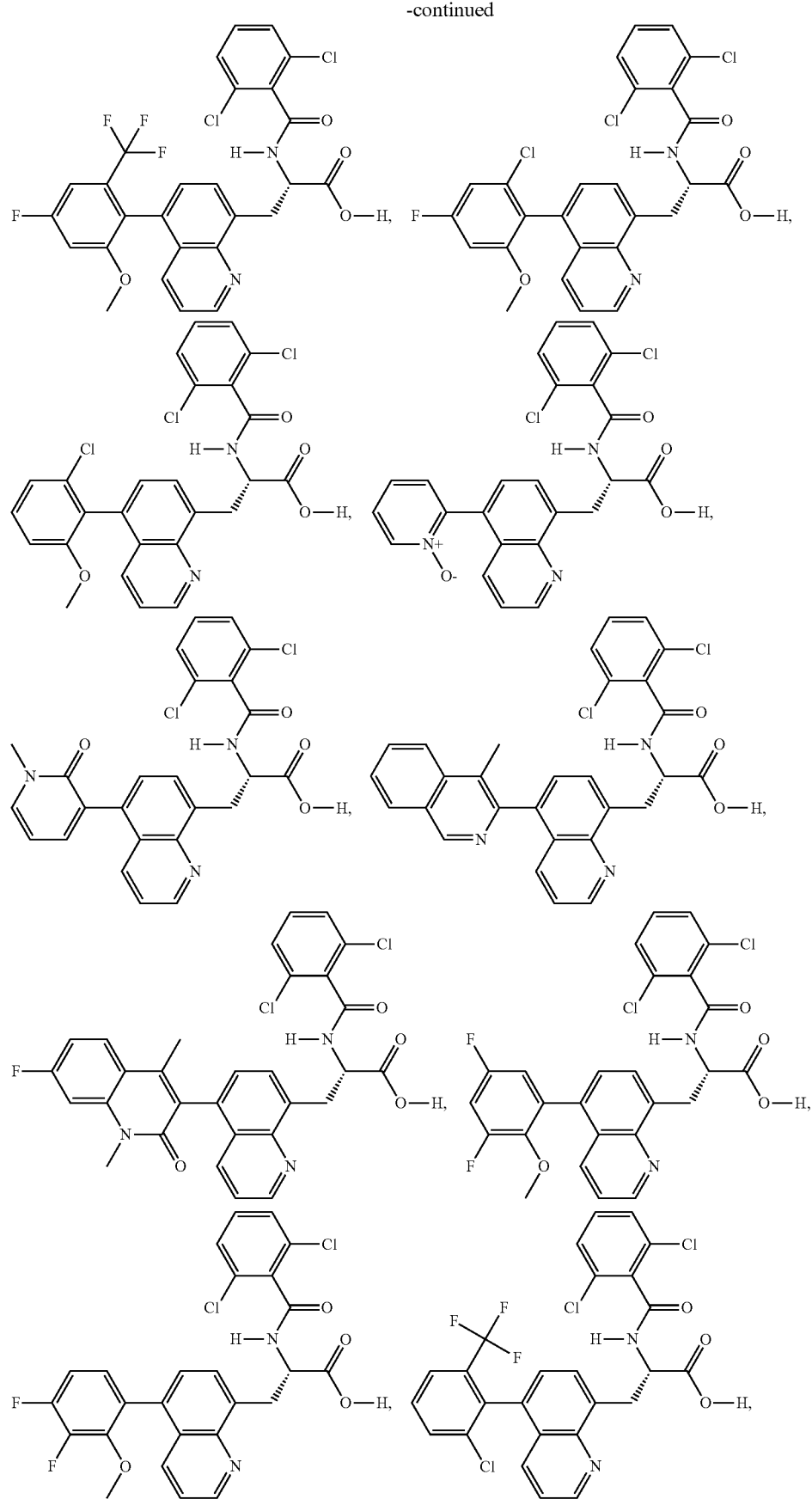

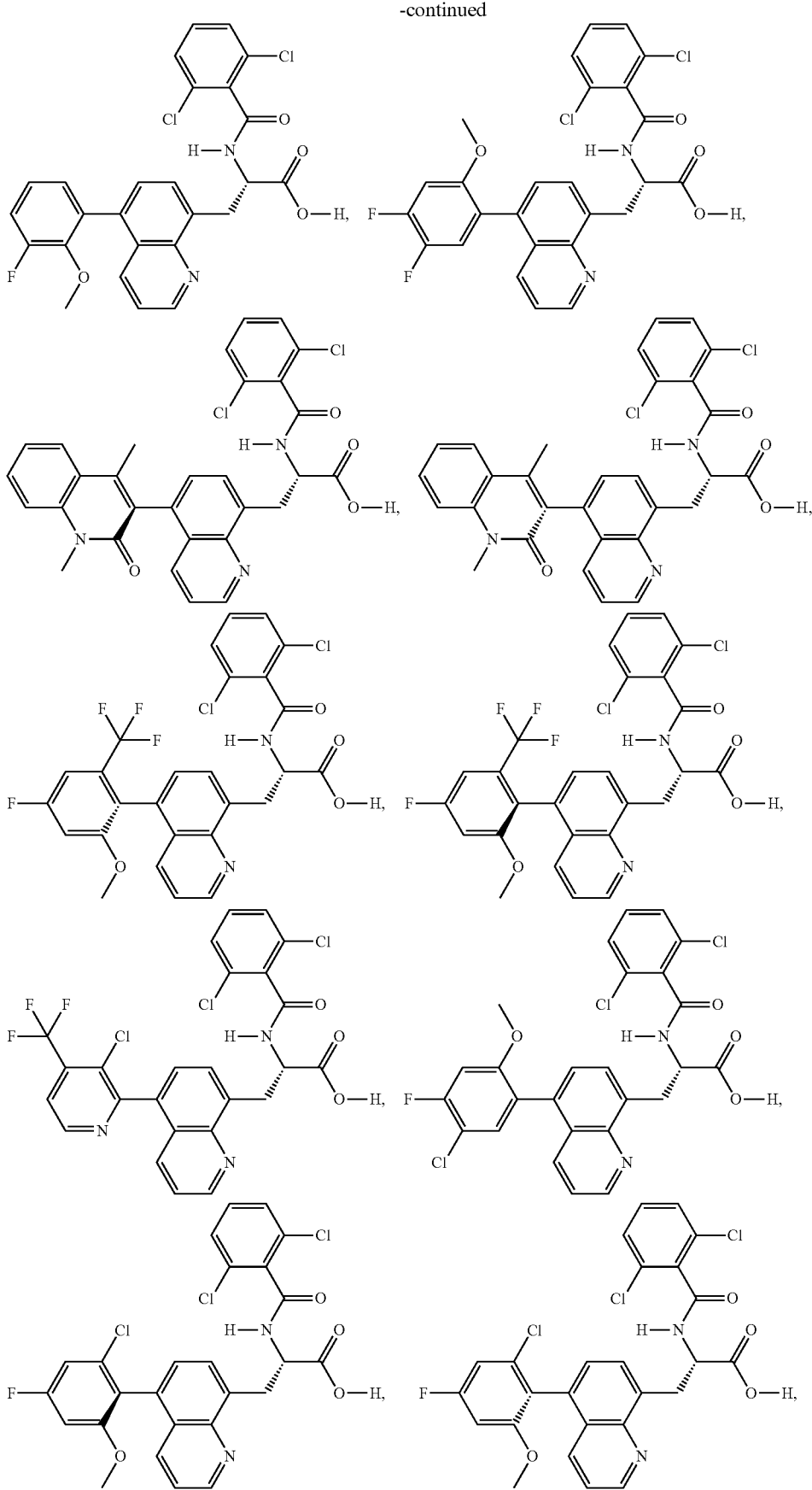

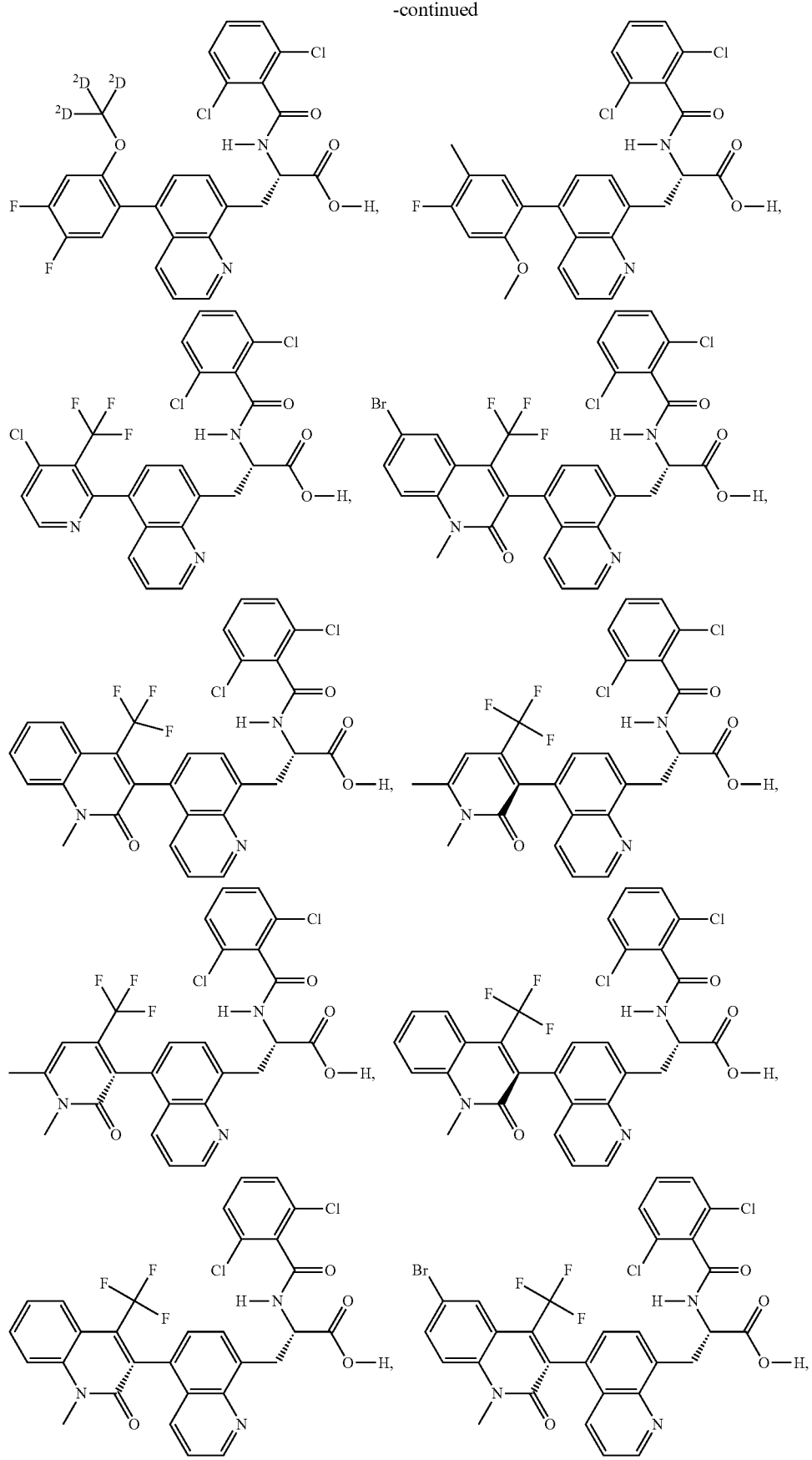

343 344
-continued
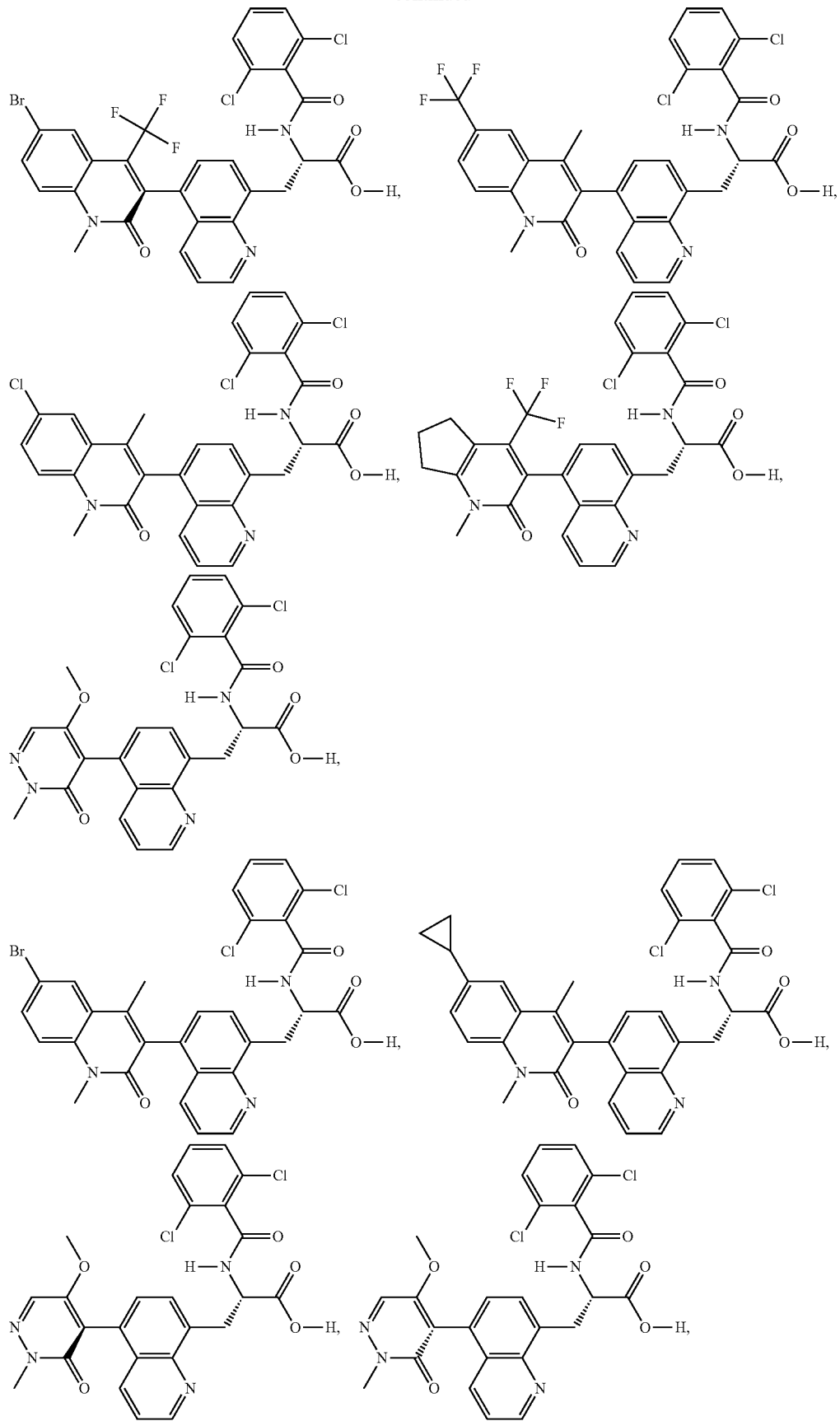

345              346
-continued
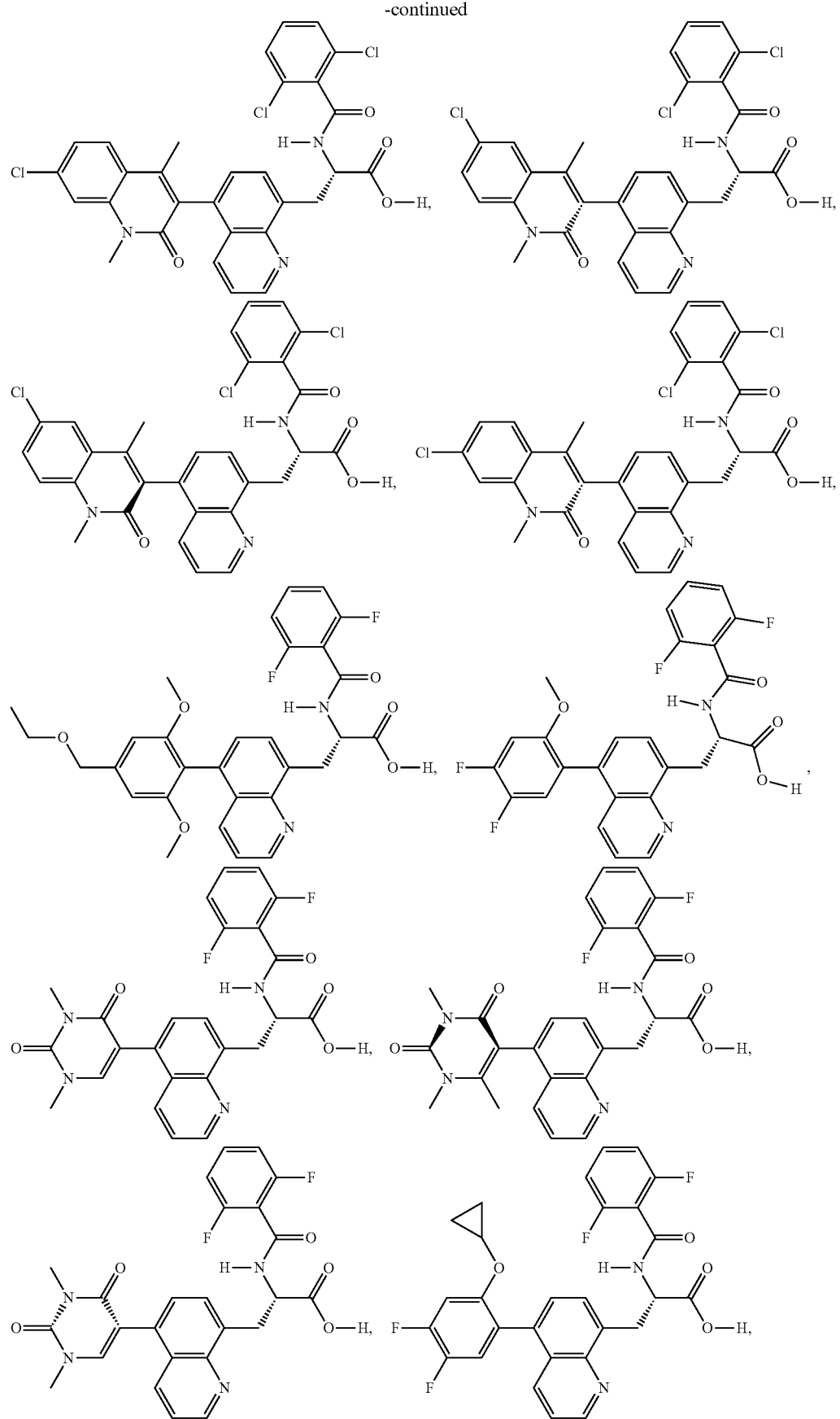

-continued
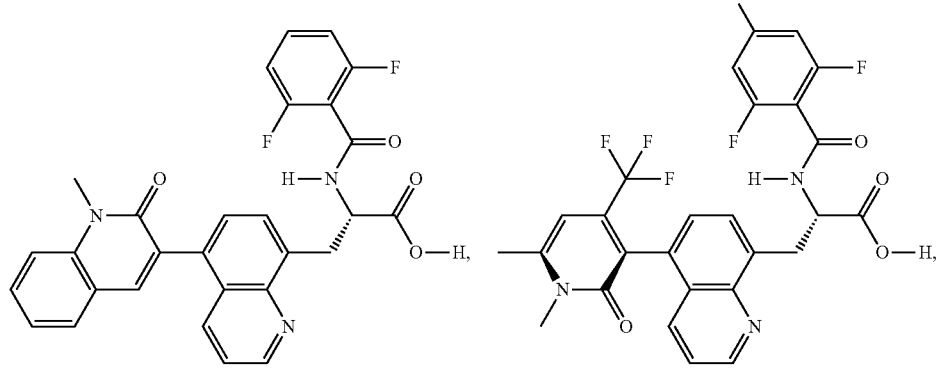
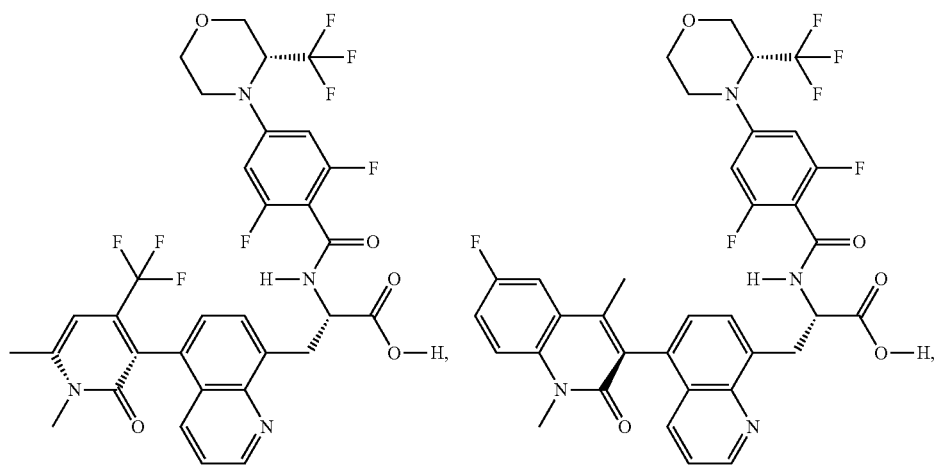
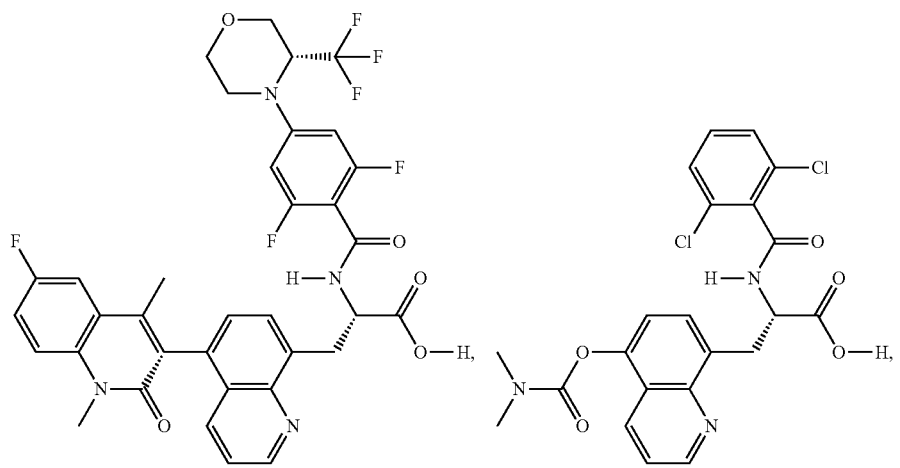

-continued
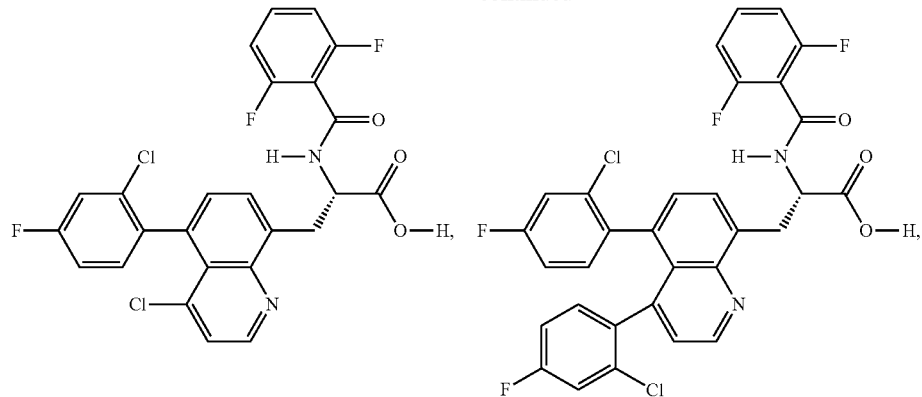
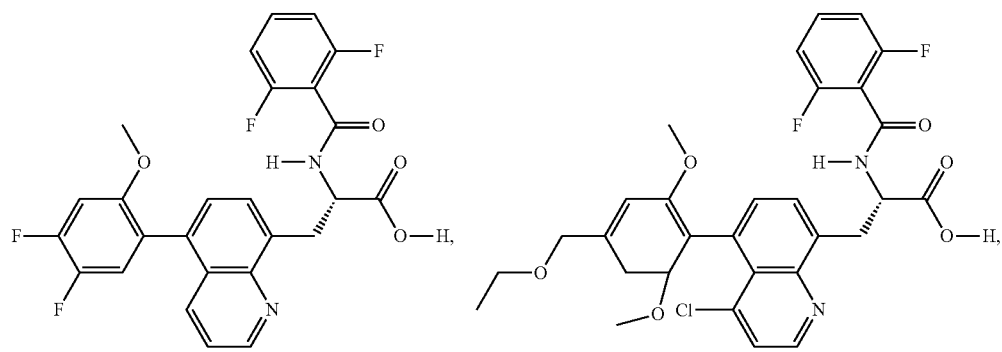
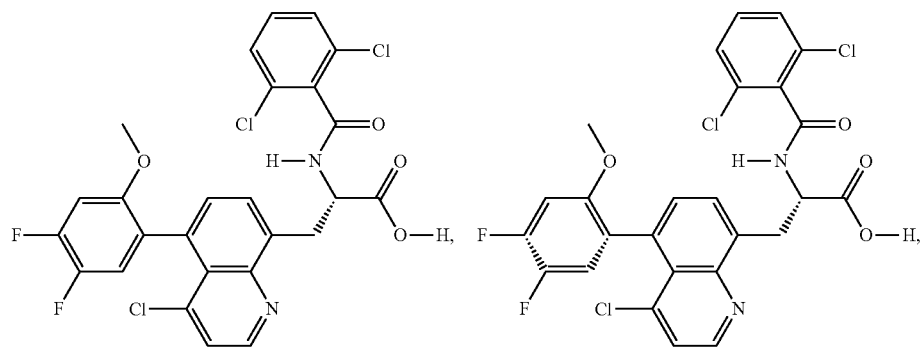
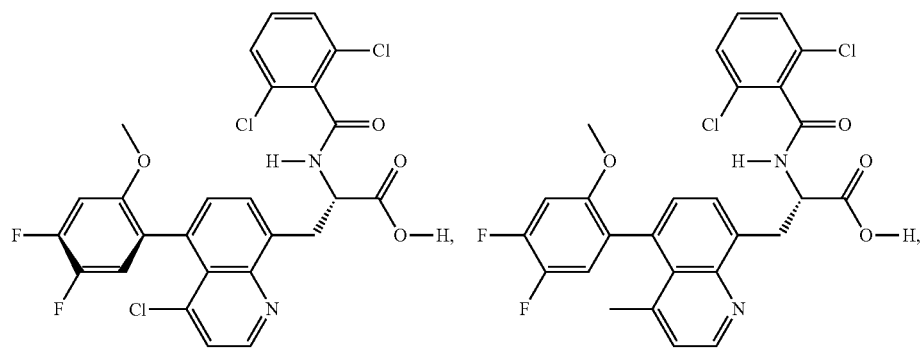

351
352
-continued
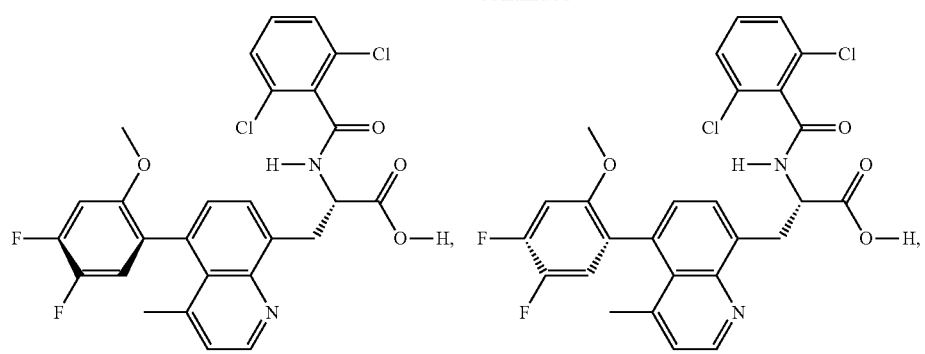
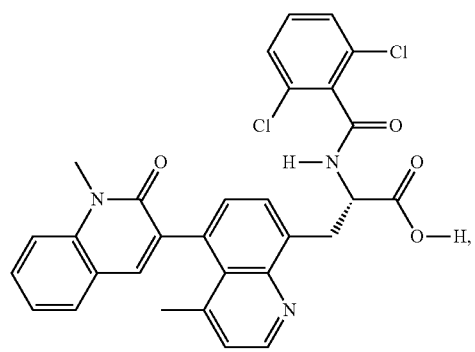
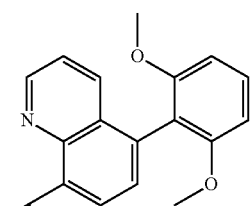
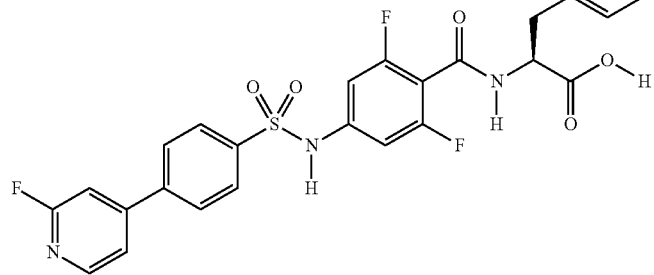
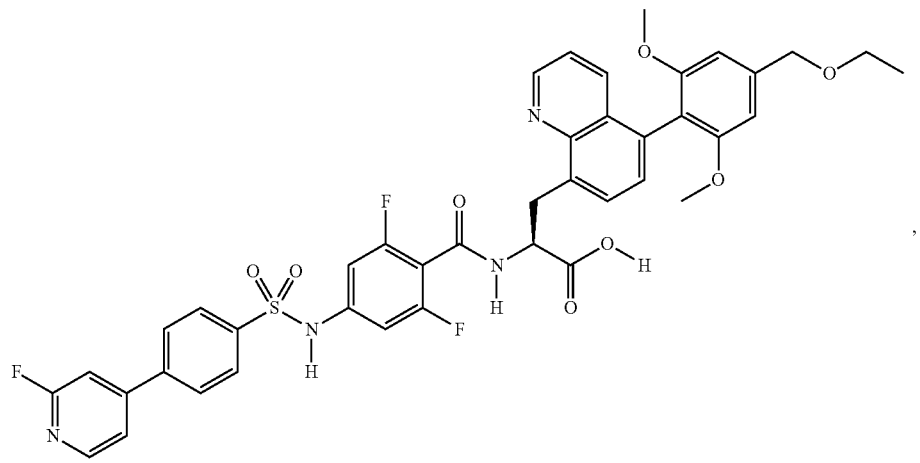

353 354
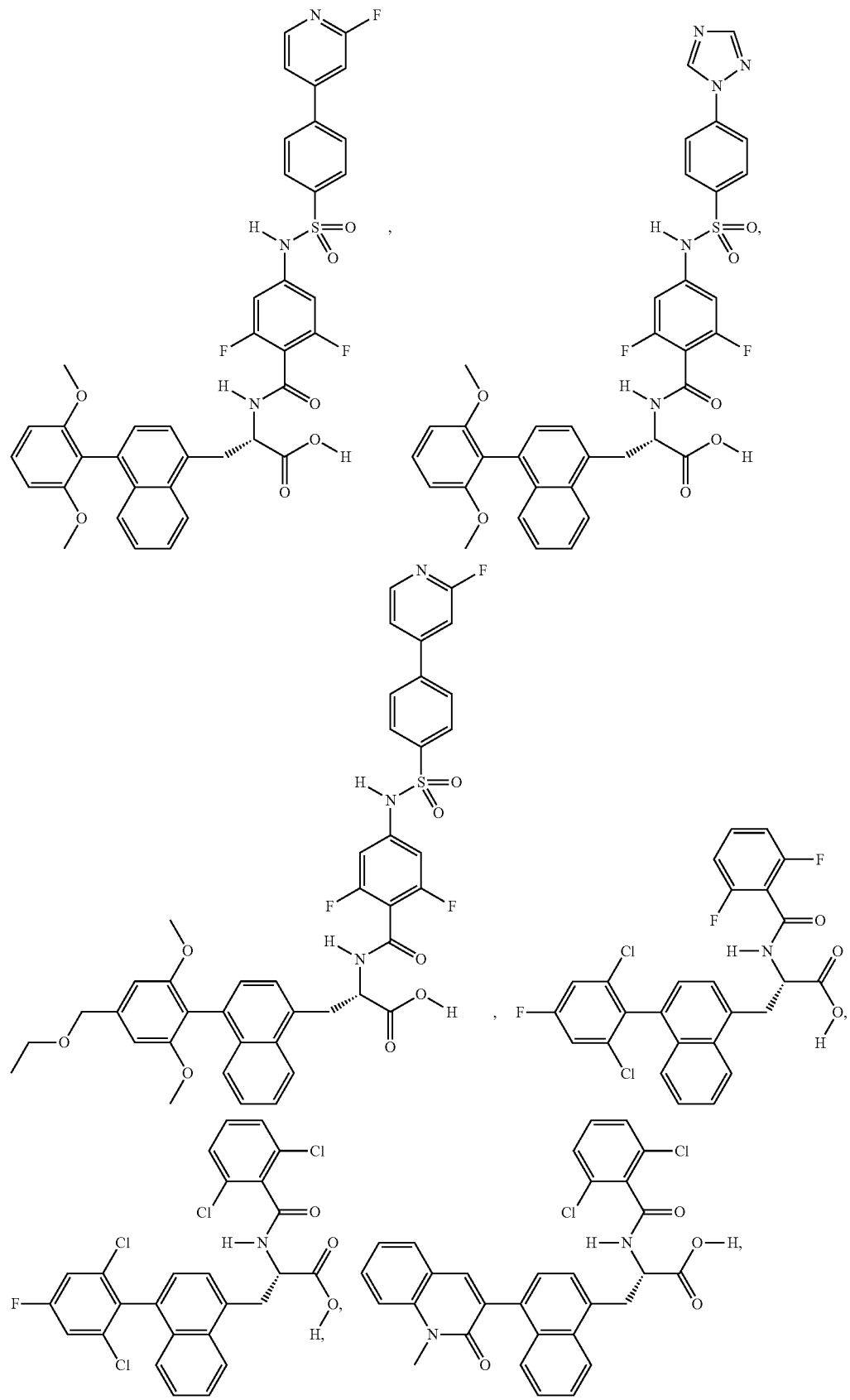

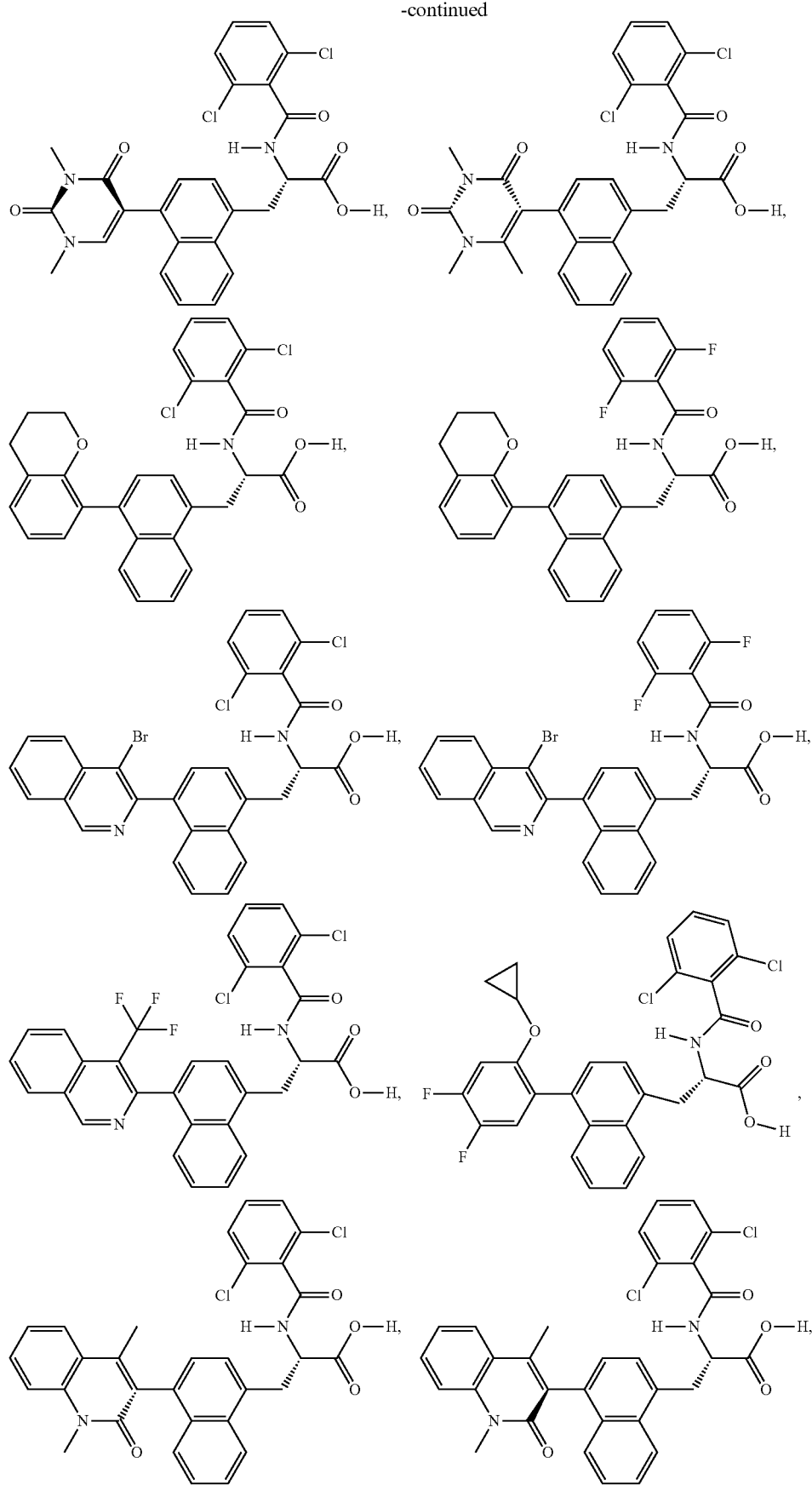

357 358
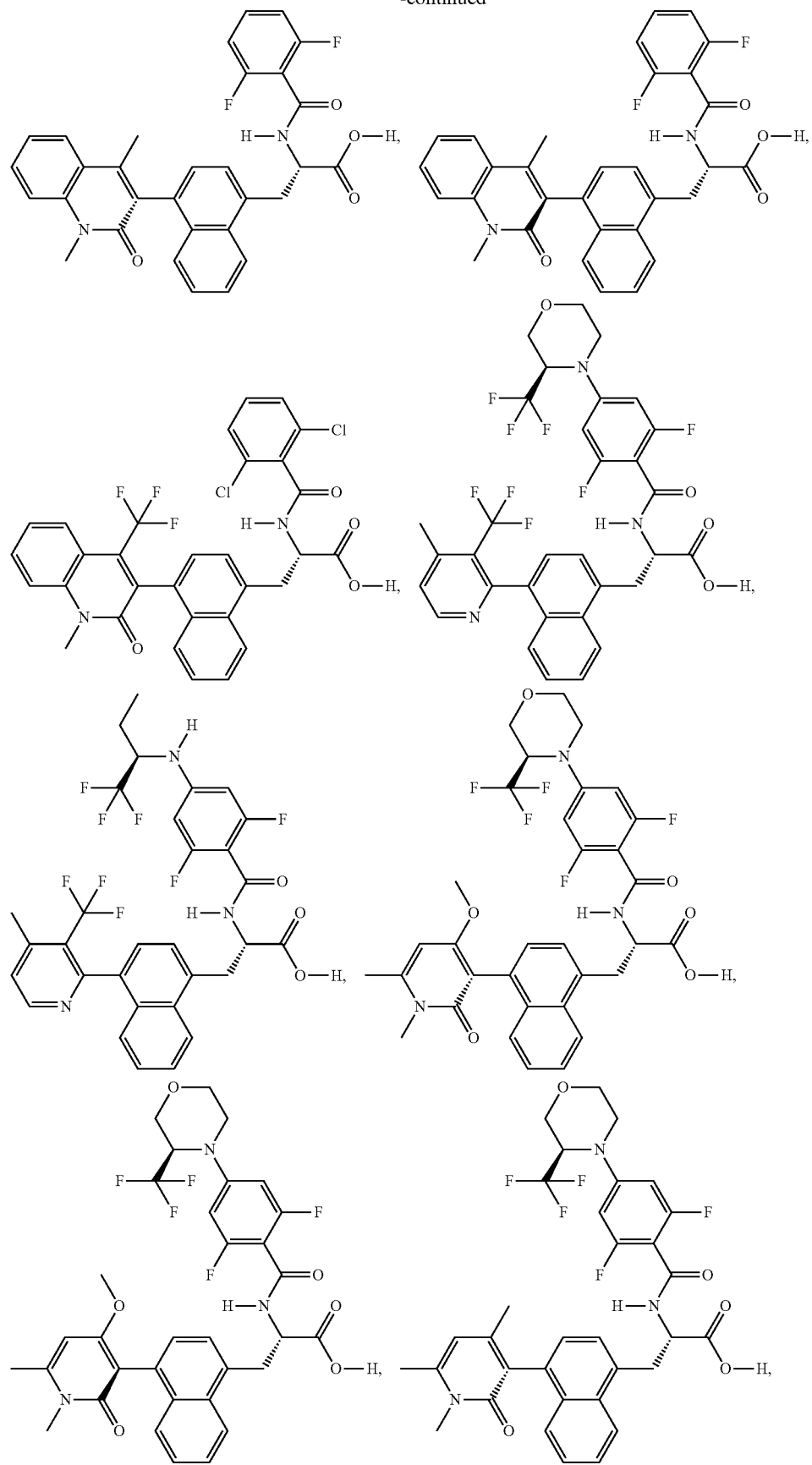

-continued
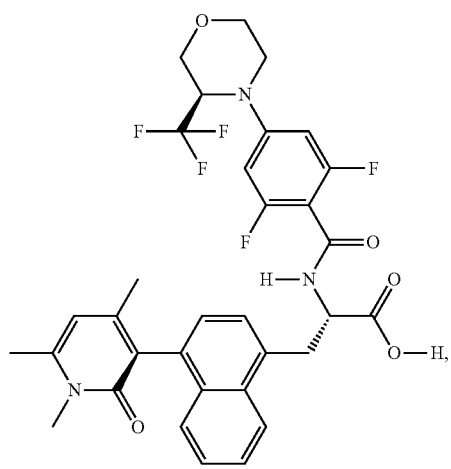
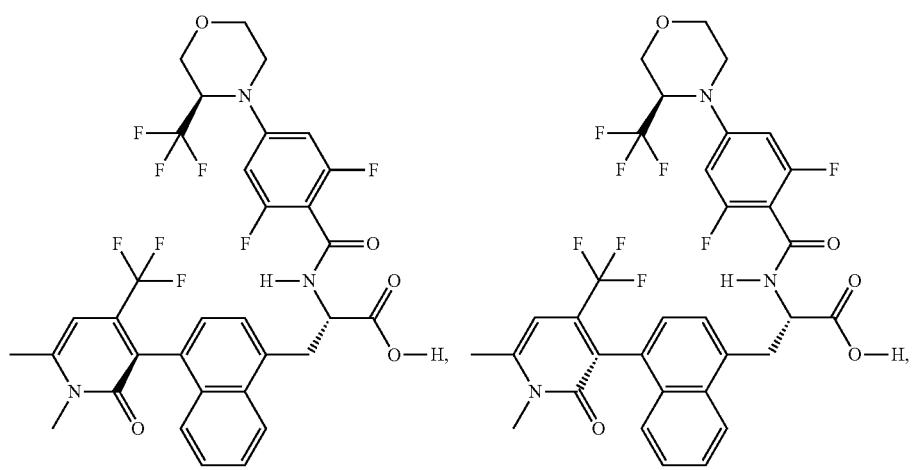
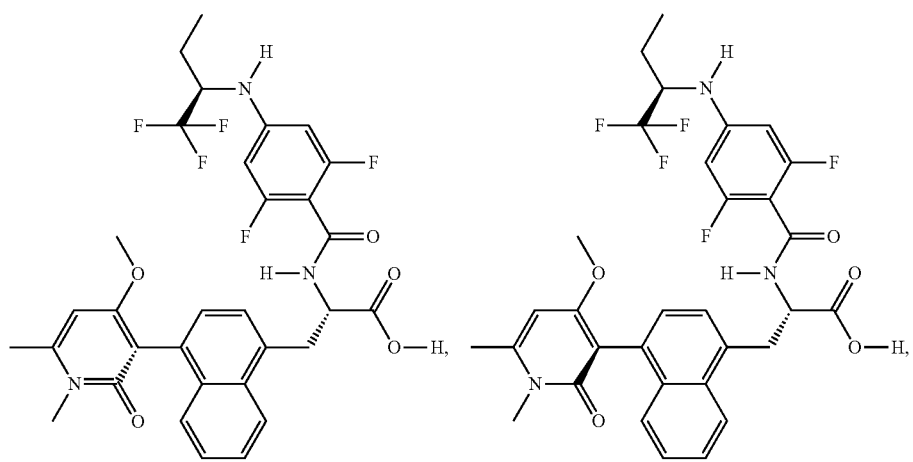

361
362
-continued
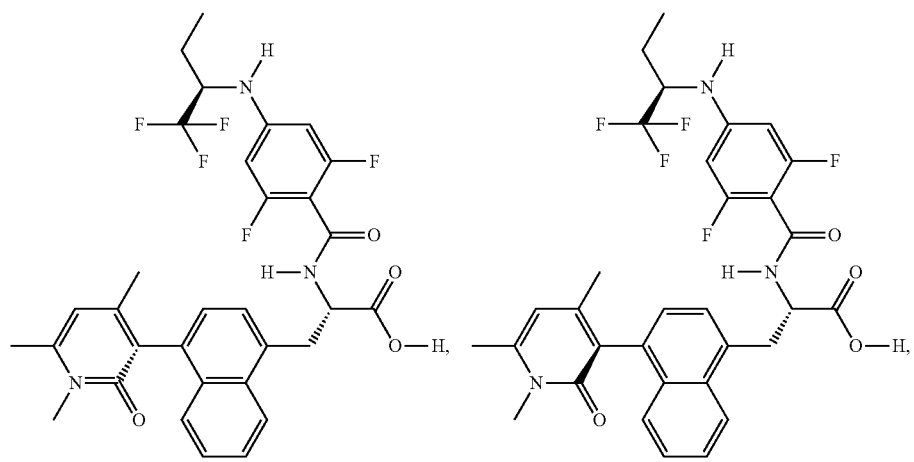
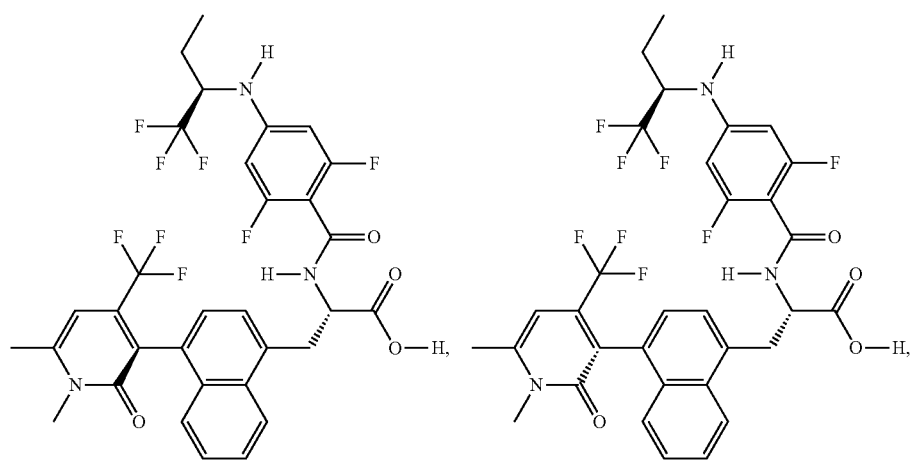
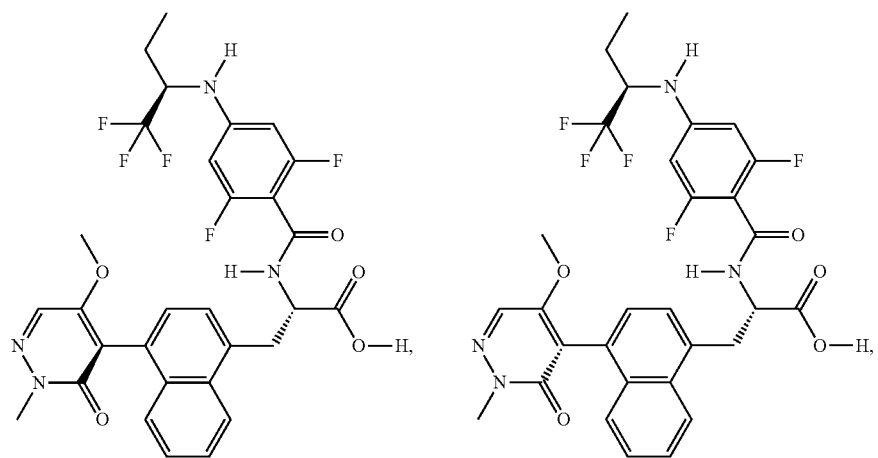

363 364
-continued
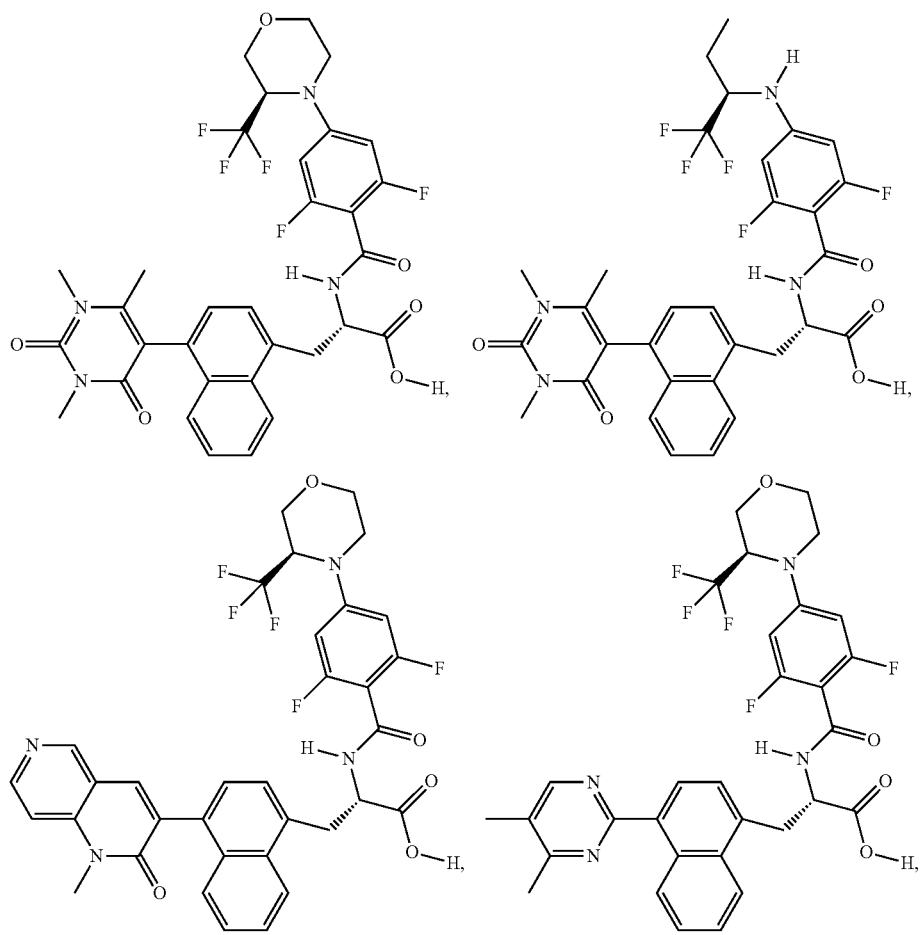
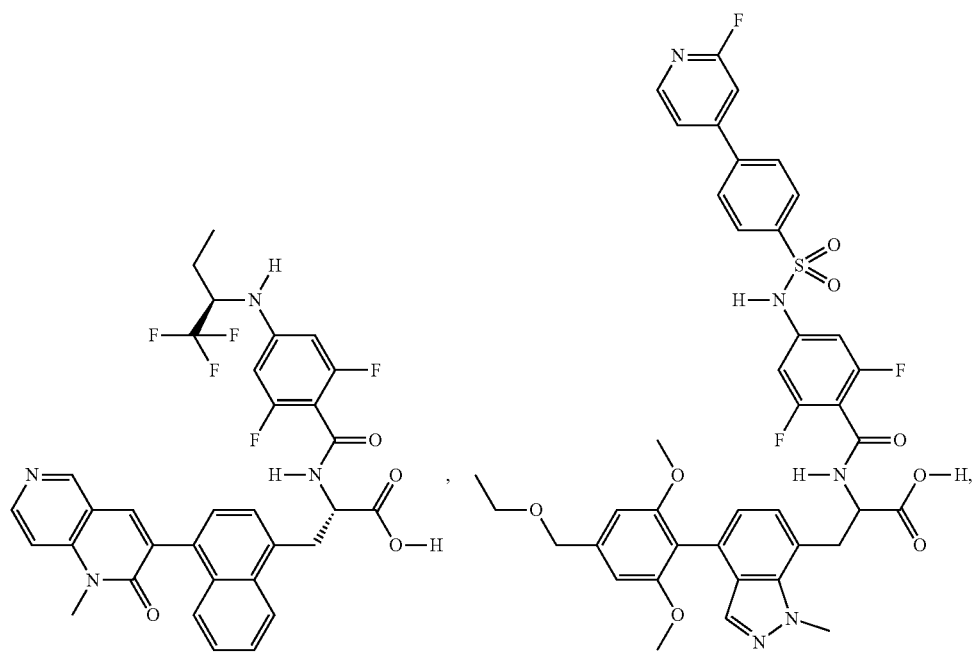

365
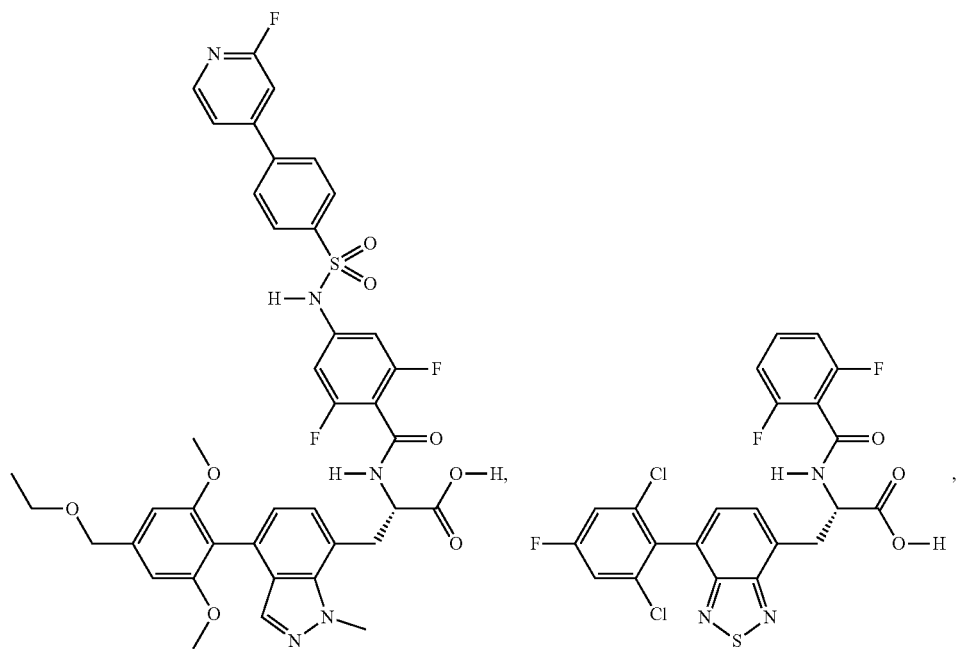
366
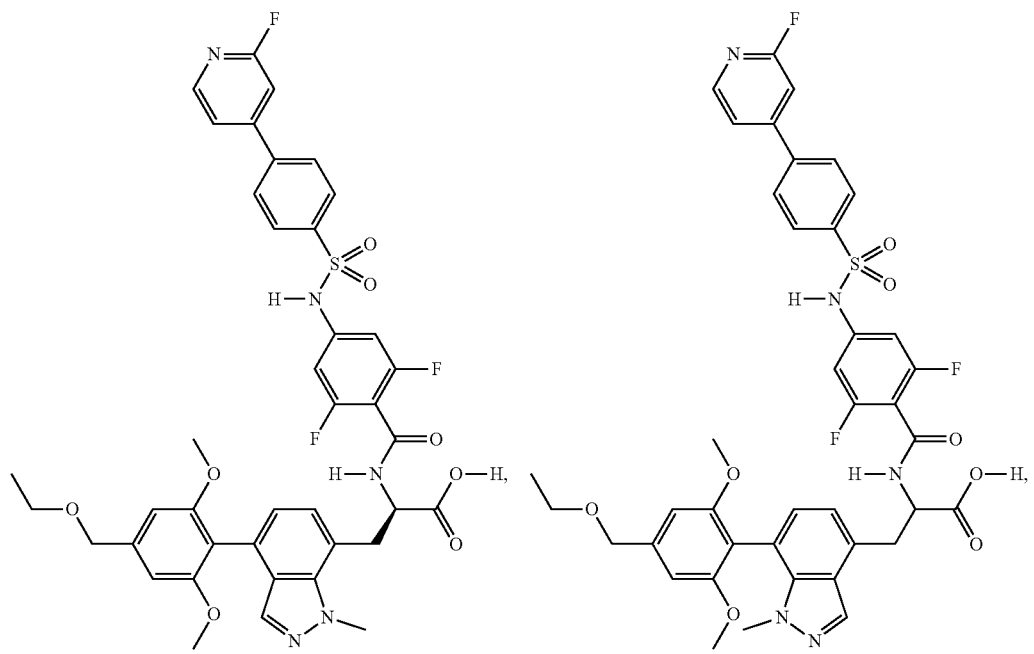

367 368
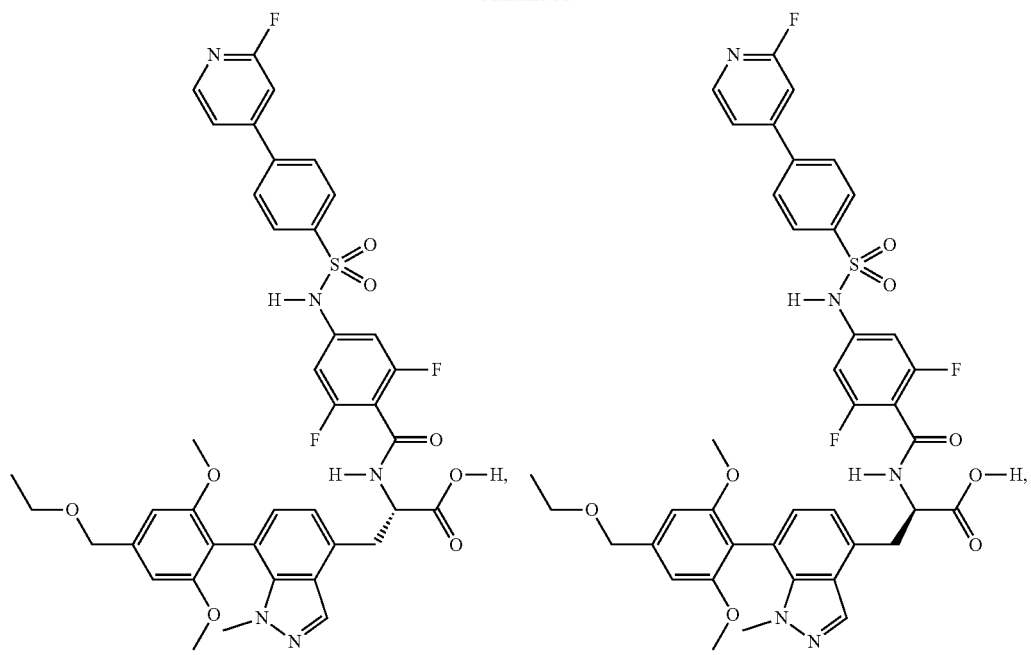
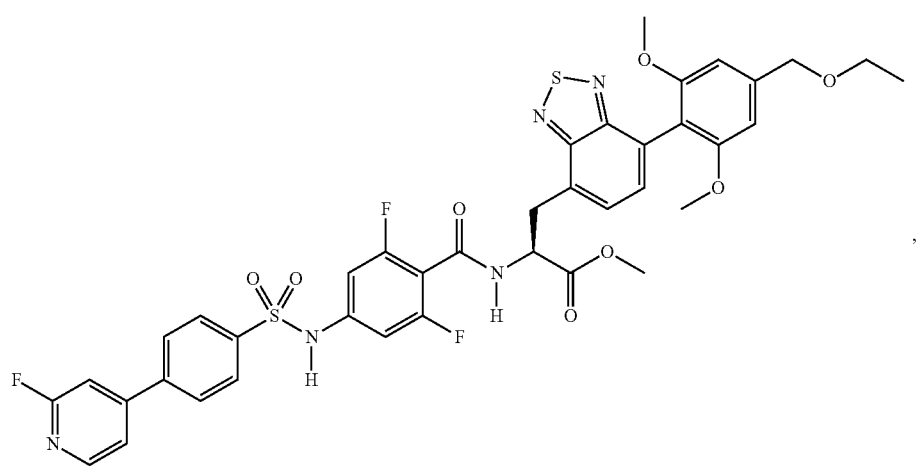 [SMILES: CCOCc1cc(OC)c(-c2ccc(C[C@H](NC(=O)c3c(F)cc(NS(=O)(=O)c4ccc(-c5ccnc(F)c5)cc4)cc3F)C(=O)OC)c3nsnc23)c(OC)c1 ; ","]

-continued
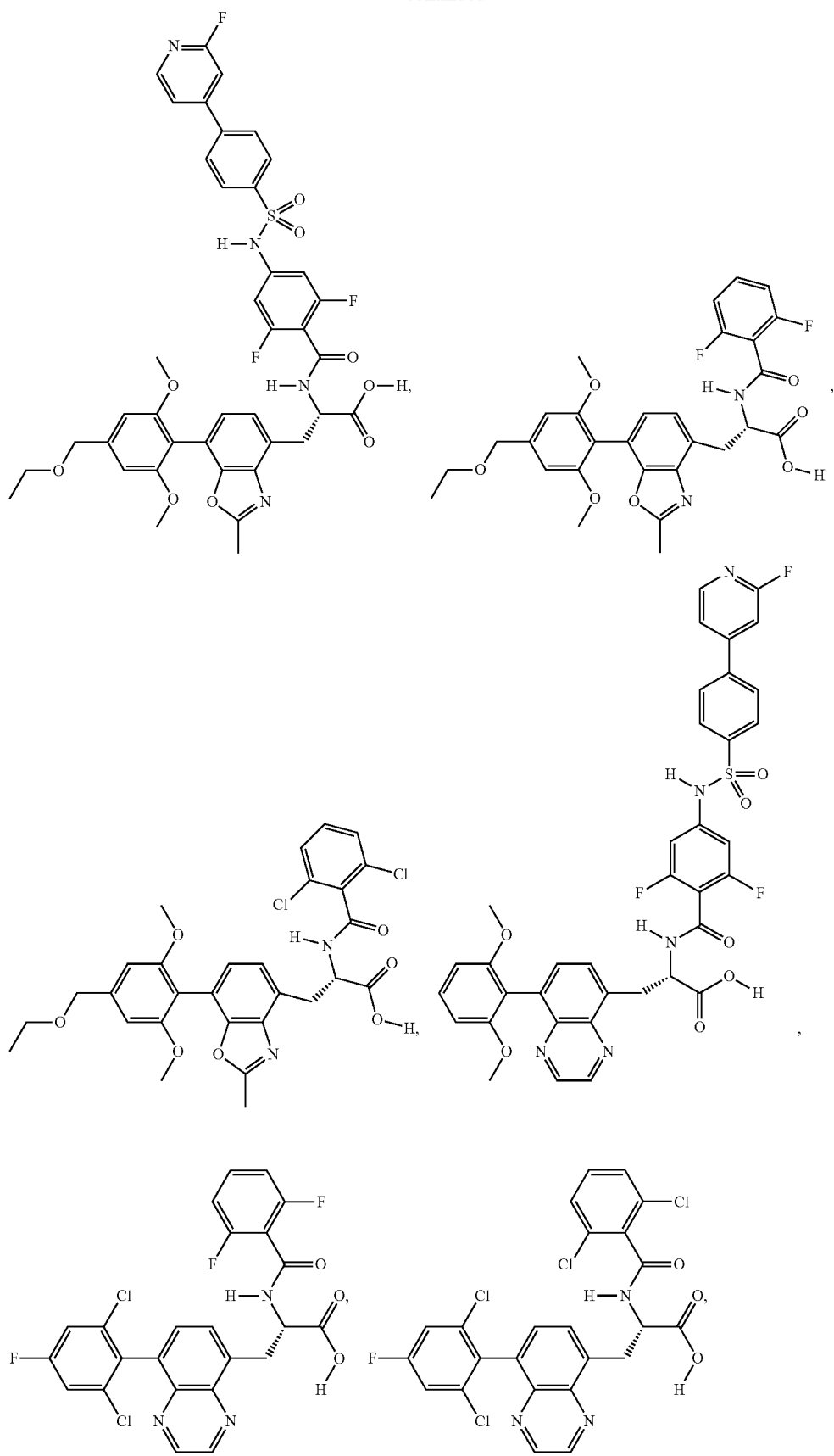

-continued
371
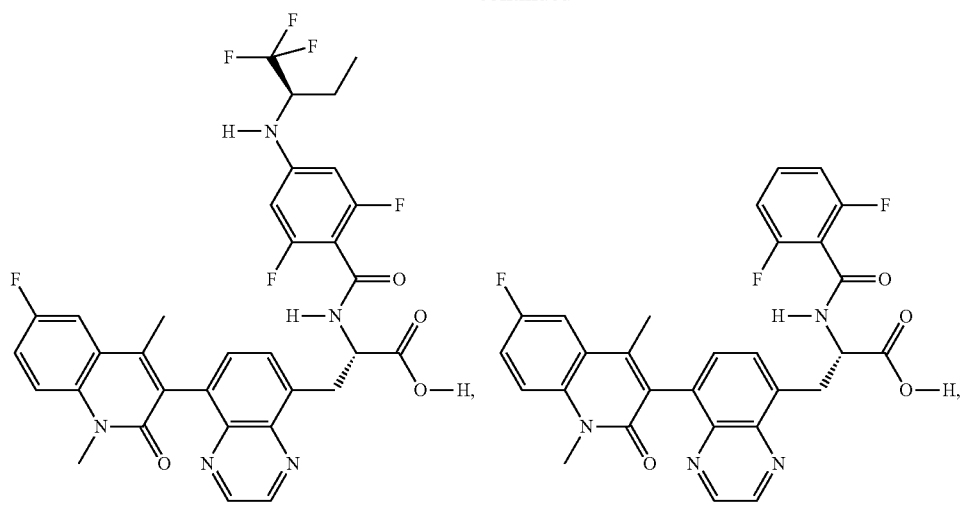
372
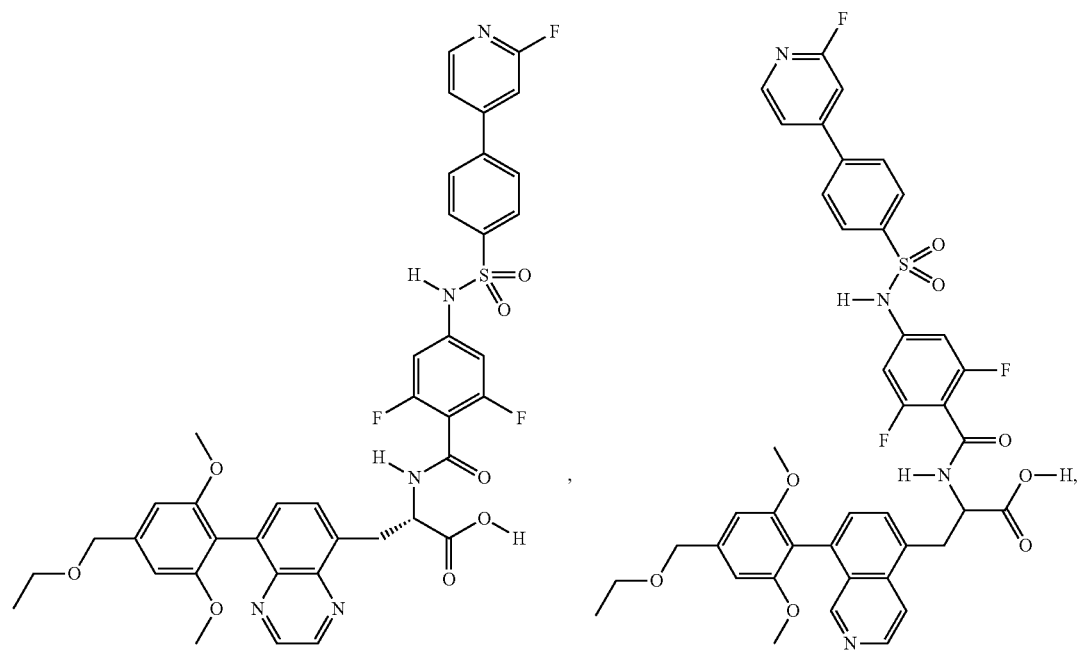

373 374
-continued
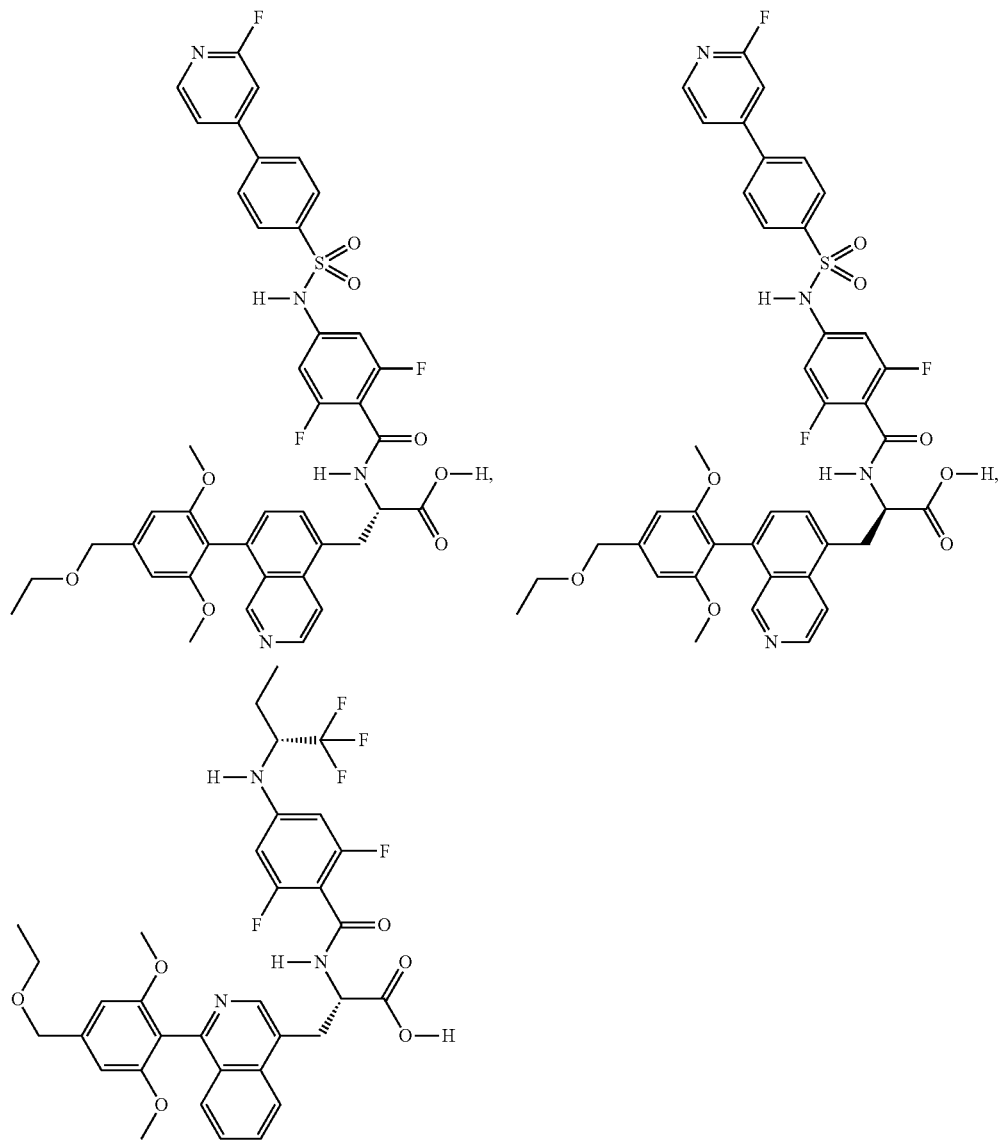
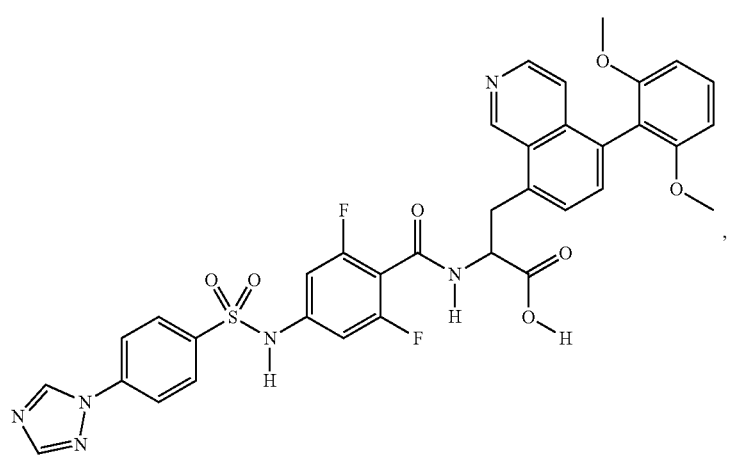

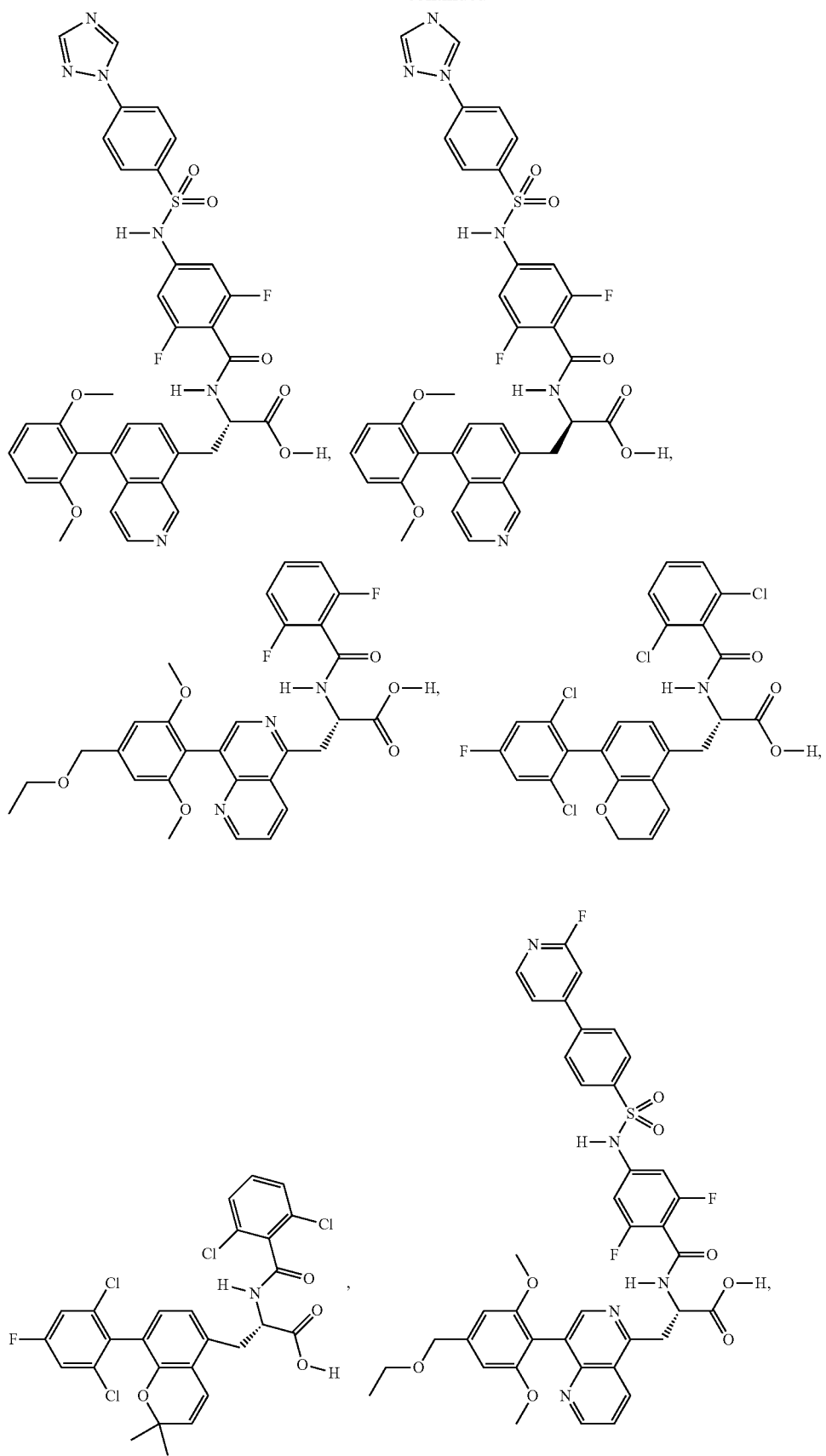

377 378
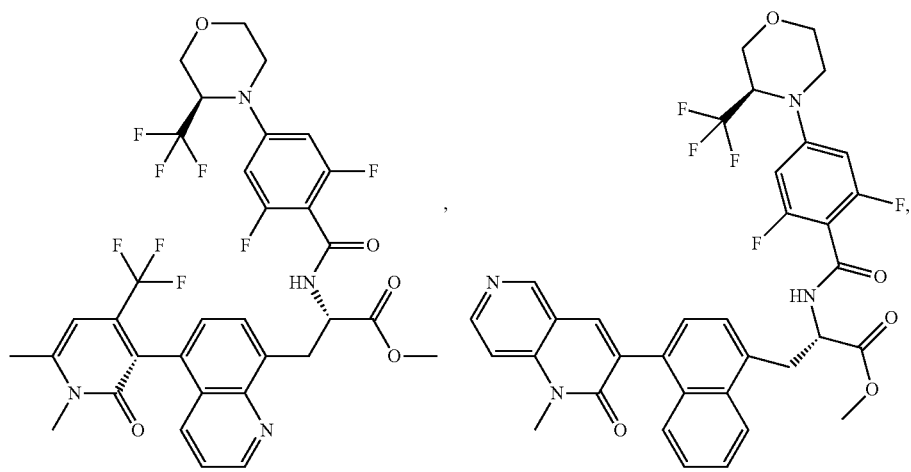
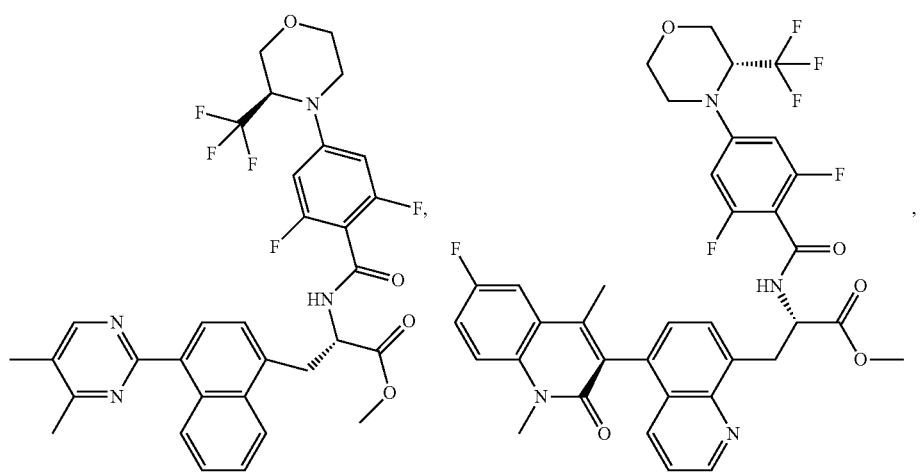
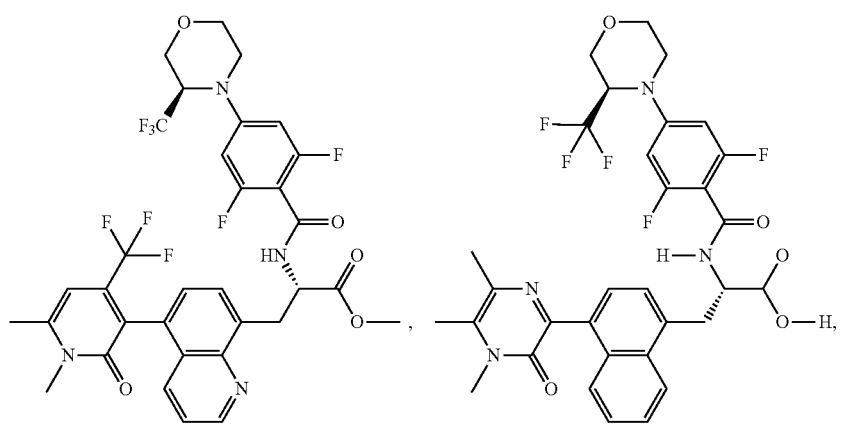

-continued

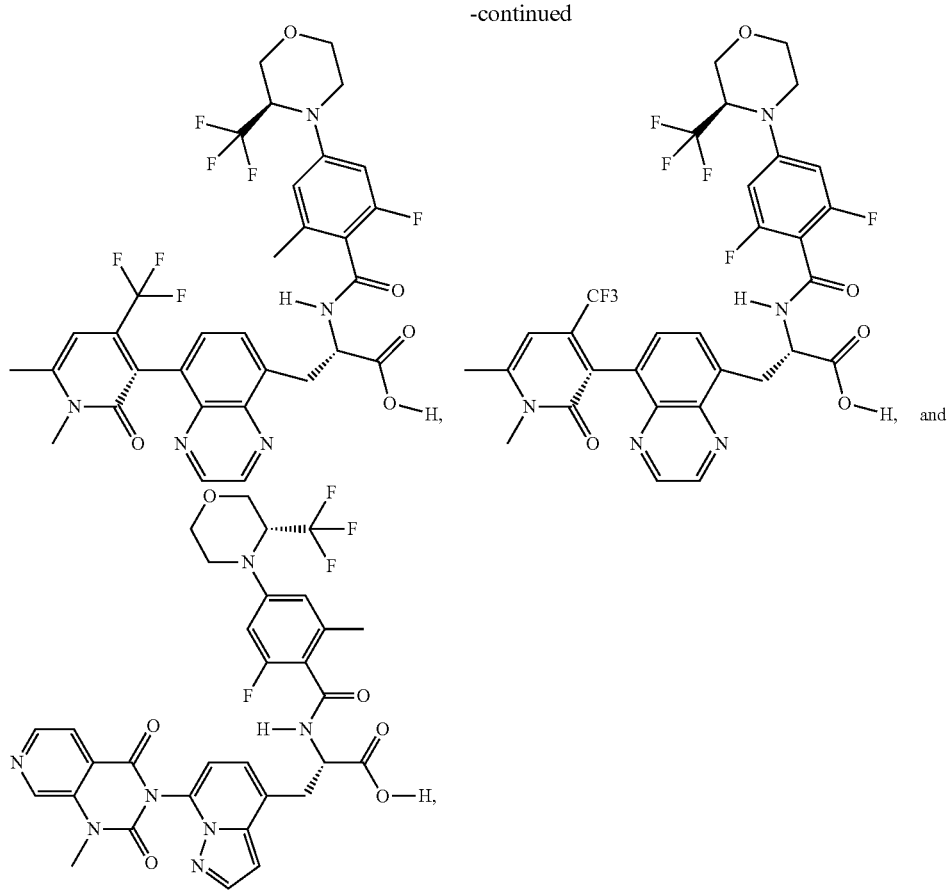

15. A pharmaceutical composition comprising a compound of claim 1, or a pharmaceutically acceptable salt thereof, and at least one pharmaceutically acceptable carrier.

16. The pharmaceutical composition of claim 15, further comprising at least one or more additional therapeutic agents.

17. A method for treating an inflammatory disease or condition mediated, at least in part, by α4β7 integrin comprising administrating to a subject an effective amount of the compound of claim 1, or a pharmaceutically acceptable salt thereof.

18. The method of claim 17, wherein the inflammatory disease or condition is selected from inflammatory bowel disease (IBD), Ulcerative colitis, Crohn's disease, graft-versus-host disease (GVHD), and primary sclerosing cholangitis (PSC).

19. The pharmaceutical composition of claim 16, wherein the at least one or more additional therapeutic agents are independently selected from JAK tyrosine kinase inhibitors, Tumor Progression Locus 2 (TPL2) inhibitors, and IRAK4 inhibitors.

20. The pharmaceutical composition of claim 19, wherein the additional therapeutic agent is a JAK tyrosine kinase inhibitor, and wherein the JAK tyrosine kinase inhibitor is Filgotinib.

* * * * *